(12) United States Patent
Zhao et al.

(10) Patent No.: US 10,780,120 B2
(45) Date of Patent: Sep. 22, 2020

(54) PROSTATE-SPECIFIC MEMBRANE ANTIGEN CARS AND METHODS OF USE THEREOF

(71) Applicant: The Trustees of the University of Pennsylvania, Philadelphia, PA (US)

(72) Inventors: Yangbing Zhao, Lumberton, NJ (US); Szu Hua Sharon Lin, Philadelphia, PA (US); Xiaojun Liu, Wallingford, PA (US); Anne Chew, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/293,298

(22) Filed: Mar. 5, 2019

(65) Prior Publication Data

US 2019/0275083 A1    Sep. 12, 2019

Related U.S. Application Data

(60) Provisional application No. 62/639,321, filed on Mar. 6, 2018.

(51) Int. Cl.
| | | |
|---|---|---|
| *A61K 35/17* | (2015.01) | |
| *A61K 31/661* | (2006.01) | |
| *A61K 31/7076* | (2006.01) | |
| *A61P 35/04* | (2006.01) | |
| *A61P 35/00* | (2006.01) | |
| *C07K 14/705* | (2006.01) | |
| *C07K 14/725* | (2006.01) | |
| *C07K 16/30* | (2006.01) | |

(52) U.S. Cl.
CPC ............ *A61K 35/17* (2013.01); *A61K 31/661* (2013.01); *A61K 31/7076* (2013.01); *A61P 35/00* (2018.01); *A61P 35/04* (2018.01); *C07K 14/7051* (2013.01); *C07K 14/70517* (2013.01); *C07K 14/70575* (2013.01); *C07K 16/3069* (2013.01); *C07K 2317/622* (2013.01); *C07K 2319/03* (2013.01)

(58) Field of Classification Search
CPC .... A61K 2039/5156; A61K 2039/5158; A61K 2039/884; A61K 31/661; A61K 31/7076; A61K 35/17; A61K 38/00; A61K 39/001195; A61P 35/00; A61P 35/04; C07K 14/00; C07K 14/7051; C07K 14/70517; C07K 14/70575; C07K 16/2818; C07K 16/2827; C07K 16/2863; C07K 16/3069; C07K 2317/31; C07K 2317/622; C07K 2319/03; C07K 2319/32; C07K 2319/33
USPC ......... 424/130.1, 172.1, 174.1, 199.1, 204.1, 424/246.1, 277.1; 514/25, 44
See application file for complete search history.

(56) References Cited

U.S. PATENT DOCUMENTS

| | | | |
|---|---|---|---|
| 7,446,190 B2 | 11/2008 | Sadelain et al. | |
| 2011/0262439 A1* | 10/2011 | Kufer | C07K 16/2809 424/135.1 |
| 2017/0209492 A1 | 7/2017 | June et al. | |
| 2017/0218337 A1 | 8/2017 | Friedman | |
| 2017/0335281 A1 | 11/2017 | Loew et al. | |
| 2018/0273601 A1* | 9/2018 | Adusumilli | A61K 39/0011 |

FOREIGN PATENT DOCUMENTS

| | | |
|---|---|---|
| WO | 9210591 A1 | 6/1992 |
| WO | 9215322 A1 | 9/1992 |
| WO | 9309228 A1 | 5/1993 |
| WO | 9319163 A1 | 9/1993 |
| WO | 9409815 A1 | 5/1994 |
| WO | 9409820 A1 | 5/1994 |
| WO | 9502686 A1 | 1/1995 |
| WO | 9623814 A1 | 8/1996 |
| WO | 9625178 A1 | 8/1996 |
| WO | 9625953 A1 | 8/1996 |
| WO | 9626265 A1 | 8/1996 |
| WO | 9735616 A1 | 10/1997 |
| WO | 9803873 A1 | 1/1998 |
| WO | 9848024 A1 | 10/1998 |
| WO | 9913912 A1 | 3/1999 |
| WO | 9965948 A1 | 12/1999 |
| WO | 0014257 A1 | 3/2000 |
| WO | 0040227 A2 | 7/2000 |

(Continued)

OTHER PUBLICATIONS

PCT/US2019/020729—International Search Report and Written Opinion dated Jul. 26, 2019.

(Continued)

*Primary Examiner* — Janet L Epps-Smith

(74) *Attorney, Agent, or Firm* — Saul Ewing Arnstein & Lehr LLP; Kathryn Doyle

(57) ABSTRACT

The present disclosure provides modified immune cells (e.g., modified T cells) comprising a chimeric antigen receptor (CAR) having affinity for a prostate-specific membrane antigen (PSMA) (e.g., human PSMA). The present disclosure provides modified immune cells (e.g., modified T cells) comprising a CAR having affinity for PSMA and a dominant negative receptor and/or a switch receptor. The present disclosure provides modified immune cells (e.g., modified T cells) comprising a CAR having affinity for PSMA and a dominant negative receptor and/or a switch receptor, wherein the modified cell is capable of expressing and secreting a bispecific antibody.

3 Claims, 59 Drawing Sheets

Specification includes a Sequence Listing.

(56) References Cited

FOREIGN PATENT DOCUMENTS

| WO | 0109192 | A1 | 2/2001 | | |
|---|---|---|---|---|---|
| WO | 02098897 | A2 | 12/2002 | | |
| WO | 03034903 | A2 | 5/2003 | | |
| WO | 2004067570 | A2 | 8/2004 | | |
| WO | 2004098535 | A2 | 11/2004 | | |
| WO | 2005044996 | A2 | 5/2005 | | |
| WO | 2011069019 | A2 | 6/2011 | | |
| WO | 2012031744 | A1 | 3/2012 | | |
| WO | 2012079000 | A1 | 6/2012 | | |
| WO | 2012099973 | A2 | 7/2012 | | |
| WO | 2012138858 | A1 | 10/2012 | | |
| WO | WO-2013059593 | A1 | * | 4/2013 | ....... C07K 14/70521 |
| WO | 2013126726 | A1 | 8/2013 | | |
| WO | 2014055097 | A1 | 4/2014 | | |
| WO | 2014172584 | A1 | 10/2014 | | |
| WO | 2015142675 | A2 | 9/2015 | | |
| WO | WO-2016044383 | A1 | * | 3/2016 | ....... A61K 39/39558 |
| WO | 2016055551 | A1 | 4/2016 | | |
| WO | 2016061574 | A1 | 4/2016 | | |
| WO | 2016069282 | A1 | 5/2016 | | |
| WO | 2016210293 | A1 | 12/2016 | | |
| WO | 2017040195 | A1 | 3/2017 | | |
| WO | 2017040945 | A1 | 3/2017 | | |
| WO | 2017070649 | A1 | 4/2017 | | |
| WO | 2016057917 | A9 | 6/2017 | | |
| WO | 2017100428 | A1 | 6/2017 | | |
| WO | 2017212250 | A1 | 12/2017 | | |
| WO | 2018033749 | A1 | 2/2018 | | |
| WO | 2018044866 | A1 | 3/2018 | | |
| WO | 2018140725 | A1 | 8/2018 | | |
| WO | 2018191490 | A1 | 10/2018 | | |

OTHER PUBLICATIONS

Liu, et al., "A Chimeric Switch-Receptor Targeting PD1 Aguments the Efficacy of Second-Generation CAR T Cells in Advanced Solid Tumors.", 2016, Cancer Research 76(6):1578-1590 (Mar. 15, 2016).
Bendle, et al., "Blockade of TGF-beta Signaling Greatly Enhances the Efficacy of TCR Gene Therapy of Cancer.", J Immunol 2013; 191:3232-3239.
Bollard, et al., Adapting a transforming growth factor beta-related tumor protection strategy to enhance antitumor immunity, Blood 99 ,2002 ,3179-3187.
Foster, et al., "Antitumor Activity of EBV-specific T Lymphocytes Transduced With a Dominant Negative TGF-beta Receptor.", J Immunother. Jun. 2008 ; 31(5): 500-505.
Junghans, et al., Abstract C13: Phase I trial of anti-PSMA designer T cells in advanced prostate cancer, Cancer Research DOI: 10.1158/ 1538-7445.PRCA2012-C13 Published Feb. 2012.
Kloss, et al., "Combinatorial antigen recognition with balanced signaling promotes selective tumor eradication by engineered T cells.", Nat Biotechnol. Jan. 2013 ; 31(1): 71-75.
Liu, et al., "Monoclonial Antibodies to the Extracellular Domain of Prostate-specific Membrane Antigen Also React with Tumor Vascular Endothelium.", 1997 Cancer Research, 57:3629-3634.
Santoro, et al., T cells bearing a chimeric antigen receptor agains prostate-specific membrane antigen mediate vascular disruption and result in tumor regression., 2015, Cancer Immunology Research, 3(1):68-84.
Wieser, et al., "Signaling Activity of Transforming Growth Factor Beta Type II Receptors Lacking Specific Domains in the Cytoplasmic Region.", 1993 Molecular and Cellular Biology, 13(12):7239-7247.

* cited by examiner

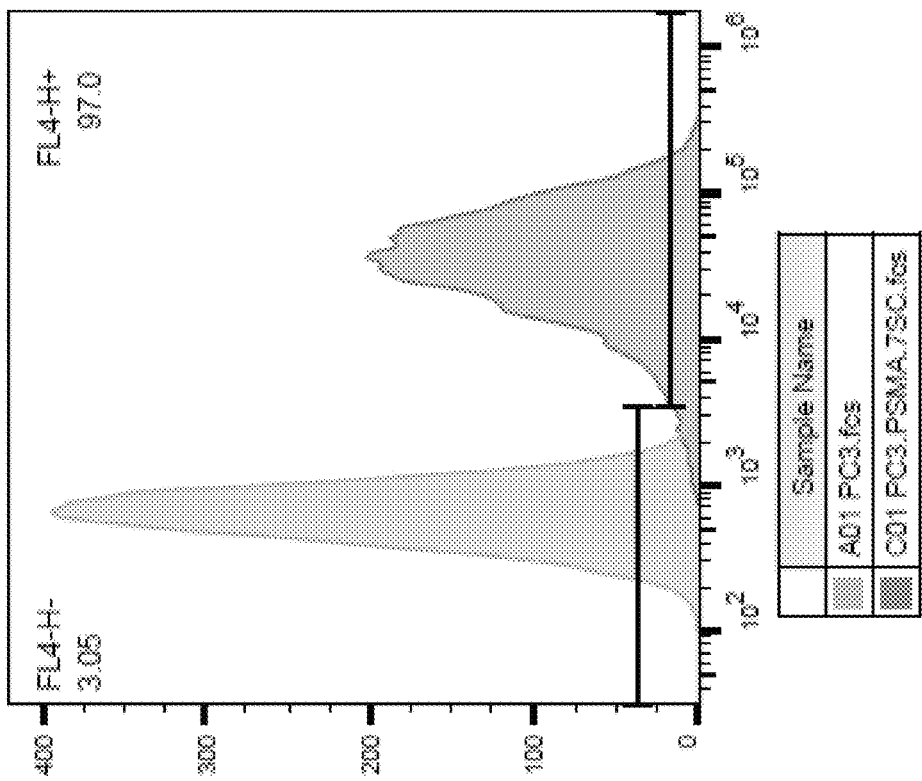
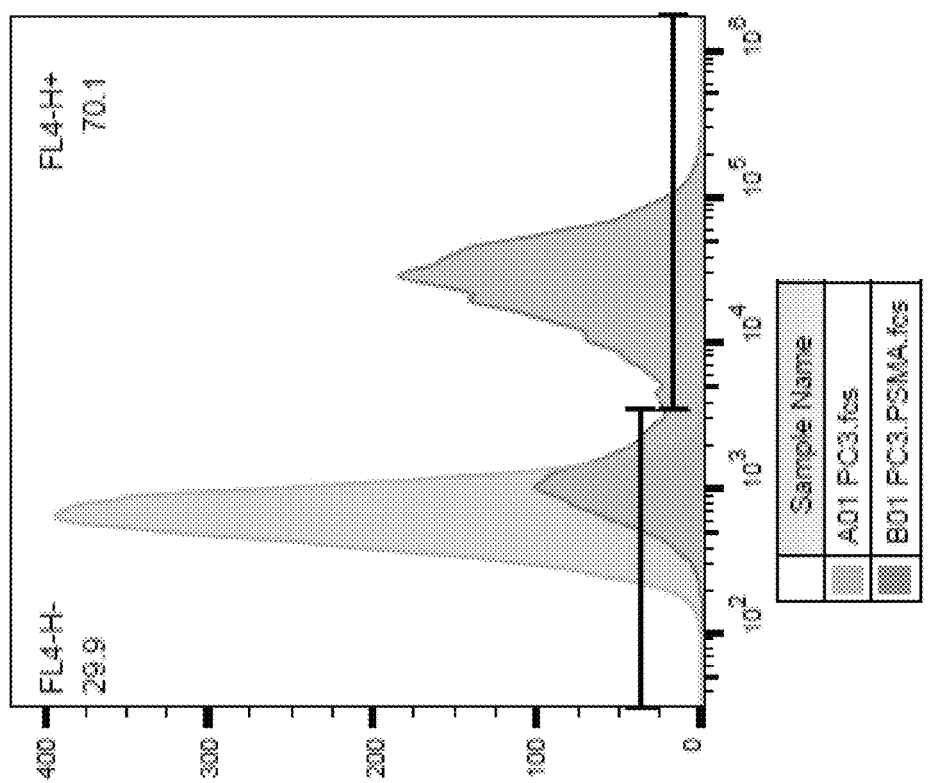
Fig. 1D

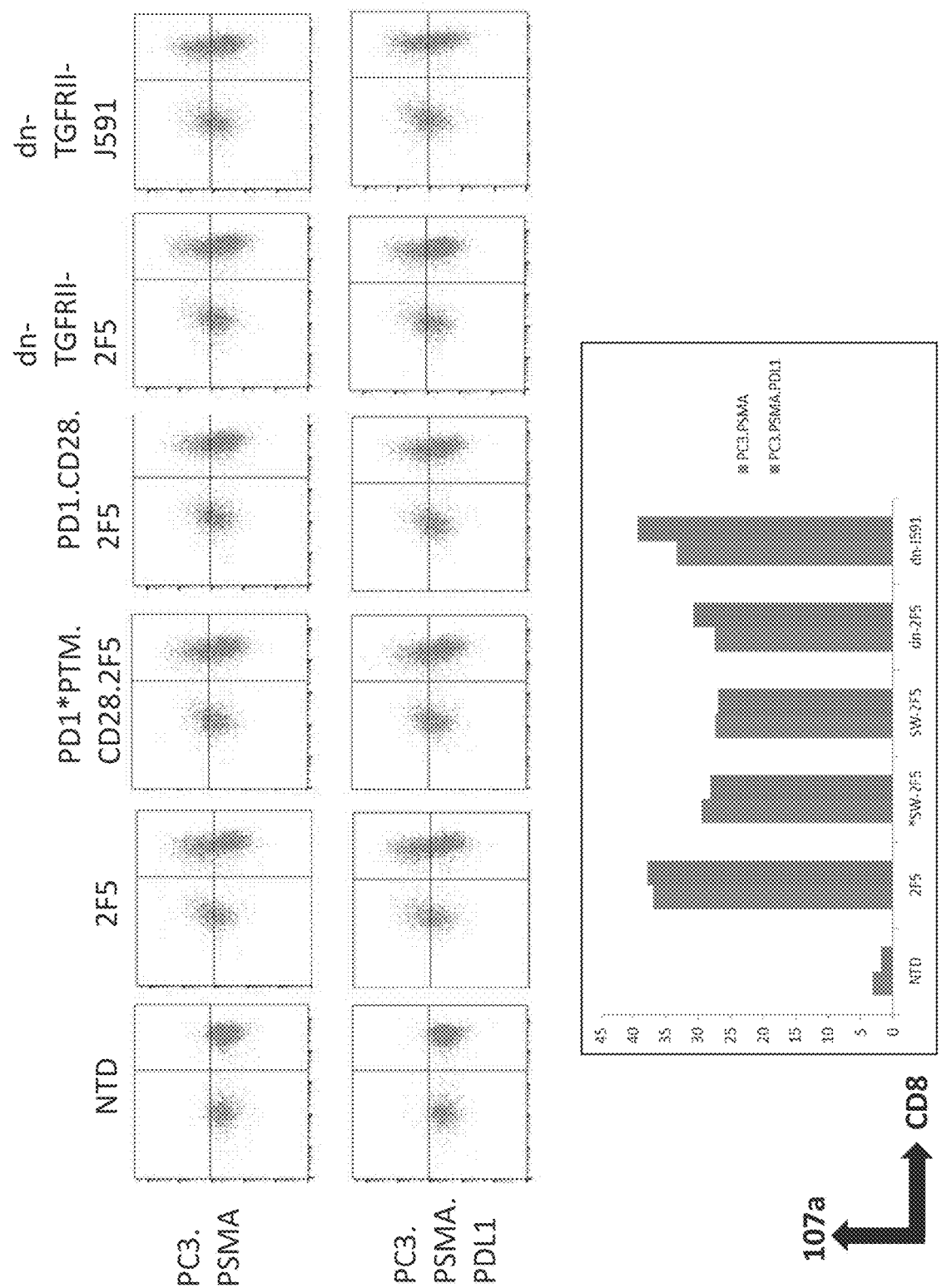

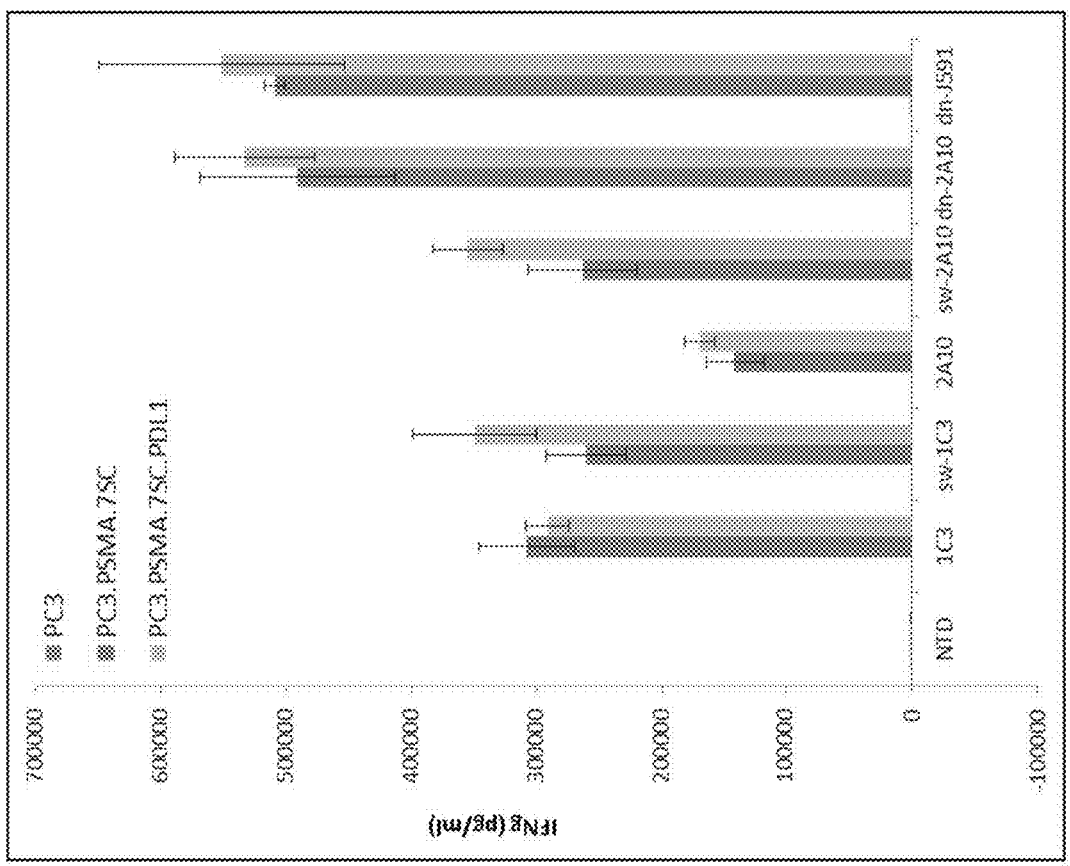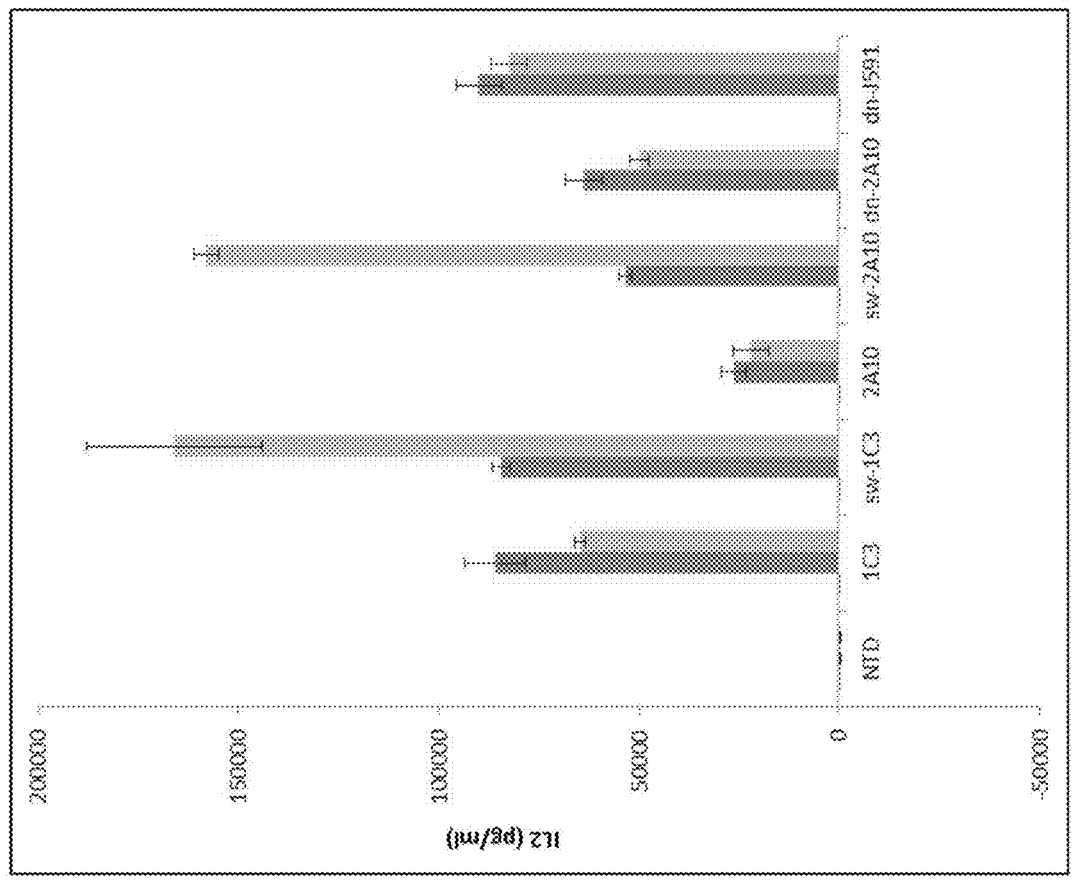
Fig. 5F

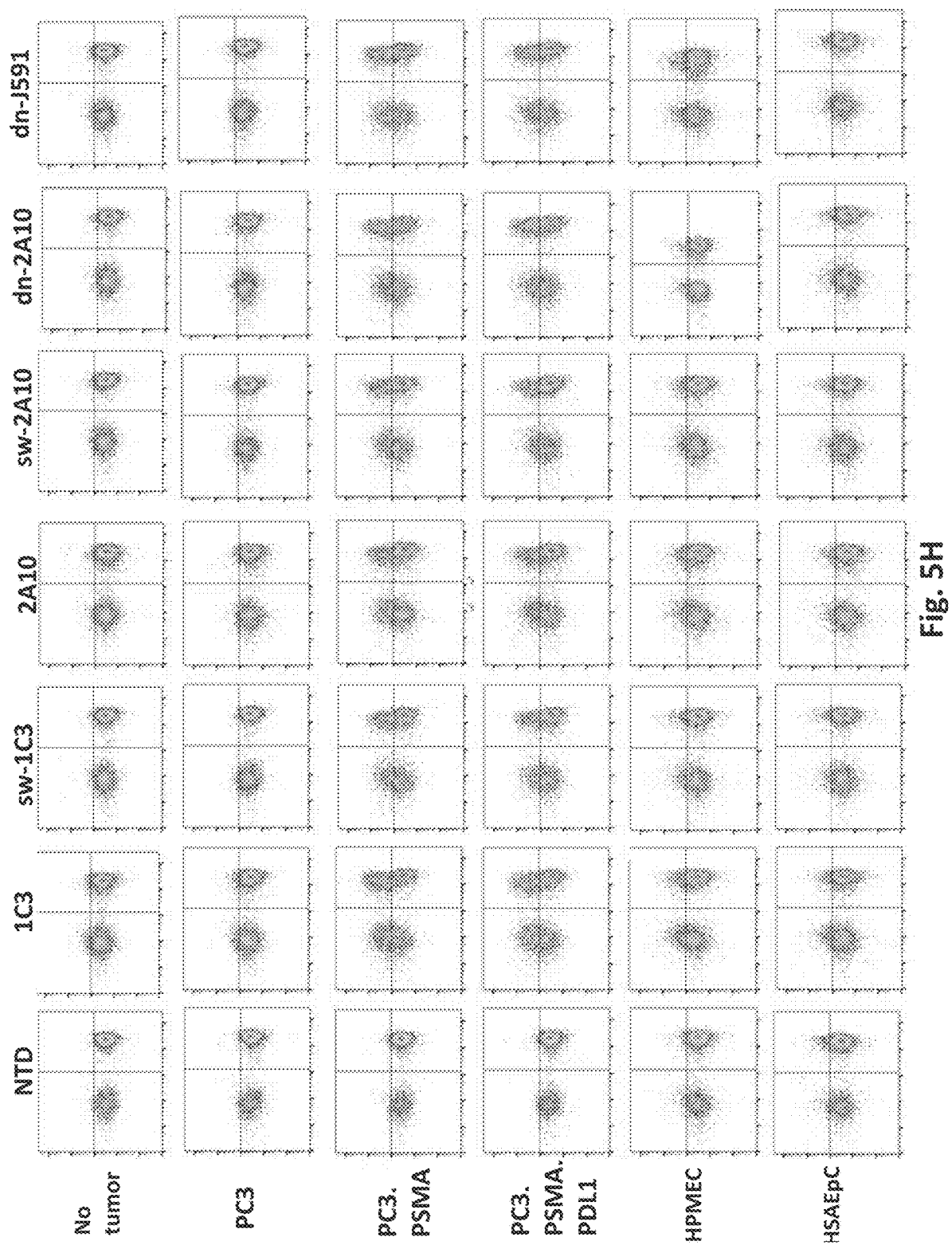

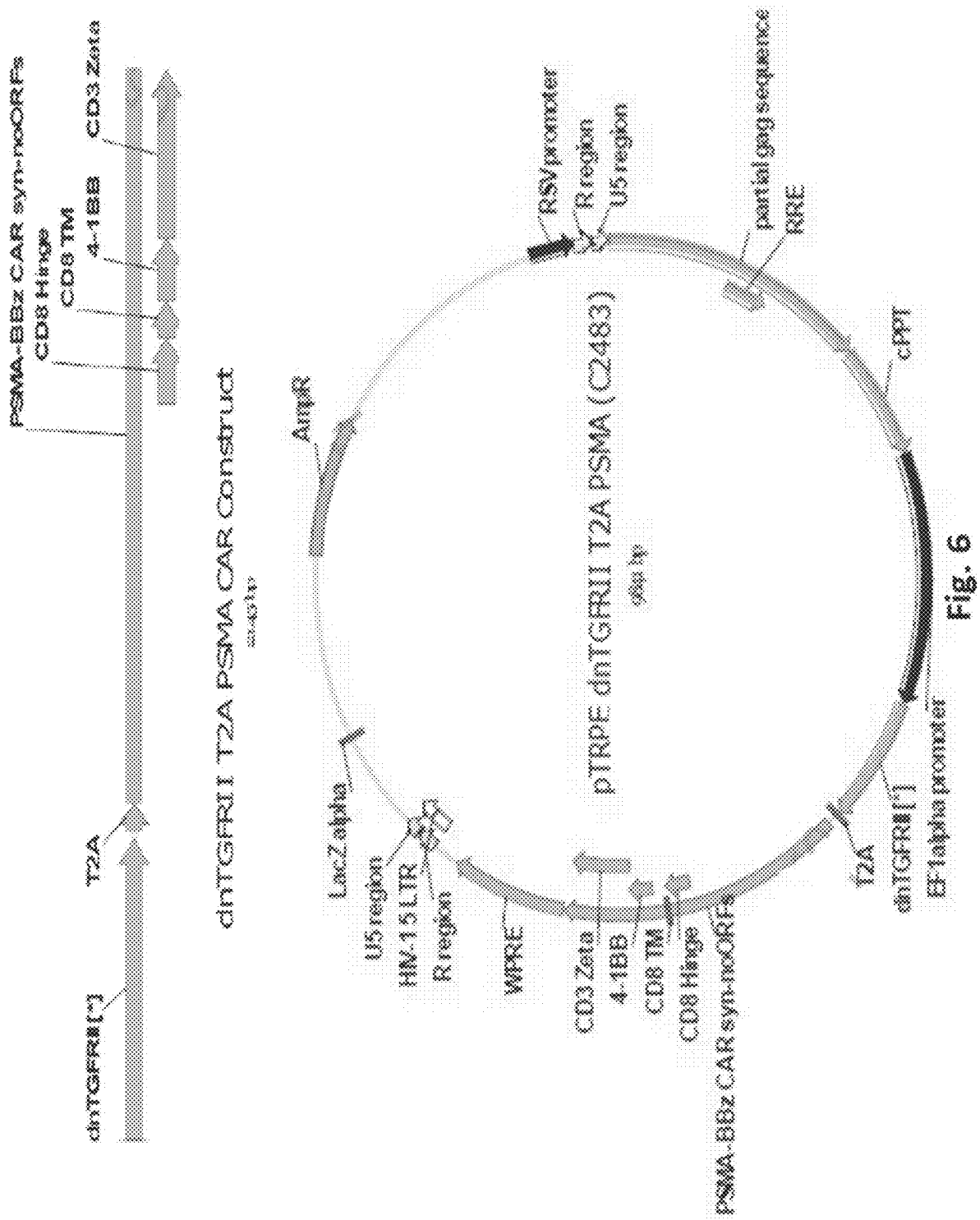

| | |
|---|---|
| D | PD1*CD28.2F5.BBZ |
| B | 2F5.BBZ |
| L | PD1*BB.2F5ICOSzYMNM |
| P | PD1*BB.Tim3CD28.2F5ICOSzYMNM |
| K | PD1*BB.2F5ICOSz |
| J | PD1*CD28.2F5ICOSzYMNM |
| F | 2F5.ICOSzYMNM |
| H | PD1CD28.2F5ICOSzYMNM |
| O | PD1*BB.Tim3CD28.2F5ICOSz |
| E | 2F5.ICOSz |
| N | Tim3CD28.2F5.ICOSzYMNM |
| I | PD1*CD28.2F5ICOSz |
| C | PD1.CD28.2F5.BBZ |
| G | PD1CD28.2F5ICOSz |
| A | NTD |
| M | Tim3CD28.2F5ICOSz |

Fig. 14G

SEQUENCE LISTING

```
<160> NUMBER OF SEQ ID NOS: 236

<210> SEQ ID NO 1
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 1

Gly Ser Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: linker
<220> FEATURE:
```

```
<221> NAME/KEY: REPEAT
<222> LOCATION: (1)..(4)
<223> OTHER INFORMATION: repeat n times, where n represents an integer
      of at least 1

<400> SEQUENCE: 2

Gly Gly Gly Ser
1

<210> SEQ ID NO 3
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 3

Gly Gly Gly Gly Ser
1               5

<210> SEQ ID NO 4
<211> LENGTH: 4
<212> TYPE: PRT
<213> ORGANISM: Artificial Sequence
<220> FEATURE:
<223> OTHER INFORMATION: linker

<400> SEQUENCE: 4

Gly Gly Ser Gly
1

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Gly Ser Gly Gly
1               5

<210> SEQ ID NO 6
<211> LENGTH: 5
<212> TYPE: PRT
<213> ORGANISM: Artificial Sequence
<220> FEATURE:
<223> OTHER INFORMATION: linker

<400> SEQUENCE: 6

Gly Ser Gly Ser Gly
1               5

<210> SEQ ID NO 7
<211> LENGTH: 5
<212> TYPE: PRT
<213> ORGANISM: Artificial Sequence
<220> FEATURE:
<223> OTHER INFORMATION: linker

<400> SEQUENCE: 7

Gly Ser Gly Gly Gly
1               5
```

<210> SEQ ID NO 8
<211> LENGTH: 5
<212> TYPE: PRT
<213> ORGANISM: Artificial Sequence
<220> FEATURE:
<223> OTHER INFORMATION: linker

<400> SEQUENCE: 8

Gly Gly Gly Ser Gly
1               5

<210> SEQ ID NO 9
<211> LENGTH: 5
<212> TYPE: PRT
<213> ORGANISM: Artificial Sequence
<220> FEATURE:
<223> OTHER INFORMATION: linker

<400> SEQUENCE: 9

Gly Ser Ser Ser Gly
1               5

<210> SEQ ID NO 10
<211> LENGTH: 5
<212> TYPE: PRT
<213> ORGANISM: Artificial Sequence
<220> FEATURE:
<223> OTHER INFORMATION: linker

<400> SEQUENCE: 10

Gly Gly Gly Gly Ser
1               5

<210> SEQ ID NO 11
<211> LENGTH: 15
<212> TYPE: PRT
<213> ORGANISM: Artificial Sequence
<220> FEATURE:
<223> OTHER INFORMATION: linker

<400> SEQUENCE: 11

Gly Gly Gly Gly Ser Gly Gly Gly Ser Gly Gly Gly Gly Ser
1               5                   10                  15

<210> SEQ ID NO 12
<211> LENGTH: 45
<212> TYPE: DNA
<213> ORGANISM: Artificial Sequence
<220> FEATURE:
<223> OTHER INFORMATION: linker

<400> SEQUENCE: 12
ggtggcggtg gctcgggcgg tggtgggtcg ggtggcggcg gatct      45

<210> SEQ ID NO 13
<211> LENGTH: 237
<212> TYPE: PRT
<213> ORGANISM: Mus musculus

<400> SEQUENCE: 13

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

```
Val Asp Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Ala Asp Tyr Phe Cys Gln Gln Tyr Asn Ser Tyr Pro Leu
                 85                  90                  95

Thr Phe Gly Ala Gly Thr Met Leu Asp Leu Lys Gly Gly Gly Gly Ser
             100                 105                 110

Gly Gly Gly Gly Ser Ser Gly Gly Ser Glu Val Gln Leu Gln Gln
             115                 120                 125

Ser Gly Pro Glu Leu Val Lys Pro Gly Thr Ser Val Arg Ile Ser Cys
 130                 135                 140

Lys Thr Ser Gly Tyr Thr Phe Thr Glu Tyr Thr Ile His Trp Val Lys
 145                 150                 155                 160

Gln Ser His Gly Lys Ser Leu Glu Trp Ile Gly Asn Ile Asn Pro Asn
                 165                 170                 175

Asn Gly Gly Thr Thr Tyr Asn Gln Lys Phe Glu Asp Lys Ala Thr Leu
             180                 185                 190

Thr Val Asp Lys Ser Ser Ser Thr Ala Tyr Met Glu Leu Arg Ser Leu
         195                 200                 205

Thr Ser Glu Asp Ser Ala Val Tyr Tyr Cys Ala Ala Gly Trp Asn Phe
 210                 215                 220

Asp Tyr Trp Gly Gln Gly Thr Thr Leu Thr Val Ser Ser
 225                 230                 235

<210> SEQ ID NO 14
<211> LENGTH: 260
<212> TYPE: PRT
<213> ORGANISM: Mus musculus

<400> SEQUENCE: 14

Met Ala Leu Pro Val Thr Ala Leu Leu Leu Pro Leu Ala Leu Leu Leu
 1               5                  10                  15

His Ala Ala Arg Pro Gly Ser Asp Ile Val Met Thr Gln Ser His Lys
                 20                  25                  30

Phe Met Ser Thr Ser Val Gly Asp Arg Val Ser Ile Ile Cys Lys Ala
             35                  40                  45

Ser Gln Asp Val Gly Thr Ala Val Asp Trp Tyr Gln Gln Lys Pro Gly
 50                  55                  60

Gln Ser Pro Lys Leu Leu Ile Tyr Trp Ala Ser Thr Arg His Thr Gly
 65                  70                  75                  80

Val Pro Asp Arg Phe Thr Gly Ser Gly Ser Gly Thr Asp Phe Thr Leu
                 85                  90                  95

Thr Ile Thr Asn Val Gln Ser Glu Asp Leu Ala Asp Tyr Phe Cys Gln
             100                 105                 110

Gln Tyr Asn Ser Tyr Pro Leu Thr Phe Gly Ala Gly Thr Met Leu Asp
             115                 120                 125

Leu Lys Gly Gly Gly Gly Ser Gly Gly Gly Gly Ser Ser Gly Gly Gly
 130                 135                 140

Ser Glu Val Gln Leu Gln Gln Ser Gly Pro Glu Leu Val Lys Pro Gly
 145                 150                 155                 160

Thr Ser Val Arg Ile Ser Cys Lys Thr Ser Gly Tyr Thr Phe Thr Glu
                 165                 170                 175
```

Tyr Thr Ile His Trp Val Lys Gln Ser His Gly Lys Ser Leu Glu Trp
            180                 185                 190

Ile Gly Asn Ile Asn Pro Asn Asn Gly Gly Thr Thr Tyr Asn Gln Lys
        195                 200                 205

Phe Glu Asp Lys Ala Thr Leu Thr Val Asp Lys Ser Ser Ser Thr Ala
    210                 215                 220

Tyr Met Glu Leu Arg Ser Leu Thr Ser Glu Asp Ser Ala Val Tyr Tyr
225                 230                 235                 240

Cys Ala Ala Gly Trp Asn Phe Asp Tyr Trp Gly Gln Gly Thr Thr Leu
                245                 250                 255

Thr Val Ser Ser
            260

<210> SEQ ID NO 15
<211> LENGTH: 780
<212> TYPE: DNA
<213> ORGANISM: Mus musculus

<400> SEQUENCE: 15
atggccctgc ctgtgacagc cctgctgctg cctctggctc tgctgctgca cgccgccaga    60
cctggatctg acattgtgat gacccagtct cacaaattca tgtccacatc agtaggagac   120
agggtcagca tcatctgtaa ggccagtcaa gatgtgggta ctgctgtaga ctggtatcaa   180
cagaaaccag gacaatctcc taaactactg atttattggg catccactcg gcacactgga   240
gtccctgatc gcttcacagg cagtggatct gggacagact tcactctcac cattactaac   300
gttcagtctg aagacttggc agattatttc tgtcagcaat ataacagcta tcctctcacg   360
ttcggtgctg ggaccatgct ggacctgaaa ggaggcggag gatctggcgg cggaggaagt   420
tctggcggag gcagcgaggt gcagctgcag cagagcggac ccgagctcgt gaagcctgga   480
acaagcgtgc ggatcagctg caagaccagc ggctacacct tcaccgagta caccatccac   540
tgggtcaagc agtcccacgg caagagcctg gagtggatcg gcaatatcaa ccccaacaac   600
ggcggcacca cctacaacca gaagttcgag gacaaggcca ccctgaccgt ggacaagagc   660
agcagcaccg cctacatgga actgcggagc ctgaccagca ggacagcgc cgtgtactat   720
tgtgccgccg gttggaactt cgactactgg ggccagggca acccctgac agtgtctagc   780

<210> SEQ ID NO 16
<211> LENGTH: 107
<212> TYPE: PRT
<213> ORGANISM: Mus musculus

<400> SEQUENCE: 16

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Met Leu Asp Leu Lys
            100                 105

<210> SEQ ID NO 17
<211> LENGTH: 321
<212> TYPE: DNA
<213> ORGANISM: Mus musculus

<400> SEQUENCE: 17
gacattgtga tgacccagtc tcacaaattc atgtccacat cagtaggaga cagggtcagc    60
atcatctgta aggccagtca agatgtgggt actgctgtag actggtatca acagaaacca   120
ggacaatctc ctaaactact gatttattgg gcatccactc ggcacactgg agtccctgat   180
cgcttcacag gcagtggatc tgggacagac ttcactctca ccattactaa cgttcagtct   240
gaagacttgg cagattattt ctgtcagcaa tataacagct atcctctcac gttcggtgct   300
gggaccatgc tggacctgaa a                                             321

<210> SEQ ID NO 18
<211> LENGTH: 11
<212> TYPE: PRT
<213> ORGANISM: Mus musculus

<400> SEQUENCE: 18

Lys Ala Ser Gln Asp Val Gly Thr Ala Val Asp
1               5                   10

<210> SEQ ID NO 19
<211> LENGTH: 7
<212> TYPE: PRT
<213> ORGANISM: Mus musculus

<400> SEQUENCE: 19

Trp Ala Ser Thr Arg His Thr
1               5

<210> SEQ ID NO 20
<211> LENGTH: 9
<212> TYPE: PRT
<213> ORGANISM: Mus musculus

<400> SEQUENCE: 20

Gln Gln Tyr Asn Ser Tyr Pro Leu Thr
1               5

<210> SEQ ID NO 21
<211> LENGTH: 115
<212> TYPE: PRT
<213> ORGANISM: Mus musculus

<400> SEQUENCE: 21

Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

```
Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
        100                 105                 110

Val Ser Ser
        115

<210> SEQ ID NO 22
<211> LENGTH: 345
<212> TYPE: DNA
<213> ORGANISM: Mus musculus

<400> SEQUENCE: 22
gaggtgcagc tgcagcagag cggacccgag ctcgtgaagc ctggaacaag cgtgcggatc    60
agctgcaaga ccagcggcta caccttcacc gagtacacca tccactgggt caagcagtcc   120
cacggcaaga gcctggagtg gatcggcaat atcaaccccca acaacggcgg caccacctac   180
aaccagaagt tcgaggacaa ggccaccctg accgtggaca gagcagcag caccgcctac   240 atggaactgc ggagcctgac cagcgaggac agcgccgtgt actattgtgc cgccggttgg   300
aacttcgact actggggcca gggcacaacc ctgacagtgt ctagc               345

<210> SEQ ID NO 23
<211> LENGTH: 10
<212> TYPE: PRT
<213> ORGANISM: Mus musculus

<400> SEQUENCE: 23

Gly Tyr Thr Phe Thr Glu Tyr Thr Ile His
1               5                   10

<210> SEQ ID NO 24
<211> LENGTH: 17
<212> TYPE: PRT
<213> ORGANISM: Mus musculus

<400> SEQUENCE: 24

Asn Ile Asn Pro Asn Asn Gly Gly Thr Thr Tyr Asn Gln Lys Phe Glu
1               5                   10                  15

Asp

<210> SEQ ID NO 25
<211> LENGTH: 6
<212> TYPE: PRT
<213> ORGANISM: Mus musculus

<400> SEQUENCE: 25

Gly Trp Asn Phe Asp Tyr
1               5

<210> SEQ ID NO 26
<211> LENGTH: 267
<212> TYPE: PRT
<213> ORGANISM: Homo sapiens

<400> SEQUENCE: 26

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
```

```
            35                  40                  45
Thr Phe Ser Ser Tyr Ala Met His Trp Val Arg Gln Ala Pro Gly Lys
 50                  55                  60

Gly Leu Glu Trp Val Ala Val Ile Ser Tyr Asp Gly Asn Asn Lys Tyr
 65                  70                  75                  80

Tyr Ala Asp Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ala Val Pro Trp Gly Ser Arg Tyr Tyr
            115                 120                 125

Tyr Tyr Gly Met Asp Val Trp Gly Gln Gly Thr Val Thr Val Ser
    130                 135                 140

Ser Gly Gly Gly Gly Ser Gly Gly Gly Ser Gly Gly Gly Gly Ser
145                 150                 155                 160

Ala Ile Gln Leu Thr Gln Ser Pro Ser Ser Leu Ser Ala Ser Val Gly
                165                 170                 175

Asp Arg Val Thr Ile Thr Cys Arg Ala Ser Gln Gly Ile Ser Ser Ala
            180                 185                 190

Leu Ala Trp Tyr Gln Gln Lys Ser Gly Lys Ala Pro Lys Leu Leu Ile
            195                 200                 205

Phe Asp Ala Ser Ser Leu Glu Ser Gly Val Pro Ser Arg Phe Ser Gly
    210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Val Glu Ile Lys
            260                 265

<210> SEQ ID NO 27
<211> LENGTH: 801
<212> TYPE: DNA
<213> ORGANISM: Homo sapiens

<400> SEQUENCE: 27
atggccttac cagtgaccgc cttgctcctg ccgctggcct tgctgctcca cgccgccagg      60
ccgcaggtgc aactggtgga gtctggggga ggcgtggtcc agcctgggag gtccctgaga     120
ctctcctgtg cagcctctgg attcaccttc agtagctatg ctatgcactg ggtccgccag     180
gctccaggca aggggctgga gtgggtggca gttatatcat atgatggaaa caataaatac     240
tacgcagact ccgtgaaggg ccgattcacc atctccagag acaattccaa gaacacgctg     300
tatctgcaaa tgaacagcct gagagctgag gacacggctg tgtattactg tgcgagagcc     360
gtccctgggg atcgaggta ctactactac ggtatggacg tctggggcca agggaccacg     420
gtcaccgtct cctcaggtgg cggtggctcg ggcggtggtg gtcgggtgg cggcggatct     480 gccatccagt tgacccagtc tccatcctcc ctgtctgcat ctgtaggaga cagagtcacc     540
atcacttgcc gggcaagtca gggcattagc agtgctttag cctggtatca gcagaaatca     600
gggaaagctc ctaagctcct gatctttgat gcctccagtt tggaaagtgg ggtcccatca     660
aggttcagcg gcagtggatc tgggacagat ttcactctca ccatcagcag cctgcagcct     720
gaagattttg caacttatta ctgtcaacag tttaacagtt atcctctcac tttcggcgga     780
gggaccaagg tggagatcaa a                                              801
```

<210> SEQ ID NO 28
<211> LENGTH: 125
<212> TYPE: PRT
<213> ORGANISM: Homo sapiens

<400> SEQUENCE: 28

```
Pro Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Ala Met His Trp Val Arg Gln Ala Pro Gly Lys Gly Leu Glu Trp
        35                  40                  45

Val Ala Val Ile Ser Tyr Asp Gly Asn Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Ala Val Pro Trp Gly Ser Arg Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 29
<211> LENGTH: 375
<212> TYPE: DNA
<213> ORGANISM: Homo sapiens

<400> SEQUENCE: 29

```
ccgcaggtgc aactggtgga gtctggggga ggcgtggtcc agcctgggag gtccctgaga      60
ctctcctgtg cagcctctgg attcaccttc agtagctatg ctatgcactg ggtccgccag     120
gctccaggca aggggctgga gtgggtggca gttatatcat atgatggaaa caataaatac     180
tacgcagact ccgtgaaggg ccgattcacc atctccagag acaattccaa gaacacgctg     240
tatctgcaaa tgaacagcct gagagctgag gacacggctg tgtattactg tgcgagagcc     300 gtccctggg gatcgaggta ctactactac ggtatggacg tctggggcca agggaccacg     360
gtcaccgtct cctca                                                     375
```

<210> SEQ ID NO 30
<211> LENGTH: 5
<212> TYPE: PRT
<213> ORGANISM: Homo sapiens

<400> SEQUENCE: 30

```
Ser Tyr Ala Met His
1               5
```

<210> SEQ ID NO 31
<211> LENGTH: 17
<212> TYPE: PRT
<213> ORGANISM: Homo sapiens

<400> SEQUENCE: 31

```
Val Ile Ser Tyr Asp Gly Asn Asn Lys Tyr Tyr Ala Asp Ser Val Lys
1               5                   10                  15

Gly
```

<210> SEQ ID NO 32
<211> LENGTH: 15
<212> TYPE: PRT
<213> ORGANISM: Homo sapiens

<400> SEQUENCE: 32

Ala Val Pro Trp Gly Ser Arg Tyr Tyr Tyr Gly Met Asp Val
1               5                   10                  15

<210> SEQ ID NO 33
<211> LENGTH: 107
<212> TYPE: PRT
<213> ORGANISM: Homo sapiens

<400> SEQUENCE: 33

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Ser Gly Lys Ala Pro Lys Leu Leu Ile
            35                  40                  45

Phe Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 34
<211> LENGTH: 321
<212> TYPE: DNA
<213> ORGANISM: Homo sapiens

<400> SEQUENCE: 34
gccatccagt tgacccagtc tccatcctcc ctgtctgcat ctgtaggaga cagagtcacc      60
atcacttgcc gggcaagtca gggcattagc agtgctttag cctggtatca gcagaaatca     120
gggaaagctc ctaagctcct gatctttgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaacagtt atcctctcac tttcggcgga     300
gggaccaagg tggagatcaa a                                               321

<210> SEQ ID NO 35
<211> LENGTH: 11
<212> TYPE: PRT
<213> ORGANISM: Homo sapiens

<400> SEQUENCE: 35

Arg Ala Ser Gln Gly Ile Ser Ser Ala Leu Ala
1               5                   10

<210> SEQ ID NO 36
<211> LENGTH: 7
<212> TYPE: PRT
<213> ORGANISM: Homo sapiens

<400> SEQUENCE: 36

Asp Ala Ser Ser Leu Glu Ser
1               5

<210> SEQ ID NO 37
<211> LENGTH: 9
<212> TYPE: PRT
<213> ORGANISM: Homo sapiens

<400> SEQUENCE: 37

Gln Gln Phe Asn Ser Tyr Pro Leu Thr
1               5

<210> SEQ ID NO 38
<211> LENGTH: 262
<212> TYPE: PRT
<213> ORGANISM: Homo sapiens

<400> SEQUENCE: 38

Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
                20                  25                  30

Lys Lys Pro Gly Glu Ser Leu Lys Ile Ser Cys Lys Gly Ser Gly Tyr
            35                  40                  45

Ser Phe Thr Ser Asn Trp Ile Gly Trp Val Arg Gln Met Pro Gly Lys
    50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Ser Ser Leu Lys Ala Ser Asp Thr
            100                 105                 110

Ala Met Tyr Tyr Cys Ala Arg Gln Thr Gly Phe Leu Trp Ser Ser Asp
        115                 120                 125

Leu Trp Gly Arg Gly Thr Leu Val Thr Val Ser Ser Gly Gly Gly Gly
130                 135                 140

Ser Gly Gly Gly Gly Ser Gly Gly Gly Gly Ser Ala Ile Gln Leu Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Ser Ala Leu Ala Trp Tyr Gln
            180                 185                 190

Gln Lys Pro Gly Lys Ala Pro Lys Leu Leu Ile Tyr Asp Ala Ser Ser
        195                 200                 205

Leu Glu Ser Gly Val Pro Ser Arg Phe Ser Gly Tyr Gly Ser Gly Thr
210                 215                 220

Asp Phe Thr Leu Thr Ile Asn Ser Leu Gln Pro Glu Asp Phe Ala Thr
225                 230                 235                 240

Tyr Tyr Cys Gln Gln Phe Asn Ser Tyr Pro Leu Thr Phe Gly Gly Gly
                245                 250                 255

Thr Lys Val Glu Ile Lys
            260

<210> SEQ ID NO 39
<211> LENGTH: 786
<212> TYPE: DNA
<213> ORGANISM: Homo sapiens

<400> SEQUENCE: 39

```
atggccttac cagtgaccgc cttgctcctg ccgctggcct tgctgctcca cgccgccagg      60
ccggaggtgc agctggtgca gtctggagca gaggtgaaaa agcccgggga gtctctgaag     120
atctcctgta agggttctgg atacagcttt accagtaact ggatcggctg ggtgcgccag     180
atgcccggga aaggcctgga gtggatgggg atcatctatc ctggtgactc tgataccaga     240
tacagcccgt ccttccaagg ccaggtcacc atctcagccg acaagtccat cagcaccgcc     300
tacctgcagt ggagcagcct gaaggcctcg gacaccgcca tgtattactg cgcgaggcaa     360
actggtttcc tctggtcctc cgatctctgg ggccgtggca ccctggtcac tgtctcctca     420
ggtggcggtg gctcgggcgg tggtgggtcg ggtggcggcg gatctgccat ccagttgacc     480
cagtctccat cctccctgtc tgcatctgta ggagacagag tcaccatcac ttgccgggca     540
agtcaggaca ttagcagtgc tttagcctgg tatcaacaga aaccagggaa agctcctaag     600
ctcctgatct atgatgcctc cagtttggaa agtggggtcc catcaaggtt cagcggctat     660
ggatctggga cagatttcac tctcaccatc aacagcctgc agcctgaaga ttttgcaact     720
tattactgtc aacagtttaa tagttacccg ctcactttcg gcggagggac caaggtggag     780
atcaaa                                                                786
```

<210> SEQ ID NO 40
<211> LENGTH: 120
<212> TYPE: PRT
<213> ORGANISM: Homo sapiens

<400> SEQUENCE: 40

```
Pro Glu Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Ser
            20                  25                  30

Asn Trp Ile Gly Trp Val Arg Gln Met Pro Gly Lys Gly Leu Glu Trp
        35                  40                  45

Met Gly Ile Ile Tyr Pro Gly Asp Ser Asp Thr Arg Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Gln Thr Gly Phe Leu Trp Ser Ser Asp Leu Trp Gly Arg
            100                 105                 110

Gly Thr Leu Val Thr Val Ser Ser
        115                 120
```

<210> SEQ ID NO 41
<211> LENGTH: 360
<212> TYPE: DNA
<213> ORGANISM: Homo sapiens

<400> SEQUENCE: 41

```
ccggaggtgc agctggtgca gtctggagca gaggtgaaaa agcccgggga gtctctgaag      60
atctcctgta agggttctgg atacagcttt accagtaact ggatcggctg ggtgcgccag     120
atgcccggga aaggcctgga gtggatgggg atcatctatc ctggtgactc tgataccaga     180
tacagcccgt ccttccaagg ccaggtcacc atctcagccg acaagtccat cagcaccgcc     240
tacctgcagt ggagcagcct gaaggcctcg gacaccgcca tgtattactg cgcgaggcaa     300
```

```
actggtttcc tctggtcctc cgatctctgg ggccgtggca ccctggtcac tgtctcctca    360
```

<210> SEQ ID NO 42
<211> LENGTH: 5
<212> TYPE: PRT
<213> ORGANISM: Homo sapiens

<400> SEQUENCE: 42

Ser Asn Trp Ile Gly
1               5

<210> SEQ ID NO 43
<211> LENGTH: 17
<212> TYPE: PRT
<213> ORGANISM: Homo sapiens

<400> SEQUENCE: 43

Ile Ile Tyr Pro Gly Asp Ser Asp Thr Arg Tyr Ser Pro Ser Phe Gln
1               5                   10                  15

Gly

<210> SEQ ID NO 44
<211> LENGTH: 10
<212> TYPE: PRT
<213> ORGANISM: Homo sapiens

<400> SEQUENCE: 44

Gln Thr Gly Phe Leu Trp Ser Ser Asp Leu
1               5                   10

<210> SEQ ID NO 45
<211> LENGTH: 107
<212> TYPE: PRT
<213> ORGANISM: Homo sapiens

<400> SEQUENCE: 45

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Tyr Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 46
<211> LENGTH: 321
<212> TYPE: DNA
<213> ORGANISM: Homo sapiens

<400> SEQUENCE: 46

```
gccatccagt tgacccagtc tccatcctcc ctgtctgcat ctgtaggaga cagagtcacc    60
atcacttgcc gggcaagtca ggacattagc agtgctttag cctggtatca acagaaacca   120
```

```
gggaaagctc ctaagctcct gatctatgat gcctccagtt tggaaagtgg ggtcccatca      180
aggttcagcg gctatggatc tgggacagat ttcactctca ccatcaacag cctgcagcct      240
gaagattttg caacttatta ctgtcaacag tttaatagtt acccgctcac tttcggcgga      300
gggaccaagg tggagatcaa a                                                321
```

```
<210> SEQ ID NO 47
<211> LENGTH: 11
<212> TYPE: PRT
<213> ORGANISM: Homo sapiens

<400> SEQUENCE: 47
```

Cys Arg Ala Ser Gln Asp Ile Ser Ser Ala Leu
1               5                   10

```
<210> SEQ ID NO 48
<211> LENGTH: 8
<212> TYPE: PRT
<213> ORGANISM: Homo sapiens

<400> SEQUENCE: 48
```

Tyr Asp Ala Ser Ser Leu Glu Ser
1               5

```
<210> SEQ ID NO 49
<211> LENGTH: 10
<212> TYPE: PRT
<213> ORGANISM: Homo sapiens

<400> SEQUENCE: 49
```

Cys Gln Gln Phe Asn Ser Tyr Pro Leu Thr
1               5                   10

```
<210> SEQ ID NO 50
<211> LENGTH: 264
<212> TYPE: PRT
<213> ORGANISM: Homo sapiens

<400> SEQUENCE: 50
```

Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
                20                  25                  30

Lys Lys Pro Gly Glu Ser Leu Lys Ile Ser Cys Lys Gly Ser Gly Tyr
            35                  40                  45

Ser Phe Thr Ser Asn Trp Ile Gly Trp Val Arg Gln Met Pro Gly Lys
        50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Asn Ser Leu Lys Ala Ser Asp Thr
            100                 105                 110

Ala Met Tyr Tyr Cys Ala Arg Gln Thr Gly Phe Leu Trp Ser Phe Asp
        115                 120                 125

Leu Trp Gly Arg Gly Thr Leu Val Thr Val Ser Ser Gly Gly Gly Gly
    130                 135                 140

Ser Gly Gly Gly Gly Ser Gly Gly Gly Gly Ser Ala Ile Gln Leu Thr
145                 150                 155                 160

Gln Ser Pro Ser Ser Leu Ser Ala Ser Val Gly Asp Arg Val Thr Ile
              165                 170                 175

Thr Cys Arg Ala Ser Gln Asp Ile Ser Ser Ala Leu Ala Trp Tyr Gln
        180                 185                 190

Gln Lys Pro Gly Lys Ala Pro Lys Leu Leu Ile Tyr Asp Ala Ser Ser
            195                 200                 205

Leu Glu Ser Gly Val Pro Ser Arg Phe Ser Gly Ser Gly Ser Gly Thr
        210                 215                 220

Asp Phe Thr Leu Thr Ile Ser Ser Leu Gln Pro Glu Asp Phe Ala Thr
225                 230                 235                 240

Tyr Tyr Cys Gln Gln Phe Asn Ser Tyr Pro Leu Thr Phe Gly Gly Gly
                245                 250                 255

Thr Lys Val Glu Ile Lys Ile Lys
            260

<210> SEQ ID NO 51
<211> LENGTH: 792
<212> TYPE: DNA
<213> ORGANISM: Homo sapiens

<400> SEQUENCE: 51 atggcttac cagtgaccgc cttgctcctg ccgctggcct tgctgctcca cgccgccagg      60
ccggaggtgc agctggtgca gtctggagca gaggtgaaaa agcccgggga gtctctgaag    120
atctcctgta agggttctgg atacagtttt accagcaact ggatcggctg ggtgcgccag    180
atgcccggga aggcctgga gtggatgggg atcatctatc ctggtgactc tgataccaga    240
tacagcccgt ccttccaagg ccaggtcacc atctcagccg acaagtccat cagcaccgcc    300
tacctgcagt ggaacagcct gaaggcctcg gacaccgcca tgtattactg tgcgagacaa    360
actggtttcc tctggtcctt cgatctctgg ggccgtggca ccctggtcac tgtctcctca    420
ggtggcggtg gctcgggcgg tgtgggtcg ggtggcggcg atctgccat ccagttgacc      480
cagtctccat cctccctgtc tgcatctgta ggagacagag tcaccatcac ttgccgggca    540
agtcaggaca ttagcagtgc tttagcctgg tatcagcaga aaccggggaa agctcctaag    600
ctcctgatct atgatgcctc cagtttggaa agtggggtcc catcaaggtt cagcggcagt    660
ggatctggga cagatttcac tctcaccatc agcagcctgc agcctgaaga ttttgcaact    720
tattactgtc aacagtttaa tagttacccg ctcactttcg gcggagggac caaggtggag    780
atcaaaatca aa                                                         792

<210> SEQ ID NO 52
<211> LENGTH: 120
<212> TYPE: PRT
<213> ORGANISM: Homo sapiens

<400> SEQUENCE: 52

Pro Glu Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Ser
            20                  25                  30

Asn Trp Ile Gly Trp Val Arg Gln Met Pro Gly Lys Gly Leu Glu Trp
        35                  40                  45

Met Gly Ile Ile Tyr Pro Gly Asp Ser Asp Thr Arg Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Asn Ser Leu Lys Ala Ser Asp Thr Ala Met Tyr Tyr
            85                  90                  95

Cys Ala Arg Gln Thr Gly Phe Leu Trp Ser Phe Asp Leu Trp Gly Arg
        100                 105                 110

Gly Thr Leu Val Thr Val Ser Ser
        115                 120

<210> SEQ ID NO 53
<211> LENGTH: 360
<212> TYPE: DNA
<213> ORGANISM: Homo sapiens

<400> SEQUENCE: 53
ccggaggtgc agctggtgca gtctggagca gaggtgaaaa agcccgggga gtctctgaag     60
atctcctgta agggttctgg atacagtttt accagcaact ggatcggctg ggtgcgccag    120
atgcccggga aaggcctgga gtggatgggg atcatctatc ctggtgactc tgataccaga    180
tacagcccgt ccttccaagg ccaggtcacc atctcagccg acaagtccat cagcaccgcc    240
tacctgcagt ggaacagcct gaaggcctcg gacaccgcca tgtattactg tgcgagacaa    300
actggttttc tctggtcctt cgatctctgg ggccgtggca ccctggtcac tgtctcctca    360

<210> SEQ ID NO 54
<211> LENGTH: 5
<212> TYPE: PRT
<213> ORGANISM: Homo sapiens

<400> SEQUENCE: 54

Ser Asn Trp Ile Gly
1               5

<210> SEQ ID NO 55
<211> LENGTH: 17
<212> TYPE: PRT
<213> ORGANISM: Homo sapiens

<400> SEQUENCE: 55

Ile Ile Tyr Pro Gly Asp Ser Asp Thr Arg Tyr Ser Pro Ser Phe Gln
1               5                   10                  15

Gly

<210> SEQ ID NO 56
<211> LENGTH: 10
<212> TYPE: PRT
<213> ORGANISM: Homo sapiens

<400> SEQUENCE: 56

Gln Thr Gly Phe Leu Trp Ser Phe Asp Leu
1               5                   10

<210> SEQ ID NO 57
<211> LENGTH: 109
<212> TYPE: PRT
<213> ORGANISM: Homo sapiens

<400> SEQUENCE: 57

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

```
Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys Ile Lys
                100                 105
```

<210> SEQ ID NO 58
<211> LENGTH: 327
<212> TYPE: DNA
<213> ORGANISM: Homo sapiens

<400> SEQUENCE: 58

```
gccatccagt tgacccagtc tccatcctcc ctgtctgcat ctgtaggaga cagagtcacc    60
atcacttgcc gggcaagtca ggacattagc agtgctttag cctggtatca gcagaaaccg   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgctcac tttcggcgga   300
gggaccaagg tggagatcaa atcaaa                                        327
```

<210> SEQ ID NO 59
<211> LENGTH: 11
<212> TYPE: PRT
<213> ORGANISM: Homo sapiens

<400> SEQUENCE: 59

```
Arg Ala Ser Gln Asp Ile Ser Ser Ala Leu Ala
 1               5                  10
```

<210> SEQ ID NO 60
<211> LENGTH: 7
<212> TYPE: PRT
<213> ORGANISM: Homo sapiens

<400> SEQUENCE: 60

```
Asp Ala Ser Ser Leu Glu Ser
 1               5
```

<210> SEQ ID NO 61
<211> LENGTH: 9
<212> TYPE: PRT
<213> ORGANISM: Homo sapiens

<400> SEQUENCE: 61

```
Gln Gln Phe Asn Ser Tyr Pro Leu Thr
 1               5
```

<210> SEQ ID NO 62
<211> LENGTH: 265
<212> TYPE: PRT
<213> ORGANISM: Homo sapiens

<400> SEQUENCE: 62

```
Met Ala Leu Pro Val Thr Ala Leu Leu Leu Pro Leu Ala Leu Leu Leu
 1               5                  10                  15
```

His Ala Ala Arg Pro Glu Val Gln Leu Val Gln Ser Gly Glu Val
            20                  25                  30

Lys Lys Pro Gly Glu Ser Leu Lys Ile Ser Cys Lys Gly Ser Gly Tyr
        35                  40                  45

Ser Phe Thr Asn Tyr Trp Ile Gly Trp Val Arg Gln Met Pro Gly Lys
    50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Ser Ser Leu Lys Ala Ser Asp Thr
            100                 105                 110

Ala Met Tyr Tyr Cys Ala Ser Pro Gly Tyr Thr Ser Ser Trp Thr Ser
        115                 120                 125

Phe Asp Tyr Trp Gly Gln Gly Thr Leu Val Thr Val Ser Ser Gly Gly
    130                 135                 140

Gly Gly Ser Gly Gly Gly Ser Gly Gly Gly Ser Glu Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Ser Ser Tyr Leu Ala Trp
            180                 185                 190

Tyr Gln Gln Lys Pro Gly Gln Ala Pro Arg Leu Leu Ile Tyr Asp Ala
        195                 200                 205

Ser Asn Arg Ala Thr Gly Ile Pro Ala Arg Phe Ser Gly Ser Gly Ser
    210                 215                 220

Gly Thr Asp Phe Thr Leu Thr Ile Ser Ser Leu Glu Pro Glu Asp Phe
225                 230                 235                 240

Ala Val Tyr Tyr Cys Gln Gln Arg Ser Asn Trp Pro Leu Phe Thr Phe
                245                 250                 255

Gly Pro Gly Thr Lys Val Asp Ile Lys
                260                 265

<210> SEQ ID NO 63
<211> LENGTH: 795
<212> TYPE: DNA
<213> ORGANISM: Homo sapiens

<400> SEQUENCE: 63 atggcttac cagtgaccgc cttgctcctg ccgctggcct tgctgctcca cgccgccagg     60
ccggaggtgc agctggtgca gtctggatca gaggtgaaaa agcccgggga gtctctgaag    120
atctcctgta agggttctgg atacagcttt accaactact ggatcggctg ggtgcgccag    180
atgcccggga aaggcctgga gtggatgggg atcatctatc ctggtgactc tgataccaga    240
tacagcccgt ccttccaagg ccaggtcacc atctcagccg acaagtccat cagcaccgcc    300
tatctgcagt ggagcagcct gaaggcctcg gacaccgcca tgtattactg tgcgagtccc    360
gggtatacca gcagttggac ttcttttgac tactggggcc agggaaccct ggtcaccgtc    420
tcctcaggtg gcggtggctc gggcggtggt gggtcgggtg gcggcggatc tgaaattgtg    480
ttgacacagt ctccagccac cctgtctttg tctccagggg aaagagccac cctctcctgc    540
agggccagtc agagtgttag cagctactta gcctggtacc aacagaaacc tggccaggct    600
cccaggctcc tcatctatga tgcatccaac agggccactg gcatcccagc caggttcagt    660
ggcagtgggt ctgggacaga cttcactctc accatcagca gcctagagcc tgaagatttt    720

```
gcagtttatt actgtcagca gcgtagcaac tggcccctat tcactttcgg ccctgggacc    780
aaagtggata tcaaa                                                     795
```

<210> SEQ ID NO 64
<211> LENGTH: 122
<212> TYPE: PRT
<213> ORGANISM: Homo sapiens

<400> SEQUENCE: 64

```
Pro Glu Val Gln Leu Val Gln Ser Gly Ser Glu Val Lys Lys Pro Gly
1               5                   10                  15

Glu Ser Leu Lys Ile Ser Cys Lys Gly Ser Gly Tyr Ser Phe Thr Asn
            20                  25                  30

Tyr Trp Ile Gly Trp Val Arg Gln Met Pro Gly Lys Gly Leu Glu Trp
        35                  40                  45

Met Gly Ile Ile Tyr Pro Gly Asp Ser Asp Thr Arg Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Ser Pro Gly Tyr Thr Ser Ser Trp Thr Ser Phe Asp Tyr Trp
            100                 105                 110

Gly Gln Gly Thr Leu Val Thr Val Ser Ser
        115                 120
```

<210> SEQ ID NO 65
<211> LENGTH: 366
<212> TYPE: DNA
<213> ORGANISM: Homo sapiens

<400> SEQUENCE: 65

```
ccggaggtgc agctggtgca gtctggatca gaggtgaaaa agcccgggga gtctctgaag    60
atctcctgta agggttctgg atacagcttt accaactact ggatcggctg ggtgcgccag   120
atgcccggga aaggcctgga gtggatgggg atcatctatc ctggtgactc tgataccaga   180
tacagcccgt ccttccaagg ccaggtcacc atctcagccg acaagtccat cagcaccgcc   240
tatctgcagt ggagcagcct gaaggcctcg gacaccgcca tgtattactg tgcgagtccc   300
gggtatacca gcagttggac ttctttgac tactggggcc agggaaccct ggtcaccgtc   360
tcctca                                                             366
```

<210> SEQ ID NO 66
<211> LENGTH: 4
<212> TYPE: PRT
<213> ORGANISM: Homo sapiens

<400> SEQUENCE: 66

```
Thr Asn Tyr Trp
1
```

<210> SEQ ID NO 67
<211> LENGTH: 18
<212> TYPE: PRT
<213> ORGANISM: Homo sapiens

<400> SEQUENCE: 67

```
Gly Ile Ile Tyr Pro Gly Asp Ser Asp Thr Arg Tyr Ser Pro Ser Phe
```

<210> SEQ ID NO 68
<211> LENGTH: 10
<212> TYPE: PRT
<213> ORGANISM: Homo sapiens

<400> SEQUENCE: 68

Ser Pro Gly Tyr Thr Ser Ser Trp Thr Ser
1               5                   10

<210> SEQ ID NO 69
<211> LENGTH: 108
<212> TYPE: PRT
<213> ORGANISM: Homo sapiens

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Phe Thr Phe Gly Pro Gly Thr Lys Val Asp Ile Lys
            100                 105

<210> SEQ ID NO 70
<211> LENGTH: 324
<212> TYPE: DNA
<213> ORGANISM: Homo sapiens

<400> SEQUENCE: 70
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcccctatt cactttcggc     300
cctgggacca aagtggatat caaa                                            324

<210> SEQ ID NO 71
<211> LENGTH: 11
<212> TYPE: PRT
<213> ORGANISM: Homo sapiens

<400> SEQUENCE: 71

Cys Arg Ala Ser Gln Ser Val Ser Ser Tyr Leu
1               5                   10

<210> SEQ ID NO 72
<211> LENGTH: 8
<212> TYPE: PRT

```
<213> ORGANISM: Homo sapiens

<400> SEQUENCE: 72

Tyr Asp Ala Ser Asn Arg Ala Thr
1               5

<210> SEQ ID NO 73
<211> LENGTH: 11
<212> TYPE: PRT
<213> ORGANISM: Homo sapiens

<400> SEQUENCE: 73

Cys Gln Gln Arg Ser Asn Trp Pro Leu Phe Thr
1               5                   10

<210> SEQ ID NO 74
<211> LENGTH: 5
<212> TYPE: PRT
<213> ORGANISM: Artificial Sequence
<220> FEATURE:
<223> OTHER INFORMATION: hinge

<400> SEQUENCE: 74

Asp Lys Thr His Thr
1               5

<210> SEQ ID NO 75
<211> LENGTH: 4
<212> TYPE: PRT
<213> ORGANISM: Artificial Sequence
<220> FEATURE:
<223> OTHER INFORMATION: hinge

<400> SEQUENCE: 75

Cys Pro Pro Cys
1

<210> SEQ ID NO 76
<211> LENGTH: 15
<212> TYPE: PRT
<213> ORGANISM: Artificial Sequence
<220> FEATURE:
<223> OTHER INFORMATION: hinge

<400> SEQUENCE: 76

Cys Pro Glu Pro Lys Ser Cys Asp Thr Pro Pro Cys Pro Arg
1               5                   10                  15

<210> SEQ ID NO 77
<211> LENGTH: 12
<212> TYPE: PRT
<213> ORGANISM: Artificial Sequence
<220> FEATURE:
<223> OTHER INFORMATION: hinge

<400> SEQUENCE: 77

Glu Leu Lys Thr Pro Leu Gly Asp Thr Thr His Thr
1               5                   10

<210> SEQ ID NO 78
<211> LENGTH: 10
<212> TYPE: PRT
<213> ORGANISM: Artificial Sequence
<220> FEATURE:
<223> OTHER INFORMATION: hinge

<400> SEQUENCE: 78
```

```
Lys Ser Cys Asp Lys Thr His Thr Cys Pro
1               5                   10
```

<210> SEQ ID NO 79
<211> LENGTH: 7
<212> TYPE: PRT
<213> ORGANISM: Artificial Sequence
<220> FEATURE:
<223> OTHER INFORMATION: hinge

<400> SEQUENCE: 79

```
Lys Cys Cys Val Asp Cys Pro
1               5
```

<210> SEQ ID NO 80
<211> LENGTH: 7
<212> TYPE: PRT
<213> ORGANISM: Artificial Sequence
<220> FEATURE:
<223> OTHER INFORMATION: hinge

<400> SEQUENCE: 80

```
Lys Tyr Gly Pro Pro Cys Pro
1               5
```

<210> SEQ ID NO 81
<211> LENGTH: 15
<212> TYPE: PRT
<213> ORGANISM: Artificial Sequence
<220> FEATURE:
<223> OTHER INFORMATION: hinge

<400> SEQUENCE: 81

```
Glu Pro Lys Ser Cys Asp Lys Thr His Thr Cys Pro Pro Cys Pro
1               5                   10                  15
```

<210> SEQ ID NO 82
<211> LENGTH: 12
<212> TYPE: PRT
<213> ORGANISM: Artificial Sequence
<220> FEATURE:
<223> OTHER INFORMATION: hinge

<400> SEQUENCE: 82

```
Glu Arg Lys Cys Cys Val Glu Cys Pro Pro Cys Pro
1               5                   10
```

<210> SEQ ID NO 83
<211> LENGTH: 17
<212> TYPE: PRT
<213> ORGANISM: Artificial Sequence
<220> FEATURE:
<223> OTHER INFORMATION: hinge

<400> SEQUENCE: 83

```
Glu Leu Lys Thr Pro Leu Gly Asp Thr Thr His Thr Cys Pro Arg Cys
1               5                   10                  15
Pro
```

<210> SEQ ID NO 84
<211> LENGTH: 12
<212> TYPE: PRT
<213> ORGANISM: Artificial Sequence
<220> FEATURE:
<223> OTHER INFORMATION: hinge

<400> SEQUENCE: 84

Ser Pro Asn Met Val Pro His Ala His His Ala Gln
1               5                   10

<210> SEQ ID NO 85
<211> LENGTH: 15
<212> TYPE: PRT
<213> ORGANISM: Artificial Sequence
<220> FEATURE:
<223> OTHER INFORMATION: hinge

<400> SEQUENCE: 85

Glu Pro Lys Ser Cys Asp Lys Thr Tyr Thr Cys Pro Pro Cys Pro
1               5                   10                  15

<210> SEQ ID NO 86
<211> LENGTH: 45
<212> TYPE: PRT
<213> ORGANISM: Artificial Sequence
<220> FEATURE:
<223> OTHER INFORMATION: CD8 hinge

<400> SEQUENCE: 86

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 87
<211> LENGTH: 135
<212> TYPE: DNA
<213> ORGANISM: Artificial Sequence
<220> FEATURE:
<223> OTHER INFORMATION: CD8 hinge

<400> SEQUENCE: 87
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat                                                     135

<210> SEQ ID NO 88
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 88

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 89
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 89

```
atctacatct gggcgcccett ggccgggact tgtggggtcc ttctcctgtc actggttatc    60
accctttact gc                                                          72
```

<210> SEQ ID NO 90
<211> LENGTH: 69
<212> TYPE: PRT
<213> ORGANISM: Artificial Sequence
<220> FEATURE:
<223> OTHER INFORMATION: CD8 hinge and CD8 transmembrane domain

<400> SEQUENCE: 90

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 91
<211> LENGTH: 207
<212> TYPE: DNA
<213> ORGANISM: Artificial Sequence
<220> FEATURE:
<223> OTHER INFORMATION: CD8 hinge and CD8 transmembrane domain

<400> SEQUENCE: 91

```
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgatatcta catctgggcg cccttggccg ggacttgtgg ggtccttctc   180
ctgtcactgg ttatcaccct ttactgc                                        207
```

<210> SEQ ID NO 92
<211> LENGTH: 42
<212> TYPE: PRT
<213> ORGANISM: Artificial Sequence
<220> FEATURE:
<223> OTHER INFORMATION: 4-1BB

<400> SEQUENCE: 92

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 93
<211> LENGTH: 126
<212> TYPE: DNA
<213> ORGANISM: Artificial Sequence
<220> FEATURE:
<223> OTHER INFORMATION: 4-1BB

<400> SEQUENCE: 93

```
aaacggggca gaaagaaact cctgtatata ttcaaacaac catttatgag accagtacaa    60
actactcaag aggaagacgg ctgtagctgc cgatttccag aagaagaaga aggaggatgt   120
```

```
<210> SEQ ID NO 94
<211> LENGTH: 126
<212> TYPE: DNA
<213> ORGANISM: Artificial Sequence
<220> FEATURE:
<223> OTHER INFORMATION: 4-1BB

<400> SEQUENCE: 94
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 95
<211> LENGTH: 35
<212> TYPE: PRT
<213> ORGANISM: Artificial Sequence
<220> FEATURE:
<223> OTHER INFORMATION: ICOS(YMNM)

<400> SEQUENCE: 95
```

Thr Lys Lys Lys Tyr Ser Ser Ser Val His Asp Pro Asn Gly Glu Tyr
1               5                   10                  15

Met Asn Met Arg Ala Val Asn Thr Ala Lys Lys Ser Arg Leu Thr Asp
            20                  25                  30

Val Thr Leu
        35

```
<210> SEQ ID NO 96
<211> LENGTH: 105
<212> TYPE: DNA
<213> ORGANISM: Artificial Sequence
<220> FEATURE:
<223> OTHER INFORMATION: ICOS(YMNM)

<400> SEQUENCE: 96
acaaaaaaga agtattcatc cagtgtgcac gaccctaacg gtgaatacat gaacatgaga      60
gcagtgaaca cagccaaaaa atccagactc acagatgtga cccta                    105

<210> SEQ ID NO 97
<211> LENGTH: 112
<212> TYPE: PRT
<213> ORGANISM: Artificial Sequence
<220> FEATURE:
<223> OTHER INFORMATION: CD3 zeta domain

<400> SEQUENCE: 97
```

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 98
<211> LENGTH: 336
<212> TYPE: DNA
<213> ORGANISM: Artificial Sequence
<220> FEATURE:
<223> OTHER INFORMATION: CD3 zeta domain

<400> SEQUENCE: 98
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                              336

<210> SEQ ID NO 99
<211> LENGTH: 336
<212> TYPE: DNA
<213> ORGANISM: Artificial Sequence
<220> FEATURE:
<223> OTHER INFORMATION: CD3 zeta domain

<400> SEQUENCE: 99
agagtgaagt tcagcaggag cgcagacgcc cccgcgtaca agcagggcca gaaccagctc      60
tataacgagc tcaatctagg acgaagagag gagtacgacg ttttggacaa gagacgtggc     120
cgggaccctg agatggggg aaagccgaga aggaagaacc ctcaggaagg cctgtacaac     180
gaactgcaga aagataagat ggcggaggcc tacagtgaga ttgggatgaa aggcgagcgc     240
cggaggggca aggggcacga cggcctttac cagggtctca gtacagccac caaggacacc     300
tacgacgccc ttcacatgca ggccctgccc cctcgc                              336

<210> SEQ ID NO 100
<211> LENGTH: 112
<212> TYPE: PRT
<213> ORGANISM: Artificial Sequence
<220> FEATURE:
<223> OTHER INFORMATION: CD3 zeta domain

<400> SEQUENCE: 100

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 101
<211> LENGTH: 336
<212> TYPE: DNA
<213> ORGANISM: Artificial Sequence
<220> FEATURE:
<223> OTHER INFORMATION: CD3 zeta domain

<400> SEQUENCE: 101

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 102
<211> LENGTH: 154
<212> TYPE: PRT
<213> ORGANISM: Artificial Sequence
<220> FEATURE:
<223> OTHER INFORMATION: 4-1BB domain and CD3 zeta domain

<400> SEQUENCE: 102

```
Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Lys Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150
```

<210> SEQ ID NO 103
<211> LENGTH: 462
<212> TYPE: DNA
<213> ORGANISM: Artificial Sequence
<220> FEATURE:
<223> OTHER INFORMATION: 4-1BB domain and CD3 zeta domain

<400> SEQUENCE: 103

```
aaacggggca gaaagaaact cctgtatata ttcaaacaac catttatgag accagtacaa      60
actactcaag aggaagacgg ctgtagctgc cgatttccag aagaagaaga aggaggatgt     120
gaactgagag tgaagttcag caggagcgca gacgcccccg cgtacaagca gggccagaac     180
cagctctata cgagctcaa tctaggacga agagaggagt acgacgtttt ggacaagaga     240
```

```
cgtggccggg accctgagat gggggaaag ccgagaagga agaaccctca ggaaggcctg      300
tacaacgaac tgcagaaaga taagatggcg gaggcctaca gtgagattgg gatgaaaggc      360
gagcgccgga ggggcaaggg gcacgacggc ctttaccagg gtctcagtac agccaccaag      420
gacacctacg acgcccttca catgcaggcc ctgccccctc gc                        462
```

<210> SEQ ID NO 104
<211> LENGTH: 462
<212> TYPE: DNA
<213> ORGANISM: Artificial Sequence
<220> FEATURE:
<223> OTHER INFORMATION: 4-1BB domain and CD3 zeta domain

<400> SEQUENCE: 104

```
aaacggggca gaaagaaact cctgtatata ttcaaacaac catttatgag accagtacaa       60
actactcaag aggaagatgg ctgtagctgc cgatttccag aagaagaaga aggaggatgt      120
gaactgagag tgaagttcag caggagcgca gacgcccccg cgtacaagca gggccagaac      180
cagctctata acgagctcaa tctaggacga agagaggagt acgatgtttt ggacaagaga      240
cgtggccggg accctgagat gggggaaag ccgagaagga agaaccctca ggaaggcctg      300
tacaatgaac tgcagaaaga taagatggcg gaggcctaca gtgagattgg gatgaaaggc      360
gagcgccgga ggggcaaggg gcacgatggc ctttaccagg gtctcagtac agccaccaag      420
gacacctacg acgcccttca catgcaggcc ctgccccctc gc                        462
```

<210> SEQ ID NO 105
<211> LENGTH: 487
<212> TYPE: PRT
<213> ORGANISM: Artificial Sequence
<220> FEATURE:
<223> OTHER INFORMATION: J591 murine PSMA-CAR

<400> SEQUENCE: 105

```
Met Ala Leu Pro Val Thr Ala Leu Leu Leu Pro Leu Ala Leu Leu Leu
1               5                   10                  15

His Ala Ala Arg Pro Gly Ser Asp Ile Val Met Thr Gln Ser His Lys
            20                  25                  30

Phe Met Ser Thr Ser Val Gly Asp Arg Val Ser Ile Ile Cys Lys Ala
        35                  40                  45

Ser Gln Asp Val Gly Thr Ala Val Asp Trp Tyr Gln Gln Lys Pro Gly
    50                  55                  60

Gln Ser Pro Lys Leu Leu Ile Tyr Trp Ala Ser Thr Arg His Thr Gly
65                  70                  75                  80

Val Pro Asp Arg Phe Thr Gly Ser Gly Ser Gly Thr Asp Phe Thr Leu
                85                  90                  95

Thr Ile Thr Asn Val Gln Ser Glu Asp Leu Ala Asp Tyr Phe Cys Gln
            100                 105                 110

Gln Tyr Asn Ser Tyr Pro Leu Thr Phe Gly Ala Gly Thr Met Leu Asp
        115                 120                 125

Leu Lys Gly Gly Gly Gly Ser Gly Gly Gly Gly Ser Ser Gly Gly Gly
    130                 135                 140

Ser Glu Val Gln Leu Gln Gln Ser Gly Pro Glu Leu Val Lys Pro Gly
145                 150                 155                 160

Thr Ser Val Arg Ile Ser Cys Lys Thr Ser Gly Tyr Thr Phe Thr Glu
                165                 170                 175

Tyr Thr Ile His Trp Val Lys Gln Ser His Gly Lys Ser Leu Glu Trp
```

180                 185                 190
Ile Gly Asn Ile Asn Pro Asn Asn Gly Gly Thr Thr Tyr Asn Gln Lys
            195                 200                 205

Phe Glu Asp Lys Ala Thr Leu Thr Val Asp Lys Ser Ser Ser Thr Ala
        210                 215                 220

Tyr Met Glu Leu Arg Ser Leu Thr Ser Glu Asp Ser Ala Val Tyr Tyr
225                 230                 235                 240

Cys Ala Ala Gly Trp Asn Phe Asp Tyr Trp Gly Gln Gly Thr Thr Leu
                245                 250                 255

Thr Val Ser Ser Ala Ser Ser Gly Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
                295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 106
<211> LENGTH: 1461
<212> TYPE: DNA
<213> ORGANISM: Artificial Sequence
<220> FEATURE:
<223> OTHER INFORMATION: J591 murine PSMA-CAR

<400> SEQUENCE: 106
atggccctgc ctgtgacagc cctgctgctg cctctggctc tgctgctgca cgccgccaga      60
cctggatctg acattgtgat gacccagtct cacaaattca tgtccacatc agtaggagac     120
agggtcagca tcatctgtaa ggccagtcaa gatgtgggta ctgctgtaga ctggtatcaa    180
cagaaaccag gacaatctcc taaactactg atttattggg catccactcg gcacactgga    240
gtccctgatc gcttcacagg cagtggatct gggacagact cactctcac cattactaac    300

```
gttcagtctg aagacttggc agattatttc tgtcagcaat ataacagcta tcctctcacg    360
ttcggtgctg ggaccatgct ggacctgaaa ggaggcggag gatctggcgg cggaggaagt    420
tctggcggag gcagcgaggt gcagctgcag cagagcggac ccgagctcgt gaagcctgga    480
acaagcgtgc ggatcagctg caagaccagc ggctacacct tcaccgagta caccatccac    540
tgggtcaagc agtcccacgg caagagcctg gagtggatcg gcaatatcaa ccccaacaac    600
ggcggcacca cctacaacca gaagttcgag gacaaggcca ccctgaccgt ggacaagagc    660
agcagcaccg cctacatgga actgcggagc ctgaccagca ggacagcgc cgtgtactat    720
tgtgccgccg gttggaactt cgactactgg ggccagggca aaccctgac agtgtctagc    780
gctagctccg gaaccacgac gccagcgccg cgaccaccaa caccggcgcc caccatcgcg    840
tcgcagcccc tgtccctgcg cccagaggcg tgccggccag cggcgggggg cgcagtgcac    900
acgagggggc tggacttcgc ctgtgatatc tacatctggg cgcccttggc cgggacttgt    960
ggggtccttc tcctgtcact ggttatcacc ctttactgca aacgggcag aaagaaactc   1020
ctgtatatat tcaaacaacc atttatgaga ccagtacaaa ctactcaaga ggaagacggc   1080
tgtagctgcc gatttccaga agaagaagaa ggaggatgtg aactgagagt gaagttcagc   1140
aggagcgcag acgcccccgc gtacaagcag gccagaacc agctctataa cgagctcaat   1200
ctaggacgaa gagaggagta cgacgttttg gacaagagac gtggccggga ccctgagatg   1260
ggggaaagc cgagaaggaa gaaccctcag gaaggcctgt acaacgaact gcagaaagat   1320
aagatggcgg aggcctacag tgagattggg atgaaaggcg agcgccggag gggcaagggg   1380
cacgacggcc tttaccaggg tctcagtaca gccaccaagg acacctacga cgcccttcac   1440
atgcaggccc tgccccctcg c                                            1461

<210> SEQ ID NO 107
<211> LENGTH: 490
<212> TYPE: PRT
<213> ORGANISM: Artificial Sequence
<220> FEATURE:
<223> OTHER INFORMATION: 1C3 human PSMA-CAR

<400> SEQUENCE: 107

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Ala Met His Trp Val Arg Gln Ala Pro Gly Lys
    50                  55                  60

Gly Leu Glu Trp Val Ala Val Ile Ser Tyr Asp Gly Asn Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ala Val Pro Trp Gly Ser Arg Tyr Tyr
        115                 120                 125

Tyr Tyr Gly Met Asp Val Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160
```

Ala Ile Gln Leu Thr Gln Ser Pro Ser Ser Leu Ser Ala Ser Val Gly
                165                 170                 175

Asp Arg Val Thr Ile Thr Cys Arg Ala Ser Gln Gly Ile Ser Ser Ala
            180                 185                 190

Leu Ala Trp Tyr Gln Gln Lys Ser Gly Lys Ala Pro Lys Leu Leu Ile
        195                 200                 205

Phe Asp Ala Ser Ser Leu Glu Ser Gly Val Pro Ser Arg Phe Ser Gly
    210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys Gln Gln Phe Asn Ser Tyr Pro Leu
                245                 250                 255

Thr Phe Gly Gly Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 108
<211> LENGTH: 1470
<212> TYPE: DNA
<213> ORGANISM: Artificial Sequence
<220> FEATURE:
<223> OTHER INFORMATION: 1C3 human PSMA-CAR

<400> SEQUENCE: 108
atggcctTac cagtgaccgc cttgctcctg ccgctggcct tgctgctcca cgccgccagg      60
ccgcaggtgc aactggtgga gtctggggga ggcgtggtcc agcctgggag gtccctgaga     120
ctctcctgtg cagcctctgg attcaccttc agtagctatg ctatgcactg ggtccgccag     180

```
gctccaggca agggctgga gtgggtggca gttatatcat atgatggaaa caataaatac    240
tacgcagact ccgtgaaggg ccgattcacc atctccagag acaattccaa gaacacgctg    300
tatctgcaaa tgaacagcct gagagctgag gacacggctg tgtattactg tgcgagagcc    360 gtccctggg gatcgaggta ctactactac ggtatggacg tctggggcca agggaccacg    420
gtcaccgtct cctcaggtgg cggtggctcg ggcggtggtg gtcgggtgg cggcggatct    480 gccatccagt tgacccagtc tccatcctcc ctgtctgcat ctgtaggaga cagagtcacc    540
atcacttgcc gggcaagtca gggcattagc agtgctttag cctggtatca gcagaaatca    600
gggaaagctc ctaagctcct gatctttgat gcctccagtt tggaaagtgg ggtcccatca    660
aggttcagcg gcagtggatc tgggacagat ttcactctca ccatcagcag cctgcagcct    720
gaagattttg caacttatta ctgtcaacag tttaacagtt atcctctcac tttcggcgga    780
gggaccaagg tggagatcaa accacgacg ccagcgccgc gaccaccaac accggcgccc    840
accatcgcgt cgcagcccct gtccctgcgc ccagaggcgt gccggccagc ggcgggggc    900 gcagtgcaca cgagggggct ggacttcgcc tgtgatatct acatctgggc gcccttggcc    960
gggacttgtg ggtccttct cctgtcactg gttatcaccc tttactgcaa acggggcaga    1020
aagaaactcc tgtatatatt caaacaacca tttatgagac cagtacaaac tactcaagag    1080
gaagacggct gtagctgccg atttccagaa gaagaagaag gaggatgtga actgagagtg    1140
aagttcagca ggagcgcaga cgcccccgcg tacaagcagg gccagaacca gctctataac    1200
gagctcaatc taggacgaag agaggagtac gacgttttgg acaagagacg tggccgggac    1260
cctgagatgg ggggaaagcc gagaaggaag aaccctcagg aaggcctgta caacgaactg    1320
cagaaagata gatggcgga ggcctacagt gagattggga tgaaaggcga gcgccggagg    1380 ggcaagggc acgacggcct ttaccagggt ctcagtacag ccaccaagga cacctacgac    1440
gcccttcaca tgcaggccct gccccctcgc                                     1470
```

<210> SEQ ID NO 109
<211> LENGTH: 485
<212> TYPE: PRT
<213> ORGANISM: Artificial Sequence
<220> FEATURE:
<223> OTHER INFORMATION: 2A10 human PSMA-CAR

<400> SEQUENCE: 109

```
Met Ala Leu Pro Val Thr Ala Leu Leu Leu Pro Leu Ala Leu Leu Leu
1               5                  10                  15

His Ala Ala Arg Pro Glu Val Gln Leu Val Gln Ser Gly Ala Glu Val
            20                  25                  30

Lys Lys Pro Gly Glu Ser Leu Lys Ile Ser Cys Lys Gly Ser Gly Tyr
        35                  40                  45

Ser Phe Thr Ser Asn Trp Ile Gly Trp Val Arg Gln Met Pro Gly Lys
    50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Ser Ser Leu Lys Ala Ser Asp Thr
            100                 105                 110

Ala Met Tyr Tyr Cys Ala Arg Gln Thr Gly Phe Leu Trp Ser Ser Asp
        115                 120                 125
```

Leu Trp Gly Arg Gly Thr Leu Val Thr Val Ser Ser Gly Gly Gly
130                 135                 140

Ser Gly Gly Gly Gly Ser Gly Gly Gly Ser Ala Ile Gln Leu Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Ser Ala Leu Ala Trp Tyr Gln
            180                 185                 190

Gln Lys Pro Gly Lys Ala Pro Lys Leu Leu Ile Tyr Asp Ala Ser Ser
        195                 200                 205

Leu Glu Ser Gly Val Pro Ser Arg Phe Ser Gly Tyr Gly Ser Gly Thr
210                 215                 220

Asp Phe Thr Leu Thr Ile Asn Ser Leu Gln Pro Glu Asp Phe Ala Thr
225                 230                 235                 240

Tyr Tyr Cys Gln Gln Phe Asn Ser Tyr Pro Leu Thr Phe Gly Gly Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 110
<211> LENGTH: 1455
<212> TYPE: DNA
<213> ORGANISM: Artificial Sequence
<220> FEATURE:
<223> OTHER INFORMATION: 2A10 human PSMA-CAR

<400> SEQUENCE: 110

| | |
|---|---:|
| atggccttac cagtgaccgc cttgctcctg ccgctggcct tgctgctcca cgccgccagg | 60 |
| ccggaggtgc agctggtgca gtctggagca gaggtgaaaa agcccgggga gtctctgaag | 120 |
| atctcctgta agggttctgg atacagcttt accagtaact ggatcggctg ggtgcgccag | 180 |
| atgcccggga aaggcctgga gtggatgggg atcatctatc ctggtgactc tgataccaga | 240 |
| tacagcccgt ccttccaagg ccaggtcacc atctcagccg acaagtccat cagcaccgcc | 300 |
| tacctgcagt ggagcagcct gaaggcctcg gacaccgcca tgtattactg tgcgaggcaa | 360 |
| actggtttcc tctggtcctc cgatctctgg ggccgtggca ccctggtcac tgtctcctca | 420 |
| ggtggcggtg gctcgggcgg tgtgggtcg gtggcggcg atctgccat ccagttgacc | 480 |
| cagtctccat cctccctgtc tgcatctgta ggagacagag tcaccatcac ttgccgggca | 540 |
| agtcaggaca ttagcagtgc tttagcctgg tatcaacaga aaccagggaa agctcctaag | 600 |
| ctcctgatct atgatgcctc agtttggaa agtggggtcc catcaaggtt cagcggctat | 660 |
| ggatctggga cagatttcac tctcaccatc aacagcctgc agcctgaaga ttttgcaact | 720 |
| tattactgtc aacagtttaa tagttacccg ctcacttcg cgcgagggac caaggtggag | 780 |
| atcaaaacca cgacgccagc gccgcgacca ccaacaccgg cgcccaccat cgcgtcgcag | 840 |
| ccctgtcc tgcgcccaga ggcgtgccgg ccagcggcgg ggggcgcagt gcacacgagg | 900 |
| gggctggact tcgcctgtga tatctacatc tgggcgccct tggccgggac ttgtggggtc | 960 |
| cttctcctgt cactggttat cacccttac tgcaaacggg gcagaaagaa actcctgtat | 1020 |
| atattcaaac aaccatttat gagaccagta caaactactc aagaggaaga cggctgtagc | 1080 |
| tgccgatttc cagaagaaga agaaggagga tgtgaactga gagtgaagtt cagcaggagc | 1140 |
| gcagacgccc ccgcgtacaa gcagggccag aaccagctct ataacgagct caatctagga | 1200 |
| cgaagagagg agtacgacgt tttggacaag agacgtggcc gggaccctga tgggggga | 1260 |
| aagccgagaa ggaagaaccc tcaggaaggc ctgtacaacg aactgcagaa agataagatg | 1320 |
| gcggaggcct acagtgagat tgggatgaaa ggcgagcgcc ggaggggcaa ggggcacgac | 1380 |
| ggcctttacc agggtctcag tacagccacc aaggacacct acgacgccct tcacatgcag | 1440 |
| gccctgcccc ctcgc | 1455 |

<210> SEQ ID NO 111
<211> LENGTH: 487
<212> TYPE: PRT
<213> ORGANISM: Artificial Sequence
<220> FEATURE:
<223> OTHER INFORMATION: 2F5 human PSMA-CAR

<400> SEQUENCE: 111

```
Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
                20                  25                  30

Lys Lys Pro Gly Glu Ser Leu Lys Ile Ser Cys Lys Gly Ser Gly Tyr
            35                  40                  45

Ser Phe Thr Ser Asn Trp Ile Gly Trp Val Arg Gln Met Pro Gly Lys
        50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Asn Ser Leu Lys Ala Ser Asp Thr
```

```
                100             105             110
Ala Met Tyr Tyr Cys Ala Arg Gln Thr Gly Phe Leu Trp Ser Phe Asp
            115                 120                 125
Leu Trp Gly Arg Gly Thr Leu Val Thr Val Ser Ser Gly Gly Gly Gly
130                 135                 140
Ser Gly Gly Gly Gly Ser Gly Gly Gly Gly Ser Ala Ile Gln Leu Thr
145                 150                 155                 160
Gln Ser Pro Ser Ser Leu Ser Ala Ser Val Gly Asp Arg Val Thr Ile
                165                 170                 175
Thr Cys Arg Ala Ser Gln Asp Ile Ser Ser Ala Leu Ala Trp Tyr Gln
                180                 185                 190
Gln Lys Pro Gly Lys Ala Pro Lys Leu Leu Ile Tyr Asp Ala Ser Ser
                195                 200                 205
Leu Glu Ser Gly Val Pro Ser Arg Phe Ser Gly Ser Gly Ser Gly Thr
                210                 215                 220
Asp Phe Thr Leu Thr Ile Ser Ser Leu Gln Pro Glu Asp Phe Ala Thr
225                 230                 235                 240
Tyr Tyr Cys Gln Gln Phe Asn Ser Tyr Pro Leu Thr Phe Gly Gly Gly
                245                 250                 255
Thr Lys Val Glu Ile Lys Ile Lys Thr Thr Pro Ala Pro Arg Pro
                260                 265                 270
Pro Thr Pro Ala Pro Thr Ile Ala Ser Gln Pro Leu Ser Leu Arg Pro
                275                 280                 285
Glu Ala Cys Arg Pro Ala Ala Gly Gly Ala Val His Thr Arg Gly Leu
                290                 295                 300
Asp Phe Ala Cys Asp Ile Tyr Ile Trp Ala Pro Leu Ala Gly Thr Cys
305                 310                 315                 320
Gly Val Leu Leu Leu Ser Leu Val Ile Thr Leu Tyr Cys Lys Arg Gly
                325                 330                 335
Arg Lys Lys Leu Leu Tyr Ile Phe Lys Gln Pro Phe Met Arg Pro Val
                340                 345                 350
Gln Thr Thr Gln Glu Glu Asp Gly Cys Ser Cys Arg Phe Pro Glu Glu
                355                 360                 365
Glu Glu Gly Gly Cys Glu Leu Arg Val Lys Phe Ser Arg Ser Ala Asp
                370                 375                 380
Ala Pro Ala Tyr Lys Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Arg Arg Lys Asn Pro Gln Glu Gly
                420                 425                 430
Leu Tyr Asn Glu Leu Gln Lys Asp Lys Met Ala Glu Ala Tyr Ser Glu
                435                 440                 445
Ile Gly Met Lys Gly Glu Arg Arg Arg Gly Lys Gly His Asp Gly Leu
                450                 455                 460
Tyr Gln Gly Leu Ser Thr Ala Thr Lys Asp Thr Tyr Asp Ala Leu His
465                 470                 475                 480
Met Gln Ala Leu Pro Pro Arg
                485

<210> SEQ ID NO 112
<211> LENGTH: 1461
<212> TYPE: DNA
<213> ORGANISM: Artificial Sequence
```

<220> FEATURE:
<223> OTHER INFORMATION: 2F5 human PSMA-CAR

<400> SEQUENCE: 112

```
atggccttac cagtgaccgc cttgctcctg ccgctggcct tgctgctcca cgccgccagg      60
ccggaggtgc agctggtgca gtctggagca gaggtgaaaa agcccgggga gtctctgaag     120
atctcctgta agggttctgg atacagtttt accagcaact ggatcggctg ggtgcgccag     180
atgcccggga aaggcctgga gtggatgggg atcatctatc ctggtgactc tgataccaga     240
tacagcccgt ccttccaagg ccaggtcacc atctcagccg acaagtccat cagcaccgcc     300
tacctgcagt ggaacagcct gaaggcctcg gacaccgcca tgtattactg tgcgagacaa     360
actggtttcc tctggtcctt cgatctctgg ggccgtggca ccctggtcac tgtctcctca     420
ggtggcggtg gctcgggcgg tggtgggtcg ggtggcggcg atctgccat ccagttgacc      480
cagtctccat cctccctgtc tgcatctgta ggagacagag tcaccatcac ttgccgggca     540
agtcaggaca ttagcagtgc tttagcctgg tatcagcaga accggggaa agctcctaag      600
ctcctgatct atgatgcctc cagtttggaa agtggggtcc catcaaggtt cagcggcagt     660
ggatctggga cagatttcac tctcaccatc agcagcctgc agcctgaaga ttttgcaact     720
tattactgtc aacagtttaa tagttacccg ctcactttcg gcggagggac caaggtggag     780
atcaaaatca aaccacgac gccagcgccg cgaccaccaa caccggcgcc caccatcgcg      840
tcgcagcccc tgtccctgcg cccagaggcg tgccggccag cggcgggggg cgcagtgcac     900
acgaggggc tggacttcgc ctgtgatatc tacatctggg cgcccttggc cgggacttgt      960
ggggtccttc tcctgtcact ggttatcacc ctttactgca acggggcag aaagaaactc     1020
ctgtatatat tcaaacaacc atttatgaga ccagtacaaa ctactcaaga ggaagacggc    1080
tgtagctgcc gatttccaga agaagaagaa ggaggatgtg aactgagagt gaagttcagc    1140
aggagcgcag acgccccgc gtacaagcag ggccagaacc agctctataa cgagctcaat    1200
ctaggacgaa gagaggagta cgacgttttg gacaagagac gtggccggga ccctgagatg    1260
gggggaaagc cgagaaggaa gaaccctcag gaaggcctgt acaacgaact gcagaaagat    1320
aagatggcgg aggcctacag tgagattggg atgaaaggcg agcgccggag gggcaagggg    1380
cacgacggcc tttaccaggg tctcagtaca gccaccaagg acacctacga cgcccttcac    1440
atgcaggccc tgccccctcg c                                             1461
```

<210> SEQ ID NO 113
<211> LENGTH: 488
<212> TYPE: PRT
<213> ORGANISM: Artificial Sequence
<220> FEATURE:
<223> OTHER INFORMATION: 2C6 human PSMA-CAR

<400> SEQUENCE: 113

Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ser Glu Val
                20                  25                  30

Lys Lys Pro Gly Glu Ser Leu Lys Ile Ser Cys Lys Gly Ser Gly Tyr
            35                  40                  45

Ser Phe Thr Asn Tyr Trp Ile Gly Trp Val Arg Gln Met Pro Gly Lys
        50                  55                  60

Gly Leu Glu Trp Met Gly Ile Ile Tyr Pro Gly Asp Ser Asp Thr Arg
65                  70                  75                  80

```
Tyr Ser Pro Ser Phe Gln Gly Gln Val Thr Ile Ser Ala Asp Lys Ser
                85                  90                  95

Ile Ser Thr Ala Tyr Leu Gln Trp Ser Ser Leu Lys Ala Ser Asp Thr
                100                 105                 110

Ala Met Tyr Tyr Cys Ala Ser Pro Gly Tyr Thr Ser Ser Trp Thr Ser
                115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Ser Glu Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Ser Ser Tyr Leu Ala Trp
                180                 185                 190

Tyr Gln Gln Lys Pro Gly Gln Ala Pro Arg Leu Leu Ile Tyr Asp Ala
                195                 200                 205

Ser Asn Arg Ala Thr Gly Ile Pro Ala Arg Phe Ser Gly Ser Gly Ser
    210                 215                 220

Gly Thr Asp Phe Thr Leu Thr Ile Ser Ser Leu Glu Pro Glu Asp Phe
225                 230                 235                 240

Ala Val Tyr Tyr Cys Gln Gln Arg Ser Asn Trp Pro Leu Phe Thr Phe
                245                 250                 255

Gly Pro Gly Thr Lys Val Asp Ile Lys Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
                355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
    435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 114
<211> LENGTH: 1464
<212> TYPE: DNA
<213> ORGANISM: Artificial Sequence
<220> FEATURE:
<223> OTHER INFORMATION: 2C6 human PSMA-CAR

<400> SEQUENCE: 114

```
atggccttac cagtgaccgc cttgctcctg ccgctggcct tgctgctcca cgccgccagg      60
ccggaggtgc agctggtgca gtctggatca gaggtgaaaa agcccgggga gtctctgaag     120
atctcctgta agggttctgg atacagcttt accaactact ggatcggctg ggtgcgccag     180
atgcccggga aaggcctgga gtggatgggg atcatctatc ctggtgactc tgataccaga     240
tacagcccgt ccttccaagg ccaggtcacc atctcagccg acaagtccat cagcaccgcc     300
tatctgcagt ggagcagcct gaaggcctcg gacaccgcca tgtattactg tgcgagtccc     360
gggtatacca gcagttggac ttcttttgac tactggggcc agggaaccct ggtcaccgtc     420
tcctcaggtg gcggtggctc gggcggtggt gggtcgggtg gcggcggatc tgaaattgtg     480
ttgacacagt ctccagccac cctgtctttg tctccagggg aaagagccac cctctcctgc     540
agggccagtc agagtgttag cagctactta gcctggtacc aacagaaacc tggccaggct     600
cccaggctcc tcatctatga tgcatccaac agggccactg gcatcccagc caggttcagt     660
ggcagtgggt ctgggacaga cttcactctc accatcagca gcctagagcc tgaagatttt     720
gcagtttatt actgtcagca gcgtagcaac tggcccctat tcactttcgg ccctgggacc     780
aaagtggata tcaaaaccac gacgccagcg ccgcgaccac caacaccggc gccaccatc      840
gcgtcgcagc ccctgtccct gcgcccagag gcgtgccggc cagcggcggg gggcgcagtg     900
cacacgaggg gctggacttt cgcctgtgat atctacatct gggcgccctt ggccgggact     960
tgtggggtcc ttctcctgtc actggttatc accctttact gcaaacgggg cagaaagaaa    1020
ctcctgtata tattcaaaca accatttatg agaccagtac aaactactca agaggaagac    1080
ggctgtagct gccgatttcc agaagaagaa gaaggaggat gtgaactgag agtgaagttc    1140
agcaggagcg cagacgcccc cgcgtacaag cagggccaga accagctcta taacgagctc    1200
aatctaggac gaagagagga gtacgacgtt ttggacaaga cgtggccg ggaccctgag       1260
atgggggga agccgagaag gaagaaccct caggaaggcc tgtacaacga actgcagaaa    1320
gataagatgg cggaggccta cagtgagatt gggatgaaag gcgagcgccg gaggggcaag    1380
gggcacgacg gcctttacca gggtctcagt acagccacca ggacaccta cgacgccctt    1440
cacatgcagg ccctgccccc tcgc                                           1464
```

<210> SEQ ID NO 115
<211> LENGTH: 201
<212> TYPE: PRT
<213> ORGANISM: Artificial Sequence
<220> FEATURE:
<223> OTHER INFORMATION: TGFBRII-DN

<400> SEQUENCE: 115

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

```
Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Ser Gly
        195                 200
```

```
<210> SEQ ID NO 116
<211> LENGTH: 603
<212> TYPE: DNA
<213> ORGANISM: Artificial Sequence
<220> FEATURE:
<223> OTHER INFORMATION: TGFBRII-DN

<400> SEQUENCE: 116
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120
aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga ggaaaaaaa aaagcctggt gagactttct tcatgtgttc ctgtagctct    420
gatgagtgca atgacaacat catcttctca gaagaatata caccagcaa tcctgacttg    480
ttgctagtca tatttcaagt gacaggcatc agcctcctgc caccactggg agttgccata    540
tctgtcatca tcatcttcta ctgctaccgc gttaaccggc agcagaagct gagttcatcc    600
gga                                                                   603
```

```
<210> SEQ ID NO 117
<211> LENGTH: 238
<212> TYPE: PRT
<213> ORGANISM: Artificial Sequence
<220> FEATURE:
<223> OTHER INFORMATION: PD1-CTM-CD28 switch receptor

<400> SEQUENCE: 117

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
```

```
                35                    40                    45
Asn Ala Thr Phe Thr Cys Ser Phe Ser Asn Thr Ser Glu Ser Phe Val
 50                      55                      60
Leu Asn Trp Tyr Arg Met Ser Pro Ser Asn Gln Thr Asp Lys Leu Ala
 65                      70                      75                      80
Ala Phe Pro Glu Asp Arg Ser Gln Pro Gly Gln Asp Cys Arg Phe Arg
                 85                      90                      95
Val Thr Gln Leu Pro Asn Gly Arg Asp Phe His Met Ser Val Val Arg
                100                     105                     110
Ala Arg Arg Asn Asp Ser Gly Thr Tyr Leu Cys Gly Ala Ile Ser Leu
                115                     120                     125
Ala Pro Lys Ala Gln Ile Lys Glu Ser Leu Arg Ala Glu Leu Arg Val
130                     135                     140
Thr Glu Arg Arg Ala Glu Val Pro Thr Ala His Pro Ser Pro Ser Pro
145                     150                     155                     160
Arg Pro Ala Gly Gln Phe Gln Thr Leu Val Phe Trp Val Leu Val Val
                165                     170                     175
Val Gly Gly Val Leu Ala Cys Tyr Ser Leu Leu Val Thr Val Ala Phe
                180                     185                     190
Ile Ile Phe Trp Val Arg Ser Lys Arg Ser Arg Leu Leu His Ser Asp
                195                     200                     205
Tyr Met Asn Met Thr Pro Arg Arg Pro Gly Pro Thr Arg Lys His Tyr
210                     215                     220
Gln Pro Tyr Ala Pro Pro Arg Asp Phe Ala Ala Tyr Arg Ser
225                     230                     235

<210> SEQ ID NO 118
<211> LENGTH: 714
<212> TYPE: DNA
<213> ORGANISM: Artificial Sequence
<220> FEATURE:
<223> OTHER INFORMATION: PD1-CTM-CD28 switch receptor

<400> SEQUENCE: 118
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag ccctcaccc     480 aggccagccg gccagttcca aaccctggtg ttttgggtgc tggtggtggt tggtggagtc     540
ctggcttgct atagcttgct agtaacagtg gcctttatta ttttctgggt gaggagtaag     600
aggagcaggc tcctgcacag tgactacatg aacatgactc ccgccgccc cgggcccacc     660 cgcaagcatt accagcccta tgccccacca cgcgacttcg cagcctatcg ctcc           714

<210> SEQ ID NO 119
<211> LENGTH: 232
<212> TYPE: PRT
<213> ORGANISM: Artificial Sequence
<220> FEATURE:
<223> OTHER INFORMATION: PD1-PTM-CD28 switch receptor
```

<400> SEQUENCE: 119

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Ser Lys Arg Ser Arg Leu Leu His Ser Asp Tyr Met Asn Met Thr Pro
        195                 200                 205

Arg Arg Pro Gly Pro Thr Arg Lys His Tyr Gln Pro Tyr Ala Pro Pro
    210                 215                 220

Arg Asp Phe Ala Ala Tyr Arg Ser
225                 230
```

<210> SEQ ID NO 120
<211> LENGTH: 696
<212> TYPE: DNA
<213> ORGANISM: Artificial Sequence
<220> FEATURE:
<223> OTHER INFORMATION: PD1-PTM-CD28 switch receptor

<400> SEQUENCE: 120

```
atgcagatcc cacaggcgcc ctggccagtc gtctgggcgg tgctacaact gggctggcgg    60
ccaggatggt tcttagactc cccagacagg ccctggaacc cccccacctt ctccccagcc   120
ctgctcgtgg tgaccgaagg ggacaacgcc accttcacct gcagcttctc caacacatcg   180
gagagcttcg tgctaaactg gtaccgcatg agccccagca accagacgga caagctggcc   240
gccttccccg aggaccgcag ccagcccggc caggactgcc gcttccgtgt cacacaactg   300
cccaacgggc gtgacttcca catgagcgtg gtcagggccc ggcgcaatga cagcggcacc   360
tacctctgtg gggccatctc cctggccccc aaggcgcaga tcaaagagag cctgcgggca   420
gagctcaggg tgacagagag aagggcagaa gtgcccacag cccaccccag ccctcacccc   480
aggccagccg gccagttcca aaccctggtg gttggtgtcg tgggcggcct gctgggcagc   540
ctggtgctgc tagtctgggt cctggccgtc atcaggagta agaggagcag gctcctgcac   600
agtgactaca tgaacatgac tccccgccgc cccgggccca ccgcaagca ttaccagccc   660
```
tatgccccac cacgcgactt cgcagcctat cgctcc    696

<210> SEQ ID NO 121
<211> LENGTH: 232
<212> TYPE: PRT
<213> ORGANISM: Artificial Sequence
<220> FEATURE:
<223> OTHER INFORMATION: PD1A132L-PTM-CD28 switch receptor

<400> SEQUENCE: 121

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Ser Lys Arg Ser Arg Leu Leu His Ser Asp Tyr Met Asn Met Thr Pro
        195                 200                 205

Arg Arg Pro Gly Pro Thr Arg Lys His Tyr Gln Pro Tyr Ala Pro Pro
    210                 215                 220

Arg Asp Phe Ala Ala Tyr Arg Ser
225                 230
```

<210> SEQ ID NO 122
<211> LENGTH: 693
<212> TYPE: DNA
<213> ORGANISM: Artificial Sequence
<220> FEATURE:
<223> OTHER INFORMATION: PD1A132L-PTM-CD28 switch receptor

<400> SEQUENCE: 122
atgcagatcc cacaggcgcc ctggccagtc gtctgggcgg tgctacaact gggctggcgg    60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agcccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360

```
tacctctgtg gggccatctc cctggccccc aagctgcaga tcaaagagag cctgcgggca      420
gagctcaggg tgacagagag aagggcagaa gtgcccacag cccacccccag cccctcaccc     480 aggccagccg gccagttcca aaccctggtg gttggtgtcg tgggcggcct gctgggcagc      540
ctggtgctgc tagtctgggt cctggccgtc atcaggagta agaggagcag gctcctgcac      600
agtgactaca tgaacatgac tccccgccgc cccgggccca cccgcaagca ttaccagccc      660
tatgccccac cacgcgactt cgcagcctat cgc                                   693
```

\<210\> SEQ ID NO 123
\<211\> LENGTH: 238
\<212\> TYPE: PRT
\<213\> ORGANISM: Artificial Sequence
\<220\> FEATURE:
\<223\> OTHER INFORMATION: TGFBR-IL12RB1 receptor

\<400\> SEQUENCE: 123

```
Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Arg Ala Ala Arg His Leu Cys Pro Pro Leu Pro Thr Pro
145                 150                 155                 160

Cys Ala Ser Ser Ala Ile Glu Phe Pro Gly Gly Lys Glu Thr Trp Gln
                165                 170                 175

Trp Ile Asn Pro Val Asp Phe Gln Glu Glu Ala Ser Leu Gln Glu Ala
            180                 185                 190

Leu Val Val Glu Met Ser Trp Asp Lys Gly Glu Arg Thr Glu Pro Leu
        195                 200                 205

Glu Lys Thr Glu Leu Pro Glu Gly Ala Pro Glu Leu Ala Leu Asp Thr
    210                 215                 220

Glu Leu Ser Leu Glu Asp Gly Asp Arg Cys Lys Ala Lys Met
225                 230                 235
```

\<210\> SEQ ID NO 124
\<211\> LENGTH: 714
\<212\> TYPE: DNA
\<213\> ORGANISM: Artificial Sequence
\<220\> FEATURE:
\<223\> OTHER INFORMATION: TGFBR-IL12RB1 receptor

\<400\> SEQUENCE: 124

```
atggaggcgg cggtcgctgc tccgcgtccc cggctgctcc tcctcgtgct ggcggcggcg      60
```

```
gcggcggcgg cggcggcgct gctcccgggg gcgacggcgt tacagtgttt ctgccacctc    120
tgtacaaaag acaattttac ttgtgtgaca gatgggctct gctttgtctc tgtcacagag    180
accacagaca aagttataca caacagcatg tgtatagctg aaattgactt aattcctcga    240
gataggccgt ttgtatgtgc accctcttca aaaactgggt ctgtgactac aacatattgc    300
tgcaatcagg accattgcaa taaaatagaa cttccaacta ctgtaaagtc atcacctggc    360
cttggtcctg tggaactggc agctgtcatt gctggaccag tgtgcttcgt ctgcatctca    420
ctcatgttga tggtctatat cagggccgca cggcacctgt gcccgccgct gcccacaccc    480
tgtgccagct ccgccattga gttccctgga gggaaggaga cttggcagtg gatcaaccca    540
gtggacttcc aggaagaggc atccctgcag gaggccctgg tggtagagat gtcctgggac    600
aaaggcgaga ggactgagcc tctcgagaag acagagctac ctgagggtgc ccctgagctg    660
gccctggata cagagttgtc cttggaggat ggagacaggt gcaaggccaa gatg           714
```

<210> SEQ ID NO 125
<211> LENGTH: 403
<212> TYPE: PRT
<213> ORGANISM: Artificial Sequence
<220> FEATURE:
<223> OTHER INFORMATION: TGFBR-IL12RB2 receptor

<400> SEQUENCE: 125

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Gln Gln Lys Val Phe
            180                 185                 190

Val Leu Leu Ala Ala Leu Arg Pro Gln Trp Cys Ser Arg Glu Ile Pro
        195                 200                 205

Asp Pro Ala Asn Ser Thr Cys Ala Lys Lys Tyr Pro Ile Ala Glu Glu
    210                 215                 220

Lys Thr Gln Leu Pro Leu Asp Arg Leu Leu Ile Asp Trp Pro Thr Pro
225                 230                 235                 240

Glu Asp Pro Glu Pro Leu Val Ile Ser Glu Val Leu His Gln Val Thr
```

```
                245                 250                 255
Pro Val Phe Arg His Pro Pro Cys Ser Asn Trp Pro Gln Arg Glu Lys
        260                 265                 270
Gly Ile Gln Gly His Gln Ala Ser Glu Lys Asp Met Met His Ser Ala
        275                 280                 285
Ser Ser Pro Pro Pro Arg Ala Leu Gln Ala Glu Ser Arg Gln Leu
        290                 295                 300
Val Asp Leu Tyr Lys Val Leu Glu Ser Arg Gly Ser Asp Pro Lys Pro
305                 310                 315                 320
Glu Asn Pro Ala Cys Pro Trp Thr Val Leu Pro Ala Gly Asp Leu Pro
                325                 330                 335
Thr His Asp Gly Tyr Leu Pro Ser Asn Ile Asp Asp Leu Pro Ser His
                340                 345                 350
Glu Ala Pro Leu Ala Asp Ser Leu Glu Glu Leu Glu Pro Gln His Ile
                355                 360                 365
Ser Leu Ser Val Phe Pro Ser Ser Ser Leu His Pro Leu Thr Phe Ser
        370                 375                 380
Cys Gly Asp Lys Leu Thr Leu Asp Gln Leu Lys Met Arg Cys Asp Ser
385                 390                 395                 400
Leu Met Leu
```

<210> SEQ ID NO 126
<211> LENGTH: 1209
<212> TYPE: DNA
<213> ORGANISM: Artificial Sequence
<220> FEATURE:
<223> OTHER INFORMATION: TGFBR-IL12RB2 receptor

<400> SEQUENCE: 126

```
atgggtcggg ggctgctcag gggcctgtgg ccgctgcaca tcgtcctgtg gacgcgtatc      60
gccagcacga tcccaccgca cgttcagaag tcggttaata cgacatgat agtcactgac      120
aacaacggtg cagtcaagtt tccacaactg tgtaaatttt gtgatgtgag attttccacc      180
tgtgacaacc agaaatcctg catgagcaac tgcagcatca cctccatctg tgagaagcca      240
caggaagtct gtgtggctgt atggagaaag aatgacgaga cataacact agagacagtt      300
tgccatgacc ccaagctccc ctaccatgac tttattctgg aagatgctgc ttctccaaag      360
tgcattatga aggaaaaaaa aaagcctggt gagactttct tcatgtgttc ctgtagctct      420
gatgagtgca atgacaacat catcttctca gaagaatata caccagcaa tcctgacttg      480
ttgctagtca tatttcaagt gacaggcatc agcctcctgc caccactggg agttgccata      540
tctgtcatca tcatcttcta ccagcaaaag gtgtttgttc cctagcagc cctcagacct      600
cagtggtgta gcagagaaat tccagatcca gcaaatagca cttgcgctaa gaatatcccc      660
attgcagagg agaagacaca gctgcccttg acaggctcc tgatagactg gcccacgcct      720
gaagatcctg aaccgctggt catcagtgaa gtccttcatc aagtgacccc agttttcaga      780
catcccccct gctccaactg gccacaaagg gaaaaggaa tccaaggtca tcaggcctct      840
gagaaagaca tgatgcacag tgcctcaagc ccaccacctc caagagctct ccaagctgag      900
agcagacaac tggtggatct gtacaaggtg ctggagagca gggcctccga cccaaagcca      960
gaaaacccag cctgtccctg acggtgctcc ccagcaggtg accttccac ccatgatggc     1020
tacttacccc tcaacataga tgacctcccc tcacatgagg cacctctcgc tgactctctg     1080
gaagaactgg agcctcagca catctccctt tctgttttcc cctcaagttc tcttcaccca     1140
```

```
ctcaccttct cctgtggtga taagctgact ctggatcagt taaagatgag gtgtgactcc    1200
ctcatgctc                                                            1209
```

<210> SEQ ID NO 127
<211> LENGTH: 268
<212> TYPE: PRT
<213> ORGANISM: Artificial Sequence
<220> FEATURE:
<223> OTHER INFORMATION: TIM3-CD28 receptor

<400> SEQUENCE: 127

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Phe Trp Val Leu Val Val Val Gly
        195                 200                 205

Gly Val Leu Ala Cys Tyr Ser Leu Leu Val Thr Val Ala Phe Ile Ile
    210                 215                 220

Phe Trp Val Arg Ser Lys Arg Ser Arg Leu Leu His Ser Asp Tyr Met
225                 230                 235                 240

Asn Met Thr Pro Arg Arg Pro Gly Pro Thr Arg Lys His Tyr Gln Pro
                245                 250                 255

Tyr Ala Pro Pro Arg Asp Phe Ala Ala Tyr Arg Ser
            260                 265
```

<210> SEQ ID NO 128
<211> LENGTH: 804
<212> TYPE: DNA
<213> ORGANISM: Artificial Sequence
<220> FEATURE:
<223> OTHER INFORMATION: TIM3-CD28 receptor

<400> SEQUENCE: 128

```
atgttttcac atcttccctt tgactgtgtc ctgctgctgc tgctgctact acttacaagg    60
tcctcagaag tggaatacag agcggaggtc ggtcagaatg cctatctgcc ctgcttctac   120
```

```
acccccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc gaatcccaaa tcccaggcat aatgaatgat    360
gaaaaattta acctgaagtt ggtcatcaaa ccagccaagg tcaccctgc accgactcgg     420
cagagagact tcactgcagc ctttccaagg atgcttacca ccaggggaca tggcccagca    480
gagacacaga cactggggag cctccctgac ataaatctaa cacaaatatc cacattggcc    540
aatgagttac gggactctag gttggccaat gacttacggg actccggagc aaccatcaga    600
ttttgggtgc tggtggtggt tggtggagtc ctggcttgct atagcttact agtaacagtg    660
gcctttatta ttttctgggt gaggagtaag aggagcaggc tcctgcacag tgactacatg    720
aacatgactc cccgccgccc cgggcccacc cgcaagcatt accagcccta tgccccacca    780
cgcgacttcg cagcctatcg ctcc                                            804
```

<210> SEQ ID NO 129
<211> LENGTH: 503
<212> TYPE: PRT
<213> ORGANISM: Artificial Sequence
<220> FEATURE:
<223> OTHER INFORMATION: 13G4-1211 PD-L1/CD28 bispecific antibody
<400> SEQUENCE: 129

Met Gly Trp Ser Cys Ile Ile Leu Phe Leu Val Ala Thr Ala Thr Gly
1               5                   10                  15

Val His Ser Ala Ile Gln Leu Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Ser Ala Leu Ala Trp Tyr Gln Gln Lys Pro Gly Lys Ala Pro Lys
    50                  55                  60

Leu Leu Ile Tyr Asp Ala Ser Ser Leu Glu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Phe Asn Ser
            100                 105                 110

Tyr Pro Phe Thr Phe Gly Pro Gly Thr Lys Val Asp Ile Lys Ser Gly
        115                 120                 125

Gly Gly Gly Ser Glu Val Gln Leu Val Glu Ser Gly Gly Gly Leu Val
    130                 135                 140

Gln Pro Gly Arg Ser Leu Arg Leu Ser Cys Ala Ala Ser Gly Ile Thr
145                 150                 155                 160

Phe Asp Asp Tyr Gly Met His Trp Val Arg Gln Ala Pro Gly Lys Gly
                165                 170                 175

Leu Glu Trp Val Ser Gly Ile Ser Trp Asn Arg Gly Arg Ile Glu Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Leu Tyr Tyr Cys Ala Lys Gly Arg Phe Arg Tyr Phe Asp Trp Phe Leu
225                 230                 235                 240

```
Asp Tyr Trp Gly Gln Gly Thr Leu Val Thr Val Ser Ser Gly Gly Gly
                245                 250                 255

Gly Ser Gln Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
        275                 280                 285

Ser Tyr Tyr Ile His Trp Val Arg Gln Ala Pro Gly Gln Gly Leu Glu
    290                 295                 300

Trp Ile Gly Cys Ile Tyr Pro Gly Asn Val Thr Asn Tyr Asn Glu
305                 310                 315                 320

Lys Phe Lys Asp Arg Ala Thr Leu Thr Val Asp Thr Ser Ile Ser Thr
                325                 330                 335

Ala Tyr Met Glu Leu Ser Arg Leu Arg Ser Asp Asp Thr Ala Val Tyr
            340                 345                 350

Phe Cys Thr Arg Ser His Tyr Gly Leu Asp Trp Asn Phe Asp Val Trp
        355                 360                 365

Gly Gln Gly Thr Thr Val Thr Val Ser Ser Val Glu Gly Gly Ser Gly
    370                 375                 380

Gly Ser Gly Gly Ser Gly Gly Ser Gly Gly Val Met Asp Ile Gln
385                 390                 395                 400

Met Thr Gln Ser Pro Ser Ser Leu Ser Ala Ser Val Gly Asp Arg Val
                405                 410                 415

Thr Ile Thr Cys His Ala Ser Gln Asn Ile Tyr Val Trp Leu Asn Trp
            420                 425                 430

Tyr Gln Gln Lys Pro Gly Lys Ala Pro Lys Leu Leu Ile Tyr Lys Ala
        435                 440                 445

Ser Asn Leu His Thr Gly Val Pro Ser Arg Phe Ser Gly Ser Gly Ser
    450                 455                 460

Gly Thr Asp Phe Thr Leu Thr Ile Ser Ser Leu Gln Pro Glu Asp Phe
465                 470                 475                 480

Ala Thr Tyr Tyr Cys Gln Gln Gly Gln Thr Tyr Pro Tyr Thr Phe Gly
                485                 490                 495

Gly Gly Thr Lys Val Glu Ile
            500

<210> SEQ ID NO 130
<211> LENGTH: 1508
<212> TYPE: DNA
<213> ORGANISM: Artificial Sequence
<220> FEATURE:
<223> OTHER INFORMATION: 13G4-1211 PD-L1/CD28 bispecific antibody

<400> SEQUENCE: 130
atggggtggt cgtgtatcat cctgttcctg gtcgcgacag caaccggcgt gcattcggcc      60
atacagctga cccagagccc ctcctccctc tccgcttccg tggggaccg cgtgacaatc     120 acgtgccgcg ccagccaggg aatctcctcg gccctcgcct ggtaccagca gaaaccggg     180 aaggctccca agctgctcat ctacgatgcc tcctcgcttg agtcgggcgt gccatccagg    240
ttctccggat ccgggtccgg aaccgacttt acactcacga tttcctctct gcagcccgag    300
gacttcgcca catactactg tcagcagttc aactcctacc cattcacctt cggcccgggc    360
accaaggtgg acatcaagtc tggcggggga ggctccgaag tccagctcgt ggaatccggg    420
ggcggtctcg tgcagccagg ccggagtctg cgcctgtctt gcgctgcctc ggggatcact    480
ttcgacgact acggcatgca ttgggttcgc caggccccag gaaggggtt ggagtgggtc     540
```

```
agtggcattt catggaacag ggggcgcatc gaatacgccg actccgttaa gggcagattc    600
accatctcgc gcgataacgc caaaaacagt ctctacctcc agatgaactc gcttcgagca    660
gaggatactg ccctgtacta ttgcgcgaag ggacgcttcc gctactttga ctggtttctg    720
gactactggg gccaggggac actggtgacg gtgtcgtcgg ggggcggggg gagtcaggtg    780
cagctggtgc agtccggagc cgaggtaaag aagccaggcg cttccgtcaa ggtgtcatgc    840
aaggcctcag gctacacctt cacaagctat tacatccact gggtgcgcca agctcccggt    900
cagggcttgg agtggatcgg gtgcatttac ccagggaacg tcaacacaaa ctacaacgag    960
aagttcaagg atcgggcaac cctgaccgtg gacacatcca tctctaccgc ctacatggag    1020
ctgtcacgcc tgcgctctga tgacaccgca gtgtacttct gtaccaggag tcactacggc    1080
ctggactgga actttgatgt ctggggccag ggaaccaccg tgacggtgtc cagtgtggag    1140
ggcggtagtg gcggctctgg tgggtccgga ggctcaggcg gcgtgatgga tgacattcag    1200
atgacccaga gtccctcctc cctctccgct tccgtcggag accgcgtgac catcacttgt    1260
cacgcctcac agaatatcta cgtgtggctg aactggtacc aacagaagcc cggcaaggcc    1320
cccaagctgc ttatctataa agcgtccaac ctccacacgg gagtcccttc ccgcttctcc    1380
ggatccggca gtgggacgga cttcacactc acaatctcgt cgctgcagcc agaggacttt    1440
gcgacgtact actgccagca gggccagacc tacccatata ctttcggcgg cgggaccaag    1500
gtggagat                                                             1508
```

<210> SEQ ID NO 131
<211> LENGTH: 500
<212> TYPE: PRT
<213> ORGANISM: Artificial Sequence
<220> FEATURE:
<223> OTHER INFORMATION: 10A5-1412 PD-L1/CD28 bispecific antibody

<400> SEQUENCE: 131

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
             20                  25                  30

Ser Val Gly Asp Arg Val Thr Ile Thr Cys Arg Ala Ser Gln Gly Ile
         35                  40                  45

Ser Ser Trp Leu Ala Trp Tyr Gln Gln Lys Pro Glu Lys Ala Pro Lys
     50                  55                  60

Ser Leu Ile Tyr Ala Ala Ser Ser Leu Gln Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Tyr Asn Ser
            100                 105                 110

Tyr Pro Tyr Thr Phe Gly Gln Gly Thr Lys Leu Glu Ile Lys Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Asp Val His Trp Val Arg Gln Ala Pro Gly Gln Arg
                165                 170                 175

Leu Glu Trp Met Gly Trp Leu His Ala Asp Thr Gly Ile Thr Lys Phe
            180                 185                 190
```

Ser Gln Lys Phe Gln Gly Arg Val Thr Ile Thr Arg Asp Thr Ser Ala
              195                 200                 205

Ser Thr Ala Tyr Met Glu Leu Ser Ser Leu Arg Ser Glu Asp Thr Ala
         210                 215                 220

Val Tyr Tyr Cys Ala Arg Glu Arg Ile Gln Leu Trp Phe Asp Tyr Trp
225                 230                 235                 240

Gly Gln Gly Thr Leu Val Thr Val Ser Gly Gly Gly Ser Gln
             245                 250                 255

Val Gln Leu Val Gln Ser Gly Ala Glu Val Lys Lys Pro Gly Ala Ser
             260                 265                 270

Val Lys Val Ser Cys Lys Ala Ser Gly Tyr Thr Phe Thr Ser Tyr Tyr
         275                 280                 285

Ile His Trp Val Arg Gln Ala Pro Gly Gln Gly Leu Glu Trp Ile Gly
     290                 295                 300

Cys Ile Tyr Pro Gly Asn Val Asn Thr Asn Tyr Asn Glu Lys Phe Lys
305                 310                 315                 320

Asp Arg Ala Thr Leu Thr Val Asp Thr Ser Ile Ser Thr Ala Tyr Met
                 325                 330                 335

Glu Leu Ser Arg Leu Arg Ser Asp Asp Thr Ala Val Tyr Phe Cys Thr
             340                 345                 350

Arg Ser His Tyr Gly Leu Asp Trp Asn Phe Asp Val Trp Gly Gln Gly
         355                 360                 365

Thr Thr Val Thr Val Ser Ser Val Glu Gly Gly Ser Gly Gly Ser Gly
     370                 375                 380

Gly Ser Gly Gly Ser Gly Gly Val Met Asp Asp Ile Gln Met Thr Gln
385                 390                 395                 400

Ser Pro Ser Ser Leu Ser Ala Ser Val Gly Asp Arg Val Thr Ile Thr
                 405                 410                 415

Cys His Ala Ser Gln Asn Ile Tyr Val Trp Leu Asn Trp Tyr Gln Gln
             420                 425                 430

Lys Pro Gly Lys Ala Pro Lys Leu Leu Ile Tyr Lys Ala Ser Asn Leu
         435                 440                 445

His Thr Gly Val Pro Ser Arg Phe Ser Gly Ser Gly Ser Gly Thr Asp
     450                 455                 460

Phe Thr Leu Thr Ile Ser Ser Leu Gln Pro Glu Asp Phe Ala Thr Tyr
465                 470                 475                 480

Tyr Cys Gln Gln Gly Gln Thr Tyr Pro Tyr Thr Phe Gly Gly Gly Thr
                 485                 490                 495

Lys Val Glu Ile
         500

<210> SEQ ID NO 132
<211> LENGTH: 1499
<212> TYPE: DNA
<213> ORGANISM: Artificial Sequence
<220> FEATURE:
<223> OTHER INFORMATION: 10A5-1412 PD-L1/CD28 bispecific antibody

<400> SEQUENCE: 132
atgggctgga gttgcatcat tctcttcctc gtggcgaccg caacaggggt gcactccgac    60
atccagatga cccagtcccc gagttccctg tctgcttccg tgggagatcg cgtgactatc   120
acctgccggg cttcccaggg catctcttcc tggctggcgt ggtaccagca gaaaccagaa   180
aaggctccta agtccctgat ctacgcagct tcgtccctcc aatccggcgt ccctctcgc   240

```
ttctccggct ccggatccgg caccgacttc acgctgacaa tctcgagttt gcagcccgag    300
gacttcgcca cctactactg ccagcagtac aactcctacc cttacacctt cggccagggc    360
acaaagctcg aaatcaagtc ggggggggc gggtcgcagg tccagctggt gcagtccggc     420
```

Pro Gly Ser Ser Val Lys Val Ser Cys Lys Thr Ser Gly Asp Thr Phe
145                 150                 155                 160

Ser Ser Tyr Ala Ile Ser Trp Val Arg Gln Ala Pro Gly Gln Gly Leu
            165                 170                 175

Glu Trp Met Gly Gly Ile Ile Pro Ile Phe Gly Arg Ala His Tyr Ala
        180                 185                 190

Gln Lys Phe Gln Gly Arg Val Thr Ile Thr Ala Asp Glu Ser Thr Ser
    195                 200                 205

Thr Ala Tyr Met Glu Leu Ser Ser Leu Arg Ser Glu Asp Thr Ala Val
210                 215                 220

Tyr Phe Cys Ala Arg Lys Phe His Phe Val Ser Gly Ser Pro Phe Gly
225                 230                 235                 240

Met Asp Val Trp Gly Gln Gly Thr Val Thr Val Ser Ser Gly Gly Ser
            245                 250                 255

Ser Gly Gly Gly Gly Ser Gln Val Gln Leu Val Gln Ser Gly Ala Glu
        260                 265                 270

Val Lys Lys Pro Gly Ala Ser Val Lys Val Ser Cys Lys Ala Ser Gly
    275                 280                 285

Tyr Thr Phe Thr Ser Tyr Tyr Ile His Trp Val Arg Gln Ala Pro Gly
290                 295                 300

Gln Gly Leu Glu Trp Ile Gly Cys Ile Tyr Pro Gly Asn Val Asn Thr
305                 310                 315                 320

Asn Tyr Asn Glu Lys Phe Lys Asp Arg Ala Thr Leu Thr Val Asp Thr
            325                 330                 335

Ser Ile Ser Thr Ala Tyr Met Glu Leu Ser Arg Leu Arg Ser Asp Asp
        340                 345                 350

Thr Ala Val Tyr Phe Cys Thr Arg Ser His Tyr Gly Leu Asp Trp Asn
    355                 360                 365

Phe Asp Val Trp Gly Gln Gly Thr Val Thr Val Ser Ser Val Glu
370                 375                 380

Gly Gly Ser Gly Gly Ser Gly Gly Ser Gly Gly Ser Gly Gly Val Met
385                 390                 395                 400

Asp Asp Ile Gln Met Thr Gln Ser Pro Ser Ser Leu Ser Ala Ser Val
            405                 410                 415

Gly Asp Arg Val Thr Ile Thr Cys His Ala Ser Gln Asn Ile Tyr Val
        420                 425                 430

Trp Leu Asn Trp Tyr Gln Gln Lys Pro Gly Lys Ala Pro Lys Leu Leu
    435                 440                 445

Ile Tyr Lys Ala Ser Asn Leu His Thr Gly Val Pro Ser Arg Phe Ser
450                 455                 460

Gly Ser Gly Ser Gly Thr Asp Phe Thr Leu Thr Ile Ser Ser Leu Gln
465                 470                 475                 480

Pro Glu Asp Phe Ala Thr Tyr Tyr Cys Gln Gln Gly Gln Thr Tyr Pro
            485                 490                 495

Tyr Thr Phe Gly Gly Gly Thr Lys Val Glu Ile
        500                 505

<210> SEQ ID NO 134
<211> LENGTH: 1520
<212> TYPE: DNA
<213> ORGANISM: Artificial Sequence
<220> FEATURE:
<223> OTHER INFORMATION: 1B12-1412 PD-L1/CD28 bispecific antibody

<400> SEQUENCE: 134

-continued

```
atgggctgga gttgcatcat cctctttcta gtcgccacgg ccaccggcgt acactcagag    60
atcgtgctga cacagtcgcc tgcgacgctg tcgctcagtc caggggagcg cgctactctc   120
tcctgccgcg cgtcgcagag cgtgtcgtcc tacttggcct ggtaccagca gaagcctggc   180
caggctccgc gcctgctgat atacgacgcc tcgaacagag ccacgggcat ccccgcccgt   240
tttagtggct ccgggtcggg gaccgacttc actctgacaa tctcatccct cgagcccgag   300
gatttcgccg tgtactactg tcagcagcgc tcgaattggc caaccttcgg caggggacg    360 aaagttgaga tcaaaagcgg cggcgggggc agccaggtcc agctcgtcca gtctggcgcc   420
gaggtcaaaa agccgggctc ttcggtcaag gtcctgca agacttccgg cgacaccttc    480
tcctcctatg ctatctcctg ggtgcggcag gccccggggc agggcctgga gtggatggga   540
ggcatcatcc caatctttgg gagggcccac tacgcccaga gttccaggg acgcgtgaca   600 atcaccgcag acgagtccac atccactgcc tacatggagt tgtcctcgct ccggtcggag   660
gatactgccg tgtacttctg cgcccggaag ttccacttcg tgtcaggctc ccccttcggg   720
atggacgtgt ggggacaagg aaccgtgacg gtgtcgtcgg ggggctcgtc gggggggcggg   780 gggagtcagg tgcagctggt gcagtccgga gccgaggtaa agaagccagg cgcttccgtc   840
aaggtgtcat gcaaggcctc aggctacacc ttcacaagct attacatcca ctgggtgcgc   900
caagctcccg gtcagggctt ggagtggatc gggtgcattt acccagggaa cgtcaacaca   960
aactacaacg agaagttcaa ggatcgggca accctgaccg tggacacatc catctctacc  1020
gcctacatgg agctgtcacg cctgcgctct gatgacaccg cagtgtactt ctgtaccagg  1080
agtcactacg gcctggactg gaactttgat gtctggggcc agggaaccac cgtgacggtg  1140
tccagtgtgg agggcggtag tggcggctct ggtgggtccg gaggctcagg cggcgtgatg  1200
gatgacattc agatgaccca gagtccctcc tccctctccg cttccgtcgg agaccgcgtg  1260
accatcactt gtcacgcctc acagaatatc tacgtgtggc tgaactggta ccaacagaag  1320
cccggcaagg cccccaagct gcttatctat aaagcgtcca acctccacac gggagtccct  1380
tcccgcttct ccggatccgg cagtgggacg gacttcacac tcacaatctc gtcgctgcag  1440
ccagaggact tgcgacgta ctactgccag cagggccaga cctacccata ctctttcggc   1500
ggcgggacca aggtggagat                                               1520
```

<210> SEQ ID NO 135
<211> LENGTH: 504
<212> TYPE: PRT
<213> ORGANISM: Artificial Sequence
<220> FEATURE:
<223> OTHER INFORMATION: TGFBR-1-1412 TGFBRII/CD28 bispecific antibody

<400> SEQUENCE: 135

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Arg Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95
```

```
Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Ser Gly
            115                 120                 125

Gly Gly Gly Ser Gln Leu Gln Val Gln Glu Ser Gly Pro Gly Leu Val
            130                 135                 140

Lys Pro Ser Glu Thr Leu Ser Leu Thr Cys Thr Val Ser Gly Gly Ser
145                 150                 155                 160

Ile Ser Asn Ser Tyr Phe Ser Trp Gly Trp Ile Arg Gln Pro Pro Gly
                165                 170                 175

Lys Gly Leu Glu Trp Ile Gly Ser Phe Tyr Tyr Gly Glu Lys Thr Tyr
            180                 185                 190

Tyr Asn Pro Ser Leu Lys Ser Arg Ala Thr Ile Ser Ile Asp Thr Ser
            195                 200                 205

Lys Ser Gln Phe Ser Leu Lys Leu Ser Ser Val Thr Ala Ala Asp Thr
            210                 215                 220

Ala Val Tyr Tyr Cys Pro Arg Gly Pro Thr Met Ile Arg Gly Val Ile
225                 230                 235                 240

Asp Ser Trp Gly Gln Gly Thr Leu Val Thr Val Ser Ser Gly Gly Gly
            245                 250                 255

Gly Ser Gln Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
            275                 280                 285

Ser Tyr Tyr Ile His Trp Val Arg Gln Ala Pro Gly Gln Gly Leu Glu
            290                 295                 300

Trp Ile Gly Cys Ile Tyr Pro Gly Asn Val Asn Thr Asn Tyr Asn Glu
305                 310                 315                 320

Lys Phe Lys Asp Arg Ala Thr Leu Thr Val Asp Thr Ser Ile Ser Thr
            325                 330                 335

Ala Tyr Met Glu Leu Ser Arg Leu Arg Ser Asp Asp Thr Ala Val Tyr
            340                 345                 350

Phe Cys Thr Arg Ser His Tyr Gly Leu Asp Trp Asn Phe Asp Val Trp
            355                 360                 365

Gly Gln Gly Thr Thr Val Thr Val Ser Ser Val Glu Gly Gly Ser Gly
            370                 375                 380

Gly Ser Gly Gly Ser Gly Gly Ser Gly Gly Val Met Asp Asp Ile Gln
385                 390                 395                 400

Met Thr Gln Ser Pro Ser Ser Leu Ser Ala Ser Val Gly Asp Arg Val
            405                 410                 415

Thr Ile Thr Cys His Ala Ser Gln Asn Ile Tyr Val Trp Leu Asn Trp
            420                 425                 430

Tyr Gln Gln Lys Pro Gly Lys Ala Pro Lys Leu Leu Ile Tyr Lys Ala
            435                 440                 445

Ser Asn Leu His Thr Gly Val Pro Ser Arg Phe Ser Gly Ser Gly Ser
            450                 455                 460

Gly Thr Asp Phe Thr Leu Thr Ile Ser Ser Leu Gln Pro Glu Asp Phe
465                 470                 475                 480

Ala Thr Tyr Tyr Cys Gln Gln Gly Gln Thr Tyr Pro Tyr Thr Phe Gly
            485                 490                 495

Gly Gly Thr Lys Val Glu Ile Lys
            500
```

<210> SEQ ID NO 136
<211> LENGTH: 1512
<212> TYPE: DNA
<213> ORGANISM: Artificial Sequence
<220> FEATURE:
<223> OTHER INFORMATION: TGFBR-1-1412 TGFBRII/CD28 bispecific antibody

<400> SEQUENCE: 136

```
atgggttggt cctgcatcat cctgtttctc gtggccaccg ccaccggcgt gcactccgaa      60
attgtgttga cacagtctcc agccaccctg tctttgtctc aggggaaag agccaccctc     120
tcctgcaggg ccagtcagag tgttcgcagc tacttagcct ggtaccaaca gaaacctggc    180
caggctccca ggctcctcat ctatgatgca tccaacaggg ccactggcat cccagccagg    240
ttcagtggca gtgggtctgg gacagacttc actctcacca tcagcagcct agagcctgaa    300
gattttgcag tttattactg tcagcagcgt agcaactggc ctccgacgtt cggccaaggg    360
accaaggtgg aaatcaaaag tggagggggc ggttcacagc tgcaggtgca ggagtcgggc    420
ccaggactgg tgaagccttc ggagaccctg tccctcacct gcactgtctc tggtggctcc    480
atcagcaaca gttatttctc ctggggctgg atccgccagc ccccagggaa gggactggag    540
tggattggga gtttctatta tggtgaaaaa acctactaca acccgtccct caagagccga    600
gccaccatat ccattgacac gtccaagagc cagttctccc tgaagctgag ctctgtgacc    660
gccgcagaca cggctgtgta ttactgtccg agagggccta ctatgattcg ggagttata    720
gactcctggg gccagggaac cctggtgacg gtgtcgtcgg ggggcggggg gagtcaggtg    780
cagctggtgc agtccggagc cgaggtaaag aagccaggcg cttccgtcaa ggtgtcatgc    840
aaggcctcag gctacacctt cacaagctat acatccact gggtgcgcca agctcccggt    900
cagggcttgg agtggatcgg gtgcatttac ccagggaacg tcaacacaaa ctacaacgag    960
aagttcaagg atcgggcaac cctgaccgtg gacacatcca tctctaccgc ctacatggag   1020
ctgtcacgcc tgcgctctga tgacaccgca gtgtacttct gtaccaggag tcactacggc   1080
ctggactgga actttgatgt ctggggccag ggaaccaccg tgacggtgtc cagtgtggag   1140
ggcggtagtg gcgggctctgg tgggtccgga ggctcaggcg gcgtgatgga tgacattcag   1200
atgacccaga gtccctcctc cctctccgct tccgtcggag accgcgtgac catcacttgt   1260
cacgcctcac agaatatcta cgtgtggctg aactggtacc aacagaagcc cggcaaggcc   1320
cccaagctgc ttatctataa agcgtccaac ctccacacgg agtcccttc ccgcttctcc   1380
ggatccggca gtgggacgga cttcacactc acaatctcgt cgctgcagcc agaggacttt   1440
gcgacgtact actgccagca gggccagacc tacccatata ctttcggcgg cgggaccaag   1500
gtggagatta ag                                                        1512
```

<210> SEQ ID NO 137
<211> LENGTH: 504
<212> TYPE: PRT
<213> ORGANISM: Artificial Sequence
<220> FEATURE:
<223> OTHER INFORMATION: TGFBR-3-1412 TGFBRII/CD28 bispecific antibody

<400> SEQUENCE: 137

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
```

```
            35                  40                  45
Arg Ser Phe Leu Ala Trp Tyr Gln Gln Lys Pro Gly Gln Ala Pro Arg
 50                  55                  60

Leu Leu Ile Tyr Asp Ala Ser Asn Arg Ala Thr Gly Ile Pro Ala Arg
 65                  70                  75                  80

Phe Ser Gly Ser Gly Ser Gly Thr Asp Phe Thr Leu Thr Ile Ser Ser
                 85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Ser Gly
        115                 120                 125

Gly Gly Gly Ser Gln Leu Gln Leu Gln Glu Ser Gly Pro Gly Leu Val
    130                 135                 140

Lys Pro Ser Glu Thr Leu Ser Leu Thr Cys Thr Val Ser Gly Gly Ser
145                 150                 155                 160

Ile Ser Ser Ser Tyr Ser Trp Gly Trp Ile Arg Gln Pro Pro Gly
                165                 170                 175

Lys Gly Leu Glu Trp Ile Gly Ser Phe Tyr Tyr Ser Gly Ile Thr Tyr
            180                 185                 190

Tyr Ser Pro Ser Leu Lys Ser Arg Ile Ile Ile Ser Glu Asp Thr Ser
        195                 200                 205

Lys Asn Gln Phe Ser Leu Lys Leu Ser Ser Val Thr Ala Ala Asp Thr
210                 215                 220

Ala Val Tyr Tyr Cys Ala Ser Gly Phe Thr Met Ile Arg Gly Ala Leu
225                 230                 235                 240

Asp Tyr Trp Gly Gln Gly Thr Leu Val Thr Val Ser Ser Gly Gly Gly
                245                 250                 255

Gly Ser Gln Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
        275                 280                 285

Ser Tyr Tyr Ile His Trp Val Arg Gln Ala Pro Gly Gln Gly Leu Glu
    290                 295                 300

Trp Ile Gly Cys Ile Tyr Pro Gly Asn Val Asn Thr Asn Tyr Asn Glu
305                 310                 315                 320

Lys Phe Lys Asp Arg Ala Thr Leu Thr Val Asp Thr Ser Ile Ser Thr
                325                 330                 335

Ala Tyr Met Glu Leu Ser Arg Leu Arg Ser Asp Asp Thr Ala Val Tyr
            340                 345                 350

Phe Cys Thr Arg Ser His Tyr Gly Leu Asp Trp Asn Phe Asp Val Trp
        355                 360                 365

Gly Gln Gly Thr Thr Val Thr Val Ser Ser Val Glu Gly Gly Ser Gly
    370                 375                 380

Gly Ser Gly Gly Ser Gly Gly Ser Gly Gly Val Met Asp Asp Ile Gln
385                 390                 395                 400

Met Thr Gln Ser Pro Ser Ser Leu Ser Ala Ser Val Gly Asp Arg Val
                405                 410                 415

Thr Ile Thr Cys His Ala Ser Gln Asn Ile Tyr Val Trp Leu Asn Trp
            420                 425                 430

Tyr Gln Gln Lys Pro Gly Lys Ala Pro Lys Leu Leu Ile Tyr Lys Ala
        435                 440                 445

Ser Asn Leu His Thr Gly Val Pro Ser Arg Phe Ser Gly Ser Gly Ser
    450                 455                 460
```

Gly Thr Asp Phe Thr Leu Thr Ile Ser Ser Leu Gln Pro Glu Asp Phe
465                 470                 475                 480

Ala Thr Tyr Tyr Cys Gln Gln Gly Gln Thr Tyr Pro Tyr Thr Phe Gly
            485                 490                 495

Gly Gly Thr Lys Val Glu Ile Lys
            500

<210> SEQ ID NO 138
<211> LENGTH: 1512
<212> TYPE: DNA
<213> ORGANISM: Artificial Sequence
<220> FEATURE:
<223> OTHER INFORMATION: TGFBR-3-1412 TGFBRII/CD28 bispecific antibody

<400> SEQUENCE: 138

```
atgggttggt cctgcatcat cctgtttctc gtggccaccg ccaccggcgt gcactccgaa      60
attgtgttga cacagtctcc agccaccctg tctttgtctc caggggaaag agccacccct     120
tcctgcaggg ccagtcagag tgttagaagt ttcttagcct ggtaccaaca gaaacctggc     180
caggctccca ggctcctcat ctatgatgca tccaacaggg ccactggcat cccagccagg     240
ttcagtggca gtgggtctgg gacagacttc actctcacca tcagcagcct agagcctgaa     300
gattttgcag tttattactg tcagcagcgt agcaactggc ctccgacgtt cggccaaggg     360
accaaggtgg aaatcaaaag tggaggggc ggttcacagc tacagctgca ggagtcgggc      420
ccaggactgg tgaagccttc ggagacccta tccctcacct gcactgtctc tggtggctcc     480
atcagcagta gtagttactc ctgggctgg atccgccagc ccccagggaa gggcctggag      540
tggattggga gtttctatta cagtgggatc acctactaca gcccgtccct caagagtcga     600
attatcatat ccgaagacac gtccaagaac cagttctccc tgaagctgag ttctgtgacc     660
gccgcagaca cggctgtgta ttactgtgcg agcgggttta ctatgattcg gggagccctt     720
gactactggg gccagggaac cctggtgacg gtgtcgtcgg ggggcggggg gagtcaggtg     780
cagctggtgc agtccggagc cgaggtaaag aagccaggcg cttccgtcaa ggtgtcatgc     840
aaggcctcag gctacacctt cacaagctat tacatccact gggtgcgcca agctcccggt     900
cagggcttgg agtggatcgg gtgcatttac ccagggaacg tcaacacaaa ctacaacgag     960
aagttcaagg gtcgggcaac cctgaccgtg gacacatcca tctctaccgc ctacatggag    1020
ctgtcacgcc tgcgctctga tgacaccgca gtgtacttct gtaccaggag tcactacggc    1080
ctggactgga ctttgatgt ctggggccag ggaaccaccg tgacggtgtc cagtgtggag     1140
ggcggtagtg gcggctctgg tgggtccgga ggctcaggcg gcgtgatgga tgacattcag    1200
atgacccaga gtccctcctc cctctccgct tccgtcggag accgcgtgac catcacttgt    1260
cacgcctcac agaatatcta cgtgtggctg aactggtacc aacagaagcc cggcaaggcc    1320
cccaagctgc ttatctataa agcgtccaac ctccacacgg gagtcccttc ccgcttctcc    1380
ggatccggca gtgggacgga cttcacactc acaatctcgt cgctgcagcc agaggacttt    1440
gcgacgtact actgccagca gggccagacc tacccatata ctttcggcgg cgggaccaag    1500
gtggagatta ag                                                        1512
```

<210> SEQ ID NO 139
<211> LENGTH: 18
<212> TYPE: PRT
<213> ORGANISM: Artificial Sequence
<220> FEATURE:
<223> OTHER INFORMATION: T2A

```
<400> SEQUENCE: 139

Glu Gly Arg Gly Ser Leu Leu Thr Cys Gly Asp Val Glu Glu Asn Pro
1               5                   10                  15

Gly Pro

<210> SEQ ID NO 140
<211> LENGTH: 54
<212> TYPE: DNA
<213> ORGANISM: Artificial Sequence
<220> FEATURE:
<223> OTHER INFORMATION: T2A

<400> SEQUENCE: 140
gagggcagag gaagtcttct aacatgcggt gacgtggagg agaatcccgg ccct        54

<210> SEQ ID NO 141
<211> LENGTH: 7
<212> TYPE: PRT
<213> ORGANISM: Artificial Sequence
<220> FEATURE:
<223> OTHER INFORMATION: spacer

<400> SEQUENCE: 141

Ser Gly Arg Ser Gly Gly Gly
1               5

<210> SEQ ID NO 142
<211> LENGTH: 21
<212> TYPE: DNA
<213> ORGANISM: Artificial Sequence
<220> FEATURE:
<223> OTHER INFORMATION: spacer

<400> SEQUENCE: 142
tccggaagat ctggcggcgg a                                           21

<210> SEQ ID NO 143
<211> LENGTH: 22
<212> TYPE: PRT
<213> ORGANISM: Artificial Sequence
<220> FEATURE:
<223> OTHER INFORMATION: F2A

<400> SEQUENCE: 143

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 144
<211> LENGTH: 66
<212> TYPE: DNA
<213> ORGANISM: Artificial Sequence
<220> FEATURE:
<223> OTHER INFORMATION: F2A

<400> SEQUENCE: 144
gtgaaacaga ctttgaattt tgaccttctc aagttggcgg agacgtgga gtccaaccca   60 gggccg                                                            66

<210> SEQ ID NO 145
<211> LENGTH: 4
<212> TYPE: PRT
```

```
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 145

Arg Xaa Lys Arg
1

<210> SEQ ID NO 146
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 146

Arg Xaa Arg Arg
1

<210> SEQ ID NO 147
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 147

Arg Xaa Xaa Arg
1

<210> SEQ ID NO 148
<211> LENGTH: 4
<212> TYPE: PRT
<213> ORGANISM: Artificial Sequence
<220> FEATURE:
<223> OTHER INFORMATION: furin cleavage site

<400> SEQUENCE: 148

Arg Gln Lys Arg
1

<210> SEQ ID NO 149
<211> LENGTH: 5
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 149

Xaa Arg Xaa Xaa Arg
```

<210> SEQ ID NO 150
<211> LENGTH: 96
<212> TYPE: DNA
<213> ORGANISM: Artificial Sequence
<220> FEATURE:
<223> OTHER INFORMATION: F-GS2-T2A linker

<400> SEQUENCE: 150
cgtgcgaaga ggggcggcgg gggctccggc gggggaggca gtgagggccg cggctccctg    60
ctgacctgcg agatgtaga agagaaccca ggcccc    96

<210> SEQ ID NO 151
<211> LENGTH: 32
<212> TYPE: PRT
<213> ORGANISM: Artificial Sequence
<220> FEATURE:
<223> OTHER INFORMATION: F-GS2-T2A linker

<400> SEQUENCE: 151

Arg Ala Lys Arg Gly Gly Gly Gly Ser Gly Gly Gly Gly Ser Glu Gly
1               5                   10                  15

Arg Gly Ser Leu Leu Thr Cys Gly Asp Val Glu Glu Asn Pro Gly Pro
            20                  25                  30

<210> SEQ ID NO 152
<211> LENGTH: 2142
<212> TYPE: DNA
<213> ORGANISM: Artificial Sequence
<220> FEATURE:
<223> OTHER INFORMATION: TGFbRDN-PSMA-CAR

<400> SEQUENCE: 152
atgggtcggg ggctgctcag gggcctgtgg ccgctgcaca tcgtcctgtg gacgcgtatc    60
gccagcacga tcccaccgca cgttcagaag tcggttaata cgacatgat agtcactgac   120 aacaacggtg cagtcaagtt tccacaactg tgtaattttt gtgatgtgag attttccacc   180
tgtgacaacc agaaatcctg catgagcaac tgcagcatca cctccatctg tgagaagcca   240
caggaagtct gtgtggctgt atggagaaag aatgacgaga acataacact agagacagtt   300
tgccatgacc ccaagctccc ctaccatgac tttattctgg aagatgctgc ttctccaaag   360
tgcattatga aggaaaaaaa aaagcctggt gagactttct catgtgttc ctgtagctct   420 gatgagtgca atgacaacat catcttctca gaagaatata acaccagcaa tcctgacttg   480
ttgctagtca tatttcaagt gacaggcatc agcctcctgc caccactggg agttgccata   540
tctgtcatca tcatcttcta ctgctaccgc gttaaccggc agcagaagct gagttcatcc   600
ggaagatctg gcggcggaga gggcagagga agtcttctaa catgcggtga cgtggaggag   660
aatcccggcc ctagagccac catggccctg cctgtgacag ccctgctgct gcctctggct   720
ctgctgctgc acgccgccag acctggatct gacattgtga tgacccagtc tcacaaattc   780
atgtccacat cagtaggaga cagggtcagc atcatctgta aggccagtca agatgtgggt   840
actgctgtag actggtatca acagaaacca ggacaatctc ctaaactact gatttattgg   900
gcatccactc ggcacactgg agtccctgat cgcttcacag gcagtggatc tgggacagac   960
ttcactctca ccattactaa cgttcagtct gaagacttgg cagattattt ctgtcagcaa  1020
tataacagct atcctctcac gttcggtgct gggaccatgc tggacctgaa aggaggcgga  1080
ggatctggcg gcggaggaag ttctggcgga ggcagcgagg tgcagctgca gcagagcgga  1140

```
cccgagctcg tgaagcctgg aacaagcgtg cggatcagct gcaagaccag cggctacacc    1200
ttcaccgagt acaccatcca ctgggtcaag cagtcccacg gcaagagcct ggagtggatc    1260
ggcaatatca accccaacaa cggcggcacc acctacaacc agaagttcga ggacaaggcc    1320
accctgaccg tggacaagag cagcagcacc gcctacatgg aactgcggag cctgaccagc    1380
gaggacagcg ccgtgtacta ttgtgccgcc ggttggaact tcgactactg gggccagggc    1440
acaaccctga cagtgtctag cgctagctcc ggaaccacga cgccagcgcc gcgaccacca    1500
acaccggcgc caccatcgc gtcgcagccc ctgtccctgc gcccagaggc gtgccggcca    1560
gcggcggggg gcgcagtgca cacgagggg ctggacttcg cctgtgatat ctacatctgg    1620
gcgcccttgg ccgggacttg tggggtcctt ctcctgtcac tggttatcac cctttactgc    1680
aaacggggca gaaagaaact cctgtatata ttcaaacaac catttatgag accagtacaa    1740
actactcaag aggaagacgg ctgtagctgc cgatttccag aagaagaaga aggaggatgt    1800
gaactgagag tgaagttcag caggagcgca gacgcccccg cgtacaagca gggccagaac    1860
cagctctata cgagctcaa tctaggacga agagaggagt acgacgtttt ggacaagaga    1920
cgtggccggg accctgagat gggggaaag ccgagaagga agaaccctca ggaaggcctg    1980
tacaacgaac tgcagaaaga taagatggcg gaggcctaca gtgagattgg gatgaaaggc    2040
gagcgccgga ggggcaaggg gcacgacggc ctttaccagg gtctcagtac agccaccaag    2100
gacacctacg acgcccttca catgcaggcc ctgccccctc gc                      2142

<210> SEQ ID NO 153
<211> LENGTH: 2151
<212> TYPE: DNA
<213> ORGANISM: Artificial Sequence
<220> FEATURE:
<223> OTHER INFORMATION: TGFbRDN-1C3PSMA-CAR

<400> SEQUENCE: 153
atgggtcggg ggctgctcag gggcctgtgg ccgctgcaca tcgtcctgtg gacgcgtatc     60
gccagcacga tcccaccgca cgttcagaag tcggttaata cgacatgat agtcactgac    120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga cataacact agagacagtt    300 tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgacttg    480
ttgctagtca tatttcaagt gacaggcatc agcctcctgc caccactggg agttgccata    540
tctgtcatca tcatcttcta ctgctaccgc gttaaccggc agcagaagct gagttcatcc    600
ggaagatctg gcggcggaga gggcagagga agtcttctaa catgcggtga cgtggaggag    660
aatcccggcc ctagagccac catggcctta ccagtgaccg ccttgctcct gccgctggcc    720
ttgctgctcc acgccgccag gccgcaggtg caactggtgg agtctggggg aggcgtggtc    780
cagcctggga ggtccctgag actctcctgt gcagcctctg gattcacctt cagtagctat    840
gctatgcact gggtccgcca ggctccaggc aaggggctgg agtgggtggc agttatatca    900
tatgatggaa acaataaata ctacgcagac tccgtgaagg gccgattcac catctccaga    960
gacaattcca agaacacgct gtatctgcaa atgaacagct gagagctga ggacacggct   1020
```

```
gtgtattact gtgcgagagc cgtccnctgg ggatcgaggt actactacta cggtatggac      1080
gtctggggcc aagggaccac ggtcaccgtc tcctcaggtg gcggtggctc gggcggtggt      1140
gggtcgggtg gcggcggatc tgccatccag ttgacccagt ctccatcctc cctgtctgca      1200
tctgtaggag acagagtcac catcacttgc cgggcaagtc agggcattag cagtgcttta      1260
gcctggtatc agcagaaatc agggaaagct cctaagctcc tgatctttga tgcctccagt      1320
ttggaaagtg gggtcccatc aaggttcagc ggcagtggat ctgggacaga tttcactctc      1380
accatcagca gcctgcagcc tgaagatttt gcaacttatt actgtcaaca gtttaacagt      1440
tatcctctca ctttcggcgg agggaccaag gtggagatca aaaccacgac gccagcgccg      1500
cgaccaccaa caccggcgcc caccatcgcg tcgcagcccc tgtccctgcg cccagaggcg      1560
tgccggccag cggcggggg cgcagtgcac acgagggggc tggacttcgc ctgtgatatc      1620
tacatctggg cgcccttggc cgggacttgt ggggtccttc tcctgtcact ggttatcacc      1680
ctttactgca aacggggcag aaagaaactc ctgtatatat tcaaacaacc atttatgaga      1740
ccagtacaaa ctactcaaga ggaagacggc tgtagctgcc gatttccaga agaagaagaa      1800
ggaggatgtg aactgagagt gaagttcagc aggagcgcag acgcccccgc gtacaagcag      1860
ggccagaacc agctctataa cgagctcaat ctaggacgaa gagaggagta cgacgttttg      1920
gacaagagac gtggccggga ccctgagatg ggggaaagc cgagaaggaa gaaccctcag      1980
gaaggcctgt acaacgaact gcagaaagat aagatggcgg aggcctacag tgagattggg      2040
atgaaaggcg agcgccggag gggcaagggg cacgacggcc tttaccaggg tctcagtaca      2100
gccaccaagg acacctacga cgcccttcac atgcaggccc tgccccctcg c            2151

<210> SEQ ID NO 154
<211> LENGTH: 2136
<212> TYPE: DNA
<213> ORGANISM: Artificial Sequence
<220> FEATURE:
<223> OTHER INFORMATION: TGFbRDN-2A10PSMA-CAR

<400> SEQUENCE: 154
atgggtcggg ggctgctcag gggcctgtgg ccgctgcaca tcgtcctgtg gacgcgtatc        60
gccagcacga tcccaccgca cgttcagaag tcggttaata cgacatgat agtcactgac       120 aacaacggtg cagtcaagtt tccacaactg tgtaaatttt gtgatgtgag atttccacc       180 tgtgacaacc agaaatcctg catgagcaac tgcagcatca cctccatctg tgagaagcca       240
caggaagtct gtgtggctgt atggagaaag aatgacgaga acataacact agagacagtt       300
tgccatgacc ccaagctccc ctaccatgac tttattctgg aagatgctgc ttctccaaag       360
tgcattatga aggaaaaaaa aaagcctggt gagactttct tcatgtgttc ctgtagctct       420
gatgagtgca atgacaacat catcttctca gaagaatata caccagcaa tcctgacttg       480 ttgctagtca tatttcaagt gacaggcatc agcctcctgc caccactggg agttgccata       540
tctgtcatca tcatcttcta ctgctaccgc gttaaccggc agcagaagct gagttcatcc       600
ggaagatctg gcggcggaga gggcagagga agtcttctaa catgcggtga cgtggaggag       660
aatcccggcc ctagagccac catggcctta ccagtgaccg ccttgctcct gccgctggcc       720
ttgctgctcc acgccgccag gccggaggtg cagctggtgc agtctggagc agaggtgaaa       780
aagcccgggg agtctctgaa gatctcctgt aagggttctg gatacagctt taccagtaac       840
tggatcggct gggtgcgcca gatgcccggg aaaggcctgg agtggatggg gatcatctat       900
cctggtgact ctgataccag atacagcccg tccttccaag gccaggtcac catctcagcc       960
```

```
gacaagtcca tcagcaccgc ctacctgcag tggagcagcc tgaaggcctc ggacaccgcc    1020
atgtattact gtgcgaggca aactggtttc ctctggtcct ccgatctctg gggccgtggc    1080
accctggtca ctgtctcctc aggtggcggt ggctcgggcg tggtgggtc gggtggcggc     1140 ggatctgcca tccagttgac ccagtctcca tcctccctgt ctgcatctgt aggagacaga    1200
gtcaccatca cttgccgggc aagtcaggac attagcagtg ctttagcctg gtatcaacag    1260
aaaccaggga agctcctaa gctcctgatc tatgatgcct ccagtttgga aagtggggtc     1320
ccatcaaggt tcagcggcta tggatctggg acagatttca ctctcaccat caacagcctg    1380
cagcctgaag attttgcaac ttattactgt caacagttta atagttaccc gctcactttc    1440
ggcggaggga ccaaggtgga gatcaaaacc acgacgccag cgccgcgacc accaacaccg    1500
gcgcccacca tcgcgtcgca gcccctgtcc ctgcgcccag aggcgtgccg gccagcggcg    1560
gggggcgcag tgcacacgag ggggctggac ttcgcctgtg atatctacat ctgggcgccc    1620
ttggccggga cttgtggggt ccttctcctg tcactggtta tcacccttta ctgcaaacgg    1680
ggcagaaaga aactcctgta tatattcaaa caaccattta tgagaccagt acaaactact    1740
caagaggaag acggctgtag ctgccgattt ccagaagaag aagaaggagg atgtgaactg    1800
agagtgaagt tcagcaggag cgcagacgcc cccgcgtaca gcagggcca gaaccagctc     1860 tataacgagc tcaatctagg acgaagagag gagtacgacg ttttggacaa gagacgtggc    1920
cgggaccctg agatgggggg aaagccgaga aggaagaacc ctcaggaagg cctgtacaac    1980
gaactgcaga agataagat ggcggaggcc tacagtgaga ttgggatgaa aggcgagcgc      2040
cggaggggca aggggcacga cggcctttac cagggtctca gtacagccac caaggacacc    2100
tacgacgccc ttcacatgca ggccctgccc cctcgc                              2136

<210> SEQ ID NO 155
<211> LENGTH: 2142
<212> TYPE: DNA
<213> ORGANISM: Artificial Sequence
<220> FEATURE:
<223> OTHER INFORMATION: TGFbRDN-2F5PSMA-CAR

<400> SEQUENCE: 155
atgggtcggg ggctgctcag gggcctgtgg ccgctgcaca tcgtcctgtg gacgcgtatc       60
gccagcacga tccaccgcca cgttcagaag tcggttaata cgacatgat agtcactgac      120 aacaacggtg cagtcaagtt tccacaactg tgtaaatttt gtgatgtgag attttccacc     180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgacttg    480
ttgctagtca tatttcaagt gacaggcatc agcctcctgc caccactggg agttgccata    540
tctgtcatca tcatcttcta ctgctaccgc gttaaccggc agcagaagct gagttcatcc    600
ggaagatctg gcggcggaga gggcagagga agtcttctaa catgcggtga cgtggaggag    660
aatcccggcc ctagagccac catggcctta ccagtgaccg ccttgctcct gccgctggcc    720
ttgctgctcc acgccgccag gccggaggtg cagctggtgc agtctggagc agaggtgaaa    780
aagcccgggg agtctctgaa gatctcctgt aagggttctg gatacagttt taccagcaac    840
```

```
tggatcggct gggtgcgcca gatgcccggg aaaggcctgg agtggatggg gatcatctat      900
cctggtgact ctgataccag atacagcccg tccttccaag gccaggtcac catctcagcc      960
gacaagtcca tcagcaccgc ctacctgcag tggaacagcc tgaaggcctc ggacaccgcc     1020
atgtattact gtgcgagaca aactggtttc ctctggtcct tcgatctctg gggccgtggc     1080
accctggtca ctgtctcctc aggtggcggt ggctcgggcg gtggtgggtc gggtggcggc     1140
ggatctgcca tccagttgac ccagtctcca tcctccctgt ctgcatctgt aggagacaga     1200
gtcaccatca cttgccgggc aagtcaggac attagcagtg ctttagcctg gtatcagcag     1260
aaaccgggga agctcctaa gctcctgatc tatgatgcct ccagtttgga aagtggggtc      1320
ccatcaaggt tcagcggcag tggatctggg acagatttca ctctcaccat cagcagcctg     1380
cagcctgaag attttgcaac ttattactgt caacagttta atagttaccc gctcactttc     1440
ggcggaggga ccaaggtgga gatcaaaatc aaaaccacga cgccagcgcc gcgaccacca     1500
acaccggcgc ccaccatcgc gtcgcagccc ctgtccctgc gcccagaggc gtgccggcca     1560
gcggcggggg gcgcagtgca cacgagggg ctggacttcg cctgtgatat ctacatctgg      1620
gcgcccttgg ccgggacttg tggggtcctt ctcctgtcac tggttatcac cctttactgc     1680
aaacggggca gaaagaaact cctgtatata ttcaaacaac catttatgag accagtacaa     1740
actactcaag aggaagacgg ctgtagctgc cgatttccag aagaagaaga aggaggatgt     1800
gaactgagag tgaagttcag caggagcgca gacgcccccg cgtacaagca gggccagaac     1860
cagctctata cgagctcaa tctaggacga agagaggagt acgacgtttt ggacaagaga      1920
cgtggccggg accctgagat ggggggaaag ccgagaagga agaaccctca ggaaggcctg     1980
tacaacgaac tgcagaaaga taagatggcg gaggcctaca gtgagattgg gatgaaaggc     2040
gagcgccgga ggggcaaggg gcacgacggc ctttaccagg gtctcagtac agccaccaag     2100
gacacctacg acgcccttca catgcaggcc ctgccccctc gc                        2142
```

<210> SEQ ID NO 156  
<211> LENGTH: 2145  
<212> TYPE: DNA  
<213> ORGANISM: Artificial Sequence  
<220> FEATURE:  
<223> OTHER INFORMATION: TGFbRDN-2C6PSMA-CAR

<400> SEQUENCE: 156

```
atgggtcggg ggctgctcag gggcctgtgg ccgctgcaca tcgtcctgtg gacgcgtatc       60
gccagcacga tcccaccgca cgttcagaag tcggttaata cgacatgat agtcactgac      120 aacaacggtg cagtcaagtt tccacaactg tgtaaatttt gtgatgtgag attttccacc     180
tgtgacaacc agaaatcctg catgagcaac tgcagcatca cctccatctg tgagaagcca     240
caggaagtct gtgtggctgt atggagaaag aatgacgaga acataacact agagacagtt     300
tgccatgacc ccaagctccc ctaccatgac tttattctgg aagatgctgc ttctccaaag     360
tgcattatga aggaaaaaaa aaagcctggt gagactttct tcatgtgttc ctgtagctct     420
gatgagtgca atgacaacat catcttctca gaagaatata caccagcaa tcctgacttg      480 ttgctagtca tatttcaagt gacaggcatc agcctcctgc caccactggg agttgccata     540
tctgtcatca tcatcttcta ctgctaccgc gttaaccggc agcagaagct gagttcatcc     600
ggaagatctg gcggcggaga gggcagagga agtcttctaa catgcggtga cgtggaggag     660
aatcccggcc ctagagccac catggcctta ccagtgaccg ccttgctcct gccgctggcc     720
ttgctgctcc acgccgccag gccggaggtg cagctggtgc agtctggatc agaggtgaaa     780
```

```
aagcccgggg agtctctgaa gatctcctgt aagggttctg gatacagctt taccaactac    840
tggatcggct gggtgcgcca gatgcccggg aaaggcctgg agtggatggg gatcatctat    900
cctggtgact ctgataccag atacagcccg tccttccaag gccaggtcac catctcagcc    960
gacaagtcca tcagcaccgc ctatctgcag tggagcagcc tgaaggcctc ggacaccgcc   1020
atgtattact gtgcgagtcc cgggtatacc agcagttgga cttcttttga ctactggggc   1080
cagggaaccc tggtcaccgt ctcctcaggt ggcggtggct cgggcggtgg tgggtcgggt   1140
ggcggcggat ctgaaattgt gttgacacag tctccagcca ccctgtcttt gtctccaggg   1200
gaaagagcca ccctctcctg cagggccagt cagagtgtta gcagctactt agcctggtac   1260
caacagaaac tggccaggc tcccaggctc ctcatctatg atgcatccaa cagggccact   1320
ggcatcccag ccaggttcag tggcagtggg tctgggacag acttcactct caccatcagc   1380
agcctagagc ctgaagattt tgcagtttat tactgtcagc agcgtagcaa ctggccccta   1440
ttcactttcg gccctgggac caaagtggat atcaaaacca cgacgccagc gccgcgacca   1500
ccaacaccgg cgcccaccat cgcgtcgcag cccctgtccc tgcgcccaga ggcgtgccgg   1560
ccagcggcgg ggggcgcagt gcacacgagg gggctggact tcgcctgtga tatctacatc   1620
tgggcgccct tggccgggac ttgtggggtc cttctcctgt cactggttat cacccttac    1680 tgcaaacggg gcagaaagaa actcctgtat atattcaaac aaccatttat gagaccagta   1740
caaactactc aagaggaaga cggctgtagc tgccgatttc cagaagaaga agaaggagga   1800
tgtgaactga gagtgaagtt cagcaggagc gcagacgccc ccgcgtacaa gcagggccag   1860
aaccagctct ataacgagct caatctagga cgaagagagg agtacgacgt tttggacaag   1920
agacgtggcc gggaccctga tgggggga aagccgagaa ggaagaaccc tcaggaaggc   1980
ctgtacaacg aactgcagaa agataagatg gcggaggcct acagtgagat tgggatgaaa   2040
ggcgagcgcc ggaggggcaa ggggcacgac ggcctttacc agggtctcag tacagccacc   2100
aaggacacct acgacgccct tcacatgcag gccctgcccc ctcgc              2145
```

<210> SEQ ID NO 157
<211> LENGTH: 2250
<212> TYPE: DNA
<213> ORGANISM: Artificial Sequence
<220> FEATURE:
<223> OTHER INFORMATION: PD1-CTM-CD28-1C3PSMA-CAR

<400> SEQUENCE: 157

```
atgcagatcc cacaggcgcc ctggccagtc gtctgggcgg tgctacaact gggctggcgg     60
ccaggatggt tcttagactc cccagacagg ccctggaacc ccccaccttt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccaccccag ccctcaccc    480 aggccagccg ccagttccaa accctggtg ttttgggtgc tggtggtggt tggtggagtc    540
ctggcttgct atagcttgct agtaacagtg gcctttatta ttttctgggt gaggagtaag    600
aggagcaggc tcctgcacag tgactacatg aacatgactc ccgccgccc cgggcccacc    660
```

| | |
|---|---|
| cgcaagcatt accagcccta tgccccacca cgcgacttcg cagcctatcg ctccgtgaaa | 720 |
| cagactttga attttgacct tctcaagttg gcgggagacg tggagtccaa cccagggccg | 780 |
| atggccttac cagtgaccgc cttgctcctg ccgctggcct tgctgctcca cgccgccagg | 840 |
| ccgcaggtgc aactggtgga gtctggggga ggcgtggtcc agcctgggag gtccctgaga | 900 |
| ctctcctgtg cagcctctgg attcaccttc agtagctatg ctatgcactg ggtccgccag | 960 |
| gctccaggca aggggctgga gtgggtggca gttatatcat atgatggaaa caataaatac | 1020 |
| tacgcagact ccgtgaaggg ccgattcacc atctccagag acaattccaa gaacacgctg | 1080 |
| tatctgcaaa tgaacagcct gagagctgag gacacggctg tgtattactg tgcgagagcc | 1140 |
| gtccccctggg gatcgaggta ctactactac ggtatggacg tctggggcca agggaccacg | 1200 |
| gtcaccgtct cctcaggtgg cggtggctcg ggcggtggtg ggtcgggtgg cggcggatct | 1260 |
| gccatccagt tgacccagtc tccatcctcc ctgtctgcat ctgtaggaga cagagtcacc | 1320 |
| atcacttgcc gggcaagtca gggcattagc agtgctttag cctggtatca gcagaaatca | 1380 |
| gggaaagctc ctaagctcct gatctttgat gcctccagtt tggaaagtgg ggtcccatca | 1440 |
| aggttcagcg gcagtggatc tgggacagat tcactctca ccatcagcag cctgcagcct | 1500 |
| gaagattttg caacttatta ctgtcaacag tttaacagtt atcctctcac tttcggcgga | 1560 |
| gggaccaagg tggagatcaa aaccacgacg ccagcgccgc gaccaccaac accggcgccc | 1620 |
| accatcgcgt cgcagcccct gtccctgcgc ccagaggcgt gccggccagc ggcggggggc | 1680 |
| gcagtgcaca cgagggggct ggacttcgcc tgtgatatct acatctgggc gcccttggcc | 1740 |
| gggacttgtg ggtccttct cctgtcactg gttatcaccc tttactgcaa acggggcaga | 1800 |
| aagaaactcc tgtatatatt caaacaacca tttatgagac cagtacaaac tactcaagag | 1860 |
| gaagatggct gtagctgccg atttccagaa gaagaagaag aggatgtgaa actgagagtg | 1920 |
| aagttcagca ggagcgcaga cgcccccgcg tacaagcagg gccagaacca gctctataac | 1980 |
| gagctcaatc taggacgaag agaggagtac gatgttttgg acaagagacg tggccgggac | 2040 |
| cctgagatgg ggggaaagcc gagaaggaag aaccctcagg aaggcctgta caatgaactg | 2100 |
| cagaaagata gatggcgga ggcctacagt gagattggga tgaaaggcga gcgccggagg | 2160 |
| ggcaaggggc acgatggcct ttaccagggt ctcagtacag ccaccaagga cacctacgac | 2220 |
| gcccttcaca tgcaggccct gccccctcgc | 2250 |

<210> SEQ ID NO 158
<211> LENGTH: 2235
<212> TYPE: DNA
<213> ORGANISM: Artificial Sequence
<220> FEATURE:
<223> OTHER INFORMATION: PD1-CTM-CD28-2A10PSMA-CAR

<400> SEQUENCE: 158

| | |
|---|---|
| atgcagatcc cacaggcgcc ctggccagtc gtctgggcgg tgctacaact gggctggcgg | 60 |
| ccaggatggt tcttagactc cccagacagg ccctggaacc ccccaccttt ctccccagcc | 120 |
| ctgctcgtgg tgaccgaagg ggacaacgcc accttcacct gcagcttctc caacacatcg | 180 |
| gagagcttcg tgctaaactg gtaccgcatg agcccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcaggccc ggcgcaatga cagcggcacc | 360 |
| tacctctgtg gggccatctc cctggccccc aaggcgcaga tcaaagagag cctgcgggca | 420 |
| gagctcaggg tgacagagag aagggcagaa gtgcccacag cccaccccag cccctcaccc | 480 |

```
aggccagccg gccagttcca aaccctggtg ttttgggtgc tggtggtggt tggtggagtc     540
ctggcttgct atagcttgct agtaacagtg gcctttatta ttttctgggt gaggagtaag     600
aggagcaggc tcctgcacag tgactacatg aacatgactc cccgccgccc cgggcccacc     660
cgcaagcatt accagcccta tgccccacca cgcgacttcg cagcctatcg ctccgtgaaa     720
cagactttga attttgacct tctcaagttg gcgggagacg tggagtccaa cccagggccg     780
atggccttac cagtgaccgc cttgctcctg ccgctggcct gctgctcca cgccgccagg      840 ccggaggtgc agctggtgca gtctggagca gaggtgaaaa agcccgggga gtctctgaag     900
atctcctgta agggttctgg atacagcttt accagtaact ggatcggctg ggtgcgccag     960
atgcccggga aaggcctgga gtggatgggg atcatctatc ctggtgactc tgataccaga    1020
tacagcccgt ccttccaagg ccaggtcacc atctcagccg acaagtccat cagcaccgcc    1080
tacctgcagt ggagcagcct gaaggcctcg acaccgcca tgtattactg cgaggcaa      1140 actggtttcc tctggtcctc cgatctctgg ggccgtggca ccctggtcac tgtctcctca    1200
ggtggcggtg gctcgggcgg tggtgggtcg ggtggcggcg gatctgccat ccagttgacc    1260
cagtctccat cctccctgtc tgcatctgta ggagacagag tcaccatcac ttgccgggca    1320
agtcaggaca ttagcagtgc tttagcctgg tatcaacaga accagggaa agctcctaag     1380 ctcctgatct atgatgcctc cagtttggaa agtggggtcc catcaaggtt cagcggctat    1440
ggatctggga cagatttcac tctcaccatc aacagcctgc agcctgaaga ttttgcaact    1500
tattactgtc aacagtttaa tagttacccg ctcactttcg gcggagggac caaggtggag    1560
atcaaaacca cgacgccagc gccgcgacca ccaacaccgg cgcccaccat cgcgtcgcag    1620
cccctgtccc tgcgcccaga ggcgtgccgg ccagcggcgg ggggcgcagt gcacacgagg    1680
gggctggact cgcctgtga tatctacatc tgggcgccct tggccgggac ttgtggggtc    1740
cttctcctgt cactggttat cacccttttac tgcaaacggg gcagaaagaa actcctgtat    1800
atattcaaac aaccatttat gagaccagta caaactactc aagaggaaga tggctgtagc    1860
tgccgatttc cagaagaaga agaaggagga tgtgaactga gagtgaagtt cagcaggagc    1920
gcagacgccc ccgcgtacaa gcagggccag aaccagctct ataacgagct caatctagga    1980
cgaagagagg agtacgatgt tttggacaag agacgtggcc gggaccctga tgggggga      2040 aagccgagaa ggaagaaccc tcaggaaggc ctgtacaatg aactgcagaa agataagatg    2100
gcggaggcct acagtgagat tgggatgaaa ggcgagcgcc ggaggggcaa ggggcacgat    2160
ggcctttacc agggtctcag tacagccacc aaggacacct cgacgccct tcacatgcag    2220 gccctgcccc ctcgc                                                     2235

<210> SEQ ID NO 159
<211> LENGTH: 2241
<212> TYPE: DNA
<213> ORGANISM: Artificial Sequence
<220> FEATURE:
<223> OTHER INFORMATION: PD1-CTM-CD28-2F5PSMA-CAR

<400> SEQUENCE: 159
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
```

```
gccttccccg aggaccgcag ccagcccggc caggactgcc gcttccgtgt cacacaactg      300
cccaacgggc gtgacttcca catgagcgtg gtcagggccc ggcgcaatga cagcggcacc      360
tacctctgtg gggccatctc cctggccccc aaggcgcaga tcaaagagag cctgcgggca      420
gagctcaggg tgacagagag aagggcagaa gtgcccacag cccaccccag cccctcaccc      480
aggccagccg ccagttccaa accctggtgt tttgggtgc tggtggtggt tggtggagtc       540
ctggcttgct atagcttgct agtaacagtg gcctttatta ttttctgggt gaggagtaag      600
aggagcaggc tcctgcacag tgactacatg aacatgactc ccgccgccc gggcccacc        660 cgcaagcatt accagcccta tgccccacca cgcgacttcg cagcctatcg ctccgtgaaa      720
cagactttga ttttgacct tctcaagttg gcgggagacg tggagtccaa cccagggccg       780
atggccttac cagtgaccgc cttgctcctg ccgctggcct tgctgctcca cgccgccagg      840
ccggaggtgc agctggtgca gtctggagca gaggtgaaaa agcccgggga gtctctgaag      900
atctcctgta agggttctgg atacagtttt accagcaact ggatcggctg ggtgcgccag      960
atgcccggga aaggcctgga gtggatgggg atcatctatc ctggtgactc tgataccaga     1020
tacagcccgt ccttccaagg ccaggtcacc atctcagccg acaagtccat cagcaccgcc     1080
tacctgcagt ggaacagcct gaaggcctcg gacaccgcca tgtattactg tgcgagacaa     1140
actggtttcc tctggtcctt cgatctctgg ggccgtggca ccctggtcac tgtctcctca     1200
ggtggcggtg gctcgggcgg tggtgggtcg ggtggcggcg atctgccat ccagttgacc      1260 cagtctccat cctccctgtc tgcatctgta ggagacagag tcaccatcac ttgccgggca     1320
agtcaggaca ttagcagtgc tttagcctgg tatcagcaga accggggaa agctcctaag      1380 ctcctgatct atgatgcctc cagtttggaa agtggggtcc catcaaggtt cagcggcagt     1440
ggatctggga cagatttcac tctcaccatc agcagcctgc agcctgaaga ttttgcaact     1500
tattactgtc aacagtttaa tagttacccg ctcactttcg gcggagggac caaggtggag     1560
atcaaaatca aaccacgac gccagcgccg cgaccaccaa caccggcgcc caccatcgcg     1620
tcgcagcccc tgtccctgcg cccagaggcg tgccggccag cggcgggggg cgcagtgcac     1680
acgagggggc tggacttcgc ctgtgatatc tacatctggg cgcccttggc cgggacttgt     1740
ggggtccttc tcctgtcact ggttatcacc ctttactgca acggggcag aaagaaactc     1800 ctgtatatat tcaaacaacc atttatgaga ccagtacaaa ctactcaaga ggaagatggc     1860
tgtagctgcc gatttccaga agaagaagaa ggaggatgtg aactgagagt gaagttcagc     1920
aggagcgcag acgcccccgc gtacaagcag ggccagaacc agctctataa cgagctcaat     1980
ctaggacgaa gagaggagta cgatgttttg gacaagagac gtggccggga ccctgagatg     2040
gggggaaagc cgagaaggaa gaaccctcag gaaggcctgt acaatgaact gcagaaagat     2100
aagatggcgg aggcctacag tgagattggg atgaaaggcg agcgccggag gggcaagggg     2160
cacgatggcc tttaccaggg tctcagtaca gccaccaagg acacctacga cgcccttcac     2220
atgcaggccc tgccccctcg c                                                2241
```

<210> SEQ ID NO 160
<211> LENGTH: 2244
<212> TYPE: DNA
<213> ORGANISM: Artificial Sequence
<220> FEATURE:
<223> OTHER INFORMATION: PD1-CTM-CD28-2C6PSMA-CAR

<400> SEQUENCE: 160

```
atgcagatcc cacaggcgcc ctggccagtc gtctgggcgg tgctacaact gggctggcgg      60
```

```
ccaggatggt tcttagactc cccagacagg ccctggaacc ccccaccctt ctccccagcc   120
ctgctcgtgg tgaccgaagg ggacaacgcc accttcacct gcagcttctc caacacatcg   180
gagagcttcg tgctaaactg gtaccgcatg agcccagca accagacgga caagctggcc    240
gccttccccg aggaccgcag ccagcccggc caggactgcc gcttccgtgt cacacaactg   300
cccaacgggc gtgacttcca catgagcgtg gtcagggccc ggcgcaatga cagcggcacc   360
tacctctgtg gggccatctc cctggccccc aaggcgcaga tcaaagagag cctgcgggca   420
gagctcaggg tgacagagag aagggcagaa gtgcccacag cccaccccag cccctcaccc   480
aggccagccg gccagttcca aaccctggtg ttttgggtgc tggtggtggt tggtggagtc   540
ctggcttgct atagcttgct agtaacagtg gcctttatta ttttctgggt gaggagtaag   600
aggagcaggc tcctgcacag tgactacatg aacatgactc cccgccgccc cgggcccacc   660
cgcaagcatt accagcccta tgccccacca cgcgacttcg cagcctatcg ctccgtgaaa   720
cagactttga atttttgacct tctcaagttg gcgggagacg tggagtccaa cccagggccg   780
atggccttac cagtgaccgc cttgctcctg ccgctggcct tgctgctcca gccgccagg    840 ccggaggtgc agctggtgca gtctggatca gaggtgaaaa agcccgggga gtctctgaag   900
atctcctgta agggttctgg atacagctt accaactact ggatcggctg ggtgcgccag   960
atgcccggga aaggcctgga gtggatgggg atcatctatc ctggtgactc tgataccaga  1020
tacagcccgt ccttccaagg ccaggtcacc atctcagccg acaagtccat cagcaccgcc  1080
tatctgcagt ggagcagcct gaaggcctcg gacaccgcca tgtattactg tgcgagtccc  1140
gggtatacca gcagttggac ttcttttgac tactggggcc agggaaccct ggtcaccgtc  1200
tcctcaggtg gcggtggctc gggcggtggt gggtcgggtg gcggcggatc tgaaattgtg  1260
ttgacacagt ctccagccac cctgtctttg tctccagggg aaagagccac cctctcctgc  1320
agggccagtc agagtgttag cagctactta gcctggtacc aacagaaacc tggccaggct  1380
cccaggctcc tcatctatga tgcatccaac agggccactg gcatcccagc caggttcagt  1440
ggcagtgggt ctgggacaga cttcactctc accatcagca gcctagagcc tgaagatttt  1500
gcagtttatt actgtcagca gcgtagcaac tggcccctat tcactttcgg ccctgggacc  1560
aaagtggata tcaaaccac gacgccagcg ccgcgaccac caacaccggc gccaccatc   1620 gcgtcgcagc cctgtccct gcgcccagag gcgtgccggc cagcggcggg gggcgcagtg   1680
cacacgaggg gctggacttt cgcctgtgat atctacatct gggcgccctt ggccgggact   1740 tgtgggtcc ttctcctgtc actggttatc acccttact gcaaacgggg cagaaagaaa   1800
ctcctgtata tattcaaaca accatttatg agaccagtac aaactactca agaggaagat   1860
ggctgtagct gccgattcc agaagaagaa gaaggaggat gtgaactgag agtgaagttc   1920
agcaggagcg cagacgcccc cgcgtacaag cagggccaga accagctcta taacgagctc   1980
aatctaggac gaagagagga gtacgatgtt ttggacaaga cgtggccg ggaccctgag    2040 atgggggaa agccgagaag gaagaaccct caggaaggcc tgtacaatga actgcagaaa   2100
gataagatgg cggaggccta cagtgagatt gggatgaaag gcgagcgccg gaggggcaag   2160
gggcacgatg gcctttacca gggtctcagt acagccacca aggacaccta cgacgccctt   2220
cacatgcagg ccctgccccc tcgc                                        2244
```

<210> SEQ ID NO 161
<211> LENGTH: 2232
<212> TYPE: DNA

<213> ORGANISM: Artificial Sequence
<220> FEATURE:
<223> OTHER INFORMATION: PD1A132L-PTM-CD28-1C3PSMA-CAR

<400> SEQUENCE: 161

| | | | | | |
|---|---|---|---|---|---|
| atgcagatcc | cacaggcgcc | ctggccagtc | gtctgggcgg | tgctacaact | gggctggcgg | 60 |
| ccaggatggt | tcttagactc | cccagacagg | ccctggaacc | cccccacctt | ctccccagcc | 120 |
| ctgctcgtgg | tgaccgaagg | ggacaacgcc | accttcacct | gcagcttctc | caacacatcg | 180 |
| gagagcttcg | tgctaaactg | gtaccgcatg | agccccagca | accagacgga | caagctggcc | 240 |
| gccttccccg | gaggaccgcag | ccagcccggc | caggactgcc | gcttccgtgt | cacacaactg | 300 |
| cccaacgggc | gtgacttcca | catgagcgtg | gtcagggccc | ggcgcaatga | cagcggcacc | 360 |
| tacctctgtg | gggccatctc | cctggccccc | aagctgcaga | tcaaagagag | cctgcgggca | 420 |
| gagctcaggg | tgacagagag | aagggcagaa | gtgcccacag | cccaccccag | cccctcaccc | 480 |
| aggccagccg | ccagttccaa | accctggtg | gttggtgtcg | tgggcggcct | gctgggcagc | 540 |
| ctggtgctgc | tagtctgggt | cctggccgtc | atcaggagta | agaggagcag | gctcctgcac | 600 |
| agtgactaca | tgaacatgac | tccccgccgc | cccgggccca | cccgcaagca | ttaccagccc | 660 |
| tatgccccac | cacgcgactt | cgcagcctat | cgctccgtga | acagactttt | gaattttgac | 720 |
| cttctcaagt | tggcgggaga | cgtggagtcc | aacccagggc | cgatggcctt | accagtgacc | 780 |
| gccttgctcc | tgccgctggc | cttgctgctc | cacgccgcca | ggccgcaggt | gcaactggtg | 840 |
| gagtctgggg | gaggcgtggt | ccagcctggg | aggtccctga | gactctcctg | tgcagcctct | 900 |
| ggattcacct | tcagtagcta | tgctatgcac | tgggtccgcc | aggctccagg | caaggggctg | 960 |
| gagtgggtgg | cagttatatc | atatgatgga | aacaataaat | actacgcaga | ctccgtgaag | 1020 |
| ggccgattca | ccatctccag | agacaattcc | aagaacacgc | tgtatctgca | aatgaacagc | 1080 |
| ctgagagctg | aggacacggc | tgtgtattac | tgtgcgagag | ccgtcccctg | gggatcgagg | 1140 |
| tactactact | acggtatgga | cgtctggggc | caagggacca | cggtcaccgt | ctcctcaggt | 1200 |
| ggcggtggct | cgggcggtgg | tgggtcgggt | ggcggcggat | ctgccatcca | gttgacccag | 1260 |
| tctccatcct | ccctgtctgc | atctgtagga | gacagagtca | ccatcacttg | ccgggcaagt | 1320 |
| cagggcatta | gcagtgcttt | agcctggtat | cagcagaaat | cagggaaagc | tcctaagctc | 1380 |
| ctgatctttg | atgcctccag | tttggaaagt | ggggtcccat | caaggttcag | cggcagtgga | 1440 |
| tctgggacag | atttcactct | caccatcagc | agcctgcagc | ctgaagattt | tgcaacttat | 1500 |
| tactgtcaac | agtttaacag | ttatcctctc | actttcggcg | gagggaccaa | ggtggagatc | 1560 |
| aaaaccacga | cgccagcgcc | gcgaccacca | acaccggcgc | ccaccatcgc | gtcgcagccc | 1620 |
| ctgtccctgc | gcccagaggc | gtgccggcca | gcggcgggg | gcgcagtgca | cacgaggggg | 1680 |
| ctggacttcg | cctgtgatat | ctacatctgg | gcgcccttgg | ccgggacttg | tggggtcctt | 1740 |
| ctcctgtcac | tggttatcac | cctttactgc | aaacggggca | gaaagaaact | cctgtatata | 1800 |
| ttcaaacaac | catttatgag | accagtacaa | actactcaag | aggaagatgg | ctgtagctgc | 1860 |
| cgatttccag | aagaagaaga | aggaggatgt | gaactgagag | tgaagttcag | caggagcgca | 1920 |
| gacgccccg | cgtacaagca | gggccagaac | cagctctata | cgagctcaa | tctaggacga | 1980 |
| agagaggagt | acgatgtttt | ggacaagaga | cgtggccggg | accctgagat | gggggggaaag | 2040 |
| ccgagaagga | agaaccctca | ggaaggcctg | tacaatgaac | tgcagaaaga | taagatggcg | 2100 |
| gaggcctaca | gtgagattgg | gatgaaaggc | gagcgccgga | ggggcaaggg | gcacgatggc | 2160 |
| ctttaccagg | gtctcagtac | agccaccaag | gacacctacg | acgcccttca | catgcaggcc | 2220 | ctgccccctc gc                                                 2232

<210> SEQ ID NO 162
<211> LENGTH: 2217
<212> TYPE: DNA
<213> ORGANISM: Artificial Sequence
<220> FEATURE:
<223> OTHER INFORMATION: PD1A132L-PTM-CD28-2A10PSMA-CAR

<400> SEQUENCE: 162

| | | |
|---|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc aacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcaggccc ggcgcaatga cagcggcacc | 360 |
| tacctctgtg ggccatctc cctggccccc aagctgcaga tcaaagagag cctgcgggca | 420 |
| gagctcaggg tgacagagag aagggcagaa gtgcccacag cccacccag ccctcaccc | 480 |
| aggccagccg gccagttcca aaccctggtg gttggtgtcg tgggcggcct gctgggcagc | 540 |
| ctggtgctgc tagtctgggt cctggccgtc atcaggagta agaggagcag gctcctgcac | 600 |
| agtgactaca tgaacatgac tccccgccgc cccgggccca cccgcaagca ttaccagccc | 660 |
| tatgccccac cacgcgactt cgcagcctat cgctccgtga acagactttt gaattttgac | 720 |
| cttctcaagt tggcgggaga cgtggagtcc aacccagggc cgatggcctt accagtgacc | 780 |
| gccttgctcc tgccgctggc cttgctgctc acgccgcca ggccgaggt gcagctggtg | 840 |
| cagtctggag cagaggtgaa aaagcccggg gagtctctga gatctcctg taagggttct | 900 |
| ggatacagct ttaccagtaa ctggatcggc tgggtgcgcc agatgccgg gaaaggcctg | 960 |
| gagtggatgg ggatcatcta tcctggtgac tctgatacca gatacagccc gtccttccaa | 1020 |
| ggccaggtca ccatctcagc cgacaagtcc atcagcaccg cctacctgca gtggagcagc | 1080 |
| ctgaaggcct cggacaccgc catgtattac tgtgcgaggg aaaactggttt cctctggtcc | 1140 |
| tccgatctct ggggccgtgg caccctggtc actgtctcct caggtggcgg tggctcgggc | 1200 |
| ggtggtgggt cgggtggcgg cggatctgcc atccagttga cccagtctcc atcctccctg | 1260 |
| tctgcatctg taggagacag agtcaccatc acttgccggg caagtcagga cattagcagt | 1320 |
| gctttagcct ggtatcaaca gaaaccaggg aaagctccta gctcctgat ctatgatgcc | 1380 |
| tccagtttgg aaagtggggt cccatcaagg ttcagcggct atggatctgg gacagatttc | 1440 |
| actctcacca tcaacagcct gcagcctgaa gattttgcaa cttattactg tcaacagttt | 1500 |
| aatagttacc cgctcacttt cggcggaggg accaaggtgg agatcaaaac cacgacgcca | 1560 |
| gcgccgcgac caccaacacc ggcgcccacc atcgcgtcgc agccctgtc cctgcgccca | 1620 |
| gaggcgtgcc ggcagcggc ggggggcgca gtgcacacga gggggctgga cttcgcctgt | 1680 |
| gatatctaca tctgggcgcc cttggccggg acttgtgggg tccttctcct gtcactggtt | 1740 |
| atcacccttt actgcaaacg gggcagaaag aaactcctgt atatattcaa acaaccattt | 1800 |
| atgagaccag tacaaactac tcaagaggaa gatggctgta gctgccgatt tccagaagaa | 1860 |
| gaagaaggag gatgtgaact gagagtgaag ttcagcagga gcgcagacgc ccccgcgtac | 1920 |
| aagcagggcc agaaccagct ctataacgag ctcaatctag gacgaagaga ggagtacgat | 1980 |

| gttttggaca agagacgtgg ccgggaccct gagatggggg gaaagccgag aaggaagaac | 2040 |
| cctcaggaag gcctgtacaa tgaactgcag aaagataaga tggcggaggc ctacagtgag | 2100 |
| attgggatga aaggcgagcg ccggaggggc aaggggcacg atggccttta ccagggtctc | 2160 |
| agtacagcca ccaaggacac ctacgacgcc cttcacatgc aggccctgcc ccctcgc | 2217 |

<210> SEQ ID NO 163
<211> LENGTH: 2223
<212> TYPE: DNA
<213> ORGANISM: Artificial Sequence
<220> FEATURE:
<223> OTHER INFORMATION: PD1A132L-PTM-CD28-25FPSMA-CAR

<400> SEQUENCE: 163

| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aagctgcaga tcaaagagag cctgcgggca | 420 |
| gagctcaggg tgacagagag aagggcagaa gtgcccacag cccaccccag cccctcaccc | 480 |
| aggccagccg ccagttccaa accctggtg gttggtgtcg tgggcggcct gctgggcagc | 540 |
| ctggtgctgc tagtctgggt cctggccgtc atcaggagta agaggagcag gctcctgcac | 600 |
| agtgactaca tgaacatgac tccccgccgc cccgggccca cccgcaagca ttaccagccc | 660 |
| tatgccccac cacgcgactt cgcagcctat cgctccgtga acagactttt gaattttgac | 720 |
| cttctcaagt tggcgggaga cgtggagtcc aacccagggc cgatggcctt accagtgacc | 780 |
| gccttgctcc tgccgctggc cttgctgctc acgccgcca ggccgaggt gcagctggtg | 840 |
| cagtctggag cagaggtgaa aaagcccggg gagtctctga agatctcctg taagggttct | 900 |
| ggatacagtt ttaccagcaa ctggatcggc tgggtgcgcc agatgcccgg aaaggcctg | 960 |
| gagtggatgg ggatcatcta tcctggtgac tctgatacca gatacagccc gtccttccaa | 1020 |
| ggccaggtca ccatctcagc cgacaagtcc atcagcaccg cctacctgca gtggaacagc | 1080 |
| ctgaaggcct cggacaccgc catgtattac tgtgcgagac aaactggttt cctctggtcc | 1140 |
| ttcgatctct ggggccgtgg caccctggtc actgtctcct caggtggcgg tggctcgggc | 1200 |
| ggtggtgggt cgggtggcgg cggatctgcc atccagttga cccagtctcc atcctccctg | 1260 |
| tctgcatctg taggagacag agtcaccatc acttgccggg caagtcagga cattagcagt | 1320 |
| gctttagcct ggtatcagca gaaaccgggg aaagctccta agctcctgat ctatgatgcc | 1380 |
| tccagtttgg aaagtggggt cccatcaagg ttcagcggca gtggatctgg gacagatttc | 1440 |
| actctcacca tcagcagcct gcagcctgaa gattttgcaa cttattactg tcaacagttt | 1500 |
| aatagttacc cgctcacttt cggcggaggg accaaggtgg agatcaaaat caaaaccacg | 1560 |
| acgccagcgc gcgaccacc aacaccgcg cccaccatcg cgtcgcagcc cctgtccctg | 1620 |
| cgcccagagg cgtgccggcc agcggcgggg ggcgcagtgc acacgagggg gctggacttc | 1680 |
| gcctgtgata tctacatctg ggcgcccttg gccgggactt gtgggtcct tctcctgtca | 1740 |
| ctggttatca ccctttactg caacggggc agaaagaaac tcctgtatat attcaaacaa | 1800 |
| ccatttatga ccagtacaa aactactcaa gaggaagatg gctgtagctg ccgatttcca | 1860 |

| | |
|---|---:|
| gaagaagaag aaggaggatg tgaactgaga gtgaagttca gcaggagcgc agacgccccc | 1920 |
| gcgtacaagc agggccagaa ccagctctat aacgagctca atctaggacg aagagaggag | 1980 |
| tacgatgttt tggacaagag acgtggccgg gaccctgaga tgggggggaaa gccgagaagg | 2040 |
| aagaaccctc aggaaggcct gtacaatgaa ctgcagaaag ataagatggc ggaggcctac | 2100 |
| agtgagattg ggatgaaagg cgagcgccgg aggggcaagg ggcacgatgg cctttaccag | 2160 |
| ggtctcagta cagccaccaa ggacacctac gacgcccttc acatgcaggc cctgccccct | 2220 |
| cgc | 2223 |

<210> SEQ ID NO 164
<211> LENGTH: 2226
<212> TYPE: DNA
<213> ORGANISM: Artificial Sequence
<220> FEATURE:
<223> OTHER INFORMATION: PD1A132L-PTM-CD28-2C6PSMA-CAR

<400> SEQUENCE: 164

| | |
|---|---:|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| gagagcttcg tgctaaactg gtaccgcatg agcccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcaggccc ggcgcaatga cagcggcacc | 360 |
| tacctctgtg gggccatctc cctggccccc aagctgcaga tcaaagagag cctgcgggca | 420 |
| gagctcaggg tgacagagag aagggcagaa gtgcccacag cccaccccag cccctcaccc | 480 |
| aggccagccg gccagttcca aaccctggtg gttggtgtcg tgggcggcct gctgggcagc | 540 |
| ctggtgctgc tagtctgggt cctggccgtc atcaggagta agaggagcag gctcctgcac | 600 |
| agtgactaca tgaacatgac tccccgccgc cccgggccca cccgcaagca ttaccagccc | 660 |
| tatgccccac cacgcgactt cgcagcctat cgctccgtga acagactttt gaattttgac | 720 |
| cttctcaagt tggcgggaga cgtggagtcc aacccagggc cgatggcctt accagtgacc | 780 |
| gccttgctcc tgccgctggc cttgctgctc cacgccgcca ggccggaggt gcagctggtg | 840 |
| cagtctggat cagaggtgaa aaagcccggg gagtctctga agatctcctg taaggggttct | 900 |
| ggatacagct ttaccaacta ctggatcggc tgggtgcgcc agatgccgg gaaaggcctg | 960 |
| gagtggatgg ggatcatcta tcctggtgac tctgatacca gatacagccc gtccttccaa | 1020 |
| ggccaggtca ccatctcagc cgacaagtcc atcagcaccg cctatctgca gtggagcagc | 1080 |
| ctgaaggcct cggacaccgc catgtattac tgtgcgagtc ccgggtatac cagcagttgg | 1140 |
| acttctttg actactgggg ccagggaacc ctggtcaccg tctcctcagg tggcggtggc | 1200 |
| tcgggcggtg gtgggtcggg tggcggcgga tctgaaattg tgttgacaca gtctccagcc | 1260 |
| accctgtctt tgtctccagg ggaaagagcc accctctcct gcagggccag tcagagtgtt | 1320 |
| agcagctact tagcctggta ccaacagaaa cctggccagg ctcccaggct cctcatctat | 1380 |
| gatgcatcca caggggccac tggcatccca gccaggttca gtggcagtgg gtctgggaca | 1440 |
| gacttcactc tcaccatcag cagcctagag cctgaagatt ttgcagttta ttactgtcag | 1500 |
| cagcgtagca actggcccct attcactttc ggccctggga ccaaagtgga tatcaaaacc | 1560 |
| acgacgccag cgccgcgacc accaacaccg gcgcccacca tcgcgtcgca gcccctgtcc | 1620 |

| | |
|---|---:|
| ctgcgcccag aggcgtgccg gccagcggcg gggggcgcag tgcacacgag ggggctggac | 1680 |
| ttcgcctgtg atatctacat ctgggcgccc ttggccggga cttgtggggt ccttctcctg | 1740 |
| tcactggtta tcacccttta ctgcaaacgg ggcagaaaga aactcctgta tatattcaaa | 1800 |
| caaccattta tgagaccagt acaaactact caagaggaag atggctgtag ctgccgattt | 1860 |
| ccagaagaag aagaaggagg atgtgaactg agagtgaagt tcagcaggag cgcagacgcc | 1920 |
| cccgcgtaca agcagggcca gaaccagctc tataacgagc tcaatctagg acgaagagag | 1980 |
| gagtacgatg ttttggacaa gagacgtggc cgggaccctg agatggggg aaagccgaga | 2040 |
| aggaagaacc ctcaggaagg cctgtacaat gaactgcaga agataagat ggcggaggcc | 2100 |
| tacagtgaga ttgggatgaa aggcgagcgc cggaggggca aggggcacga tggcctttac | 2160 |
| cagggtctca gtacagccac caaggacacc tacgacgccc ttcacatgca ggccctgccc | 2220 |
| cctcgc | 2226 |

<210> SEQ ID NO 165
<211> LENGTH: 2340
<212> TYPE: DNA
<213> ORGANISM: Artificial Sequence
<220> FEATURE:
<223> OTHER INFORMATION: TIM3-CD28-1C3PSMA-CAR

<400> SEQUENCE: 165

| | |
|---|---:|
| atgttttcac atcttccctt tgactgtgtc ctgctgctgc tgctgctact acttacaagg | 60 |
| tcctcagaag tggaatacag agcggaggtc ggtcagaatg cctatctgcc ctgcttctac | 120 |
| accccagccg ccccagggaa cctcgtgccc gtctgctggg gcaaaggagc ctgtcctgtg | 180 |
| tttgaatgtg gcaacgtggt gctcaggact gatgaaaggg atgtgaatta ttggacatcc | 240 |
| agatactggc taaatgggga tttccgcaaa ggagatgtgt ccctgaccat agagaatgtg | 300 |
| actctagcag acagtgggat ctactgctgc cgaatccaaa tcccaggcat aatgaatgat | 360 |
| gaaaaattta acctgaagtt ggtcatcaaa ccagccaagg tcacccctgc accgactcgg | 420 |
| cagagagact tcactgcagc ctttccaagg atgcttacca ccaggggaca tggcccagca | 480 |
| gagacacaga cactgggag cctccctgac ataaatctaa cacaaatatc acattggcc | 540 |
| aatgagttac gggactctag gttggccaat gacttacggg actccggagc aaccatcaga | 600 |
| ttttgggtgc tggtggtggt tggtggagtc ctggcttgct atagcttact agtaacagtg | 660 |
| gcctttatta ttttctgggt gaggagtaag aggagcaggc tcctgcacag tgactacatg | 720 |
| aacatgactc cccgccgccc cgggcccacc cgcaagcatt accagcccta tgccccacca | 780 |
| cgcgacttcg cagcctatcg ctccgtgaaa cagactttga attttgacct tctcaagttg | 840 |
| gcgggagacg tggagtccaa cccagggccc atggccttac cagtgaccgc cttgctcctg | 900 |
| ccgctggcct tgctgctcca cgccgccagg ccgcaggtgc aactggtgga gtctggggga | 960 |
| ggcgtggtcc agcctgggag gtccctgaga ctctcctgtg cagcctctgg attcaccttc | 1020 |
| agtagctatg ctatgcactg ggtccgccag gctccaggca aggggctgga gtgggtggca | 1080 |
| gttatatcat atgatggaaa caataaatac tacgcagact ccgtgaaggg ccgattcacc | 1140 |
| atctccagag acaattccaa gaacacgctg tatctgcaaa tgaacagcct gagagctgag | 1200 |
| gacacggctg tgtattactg tgcgagagcc gtccctgggg atcgaggta ctactactac | 1260 |
| ggtatggacg tctggggcca agggaccacg gtcaccgtct cctcaggtgg cggtggctcg | 1320 |
| ggcggtggtg ggtcgggtgg cggcggatct gccatccagt tgacccagtc tccatcctcc | 1380 |
| ctgtctgcat ctgtaggaga cagagtcacc atcacttgcc gggcaagtca gggcattagc | 1440 |

| | |
|---|---|
| agtgctttag cctggtatca gcagaaatca gggaaagctc ctaagctcct gatctttgat | 1500 |
| gcctccagtt tggaaagtgg ggtcccatca aggttcagcg gcagtggatc tgggacagat | 1560 |
| ttcactctca ccatcagcag cctgcagcct gaagattttg caacttatta ctgtcaacag | 1620 |
| tttaacagtt atcctctcac tttcggcgga gggaccaagg tggagatcaa aaccacgacg | 1680 |
| ccagcgccgc gaccaccaac accggcgccc accatcgcgt cgcagcccct gtccctgcgc | 1740 |
| ccagaggcgt gccggccagc ggcgggggc gcagtgcaca cgaggggct ggacttcgcc | 1800 |
| tgtgatatct acatctgggc gcccttggcc gggacttgtg gggtccttct cctgtcactg | 1860 |
| gttatcaccc tttactgcaa acggggcaga aagaaactcc tgtatatatt caaacaacca | 1920 |
| tttatgagac cagtacaaac tactcaagag gaagacggct gtagctgccg atttccagaa | 1980 |
| gaagaagaag gaggatgtga actgagagtg aagttcagca ggagcgcaga cgcccccgcg | 2040 |
| tacaagcagg gccagaacca gctctataac gagctcaatc taggacgaag agaggagtac | 2100 |
| gacgttttgg acaagagacg tggccggac cctgagatgg ggggaaagcc gagaaggaag | 2160 |
| aaccctcagg aaggcctgta caacgaactg cagaaagata agatggcgga ggcctacagt | 2220 |
| gagattggga tgaaaggcga gcgccggagg ggcaaggggc acgacggcct ttaccagggt | 2280 |
| ctcagtacag ccaccaagga cacctacgac gcccttcaca tgcaggccct gccccctcgc | 2340 |

<210> SEQ ID NO 166
<211> LENGTH: 2325
<212> TYPE: DNA
<213> ORGANISM: Artificial Sequence
<220> FEATURE:
<223> OTHER INFORMATION: TIM3-CD28-2A10PSMA-CAR

<400> SEQUENCE: 166

| | |
|---|---|
| atgttttcac atcttccctt tgactgtgtc ctgctgctgc tgctgctact acttacaagg | 60 |
| tcctcagaag tggaatacag agcggaggtc ggtcagaatg cctatctgcc ctgcttctac | 120 |
| accccagccg ccccagggaa cctcgtgccc gtctgctggg gcaaggagc ctgtcctgtg | 180 |
| tttgaatgtg gcaacgtggt gctcaggact gatgaaaggg atgtgaatta ttggacatcc | 240 |
| agatactggc taaatgggga tttccgcaaa ggagatgtgt ccctgaccat agaaaatgtg | 300 |
| actctagcag acagtgggat ctactgctgc cgaatccaaa tcccaggcat aatgaatgat | 360 |
| gaaaaattta acctgaagtt ggtcatcaaa ccagccaagg tcacccctgc accgactcgg | 420 |
| cagagagact tcactgcagc ctttccaagg atgcttacca ccaggggaca tggcccagca | 480 |
| gagacacaga cactggggag cctccctgac ataaatctaa cacaaatatc acattggcc | 540 |
| aatgagttac gggactctag gttggccaat gacttacggg actccggagc aaccatcaga | 600 |
| ttttgggtgc tggtggtggt tggtggagtc ctggcttgct atagcttact agtaacagtg | 660 |
| gcctttatta ttttctgggt gaggagtaag aggagcaggc cctgcacag tgactacatg | 720 |
| aacatgactc cccgccgccc cgggcccacc cgcaagcatt accagcccta tgccccacca | 780 |
| cgcgacttcg cagcctatcg ctccgtgaaa cagactttga attttgacct tctcaagttg | 840 |
| gcgggagacg tggagtccaa cccagggccg atggccttac cagtgaccgc cttgctcctg | 900 |
| ccgctggcct tgctgctcca cgccgccagg ccggaggtgc agctggtgca gtctggagca | 960 |
| gaggtgaaaa agcccgggga gtctctgaag atcctctgta agggttctgg atacagcttt | 1020 |
| accagtaact ggatcggctg ggtgcgccaa atgcccggga aaggcctgga gtggatgggg | 1080 |
| atcatctatc ctggtgactc tgataccaga tacagcccgt ccttccaagg ccaggtcacc | 1140 |

-continued

```
atctcagccg acaagtccat cagcaccgcc tacctgcagt ggagcagcct gaaggcctcg   1200
gacaccgcca tgtattactg tgcgaggcaa actggtttcc tctggtcctc cgatctctgg   1260
ggccgtggca ccctggtcac tgtctcctca ggtggcggtg gctcgggcgg tggtgggtcg   1320
ggtggcggcg gatctgccat ccagttgacc cagtctccat cctccctgtc tgcatctgta   1380
ggagacagag tcaccatcac ttgccgggca agtcaggaca ttagcagtgc tttagcctgg   1440
tatcaacaga aaccagggaa agctcctaag ctcctgatct atgatgcctc cagtttggaa   1500 agtgggtcc catcaaggtt cagcggctat ggatctggga cagatttcac tctcaccatc   1560
aacagcctgc agcctgaaga ttttgcaact tattactgtc aacagtttaa tagttacccg   1620
ctcactttcg gcggagggac caaggtggag atcaaaacca cgacgccagc gccgcgacca   1680
ccaacaccgg cgcccaccat cgcgtcgcag cccctgtccc tgcgcccaga ggcgtgccgg   1740
ccagcggcgg ggggcgcagt gcacacgagg gggctggact tcgcctgtga tatctacatc   1800
tgggcgccct tggccgggac ttgtgggtc cttctcctgt cactggttat caccctttac   1860
tgcaaacggg gcagaaagaa actcctgtat atattcaaac aaccatttat gagaccagta   1920
caaactactc aagaggaaga tggctgtagc tgccgatttc agaagaaga agaaggagga   1980 tgtgaactga gagtgaagtt cagcaggagc gcagacgccc ccgcgtacaa gcagggccag   2040
aaccagctct ataacgagct caatctagga cgaagagagg agtacgatgt tttggacaag   2100
agacgtggcc gggaccctga gatggggga aagccgagaa ggaagaaccc tcaggaaggc   2160
ctgtacaatg aactgcagaa agataagatg gcggaggcct acagtgagat tgggatgaaa   2220
ggcgagcgcc ggaggggcaa ggggcacgat ggcctttacc agggtctcag tacagccacc   2280
aaggacacct acgacgccct tcacatgcag gccctgcccc ctcgc              2325
```

<210> SEQ ID NO 167
<211> LENGTH: 2331
<212> TYPE: DNA
<213> ORGANISM: Artificial Sequence
<220> FEATURE:
<223> OTHER INFORMATION: TIM3-CD28-25FPSMA-CAR

<400> SEQUENCE: 167

```
atgttttcac atcttcccct tgactgtgtc ctgctgctgc tgctgctact acttacaagg    60
tcctcagaag tggaatacag agcggaggtc ggtcagaatg cctatctgcc ctgcttctac   120
accccagccg ccccagggaa cctcgtgccc gtctgctggg gcaaggagc ctgtcctgtg    180 tttgaatgtg gcaacgtggt gctcaggact gatgaaaggg atgtgaatta ttggacatcc   240
agatactggc taaatgggga tttccgcaaa ggagatgtgt ccctgaccat agagaatgtg   300
actctagcag acagtgggat ctactgctgc cgaatccaaa tcccaggcat aatgaatgat   360
gaaaaattta acctgaagtt ggtcatcaaa ccagccaagg tcacccctgc accgactcgg   420
cagagagact tcactgcagc ctttccaagg atgcttacca ccaggggaca tggcccagca   480
gagacacaga cactggggag cctccctgac ataaatctaa cacaaatatc cacattggcc   540
aatgagttac gggactctag gttggccaat gacttacggg actccggagc aaccatcaga   600
ttttgggtgc tggtggtggt tggtggagtc ctggcttgct atagcttact agtaacagtg   660
gcctttatta ttttctgggt gaggagtaag aggagcaggc tcctgcacag tgactacatg   720
aacatgactc cccgccgccc cgggcccacc cgcaagcatt accagcccta tgccccacca   780
cgcgacttcg cagcctatcg ctccgtgaaa cagactttga attttgacct tctcaagttg   840
gcgggagacg tggagtccaa cccagggccg atggccttac cagtgaccgc cttgctcctg   900
```

```
ccgctggcct tgctgctcca cgccgccagg ccggaggtgc agctggtgca gtctggagca    960
gaggtgaaaa agcccgggga gtctctgaag atctcctgta agggttctgg atacagtttt   1020
accagcaact ggatcggctg ggtgcgccag atgcccggga aggcctggag tggatgggg    1080
atcatctatc ctggtgactc tgataccaga tacagcccgt ccttccaagg ccaggtcacc   1140
atctcagccg acaagtccat cagcaccgcc tacctgcagt ggaacagcct gaaggcctcg   1200
gacaccgcca tgtattactg tgcgagacaa actggtttcc tctggtcctt cgatctctgg   1260
ggccgtggca ccctggtcac tgtctcctca ggtggcggtg gctcgggcgg tggtgggtcg   1320
ggtggcggcg gatctgccat ccagttgacc cagtctccat cctccctgtc tgcatctgta   1380
ggagacagag tcaccatcac ttgccgggca agtcaggaca ttagcagtgc tttagcctgg   1440
tatcagcaga aaccggggaa agctcctaag ctcctgatct atgatgcctc cagtttggaa   1500
agtggggtcc catcaaggtt cagcggcagt ggatctggga cagatttcac tctcaccatc   1560
agcagcctgc agcctgaaga ttttgcaact tattactgtc aacagtttaa tagttacccg   1620
ctcacttctcg gcggagggac caaggtggag atcaaaatca aaccacgac gccagcgccg   1680
cgaccaccaa caccggcgcc caccatcgcg tcgcagcccc tgtccctgcg cccagaggcg   1740
tgccggccag cggcgggggg cgcagtgcac acgagggggc tggacttcgc ctgtgatatc   1800
tacatctggg cgcccttggc cgggacttgt ggggtccttc tcctgtcact ggttatcacc   1860
ctttactgca acggggcag aaagaaactc ctgtatatat tcaaacaacc atttatgaga   1920
ccagtacaaa ctactcaaga ggaagacggc tgtagctgcc gatttccaga agaagaagaa   1980
ggaggatgtg aactgagagt gaagttcagc aggagcgcag acgccccgc gtacaagcag   2040
ggccagaacc agctctataa cgagctcaat ctaggacgaa gagaggagta cgacgttttg   2100
gacaagagac gtggccggga ccctgagatg ggggaaagc cgagaaggaa gaaccctcag   2160
gaaggcctgt acaacgaact gcagaaagat aagatggcgg aggcctacag tgagattggg   2220
atgaaaggcg agcgccggag gggcaagggg cacgacggcc tttaccaggg tctcagtaca   2280
gccaccaagg acacctacga cgcccttcac atgcaggccc tgccccctcg c            2331
```

<210> SEQ ID NO 168
<211> LENGTH: 2334
<212> TYPE: DNA
<213> ORGANISM: Artificial Sequence
<220> FEATURE:
<223> OTHER INFORMATION: TIM3-CD28-2C6PSMA-CAR

<400> SEQUENCE: 168

```
atgttttcac atcttcccctt tgactgtgtc ctgctgctgc tgctgctact acttacaagg     60
tcctcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc cgaatccaaa tcccaggcat aatgaatgat    360
gaaaaattta acctgaagtt ggtcatcaaa ccagccaagg tcacccctgc accgactcgg    420
cagagagact tcactgcagc ctttccaagg atgcttacca ccaggggaca tggcccagca    480
gagacacaga cactggggag cctccctgac ataaatctaa cacaaatatc cacattggcc    540
aatgagttac gggactctag gttggccaat gacttacggg actccggagc aaccatcaga    600
```

```
ttttgggtgc tggtggtggt tggtggagtc ctggcttgct atagcttact agtaacagtg    660
gcctttatta ttttctgggt gaggagtaag aggagcaggc tcctgcacag tgactacatg    720
aacatgactc cccgccgccc cgggcccacc cgcaagcatt accagcccta tgccccacca    780
cgcgacttcg cagcctatcg ctccgtgaaa cagactttga attttgacct tctcaagttg    840
gcgggagacg tggagtccaa cccagggccg atggccttac cagtgaccgc cttgctcctg    900
ccgctggcct tgctgctcca cgccgccagg ccggaggtgc agctggtgca gtctggatca    960
gaggtgaaaa agcccgggga gtctctgaag atctcctgta agggttctgg atacagcttt   1020
accaactact ggatcggctg ggtgcgccag atgcccggga aaggcctgga gtggatgggg   1080
atcatctatc ctggtgactc tgataccaga tacagcccgt ccttccaagg ccaggtcacc   1140
atctcagccg acaagtccat cagcaccgcc tatctgcagt ggagcagcct gaaggcctcg   1200
gacaccgcca tgtattactg tgcgagtccc gggtatacca gcagttggac ttcttttgac   1260
tactggggcc agggaaccct ggtcaccgtc tcctcaggtg gcggtggctc gggcggtggt   1320
gggtcgggtg gcggcggatc tgaaattgtg ttgacacagt ctccagccac cctgtctttg   1380
tctccagggg aaagagccac cctctcctgc agggccagtc agagtgttag cagctactta   1440
gcctggtacc aacagaaacc tggccaggct cccaggctcc tcatctatga tgcatccaac   1500
agggccactg gcatcccagc caggttcagt ggcagtgggt ctgggacaga cttcactctc   1560
accatcagca gcctagagcc tgaagatttt gcagtttatt actgtcagca gcgtagcaac   1620
tggcccctat tcactttcgg ccctgggacc aaagtggata tcaaaaccac gacgccagcg   1680
ccgcgaccac caacaccggc gcccaccatc gcgtcgcagc ccctgtccct gcgcccagag   1740
gcgtgccggc cagcggcggg gggcgcagtg cacacgaggg ggctggactt cgcctgtgat   1800
atctacatct gggcgccctt ggccgggact tgtggggtcc ttctcctgtc actggttatc   1860 acccttact gcaaacgggg cagaaagaaa ctcctgtata tattcaaaca accatttatg   1920
agaccagtac aaactactca agaggaagac ggctgtagct gccgatttcc agaagaagaa   1980
gaaggaggat gtgaactgag agtgaagttc agcaggagcg cagacgcccc cgcgtacaag   2040
cagggccaga accagctcta taacgagctc aatctaggac gaagagagga gtacgacgtt   2100
ttggacaaga cgtggccg ggaccctgag atggggggaa agccgagaag gaagaaccct   2160
caggaaggcc tgtacaacga actgcagaaa gataagatgg cggaggccta cagtgagatt   2220
gggatgaaag gcgagcgccg gaggggcaag gggcacgacg gcctttacca gggtctcagt   2280
acagccacca aggacaccta cgacgccctt cacatgcagg ccctgccccc tcgc         2334

<210> SEQ ID NO 169
<211> LENGTH: 821
<212> TYPE: DNA
<213> ORGANISM: Artificial Sequence
<220> FEATURE:
<223> OTHER INFORMATION: 1C3

<400> SEQUENCE: 169
atggccttac cagtgaccgc cttgctcctg ccgctggcct tgctgctcca cgccgccagg     60
ccgcaggtgc aactggtgga gtctggggga ggcgtggtcc agcctgggag gtccctgaga    120
ctctcctgtg cagcctctgg attcaccttc agtagctatg ctatgcactg ggtccgccag    180
gctccaggca aggggctgga gtgggtggca gttatatcat atgatggaaa caataaatac    240
tacgcagact ccgtgaaggg ccgattcacc atctccagag acaattccaa gaacacgctg    300
tatctgcaaa tgaacagcct gagagctgag gacacggctg tgtattactg tgcgagagcc    360
```

```
gtcccctggg gatcgaggta ctactactac ggtatggacg tctggggcca agggaccacg    420
gtcaccgtct cctcaggtgg cggtggctcg ggcggtggtg ggtcgggtgg cggcggatct    480
gccatccagt tgacccagtc tccatcctcc ctgtctgcat ctgtaggaga cagagtcacc    540
atcacttgcc gggcaagtca gggcattagc agtgctttag cctggtatca gcagaaatca    600
gggaaagctc ctaagctcct gatctttgat gcctccagtt tggaaagtgg ggtcccatca    660
aggttcagcg gcagtggatc tgggacagat ttcactctca ccatcagcag cctgcagcct    720
gaagattttg caacttatta ctgtcaacag tttaacagtt atcctctcac tttcggcgga    780
gggaccaagg tggagatcaa aaccacgacg ccagcgccgc g                        821

<210> SEQ ID NO 170
<211> LENGTH: 806
<212> TYPE: DNA
<213> ORGANISM: Artificial Sequence
<220> FEATURE:
<223> OTHER INFORMATION: 2A10

<400> SEQUENCE: 170
atggccttac cagtgaccgc cttgctcctg ccgctggcct tgctgctcca cgccgccagg     60
ccggaggtgc agctggtgca gtctggagca gaggtgaaaa agcccgggga gtctctgaag    120
atctcctgta agggttctgg atacagcttt accagtaact ggatcggctg ggtgcgccag    180
atgcccggga aaggcctgga gtggatgggg atcatctatc ctggtgactc tgataccaga    240
tacagcccgt ccttccaagg ccaggtcacc atctcagccg acaagtccat cagcaccgcc    300
tacctgcagt ggagcagcct gaaggcctcg acaccgcca tgtattactg tgcgaggcaa     360 actggttttcc tctggtcctc cgatctctgg ggccgtggca ccctggtcac tgtctcctca    420
ggtggcggtg gctcgggcgg tggtgggtcg ggtggcggcg gatctgccat ccagttgacc    480
cagtctccat cctccctgtc tgcatctgta ggagacagag tcaccatcac ttgccgggca    540
agtcaggaca ttagcagtgc tttagcctgg tatcaacaga accagggaa agctcctaag    600 ctcctgatct atgatgcctc cagttttgaa agtggggtcc catcaaggtt cagcggctat    660
ggatctggga cagatttcac tctcaccatc aacagcctgc agcctgaaga ttttgcaact    720
tattactgtc aacagtttaa tagttacccg ctcactttcg gcggagggac caaggtggag    780
atcaaaacca cgacgccagc gccgcg                                         806

<210> SEQ ID NO 171
<211> LENGTH: 812
<212> TYPE: DNA
<213> ORGANISM: Artificial Sequence
<220> FEATURE:
<223> OTHER INFORMATION: 2F5

<400> SEQUENCE: 171
atggccttac cagtgaccgc cttgctcctg ccgctggcct tgctgctcca cgccgccagg     60
ccggaggtgc agctggtgca gtctggagca gaggtgaaaa agcccgggga gtctctgaag    120
atctcctgta agggttctgg atacagttttt accagcaact ggatcggctg ggtgcgccag    180
atgcccggga aaggcctgga gtggatgggg atcatctatc ctggtgactc tgataccaga    240
tacagcccgt ccttccaagg ccaggtcacc atctcagccg acaagtccat cagcaccgcc    300
tacctgcagt ggaacagcct gaaggcctcg acaccgcca tgtattactg tgcgagacaa     360 actggttttcc tctggtccttt cgatctctgg ggccgtggca ccctggtcac tgtctcctca    420
```

```
ggtggcggtg gctcgggcgg tggtgggtcg ggtggcggcg atctgccat  ccagttgacc    480 cagtctccat cctccctgtc tgcatctgta ggagacagag tcaccatcac ttgccgggca    540
agtcaggaca ttagcagtgc tttagcctgg tatcagcaga aaccggggaa agctcctaag    600
ctcctgatct atgatgcctc cagtttggaa agtggggtcc catcaaggtt cagcggcagt    660
ggatctggga cagatttcac tctcaccatc agcagcctgc agcctgaaga ttttgcaact    720
tattactgtc aacagtttaa tagttacccg ctcactttcg gcggagggac caaggtggag    780
atcaaaatca aaaccacgac gccagcgccg cg                                  812

<210> SEQ ID NO 172
<211> LENGTH: 815
<212> TYPE: DNA
<213> ORGANISM: Artificial Sequence
<220> FEATURE:
<223> OTHER INFORMATION: 2C6

<400> SEQUENCE: 172
atggccttac cagtgaccgc cttgctcctg ccgctggcct tgctgctcca cgccgccagg     60
ccggaggtgc agctggtgca gtctggatca gaggtgaaaa agcccgggga gtctctgaag    120
atctcctgta agggttctgg atacagcttt accaactact ggatcggctg ggtgcgccag    180
atgcccggga aaggcctgga gtggatgggg atcatctatc ctggtgactc tgataccaga    240
tacagcccgt ccttccaagg ccaggtcacc atctcagccg acaagtccat cagcaccgcc    300
tatctgcagt ggagcagcct gaaggcctcg gacaccgcca tgtattactg tgcgagtccc    360
gggtatacca gcagttggac ttcttttgac tactggggcc agggaaccct ggtcaccgtc    420
tcctcaggtg gcggtggctc gggcggtggt gggtcgggtg gcggcggatc tgaaattgtg    480
ttgacacagt ctccagccac cctgtctttg tctccagggg aaagagccac cctctcctgc    540
agggccagtc agagtgttag cagctactta gcctggtacc aacagaaacc tggccaggct    600
cccaggctcc tcatctatga tgcatccaac agggccactg gcatcccagc caggttcagt    660
ggcagtgggt ctgggacaga cttcactctc accatcagca gcctagagcc tgaagatttt    720
gcagtttatt actgtcagca gcgtagcaac tggcccctat tcactttcgg ccctgggacc    780
aaagtggata tcaaaaccac gacgccagcg ccgcg                              815

<210> SEQ ID NO 173
<211> LENGTH: 780
<212> TYPE: DNA
<213> ORGANISM: Artificial Sequence
<220> FEATURE:
<223> OTHER INFORMATION: PD1.CD28-F2A

<400> SEQUENCE: 173
atgcagatcc cacaggcgcc ctggccagtc gtctgggcgg tgctacaact gggctggcgg     60
ccaggatggt tcttagactc cccagacagg ccctggaacc ccccaccctt ctccccagcc    120
ctgctcgtgg tgaccgaagg ggacaacgcc accttcacct gcagcttctc aacacatcg    180 gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggcccc aaggcgcaga tcaaagagag cctgcgggca    420
gagctcaggg tgacagagag aagggcagaa gtgcccacag cccacccag ccctcaccc    480 aggccagccg ccagttcca aaccctggtg tttgggtgc tggtggtggt tggtggagtc    540
```

```
ctggcttgct atagcttgct agtaacagtg gcctttatta ttttctgggt gaggagtaag     600
aggagcaggc tcctgcacag tgactacatg aacatgactc cccgccgccc cgggcccacc     660
cgcaagcatt accagcccta tgccccacca cgcgacttcg cagcctatcg ctccgtgaaa     720
cagactttga attttgacct tctcaagttg gcgggagacg tggagtccaa cccagggccg     780
```

<210> SEQ ID NO 174
<211> LENGTH: 762
<212> TYPE: DNA
<213> ORGANISM: Artificial Sequence
<220> FEATURE:
<223> OTHER INFORMATION: PD1A132L-PTM.CD28-F2A

<400> SEQUENCE: 174

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aagctgcaga tcaaagagag cctgcgggca     420
gagctcaggg tgacagagag aagggcagaa gtgcccacag cccaccccag ccctcacccc     480
aggccagccg ccagttccaa accctggtg gttggtgtcg tggcggcct gctgggcagc     540 ctggtgctgc tagtctgggt cctggccgtc atcaggagta agaggagcag gctcctgcac     600
agtgactaca tgaacatgac tccccgccgc cccgggccca cccgcaagca ttaccagccc     660
tatgccccac cacgcgactt cgcagcctat cgctccgtga acagacttt gaatttgac     720 cttctcaagt tggcgggaga cgtggagtcc aacccagggc cg                        762
```

<210> SEQ ID NO 175
<211> LENGTH: 681
<212> TYPE: DNA
<213> ORGANISM: Artificial Sequence
<220> FEATURE:
<223> OTHER INFORMATION: dnTGFRBII-T2A

<400> SEQUENCE: 175

```
atgggtcggg ggctgctcag gggcctgtgg ccgctgcaca tcgtcctgtg gacgcgtatc      60
gccagcacga tccaccgca cgttcagaag tcggttaata cgacatgat agtcactgac     120 aacaacggtg cagtcaagtt tccacaactg tgtaaatttt gtgatgtgag attttccacc     180
tgtgacaacc agaaatcctg catgagcaac tgcagcatca cctccatctg tgagaagcca     240
caggaagtct gtgtggctgt atggagaaag aatgacgaga acataacact agagacagtt     300
tgccatgacc ccaagctccc ctaccatgac tttattctgg aagatgctgc ttctccaaag     360
tgcattatga aggaaaaaaa aaagcctggt gagactttct tcatgtgttc ctgtagctct     420
gatgagtgca atgacaacat catcttctca gaagaatata acaccagcaa tcctgacttg     480
ttgctagtca tatttcaagt gacaggcatc agcctcctgc caccactggg agttgccata     540
tctgtcatca tcatcttcta ctgctaccgc gttaaccggc agcagaagct gagttcatcc     600
ggaagatctg gcggcggaga gggcagagga agtcttctaa catgcggtga cgtggaggag     660
aatcccggcc ctagagccac c                                              681
```

<210> SEQ ID NO 176
<211> LENGTH: 20
<212> TYPE: DNA
<213> ORGANISM: Artificial Sequence
<220> FEATURE:
<223> OTHER INFORMATION: primer

<400> SEQUENCE: 176
aggaagtctc aaagtgccct							20

<210> SEQ ID NO 177
<211> LENGTH: 20
<212> TYPE: DNA
<213> ORGANISM: Artificial Sequence
<220> FEATURE:
<223> OTHER INFORMATION: primer

<400> SEQUENCE: 177
gaacaacagc tgctccactc							20

<210> SEQ ID NO 178
<211> LENGTH: 25
<212> TYPE: DNA
<213> ORGANISM: Artificial Sequence
<220> FEATURE:
<223> OTHER INFORMATION: primer

<400> SEQUENCE: 178
gctacactga gcaccaggtg gtctc						25

<210> SEQ ID NO 179
<211> LENGTH: 25
<212> TYPE: DNA
<213> ORGANISM: Artificial Sequence
<220> FEATURE:
<223> OTHER INFORMATION: primer

<400> SEQUENCE: 179
cccagcagtg agggtctctc tcttc						25

<210> SEQ ID NO 180
<211> LENGTH: 711
<212> TYPE: DNA
<213> ORGANISM: Artificial Sequence
<220> FEATURE:
<223> OTHER INFORMATION: J591 PSMA scFv

<400> SEQUENCE: 180
gacattgtga tgacccagtc tcacaaattc atgtccacat cagtaggaga cagggtcagc      60
atcatctgta aggccagtca agatgtgggt actgctgtag actggtatca acagaaacca     120
ggacaatctc ctaaactact gatttattgg gcatccactc ggcacactgg agtccctgat     180
cgcttcacag gcagtggatc tgggacagac ttcactctca ccattactaa cgttcagtct     240
gaagacttgg cagattattt ctgtcagcaa tataacagct atcctctcac gttcggtgct     300
gggaccatgc tggacctgaa aggaggcgga ggatctggcg gcggaggaag ttctggcgga     360
ggcagcgagg tgcagctgca gcagagcgga cccgagctcg tgaagcctgg aacaagcgtg     420
cggatcagct gcaagaccag cggctacacc ttcaccgagt acaccatcca ctgggtcaag     480
cagtcccacg gcaagagcct ggagtggatc ggcaatatca ccccaacaa cggcggcacc      540 acctacaacc agaagttcga ggacaaggcc accctgaccg tggacaagag cagcagcacc     600
gcctacatgg aactgcggag cctgaccagc gaggacagcg ccgtgtacta ttgtgccgcc     660

```
ggttggaact tcgactactg gggccagggc acaaccctga cagtgtctag c            711
```

<210> SEQ ID NO 181
<211> LENGTH: 108
<212> TYPE: PRT
<213> ORGANISM: Artificial Sequence
<220> FEATURE:
<223> OTHER INFORMATION: J591 VL
<400> SEQUENCE: 181

```
Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Ala Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Lys Leu Glu Ile Lys Arg
            100                 105
```

<210> SEQ ID NO 182
<211> LENGTH: 115
<212> TYPE: PRT
<213> ORGANISM: Artificial Sequence
<220> FEATURE:
<223> OTHER INFORMATION: J591 VH
<400> SEQUENCE: 182

```
Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
        115
```

<210> SEQ ID NO 183
<211> LENGTH: 115
<212> TYPE: PRT
<213> ORGANISM: Artificial Sequence
<220> FEATURE:
<223> OTHER INFORMATION: Humanized PSMA VH consensus
<220> FEATURE:
<221> NAME/KEY: misc_feature
<222> LOCATION: (9)..(9)
<223> OTHER INFORMATION: X is A or P
<220> FEATURE:
<221> NAME/KEY: misc_feature
<222> LOCATION: (11)..(11)
<223> OTHER INFORMATION: X is V or L
<220> FEATURE:
<221> NAME/KEY: misc_feature
<222> LOCATION: (24)..(24)
<223> OTHER INFORMATION: X is A or T
<220> FEATURE:
<221> NAME/KEY: misc_feature
<222> LOCATION: (38)..(38)
<223> OTHER INFORMATION: X is R or K
<220> FEATURE:
<221> NAME/KEY: misc_feature
<222> LOCATION: (41)..(41)
<223> OTHER INFORMATION: X is P or H
<220> FEATURE:
<221> NAME/KEY: misc_feature
<222> LOCATION: (55)..(55)
<223> OTHER INFORMATION: X is N or Q
<220> FEATURE:
<221> NAME/KEY: misc_feature
<222> LOCATION: (68)..(68)
<223> OTHER INFORMATION: X is V or A
<220> FEATURE:
<221> NAME/KEY: misc_feature
<222> LOCATION: (70)..(70)
<223> OTHER INFORMATION: X is I or L

<400> SEQUENCE: 183

Glu Val Gln Leu Val Gln Ser Gly Xaa Glu Xaa Lys Lys Pro Gly Ala
1               5                   10                  15

Ser Val Lys Val Ser Cys Lys Xaa Ser Gly Tyr Thr Phe Thr Glu Tyr
                20                  25                  30

Thr Ile His Trp Val Xaa Gln Ala Xaa Gly Lys Gly Leu Glu Trp Ile
            35                  40                  45

Gly Asn Ile Asn Pro Asn Xaa Gly Gly Thr Thr Tyr Asn Gln Lys Phe
        50                  55                  60

Glu Asp Arg Xaa Thr Xaa Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 184
<211> LENGTH: 107
<212> TYPE: PRT
<213> ORGANISM: Artificial Sequence
<220> FEATURE:
<223> OTHER INFORMATION: Humanized PSMA VL consensus
<220> FEATURE:
<221> NAME/KEY: misc_feature
<222> LOCATION: (3)..(3)
<223> OTHER INFORMATION: X is Q or V
<220> FEATURE:
<221> NAME/KEY: misc_feature
<222> LOCATION: (10)..(10)
<223> OTHER INFORMATION: X is T or F
<220> FEATURE:
<221> NAME/KEY: misc_feature
<222> LOCATION: (63)..(63)
<223> OTHER INFORMATION: X is S or T
<220> FEATURE:
<221> NAME/KEY: misc_feature
<222> LOCATION: (80)..(80)
<223> OTHER INFORMATION: X is P or S
<220> FEATURE:

```
<221> NAME/KEY: misc_feature
<222> LOCATION: (85)..(85)
<223> OTHER INFORMATION: X is V or D
<220> FEATURE:
<221> NAME/KEY: misc_feature
<222> LOCATION: (87)..(87)
<223> OTHER INFORMATION: X is Y or F
<220> FEATURE:
<221> NAME/KEY: misc_feature
<222> LOCATION: (103)..(103)
<223> OTHER INFORMATION: X is K or M

<400> SEQUENCE: 184

Asp Ile Xaa Met Thr Gln Ser Pro Ser Xaa Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Xaa Gly
50                  55                  60

Ser Gly Ser Gly Thr Asp Phe Thr Leu Thr Ile Ser Arg Leu Gln Xaa
65                  70                  75                  80

Glu Asp Phe Ala Xaa Tyr Xaa Cys Gln Gln Tyr Asn Ser Tyr Pro Leu
                85                  90                  95

Thr Phe Gly Gln Gly Thr Xaa Val Asp Ile Lys
            100                 105

<210> SEQ ID NO 185
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 185

Glu Val Gln Leu Val Gln Ser Gly Pro Glu Leu Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Lys Gln Ala His Gly Lys Gly Leu Glu Trp Ile
        35                  40                  45

Gly Asn Ile Asn Pro Asn Asn Gly Gly Thr Thr Tyr Asn Gln Lys Phe
50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 186
<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 186
```

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
            35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Arg Leu Gln Ser
65                  70                  75                  80

Glu Asp Phe Ala Asp Tyr Phe Cys Gln Gln Tyr Asn Ser Tyr Pro Leu
                85                  90                  95

Thr Phe Gly Gln Gly Thr Met Val Asp Ile Lys
            100                 105
```

<210> SEQ ID NO 187
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 187

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
50                  55                  60

Glu Asp Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115
```

<210> SEQ ID NO 188
<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 188

```
Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
            35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Arg Leu Gln Ser
65                  70                  75                  80
```

Glu Asp Phe Ala Asp Tyr Phe Cys Gln Gln Tyr Asn Ser Tyr Pro Leu
            85                  90                  95

Thr Phe Gly Gln Gly Thr Lys Val Asp Ile Lys
            100                 105

<210> SEQ ID NO 189
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 189

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 190
<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 190

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 191
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 191

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Gly Gly Thr Thr Tyr Asn Gln Lys Phe
50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 192
<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 192

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 193
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 193

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Gln Gly Gly Thr Thr Tyr Asn Gln Lys Phe
50                  55                  60

```
Glu Asp Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 194
<211> LENGTH: 115
<212> TYPE: PRT
<213> ORGANISM: Artificial Sequence
<220> FEATURE:
<223> OTHER INFORMATION: Humanized PSMA VH consensus
<220> FEATURE:
<221> NAME/KEY: misc_feature
<222> LOCATION: (9)..(9)
<223> OTHER INFORMATION: X is A or P
<220> FEATURE:
<221> NAME/KEY: misc_feature
<222> LOCATION: (11)..(11)
<223> OTHER INFORMATION: X is V or L
<220> FEATURE:
<221> NAME/KEY: misc_feature
<222> LOCATION: (24)..(24)
<223> OTHER INFORMATION: X is A or T
<220> FEATURE:
<221> NAME/KEY: misc_feature
<222> LOCATION: (38)..(38)
<223> OTHER INFORMATION: X is R or K
<220> FEATURE:
<221> NAME/KEY: misc_feature
<222> LOCATION: (41)..(41)
<223> OTHER INFORMATION: X is P or H
<220> FEATURE:
<221> NAME/KEY: misc_feature
<222> LOCATION: (55)..(55)
<223> OTHER INFORMATION: X is N or Q
<220> FEATURE:
<221> NAME/KEY: misc_feature
<222> LOCATION: (68)..(68)
<223> OTHER INFORMATION: X is V or A
<220> FEATURE:
<221> NAME/KEY: misc_feature
<222> LOCATION: (70)..(70)
<223> OTHER INFORMATION: X is I or L
<220> FEATURE:
<221> NAME/KEY: misc_feature
<222> LOCATION: (86)..(86)
<223> OTHER INFORMATION: X is L or P
<220> FEATURE:
<221> NAME/KEY: misc_feature
<222> LOCATION: (98)..(102)
<223> OTHER INFORMATION: is AYWLF, GGWTF, or GAWTM

<400> SEQUENCE: 194

Glu Val Gln Leu Val Gln Ser Gly Xaa Glu Xaa Lys Lys Pro Gly Ala
 1               5                  10                  15

Ser Val Lys Val Ser Cys Lys Xaa Ser Gly Tyr Thr Phe Thr Glu Tyr
             20                  25                  30

Thr Ile His Trp Val Xaa Gln Ala Xaa Gly Lys Gly Leu Glu Trp Ile
         35                  40                  45

Gly Asn Ile Asn Pro Asn Xaa Gly Gly Thr Thr Tyr Asn Gln Lys Phe
     50                  55                  60

Glu Asp Arg Xaa Thr Xaa Thr Val Asp Lys Ser Thr Ser Thr Ala Tyr
 65                  70                  75                  80

Met Glu Leu Ser Ser Xaa Arg Ser Glu Asp Thr Ala Val Tyr Tyr Cys
```

```
                        85                  90                  95
Ala Xaa Xaa Xaa Xaa Asp Tyr Trp Gly Gln Gly Thr Thr Val Thr
            100                 105                 110

Val Ser Ser
        115

<210> SEQ ID NO 195
<211> LENGTH: 106
<212> TYPE: PRT
<213> ORGANISM: Artificial Sequence
<220> FEATURE:
<223> OTHER INFORMATION: Humanized PSMA VL consensus
<220> FEATURE:
<221> NAME/KEY: misc_feature
<222> LOCATION: (3)..(3)
<223> OTHER INFORMATION: X is Q or V
<220> FEATURE:
<221> NAME/KEY: misc_feature
<222> LOCATION: (10)..(10)
<223> OTHER INFORMATION: X is T or F
<220> FEATURE:
<221> NAME/KEY: misc_feature
<222> LOCATION: (63)..(63)
<223> OTHER INFORMATION: X is S or T
<220> FEATURE:
<221> NAME/KEY: misc_feature
<222> LOCATION: (80)..(80)
<223> OTHER INFORMATION: X is P or S
<220> FEATURE:
<221> NAME/KEY: misc_feature
<222> LOCATION: (85)..(85)
<223> OTHER INFORMATION: X is V or D
<220> FEATURE:
<221> NAME/KEY: misc_feature
<222> LOCATION: (87)..(87)
<223> OTHER INFORMATION: X is Y or F
<220> FEATURE:
<221> NAME/KEY: misc_feature
<222> LOCATION: (91)..(95)
<223> OTHER INFORMATION: is FTRYP or YNAYS
<220> FEATURE:
<221> NAME/KEY: misc_feature
<222> LOCATION: (103)..(103)
<223> OTHER INFORMATION: X is K or M

<400> SEQUENCE: 195

Asp Ile Xaa Met Thr Gln Ser Pro Ser Xaa Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Xaa Gly
    50                  55                  60

Ser Gly Ser Gly Thr Asp Phe Thr Leu Thr Ile Ser Arg Leu Gln Xaa
65                  70                  75                  80

Glu Asp Phe Ala Xaa Tyr Xaa Cys Gln Gln Xaa Xaa Xaa Xaa Xaa Leu
                85                  90                  95

Thr Phe Gly Gln Gly Thr Val Asp Ile Lys
            100                 105

<210> SEQ ID NO 196
<211> LENGTH: 115
<212> TYPE: PRT
<213> ORGANISM: Artificial Sequence
<220> FEATURE:
<223> OTHER INFORMATION: Humanized PSMA VH
```

-continued

```
<400> SEQUENCE: 196

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Tyr Trp Leu Phe Asp Tyr Trp Gly Gln Gly Thr Thr Val Thr
            100                 105                 110

Val Ser Ser
        115

<210> SEQ ID NO 197
<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 197

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 198
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 198

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60
```

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Trp Thr Phe Asp Tyr Trp Gly Gln Gly Thr Thr Val Thr
            100                 105                 110

Val Ser Ser
        115

<210> SEQ ID NO 199
<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 199

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Phe Thr Arg Tyr Pro Leu
                85                  90                  95

Thr Phe Gly Gln Gly Thr Lys Val Asp Ile Lys
            100                 105

<210> SEQ ID NO 200
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 200

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ala Trp Thr Met Asp Tyr Trp Gly Gln Gly Thr Thr Val Thr
            100                 105                 110

Val Ser Ser
        115

<210> SEQ ID NO 201

<211> LENGTH: 107
<212> TYPE: PRT
<213> ORGANISM: Artificial Sequence
<220> FEATURE:
<223> OTHER INFORMATION: Humanized PSMA VL

<400> SEQUENCE: 201

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ala Tyr Ser Leu
                85                  90                  95

Thr Phe Gly Gln Gly Thr Lys Val Asp Ile Lys
            100                 105

<210> SEQ ID NO 202
<211> LENGTH: 115
<212> TYPE: PRT
<213> ORGANISM: Artificial Sequence
<220> FEATURE:
<223> OTHER INFORMATION: Humanized PSMA VH

<400> SEQUENCE: 202

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Pro Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 203
<211> LENGTH: 35
<212> TYPE: PRT
<213> ORGANISM: Artificial Sequence
<220> FEATURE:
<223> OTHER INFORMATION: ICOS ICD

<400> SEQUENCE: 203

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
    35

<210> SEQ ID NO 204
<211> LENGTH: 105
<212> TYPE: DNA
<213> ORGANISM: Artificial Sequence
<220> FEATURE:
<223> OTHER INFORMATION: ICOS ICD

<400> SEQUENCE: 204
acaaaaaaga agtattcatc cagtgtgcac gaccctaacg gtgaatacat gttcatgaga    60
gcagtgaaca cagccaaaaa atccagactc acagatgtga cccta                  105

<210> SEQ ID NO 205
<211> LENGTH: 148
<212> TYPE: PRT
<213> ORGANISM: Artificial Sequence
<220> FEATURE:
<223> OTHER INFORMATION: ICOS CD3zeta ICD

<400> SEQUENCE: 205

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu Arg Val Lys Phe Ser Arg Ser Ala Asp Ala Pro Ala Tyr
        35                  40                  45

Gln Gln Gly Gln Asn Gln Leu Tyr Asn Glu Leu Asn Leu Gly Arg Arg
    50                  55                  60

Glu Glu Tyr Asp Val Leu Asp Lys Arg Arg Gly Arg Asp Pro Glu Met
65                  70                  75                  80

Gly Gly Lys Pro Gln Arg Arg Lys Asn Pro Gln Glu Gly Leu Tyr Asn
                85                  90                  95

Glu Leu Gln Lys Asp Lys Met Ala Glu Ala Tyr Ser Glu Ile Gly Met
            100                 105                 110

Lys Gly Glu Arg Arg Arg Gly Lys Gly His Asp Gly Leu Tyr Gln Gly
        115                 120                 125

Leu Ser Thr Ala Thr Lys Asp Thr Tyr Asp Ala Leu His Met Gln Ala
    130                 135                 140

Leu Pro Pro Arg
145

<210> SEQ ID NO 206
<211> LENGTH: 444
<212> TYPE: DNA
<213> ORGANISM: Artificial Sequence
<220> FEATURE:
<223> OTHER INFORMATION: ICOS CD3zeta ICD

<400> SEQUENCE: 206
acaaaaaaga agtattcatc cagtgtgcac gaccctaacg gtgaatacat gttcatgaga    60
gcagtgaaca cagccaaaaa atccagactc acagatgtga ccctaagagt gaagttcagc   120
aggagcgcag acgcccccgc gtaccagcag ggccagaacc agctctataa cgagctcaat   180
ctaggacgaa gagaggagta cgatgttttg gacaagagac gtggccggga ccctgagatg   240
gggggaaagc cgcagagaag gaagaaccct caggaaggcc tgtacaatga actgcagaaa   300
gataagatgg cggaggccta cagtgagatt gggatgaaag cgagcgccg gaggggcaag   360

```
gggcacgatg gcctttacca gggtctcagt acagccacca aggacaccta cgacgccctt    420
cacatgcagg ccctgccccc tcgc                                          444
```

<210> SEQ ID NO 207
<211> LENGTH: 148
<212> TYPE: PRT
<213> ORGANISM: Artificial Sequence
<220> FEATURE:
<223> OTHER INFORMATION: variant ICOS CD3zeta ICD

<400> SEQUENCE: 207

```
Thr Lys Lys Lys Tyr Ser Ser Ser Val His Asp Pro Asn Gly Glu Tyr
1               5                   10                  15

Met Asn Met Arg Ala Val Asn Thr Ala Lys Lys Ser Arg Leu Thr Asp
            20                  25                  30

Val Thr Leu Arg Val Lys Phe Ser Arg Ser Ala Asp Ala Pro Ala Tyr
        35                  40                  45

Gln Gln Gly Gln Asn Gln Leu Tyr Asn Glu Leu Asn Leu Gly Arg Arg
    50                  55                  60

Glu Glu Tyr Asp Val Leu Asp Lys Arg Arg Gly Arg Asp Pro Glu Met
65                  70                  75                  80

Gly Gly Lys Pro Gln Arg Arg Lys Asn Pro Gln Glu Gly Leu Tyr Asn
                85                  90                  95

Glu Leu Gln Lys Asp Lys Met Ala Glu Ala Tyr Ser Glu Ile Gly Met
            100                 105                 110

Lys Gly Glu Arg Arg Arg Gly Lys Gly His Asp Gly Leu Tyr Gln Gly
        115                 120                 125

Leu Ser Thr Ala Thr Lys Asp Thr Tyr Asp Ala Leu His Met Gln Ala
    130                 135                 140

Leu Pro Pro Arg
145
```

<210> SEQ ID NO 208
<211> LENGTH: 444
<212> TYPE: DNA
<213> ORGANISM: Artificial Sequence
<220> FEATURE:
<223> OTHER INFORMATION: variant ICOS CD3zeta ICD

<400> SEQUENCE: 208

```
acaaaaaaga agtattcatc cagtgtgcac gaccctaacg gtgaatacat gaacatgaga    60
gcagtgaaca cagccaaaaa atccagactc acagatgtga ccctaagagt gaagttcagc   120
aggagcgcag acgccccgc gtaccagcag ggccagaacc agctctataa cgagctcaat    180
ctaggacgaa gagaggagta cgatgttttg gacaagagac gtggccggga ccctgagatg   240
gggggaaagc cgcagagaag gaagaaccct caggaaggcc tgtacaatga actgcagaaa   300
gataagatgg cggaggccta cagtgagatt gggatgaaag cgagcgccg gaggggcaag    360 gggcacgatg gcctttacca gggtctcagt acagccacca aggacaccta cgacgccctt   420
cacatgcagg ccctgccccc tcgc                                          444
```

<210> SEQ ID NO 209
<211> LENGTH: 481
<212> TYPE: PRT
<213> ORGANISM: Artificial Sequence
<220> FEATURE:
<223> OTHER INFORMATION: 2F5 human PSMA-CAR ICOS CD3z

<400> SEQUENCE: 209

-continued

```
Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
            20                  25                  30

Lys Lys Pro Gly Glu Ser Leu Lys Ile Ser Cys Lys Gly Ser Gly Tyr
        35                  40                  45

Ser Phe Thr Ser Asn Trp Ile Gly Trp Val Arg Gln Met Pro Gly Lys
    50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Asn Ser Leu Lys Ala Ser Asp Thr
            100                 105                 110

Ala Met Tyr Tyr Cys Ala Arg Gln Thr Gly Phe Leu Trp Ser Phe Asp
        115                 120                 125

Leu Trp Gly Arg Gly Thr Leu Val Thr Val Ser Ser Gly Gly Gly Gly
    130                 135                 140

Ser Gly Gly Gly Gly Ser Gly Gly Gly Gly Ser Ala Ile Gln Leu Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Ser Ala Leu Ala Trp Tyr Gln
            180                 185                 190

Gln Lys Pro Gly Lys Ala Pro Lys Leu Leu Ile Tyr Asp Ala Ser Ser
        195                 200                 205

Leu Glu Ser Gly Val Pro Ser Arg Phe Ser Gly Ser Gly Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Phe Asn Ser Tyr Pro Leu Thr Phe Gly Gly Gly
                245                 250                 255

Thr Lys Val Glu Ile Lys Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Phe Trp Leu Pro Ile Gly Cys Ala Ala Phe Val
305                 310                 315                 320

Val Val Cys Ile Leu Gly Cys Ile Leu Ile Cys Trp Leu Thr Lys Lys
                325                 330                 335

Lys Tyr Ser Ser Ser Val His Asp Pro Asn Gly Glu Tyr Met Phe Met
            340                 345                 350

Arg Ala Val Asn Thr Ala Lys Lys Ser Arg Leu Thr Asp Val Thr Leu
        355                 360                 365

Arg Val Lys Phe Ser Arg Ser Ala Asp Ala Pro Ala Tyr Gln Gln Gly
    370                 375                 380

Gln Asn Gln Leu Tyr Asn Glu Leu Asn Leu Gly Arg Arg Glu Glu Tyr
385                 390                 395                 400

Asp Val Leu Asp Lys Arg Gly Arg Asp Pro Glu Met Gly Gly Lys
                405                 410                 415
```

Pro Gln Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
465                 470                 475                 480

Arg

<210> SEQ ID NO 210
<211> LENGTH: 1443
<212> TYPE: DNA
<213> ORGANISM: Artificial Sequence
<220> FEATURE:
<223> OTHER INFORMATION: 2F5 human PSMA-CAR ICOS CD3z

<400> SEQUENCE: 210

| | | |
|---|---|---|
| atggccttac cagtgaccgc cttgctcctg ccgctggcct tgctgctcca cgccgccagg | | 60 |
| ccggaggtgc agctggtgca gtctggagca gaggtgaaaa agcccgggga gtctctgaag | | 120 |
| atctcctgta agggttctgg atacagtttt accagcaact ggatcggctg ggtgcgccag | | 180 |
| atgcccggga aaggcctgga gtggatgggg atcatctatc ctggtgactc tgataccaga | | 240 |
| tacagcccgt ccttccaagg ccaggtcacc atctcagccg acaagtccat cagcaccgcc | | 300 |
| tacctgcagt ggaacagcct gaaggcctcg gacaccgcca tgtattactg cgagacaa | | 360 |
| actggttttcc tctggtcctt cgatctctgg ggccgtggca ccctggtcac tgtctcctca | | 420 |
| ggtggcggtg gctcgggcgg tggtgggtcg ggtggcggcg gatctgccat ccagttgacc | | 480 |
| cagtctccat cctccctgtc tgcatctgta ggagacagag tcaccatcac ttgccgggca | | 540 |
| agtcaggaca ttagcagtgc tttagcctgg tatcagcaga aaccggggaa agctcctaag | | 600 |
| ctcctgatct atgatgcctc cagttttggaa agtggggtcc catcaaggtt cagcggcagt | | 660 |
| ggatctggga cagatttcac tctcaccatc agcagcctgc agcctgaaga ttttgcaact | | 720 |
| tattactgtc aacagtttaa tagttacccg ctcacttttcg gcggagggac caaggtggag | | 780 |
| atcaaaatca aaccacgac gccagcgccg cgaccaccaa caccggcgcc caccatcgcg | | 840 |
| tcgcagcccc tgtccctgcg cccagaggcg tgccggccag cggcgggggg cgcagtgcac | | 900 |
| acgaggggc tggacttcgc ctgtgatttc tggttaccca taggatgtgc agcctttgtt | | 960 |
| gtagtctgca ttttgggatg catacttatt tgttggctta caaaaagaa gtattcatcc | | 1020 |
| agtgtgcacg accctaacgg tgaatacatg ttcatgagag cagtgaacac agccaaaaaa | | 1080 |
| tccagactca cagatgtgac cctaagagtg aagttcagca ggagcgcaga cgcccccgcg | | 1140 |
| taccagcagg gccagaacca gctctataac gagctcaatc taggacgaag agaggagtac | | 1200 |
| gatgttttgg acaagagacg tggccgggac cctgagatgg ggggaaagcc gcagagaagg | | 1260 |
| aagaaccctc aggaaggcct gtacaatgaa ctgcagaaag ataagatggc ggaggcctac | | 1320 |
| agtgagattg gatgaaagg cgagcgccgg aggggcaagg gcacgatgg cctttaccag | | 1380 |
| ggtctcagta cagccaccaa ggacacctac gacgcccttc acatgcaggc cctgccccct | | 1440 |
| cgc | | 1443 |

<210> SEQ ID NO 211
<211> LENGTH: 481
<212> TYPE: PRT
<213> ORGANISM: Artificial Sequence
<220> FEATURE:
<223> OTHER INFORMATION: 2F5 human PSMA-CAR varICOS CD3z

<400> SEQUENCE: 211

```
Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
            20                  25                  30

Lys Lys Pro Gly Glu Ser Leu Lys Ile Ser Cys Lys Gly Ser Gly Tyr
        35                  40                  45

Ser Phe Thr Ser Asn Trp Ile Gly Trp Val Arg Gln Met Pro Gly Lys
    50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Asn Ser Leu Lys Ala Ser Asp Thr
            100                 105                 110

Ala Met Tyr Tyr Cys Ala Arg Gln Thr Gly Phe Leu Trp Ser Phe Asp
        115                 120                 125

Leu Trp Gly Arg Gly Thr Leu Val Thr Val Ser Ser Gly Gly Gly Gly
    130                 135                 140

Ser Gly Gly Gly Gly Ser Gly Gly Gly Gly Ser Ala Ile Gln Leu Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Ser Ala Leu Ala Trp Tyr Gln
            180                 185                 190

Gln Lys Pro Gly Lys Ala Pro Lys Leu Leu Ile Tyr Asp Ala Ser Ser
        195                 200                 205

Leu Glu Ser Gly Val Pro Ser Arg Phe Ser Gly Ser Gly Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Phe Asn Ser Tyr Pro Leu Thr Phe Gly Gly Gly
                245                 250                 255

Thr Lys Val Glu Ile Lys Ile Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Phe Trp Leu Pro Ile Gly Cys Ala Ala Phe Val
305                 310                 315                 320

Val Val Cys Ile Leu Gly Cys Ile Leu Ile Cys Trp Leu Thr Lys Lys
                325                 330                 335

Lys Tyr Ser Ser Ser Val His Asp Pro Asn Gly Glu Tyr Met Asn Met
            340                 345                 350

Arg Ala Val Asn Thr Ala Lys Lys Ser Arg Leu Thr Asp Val Thr Leu
        355                 360                 365

Arg Val Lys Phe Ser Arg Ser Ala Asp Ala Pro Ala Tyr Gln Gln Gly
    370                 375                 380

Gln Asn Gln Leu Tyr Asn Glu Leu Asn Leu Gly Arg Arg Glu Glu Tyr
385                 390                 395                 400
```

Asp Val Leu Asp Lys Arg Arg Gly Arg Asp Pro Glu Met Gly Gly Lys
            405                 410                 415

Pro Gln Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
450                 455                 460

Ala Thr Lys Asp Thr Tyr Asp Ala Leu His Met Gln Ala Leu Pro Pro
465                 470                 475                 480

Arg

<210> SEQ ID NO 212
<211> LENGTH: 1443
<212> TYPE: DNA
<213> ORGANISM: Artificial Sequence
<220> FEATURE:
<223> OTHER INFORMATION: 2F5 human PSMA-CAR varICOS CD3z

<400> SEQUENCE: 212

| | |
|---|---:|
| atggccttac cagtgaccgc cttgctcctg ccgctggcct tgctgctcca cgccgccagg | 60 |
| ccggaggtgc agctggtgca gtctggagca gaggtgaaaa agcccgggga gtctctgaag | 120 |
| atctcctgta agggttctgg atacagtttt accagcaact ggatcggctg gtgcgccag | 180 |
| atgcccggga aaggcctgga gtggatgggg atcatctatc ctggtgactc tgataccaga | 240 |
| tacagcccgt ccttccaagg ccaggtcacc atctcagccg acaagtccat cagcaccgcc | 300 |
| tacctgcagt ggaacagcct gaaggcctcg acaccgcca tgtattactg cgagacaa | 360 |
| actggtttcc tctggtcctt cgatctctgg ggccgtggca ccctggtcac tgtctcctca | 420 |
| ggtggcggtg gctcgggcgg tggtgggtcg ggtggcggcg gatctgccat ccagttgacc | 480 |
| cagtctccat cctccctgtc tgcatctgta ggagacagag tcaccatcac ttgccgggca | 540 |
| agtcaggaca ttagcagtgc tttagcctgg tatcagcaga accggggaa agctcctaag | 600 |
| ctcctgatct atgatgcctc cagtttggaa agtggggtcc catcaaggtt cagcggcagt | 660 |
| ggatctggga cagatttcac tctcaccatc agcagcctgc agcctgaaga ttttgcaact | 720 |
| tattactgtc aacagtttaa tagttacccg ctcactttcg gcggagggac caaggtggag | 780 |
| atcaaaatca aaccacgac gccagcgccg cgaccaccaa caccggcgcc caccatcgcg | 840 |
| tcgcagcccc tgtccctgcg cccagaggcg tgccggccag cggcggggg cgcagtgcac | 900 |
| acgagggggc tggacttcgc ctgtgatttc tggttaccca taggatgtgc agcctttgtt | 960 |
| gtagtctgca ttttgggatg catacttatt tgttggctta caaaaaagaa gtattcatcc | 1020 |
| agtgtgcacg accctaacgg tgaatacatg aacatgagag cagtgaacac agccaaaaaa | 1080 |
| tccagactca cagatgtgac cctaagagtg aagttcagca ggagcgcaga cgcccccgcg | 1140 |
| taccagcagg gccagaacca gctctataac gagctcaatc taggacgaag agaggagtac | 1200 |
| gatgttttgg acaagagacg tggccgggac cctgagatgg ggggaaagcc gcagagaagg | 1260 |
| aagaaccctc aggaaggcct gtacaatgaa ctgcagaaag ataagatggc ggaggcctac | 1320 |
| agtgagattg ggatgaaagg cgagcgccgg aggggcaagg gcacgatgg cctttaccag | 1380 |
| ggtctcagta cagccaccaa ggacacctac gacgcccttc acatgcaggc cctgcccct | 1440 |
| cgc | 1443 |

-continued

<210> SEQ ID NO 213
<211> LENGTH: 237
<212> TYPE: PRT
<213> ORGANISM: Artificial Sequence
<220> FEATURE:
<223> OTHER INFORMATION: PD1-4-1BB switch receptor

<400> SEQUENCE: 213

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Tyr Cys Lys Lys Arg Gly Arg Lys Lys Leu Leu Tyr Ile Phe Lys Gln
        195                 200                 205

Pro Phe Met Arg Pro Val Gln Thr Thr Gln Glu Glu Asp Gly Cys Ser
    210                 215                 220

Cys Arg Phe Pro Glu Glu Glu Glu Gly Gly Cys Glu Leu
225                 230                 235
```

<210> SEQ ID NO 214
<211> LENGTH: 711
<212> TYPE: DNA
<213> ORGANISM: Artificial Sequence
<220> FEATURE:
<223> OTHER INFORMATION: PD1-4-1BB switch receptor

<400> SEQUENCE: 214

```
atgcagatcc cacaggcgcc ctggccagtc gtctgggcgg tgctacaact gggctggcgg      60
ccaggatggt tcttagactc cccagacagg ccctggaacc ccccaccctt ctccccagcc     120
ctgctcgtgg tgaccgaagg ggacaacgcc accttcacct gcagcttctc caacacatcg     180
gagagcttcg tgctaaactg gtaccgcatg agcccagca accagacgga caagctggcc      240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg ggccatctc cctggccccc aaggcgcaga tcaaagagag cctgcgggca     420
gagctcaggg tgacagagag aagggcagaa gtgcccacag cccaccccag ccctcacccc    480
```

```
aggccagccg gccagttcca aaccctggtt atctacatct gggcgccctt ggccgggact    540 tgtgggtcc ttctcctgtc actggttatc acccttact gcaaaaaacg gggcagaaag    600
aaactcctgt atatattcaa acaaccattt atgagaccag tacaaactac tcaagaggaa    660
gatggctgta gctgccgatt tccagaagaa gaagaaggag gatgtgaact g            711
```

<210> SEQ ID NO 215
<211> LENGTH: 237
<212> TYPE: PRT
<213> ORGANISM: Artificial Sequence
<220> FEATURE:
<223> OTHER INFORMATION: PD1A132L-4-1BB switch receptor

<400> SEQUENCE: 215

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Tyr Cys Lys Lys Arg Gly Arg Lys Lys Leu Leu Tyr Ile Phe Lys Gln
        195                 200                 205

Pro Phe Met Arg Pro Val Gln Thr Thr Gln Glu Glu Asp Gly Cys Ser
    210                 215                 220

Cys Arg Phe Pro Glu Glu Glu Glu Gly Gly Cys Glu Leu
225                 230                 235
```

<210> SEQ ID NO 216
<211> LENGTH: 711
<212> TYPE: DNA
<213> ORGANISM: Artificial Sequence
<220> FEATURE:
<223> OTHER INFORMATION: PD1A132L-4-1BB switch receptor

<400> SEQUENCE: 216

```
atgcagatcc cacaggcgcc ctggccagtc gtctgggcgg tgctacaact gggctggcgg    60
ccaggatggt tcttagactc cccagacagg ccctggaacc cccccacctt ctccccagcc   120
ctgctcgtgg tgaccgaagg ggacaacgcc accttcacct gcagcttctc caacacatcg   180
```

```
gagagcttcg tgctaaactg gtaccgcatg agccccagca accagacgga caagctggcc      240
gccttccccg aggaccgcag ccagcccggc caggactgcc gcttccgtgt cacacaactg      300
cccaacgggc gtgacttcca catgagcgtg gtcagggccc ggcgcaatga cagcggcacc      360
tacctctgtg gggccatctc cctggccccc aagctgcaga tcaaagagag cctgcgggca      420
gagctcaggg tgacagagag aagggcagaa gtgcccacag cccacccag ccctcaccc       480 aggccagccg ccagttccaa accctggtt atctacatct gggcgccctt ggccgggact      540 tgtgggtcc ttctcctgtc actggttatc acctttact gcaaaaaacg gggcagaaag        600
aaactcctgt atatattcaa acaaccattt atgagaccag tacaaactac tcaagaggaa      660
gatggctgta gctgccgatt ccagaagaa gaagaaggag gatgtgaact g                711
```

<210> SEQ ID NO 217
<211> LENGTH: 2223
<212> TYPE: DNA
<213> ORGANISM: Artificial Sequence
<220> FEATURE:
<223> OTHER INFORMATION: PD1-CD28-F2A-2F5PSMA-CAR ICOS CD3z

<400> SEQUENCE: 217

```
atgcagatcc cacaggcgcc ctggccagtc gtctgggcgg tgctacaact gggctggcgg      60
ccaggatggt tcttagactc cccagacagg ccctggaacc ccccaccctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccacccag ccctcaccc      480 aggccagccg ccagttccaa accctggtg ttttgggtgc tggtggtggt tggtggagtc      540
ctggcttgct atagcttgct agtaacagtg gcctttatta ttttctgggt gaggagtaag     600
aggagcaggc tcctgcacag tgactacatg aacatgactc cccgccgccc cgggcccacc     660
cgcaagcatt accagcccta tgccccacca cgcgacttcg cagcctatcg ctccgtgaaa     720
cagactttga ttttgaccct tctcaagttg gcgggagacg tggagtccaa cccagggccg     780
atggccttac cagtgaccgc cttgctcctg ccgctggcct tgctgctcca cgccgccagg     840
ccggaggtgc agctggtgca gtctggagca gaggtgaaaa agcccgggga gtctctgaag     900
atctcctgta agggttctgg atacagtttt accagcaact ggatcggctg ggtgcgccag     960
atgcccggga aaggcctgga gtggatgggg atcatctatc ctggtgactc tgataccaga    1020
tacagcccgt ccttccaagg ccaggtcacc atctcagccg acaagtccat cagcaccgcc    1080
tacctgcagt ggaacagcct gaaggcctcg gacaccgcca tgtattactg tgcgagacaa    1140 actggttttcc tctggtcctt cgatctctgg ggccgtggca cctggtcac tgtctcctca    1200 ggtggcggtg gctcgggcgg tggtgggtcg ggtggcggcg gatctgccat ccagttgacc    1260
cagtctccat cctccctgtc tgcatctgta ggagacagag tcaccatcac ttgccgggca    1320
agtcaggaca ttagcagtgc tttagcctgg tatcagcaga accggggaa agctcctaag    1380 ctcctgatct atgatgcctc cagtttggaa agtggggtcc catcaaggtt cagcggcagt    1440
ggatctggga cagatttcac tctcaccatc agcagcctgc agcctgaaga ttttgcaact    1500
```

```
tattactgtc aacagtttaa tagttacccg ctcactttcg gcggagggac caaggtggag   1560
atcaaaatca aaaccacgac gccagcgccg cgaccaccaa caccggcgcc caccatcgcg   1620
tcgcagcccc tgtccctgcg cccagaggcg tgccggccag cggcgggggg cgcagtgcac   1680 acgaggggc tggacttcgc ctgtgatttc tggttaccca taggatgtgc agcctttgtt    1740
gtagtctgca ttttgggatg catacttatt tgttggctta caaaaagaa gtattcatcc    1800 agtgtgcacg accctaacgg tgaatacatg ttcatgagag cagtgaacac agccaaaaaa   1860
tccagactca cagatgtgac cctaagagtg aagttcagca ggagcgcaga cgcccccgcg   1920
taccagcagg gccagaacca gctctataac gagctcaatc taggacgaag agaggagtac   1980
gatgttttgg acaagagacg tggccgggac cctgagatgg ggggaaagcc gcagagaagg   2040
aagaaccctc aggaaggcct gtacaatgaa ctgcagaaag ataagatggc ggaggcctac   2100
agtgagattg ggatgaaagg cgagcgccgg aggggcaagg ggcacgatgg cctttaccag   2160
ggtctcagta cagccaccaa ggacacctac gacgcccttc acatgcaggc cctgccccct   2220
cgc                                                                  2223

<210> SEQ ID NO 218
<211> LENGTH: 2223
<212> TYPE: DNA
<213> ORGANISM: Artificial Sequence
<220> FEATURE:
<223> OTHER INFORMATION: PD1-CD28-2F5PSMA-CAR varICOS CD3z

<400> SEQUENCE: 218
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccacccccag cccctcaccc    480 aggccagccg ccagttcca aaccctggtg ttttgggtgc tggtggtggt tggtggagtc    540
ctggcttgct atagcttgct agtaacagtg gcctttatta tttttctgggt gaggagtaag    600 aggagcaggc tcctgcacag tgactacatg aacatgactc ccgccgccc cgggcccacc    660 cgcaagcatt accagcccta tgccccacca cgcgacttcg cagcctatcg ctccgtgaaa    720
cagactttga ttttgacct ctcaagttg gcgggagacg tggagtccaa cccagggccg     780
atggccttac cagtgaccgc cttgctcctg ccgctggcct tgctgctcca cgccgccagg    840
ccggaggtgc agctggtgca gtctggagca gaggtgaaaa agcccgggga gtctctgaag    900
atctcctgta agggttctgg atacagtttt accagcaact ggatcggctg ggtgcgccag    960
atgcccggga aaggcctgga gtggatgggg atcatctatc ctggtgactc tgataccaga   1020
tacagcccgt ccttccaagg ccaggtcacc atctcagccg acaagtccat cagcaccgcc   1080
tacctgcagt ggaacagcct gaaggcctcg gacaccgcca tgtattactg tgcgagacaa   1140
actggtttcc tctggtcctt cgatctctgg ggccgtggca ccctggtcac tgtctcctca   1200
ggtggcggtg gctcggcgg tggtgggtcg ggtggcggcg gatctgccat ccagttgacc   1260
cagtctccat cctccctgtc tgcatctgta ggagacagag tcaccatcac ttgccgggca   1320
```

```
agtcaggaca ttagcagtgc tttagcctgg tatcagcaga aaccggggaa agctcctaag   1380
ctcctgatct atgatgcctc cagtttggaa agtggggtcc catcaaggtt cagcggcagt   1440
ggatctggga cagatttcac tctcaccatc agcagcctgc agcctgaaga ttttgcaact   1500
tattactgtc aacagtttaa tagttacccg ctcactttcg gcggagggac caaggtggag   1560
atcaaaatca aaaccacgac gccagcgccg cgaccaccaa caccggcgcc caccatcgcg   1620
tcgcagcccc tgtccctgcg cccagaggcg tgccggccag gcggcggggg cgcagtgcac   1680
acgagggggc tggacttcgc ctgtgatttc tggttaccca taggatgtgc agcctttgtt   1740
gtagtctgca ttttgggatg catacttatt tgttggctta caaaaaagaa gtattcatcc   1800
agtgtgcacg accctaacgg tgaatacatg aacatgagag cagtgaacac agccaaaaaa   1860
tccagactca cagatgtgac cctaagagtg aagttcagca ggagcgcaga cgcccccgcg   1920
taccagcagg gccagaacca gctctataac gagctcaatc taggacgaag agaggagtac   1980
gatgttttgg acaagagacg tggccgggac cctgagatgg ggggaaagcc gcagagaagg   2040
aagaaccctc aggaaggcct gtacaatgaa ctgcagaaag ataagatggc ggaggcctac   2100
agtgagattg ggatgaaagg cgagcgccgg aggggcaagg ggcacgatgg cctttaccag   2160
ggtctcagta cagccaccaa ggacacctac gacgcccttc acatgcaggc cctgccccct   2220
cgc                                                                2223

<210> SEQ ID NO 219
<211> LENGTH: 2205
<212> TYPE: DNA
<213> ORGANISM: Artificial Sequence
<220> FEATURE:
<223> OTHER INFORMATION: PD1A132L-CD28-2F5PSMA-CAR ICOS CD3z

<400> SEQUENCE: 219
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aagctgcaga tcaaagagag cctgcgggca    420
gagctcaggg tgacagagag aagggcagaa gtgcccacag cccaccccag ccctcaccc    480 aggccagccg ccagttcca aaccctggtg gttggtgtcg tggcggcct gctgggcagc    540 ctggtgctgc tagtctgggt cctggccgtc atcaggagta agaggagcag gctcctgcac    600
agtgactaca tgaacatgac tccccgccgc cccgggccca cccgcaagca ttaccagccc    660
tatgccccac cacgcgactt cgcagcctat cgctccgtga acagactttt gaattttgac    720
cttctcaagt tggcgggaga cgtggagtcc aacccagggc cgatggcctt accagtgacc    780
gccttgctcc tgccgctggc cttgctgctc cacgccgcca ggccgaggt gcagctggtg    840 cagtctggag cagaggtgaa aaagcccggg gagtctctga gatcctg taagggttct    900 ggatacagtt ttaccagcaa ctggatcggc tgggtgcgcc agatgccgg gaaaggcctg    960 gagtggatgg ggatcatcta tcctggtgac tctgatacca gatacagccc gtccttccaa   1020
ggccaggtca ccatctcagc cgacaagtcc atcagcaccg cctacctgca gtggaacagc   1080
```

-continued

| | |
|---|---|
| ctgaaggcct cggacaccgc catgtattac tgtgcgagac aaactggttt cctctggtcc | 1140 |
| ttcgatctct ggggccgtgg caccctggtc actgtctcct caggtggcgg tggctcgggc | 1200 |
| ggtggtgggt cgggtggcgg cggatctgcc atccagttga cccagtctcc atcctccctg | 1260 |
| tctgcatctg taggagacag agtcaccatc acttgccggg caagtcagga cattagcagt | 1320 |
| gctttagcct ggtatcagca gaaaccgggg aaagctccta agctcctgat ctatgatgcc | 1380 |
| tccagtttgg aaagtggggt cccatcaagg ttcagcggca gtggatctgg gacagatttc | 1440 |
| actctcacca tcagcagcct gcagcctgaa gattttgcaa cttattactg tcaacagttt | 1500 |
| aatagttacc cgctcacttt cggcggaggg accaaggtgg agatcaaaat caaaaccacg | 1560 |
| acgccagcgc cgcgaccacc aacaccggcg cccaccatcg cgtcgcagcc cctgtccctg | 1620 |
| cgcccagagg cgtgccggcc agcggcgggg ggcgcagtgc acacgagggg gctggacttc | 1680 |
| gcctgtgatt tctggttacc cataggatgt gcagcctttg ttgtagtctg cattttggga | 1740 |
| tgcatactta tttgttggct acaaaaaag aagtattcat ccagtgtgca cgacccta ac | 1800 |
| ggtgaataca tgttcatgag agcagtgaac acagccaaaa atccagact cacagatgtg | 1860 |
| accctaagag tgaagttcag caggagcgca gacgcccccg cgtaccagca gggccagaac | 1920 |
| cagctctata acgagctcaa tctaggacga agagaggagt acgatgtttt ggacaagaga | 1980 |
| cgtggccggg accctgagat ggggggaaag ccgcagagaa ggaagaaccc tcaggaaggc | 2040 |
| ctgtacaatg aactgcagaa agataagatg gcggaggcct acagtgagat tgggatgaaa | 2100 |
| ggcgagcgcc ggaggggcaa ggggcacgat ggcctttacc agggtctcag tacagccacc | 2160 |
| aaggacacct acgacgccct tcacatgcag gccctgcccc ctcgc | 2205 |

<210> SEQ ID NO 220
<211> LENGTH: 2205
<212> TYPE: DNA
<213> ORGANISM: Artificial Sequence
<220> FEATURE:
<223> OTHER INFORMATION: PD1A132L-CD28-2F5PSMA-CAR varICOS CD3z

<400> SEQUENCE: 220

| | |
|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| agagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aagctgcaga tcaaagagag cctgcgggca | 420 |
| gagctcaggg tgacagagag aagggcagaa gtgcccacag cccaccccag ccctcaccc | 480 |
| aggccagccg ccagttcca accctggtg ttggtgtcg tgggcggcct gctgggcagc | 540 |
| ctggtgctgc tagtctgggt cctggccgtc atcaggagta gaggagcag gctcctgcac | 600 |
| agtgactaca tgaacatgac tccccgccgc cccgggccca ccgcaagca ttaccagccc | 660 |
| tatgccccac cacgcgactt cgcagcctat cgctccgtga acagactttt gaattttgac | 720 |
| cttctcaagt ggcgggaga cgtggagtcc aacccagggc cgatggcctt accagtgacc | 780 |
| gccttgctcc tgccgctggc cttgctgctc cacgccgcca ggccggaggt gcagctggtg | 840 |
| cagtctggag cagaggtgaa aaagcccggg gagtctctga gatctcctg taagggttct | 900 |
| ggatacagtt ttaccagcaa ctggatcggc tgggtgcgcc agatgcccgg gaaaggcctg | 960 |

```
gagtggatgg ggatcatcta tcctggtgac tctgatacca gatacagccc gtccttccaa    1020
ggccaggtca ccatctcagc cgacaagtcc atcagcaccg cctacctgca gtggaacagc    1080
ctgaaggcct cggacaccgc catgtattac tgtgcgagac aaactggttt cctctggtcc    1140
ttcgatctct ggggccgtgg caccctggtc actgtctcct caggtggcgg tggctcgggc    1200
ggtggtgggt cgggtggcgg cggatctgcc atccagttga cccagtctcc atcctccctg    1260
tctgcatctg taggagacag agtcaccatc acttgccggg caagtcagga cattagcagt    1320
gctttagcct ggtatcagca gaaaccgggg aaagctccta agctcctgat ctatgatgcc    1380
tccagtttgg aaagtggggt cccatcaagg ttcagcggca gtggatctgg gacagatttc    1440
actctcacca tcagcagcct gcagcctgaa gattttgcaa cttattactg tcaacagttt    1500
aatagttacc cgctcacttt cggcggaggg accaaggtgg agatcaaaat caaaaccacg    1560
acgccagcgc gcgaccacc aacaccggcg cccaccatcg cgtcgcagcc cctgtccctg    1620
cgcccagagg cgtgccggcc agcggcgggg ggcgcagtgc acacgagggg gctggacttc    1680
gcctgtgatt tctggttacc cataggatgt gcagcctttg ttgtagtctg cattttggga    1740
tgcatactta tttgttggct tacaaaaaag aagtattcat ccagtgtgca cgaccctaac    1800
ggtgaataca tgaacatgag agcagtgaac acagccaaaa aatccagact cacagatgtg    1860
accctaagag tgaagttcag caggagcgca gacgcccccg cgtaccagca gggccagaac    1920
cagctctata cgagctcaa tctaggacga agagaggagt acgatgtttt ggacaagaga    1980
cgtggccggg accctgagat gggggggaaag ccgcagagaa ggaagaaccc tcaggaaggc    2040
ctgtacaatg aactgcagaa agataagatg gcggaggcct acagtgagat tgggatgaaa    2100
ggcgagcgcc ggaggggcaa ggggcacgat ggcctttacc agggtctcag tacagccacc    2160
aaggacacct acgacgccct tcacatgcag gccctgcccc ctcgc                    2205
```

<210> SEQ ID NO 221
<211> LENGTH: 2220
<212> TYPE: DNA
<213> ORGANISM: Artificial Sequence
<220> FEATURE:
<223> OTHER INFORMATION: PD1A132L-41BB-2F5PSMA-CAR ICOS CD3z

<400> SEQUENCE: 221

```
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aagctgcaga tcaaagagag cctgcgggca    420
gagctcaggg tgacagagag aaagggcaga agtgcccacag cccaccccag cccctcaccc    480
aggccagccg ccagttcca aaccctggtt atctacatct gggcgcccct tggccgggact    540 tgtgggtcc ttctcctgtc actggttatc acccttact gcaaaaacg gggcagaaag    600 aaactcctgt atatattcaa acaaccattt atgagaccag tacaaactac tcaagaggaa    660 gatgctgta gctgccgatt ccagaagaa gaagaaggag atgtgaact ggtgaaacag    720 actttgaatt ttgaccttct caagttggcg ggagacgtgg agtccaaccc agggccgatg    780
```

```
gccttaccag tgaccgcctt gctcctgccg ctggccttgc tgctccacgc cgccaggccg    840
gaggtgcagc tggtgcagtc tggagcagag gtgaaaaagc ccggggagtc tctgaagatc    900
tcctgtaagg gttctggata cagttttacc agcaactgga tcggctgggt gcgccagatg    960
cccgggaaag gcctggagtg gatggggatc atctatcctg gtgactctga taccagatac   1020
agcccgtcct tccaaggcca ggtcaccatc tcagccgaca gtccatcagc accgcctac    1080 ctgcagtgga acagcctgaa ggcctcggac accgccatgt attactgtgc gagacaaact   1140
ggtttcctct ggtccttcga tctctggggc cgtggcaccc tggtcactgt ctcctcaggt   1200
ggcggtggct cgggcggtgg tgggtcgggt ggcggcggat ctgccatcca gttgacccag   1260
tctccatcct ccctgtctgc atctgtagga gacagagtca ccatcacttg ccgggcaagt   1320
caggacatta gcagtgcttt agcctggtat cagcagaaac cggggaaagc tcctaagctc   1380
ctgatctatg atgcctccag tttggaaagt ggggtcccat caaggttcag cggcagtgga   1440
tctgggacag atttcactct caccatcagc agcctgcagc ctgaagattt tgcaacttat   1500
tactgtcaac agtttaatag ttacccgctc actttcggcg agggaccaa ggtggagatc    1560 aaaatcaaaa ccacgacgcc agcgccgcga ccaccaacac cggcgcccac catcgcgtcg   1620 cagccccgt cctgcgccc agaggcgtgc cggccgcgg cggggggcgc agtgcacacg      1680
agggggctgg acttcgcctg tgatttctgg ttacccatag gatgtgcagc ctttgttgta   1740
gtctgcattt gggatgcat acttatttgt tggcttacaa aaagaagta ttcatccagt     1800 gtgcacgacc ctaacggtga atacatgttc atgagagcag tgaacacagc caaaaatcc    1860 agactcacag atgtgaccct aagagtgaag ttcagcagga gcgcagacgc ccccgcgtac   1920
cagcagggcc agaaccagct ctataacgag ctcaatctag gacgaagaga ggagtacgat   1980
gttttggaca gagacgtgg ccgggaccct gagatggggg gaaagccgca gagaaggaag    2040
aaccctcagg aaggcctgta caatgaactg cagaaagata agatggcgga ggcctacagt   2100
gagattggga tgaaaggcga gcgccggagg ggcaagggc acgatggcct ttaccagggt    2160
ctcagtacag ccaccaagga cacctacgac gcccttcaca tgcaggccct gccccctcgc   2220
```

<210> SEQ ID NO 222
<211> LENGTH: 2220
<212> TYPE: DNA
<213> ORGANISM: Artificial Sequence
<220> FEATURE:
<223> OTHER INFORMATION: PD1A132L-41BB-2F5PSMA-CAR varICOS CD3z

<400> SEQUENCE: 222

```
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aagctgcaga tcaaagagag cctgcgggca    420
gagctcaggg tgacagagag aagggcagaa gtgcccacag cccacccccag cccctcaccc    480 aggccagccg gccagttcca aaccctggtt atctacatct gggcgccctt ggccgggact    540
tgtggggtcc ttctcctgtc actggttatc acccttact gcaaaaacg gggcagaaag     600 aaactcctgt atatattcaa acaaccattt atgagaccag tacaaactac tcaagaggaa    660
```

```
gatggctgta gctgccgatt tccagaagaa gaagaaggag gatgtgaact ggtgaaacag     720
actttgaatt ttgaccttct caagttggcg ggagacgtgg agtccaaccc agggccgatg     780
gccttaccag tgaccgcctt gctcctgccg ctggccttgc tgctccacgc cgccaggccg     840
gaggtgcagc tggtgcagtc tggagcagag gtgaaaaagc ccggggagtc tctgaagatc     900
tcctgtaagg gttctggata cagttttacc agcaactgga tcggctgggt gcgccagatg     960
cccgggaaag cctggagtg gatggggatc atctatcctg gtgactctga taccagatac    1020
agcccgtcct ccaaggcca ggtcaccatc tcagccgaca gtccatcag caccgcctac     1080 ctgcagtgga cagcctgaa ggcctcggac accgccatgt attactgtgc gagacaaact    1140
ggtttcctct ggtccttcga tctctggggc cgtggcaccc tggtcactgt ctcctcaggt    1200
ggcggtggct cggggcggtgg tgggtcgggt ggcggcggat ctgccatcca gttgacccag    1260
tctccatcct ccctgtctgc atctgtagga gacagagtca ccatcacttg ccgggcaagt    1320
caggacatta gcagtgcttt agcctggtat cagcagaaac cggggaaagc tcctaagctc    1380
ctgatctatg atgcctccag tttggaaagt ggggtcccat caaggttcag cggcagtgga    1440
tctgggacag atttcactct caccatcagc agcctgcagc tgaagatttt tgcaacttat    1500
tactgtcaac agtttaatag ttacccgctc actttcggcg agggaccaa ggtggagatc    1560 aaaatcaaaa ccacgacgcc agcgccgcga ccaccaacac cggcgcccac catcgcgtcg    1620 cagccctgt ccctgcgccc agaggcgtgc cggccagcgg cggggggcgc agtgcacacg     1680
agggggctgg acttcgcctg tgatttctgg ttacccatag gatgtgcagc ctttgttgta    1740
gtctgcattt tgggatgcat acttatttgt tggcttacaa aaaagaagta ttcatccagt    1800
gtgcacgacc ctaacggtga atacatgaac atgagagcag tgaacacagc caaaaaatcc    1860
agactcacag atgtgaccct aagagtgaag ttcagcagga gcgcagacgc cccgcgtac    1920 cagcagggcc agaaccagct ctataacgag ctcaatctag gacgaagaga ggagtacgat    1980 gtttggaca agagacgtgg ccgggacct gagatggggg gaaagccgca gagaaggaag    2040
aaccctcagg aaggcctgta caatgaactg cagaaagata agatggcgga ggcctacagt    2100
gagattggga tgaaaggcga gcgccggagg ggcaaggggc acgatggcct ttaccagggt    2160
ctcagtacag ccaccaagga cacctacgac gcccttcaca tgcaggccct gccccctcgc    2220
```

<210> SEQ ID NO 223
<211> LENGTH: 2313
<212> TYPE: DNA
<213> ORGANISM: Artificial Sequence
<220> FEATURE:
<223> OTHER INFORMATION: TIM3-CD28-2F5PSMA-CAR ICOS CD3z

<400> SEQUENCE: 223

```
atgttttcac atcttcccctt tgactgtgtc ctgctgctgc tgctgctact acttacaagg      60
tcctcagaag tggaatacag agcggaggtc ggtcagaatg cctatctgcc ctgcttctac     120
accccagccg ccccagggaa cctcgtgccc gtctgctggg gcaaaggagc ctgtcctgtg     180
tttgaatgtg gcaacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc cgaatccaaa tcccaggcat aatgaatgat     360
gaaaaattta acctgaagtt ggtcatcaaa ccagccaagg tcacccctgc accgactcgg     420
cagagagact tcactgcagc ctttccaagg atgcttacca ccagggggaca tggcccagca     480
```

```
gagacacaga cactggggag cctccctgac ataaatctaa cacaaatatc cacattggcc    540
aatgagttac gggactctag gttggccaat gacttacggg actccggagc aaccatcaga    600
ttttgggtgc tggtggtggt tggtggagtc ctggcttgct atagcttact agtaacagtg    660
gcctttatta ttttctgggt gaggagtaag aggagcaggc tcctgcacag tgactacatg    720
aacatgactc cccgccgccc cgggcccacc cgcaagcatt accagcccta tgccccacca    780
cgcgacttcg cagcctatcg ctccgtgaaa cagactttga attttgacct tctcaagttg    840
gcgggagacg tggagtccaa cccagggccg atggccttac cagtgaccgc cttgctcctg    900
ccgctggcct tgctgctcca cgccgccagg ccggaggtgc agctggtgca gtctggagca    960
gaggtgaaaa agcccgggga gtctctgaag atctcctgta agggttctgg atacagtttt   1020
accagcaact ggatcggctg ggtgcgccag atgcccggga aaggcctgga gtggatgggg   1080
atcatctatc ctggtgactc tgataccaga tacagcccgt ccttccaagg ccaggtcacc   1140
atctcagccg acaagtccat cagcaccgcc tacctgcagt ggaacagcct gaaggcctcg   1200
gacaccgcca tgtattactg tgcgagacaa actggtttcc tctggtcctt cgatctctgg   1260
ggccgtggca ccctggtcac tgtctcctca ggtggcggtg gctcgggcgg tggtgggtcg   1320
ggtggcggcg gatctgccat ccagttgacc cagtctccat cctccctgtc tgcatctgta   1380
ggagacagag tcaccatcac ttgccgggca agtcaggaca ttagcagtgc tttagcctgg   1440
tatcagcaga aaccggggaa agctcctaag ctcctgatct atgatgcctc cagtttggaa   1500
agtggggtcc catcaaggtt cagcggcagt ggatctggga cagatttcac tctcaccatc   1560
agcagcctgc agcctgaaga ttttgcaact tattactgtc aacagtttaa tagttacccg   1620
ctcactttcg gcggagggac caaggtggag atcaaaatca aaccacgac gccagcgccg   1680 cgaccaccaa caccggcgcc caccatcgcg tcgcagcccc tgtccctgcg cccagaggcg   1740
tgccggccag cggcgggggg cgcagtgcac acgaggggc tggacttcgc ctgtgatttc   1800
tggttaccca taggatgtgc agcctttgtt gtagtctgca ttttgggatg catacttatt   1860
tgttggctta caaaaaagaa gtattcatcc agtgtgcacg accctaacgg tgaatacatg   1920
ttcatgagag cagtgaacac agccaaaaaa tccagactca cagatgtgac cctaagagtg   1980
aagttcagca ggagcgcaga cgcccccgcg taccagcagg gccagaacca gctctataac   2040
gagctcaatc taggacgaag agaggagtac gatgttttgg acaagagacg tggccgggac   2100
cctgagatgg ggggaaagcc gcagagaagg aagaaccctc aggaaggcct gtacaatgaa   2160
ctgcagaaag ataagatggc ggaggcctac agtgagattg ggatgaaagg cgagcgccgg   2220
aggggcaagg ggcacgatgg cctttaccag gtctcagta cagccaccaa ggacacctac   2280
gacgcccttc acatgcaggc cctgccccct cgc                                2313

<210> SEQ ID NO 224
<211> LENGTH: 2313
<212> TYPE: DNA
<213> ORGANISM: Artificial Sequence
<220> FEATURE:
<223> OTHER INFORMATION: TIM3-CD28-2F5PSMA-CAR varICOS CD3z

<400> SEQUENCE: 224
atgttttcac atcttccctt tgactgtgtc ctgctgctgc tgctgctact acttacaagg     60
tcctcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
```

```
agatactggc taaatgggga tttccgcaaa ggagatgtgt ccctgaccat agagaatgtg    300
actctagcag acagtgggat ctactgctgc cgaatccaaa tcccaggcat aatgaatgat    360
gaaaaattta acctgaagtt ggtcatcaaa ccagccaagg tcaccctgc accgactcgg    420 cagagagact tcactgcagc ctttccaagg atgcttacca ccaggggaca tggcccagca    480
gagacacaga cactggggag cctccctgac ataaatctaa cacaaatatc cacattggcc    540
aatgagttac gggactctag gttggccaat gacttacggg actccggagc aaccatcaga    600
ttttgggtgc tggtggtggt tggtggagtc ctggcttgct atagcttact agtaacagtg    660
gcctttatta ttttctgggt gaggagtaag aggagcaggc tcctgcacag tgactacatg    720
aacatgactc cccgccgccc gggcccaccc cgcaagcatt accagcccta tgccccacca    780
cgcgacttcg cagcctatcg ctccgtgaaa cagactttga attttgacct tctcaagttg    840
gcgggagacg tggagtccaa cccagggccg atggccttac cagtgaccgc cttgctcctg    900
ccgctggcct tgctgctcca cgccgccagg ccggaggtgc agctggtgca gtctggagca    960
gaggtgaaaa agcccgggga gtctctgaag atctcctgta agggttctgg atacagtttt   1020
accagcaact ggatcggctg ggtgcgccag atgcccggga aaggcctgga gtggatgggg   1080
atcatctatc ctggtgactc tgataccaga tacagcccgt ccttccaagg ccaggtcacc   1140
atctcagccg acaagtccat cagcaccgcc tacctgcagt ggaacagcct gaaggcctcg   1200
gacaccgcca tgtattactg tgcgagacaa actggttttcc tctggtcctt cgatctctgg   1260
ggccgtggca ccctggtcac tgtctcctca ggtggcggtg gctcgggcgg tggtgggtcg   1320
ggtggcggcg gatctgccat ccagttgacc cagtctccat cctccctgtc tgcatctgta   1380
ggagacagag tcaccatcac ttgccgggca agtcaggaca ttagcagtgc tttagcctgg   1440
tatcagcaga accggggaa agctcctaag ctcctgatct atgatgcctc cagtttggaa   1500
agtggggtcc catcaaggtt cagcggcagt ggatctggga cagatttcac tctcaccatc   1560
agcagcctgc agcctgaaga ttttgcaact tattactgtc aacagtttaa tagttacccg   1620
ctcactttcg gcggagggac caaggtggag atcaaaatca aaaccacgac gccagcgccg   1680
cgaccaccaa caccggcgcc caccatcgcg tcgcagcccc tgtccctgcg cccagaggcg   1740
tgccggccag cggcgggggg cgcagtgcac acgagggggc tggacttcgc ctgtgatttc   1800
tggttaccca taggatgtgc agcctttgtt gtagtctgca ttttgggatg catacttatt   1860
tgttggctta caaaaaagaa gtattcatcc agtgtgcacg accctaacgg tgaatacatg   1920
aacatgagag cagtgaacac agccaaaaaa tccagactca cagatgtgac cctaagagtg   1980
aagttcagca ggagcgcaga cgccccgcg taccagcagg gccagaacca gctctataac   2040
gagctcaatc taggacgaag agaggagtac gatgttttgg acaagagacg tggccgggac   2100
cctgagatgg ggggaaagcc gcagagaagg aagaaccctc aggaaggcct gtacaatgaa   2160
ctgcagaaag ataagatggc ggaggcctac agtgagattg ggatgaaagg cgagcgccgg   2220
aggggcaagg ggcacgatgg cctttaccag gtctcagta cagccaccaa ggacacctac   2280
gacgcccttc acatgcaggc cctgccccct cgc                                2313
```

<210> SEQ ID NO 225
<211> LENGTH: 3090
<212> TYPE: DNA
<213> ORGANISM: Artificial Sequence
<220> FEATURE:
<223> OTHER INFORMATION: PD1A132L-4-1BB-TIM3-CD28-2F5PSMA-CAR ICOS CD3z

<400> SEQUENCE: 225

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aagctgcaga tcaaagagag cctgcgggca     420
gagctcaggg tgacagagag aagggcagaa gtgcccacag cccaccccag ccctcacccc     480
aggccagccg ccagttccaa accctggtt atctacatct gggcgccctt ggccgggact     540
tgtgggggtcc ttctcctgtc actggttatc acccttact gcaaaaaacg gggcagaaag     600
aaactcctgt atatattcaa caaccattt atgagaccag tacaaactac tcaagaggaa     660
gatggctgta gctgccgatt ccagaagaa gaagaaggag gatgtgaact ggtgaagcag     720
acgttgaact cgatttgct caaacttgcc ggtgacgtgg aatccaatcc ggggccgatg     780
ttttcacatc ttccctttga ctgtgtcctg ctgctgctgc tgctactact tacaaggtcc     840
tcagaagtgg aatacagagc ggaggtcggt cagaatgcct atctgccctg cttctacacc     900
ccagccgccc cagggaacct cgtgcccgtc tgctggggca aaggagcctg tcctgtgttt     960
gaatgtggca acgtggtgct caggactgat gaaagggatg tgaattattg acatccaga    1020
tactggctaa atggggattt ccgcaaagga gatgtgtccc tgaccataga gaatgtgact    1080
ctagcagaca gtgggatcta ctgctgccga atccaaatcc caggcataat gaatgatgaa    1140
aaatttaacc tgaagttggt catcaaacca gccaaggtca cccctgcacc gactcggcag    1200
agagacttca ctgcagcctt tccaaggatg cttaccacca ggggacatgg cccagcagag    1260
acacagacac tggggagcct ccctgacata aatctaacac aaatatccac attggccaat    1320
gagttacggg actctaggtt ggccaatgac ttacgggact ccggagcaac catcagattt    1380
tgggtgctgg tggtggttgg tggagtcctg gcttgctata gcttactagt aacagtggcc    1440
tttattattt tctgggtgag gagtaagagg agcaggctcc tgcacagtga ctacatgaac    1500
atgactcccc gccgcccgg gcccaccgc aagcattacc agcccatgc ccaccacgc        1560
gacttcgcag cctatcgctc cgtgaaacag actttgaatt ttgaccttct caagttggcg    1620
ggagacgtga gtccaacccc agggccgatg gccttaccag tgaccgcctt gctcctgccg    1680
ctggccttgc tgctccacgc cgccaggccg gaggtgcagc tggtgcagtc tggagcagag    1740
gtgaaaaagc ccggggagtc tctgaagatc cctgtaagg gttctggata cagttttacc    1800
agcaactgga tcggctgggt gcgccagatg cccgggaaag gcctggagtg gatggggatc    1860
atctatcctg gtgactctga taccagatac agccgtcct tccaaggcca ggtcaccatc    1920
tcagccgaca gtccatcag caccgcctac ctgcagtgga acagcctgaa ggcctcggac    1980
accgccatgt attactgtgc gagacaaact ggtttcctct ggtccttcga tctctggggc    2040
cgtggcaccc tggtcactgt ctcctcaggt ggcggtggct cggcggtgg tgggtcgggt    2100
ggcggcggat ctgccatcca gttgacccag tctccatcct ccctgtctgc atctgtagga    2160
gacagagtca ccatcacttg ccgggcaagt caggacatta gcagtgcttt agcctggtat    2220
cagcagaaac cggggaaagc tcctaagctc ctgatctatg atgcctccag tttgaaagt     2280
ggggtcccat caaggttcag cggcagtgga tctgggacag atttcactct caccatcagc    2340
```

```
agcctgcagc ctgaagattt tgcaacttat tactgtcaac agtttaatag ttacccgctc    2400
actttcggcg gagggaccaa ggtggagatc aaaatcaaaa ccacgacgcc agcgccgcga    2460
ccaccaacac cggcgcccac catcgcgtcg cagcccctgt ccctgcgccc agaggcgtgc    2520
cggccagcgc cggggggcgc agtgcacacg aggggggctgg acttcgcctg tgatttctgg    2580
ttacccatag gatgtgcagc cttttgttgta gtctgcattt gggatgcat acttatttgt    2640 tggcttacaa aaaagaagta ttcatccagt gtgcacgacc ctaacggtga atacatgttc    2700
atgagagcag tgaacacagc caaaaaatcc agactcacag atgtgaccct aagagtgaag    2760
ttcagcagga gcgcagacgc ccccgcgtac cagcagggcc agaaccagct ctataacgag    2820
ctcaatctag gacgaagaga ggagtacgat gtttttggaca agagacgtgg ccgggaccct    2880
gagatggggg gaaagccgca gagaaggaag aaccctcagg aaggcctgta caatgaactg    2940
cagaaagata gatggcgga ggcctacagt gagattggga tgaaaggcga gcgccggagg    3000
ggcaaggggc acgatggcct ttaccagggt ctcagtacag ccaccaagga cacctacgac    3060
gcccttcaca tgcaggccct gccccctcgc                                    3090

<210> SEQ ID NO 226
<211> LENGTH: 3090
<212> TYPE: DNA
<213> ORGANISM: Artificial Sequence
<220> FEATURE:
<223> OTHER INFORMATION: PD1A132L-4-1BB-TIM3-CD28-2F5PSMA-CAR varICOS
      CD3z

<400> SEQUENCE: 226
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcaggccc ggcgcaatga cagcggcacc     360
tacctctgtg gggccatctc cctggccccc aagctgcaga tcaaagagag cctgcgggca     420
gagctcaggg tgacagagag aagggcagaa gtgcccacag cccaccccag cccctcaccc     480
aggccagccg gccagttcca aaccctggtt atctacatct gggcgccctt ggccgggact     540 tgtgggggtcc ttctcctgtc actggttatc accctttact gcaaaaaacg gggcagaaag     600
aaactcctgt atatattcaa acaaccattt atgagaccag tacaaactac tcaagaggaa     660
gatggctgta gctgccgatt ccagaagaa gaagaaggag gatgtgaact ggtgaagcag     720
acgttgaact tcgatttgct caaacttgcc ggtgacgtgg aatccaatcc ggggccgatg     780
ttttcacatc ttcccttga ctgtgtcctg ctgctgctgc tgctactact tacaaggtcc     840
tcagaagtgg aatacagagc ggaggtcggt cagaatgcct atctgccctg cttctacacc     900
ccagccgccc cagggaacct cgtgcccgtc tgctggggca aggagcctg tcctgtgttt     960 gaatgtggca acgtggtgct caggactgat gaaagggatg tgaattattg gacatccaga    1020
tactggctaa atgggatttt ccgcaaagga gatgtgtccc tgaccataga gaatgtgact    1080
ctagcagaca gtgggatcta ctgctgccga atccaaatcc caggcataat gaatgatgaa    1140
aaatttaacc tgaagttggt catcaaacca gccaaggtca cccctgcacc gactcggcag    1200
agagacttca gctgcagcct tccaaggatg cttaccacca ggggacatgg cccagcagag    1260
```

```
acacagacac tggggagcct ccctgacata aatctaacac aaatatccac attggccaat    1320
gagttacggg actctaggtt ggccaatgac ttacgggact ccggagcaac catcagattt    1380
tgggtgctgg tggtggttgg tggagtcctg gcttgctata gcttactagt aacagtggcc    1440
tttattattt tctgggtgag gagtaagagg agcaggctcc tgcacagtga ctacatgaac    1500
atgactcccc gccgccccgg gcccacccgc aagcattacc agccctatgc cccaccacgc    1560
gacttcgcag cctatcgctc cgtgaaacga actttgaatt ttgaccttct caagttggcg    1620
ggagacgtgg agtccaaccc agggccgatg gccttaccag tgaccgcctt gctcctgccg    1680
ctggccttgc tgctccacgc cgccaggccg gaggtgcagc tggtgcagtc tggagcagag    1740
gtgaaaaagc ccggggagtc tctgaagatc tcctgtaagg gttctggata cagttttacc    1800
agcaactgga tcggctgggt gcgccagatg cccgggaaag gcctggagtg gatgggggatc    1860 atctatcctg gtgactctga taccagatac agcccgtcct ccaaggcca ggtcaccatc    1920 tcagccgaca gtccatcag caccgcctac ctgcagtgga acagcctgaa ggcctcggac    1980
accgccatgt attactgtgc gagacaaact ggtttcctct ggtccttcga tctctggggc    2040
cgtggcaccc tggtcactgt ctcctcaggt ggcggtggct cgggcggtgg tgggtcgggt    2100
ggcggcggat ctgccatcca gttgacccag tctccatcct ccctgtctgc atctgtagga    2160
gacagagtca ccatcacttg ccgggcaagt caggacatta gcagtgcttt agcctggtat    2220
cagcagaaac cggggaaagc tcctaagctc ctgatctatg atgcctccag tttggaaagt    2280
ggggtcccat caaggttcag cggcagtgga tctgggacag atttcactct caccatcagc    2340
agcctgcagc ctgaagattt tgcaacttat tactgtcaac agtttaatag ttacccgctc    2400
actttcggcg gagggaccaa ggtggagatc aaaatcaaaa ccacgacgcc agcgccgcga    2460
ccaccaacac cggcgcccac catcgcgtcg cagcccctgt ccctgcgccc agaggcgtgc    2520
cggccagcgg cggggggcgc agtgcacacg agggggctgg acttcgcctg tgatttctgg    2580
ttacccatag gatgtgcagc cttgttgta gtctgcattt gggatgcat acttatttgt    2640 tggcttacaa aaagaagta ttcatccagt gtgcacgacc ctaacggtga atacatgaac    2700
atgagagcag tgaacacagc caaaaaatcc agactcacag atgtgaccct aagagtgaag    2760
ttcagcagga gcgcagacgc ccccgcgtac cagcagggcc agaaccagct ctataacgag    2820
ctcaatctag gacgaagaga ggagtacgat gttttggaca gagacgtgg ccgggaccct    2880 gagatggggg gaaagccgca gagaaggaag aaccctcagg aaggcctgta caatgaactg    2940
cagaaagata gatggcgga ggcctacagt gagattggga tgaaaggcga gcgccggagg    3000
ggcaaggggc acgatggcct ttaccagggt ctcagtacag ccaccaagga cacctacgac    3060
gcccttcaca tgcaggccct gccccctcgc                                     3090
```

<210> SEQ ID NO 227
<211> LENGTH: 741
<212> TYPE: PRT
<213> ORGANISM: Artificial Sequence
<220> FEATURE:
<223> OTHER INFORMATION: PD1-CD28-2F5PSMA-CAR ICOS CD3z

<400> SEQUENCE: 227

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

-continued

```
Asn Pro Pro Thr Phe Ser Pro Ala Leu Leu Val Val Thr Glu Gly Asp
         35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
             100                 105                 110

Ala Arg Arg Asn Asp Ser Gly Thr Tyr Leu Cys Gly Ala Ile Ser Leu
         115                 120                 125

Ala Pro Lys Ala Gln Ile Lys Glu Ser Leu Arg Ala Glu Leu Arg Val
     130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Phe Trp Val Leu Val Val
                 165                 170                 175

Val Gly Gly Val Leu Ala Cys Tyr Ser Leu Leu Val Thr Val Ala Phe
             180                 185                 190

Ile Ile Phe Trp Val Arg Ser Lys Arg Ser Arg Leu Leu His Ser Asp
         195                 200                 205

Tyr Met Asn Met Thr Pro Arg Arg Pro Gly Pro Thr Arg Lys His Tyr
     210                 215                 220

Gln Pro Tyr Ala Pro Pro Arg Asp Phe Ala Ala Tyr Arg Ser Val Lys
225                 230                 235                 240

Gln Thr Leu Asn Phe Asp Leu Leu Lys Leu Ala Gly Asp Val Glu Ser
                 245                 250                 255

Asn Pro Gly Pro Met Ala Leu Pro Val Thr Ala Leu Leu Leu Pro Leu
             260                 265                 270

Ala Leu Leu Leu His Ala Ala Arg Pro Glu Val Gln Leu Val Gln Ser
         275                 280                 285

Gly Ala Glu Val Lys Lys Pro Gly Glu Ser Leu Lys Ile Ser Cys Lys
     290                 295                 300

Gly Ser Gly Tyr Ser Phe Thr Ser Asn Trp Ile Gly Trp Val Arg Gln
305                 310                 315                 320

Met Pro Gly Lys Gly Leu Glu Trp Met Gly Ile Ile Tyr Pro Gly Asp
                 325                 330                 335

Ser Asp Thr Arg Tyr Ser Pro Ser Phe Gln Gly Gln Val Thr Ile Ser
             340                 345                 350

Ala Asp Lys Ser Ile Ser Thr Ala Tyr Leu Gln Trp Asn Ser Leu Lys
         355                 360                 365

Ala Ser Asp Thr Ala Met Tyr Tyr Cys Ala Arg Gln Thr Gly Phe Leu
     370                 375                 380

Trp Ser Phe Asp Leu Trp Gly Arg Gly Thr Leu Val Thr Val Ser Ser
385                 390                 395                 400

Gly Gly Gly Gly Ser Gly Gly Gly Ser Gly Gly Gly Gly Ser Ala
                 405                 410                 415

Ile Gln Leu Thr Gln Ser Pro Ser Ser Leu Ser Ala Ser Val Gly Asp
             420                 425                 430

Arg Val Thr Ile Thr Cys Arg Ala Ser Gln Asp Ile Ser Ser Ala Leu
         435                 440                 445

Ala Trp Tyr Gln Gln Lys Pro Gly Lys Ala Pro Lys Leu Leu Ile Tyr
```

Asp Ala Ser Ser Leu Glu Ser Gly Val Pro Ser Arg Phe Ser Gly Ser
465                 470                 475                 480

Gly Ser Gly Thr Asp Phe Thr Leu Thr Ile Ser Ser Leu Gln Pro Glu
            485                 490                 495

Asp Phe Ala Thr Tyr Tyr Cys Gln Gln Phe Asn Ser Tyr Pro Leu Thr
            500                 505                 510

Phe Gly Gly Gly Thr Lys Val Glu Ile Lys Ile Lys Thr Thr Thr Pro
            515                 520                 525

Ala Pro Arg Pro Pro Thr Pro Ala Pro Thr Ile Ala Ser Gln Pro Leu
530                 535                 540

Ser Leu Arg Pro Glu Ala Cys Arg Pro Ala Ala Gly Gly Ala Val His
545                 550                 555                 560

Thr Arg Gly Leu Asp Phe Ala Cys Asp Phe Trp Leu Pro Ile Gly Cys
            565                 570                 575

Ala Ala Phe Val Val Val Cys Ile Leu Gly Cys Ile Leu Ile Cys Trp
            580                 585                 590

Leu Thr Lys Lys Lys Tyr Ser Ser Ser Val His Asp Pro Asn Gly Glu
            595                 600                 605

Tyr Met Phe Met Arg Ala Val Asn Thr Ala Lys Lys Ser Arg Leu Thr
610                 615                 620

Asp Val Thr Leu Arg Val Lys Phe Ser Arg Ser Ala Asp Ala Pro Ala
625                 630                 635                 640

Tyr Gln Gln Gly Gln Asn Gln Leu Tyr Asn Glu Leu Asn Leu Gly Arg
            645                 650                 655

Arg Glu Glu Tyr Asp Val Leu Asp Lys Arg Arg Gly Arg Asp Pro Glu
            660                 665                 670

Met Gly Gly Lys Pro Gln Arg Arg Lys Asn Pro Gln Glu Gly Leu Tyr
            675                 680                 685

Asn Glu Leu Gln Lys Asp Lys Met Ala Glu Ala Tyr Ser Glu Ile Gly
            690                 695                 700

Met Lys Gly Glu Arg Arg Arg Gly Lys Gly His Asp Gly Leu Tyr Gln
705                 710                 715                 720

Gly Leu Ser Thr Ala Thr Lys Asp Thr Tyr Asp Ala Leu His Met Gln
            725                 730                 735

Ala Leu Pro Pro Arg
            740

<210> SEQ ID NO 228
<211> LENGTH: 735
<212> TYPE: PRT
<213> ORGANISM: Artificial Sequence
<220> FEATURE:
<223> OTHER INFORMATION: PD1-CD28-2F5PSMA-CAR varICOS CD3z

<400> SEQUENCE: 228

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala

```
                65                  70                  75                  80
Ala Phe Pro Glu Asp Arg Ser Gln Pro Gly Gln Asp Cys Arg Phe Arg
                        85                  90                  95
Val Thr Gln Leu Pro Asn Gly Arg Asp Phe His Met Ser Val Val Arg
                    100                 105                 110
Ala Arg Arg Asn Asp Ser Gly Thr Tyr Leu Cys Gly Ala Ile Ser Leu
                    115                 120                 125
Ala Pro Lys Leu Gln Ile Lys Glu Ser Leu Arg Ala Glu Leu Arg Val
                    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                    165                 170                 175
Leu Leu Gly Ser Leu Val Leu Leu Val Trp Val Leu Ala Val Ile Arg
                    180                 185                 190
Ser Lys Arg Ser Arg Leu Leu His Ser Asp Tyr Met Asn Met Thr Pro
                    195                 200                 205
Arg Arg Pro Gly Pro Thr Arg Lys His Tyr Gln Pro Tyr Ala Pro Pro
                    210                 215                 220
Arg Asp Phe Ala Ala Tyr Arg Ser Val Lys Gln Thr Leu Asn Phe Asp
225                 230                 235                 240
Leu Leu Lys Leu Ala Gly Asp Val Glu Ser Asn Pro Gly Pro Met Ala
                    245                 250                 255
Leu Pro Val Thr Ala Leu Leu Leu Pro Leu Ala Leu Leu Leu His Ala
                    260                 265                 270
Ala Arg Pro Glu Val Gln Leu Val Gln Ser Gly Ala Glu Val Lys Lys
                    275                 280                 285
Pro Gly Glu Ser Leu Lys Ile Ser Cys Lys Gly Ser Gly Tyr Ser Phe
                    290                 295                 300
Thr Ser Asn Trp Ile Gly Trp Val Arg Gln Met Pro Gly Lys Gly Leu
305                 310                 315                 320
Glu Trp Met Gly Ile Ile Tyr Pro Gly Asp Ser Asp Thr Arg Tyr Ser
                    325                 330                 335
Pro Ser Phe Gln Gly Gln Val Thr Ile Ser Ala Asp Lys Ser Ile Ser
                    340                 345                 350
Thr Ala Tyr Leu Gln Trp Asn Ser Leu Lys Ala Ser Asp Thr Ala Met
                    355                 360                 365
Tyr Tyr Cys Ala Arg Gln Thr Gly Phe Leu Trp Ser Phe Asp Leu Trp
        370                 375                 380
Gly Arg Gly Thr Leu Val Thr Val Ser Ser Gly Gly Gly Gly Ser Gly
385                 390                 395                 400
Gly Gly Gly Ser Gly Gly Gly Ser Ala Ile Gln Leu Thr Gln Ser
                    405                 410                 415
Pro Ser Ser Leu Ser Ala Ser Val Gly Asp Arg Val Thr Ile Thr Cys
                    420                 425                 430
Arg Ala Ser Gln Asp Ile Ser Ser Ala Leu Ala Trp Tyr Gln Gln Lys
                    435                 440                 445
Pro Gly Lys Ala Pro Lys Leu Leu Ile Tyr Asp Ala Ser Ser Leu Glu
                    450                 455                 460
Ser Gly Val Pro Ser Arg Phe Ser Gly Ser Gly Ser Gly Thr Asp Phe
465                 470                 475                 480
Thr Leu Thr Ile Ser Ser Leu Gln Pro Glu Asp Phe Ala Thr Tyr Tyr
                    485                 490                 495
```

Cys Gln Gln Phe Asn Ser Tyr Pro Leu Thr Phe Gly Gly Gly Thr Lys
            500                 505                 510

Val Glu Ile Lys Ile Lys Thr Thr Pro Ala Pro Arg Pro Pro Thr
            515                 520                 525

Pro Ala Pro Thr Ile Ala Ser Gln Pro Leu Ser Leu Arg Pro Glu Ala
            530                 535                 540

Cys Arg Pro Ala Ala Gly Gly Ala Val His Thr Arg Gly Leu Asp Phe
545                 550                 555                 560

Ala Cys Asp Phe Trp Leu Pro Ile Gly Cys Ala Ala Phe Val Val Val
                565                 570                 575

Cys Ile Leu Gly Cys Ile Leu Ile Cys Trp Leu Thr Lys Lys Lys Tyr
            580                 585                 590

Ser Ser Ser Val His Asp Pro Asn Gly Glu Tyr Met Phe Met Arg Ala
            595                 600                 605

Val Asn Thr Ala Lys Lys Ser Arg Leu Thr Asp Val Thr Leu Arg Val
610                 615                 620

Lys Phe Ser Arg Ser Ala Asp Ala Pro Ala Tyr Gln Gln Gly Gln Asn
625                 630                 635                 640

Gln Leu Tyr Asn Glu Leu Asn Leu Gly Arg Arg Glu Glu Tyr Asp Val
            645                 650                 655

Leu Asp Lys Arg Arg Gly Arg Asp Pro Glu Met Gly Gly Lys Pro Gln
            660                 665                 670

Arg Arg Lys Asn Pro Gln Glu Gly Leu Tyr Asn Glu Leu Gln Lys Asp
            675                 680                 685

Lys Met Ala Glu Ala Tyr Ser Glu Ile Gly Met Lys Gly Glu Arg Arg
            690                 695                 700

Arg Gly Lys Gly His Asp Gly Leu Tyr Gln Gly Leu Ser Thr Ala Thr
705                 710                 715                 720

Lys Asp Thr Tyr Asp Ala Leu His Met Gln Ala Leu Pro Pro Arg
                725                 730                 735

<210> SEQ ID NO 229
<211> LENGTH: 740
<212> TYPE: PRT
<213> ORGANISM: Artificial Sequence
<220> FEATURE:
<223> OTHER INFORMATION: PD1A132L-41BB-2F5PSMA-CAR ICOS CD3z

<400> SEQUENCE: 229

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

-continued

Ala Pro Lys Leu Gln Ile Lys Glu Ser Leu Arg Ala Glu Leu Arg Val
         130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                 165                 170                 175

Leu Ala Gly Thr Cys Gly Val Leu Leu Leu Ser Leu Val Ile Thr Leu
                 180                 185                 190

Tyr Cys Lys Lys Arg Gly Arg Lys Lys Leu Leu Tyr Ile Phe Lys Gln
             195                 200                 205

Pro Phe Met Arg Pro Val Gln Thr Thr Gln Glu Glu Asp Gly Cys Ser
        210                 215                 220

Cys Arg Phe Pro Glu Glu Glu Glu Gly Gly Cys Glu Leu Val Lys Gln
225                 230                 235                 240

Thr Leu Asn Phe Asp Leu Leu Lys Leu Ala Gly Asp Val Glu Ser Asn
                245                 250                 255

Pro Gly Pro Met Ala Leu Pro Val Thr Ala Leu Leu Leu Pro Leu Ala
                260                 265                 270

Leu Leu Leu His Ala Ala Arg Pro Glu Val Gln Leu Val Gln Ser Gly
            275                 280                 285

Ala Glu Val Lys Lys Pro Gly Glu Ser Leu Lys Ile Ser Cys Lys Gly
        290                 295                 300

Ser Gly Tyr Ser Phe Thr Ser Asn Trp Ile Gly Trp Val Arg Gln Met
305                 310                 315                 320

Pro Gly Lys Gly Leu Glu Trp Met Gly Ile Ile Tyr Pro Gly Asp Ser
                325                 330                 335

Asp Thr Arg Tyr Ser Pro Ser Phe Gln Gly Gln Val Thr Ile Ser Ala
                340                 345                 350

Asp Lys Ser Ile Ser Thr Ala Tyr Leu Gln Trp Asn Ser Leu Lys Ala
            355                 360                 365

Ser Asp Thr Ala Met Tyr Tyr Cys Ala Arg Gln Thr Gly Phe Leu Trp
        370                 375                 380

Ser Phe Asp Leu Trp Gly Arg Gly Thr Leu Val Thr Val Ser Ser Gly
385                 390                 395                 400

Gly Gly Gly Ser Gly Gly Gly Ser Gly Gly Gly Gly Ser Ala Ile
                405                 410                 415

Gln Leu Thr Gln Ser Pro Ser Ser Leu Ser Ala Ser Val Gly Asp Arg
                420                 425                 430

Val Thr Ile Thr Cys Arg Ala Ser Gln Asp Ile Ser Ser Ala Leu Ala
            435                 440                 445

Trp Tyr Gln Gln Lys Pro Gly Lys Ala Pro Lys Leu Leu Ile Tyr Asp
        450                 455                 460

Ala Ser Ser Leu Glu Ser Gly Val Pro Ser Arg Phe Ser Gly Ser Gly
465                 470                 475                 480

Ser Gly Thr Asp Phe Thr Leu Thr Ile Ser Ser Leu Gln Pro Glu Asp
                485                 490                 495

Phe Ala Thr Tyr Tyr Cys Gln Gln Phe Asn Ser Tyr Pro Leu Thr Phe
                500                 505                 510

Gly Gly Gly Thr Lys Val Glu Ile Lys Ile Lys Thr Thr Thr Pro Ala
            515                 520                 525

Pro Arg Pro Pro Thr Pro Ala Pro Thr Ile Ala Ser Gln Pro Leu Ser
        530                 535                 540

```
Leu Arg Pro Glu Ala Cys Arg Pro Ala Ala Gly Gly Ala Val His Thr
545                 550                 555                 560

Arg Gly Leu Asp Phe Ala Cys Asp Phe Trp Leu Pro Ile Gly Cys Ala
                565                 570                 575

Ala Phe Val Val Val Cys Ile Leu Gly Cys Ile Leu Ile Cys Trp Leu
            580                 585                 590

Thr Lys Lys Lys Tyr Ser Ser Val His Asp Pro Asn Gly Glu Tyr
        595                 600                 605

Met Phe Met Arg Ala Val Asn Thr Ala Lys Lys Ser Arg Leu Thr Asp
    610                 615                 620

Val Thr Leu Arg Val Lys Phe Ser Arg Ser Ala Asp Ala Pro Ala Tyr
625                 630                 635                 640

Gln Gln Gly Gln Asn Gln Leu Tyr Asn Glu Leu Asn Leu Gly Arg Arg
                645                 650                 655

Glu Glu Tyr Asp Val Leu Asp Lys Arg Arg Gly Arg Asp Pro Glu Met
                660                 665                 670

Gly Gly Lys Pro Gln Arg Arg Lys Asn Pro Gln Glu Gly Leu Tyr Asn
            675                 680                 685

Glu Leu Gln Lys Asp Lys Met Ala Glu Ala Tyr Ser Glu Ile Gly Met
690                 695                 700

Lys Gly Glu Arg Arg Arg Gly Lys Gly His Asp Gly Leu Tyr Gln Gly
705                 710                 715                 720

Leu Ser Thr Ala Thr Lys Asp Thr Tyr Asp Ala Leu His Met Gln Ala
                725                 730                 735

Leu Pro Pro Arg
            740

<210> SEQ ID NO 230
<211> LENGTH: 771
<212> TYPE: PRT
<213> ORGANISM: Artificial Sequence
<220> FEATURE:
<223> OTHER INFORMATION: TIM3-CD28-2F5PSMA-CAR ICOS CD3z

<400> SEQUENCE: 230

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
        50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160
```

-continued

```
Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Phe Trp Val Leu Val Val Val Gly
        195                 200                 205

Gly Val Leu Ala Cys Tyr Ser Leu Leu Val Thr Val Ala Phe Ile Ile
    210                 215                 220

Phe Trp Val Arg Ser Lys Arg Ser Arg Leu Leu His Ser Asp Tyr Met
225                 230                 235                 240

Asn Met Thr Pro Arg Arg Pro Gly Pro Thr Arg Lys His Tyr Gln Pro
                245                 250                 255

Tyr Ala Pro Pro Arg Asp Phe Ala Ala Tyr Arg Ser Val Lys Gln Thr
            260                 265                 270

Leu Asn Phe Asp Leu Leu Lys Leu Ala Gly Asp Val Glu Ser Asn Pro
        275                 280                 285

Gly Pro Met Ala Leu Pro Val Thr Ala Leu Leu Leu Pro Leu Ala Leu
    290                 295                 300

Leu Leu His Ala Ala Arg Pro Glu Val Gln Leu Val Gln Ser Gly Ala
305                 310                 315                 320

Glu Val Lys Lys Pro Gly Glu Ser Leu Lys Ile Ser Cys Lys Gly Ser
                325                 330                 335

Gly Tyr Ser Phe Thr Ser Asn Trp Ile Gly Trp Val Arg Gln Met Pro
            340                 345                 350

Gly Lys Gly Leu Glu Trp Met Gly Ile Ile Tyr Pro Gly Asp Ser Asp
        355                 360                 365

Thr Arg Tyr Ser Pro Ser Phe Gln Gly Gln Val Thr Ile Ser Ala Asp
    370                 375                 380

Lys Ser Ile Ser Thr Ala Tyr Leu Gln Trp Asn Ser Leu Lys Ala Ser
385                 390                 395                 400

Asp Thr Ala Met Tyr Tyr Cys Ala Arg Gln Thr Gly Phe Leu Trp Ser
                405                 410                 415

Phe Asp Leu Trp Gly Arg Gly Thr Leu Val Thr Val Ser Ser Gly Gly
            420                 425                 430

Gly Gly Ser Gly Gly Gly Gly Ser Gly Gly Gly Gly Ser Ala Ile Gln
        435                 440                 445

Leu Thr Gln Ser Pro Ser Ser Leu Ser Ala Ser Val Gly Asp Arg Val
    450                 455                 460

Thr Ile Thr Cys Arg Ala Ser Gln Asp Ile Ser Ser Ala Leu Ala Trp
465                 470                 475                 480

Tyr Gln Gln Lys Pro Gly Lys Ala Pro Lys Leu Leu Ile Tyr Asp Ala
                485                 490                 495

Ser Ser Leu Glu Ser Gly Val Pro Ser Arg Phe Ser Gly Ser Gly Ser
            500                 505                 510

Gly Thr Asp Phe Thr Leu Thr Ile Ser Ser Leu Gln Pro Glu Asp Phe
        515                 520                 525

Ala Thr Tyr Tyr Cys Gln Gln Phe Asn Ser Tyr Pro Leu Thr Phe Gly
    530                 535                 540

Gly Gly Thr Lys Val Glu Ile Lys Ile Lys Thr Thr Thr Pro Ala Pro
545                 550                 555                 560

Arg Pro Pro Thr Pro Ala Pro Thr Ile Ala Ser Gln Pro Leu Ser Leu
                565                 570                 575

Arg Pro Glu Ala Cys Arg Pro Ala Ala Gly Gly Ala Val His Thr Arg
```

-continued

```
                580                 585                 590
Gly Leu Asp Phe Ala Cys Asp Phe Trp Leu Pro Ile Gly Cys Ala Ala
            595                 600                 605

Phe Val Val Cys Ile Leu Gly Cys Ile Leu Ile Cys Trp Leu Thr
    610                 615                 620

Lys Lys Lys Tyr Ser Ser Ser Val His Asp Pro Asn Gly Glu Tyr Met
625                 630                 635                 640

Phe Met Arg Ala Val Asn Thr Ala Lys Lys Ser Arg Leu Thr Asp Val
                645                 650                 655

Thr Leu Arg Val Lys Phe Ser Arg Ser Ala Asp Ala Pro Ala Tyr Gln
            660                 665                 670

Gln Gly Gln Asn Gln Leu Tyr Asn Glu Leu Asn Leu Gly Arg Arg Glu
        675                 680                 685

Glu Tyr Asp Val Leu Asp Lys Arg Arg Gly Arg Asp Pro Glu Met Gly
    690                 695                 700

Gly Lys Pro Gln Arg Arg Lys Asn Pro Gln Glu Gly Leu Tyr Asn Glu
705                 710                 715                 720

Leu Gln Lys Asp Lys Met Ala Glu Ala Tyr Ser Glu Ile Gly Met Lys
                725                 730                 735

Gly Glu Arg Arg Arg Gly Lys Gly His Asp Gly Leu Tyr Gln Gly Leu
            740                 745                 750

Ser Thr Ala Thr Lys Asp Thr Tyr Asp Ala Leu His Met Gln Ala Leu
        755                 760                 765

Pro Pro Arg
    770

<210> SEQ ID NO 231
<211> LENGTH: 1030
<212> TYPE: PRT
<213> ORGANISM: Artificial Sequence
<220> FEATURE:
<223> OTHER INFORMATION: PD1A132L-4-1BB-TIM3-CD28-2F5PSMA-CAR ICOS CD3z

<400> SEQUENCE: 231

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
```

```
                165                 170                 175
Leu Ala Gly Thr Cys Gly Val Leu Leu Leu Ser Leu Val Ile Thr Leu
            180                 185                 190
Tyr Cys Lys Lys Arg Gly Arg Lys Leu Leu Tyr Ile Phe Lys Gln
        195                 200                 205
Pro Phe Met Arg Pro Val Gln Thr Thr Gln Glu Glu Asp Gly Cys Ser
    210                 215                 220
Cys Arg Phe Pro Glu Glu Glu Gly Gly Cys Glu Leu Val Lys Gln
225                 230                 235                 240
Thr Leu Asn Phe Asp Leu Leu Lys Leu Ala Gly Asp Val Glu Ser Asn
                245                 250                 255
Pro Gly Pro Met Phe Ser His Leu Pro Phe Asp Cys Val Leu Leu Leu
            260                 265                 270
Leu Leu Leu Leu Leu Thr Arg Ser Ser Glu Val Glu Tyr Arg Ala Glu
        275                 280                 285
Val Gly Gln Asn Ala Tyr Leu Pro Cys Phe Tyr Thr Pro Ala Ala Pro
    290                 295                 300
Gly Asn Leu Val Pro Val Cys Trp Gly Lys Gly Ala Cys Pro Val Phe
305                 310                 315                 320
Glu Cys Gly Asn Val Val Leu Arg Thr Asp Glu Arg Asp Val Asn Tyr
                325                 330                 335
Trp Thr Ser Arg Tyr Trp Leu Asn Gly Asp Phe Arg Lys Gly Asp Val
            340                 345                 350
Ser Leu Thr Ile Glu Asn Val Thr Leu Ala Asp Ser Gly Ile Tyr Cys
        355                 360                 365
Cys Arg Ile Gln Ile Pro Gly Ile Met Asn Asp Glu Lys Phe Asn Leu
    370                 375                 380
Lys Leu Val Ile Lys Pro Ala Lys Val Thr Pro Ala Pro Thr Arg Gln
385                 390                 395                 400
Arg Asp Phe Thr Ala Ala Phe Pro Arg Met Leu Thr Thr Arg Gly His
                405                 410                 415
Gly Pro Ala Glu Thr Gln Thr Leu Gly Ser Leu Pro Asp Ile Asn Leu
            420                 425                 430
Thr Gln Ile Ser Thr Leu Ala Asn Glu Leu Arg Asp Ser Arg Leu Ala
        435                 440                 445
Asn Asp Leu Arg Asp Ser Gly Ala Thr Ile Arg Phe Trp Val Leu Val
    450                 455                 460
Val Val Gly Gly Val Leu Ala Cys Tyr Ser Leu Leu Val Thr Val Ala
465                 470                 475                 480
Phe Ile Ile Phe Trp Val Arg Ser Lys Arg Ser Arg Leu Leu His Ser
                485                 490                 495
Asp Tyr Met Asn Met Thr Pro Arg Arg Pro Gly Pro Thr Arg Lys His
            500                 505                 510
Tyr Gln Pro Tyr Ala Pro Pro Arg Asp Phe Ala Ala Tyr Arg Ser Val
        515                 520                 525
Lys Gln Thr Leu Asn Phe Asp Leu Leu Lys Leu Ala Gly Asp Val Glu
    530                 535                 540
Ser Asn Pro Gly Pro Met Ala Leu Pro Val Thr Ala Leu Leu Leu Pro
545                 550                 555                 560
Leu Ala Leu Leu Leu His Ala Ala Arg Pro Glu Val Gln Leu Val Gln
                565                 570                 575
Ser Gly Ala Glu Val Lys Lys Pro Gly Glu Ser Leu Lys Ile Ser Cys
            580                 585                 590
```

-continued

```
Lys Gly Ser Gly Tyr Ser Phe Thr Ser Asn Trp Ile Gly Trp Val Arg
        595                 600                 605

Gln Met Pro Gly Lys Gly Leu Glu Trp Met Gly Ile Ile Tyr Pro Gly
610                 615                 620

Asp Ser Asp Thr Arg Tyr Ser Pro Ser Phe Gln Gly Gln Val Thr Ile
625                 630                 635                 640

Ser Ala Asp Lys Ser Ile Ser Thr Ala Tyr Leu Gln Trp Asn Ser Leu
        645                 650                 655

Lys Ala Ser Asp Thr Ala Met Tyr Tyr Cys Ala Arg Gln Thr Gly Phe
        660                 665                 670

Leu Trp Ser Phe Asp Leu Trp Gly Arg Gly Thr Leu Val Thr Val Ser
        675                 680                 685

Ser Gly Gly Gly Ser Gly Gly Gly Ser Gly Gly Gly Ser
        690                 695                 700

Ala Ile Gln Leu Thr Gln Ser Pro Ser Ser Leu Ser Ala Ser Val Gly
705                 710                 715                 720

Asp Arg Val Thr Ile Thr Cys Arg Ala Ser Gln Asp Ile Ser Ser Ala
                    725                 730                 735

Leu Ala Trp Tyr Gln Gln Lys Pro Gly Lys Ala Pro Lys Leu Leu Ile
                740                 745                 750

Tyr Asp Ala Ser Ser Leu Glu Ser Gly Val Pro Ser Arg Phe Ser Gly
                755                 760                 765

Ser Gly Ser Gly Thr Asp Phe Thr Leu Thr Ile Ser Ser Leu Gln Pro
    770                 775                 780

Glu Asp Phe Ala Thr Tyr Tyr Cys Gln Gln Phe Asn Ser Tyr Pro Leu
785                 790                 795                 800

Thr Phe Gly Gly Gly Thr Lys Val Glu Ile Lys Ile Lys Thr Thr Thr
                    805                 810                 815

Pro Ala Pro Arg Pro Pro Thr Pro Ala Pro Thr Ile Ala Ser Gln Pro
                820                 825                 830

Leu Ser Leu Arg Pro Glu Ala Cys Arg Pro Ala Ala Gly Gly Ala Val
        835                 840                 845

His Thr Arg Gly Leu Asp Phe Ala Cys Asp Phe Trp Leu Pro Ile Gly
        850                 855                 860

Cys Ala Ala Phe Val Val Val Cys Ile Leu Gly Cys Ile Leu Ile Cys
865                 870                 875                 880

Trp Leu Thr Lys Lys Lys Tyr Ser Ser Ser Val His Asp Pro Asn Gly
                    885                 890                 895

Glu Tyr Met Phe Met Arg Ala Val Asn Thr Ala Lys Lys Ser Arg Leu
                900                 905                 910

Thr Asp Val Thr Leu Arg Val Lys Phe Ser Arg Ser Ala Asp Ala Pro
                915                 920                 925

Ala Tyr Gln Gln Gly Gln Asn Gln Leu Tyr Asn Glu Leu Asn Leu Gly
        930                 935                 940

Arg Arg Glu Glu Tyr Asp Val Leu Asp Lys Arg Arg Gly Arg Asp Pro
945                 950                 955                 960

Glu Met Gly Gly Lys Pro Gln Arg Arg Lys Asn Pro Gln Glu Gly Leu
                    965                 970                 975

Tyr Asn Glu Leu Gln Lys Asp Lys Met Ala Glu Ala Tyr Ser Glu Ile
                980                 985                 990

Gly Met Lys Gly Glu Arg Arg Arg Gly Lys Gly His Asp Gly Leu Tyr
                995                 1000                1005
```

-continued

Gln Gly Leu Ser Thr Ala Thr Lys Asp Thr Tyr Asp Ala Leu His
        1010                1015                1020

Met Gln Ala Leu Pro Pro Arg
    1025                1030

<210> SEQ ID NO 232
<211> LENGTH: 741
<212> TYPE: PRT
<213> ORGANISM: Artificial Sequence
<220> FEATURE:
<223> OTHER INFORMATION: PD1-CD28-2F5PSMA-CAR varICOS CD3z

<400> SEQUENCE: 232

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65              70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Phe Trp Val Leu Val Val
            165                 170                 175

Val Gly Gly Val Leu Ala Cys Tyr Ser Leu Leu Val Thr Val Ala Phe
            180                 185                 190

Ile Ile Phe Trp Val Arg Ser Lys Arg Ser Arg Leu Leu His Ser Asp
            195                 200                 205

Tyr Met Asn Met Thr Pro Arg Arg Pro Gly Pro Thr Arg Lys His Tyr
    210                 215                 220

Gln Pro Tyr Ala Pro Pro Arg Asp Phe Ala Ala Tyr Arg Ser Val Lys
225                 230                 235                 240

Gln Thr Leu Asn Phe Asp Leu Leu Lys Leu Ala Gly Asp Val Glu Ser
            245                 250                 255

Asn Pro Gly Pro Met Ala Leu Pro Val Thr Ala Leu Leu Leu Pro Leu
            260                 265                 270

Ala Leu Leu Leu His Ala Ala Arg Pro Glu Val Gln Leu Val Gln Ser
            275                 280                 285

Gly Ala Glu Val Lys Lys Pro Gly Glu Ser Leu Lys Ile Ser Cys Lys
        290                 295                 300

Gly Ser Gly Tyr Ser Phe Thr Ser Asn Trp Ile Gly Trp Val Arg Gln
305                 310                 315                 320

Met Pro Gly Lys Gly Leu Glu Trp Met Gly Ile Ile Tyr Pro Gly Asp
            325                 330                 335

```
Ser Asp Thr Arg Tyr Ser Pro Ser Phe Gln Gly Gln Val Thr Ile Ser
            340                 345                 350

Ala Asp Lys Ser Ile Ser Thr Ala Tyr Leu Gln Trp Asn Ser Leu Lys
            355                 360                 365

Ala Ser Asp Thr Ala Met Tyr Tyr Cys Ala Arg Gln Thr Gly Phe Leu
            370                 375                 380

Trp Ser Phe Asp Leu Trp Gly Arg Gly Thr Leu Val Thr Val Ser Ser
385                 390                 395                 400

Gly Gly Gly Gly Ser Gly Gly Gly Ser Gly Gly Gly Gly Ser Ala
                405                 410                 415

Ile Gln Leu Thr Gln Ser Pro Ser Ser Leu Ser Ala Ser Val Gly Asp
            420                 425                 430

Arg Val Thr Ile Thr Cys Arg Ala Ser Gln Asp Ile Ser Ser Ala Leu
            435                 440                 445

Ala Trp Tyr Gln Gln Lys Pro Gly Lys Ala Pro Lys Leu Leu Ile Tyr
            450                 455                 460

Asp Ala Ser Ser Leu Glu Ser Gly Val Pro Ser Arg Phe Ser Gly Ser
465                 470                 475                 480

Gly Ser Gly Thr Asp Phe Thr Leu Thr Ile Ser Ser Leu Gln Pro Glu
            485                 490                 495

Asp Phe Ala Thr Tyr Tyr Cys Gln Gln Phe Asn Ser Tyr Pro Leu Thr
            500                 505                 510

Phe Gly Gly Gly Thr Lys Val Glu Ile Lys Ile Lys Thr Thr Thr Pro
            515                 520                 525

Ala Pro Arg Pro Pro Thr Pro Ala Pro Thr Ile Ala Ser Gln Pro Leu
            530                 535                 540

Ser Leu Arg Pro Glu Ala Cys Arg Pro Ala Ala Gly Gly Ala Val His
545                 550                 555                 560

Thr Arg Gly Leu Asp Phe Ala Cys Asp Phe Trp Leu Pro Ile Gly Cys
            565                 570                 575

Ala Ala Phe Val Val Val Cys Ile Leu Gly Cys Ile Leu Ile Cys Trp
            580                 585                 590

Leu Thr Lys Lys Lys Tyr Ser Ser Ser Val His Asp Pro Asn Gly Glu
            595                 600                 605

Tyr Met Asn Met Arg Ala Val Asn Thr Ala Lys Lys Ser Arg Leu Thr
            610                 615                 620

Asp Val Thr Leu Arg Val Lys Phe Ser Arg Ser Ala Asp Ala Pro Ala
625                 630                 635                 640

Tyr Gln Gln Gly Gln Asn Gln Leu Tyr Asn Glu Leu Asn Leu Gly Arg
            645                 650                 655

Arg Glu Glu Tyr Asp Val Leu Asp Lys Arg Arg Gly Arg Asp Pro Glu
            660                 665                 670

Met Gly Gly Lys Pro Gln Arg Arg Lys Asn Pro Gln Glu Gly Leu Tyr
            675                 680                 685

Asn Glu Leu Gln Lys Asp Lys Met Ala Glu Ala Tyr Ser Glu Ile Gly
            690                 695                 700

Met Lys Gly Glu Arg Arg Arg Gly Lys Gly His Asp Gly Leu Tyr Gln
705                 710                 715                 720

Gly Leu Ser Thr Ala Thr Lys Asp Thr Tyr Asp Ala Leu His Met Gln
            725                 730                 735

Ala Leu Pro Pro Arg
            740
```

<210> SEQ ID NO 233
<211> LENGTH: 735
<212> TYPE: PRT
<213> ORGANISM: Artificial Sequence
<220> FEATURE:
<223> OTHER INFORMATION: PD1A132L-CD28-2F5PSMA-CAR ICOS CD3z

<400> SEQUENCE: 233

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Ser Lys Arg Ser Arg Leu Leu His Ser Asp Tyr Met Asn Met Thr Pro
        195                 200                 205

Arg Arg Pro Gly Pro Thr Arg Lys His Tyr Gln Pro Tyr Ala Pro Pro
210                 215                 220

Arg Asp Phe Ala Ala Tyr Arg Ser Val Lys Gln Thr Leu Asn Phe Asp
225                 230                 235                 240

Leu Leu Lys Leu Ala Gly Asp Val Glu Ser Asn Pro Gly Pro Met Ala
                245                 250                 255

Leu Pro Val Thr Ala Leu Leu Leu Pro Leu Ala Leu Leu Leu His Ala
            260                 265                 270

Ala Arg Pro Glu Val Gln Leu Val Gln Ser Gly Ala Glu Val Lys Lys
        275                 280                 285

Pro Gly Glu Ser Leu Lys Ile Ser Cys Lys Gly Ser Gly Tyr Ser Phe
290                 295                 300

Thr Ser Asn Trp Ile Gly Trp Val Arg Gln Met Pro Gly Lys Gly Leu
305                 310                 315                 320

Glu Trp Met Gly Ile Ile Tyr Pro Gly Asp Ser Asp Thr Arg Tyr Ser
                325                 330                 335

Pro Ser Phe Gln Gly Gln Val Thr Ile Ser Ala Asp Lys Ser Ile Ser
            340                 345                 350

Thr Ala Tyr Leu Gln Trp Asn Ser Leu Lys Ala Ser Asp Thr Ala Met
        355                 360                 365

Tyr Tyr Cys Ala Arg Gln Thr Gly Phe Leu Trp Ser Phe Asp Leu Trp
```

```
              370                 375                 380
Gly Arg Gly Thr Leu Val Thr Val Ser Ser Gly Gly Gly Ser Gly
385                 390                 395                 400

Gly Gly Gly Ser Gly Gly Gly Ser Ala Ile Gln Leu Thr Gln Ser
                405                 410                 415

Pro Ser Ser Leu Ser Ala Ser Val Gly Asp Arg Val Thr Ile Thr Cys
            420                 425                 430

Arg Ala Ser Gln Asp Ile Ser Ser Ala Leu Ala Trp Tyr Gln Gln Lys
        435                 440                 445

Pro Gly Lys Ala Pro Lys Leu Leu Ile Tyr Asp Ala Ser Ser Leu Glu
    450                 455                 460

Ser Gly Val Pro Ser Arg Phe Ser Gly Ser Gly Ser Gly Thr Asp Phe
465                 470                 475                 480

Thr Leu Thr Ile Ser Ser Leu Gln Pro Glu Asp Phe Ala Thr Tyr Tyr
                485                 490                 495

Cys Gln Gln Phe Asn Ser Tyr Pro Leu Thr Phe Gly Gly Gly Thr Lys
            500                 505                 510

Val Glu Ile Lys Ile Lys Thr Thr Pro Ala Pro Arg Pro Pro Thr
        515                 520                 525

Pro Ala Pro Thr Ile Ala Ser Gln Pro Leu Ser Leu Arg Pro Glu Ala
    530                 535                 540

Cys Arg Pro Ala Ala Gly Gly Ala Val His Thr Arg Gly Leu Asp Phe
545                 550                 555                 560

Ala Cys Asp Phe Trp Leu Pro Ile Gly Cys Ala Ala Phe Val Val Val
                565                 570                 575

Cys Ile Leu Gly Cys Ile Leu Ile Cys Trp Leu Thr Lys Lys Lys Tyr
            580                 585                 590

Ser Ser Ser Val His Asp Pro Asn Gly Glu Tyr Met Asn Met Arg Ala
        595                 600                 605

Val Asn Thr Ala Lys Lys Ser Arg Leu Thr Asp Val Thr Leu Arg Val
    610                 615                 620

Lys Phe Ser Arg Ser Ala Asp Ala Pro Ala Tyr Gln Gln Gly Gln Asn
625                 630                 635                 640

Gln Leu Tyr Asn Glu Leu Asn Leu Gly Arg Arg Glu Glu Tyr Asp Val
                645                 650                 655

Leu Asp Lys Arg Arg Gly Arg Asp Pro Glu Met Gly Gly Lys Pro Gln
            660                 665                 670

Arg Arg Lys Asn Pro Gln Glu Gly Leu Tyr Asn Glu Leu Gln Lys Asp
        675                 680                 685

Lys Met Ala Glu Ala Tyr Ser Glu Ile Gly Met Lys Gly Glu Arg Arg
    690                 695                 700

Arg Gly Lys Gly His Asp Gly Leu Tyr Gln Gly Leu Ser Thr Ala Thr
705                 710                 715                 720

Lys Asp Thr Tyr Asp Ala Leu His Met Gln Ala Leu Pro Pro Arg
                725                 730                 735

<210> SEQ ID NO 234
<211> LENGTH: 740
<212> TYPE: PRT
<213> ORGANISM: Artificial Sequence
<220> FEATURE:
<223> OTHER INFORMATION: PD1A132L-41BB-2F5PSMA-CAR varICOS CD3z

<400> SEQUENCE: 234

Met Gln Ile Pro Gln Ala Pro Trp Pro Val Val Trp Ala Val Leu Gln
```

-continued

```
1               5                   10                  15
Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
                50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Leu Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
                180                 185                 190

Tyr Cys Lys Lys Arg Gly Arg Lys Lys Leu Leu Tyr Ile Phe Lys Gln
                195                 200                 205

Pro Phe Met Arg Pro Val Gln Thr Thr Gln Glu Glu Asp Gly Cys Ser
210                 215                 220

Cys Arg Phe Pro Glu Glu Glu Glu Gly Gly Cys Glu Leu Val Lys Gln
225                 230                 235                 240

Thr Leu Asn Phe Asp Leu Leu Lys Leu Ala Gly Asp Val Glu Ser Asn
                245                 250                 255

Pro Gly Pro Met Ala Leu Pro Val Thr Ala Leu Leu Leu Pro Leu Ala
                260                 265                 270

Leu Leu Leu His Ala Ala Arg Pro Glu Val Gln Leu Val Gln Ser Gly
                275                 280                 285

Ala Glu Val Lys Lys Pro Gly Glu Ser Leu Lys Ile Ser Cys Lys Gly
                290                 295                 300

Ser Gly Tyr Ser Phe Thr Ser Asn Trp Ile Gly Trp Val Arg Gln Met
305                 310                 315                 320

Pro Gly Lys Gly Leu Glu Trp Met Gly Ile Ile Tyr Pro Gly Asp Ser
                325                 330                 335

Asp Thr Arg Tyr Ser Pro Ser Phe Gln Gly Gln Val Thr Ile Ser Ala
                340                 345                 350

Asp Lys Ser Ile Ser Thr Ala Tyr Leu Gln Trp Asn Ser Leu Lys Ala
                355                 360                 365

Ser Asp Thr Ala Met Tyr Tyr Cys Ala Arg Gln Thr Gly Phe Leu Trp
                370                 375                 380

Ser Phe Asp Leu Trp Gly Arg Gly Thr Leu Val Thr Val Ser Ser Gly
385                 390                 395                 400

Gly Gly Gly Ser Gly Gly Gly Gly Ser Gly Gly Gly Gly Ser Ala Ile
                405                 410                 415

Gln Leu Thr Gln Ser Pro Ser Ser Leu Ser Ala Ser Val Gly Asp Arg
                420                 425                 430
```

-continued

```
Val Thr Ile Thr Cys Arg Ala Ser Gln Asp Ile Ser Ser Ala Leu Ala
            435                 440                 445

Trp Tyr Gln Gln Lys Pro Gly Lys Ala Pro Lys Leu Leu Ile Tyr Asp
    450                 455                 460

Ala Ser Ser Leu Glu Ser Gly Val Pro Ser Arg Phe Ser Gly Ser Gly
465                 470                 475                 480

Ser Gly Thr Asp Phe Thr Leu Thr Ile Ser Ser Leu Gln Pro Glu Asp
                485                 490                 495

Phe Ala Thr Tyr Tyr Cys Gln Gln Phe Asn Ser Tyr Pro Leu Thr Phe
            500                 505                 510

Gly Gly Gly Thr Lys Val Glu Ile Lys Ile Lys Thr Thr Thr Pro Ala
        515                 520                 525

Pro Arg Pro Pro Thr Pro Ala Pro Thr Ile Ala Ser Gln Pro Leu Ser
    530                 535                 540

Leu Arg Pro Glu Ala Cys Arg Pro Ala Ala Gly Gly Ala Val His Thr
545                 550                 555                 560

Arg Gly Leu Asp Phe Ala Cys Asp Phe Trp Leu Pro Ile Gly Cys Ala
                565                 570                 575

Ala Phe Val Val Val Cys Ile Leu Gly Cys Ile Leu Ile Cys Trp Leu
            580                 585                 590

Thr Lys Lys Lys Tyr Ser Ser Ser Val His Asp Pro Asn Gly Glu Tyr
        595                 600                 605

Met Asn Met Arg Ala Val Asn Thr Ala Lys Lys Ser Arg Leu Thr Asp
    610                 615                 620

Val Thr Leu Arg Val Lys Phe Ser Arg Ser Ala Asp Ala Pro Ala Tyr
625                 630                 635                 640

Gln Gln Gly Gln Asn Gln Leu Tyr Asn Glu Leu Asn Leu Gly Arg Arg
                645                 650                 655

Glu Glu Tyr Asp Val Leu Asp Lys Arg Arg Gly Arg Asp Pro Glu Met
            660                 665                 670

Gly Gly Lys Pro Gln Arg Arg Lys Asn Pro Gln Glu Gly Leu Tyr Asn
        675                 680                 685

Glu Leu Gln Lys Asp Lys Met Ala Glu Ala Tyr Ser Glu Ile Gly Met
    690                 695                 700

Lys Gly Glu Arg Arg Arg Gly Lys Gly His Asp Gly Leu Tyr Gln Gly
705                 710                 715                 720

Leu Ser Thr Ala Thr Lys Asp Thr Tyr Asp Ala Leu His Met Gln Ala
                725                 730                 735

Leu Pro Pro Arg
            740

<210> SEQ ID NO 235
<211> LENGTH: 771
<212> TYPE: PRT
<213> ORGANISM: Artificial Sequence
<220> FEATURE:
<223> OTHER INFORMATION: TIM3-CD28-2F5PSMA-CAR varICOS CD3z

<400> SEQUENCE: 235

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45
```

-continued

```
Val Pro Val Cys Trp Gly Lys Gly Ala Cys Pro Val Phe Glu Cys Gly
     50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                     85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
        130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Phe Trp Val Leu Val Val Val Gly
        195                 200                 205

Gly Val Leu Ala Cys Tyr Ser Leu Leu Val Thr Val Ala Phe Ile Ile
    210                 215                 220

Phe Trp Val Arg Ser Lys Arg Ser Arg Leu Leu His Ser Asp Tyr Met
225                 230                 235                 240

Asn Met Thr Pro Arg Arg Pro Gly Pro Thr Arg Lys His Tyr Gln Pro
                245                 250                 255

Tyr Ala Pro Pro Arg Asp Phe Ala Ala Tyr Arg Ser Val Lys Gln Thr
                260                 265                 270

Leu Asn Phe Asp Leu Leu Lys Leu Ala Gly Asp Val Glu Ser Asn Pro
            275                 280                 285

Gly Pro Met Ala Leu Pro Val Thr Ala Leu Leu Leu Pro Leu Ala Leu
        290                 295                 300

Leu Leu His Ala Ala Arg Pro Glu Val Gln Leu Val Gln Ser Gly Ala
305                 310                 315                 320

Glu Val Lys Lys Pro Gly Glu Ser Leu Lys Ile Ser Cys Lys Gly Ser
                325                 330                 335

Gly Tyr Ser Phe Thr Ser Asn Trp Ile Gly Trp Val Arg Gln Met Pro
            340                 345                 350

Gly Lys Gly Leu Glu Trp Met Gly Ile Ile Tyr Pro Gly Asp Ser Asp
        355                 360                 365

Thr Arg Tyr Ser Pro Ser Phe Gln Gly Gln Val Thr Ile Ser Ala Asp
    370                 375                 380

Lys Ser Ile Ser Thr Ala Tyr Leu Gln Trp Asn Ser Leu Lys Ala Ser
385                 390                 395                 400

Asp Thr Ala Met Tyr Tyr Cys Ala Arg Gln Thr Gly Phe Leu Trp Ser
                405                 410                 415

Phe Asp Leu Trp Gly Arg Gly Thr Leu Val Thr Val Ser Ser Gly Gly
            420                 425                 430

Gly Gly Ser Gly Gly Gly Gly Ser Gly Gly Gly Gly Ser Ala Ile Gln
        435                 440                 445

Leu Thr Gln Ser Pro Ser Ser Leu Ser Ala Ser Val Gly Asp Arg Val
    450                 455                 460
```

```
Thr Ile Thr Cys Arg Ala Ser Gln Asp Ile Ser Ser Ala Leu Ala Trp
465                 470                 475                 480

Tyr Gln Gln Lys Pro Gly Lys Ala Pro Lys Leu Leu Ile Tyr Asp Ala
                485                 490                 495

Ser Ser Leu Glu Ser Gly Val Pro Ser Arg Phe Ser Gly Ser Gly Ser
            500                 505                 510

Gly Thr Asp Phe Thr Leu Thr Ile Ser Ser Leu Gln Pro Glu Asp Phe
        515                 520                 525

Ala Thr Tyr Tyr Cys Gln Gln Phe Asn Ser Tyr Pro Leu Thr Phe Gly
    530                 535                 540

Gly Gly Thr Lys Val Glu Ile Lys Ile Lys Thr Thr Thr Pro Ala Pro
545                 550                 555                 560

Arg Pro Pro Thr Pro Ala Pro Thr Ile Ala Ser Gln Pro Leu Ser Leu
                565                 570                 575

Arg Pro Glu Ala Cys Arg Pro Ala Ala Gly Gly Ala Val His Thr Arg
            580                 585                 590

Gly Leu Asp Phe Ala Cys Asp Phe Trp Leu Pro Ile Gly Cys Ala Ala
        595                 600                 605

Phe Val Val Val Cys Ile Leu Gly Cys Ile Leu Ile Cys Trp Leu Thr
    610                 615                 620

Lys Lys Lys Tyr Ser Ser Ser Val His Asp Pro Asn Gly Glu Tyr Met
625                 630                 635                 640

Asn Met Arg Ala Val Asn Thr Ala Lys Lys Ser Arg Leu Thr Asp Val
                645                 650                 655

Thr Leu Arg Val Lys Phe Ser Arg Ser Ala Asp Ala Pro Ala Tyr Gln
            660                 665                 670

Gln Gly Gln Asn Gln Leu Tyr Asn Glu Leu Asn Leu Gly Arg Arg Glu
        675                 680                 685

Glu Tyr Asp Val Leu Asp Lys Arg Arg Gly Arg Asp Pro Glu Met Gly
    690                 695                 700

Gly Lys Pro Gln Arg Arg Lys Asn Pro Gln Glu Gly Leu Tyr Asn Glu
705                 710                 715                 720

Leu Gln Lys Asp Lys Met Ala Glu Ala Tyr Ser Glu Ile Gly Met Lys
                725                 730                 735

Gly Glu Arg Arg Arg Gly Lys Gly His Asp Gly Leu Tyr Gln Gly Leu
            740                 745                 750

Ser Thr Ala Thr Lys Asp Thr Tyr Asp Ala Leu His Met Gln Ala Leu
        755                 760                 765

Pro Pro Arg
    770

<210> SEQ ID NO 236
<211> LENGTH: 1030
<212> TYPE: PRT
<213> ORGANISM: Artificial Sequence
<220> FEATURE:
<223> OTHER INFORMATION: PD1A132L-4-1BB-TIM3-CD28-2F5PSMA-CAR varICOS
      CD3z

<400> SEQUENCE: 236

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45
```

```
Asn Ala Thr Phe Thr Cys Ser Phe Ser Asn Thr Ser Glu Ser Phe Val
         50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Leu Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Tyr Cys Lys Lys Arg Gly Arg Lys Lys Leu Leu Tyr Ile Phe Lys Gln
        195                 200                 205

Pro Phe Met Arg Pro Val Gln Thr Thr Gln Glu Glu Asp Gly Cys Ser
210                 215                 220

Cys Arg Phe Pro Glu Glu Glu Glu Gly Gly Cys Glu Leu Val Lys Gln
225                 230                 235                 240

Thr Leu Asn Phe Asp Leu Leu Lys Leu Ala Gly Asp Val Glu Ser Asn
                245                 250                 255

Pro Gly Pro Met Phe Ser His Leu Pro Phe Asp Cys Val Leu Leu Leu
            260                 265                 270

Leu Leu Leu Leu Leu Thr Arg Ser Ser Glu Val Glu Tyr Arg Ala Glu
        275                 280                 285

Val Gly Gln Asn Ala Tyr Leu Pro Cys Phe Tyr Thr Pro Ala Ala Pro
290                 295                 300

Gly Asn Leu Val Pro Val Cys Trp Gly Lys Gly Ala Cys Pro Val Phe
305                 310                 315                 320

Glu Cys Gly Asn Val Val Leu Arg Thr Asp Glu Arg Asp Val Asn Tyr
                325                 330                 335

Trp Thr Ser Arg Tyr Trp Leu Asn Gly Asp Phe Arg Lys Gly Asp Val
            340                 345                 350

Ser Leu Thr Ile Glu Asn Val Thr Leu Ala Asp Ser Gly Ile Tyr Cys
        355                 360                 365

Cys Arg Ile Gln Ile Pro Gly Ile Met Asn Asp Glu Lys Phe Asn Leu
370                 375                 380

Lys Leu Val Ile Lys Pro Ala Lys Val Thr Pro Ala Pro Thr Arg Gln
385                 390                 395                 400

Arg Asp Phe Thr Ala Ala Phe Pro Arg Met Leu Thr Thr Arg Gly His
                405                 410                 415

Gly Pro Ala Glu Thr Gln Thr Leu Gly Ser Leu Pro Asp Ile Asn Leu
            420                 425                 430

Thr Gln Ile Ser Thr Leu Ala Asn Glu Leu Arg Asp Ser Arg Leu Ala
        435                 440                 445

Asn Asp Leu Arg Asp Ser Gly Ala Thr Ile Arg Phe Trp Val Leu Val
450                 455                 460
```

```
Val Val Gly Gly Val Leu Ala Cys Tyr Ser Leu Leu Val Thr Val Ala
465                 470                 475                 480

Phe Ile Ile Phe Trp Val Arg Ser Lys Arg Ser Arg Leu Leu His Ser
                485                 490                 495

Asp Tyr Met Asn Met Thr Pro Arg Arg Pro Gly Pro Thr Arg Lys His
            500                 505                 510

Tyr Gln Pro Tyr Ala Pro Pro Arg Asp Phe Ala Ala Tyr Arg Ser Val
        515                 520                 525

Lys Gln Thr Leu Asn Phe Asp Leu Leu Lys Leu Ala Gly Asp Val Glu
    530                 535                 540

Ser Asn Pro Gly Pro Met Ala Leu Pro Val Thr Ala Leu Leu Leu Pro
545                 550                 555                 560

Leu Ala Leu Leu Leu His Ala Ala Arg Pro Glu Val Gln Leu Val Gln
                565                 570                 575

Ser Gly Ala Glu Val Lys Lys Pro Gly Glu Ser Leu Lys Ile Ser Cys
            580                 585                 590

Lys Gly Ser Gly Tyr Ser Phe Thr Ser Asn Trp Ile Gly Trp Val Arg
        595                 600                 605

Gln Met Pro Gly Lys Gly Leu Glu Trp Met Gly Ile Ile Tyr Pro Gly
    610                 615                 620

Asp Ser Asp Thr Arg Tyr Ser Pro Ser Phe Gln Gly Gln Val Thr Ile
625                 630                 635                 640

Ser Ala Asp Lys Ser Ile Ser Thr Ala Tyr Leu Gln Trp Asn Ser Leu
                645                 650                 655

Lys Ala Ser Asp Thr Ala Met Tyr Tyr Cys Ala Arg Gln Thr Gly Phe
            660                 665                 670

Leu Trp Ser Phe Asp Leu Trp Gly Arg Gly Thr Leu Val Thr Val Ser
        675                 680                 685

Ser Gly Gly Gly Gly Ser Gly Gly Gly Ser Gly Gly Gly Gly Ser
    690                 695                 700

Ala Ile Gln Leu Thr Gln Ser Pro Ser Ser Leu Ser Ala Ser Val Gly
705                 710                 715                 720

Asp Arg Val Thr Ile Thr Cys Arg Ala Ser Gln Asp Ile Ser Ser Ala
                725                 730                 735

Leu Ala Trp Tyr Gln Gln Lys Pro Gly Lys Ala Pro Lys Leu Leu Ile
            740                 745                 750

Tyr Asp Ala Ser Ser Leu Glu Ser Gly Val Pro Ser Arg Phe Ser Gly
        755                 760                 765

Ser Gly Ser Gly Thr Asp Phe Thr Leu Thr Ile Ser Ser Leu Gln Pro
770                 775                 780

Glu Asp Phe Ala Thr Tyr Tyr Cys Gln Gln Phe Asn Ser Tyr Pro Leu
785                 790                 795                 800

Thr Phe Gly Gly Gly Thr Lys Val Glu Ile Lys Ile Lys Thr Thr Thr
                805                 810                 815

Pro Ala Pro Arg Pro Pro Thr Pro Ala Pro Thr Ile Ala Ser Gln Pro
            820                 825                 830

Leu Ser Leu Arg Pro Glu Ala Cys Arg Pro Ala Ala Gly Gly Ala Val
        835                 840                 845

His Thr Arg Gly Leu Asp Phe Ala Cys Asp Phe Trp Leu Pro Ile Gly
    850                 855                 860

Cys Ala Ala Phe Val Val Val Cys Ile Leu Gly Cys Ile Leu Ile Cys
865                 870                 875                 880

Trp Leu Thr Lys Lys Lys Tyr Ser Ser Ser Val His Asp Pro Asn Gly
```

```
                    885                  890                      895
Glu Tyr Met Asn Met Arg Ala Val Asn Thr Ala Lys Lys Ser Arg Leu
                900                      905                  910

Thr Asp Val Thr Leu Arg Val Lys Phe Ser Arg Ser Ala Asp Ala Pro
            915                 920                  925

Ala Tyr Gln Gln Gly Gln Asn Gln Leu Tyr Asn Glu Leu Asn Leu Gly
        930                 935                 940

Arg Arg Glu Glu Tyr Asp Val Leu Asp Lys Arg Arg Gly Arg Asp Pro
945             950                 955                     960

Glu Met Gly Gly Lys Pro Gln Arg Arg Lys Asn Pro Gln Glu Gly Leu
                965                 970                  975

Tyr Asn Glu Leu Gln Lys Asp Lys Met Ala Glu Ala Tyr Ser Glu Ile
            980                 985                  990

Gly Met Lys Gly Glu Arg Arg Arg  Gly Lys Gly His Asp  Gly Leu Tyr
            995                 1000                1005

Gln Gly Leu Ser Thr Ala Thr  Lys Asp Thr Tyr Asp  Ala Leu His
        1010            1015                1020

Met Gln  Ala Leu Pro Pro Arg
    1025              1030
```

PROSTATE-SPECIFIC MEMBRANE ANTIGEN CARS AND METHODS OF USE THEREOF

CROSS-REFERENCE TO RELATED APPLICATION

The present application is entitled to priority under 35 U.S.C. § 119(e) to U.S. Provisional Patent Application No. 62/639,321, filed Mar. 6, 2018, which is hereby incorporated by reference in its entirety herein.

BACKGROUND OF THE INVENTION

Breaking the tolerance to self-antigens is a major challenge in the application of immunotherapy to solid malignancies. Vaccine strategies aimed at harnessing endogenous anti-tumor T cells are limited by the T cell receptor (TCR) repertoire, which can be deleted within the thymus as part of central tolerance or rendered non-functional by post-thymic mechanisms of peripheral tolerance. One strategy to overcome such obstacles is to produce genetically engineered T cells redirected toward tumor antigens using a chimeric antigen receptor (CAR) approach. CAR T cells use genetically programmed, patient-derived lymphocytes transduced with chimeric receptor genes in order to combine the antigen recognition domains of a specific antibody with the signaling domains of a TCR.

Prostate-specific membrane antigen (PSMA) is a membrane-bound protein expressed on the cell surface and is reported to be highly overexpressed in prostate cancer tissues. PSMA expression is directly correlated with advancing tumor grade and stage, and is believed to confer a selective growth advantage to prostate cancer cells. As such, PSMA may be an ideal target for immunotherapies for prostate cancer.

Another major challenge in cancer immunotherapy is the hostile microenvironment in which the targeted tumor resides. For example, immunosuppressive receptor ligands such as, PDL1 (CD274) which binds to PD1 (CD279), are up-regulated and negatively regulate T cell activity in the tumor microenvironment. In addition, TGF-β, which is over-expressed in prostate tumor cells, can act as an immunosuppressive molecule.

Thus, there is a need in the art for novel cancer immunotherapies targeting PSMA. The present invention satisfies this need.

SUMMARY OF THE INVENTION

The present invention is based on the finding that human and murine prostate-specific membrane antigen (PSMA) chimeric antigen receptor (CAR) T cells exhibit potent anti-tumor activity. The present invention is also based on the finding that PSMA-CAR T cells comprising a dominant negative receptor and/or switch receptor exhibit significantly enhanced anti-tumor activity.

Accordingly, in certain aspects, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain; and a dominant negative receptor and/or switch receptor.

In certain exemplary embodiments, the PSMA binding domain is a murine PSMA binding domain.

In certain exemplary embodiments, the PSMA binding domain is a human PSMA binding domain.

In certain exemplary embodiments, the PSMA binding domain is selected from the group consisting of an antibody, a Fab, or an scFv.

In certain exemplary embodiments, the scFv comprises the amino acid sequence set forth in any one of SEQ ID NOs:13, 14, 26, 38, 50, or 62.

In certain exemplary embodiments, the CAR comprises a transmembrane domain, and an intracellular domain.

In certain exemplary embodiments, the transmembrane domain comprises a transmembrane region derived from CD8.

In certain exemplary embodiments, the transmembrane region derived from CD8 comprises the amino acid sequence set forth in SEQ ID NO:88.

In certain exemplary embodiments, the transmembrane domain further comprises a hinge region derived from CD8.

In certain exemplary embodiments, the hinge region derived from CD8 comprises the amino acid sequence set forth in SEQ ID NO:86.

In certain exemplary embodiments, the transmembrane domain and the hinge region comprises the amino acid sequence set forth in SEQ ID NO:90.

In certain exemplary embodiments, the intracellular domain comprises a 4-1BB signaling domain and a CD3 zeta signaling domain.

In certain exemplary embodiments, the intracellular domain comprises the amino acid sequence set forth in SEQ ID NO:102.

In certain exemplary embodiments, the intracellular domain comprises an ICOS signaling domain and a CD3 zeta signaling domain.

In certain exemplary embodiments, the intracellular domain comprises a variant ICOS signaling domain and a CD3 zeta signaling domain.

In certain exemplary embodiments, the 4-1BB signaling domain comprises the amino acid sequence set forth in SEQ ID NO:92.

In certain exemplary embodiments, the ICOS signaling domain comprises the amino acid sequence set forth in SEQ ID NO:203.

In certain exemplary embodiments, the variant ICOS signaling domain comprises the amino acid sequence set forth in SEQ ID NO:95.

In certain exemplary embodiments, the CD3 zeta signaling domain comprises the amino acid sequence set forth in SEQ ID NOs:97 or 100.

In certain exemplary embodiments, the dominant negative receptor is a truncated variant of a wild-type protein associated with a negative signal.

In certain exemplary embodiments, the truncated variant of a wild-type protein associated with a negative signal (e.g. dominant negative receptor) comprises the amino acid sequence set forth in SEQ ID NO:115.

In certain exemplary embodiments, the switch receptor comprises a first domain, wherein the first domain is derived from a first polypeptide that is associated with a negative signal; and a second domain, wherein the second domain is derived from a second polypeptide that is associated with a positive signal.

In certain exemplary embodiments, the first domain comprises at least a portion of the extracellular domain of the first polypeptide that is associated with a negative signal, and wherein the second domain comprises at least a portion of the intracellular domain of the second polypeptide that is associated with a positive signal.

In certain exemplary embodiments, the switch receptor further comprises a switch receptor transmembrane domain.

In certain exemplary embodiments, the switch receptor transmembrane domain comprises the transmembrane domain of the first polypeptide that is associated with a negative signal; or the transmembrane domain of the second polypeptide that is associated with a positive signal.

In certain exemplary embodiments, the first polypeptide that is associated with a negative signal is selected from the group consisting of CTLA4, PD-1, BTLA, TIM-3, and a TGFβR.

In certain exemplary embodiments, the second polypeptide that is associated with a positive signal is selected from the group consisting of CD28, ICOS, 4-1BB, and a IL-12R.

In certain exemplary embodiments, the switch receptor comprises a first domain comprising at least a portion of the extracellular domain of PD1; a switch receptor transmembrane domain comprising at least a portion of the transmembrane domain of CD28; and a second domain comprising at least a portion of the intracellular domain of CD28.

In certain exemplary embodiments, the switch receptor comprises the amino acid sequence set forth in SEQ ID NO:117.

In certain exemplary embodiments, the switch receptor comprises a first domain comprising at least a portion of the extracellular domain of PD1; a switch receptor transmembrane domain comprising at least a portion of the transmembrane domain of PD1; and a second domain comprising at least a portion of the intracellular domain of CD28.

In certain exemplary embodiments, the switch receptor comprises the amino acid sequence set forth in SEQ ID NO:119.

In certain exemplary embodiments, the first domain comprises at least a portion of the extracellular domain of PD1 comprises an alanine (A) to leucine (L) substitution at amino acid position 132.

In certain exemplary embodiments, the switch receptor comprises the amino acid sequence set forth in SEQ ID NO:121.

In certain exemplary embodiments, the switch receptor comprises a first domain comprising at least a portion of the extracellular domain of PD1 comprising an alanine (A) to leucine (L) substitution at amino acid position 132, and a second domain comprising at least a portion of the intracellular domain of CD28.

In certain exemplary embodiments, the switch receptor comprises the amino acid sequence set forth in SEQ ID NO:121.

In certain exemplary embodiments, the switch receptor comprises a first domain comprising at least a portion of the extracellular domain of PD1 comprising an alanine (A) to leucine (L) substitution at amino acid position 132, and a second domain comprising at least a portion of the intracellular domain of 4-1BB.

In certain exemplary embodiments, the switch receptor comprises the amino acid sequence set forth in SEQ ID NO:215.

In certain exemplary embodiments, the switch receptor comprises a first domain comprising at least a portion of the extracellular domain of TIM-3; and a second domain comprising at least a portion of the intracellular domain of CD28.

In certain exemplary embodiments, the switch receptor comprises the amino acid sequence set forth in SEQ ID NO:127.

In certain exemplary embodiments, the switch receptor comprises a first domain comprising at least a portion of the extracellular domain of a TGFβR; and a second domain comprising at least a portion of the intracellular domain of IL12Rβ1.

In certain exemplary embodiments, the switch receptor comprises the amino acid sequence set forth in SEQ ID NO:123.

In certain exemplary embodiments, the switch receptor comprises a first domain comprising at least a portion of the extracellular domain of a TGFβR; and a second domain comprising at least a portion of the intracellular domain of IL12Rβ2.

In certain exemplary embodiments, the switch receptor comprises the amino acid sequence set forth in SEQ ID NO:125.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:13, 14, 16, 38, 50, or 62; and a dominant negative receptor comprising the amino acid sequence set forth in SEQ ID NO:115.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:13, 14, 16, 38, 50, or 62; and a switch receptor comprising the amino acid sequence set forth in SEQ ID NO:213 or 215.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:13, 14, 16, 38, 50, or 62; and a switch receptor comprising the amino acid sequence set forth in SEQ ID NOs:117 or 119.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:13, 14, 16, 38, 50, or 62; and a switch receptor comprising the amino acid sequence set forth in SEQ ID NO:121.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:13, 14, 16, 38, 50, or 62; and a switch receptor comprising the amino acid sequence set forth in SEQ ID NO:127.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:13, 14, 16, 38, 50, or 62; and a switch receptor comprising the amino acid sequence set forth in SEQ ID NO:123.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in any one of SEQ ID NOs:14, 16, 38, 50, or 62; and a switch receptor comprising the amino acid sequence set forth in SEQ ID NO:125.

In another aspect, the instant disclosure provides a modified immune cell or precursor cell thereof, comprising a chimeric antigen receptor (CAR) having affinity for a prostate specific membrane antigen (PSMA) on a target cell, wherein the CAR comprises a PSMA binding domain comprising the amino acid sequence set forth in SEQ ID NO:13, 14; and a dominant negative receptor comprising the amino acid sequence set forth in SEQ ID NO:115.

In certain exemplary embodiments, the CAR comprises the amino acid sequence set forth in SEQ ID NO:105.

In certain exemplary embodiments, the modified cell secretes a bispecific antibody.

In certain exemplary embodiments, the bispecific antibody comprises a first antigen binding domain and a second antigen binding domain.

In certain exemplary embodiments, the first antigen binding domain binds to a negative signal selected from the group consisting of CTLA4, PD-1, BTLA, TIM-3, and TGFβR.

In certain exemplary embodiments, the second antigen binding domain binds to a co-stimulatory molecule.

In certain exemplary embodiments, the co-stimulatory molecule is CD28.

In certain exemplary embodiments, the modified cell is a modified T cell.

In certain exemplary embodiments, the modified T cell is an autologous cell.

In certain exemplary embodiments, the modified cell is a cytotoxic T lymphocyte (CTL).

In certain exemplary embodiments, the modified cell is a Natural Killer (NK) cell.

In certain exemplary embodiments, the modified cell is a hematopoietic stem or hematopoietic progenitor cell.

In certain exemplary embodiments, the modified cell is an autologous cell.

In certain exemplary embodiments, the modified cell is derived from a human.

In certain exemplary embodiments, the modified T cell is derived from a human.

In another aspect, the instant disclosure provides an isolated nucleic acid, comprising a first nucleic acid sequence encoding a chimeric antigen receptor (CAR) having affinity for a prostate specific membrane antigen (PSMA) on a target cell, wherein the CAR comprises a PSMA binding domain; and a second nucleic acid sequence encoding a dominant negative receptor and/or a switch receptor.

In certain exemplary embodiments, the first nucleic acid sequence comprises the nucleic acid sequence set forth in any one of SEQ ID NOs: 106, 108, 110, 112, 114, 210, 212.

In certain exemplary embodiments, the second nucleic acid sequence comprises the nucleic acid sequence set forth in any one of SEQ ID NOs:116, 118, 120, 122, 124, 126, 128, 214 or 216.

In certain exemplary embodiments, the first nucleic acid sequence and the second nucleic acid sequence are separated by a linker.

In certain exemplary embodiments, the linker comprises a nucleic acid sequence encoding an internal ribosome entry site (IRES).

In certain exemplary embodiments, the linker comprises a nucleic acid sequence encoding a self-cleaving peptide.

In certain exemplary embodiments, the self-cleaving peptide is a 2A peptide.

In certain exemplary embodiments, the 2A peptide is selected from the group consisting of porcine teschovirus-1 2A (P2A), Thoseaasigna virus 2A (T2A), equine rhinitis A virus 2A (E2A), and foot-and-mouth disease virus 2A (F2A).

In certain exemplary embodiments, the 2A peptide is T2A.

In certain exemplary embodiments, the 2A peptide is F2A.

In certain exemplary embodiments, the isolated nucleic acid comprises from 5' to 3' the first nucleic acid sequence, the linker, and the second nucleic acid sequence.

In certain exemplary embodiments, the isolated nucleic acid comprises from 5' to 3' the second nucleic acid sequence, the linker, and the first nucleic acid sequence.

In another aspect, the instant disclosure provides an isolated nucleic acid, comprising a first nucleic acid sequence encoding a chimeric antigen receptor (CAR) having affinity for a prostate specific membrane antigen (PSMA) on a target cell, wherein the CAR comprises a PSMA binding domain comprising the nucleic acid sequence set forth in any one of SEQ ID NOs:180, 15, 27, 39, 51, or 63; and a second nucleic acid sequence encoding a dominant negative receptor and/or switch receptor comprising the nucleic acid sequence set forth in any one of SEQ ID NOs:116, 118, 120, 122, 124, 126, 128, 214 or 216.

In another aspect, the instant disclosure provides an isolated nucleic acid, comprising a first nucleic acid sequence encoding a chimeric antigen receptor (CAR) having affinity for a prostate specific membrane antigen (PSMA) on a target cell, wherein the CAR comprises a PSMA binding domain comprising the nucleic acid sequence set forth in SEQ ID NO:180; and a second nucleic acid sequence encoding a dominant negative receptor and/or switch receptor comprising the nucleic acid sequence set forth in SEQ ID NO:116.

In certain exemplary embodiments, the first nucleic acid sequence and the second nucleic acid sequence is separated by a linker comprising a nucleic acid sequence encoding T2A.

In certain exemplary embodiments, the first nucleic acid sequence and the second nucleic acid sequence is separated by a linker comprising a nucleic acid sequence encoding F2A.

In another aspect, the instant disclosure provides an isolated nucleic acid, comprising the nucleic acid sequence set forth in any one of SEQ ID NOs:152-168, 210, 212, and 217-226.

In certain exemplary embodiments, the nucleic acid comprises the nucleotide sequence set forth in SEQ ID NO:152.

In another aspect, the instant disclosure provides an isolated nucleic acid, comprising a nucleic acid sequence encoding a bispecific antibody set forth in any one of SEQ ID NOs:130, 132, 134, 136, or 138.

In another aspect, the instant disclosure provides an expression construct comprising the isolated nucleic acid of any of the above-described embodiments.

In certain exemplary embodiments, the expression construct is a viral vector selected from the group consisting of a retroviral vector, a lentiviral vector, an adenoviral vector, and an adeno-associated viral vector.

In certain exemplary embodiments, the expression construct is a lentiviral vector.

In certain exemplary embodiments, the lentiviral vector further comprises an EF-1α promoter.

In certain exemplary embodiments, the lentiviral vector further comprises a rev response element (RRE).

In certain exemplary embodiments, the lentiviral vector further comprises a woodchuck hepatitis virus posttranscriptional regulatory element (WPRE).

In certain exemplary embodiments, the lentiviral vector further comprises a cPPT sequence.

In certain exemplary embodiments, the lentiviral vector further comprises an EF-1α promoter, a rev response element (RRE), a woodchuck hepatitis virus posttranscriptional regulatory element (WPRE), and a cPPT sequence.

In certain exemplary embodiments, the lentiviral vector is a self-inactivating lentiviral vector.

In another aspect, the instant disclosure provides a method for generating the modified immune cell or precursor cell thereof of any of the above-described embodiments, comprising introducing into the immune cell one or more of the nucleic acid of any of the above-described embodiments, or the expression construct of any of the above-described embodiments.

In another aspect, the instant disclosure provides a method of treating cancer in a subject in need thereof, the method comprising administering to the subject a therapeutically effective composition comprising the modified immune cell of any of the above-described embodiments.

In certain exemplary embodiments, the method further comprises administering to the subject a lymphodepleting chemotherapy.

In certain exemplary embodiments, the lymphodepleting chemotherapy comprises administering to the subject a therapeutically effective amount of cyclophosphamide and/or fludarabine.

In certain exemplary embodiments, the lymphodepleting chemotherapy comprises administering to the subject a therapeutically effective amount of cyclophosphamide at about 200 mg/m$^2$/day to about 2000 mg/m$^2$/day, and/or fludarabine at about 20 mg/m$^2$/day to about 900 mg/m$^2$/day.

In certain exemplary embodiments, cyclophosphamide is administered at about 300 mg/m$^2$/day, and fludarabine is administered at about 30 mg/m$^2$/day.

In certain exemplary embodiments, the cancer is a prostate cancer selected from the group consisting of castrate-resistant prostate cancer, advanced castrate-resistant prostate cancer, and metastatic castrate-resistant prostate cancer.

In another aspect, the instant disclosure provides a method of treating prostate cancer in a subject in need thereof. The method comprises administering to the subject a lymphodepleting chemotherapy comprising a therapeutically effective amount of cyclophosphamide and a modified T cell comprising a chimeric antigen receptor (CAR) having affinity for a prostate specific membrane antigen (PSMA) on a target cell, wherein the CAR comprises a PSMA binding domain comprising an amino acid sequence set forth in SEQ ID NO:13; and a dominant negative receptor comprising an amino acid sequence set forth in SEQ ID NO:115.

In another aspect, the instant disclosure provides a method of treating metastatic castrate resistant prostate cancer in a subject in need thereof, the method comprising administering to the subject a lymphodepleting chemotherapy comprising administering to the subject a therapeutically effective amount of cyclophosphamide; and administering to the subject a modified T cell comprising a chimeric antigen receptor (CAR) having affinity for a prostate specific membrane antigen (PSMA) on a target cell, wherein the CAR comprises a PSMA binding domain comprising an amino acid sequence set forth in SEQ ID NO:13; and a dominant negative receptor comprising an amino acid sequence set forth in SEQ ID NO:115.

BRIEF DESCRIPTION OF THE DRAWINGS

The foregoing and other features and advantages of the present invention will be more fully understood from the following detailed description of illustrative embodiments taken in conjunction with the accompanying drawings. It should be understood that the present invention is not limited to the precise arrangements and instrumentalities of the embodiments shown in the drawings.

FIG. 1D illustrates results using combined PC3.PSMA single cell clones. Limited dilution was performed with PC3.PSMA cells (left panel), seven single colonies were isolated and pooled to be a new cell line, PC3.PSMA.7SC (right panel). PSMA expression was examined by Flow Cytometry.

FIG. 4F shows results using various PSMA Lenti CARs incubated with PC3.PSMA or PDL1 electroporated PC3.PSMA cells and CD107a assays performed. The cells were gated by CD3. Results from day 14 are shown.

FIG. 5F shows results using various PSMA Lenti CARs incubated with PC3, PC3.PSMA.7SC or PDL1 electroporated PC3.PSMA.PDL1 cells and ELISA assays performed. (IL-2, top panel; IFN-γ, bottom panel).

FIG. 5H shows results using various PSMA Lenti CARs incubated with tumor cells or primary human cells and CD107a assays performed. The cells were gated by CD3.

FIG. 6 is a schematic representation of a dn-TGFRβII PSMA CAR construct and pTRPE construct map.

FIG. 14G is a table listing from top to bottom, T cells transduced as indicated, in order of tumor control capability. ICOS$^{YMNM}$ is superior to WT ICOS. PD1*BB is better than PD1*CD28 when with ICOSz or ICOSzYMNM.

DETAILED DESCRIPTION

Figure 1A:
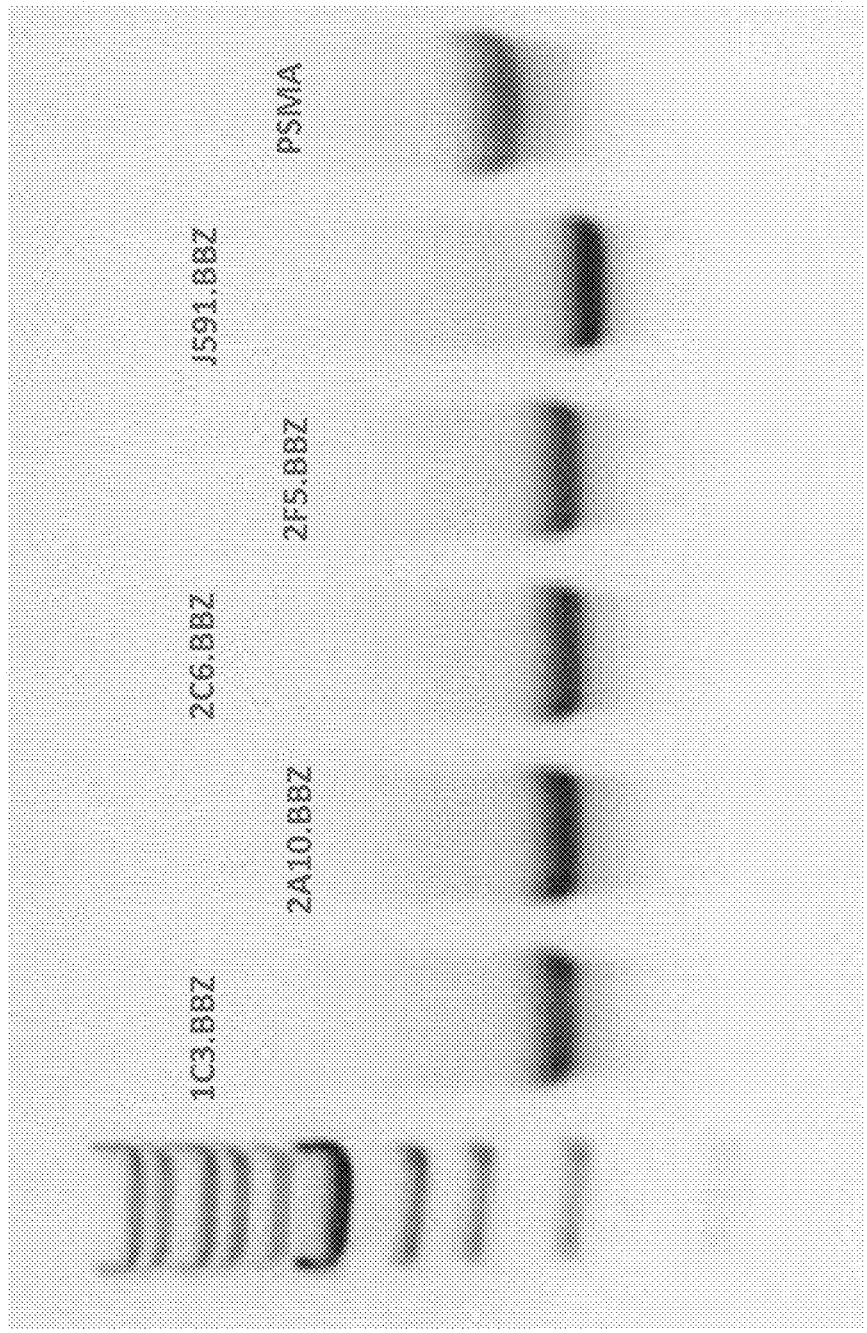
FIG. 1A illustrates results using purified IVT PSMA RNA CARs and full length PSMA RNA resolved on an agarose gel.

The present invention provides compositions and methods for modified immune cells, e.g., T cells and NK cells, or precursors thereof, e.g., modified T cells, comprising a chimeric antigen receptor (CAR). In some embodiments, the CAR comprises a prostate-specific membrane antigen (PSMA) binding domain (PSMA-CAR), and has affinity for PSMA on a target cell, e.g., a prostate cancer cell. In some embodiments, the modified immune cell comprises a PSMA-CAR comprising a murine PSMA binding domain. In some embodiments, the modified immune cell comprises a PSMA-CAR comprising a human PSMA binding domain. Also provided are methods of producing such genetically engineered cells. In some embodiments, the cells and compositions can be used in adoptive cell therapy, e.g., adoptive tumor immunotherapy.

In some embodiments, the provided immune cells comprise additional receptors, e.g., a dominant negative receptor and/or a switch receptor, to enhance the efficacy of the immune cell in the tumor microenvironment. Such cells are capable of altering or reducing the effects of immunosuppressive signals in the tumor microenvironment. The modified immune cells of the invention counteract the upregulation and/or expression of inhibitor receptor or ligands that can negatively control T cell activation and T cell function. For example, expression of certain immune checkpoint proteins, e.g., PD-1 or PD-L1, on T cells and/or in the tumor microenvironment can reduce the potency and efficacy of adoptive T cell therapy. For example, expression of TGF-β on T cells and/or in the tumor microenvironment can reduce the potency and efficacy of adoptive T cell therapy. Such immunosuppressive signals may otherwise impair certain desirable effector functions in the context of adoptive cell therapy. Tumor cells and/or cells in the tumor microenvironment often upregulate immunosuppressive proteins, e.g., PD-L1, delivering an immunosuppressive signal. Such immunosuppressive proteins may also be upregulated on T cells in the tumor microenvironment, e.g., on tumor-infiltrating T cells, which can occur following signaling through the antigen receptor or certain other activating signals. Such events may contribute to genetically engineered immune cells (e.g., PSMA targeting) T cells acquiring an exhausted phenotype, such as when present in proximity with other cells that express such protein, which in turn can lead to reduced functionality. Thus, the modified immune cells of the invention address the T cell exhaustion and/or the lack of T cell persistence that is a barrier to the efficacy and therapeutic outcomes of conventional adoptive cell therapies.

The present invention includes a PSMA CAR and its use in treating cancer. In certain embodiments, the invention includes a human PSMA CAR with a dominant negative receptor and/or a switch receptor. One of the major obstacles for cancer immunotherapy is the tumor microenvironment. Up-regulation of immunosuppressive molecules, e.g., PD-1, negatively regulates T cell activity.

The present invention is based on the finding that T cells comprising a PSMA-CAR and a dominant negative receptor and/or a switch receptor are capable of bypassing the effect of immunosuppressive molecules in the tumor microenvironment, providing continued and potent anti-tumor activity.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins (e.g., a binding fragment of an antibody). Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

Such a biological sample can include, but is not limited to a tissue sample, a tumor sample, a cell or a biological fluid.

As used herein, the term "autologous" is meant to refer to any material derived from the same individual to which it is later to be re-introduced into the individual. "Allogeneic" refers to any material derived from a different animal of the same species. "Xenogeneic" refers to any material derived from an animal of a different species.

The term "chimeric antigen receptor" or "CAR," as used herein refers to an artificial T cell receptor that is engineered to be expressed on an immune cell and specifically bind an antigen. CARs may be used as a therapy with adoptive cell transfer. T cells are removed from a patient and modified so that they express the receptors specific to an antigen or particular form of an antigen. In some embodiments, the CARs have specificity to a selected target, e.g., cells expressing a prostate-specific membrane antigen. CARs may also comprise an intracellular activation domain, a transmembrane domain and an extracellular domain comprising a tumor associated antigen binding region.

"Co-stimulatory ligand," as the term is used herein, includes a molecule on an antigen presenting cell (e.g., an artificial APC (aAPC), dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992. "Fully human" refers to an immunoglobulin, such as an antibody, or binding fragment thereof, where the whole molecule is of human origin or consists of an amino acid sequence identical to a human form of the antibody.

The term "immunoglobulin" or "Ig," as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" or "operatively linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used herein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Chimeric Antigen Receptors

The present invention provides compositions and methods for modified immune cells or precursors thereof, e.g., modified T cells, comprising a chimeric antigen receptor (CAR). Thus, in some embodiments, the immune cell has been genetically modified to express the CAR. CARs of the present invention comprise an antigen binding domain, a transmembrane domain, a hinge domain, and an intracellular signaling domain.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention. A subject CAR of the present invention may also include a spacer domain as described herein. In some embodiments, each of the antigen binding domain, transmembrane domain, and intracellular domain is separated by a linker.

Antigen Binding Domain

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular disease state of the target cell.

In an exemplary embodiment, the target cell antigen is a prostate-specific membrane antigen (PSMA). PSMA is a membrane-bound protein expressed on the cell surface and is reported to be highly overexpressed in prostate cancer tissues. PSMA expression is directly correlated with advancing tumor grade and stage, and is believed to confer a selective growth advantage to prostate cancer cells. As such, an exemplary CAR of the present disclosure has affinity for PSMA on a target cell.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In an exemplary embodiment, a CAR of the present disclosure having affinity for PSMA on a target cell may comprise a PSMA binding domain. In some embodiments, the PSMA binding domain is a murine PSMA binding domain, e.g., the PSMA binding domain is of murine origin. In some embodiments, the PSMA binding domain is a human PSMA binding domain, e.g., the PSMA binding domain is of human origin.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

In some embodiments, the antigen binding domain is selected from the group consisting of an antibody, an antigen binding fragment (Fab), and a single-chain variable fragment (scFv). In some embodiments, a PSMA binding domain of the present invention is selected from the group consisting of a PSMA-specific antibody, a PSMA-specific Fab, and a PSMA-specific scFv. In one embodiment, a PSMA binding domain is a PSMA-specific antibody. In one embodiment, a PSMA binding domain is a PSMA-specific Fab. In one embodiment, a PSMA binding domain is a PSMA-specific scFv.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., PSMA binding domain) comprises an scFv having the configuration from N-terminus to C-terminus, VH-linker-VL. In some embodiments, the antigen binding domain (e.g., PSMA binding domain) comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as (GS)$_n$, (GSGGS)$_n$ (SEQ ID NO:1), (GGGS)$_n$ (SEQ ID NO:2), and (GGGGS)$_n$ (SEQ ID NO:3), where n represents an integer of at least 1. Exemplary linker sequences can comprise amino acid sequences including, without limitation, GGSG (SEQ ID NO:4), GGSGG (SEQ ID NO:5), GSGSG (SEQ ID NO:6), GSGGG (SEQ ID NO:7), GGGSG (SEQ ID NO:8), GSSSG (SEQ ID NO:9), GGGGS (SEQ ID NO:10), GGGGSGGGGSGGGGS (SEQ ID NO:11) and the like. Those of skill in the art would be able to select the appropriate linker sequence for use in the present invention. In one embodiment, an antigen binding domain (e.g., PSMA binding domain) of the present invention comprises a heavy chain variable region (VH) and a light chain variable region (VL), wherein the VH and VL is separated by the linker sequence having the amino acid sequence GGGGSGGGGSGGGGS (SEQ ID NO:11), which may be encoded by the nucleic acid sequence

```
                                          (SEQ ID NO: 12)
GGTGGCGGTGGCTCGGGCGGTGGTGGGTCGGGTGGCGGCGGATCT.
```

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody as described elsewhere herein, or a fragment thereof.

In an exemplary embodiment, a PSMA-CAR of the present invention comprises a PSMA binding domain, e.g., PSMA-specific scFv.

(a) Murine PSMA Binding Domains and Variants Thereof

In certain embodiments, a PSMA-CAR of the present invention comprises a murine PSMA binding domain or variant thereof.

In certain embodiments, a PSMA-CAR of the present invention comprises a PSMA binding domain of a non-human PSMA antibody (e.g., a mouse or rat PSMA antibody), or a variant thereof. As is well known in the art, a murine or other non-human antibody may be raised by immunizing the non-human (e.g., a mouse) with human PSMA or a fragment thereof.

In one embodiment, the PSMA binding domain is a murine J591 PSMA binding domain that is comprised in the amino acid sequence set forth below:

```
                                          (SEQ ID NO: 14)
MALPVTALLLPLALLLHAARPGSDIVMTQSHKFMSTSVGDRVSIICKASQ

DVGTAVDWYQQKPGQSPKLLIYWASTRHTGVPDRFTGSGSGTDFTLTITN

VQSEDLADYFCQQYNSYPLTFGAGTMLDLKGGGGSGGGGSSGGGSEVQLQ

QSGPELVKPGTSVRISCKTSGYTFTEYTIHWVKQSHGKSLEWIGNINPNN

GGTTYNQKFEDKATLTVDKSSSTAYMELRSLTSEDSAVYYCAAGWNFDYW

GQGTTLTVSS,
``` which may be encoded by the nucleic acid sequence set forth below:

```
                                          (SEQ ID NO: 15)
ATGGCCCTGCCTGTGACAGCCCTGCTGCTGCCTCTGGCTCTGCTGCTGCA

CGCCGCCAGACCTGGATCTGACATTGTGATGACCCAGTCTCACAAATTCA

TGTCCACATCAGTAGGAGACAGGGTCAGCATCATCTGTAAGGCCAGTCAA

GATGTGGGTACTGCTGTAGACTGGTATCAACAGAAACCAGGACAATCTCC

TAAACTACTGATTTATTGGGCATCCACTCGGCACACTGGAGTCCCTGATC

GCTTCACAGGCAGTGGATCTGGGACAGACTTCACTCTCACCATTACTAAC

GTTCAGTCTGAAGACTTGGCAGATTATTTCTGTCAGCAATATAACAGCTA

TCCTCTCACGTTCGGTGCTGGGACCATGCTGGACCTGAAAGGAGGCGGAG

GATCTGGCGGCGGAGGAAGTTCTGGCGGAGGCAGCGAGGTGCAGCTGCAG

CAGAGCGGACCCGAGCTCGTGAAGCCTGGAACAAGCGTGCGGATCAGCTG

CAAGACCAGCGGCTACACCTTCACCGAGTACACCATCCACTGGGTCAAGC

AGTCCCACGGCAAGAGCCTGGAGTGGATCGGCAATATCAACCCCAACAAC

GGCGGCACCACCTACAACCAGAAGTTCGAGGACAAGGCCACCCTGACCGT

GGACAAGAGCAGCAGCACCGCCTACATGGAACTGCGGAGCCTGACCAGCG
```

```
AGGACAGCGCCGTGTACTATTGTGCCGCCGGTTGGAACTTCGACTACTGG

GGCCAGGGCACAACCCTGACAGTGTCTAGC.
```

Tolerable variations of the murine J591 PSMA binding domain will be known to those of skill in the art, while maintaining binding to PSMA. For example, in some embodiments, the PSMA binding domain is a murine J591 PSMA binding domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the murine J591 PSMA binding domain amino acid sequence that is comprised in SEQ ID NO:14. In one embodiment, the PSMA binding domain is a murine J591 PSMA binding domain that is comprised in the amino acid sequence set forth in SEQ ID NO:14.

In some embodiments, the PSMA binding domain is a murine J591 PSMA binding domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the murine J591 PSMA binding domain coding sequence comprised in SEQ ID NO:15. In one embodiment, the PSMA binding domain is a murine J591 PSMA binding domain encoded by the coding sequence comprised in the nucleic acid sequence set forth in SEQ ID NO:15.

In an exemplary embodiment, a PSMA-CAR of the present invention comprises a PSMA binding domain, e.g., PSMA-specific scFv. In one embodiment, the PSMA binding domain is a murine J591 PSMA binding domain comprising the amino acid sequence set forth below:

```
                                           (SEQ ID NO: 13)
DIVMTQSHKFMSTSVGDRVSIICKASQDVGTAVDWYQQKPGQSPKLLIYW

ASTRHTGVPDRFTGSGSGTDFTLTITNVQSEDLADYFCQQYNSYPLTFGA

GTMLDLKGGGGSGGGGSSGGGSEVQLQQSGPELVKPGTSVRISCKTSGYT

FTEYTIHWVKQSHGKSLEWIGNINPNNGGTTYNQKFEDKATLTVDKSSST

AYMELRSLTSEDSAVYYCAAGWNFDYWGQGTTLTVSS,
``` which may be encoded by the nucleic acid sequence set forth below:

```
                                           (SEQ ID NO: 180)
GACATTGTGATGACCCAGTCTCACAAATTCATGTCCACATCAGTAGGAGA

CAGGGTCAGCATCATCTGTAAGGCCAGTCAAGATGTGGGTACTGCTGTAG

ACTGGTATCAACAGAAACCAGGACAATCTCCTAAACTACTGATTTATTGG

GCATCCACTCGGCACACTGGAGTCCCTGATCGCTTCACAGGCAGTGGATC

TGGGACAGACTTCACTCTCACCATTACTAACGTTCAGTCTGAAGACTTGG

CAGATTATTTCTGTCAGCAATATAACAGCTATCCTCTCACGTTCGGTGCT

GGGACCATGCTGGACCTGAAAGGAGGCGGAGGATCTGGCGGCGGAGGAAG

TTCTGGCGGAGGCAGCGAGGTGCAGCTGCAGCAGAGCGGACCCGAGCTCG

TGAAGCCTGGAACAAGCGTGCGGATCAGCTGCAAGACCAGCGGCTACACC

TTCACCGAGTACACCATCCACTGGGTCAAGCAGTCCCACGGCAAGAGCCT

GGAGTGGATCGGCAATATCAACCCCAACAACGGCGGCACCACCTACAACC

AGAAGTTCGAGGACAAGGCCACCCTGACCGTGGACAAGAGCAGCAGCACC

GCCTACATGGAACTGCGGAGCCTGACCAGCGAGGACAGCGCCGTGTACTA

TTGTGCCGCCGGTTGGAACTTCGACTACTGGGGCCAGGGCACAACCCTGA

CAGTGTCTAGC
```

Tolerable variations of the murine J591 PSMA binding domain will be known to those of skill in the art, while maintaining binding to human PSMA. For example, in some embodiments, the PSMA binding domain is a murine J591 PSMA binding domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:13. In one embodiment, the PSMA binding domain is a murine J591 PSMA binding domain comprising the amino acid sequence set forth in SEQ ID NO: 13.

In some embodiments, the PSMA binding domain is a murine J591 PSMA binding domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:180. In one embodiment, the PSMA binding domain is a murine J591 PSMA binding domain encoded by the nucleic acid sequence set forth in SEQ ID NO:180.

In one embodiment, the murine J591 PSMA binding domain comprises a light chain variable region comprising the amino acid sequence set forth below:

```
                                           (SEQ ID NO: 16)
DIVMTQSHKFMSTSVGDRVSIICKASQDVGTAVDWYQQKPGQSPKLLIYW

ASTRHTGVPDRFTGSGSGTDFTLTITNVQSEDLADYFCQQYNSYPLTFGA

GTMLDLK,
``` which may be encoded by the nucleic acid sequence set forth below:

```
                                           (SEQ ID NO: 17)
GACATTGTGATGACCCAGTCTCACAAATTCATGTCCACATCAGTAGGAGA

CAGGGTCAGCATCATCTGTAAGGCCAGTCAAGATGTGGGTACTGCTGTAG

ACTGGTATCAACAGAAACCAGGACAATCTCCTAAACTACTGATTTATTGG

GCATCCACTCGGCACACTGGAGTCCCTGATCGCTTCACAGGCAGTGGATC

TGGGACAGACTTCACTCTCACCATTACTAACGTTCAGTCTGAAGACTTGG

CAGATTATTTCTGTCAGCAATATAACAGCTATCCTCTCACGTTCGGTGCT

GGGACCATGCTGGACCTGAAA.
```

Tolerable variations of the light chain variable region will be known to those of skill in the art, while maintaining its contribution to the binding of human PSMA. For example, in some embodiments, the murine J591 PSMA binding domain comprises a light chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:16. In one embodiment, the murine J591 PSMA binding domain comprises a light chain variable region comprising the amino acid sequence set forth in SEQ ID NO:16.

In some embodiments, the murine J591 PSMA binding domain comprises a light chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:17. In one embodiment, the murine J591 PSMA binding domain comprises a light chain variable region encoded by the nucleic acid sequence set forth in SEQ ID NO:17.

In one embodiment, the murine J591 PSMA binding domain comprises the light chain variable region described in NCBI GenBank sequence database ID: CCA78125.1, comprising the amino acid sequence set forth below:

```
                                         (SEQ ID NO: 181)
DIVMTQSHKFMSTSVGDRVSIICKASQDVGTAVDWYQQKPGQSPKLLIYW

ASTRHTGVPDRFTGSGSGTDFTLAITNVQSEDLADYFCQQYNSYPLTFGA

GTKLEIKR
```

Tolerable variations of the light chain variable region will be known to those of skill in the art, while maintaining its contribution to the binding of human PSMA. For example, in some embodiments, the murine J591 PSMA binding domain comprises a light chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:181. In one embodiment, the murine J591 PSMA binding domain comprises a light chain variable region comprising the amino acid sequence set forth in SEQ ID NO:181. The light chain variable region of the murine J591 PSMA binding domain comprises three light chain complementarity-determining regions (CDRs). As used herein, a "complementarity-determining region" or "CDR" refers to a region of the variable chain of an antigen binding molecule that binds to a specific antigen. Accordingly, a murine J591 PSMA binding domain may comprise a light chain variable region that comprises a CDR1 represented by the amino acid sequence KASQDVGTAVD (SEQ ID NO:18); a CDR2 represented by the amino acid sequence WASTRHT (SEQ ID NO:19); and a CDR3 represented by the amino acid sequence QQYNSYPLT (SEQ ID NO:20). Tolerable variations to the CDRs of the light chain will be known to those of skill in the art, while maintaining its contribution to the binding of PSMA. For example, a murine J591 PSMA binding domain may comprise a light chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:18. For example, a murine J591 PSMA binding domain may comprise a light chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:19. For example, a murine J591 PSMA binding domain may comprise a light chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:20. In one embodiment, the murine J591 PSMA binding domain comprises a light chain variable region comprising the three aforementioned light chain variable region CDRs.

In one embodiment, the murine J591 PSMA binding domain comprises a heavy chain variable region comprising the amino acid sequence set forth below:

```
                                          (SEQ ID NO: 21)
EVQLQQSGPELVKPGTSVRISCKTSGYTFTEYTIHWVKQSHGKSLEWIGN

INPNNGGTTYNQKFEDKATLTVDKSSSTAYMELRSLTSEDSAVYYCAAGW

NFDYWGQGTTLTVSS,
``` which may be encoded by the nucleic acid sequence set forth below:

```
                                          (SEQ ID NO: 22)
GAGGTGCAGCTGCAGCAGAGCGGACCCGAGCTCGTGAAGCCTGGAACAAG

CGTGCGGATCAGCTGCAAGACCAGCGGCTACACCTTCACCGAGTACACCA

TCCACTGGGTCAAGCAGTCCCACGGCAAGAGCCTGGAGTGGATCGGCAAT

ATCAACCCCAACAACGGCGGCACCACCTACAACCAGAAGTTCGAGGACAA

GGCCACCCTGACCGTGGACAAGAGCAGCAGCACCGCCTACATGGAACTGC

GGAGCCTGACCAGCGAGGACAGCGCCGTGTACTATTGTGCCGCCGGTTGG

AACTTCGACTACTGGGGCCAGGGCACAACCCTGACAGTGTCTAGC.
```

Tolerable variations of the heavy chain variable region will be known to those of skill in the art, while maintaining its contribution to the binding of human PSMA. For example, in some embodiments, the murine J591 PSMA binding domain comprises a heavy chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:21. In one embodiment, the murine J591 PSMA binding domain comprises a heavy chain variable region comprising the amino acid sequence set forth in SEQ ID NO:21.

In some embodiments, the murine J591 PSMA binding domain comprises a heavy chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:22. In one embodiment, the murine J591 PSMA binding domain comprises a heavy chain variable region encoded by the nucleic acid sequence set forth in SEQ ID NO:22.

In one embodiment, the murine J591 PSMA binding domain comprises the heavy chain variable region described in NCBI GenBank sequence database ID: CCA78124.1, comprising the amino acid sequence set forth below:

(SEQ ID NO: 182)
EVQLQQSGPELVKPGTSVRISCKTSGYTFTEYTIHWVKQSHGKSLEWIGN

INPNNGGTTYNQKFEDKATLTVDKSSSTAYMELRSLTSEDSAVYYCAAGW

NFDYWGQGTTLTVSS

Tolerable variations of the heavy chain variable region will be known to those of skill in the art, while maintaining its contribution to the binding of PSMA. For example, in some embodiments, the murine J591 PSMA binding domain comprises a heavy chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:182. In one embodiment, the murine J591 PSMA binding domain comprises a heavy chain variable region comprising the amino acid sequence set forth in SEQ ID NO:182.

The heavy chain variable region of the murine J591 PSMA binding domain comprises three heavy chain complementarity-determining regions (CDRs). Accordingly, a murine J591 PSMA binding domain may comprise a heavy chain variable region that comprises a CDR1 represented by the amino acid sequence GYTFTEYTIH (SEQ ID NO:23); a CDR2 represented by the amino acid sequence NINPNNGGTTYNQKFED (SEQ ID NO:24); and a CDR3 represented by the amino acid sequence GWNFDY (SEQ ID NO:25). Tolerable variations to the CDRs of the heavy chain will be known to those of skill in the art, while maintaining its contribution to the binding of human PSMA. For example, a murine J591 PSMA binding domain may comprise a heavy chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:23. For example, a murine J591 PSMA binding domain may comprise a heavy chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:24. For example, a murine J591 PSMA binding domain may comprise a heavy chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:25. In one embodiment, the murine J591 PSMA binding domain comprises a heavy chain variable region comprising the three aforementioned heavy chain variable region CDRs.

In one embodiment, the PSMA binding domain is a murine J591 PSMA binding domain comprising an amino acid sequence that comprises at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequences set forth in SEQ ID NOs:16 and 21.

In one embodiment, the PSMA binding domain is a murine J591 PSMA binding domain comprising an amino acid sequence that comprises at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequences set forth in SEQ ID NOs:181 and 182

(b) Humanized PSMA Binding Domains

In certain embodiments, a PSMA-CAR of the present invention comprises a humanized variant of a PSMA binding domain of a non-human PSMA antibody, or a variant or fragment thereof. In certain exemplary embodiments, the PSMA CAR comprises a humanized variant of the murine J591 antibody which binds human PSMA. Methods for humanizing murine antibodies are well known in the art.

In one embodiment, the PSMA binding domain is a humanized PSMA-specific binding domain. In certain embodiments, the PSMA binding domain is a humanized J591 PSMA binding domain. In certain embodiments, the PSMA binding domain comprises any of the heavy and light chain variable regions disclosed in PCT Publication Nos. WO2017212250A1 and WO2018033749A1, the disclosures of which are hereby incorporated herein by reference in their entirety. For example, a PSMA binding domain of the present invention can comprise an scFv comprising any of the heavy and light chain variable regions disclosed therein. Accordingly, a PSMA-CAR of the present invention comprises a humanized variant of the murine J591 antibody which binds human PSMA, as disclosed in WO2017212250A1 and WO2018033749A1.

In certain embodiments, a PSMA binding domain of the present invention can comprise a heavy chain variable region and a light chain variable region of any of those set forth in Table 19:

TABLE 19

Humanized PSMA binding heavy and light chain variable sequences

| Heavy Chain Variable Region Sequences | Light Chain Variable Region Sequences |
|---|---|
| VH Consensus Sequence<br>SEQ ID NO: 183<br>EVQLVQSGX$_1$EX$_2$KKPGASVKVSCKX$_3$<br>SGYTFTEYTIHWVX$_4$QAX$_5$GKGLEWIG<br>NINPNX$_6$GGTTYNQKFEDRX$_7$TX$_8$TVD<br>KSTSTAYMELSSLRSEDTAVYYCAAG<br>WNFDYWGQGTTVTSS<br>wherein:<br>X$_1$ is A or P;<br>X$_2$ is V or L;<br>X$_3$ is A or T;<br>X$_4$ is R or K;<br>X$_5$ is P or H;<br>X$_6$ is N or Q;<br>X$_7$ is V or A; and<br>X$_8$ is I or L. | VL Consensus Sequence<br>SEQ ID NO: 184<br>DIX$_1$MTQSPSX$_2$LSASVGDRVTITCKASQDV<br>GTAVDWYQQKPGQAPKLLIYWASTRHTG<br>VPDRFX$_3$GSGSGTDFTLTISRLQX$_4$EDFAX$_5$Y<br>X$_6$CQQYNSYPLTFGQGTX$_7$VDIK<br>wherein:<br>X$_1$ is Q or V;<br>X$_2$ is T or F;<br>X$_3$ is S or T;<br>X$_4$ is P or S;<br>X$_5$ is V or D;<br>X$_6$ is Y or F; and<br>X$_7$ is K or M. |
| SEQ ID NO: 185<br>EVQLVQSGPELKKPGASVKVSCKTSG<br>YTFTEYTIHWVKQAHGKGLEWIGNIN<br>PNNGGTTYNQKFEDRATLTVDKSTST<br>AYMELSSLRSEDTAVYYCAAGWNFD<br>YWGQGTTVTSS | SEQ ID NO: 186<br>DIVMTQSPSFLSASVGDRVTITCKASQDVG<br>TAVDWYQQKPGQAPKLLIYWASTRHTGV<br>PDRFTGSGSGTDFTLTISRLQSEDFADYFCQ<br>QYNSYPLTFGQGTMVDIK |
| SEQ ID NO: 187<br>EVQLVQSGAEVKKPGASVKVSCKTSG<br>YTFTEYTIHWVKQAPGKGLEWIGNIN<br>PNNGGTTYNQKFEDRATITVDKSTST<br>AYMELSSLRSEDTAVYYCAAGWNFD<br>YWGQGTTVTSS | SEQ ID NO: 188<br>DIVMTQSPSTLSASVGDRVTITCKASQDVG<br>TAVDWYQQKPGQAPKLLIYWASTRHTGV<br>PDRFTGSGSGTDFTLTISRLQSEDFADYFCQ<br>QYNSYPLTFGQGTKVDIK |
| SEQ ID NO: 189<br>EVQLVQSGAEVKKPGASVKVSCKTSG<br>YTFTEYTIHWVRQAPGKGLEWIGNIN<br>PNNGGTTYNQKFEDRATITVDKSTST<br>AYMELSSLRSEDTAVYYCAAGWNFD<br>YWGQGTTVTSS | SEQ ID NO: 190<br>DIVMTQSPSTLSASVGDRVTITCKASQDVG<br>TAVDWYQQKPGQAPKLLIYWASTRHTGV<br>PDRFSGSGSGTDFTLTISRLQPEDFADYYCQ<br>QYNSYPLTFGQGTKVDIK |
| SEQ ID NO: 191<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAAGWNF<br>DYWGQGTTVTSS | SEQ ID NO: 192<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ<br>QYNSYPLTFGQGTKVDIK |
| SEQ ID NO: 193<br>EVQLVQSGAEVKKPGASVKVSCKAS<br>GYTFTEYTIHWVRQAPGKGLEWIGNI<br>NPNQGGTTYNQKFEDRVTITVDKSTS<br>TAYMELSSLRSEDTAVYYCAAGWNF<br>DYWGQGTTVTSS | |
| VH Consensus Sequence<br>SEQ ID NO: 194<br>EVQLVQSGX$_1$EX$_2$KKPGASVKVSCKX$_3$<br>SGYTFTEYTIHWVX$_4$QAX$_5$GKGLEWIG<br>NINPNX$_6$GGTTYNQKFEDRX$_7$TX$_8$TVD<br>KSTSTAYMELSSX$_9$RSEDTAVYYCAX$_{10}$<br>X$_{11}$X$_{12}$X$_{13}$X$_{14}$DYWGQGTTVTSS<br>wherein:<br>X$_1$ is A or P;<br>X$_2$ is V or L;<br>X$_3$ is A or T;<br>X$_4$ is R or K;<br>X$_5$ is P or H;<br>X$_6$ is N or Q;<br>X$_7$ is V or A;<br>X$_8$ is I or L;<br>X$_9$ is L or P; and<br>X$_{10}$-X$_{14}$ is AYWLF, GGWTF, or GAWTM. | VL Consensus Sequence<br>SEQ ID NO: 195<br>DIX$_1$MTQSPSX$_2$LSASVGDRVTITCKASQDV<br>GTAVDWYQQKPGQAPKLLIYWASTRHTG<br>VPDRFX$_3$GSGSGTDFTLTISRLQX$_4$EDFAX$_5$Y<br>X$_6$CQQX$_7$X$_8$X$_9$X$_{10}$X$_{11}$LTFGQGTX$_{12}$VDIK<br>wherein:<br>X$_1$ is Q or V;<br>X$_2$ is T or F;<br>X$_3$ is S or T;<br>X$_4$ is P or S;<br>X$_5$ is V or D;<br>X$_6$ is Y or F;<br>X$_7$-X$_{11}$ is FTRYP or YNAYS; and<br>X$_{12}$ is K or M. |
| SEQ ID NO: 196<br>EVQLVQSGAEVKKPGASVKVSCKAS<br>GYTFTEYTIHWVRQAPGKGLEWIGNI<br>NPNNGGTTYNQKFEDRVTITVDKSTS | SEQ ID NO: 197<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ |

TABLE 19-continued

Humanized PSMA binding heavy and light chain variable sequences

| Heavy Chain Variable Region Sequences | Light Chain Variable Region Sequences |
|---|---|
| TAYMELSSLRSEDTAVYYCAAYWLF DYWGQGTTVTVSS | QYNSYPLTFGQGTKVDIK |
| SEQ ID NO: 198<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAGGWTF<br>DYWGQGTTVTVSS | SEQ ID NO: 199<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ<br>QFTRYPLTFGQGTKVDIK |
| SEQ ID NO: 200<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAGAWTM<br>DYWGQGTTVTVSS | SEQ ID NO: 201<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ<br>QYNAYSLTFGQGTKVDIK |
| SEQ ID NO: 202<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSPRSEDTAVYYCAAGWNF<br>DYWGQGTTVTVSS | |

(c) Human PSMA Binding Domains

In certain embodiments, a PSMA-CAR of the present invention comprises a PSMA binding domain of a human PSMA antibody, or a variant thereof. In one embodiment, the PSMA binding domain is a human 1C3 PSMA binding domain comprising the amino acid sequence set forth below:

(SEQ ID NO: 26)
MALPVTALLLPLALLLHAARPQVQLVESGGGVVQPGRSLRLSCAASGFTF

SSYAMHWVRQAPGKGLEWVAVISYDGNNKYYADSVKGRFTISRDNSKNT

LYLQMNSLRAEDTAVYYCARAVPWGSRYYYYGMDVWGQGTTVTVSSGG

GGSGGGGSGGGGSAIQLTQSPSSLSASVGDRVTITCRASQGISSALAWYQ

QKSGKAPKLLIFDASSLESGVPSRFSGSGSGTDFTLTISSLQPEDFATY

YCQQFNSYPLTFGGGTKVEIK, which may be encoded by the nucleic acid sequence set forth below:

(SEQ ID NO: 27)
ATGGCCTTACCAGTGACCGCCTTGCTCCTGCCGCTGGCCTTGCTGCTCCA

CGCCGCCAGGCCGCAGGTGCAACTGGTGGAGTCTGGGGGAGGCGTGGTCC

AGCCTGGGAGGTCCCTGAGACTCTCCTGTGCAGCCTCTGGATTCACCTTC

AGTAGCTATGCTATGCACTGGGTCCGCCAGGCTCCAGGCAAGGGGCTGGA

GTGGGTGGCAGTTATATCATATGATGGAAACAATAAATACTACGCAGACT

CCGTGAAGGGCCGATTCACCATCTCCAGAGACAATTCCAAGAACACGCTG

TATCTGCAAATGAACAGCCTGAGAGCTGAGGACACGGCTGTGTATTACTG

TGCGAGAGCCGTCCCCTGGGGATCGAGGTACTACTACTACGGTATGGACG

TCTGGGGCCAAGGGACCACGGTCACCGTCTCCTCAGGTGGCGGTGGCTCG

GGCGGTGGTGGGTCGGGTGGCGGCGGATCTGCCATCCAGTTGACCCAGTC

TCCATCCTCCCTGTCTGCATCTGTAGGAGACAGAGTCACCATCACTTGCC

GGGCAAGTCAGGGCATTAGCAGTGCTTTAGCCTGGTATCAGCAGAAATCA

GGGAAAGCTCCTAAGCTCCTGATCTTTGATGCCTCCAGTTTGGAAAGTGG

GGTCCCATCAAGGTTCAGCGGCAGTGGATCTGGGACAGATTTCACTCTCA

CCATCAGCAGCCTGCAGCCTGAAGATTTTGCAACTTATTACTGTCAACAG

TTTAACAGTTATCCTCTCACTTTCGGCGGAGGGACCAAGGTGGAGA

TCAAA.

Tolerable variations of the human 1C3 PSMA binding domain will be known to those of skill in the art, while maintaining binding to human PSMA. For example, in some embodiments, the PSMA binding domain is a human 1C3 PSMA binding domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:26. In one embodiment, the PSMA binding domain is a human 1C3 PSMA binding domain comprising the amino acid sequence set forth in SEQ ID NO:26.

In some embodiments, the PSMA binding domain is a human 1C3 PSMA binding domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:27. In one embodiment, the PSMA binding domain is a human 1C3 PSMA binding domain encoded by the nucleic acid sequence set forth in SEQ ID NO:27.

In one embodiment, the human 1C3 PSMA binding domain comprises a heavy chain variable region comprising the amino acid sequence set forth below:

(SEQ ID NO: 28)
PQVQLVESGGGVVQPGRSLRLSCAASGFTFSSYAMHWVRQAPGKGLEWVA

VISYDGNNKYYADSVKGRFTISRDNSKNTLYLQMNSLRAEDTAVYYCARA

VPWGSRYYYYGMDVWGQGTTVTVSS, which may be encoded by the nucleic acid sequence set forth below:

(SEQ ID NO: 29)
CCGCAGGTGCAACTGGTGGAGTCTGGGGGAGGCGTGGTCCAGCCTGGGAG

GTCCCTGAGACTCTCCTGTGCAGCCTCTGGATTCACCTTCAGTAGCTATG

CTATGCACTGGGTCCGCCAGGCTCCAGGCAAGGGGCTGGAGTGGGTGGCA

GTTATATCATATGATGGAAACAATAAATACTACGCAGACTCCGTGAAGGG

CCGATTCACCATCTCCAGAGACAATTCCAAGAACACGCTGTATCTGCAAA

TGAACAGCCTGAGAGCTGAGGACACGGCTGTGTATTACTGTGCGAGAGCC

GTCCCCTGGGGATCGAGGTACTACTACTACGGTATGGACGTCTGGGGCCA

AGGGACCACGGTCACCGTCTCCTCA.

Tolerable variations of the heavy chain variable region will be known to those of skill in the art, while maintaining its contribution to the binding of human PSMA. For example, in some embodiments, the human 1C3 PSMA binding domain comprises a heavy chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:28. In one embodiment, the human 1C3 PSMA binding domain comprises a heavy chain variable region comprising the amino acid sequence set forth in SEQ ID NO:28.

In some embodiments, the human 1C3 PSMA binding domain comprises a heavy chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:29. In one embodiment, the human 1C3 PSMA binding domain comprises a heavy chain variable region encoded by the nucleic acid sequence set forth in SEQ ID NO:29.

The heavy chain variable region of the human 1C3 PSMA binding domain comprises three heavy chain complementarity-determining regions (CDRs). Accordingly, a human 1C3 PSMA binding domain may comprise a heavy chain variable region that comprises a CDR1 represented by the amino acid sequence SYAMH (SEQ ID NO:30); a CDR2 represented by the amino acid sequence VISYDGNNKYYADSVKG (SEQ ID NO:31); and a CDR3 represented by the amino acid sequence AVPWGSRYYYYGMDV (SEQ ID NO:32). Tolerable variations to the CDRs of the heavy chain will be known to those of skill in the art, while maintaining its contribution to the binding of PSMA. For example, a human 1C3 PSMA binding domain may comprise a heavy chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:30. For example, a human 1C3 PSMA binding domain may comprise a heavy chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:31. For example, a human 1C3 PSMA binding domain may comprise a heavy chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:32. In one embodiment, the human 1C3 PSMA binding domain comprises a heavy chain variable region comprising the three aforementioned heavy chain variable region CDRs.

In one embodiment, the human 1C3 PSMA binding domain comprises a light chain variable region comprising the amino acid sequence set forth below:

(SEQ ID NO: 33)
AIQLTQSPSSLSASVGDRVTITCRASQGISSALAWYQQKSGKAPKLLIFD

ASSLESGVPSRFSGSGSGTDFTLTISSLQPEDFATYYCQQFNSYPLTFGG

GTKVEIK, which may be encoded by the nucleic acid sequence set forth below:

(SEQ ID NO: 34)
GCCATCCAGTTGACCCAGTCTCCATCCTCCCTGTCTGCATCTGTAGGAGA

CAGAGTCACCATCACTTGCCGGGCAAGTCAGGGCATTAGCAGTGCTTTAG

CCTGGTATCAGCAGAAATCAGGGAAAGCTCCTAAGCTCCTGATCTTTGAT

GCCTCCAGTTTGGAAAGTGGGGTCCCATCAAGGTTCAGCGGCAGTGGATC

TGGGACAGATTTCACTCTCACCATCAGCAGCCTGCAGCCTGAAGATTTTG

CAACTTATTACTGTCAACAGTTTAACAGTTATCCTCTCACTTTCGGCGGA

GGGACCAAGGTGGAGATCAAA.

Tolerable variations of the light chain variable region will be known to those of skill in the art, while maintaining its contribution to the binding of human PSMA. For example, in some embodiments, the human 1C3 PSMA binding domain comprises a light chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:33. In one embodiment, the human 1C3 PSMA binding domain comprises a light chain variable region comprising the amino acid sequence set forth in SEQ ID NO:33.

In some embodiments, the human 1C3 PSMA binding domain comprises a light chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:34. In one embodiment, the human 1C3 PSMA binding domain comprises a light chain variable region encoded by the nucleic acid sequence set forth in SEQ ID NO:34.

The light chain variable region of the human 1C3 PSMA binding domain comprises three light chain complementarity-determining regions (CDRs). Accordingly, a human 1C3 PSMA binding domain may comprise a light chain variable region that comprises a CDR1 represented by the amino acid sequence RASQGISSALA (SEQ ID NO:35); a CDR2 represented by the amino acid sequence DASSLES (SEQ ID NO:36); and a CDR3 represented by the amino acid sequence QQFNSYPLT (SEQ ID NO:37). Tolerable variations to the CDRs of the light chain will be known to those of skill in the art, while maintaining its contribution to the binding of PSMA. For example, a human 1C3 PSMA binding domain may comprise a light chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:35. For example, a human 1C3 PSMA binding domain may comprise a light chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:36. For example, a human 1C3 PSMA binding domain may comprise a light chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:37. In one embodiment, the human 1C3 PSMA binding domain comprises a light chain variable region comprising the three aforementioned light chain variable region CDRs.

In one embodiment, the PSMA binding domain is a human 2A10 PSMA binding domain comprising the amino acid sequence set forth below:

(SEQ ID NO: 38)
MALPVTALLLPLALLLHAARPEVQLVQSGAEVKKPGESLKISCKGSGYSF

TSNWIGWVRQMPGKGLEWMGIIYPGDSDTRYSPSFQGQVTISADKSISTA

YLQWSSLKASDTAMYYCARQTGFLWSSDLWGRGTLVTVSSGGGGSGGGGS

GGGGSAIQLTQSPSSLSASVGDRVTITCRASQDISSALAWYQQKPGKAPK

LLIYDASSLESGVPSRFSGYGSGTDFTLTINSLQPEDFATYYCQQFNSYP

LTFGGGTKVEIK, which may be encoded by the nucleic acid sequence set forth below:

(SEQ ID NO: 39)
ATGGCCTTACCAGTGACCGCCTTGCTCCTGCCGCTGGCCTTGCTGCTCCA

CGCCGCCAGGCCGGAGGTGCAGCTGGTGCAGTCTGGAGCAGAGGTGAAAA

AGCCCGGGGAGTCTCTGAAGATCTCCTGTAAGGGTTCTGGATACAGCTTT

ACCAGTAACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TACCTGCAGTGGAGCAGCCTGAAGGCCTCGGACACCGCCATGTATTACTG

TGCGAGGCAAACTGGTTTCCTCTGGTCCTCCGATCTCTGGGGCCGTGGCA

CCCTGGTCACTGTCTCCTCAGGTGGCGGTGGCTCGGGCGGTGGTGGGTCG

GGTGGCGGCGGATCTGCCATCCAGTTGACCCAGTCTCCATCCTCCCTGTC

TGCATCTGTAGGAGACAGAGTCACCATCACTTGCCGGGCAAGTCAGGACA

TTAGCAGTGCTTTAGCCTGGTATCAACAGAAACCAGGGAAAGCTCCTAAG

CTCCTGATCTATGATGCCTCCAGTTTGGAAAGTGGGGTCCCATCAAGGTT

CAGCGGCTATGGATCTGGGACAGATTTCACTCTCACCATCAACAGCCTGC

AGCCTGAAGATTTTGCAACTTATTACTGTCAACAGTTTAATAGTTACCCG

CTCACTTTCGGCGGAGGGACCAAGGTGGAGATCAAA.

Tolerable variations of the human 2A10 PSMA binding domain will be known to those of skill in the art, while maintaining binding to human PSMA. For example, in some embodiments, the PSMA binding domain is a human 2A10 PSMA binding domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:38. In one embodiment, the PSMA binding domain is a human 2A10 PSMA binding domain comprising the amino acid sequence set forth in SEQ ID NO:38.

In some embodiments, the PSMA binding domain is a human 2A10 PSMA binding domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:39. In one embodiment, the PSMA binding domain is a human 2A10 PSMA binding domain encoded by the nucleic acid sequence set forth in SEQ ID NO:39.

In one embodiment, the human 2A10 PSMA binding domain comprises a heavy chain variable region comprising the amino acid sequence set forth below:

(SEQ ID NO: 40)
PEVQLVQSGAEVKKPGESLKISCKGSGYSFTSNWIGWVRQMPGKGLEWMG

IIYPGDSDTRYSPSFQGQVTISADKSISTAYLQWSSLKASDTAMYYCARQ

TGFLWSSDLWGRGTLVTVSS, which may be encoded by the nucleic acid sequence set forth below:

```
                                            (SEQ ID NO: 41)
CCGGAGGTGCAGCTGGTGCAGTCTGGAGCAGAGGTGAAAAAGCCCGGGGA

GTCTCTGAAGATCTCCTGTAAGGGTTCTGGATACAGCTTTACCAGTAACT

GGATCGGCTGGGTGCGCCAGATGCCCGGGAAAGGCCTGGAGTGGATGGGG

ATCATCTATCCTGGTGACTCTGATACCAGATACAGCCCGTCCTTCCAAGG

CCAGGTCACCATCTCAGCCGACAAGTCCATCAGCACCGCCTACCTGCAGT

GGAGCAGCCTGAAGGCCTCGGACACCGCCATGTATTACTGTGCGAGGCAA

ACTGGTTTCCTCTGGTCCTCCGATCTCTGGGGCCGTGGCACCCTGGTCAC

TGTCTCCTCA.
```

Tolerable variations of the heavy chain variable region will be known to those of skill in the art, while maintaining its contribution to the binding of human PSMA. For example, in some embodiments, the human 2A10 PSMA binding domain comprises a heavy chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:40. In one embodiment, the human 2A10 PSMA binding domain comprises a heavy chain variable region comprising the amino acid sequence set forth in SEQ ID NO:40.

In some embodiments, the human 2A10 PSMA binding domain comprises a heavy chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:41. In one embodiment, the human 2A10 PSMA binding domain comprises a heavy chain variable region encoded by the nucleic acid sequence set forth in SEQ ID NO:41.

The heavy chain variable region of the human 2A10 PSMA binding domain comprises three heavy chain complementarity-determining regions (CDRs). Accordingly, a human 2A10 PSMA binding domain may comprise a heavy chain variable region that comprises a CDR1 represented by the amino acid sequence SNWIG (SEQ ID NO:42); a CDR2 represented by the amino acid sequence IIYPGDSDTRYSPSFQG (SEQ ID NO:43); and a CDR3 represented by the amino acid sequence QTGFLWSSDL (SEQ ID NO:44). Tolerable variations to the CDRs of the heavy chain will be known to those of skill in the art, while maintaining its contribution to the binding of human PSMA. For example, a human 2A10 PSMA binding domain may comprise a heavy chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:42. For example, a human 2A10 PSMA binding domain may comprise a heavy chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:43. For example, a human 2A10 PSMA binding domain may comprise a heavy chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:44. In one embodiment, the human 2A10 PSMA binding domain comprises a heavy chain variable region comprising the three aforementioned heavy chain variable region CDRs.

In one embodiment, the human 2A10 PSMA binding domain comprises a light chain variable region comprising the amino acid sequence set forth below:

```
                                            (SEQ ID NO: 45)
AIQLTQSPSSLSASVGDRVTITCRASQDISSALAWYQQKPGKAPKLLIYD

ASSLESGVPSRFSGYGSGTDFTLTINSLQPEDFATYYCQQFNSYPLTFGG

GTKVEIK,
``` which may be encoded by the nucleic acid sequence set forth below:

```
                                            (SEQ ID NO: 46)
GCCATCCAGTTGACCCAGTCTCCATCCTCCCTGTCTGCATCTGTAGGAGA

CAGAGTCACCATCACTTGCCGGGCAAGTCAGGACATTAGCAGTGCTTTAG

CCTGGTATCAACAGAAACCAGGGAAAGCTCCTAAGCTCCTGATCTATGAT

GCCTCCAGTTTGGAAAGTGGGGTCCCATCAAGGTTCAGCGGCTATGGATC

TGGGACAGATTTCACTCTCACCATCAACAGCCTGCAGCCTGAAGATTTTG

CAACTTATTACTGTCAACAGTTTAATAGTTACCCGCTCACTTTCGGCGGA

GGGACCAAGGTGGAGATCAAA.
```

Tolerable variations of the light chain variable region will be known to those of skill in the art, while maintaining its contribution to the binding of human PSMA. For example, in some embodiments, the human 2A10 PSMA binding domain comprises a light chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:45. In one embodiment, the human 2A10 PSMA binding domain comprises a light chain variable region comprising the amino acid sequence set forth in SEQ ID NO:45.

In some embodiments, the human 2A10 PSMA binding domain comprises a light chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:46. In one embodiment, the human 2A10 PSMA binding domain comprises a light chain variable region encoded by the nucleic acid sequence set forth in SEQ ID NO:46.

The light chain variable region of the human 2A10 PSMA binding domain comprises three light chain complementarity-determining regions (CDRs). Accordingly, a human 2A10 PSMA binding domain may comprise a light chain variable region that comprises a CDR1 represented by the amino acid sequence CRASQDISSAL (SEQ ID NO:47); a CDR2 represented by the amino acid sequence YDASSLES (SEQ ID NO:48); and a CDR3 represented by the amino acid sequence CQQFNSYPLT (SEQ ID NO:49). Tolerable variations to the CDRs of the light chain will be known to those of skill in the art, while maintaining its contribution to the binding of PSMA. For example, a human 2A10 PSMA binding domain may comprise a light chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:47. For example, a human 2A10 PSMA binding domain may comprise a light chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:48. For example, a human 2A10 PSMA binding domain may comprise a light chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:49. In one embodiment, the human 2A10 PSMA binding domain comprises a light chain variable region comprising the three aforementioned light chain variable region CDRs.

In one embodiment, the PSMA binding domain is a human 2F5 PSMA binding domain comprising the amino acid sequence set forth below:

```
                                        (SEQ ID NO: 50)
MALPVTALLLPLALLLHAARPEVQLVQSGAEVKKPGESLKISCKGSGYSF

TSNWIGWVRQMPGKGLEWMGIIYPGDSDTRYSPSFQGQVTISADKSISTA

YLQWNSLKASDTAMYYCARQTGFLWSFDLWGRGTLVTVSSGGGGSGGGGS

GGGGSAIQLTQSPSSLSASVGDRVTITCRASQDISSALAWYQQKPGKAPK

LLIYDASSLESGVPSRFSGSGSGTDFTLTISSLQPEDFATYYCQQFNSYP

LTFGGGTKVEIKIK,
``` which may be encoded by the nucleic acid sequence set forth below:

```
                                        (SEQ ID NO: 51)
ATGGCCTTACCAGTGACCGCCTTGCTCCTGCCGCTGGCCTTGCTGCTCCA
```

-continued
```
CGCCGCCAGGCCGGAGGTGCAGCTGGTGCAGTCTGGAGCAGAGGTGAAAA

AGCCCGGGGAGTCTCTGAAGATCTCCTGTAAGGGTTCTGGATACAGTTTT

ACCAGCAACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TACCTGCAGTGGAACAGCCTGAAGGCCTCGGACACCGCCATGTATTACTG

TGCGAGACAAACTGGTTTCCTCTGGTCCTTCGATCTCTGGGGCCGTGGCA

CCCTGGTCACTGTCTCCTCAGGTGGCGGTGGCTCGGGCGGTGGTGGGTCG

GGTGGCGGCGGATCTGCCATCCAGTTGACCCAGTCTCCATCCTCCCTGTC

TGCATCTGTAGGAGACAGAGTCACCATCACTTGCCGGGCAAGTCAGGACA

TTAGCAGTGCTTTAGCCTGGTATCAGCAGAAACCGGGGAAAGCTCCTAAG

CTCCTGATCTATGATGCCTCCAGTTTGGAAAGTGGGGTCCCATCAAGGTT

CAGCGGCAGTGGATCTGGGACAGATTTCACTCTCACCATCAGCAGCCTGC

AGCCTGAAGATTTTGCAACTTATTACTGTCAACAGTTTAATAGTTACCCG

CTCACTTTCGGCGGAGGGACCAAGGTGGAGATCAAAATCAAA.
```

Tolerable variations of the human 2F5 PSMA binding domain will be known to those of skill in the art, while maintaining binding to human PSMA. For example, in some embodiments, the PSMA binding domain is a human 2F5 PSMA binding domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:50. In one embodiment, the PSMA binding domain is a human 2F5 PSMA binding domain comprising the amino acid sequence set forth in SEQ ID NO:50.

In some embodiments, the PSMA binding domain is a human 2F5 PSMA binding domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:51. In one embodiment, the PSMA binding domain is a human 2F5 PSMA binding domain encoded by the nucleic acid sequence set forth in SEQ ID NO:51.

In one embodiment, the human 2F5 PSMA binding domain comprises a heavy chain variable region comprising the amino acid sequence set forth below:

```
                                        (SEQ ID NO: 52)
PEVQLVQSGAEVKKPGESLKISCKGSGYSFTSNWIGWVRQMPGKGLEWMG

IIYPGDSDTRYSPSFQGQVTISADKSISTAYLQWNSLKASDTAMYYCARQ

TGFLWSFDLWGRGTLVTVSS,
``` which may be encoded by the nucleic acid sequence set forth below:

```
                                              (SEQ ID NO: 53)
CCGGAGGTGCAGCTGGTGCAGTCTGGAGCAGAGGTGAAAAAGCCCGGGGA

GTCTCTGAAGATCTCCTGTAAGGGTTCTGGATACAGTTTTACCAGCAACT

GGATCGGCTGGGTGCGCCAGATGCCCGGGAAAGGCCTGGAGTGGATGGGG

ATCATCTATCCTGGTGACTCTGATACCAGATACAGCCCGTCCTTCCAAGG

CCAGGTCACCATCTCAGCCGACAAGTCCATCAGCACCGCCTACCTGCAGT

GGAACAGCCTGAAGGCCTCGGACACCGCCATGTATTACTGTGCGAGACAA

ACTGGTTTCCTCTGGTCCTTCGATCTCTGGGGCCGTGGCACCCTGGTCAC

TGTCTCCTCA.
```

Tolerable variations of the heavy chain variable region will be known to those of skill in the art, while maintaining its contribution to the binding of human PSMA. For example, in some embodiments, the human 2F5 PSMA binding domain comprises a heavy chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:52. In one embodiment, the human 2F5 PSMA binding domain comprises a heavy chain variable region comprising the amino acid sequence set forth in SEQ ID NO:52.

In some embodiments, the human 2F5 PSMA binding domain comprises a heavy chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:53. In one embodiment, the human 2F5 PSMA binding domain comprises a heavy chain variable region encoded by the nucleic acid sequence set forth in SEQ ID NO:53.

The heavy chain variable region of the human 2F5 PSMA binding domain comprises three heavy chain complementarity-determining regions (CDRs). Accordingly, a human 2F5 PSMA binding domain may comprise a heavy chain variable region that comprises a CDR1 represented by the amino acid sequence SNWIG (SEQ ID NO:54); a CDR2 represented by the amino acid sequence IIYPGDSDTRYSPSFQG (SEQ ID NO:55); and a CDR3 represented by the amino acid sequence QTGFLWSFDL (SEQ ID NO:56). Tolerable variations to the CDRs of the heavy chain will be known to those of skill in the art, while maintaining its contribution to the binding of PSMA. For example, a human 2F5 PSMA binding domain may comprise a heavy chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:54. For example, a human 2F5 PSMA binding domain may comprise a heavy chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:55. For example, a human 2F5 PSMA binding domain may comprise a heavy chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:56. In one embodiment, the human 2F5 PSMA binding domain comprises a heavy chain variable region comprising the three aforementioned heavy chain variable region CDRs.

In one embodiment, the human 2F5 PSMA binding domain comprises a light chain variable region comprising the amino acid sequence set forth below:

```
                                              (SEQ ID NO: 57)
AIQLTQSPSSLSASVGDRVTITCRASQDISSALAWYQQKPGKAPKLLIYD

ASSLESGVPSRFSGSGSGTDFTLTISSLQPEDFATYYCQQFNSYPLTFGG

GTKVEIKIK,
``` which may be encoded by the nucleic acid sequence set forth below:

```
                                              (SEQ ID NO: 58)
GCCATCCAGTTGACCCAGTCTCCATCCTCCCTGTCTGCATCTGTAGGAGA

CAGAGTCACCATCACTTGCCGGGCAAGTCAGGACATTAGCAGTGCTTTAG

CCTGGTATCAGCAGAAACCGGGGAAAGCTCCTAAGCTCCTGATCTATGAT

GCCTCCAGTTTGGAAAGTGGGGTCCCATCAAGGTTCAGCGGCAGTGGATC

TGGGACAGATTTCACTCTCACCATCAGCAGCCTGCAGCCTGAAGATTTTG

CAACTTATTACTGTCAACAGTTTAATAGTTACCCGCTCACTTTCGGCGGA

GGGACCAAGGTGGAGATCAAAATCAAA.
```

Tolerable variations of the light chain variable region will be known to those of skill in the art, while maintaining its contribution to the binding of human PSMA. For example, in some embodiments, the human 2F5 PSMA binding domain comprises a light chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:57. In one embodiment, the human 2F5 PSMA binding domain comprises a light chain variable region comprising the amino acid sequence set forth in SEQ ID NO:57.

In some embodiments, the human 2F5 PSMA binding domain comprises a light chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:58. In one embodiment, the human 2F5 PSMA binding domain comprises a light chain variable region encoded by the nucleic acid sequence set forth in SEQ ID NO:58.

The light chain variable region of the human 2F5 PSMA binding domain comprises three light chain complementarity-determining regions (CDRs). Accordingly, a human 2F5 PSMA binding domain may comprise a light chain variable region that comprises a CDR1 represented by the amino acid sequence RASQDISSALA (SEQ ID NO:59); a CDR2 represented by the amino acid sequence DASSLES (SEQ ID NO:60); and a CDR3 represented by the amino acid sequence QQFNSYPLT (SEQ ID NO:61). Tolerable variations to the CDRs of the light chain will be known to those of skill in the art, while maintaining its contribution to the binding of PSMA. For example, a human 2F5 PSMA binding domain may comprise a light chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:59. For example, a human 2F5 PSMA binding domain may comprise a light chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:60. For example, a human 2F5 PSMA binding domain may comprise a light chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:61. In one embodiment, the human 2F5 PSMA binding domain comprises a light chain variable region comprising the three aforementioned light chain variable region CDRs.

In one embodiment, the PSMA binding domain is a human 2C6 PSMA binding domain comprising the amino acid sequence set forth below:

```
                                            (SEQ ID NO: 62)
MALPVTALLLPLALLLHAARPEVQLVQSGSEVKKPGESLKISCKGSGYSF

TNYWIGWVRQMPGKGLEWMGIIYPGDSDTRYSPSFQGQVTISADKSISTA

YLQWSSLKASDTAMYYCASPGYTSSWTSFDYWGQGTLVTVSSGGGGSGGG

GSGGGGSEIVLTQSPATLSLSPGERATLSCRASQSVSSYLAWYQQKPGQA

PRLLIYDASNRATGIPARFSGSGSGTDFTLTISSLEPEDFAVYYCQQRSN

WPLFTFGPGTKVDIK,
``` which may be encoded by the nucleic acid sequence set forth below:

```
                                            (SEQ ID NO: 63)
ATGGCCTTACCAGTGACCGCCTTGCTCCTGCCGCTGGCCTTGCTGCTCCA

CGCCGCCAGGCCGGAGGTGCAGCTGGTGCAGTCTGGATCAGAGGTGAAAA

AGCCCGGGGAGTCTCTGAAGATCTCCTGTAAGGGTTCTGGATACAGCTTT
```

```
                       -continued
ACCAACTACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TATCTGCAGTGGAGCAGCCTGAAGGCCTCGGACACCGCCATGTATTACTG

TGCGAGTCCCGGGTATACCAGCAGTTGGACTTCTTTTGACTACTGGGGCC

AGGGAACCCTGGTCACCGTCTCCTCAGGTGGCGGTGGCTCGGGCGGTGGT

GGGTCGGGTGGCGGCGGATCTGAAATTGTGTTGACACAGTCTCCAGCCAC

CCTGTCTTTGTCTCCAGGGGAAAGAGCCACCCTCTCCTGCAGGGCCAGTC

AGAGTGTTAGCAGCTACTTAGCCTGGTACCAACAGAAACCTGGCCAGGCT

CCCAGGCTCCTCATCTATGATGCATCCAACAGGGCCACTGGCATCCCAGC

CAGGTTCAGTGGCAGTGGGTCTGGGACAGACTTCACTCTCACCATCAGCA

GCCTAGAGCCTGAAGATTTTGCAGTTTATTACTGTCAGCAGCGTAGCAAC

TGGCCCCTATTCACTTTCGGCCCTGGGACCAAAGTGGATATCAAA.
```

Tolerable variations of the human 2C6 PSMA binding domain will be known to those of skill in the art, while maintaining binding to human PSMA. For example, in some embodiments, the PSMA binding domain is a human 2C6 PSMA binding domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:62. In one embodiment, the PSMA binding domain is a human 2C6 PSMA binding domain comprising the amino acid sequence set forth in SEQ ID NO:62.

In some embodiments, the PSMA binding domain is a human 2C6 PSMA binding domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:63. In one embodiment, the PSMA binding domain is a human 2C6 PSMA binding domain encoded by the nucleic acid sequence set forth in SEQ ID NO:63.

In one embodiment, the human 2C6 PSMA binding domain comprises a heavy chain variable region comprising the amino acid sequence set forth below:

```
                                            (SEQ ID NO: 64)
PEVQLVQSGSEVKKPGESLKISCKGSGYSFTNYWIGWVRQMPGKGLEWMG

IIYPGDSDTRYSPSFQGQVTISADKSISTAYLQWSSLKASDTAMYYCASP

GYTSSWTSFDYWGQGTLVTVSS,
``` which may be encoded by the nucleic acid sequence set forth below:

```
                                            (SEQ ID NO: 65)
CCGGAGGTGCAGCTGGTGCAGTCTGGATCAGAGGTGAAAAAGCCCGGGGA

GTCTCTGAAGATCTCCTGTAAGGGTTCTGGATACAGCTTTACCAACTACT
```

```
-continued
GGATCGGCTGGGTGCGCCAGATGCCCGGGAAAGGCCTGGAGTGGATGGGG

ATCATCTATCCTGGTGACTCTGATACCAGATACAGCCCGTCCTTCCAAGG

CCAGGTCACCATCTCAGCCGACAAGTCCATCAGCACCGCCTATCTGCAGT

GGAGCAGCCTGAAGGCCTCGGACACCGCCATGTATTACTGTGCGAGTCCC

GGGTATACCAGCAGTTGGACTTCTTTTGACTACTGGGGCCAGGGAACCCT

GGTCACCGTCTCCTCA.
```

Tolerable variations of the heavy chain variable region will be known to those of skill in the art, while maintaining its contribution to the binding of human PSMA. For example, in some embodiments, the human 2C6 PSMA binding domain comprises a heavy chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:64. In one embodiment, the human 2C6 PSMA binding domain comprises a heavy chain variable region comprising the amino acid sequence set forth in SEQ ID NO:64.

In some embodiments, the human 2C6 PSMA binding domain comprises a heavy chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:65. In one embodiment, the human 2C6 PSMA binding domain comprises a heavy chain variable region encoded by the nucleic acid sequence set forth in SEQ ID NO:65.

The heavy chain variable region of the human 2C6 PSMA binding domain comprises three heavy chain complementarity-determining regions (CDRs). Accordingly, a human 2C6 PSMA binding domain may comprise a heavy chain variable region that comprises a CDR1 represented by the amino acid sequence TNYWI (SEQ ID NO:66); a CDR2 represented by the amino acid sequence GIIYPGDS-DTRYSPSFQG (SEQ ID NO:67); and a CDR3 represented by the amino acid sequence SPGYTSSWTS (SEQ ID NO:68). Tolerable variations to the CDRs of the heavy chain will be known to those of skill in the art, while maintaining its contribution to the binding of PSMA. For example, a human 2C6 PSMA binding domain may comprise a heavy chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:66. For example, a human 2C6 PSMA binding domain may comprise a heavy chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:67. For example, a human 2C6 PSMA binding domain may comprise a heavy chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:68. In one embodiment, the human 2C6 PSMA binding domain comprises a heavy chain variable region comprising the three aforementioned heavy chain variable region CDRs.

In one embodiment, the human 2C6 PSMA binding domain comprises a light chain variable region comprising the amino acid sequence set forth below:

```
                                        (SEQ ID NO: 69)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPLFTFG

PGTKVDIK,
``` which may be encoded by the nucleic acid sequence set forth below:

```
                                        (SEQ ID NO: 70)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCCCTATTCACTTTCGGC

CCTGGGACCAAAGTGGATATCAAA.
```

Tolerable variations of the light chain variable region will be known to those of skill in the art, while maintaining its contribution to the binding of human PSMA. For example, in some embodiments, the human 2C6 PSMA binding domain comprises a light chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:69. In one embodiment, the human 2C6 PSMA binding domain comprises a light chain variable region comprising the amino acid sequence set forth in SEQ ID NO:69.

In some embodiments, the human 2C6 PSMA binding domain comprises a light chain variable region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:70. In one embodiment, the human 2C6 PSMA binding domain comprises a light chain variable region encoded by the nucleic acid sequence set forth in SEQ ID NO:70.

The light chain variable region of the human 2C6 PSMA binding domain comprises three light chain complementarity-determining regions (CDRs). Accordingly, a human 2C6 PSMA binding domain may comprise a light chain variable region that comprises a CDR1 represented by the amino acid sequence CRASQSVSSYL (SEQ ID NO:71); a CDR2 represented by the amino acid sequence YDASNRAT (SEQ ID NO:72); and a CDR3 represented by the amino acid sequence CQQRSNWPLFT (SEQ ID NO:73). Tolerable variations to the CDRs of the light chain will be known to those of skill in the art, while maintaining its contribution to the binding of PSMA. For example, a human 2C6 PSMA binding domain may comprise a light chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:71. For example, a human 2C6 PSMA binding domain may comprise a light chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:72. For example, a human 2C6 PSMA binding domain may comprise a light chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:73. In one embodiment, the human 2C6 PSMA binding domain comprises a light chain variable region comprising the three aforementioned light chain variable region CDRs.

Transmembrane Domain

CARs (e.g., PSMA-CARs) of the present invention comprise may comprise a transmembrane domain that connects the antigen binding domain of the CAR to the intracellular domain of the CAR. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include an hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, hinge regions include glycine polymers $(G)_n$, glycine-serine polymers (including, for example, $(GS)_n$, $(GSGGS)_n$ (SEQ ID NO:1) and $(GGGS)_n$ (SEQ ID NO:2), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:4), GGSGG (SEQ ID NO:5), GSGSG (SEQ ID NO:6), GSGGG (SEQ ID NO:7), GGGSG (SEQ ID NO:8), GSSSG (SEQ ID NO:9), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res*. (1986) 14(4): 1779-1789. As non-limiting examples, an immunoglobulin hinge region can include one of the following amino acid sequences: DKTHT (SEQ ID NO:74); CPPC (SEQ ID NO:75); CPEPKSCDTPPPCPR (SEQ ID NO:76) (see, e.g., Glaser et al., *J. Biol. Chem.* (2005) 280:41494-41503); ELKTPLGDTTHT (SEQ ID NO:77); KSCDKTHTCP (SEQ ID NO:78); KCCVDCP (SEQ ID NO:79); KYGPPCP (SEQ ID NO:80); EPKSCDKTHTCPPCP (SEQ ID NO:81) (human IgG1 hinge); ERKCCVECPPCP (SEQ ID NO:82) (human IgG2 hinge); ELKTPLGDTTHTCPRCP (SEQ ID NO:83) (human IgG3 hinge); SPNMVPHAHHAQ (SEQ ID NO:84) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:85); see, e.g., Yan et al., *J. Biol. Chem.* (2012) 287: 5891-5897. In one embodiment, the hinge region can comprise an amino acid sequence derived from human CD8, or a variant thereof.

The transmembrane domain may be combined with any hinge region and/or may comprise one or more transmembrane domains described herein. In one embodiment, the transmembrane domain comprises a CD8 transmembrane domain. In one embodiment, the transmembrane domain comprises a CD8 hinge region and a CD8 transmembrane domain. In some embodiments, a subject CAR comprises a CD8 hinge region having the amino acid sequence set forth below:

```
                                         (SEQ ID NO: 86)
TTTPAPRPPTPAPTIASQPLSLRPEACRPAAGGAVHTRGLDFACD,
``` which may be encoded by the nucleic acid sequence set forth below:

```
                                         (SEQ ID NO: 87)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGCG

CAGTGCACACGAGGGGGCTGGACTTCGCCTGTGAT.
```

Tolerable variations of the transmembrane domain will be known to those of skill in the art, while maintaining its intended function. For example, in some embodiments, a subject CAR of the present invention comprises a transmembrane domain comprising a CD8 hinge region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:86. In one embodiment, the CAR comprises a transmembrane domain comprising a CD8 hinge region comprising the amino acid sequence set forth in SEQ ID NO:86.

In some embodiments, a subject CAR of the present invention comprises a transmembrane domain comprising a CD8 hinge region encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:87. In one embodiment, the CAR comprises a transmembrane domain comprising a CD8 hinge region encoded by the nucleic acid sequence set forth in SEQ ID NO:87.

In some embodiments, a subject CAR comprises a CD8 transmembrane domain having the amino acid sequence set forth below:

```
                                         (SEQ ID NO: 88)
               IYIWAPLAGTCGVLLLSLVITLYC,
``` which may be encoded by the nucleic acid sequence set forth below:

```
                                         (SEQ ID NO: 89)
ATCTACATCTGGGCGCCCTTGGCCGGGACTTGTGGGGTCCTTCTCCTGTC

ACTGGTTATCACCCTTTACTGC.
```

Tolerable variations of the transmembrane domain will be known to those of skill in the art, while maintaining its intended function. For example, in some embodiments, a subject CAR of the present invention comprises a transmembrane domain comprising a CD8 transmembrane domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:88. In one embodiment, the CAR comprises a transmembrane domain comprising a CD8 transmembrane domain comprising the amino acid sequence set forth in SEQ ID NO:88.

In some embodiments, a subject CAR of the present invention comprises a transmembrane domain comprising a CD8 transmembrane domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:89. In one embodiment, the CAR comprises a transmembrane domain comprising a CD8 transmembrane domain encoded by the acid sequence set forth in SEQ ID NO:89.

In some embodiments, the transmembrane domain comprises a CD8 hinge region and a CD8 transmembrane domain, having the amino acid sequence set forth below:

(SEQ ID NO: 90)
TTTPAPRPPTPAPTIASQPLSLRPEACRPAAGGAVHTRGLDFACDIYIWA

PLAGTCGVLLLSLVITLYC, which may be encoded by the nucleic acid sequence set forth below:

(SEQ ID NO: 91)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGATATCTACATCTGGGCG

CCCTTGGCCGGGACTTGTGGGGTCCTTCTCCTGTCACTGGTTATCACCCT

TTACTGC.

Tolerable variations of the transmembrane domain will be known to those of skill in the art, while maintaining its intended function. For example, in some embodiments, a subject CAR of the present invention comprises a transmembrane domain comprising a CD8 hinge region and a CD8 transmembrane domain, comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:90. In one embodiment, the CAR comprises a transmembrane domain comprising a CD8 hinge region and a CD8 transmembrane domain, comprising the amino acid sequence set forth in SEQ ID NO:90.

In some embodiments, a subject CAR of the present invention comprises a transmembrane domain comprising a CD8 hinge region and a CD8 transmembrane domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:91. In one embodiment, the CAR comprises a transmembrane domain comprising a CD8 hinge region and a CD8 transmembrane domain, encoded by the nucleic acid sequence set forth in SEQ ID NO:91.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, e.g., 10 to 100 amino acids, or 25 to 50 amino acids. In some embodiments, the spacer domain may be a short oligo- or polypeptide linker, e.g., between 2 and 10 amino acids in length. For example, glycine-serine doublet provides a particularly suitable linker between the transmembrane domain and the intracellular signaling domain of the subject CAR.

Intracellular Signaling Domain

A subject CAR of the present invention also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In one embodiment, the intracellular signaling domain of the CAR includes any portion of one or more co-stimulatory molecules, such as at least one signaling domain from CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon Rib), CD79a, CD79b, Fcgamma Rlla, DAP10, DAP 12, T cell receptor (TCR), CD8, CD27, CD28, 4-IBB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD 160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD 103, ITGAL, CD 11 a, LFA-1, ITGAM, CD lib, ITGAX, CD 11c, ITGB1, CD29, ITGB2, CD 18, LFA-1, ITGB7, TNFR2, TRANCE/RANKL, DNAM1 (CD226), SLAMF4 (CD244, 2B4), CD84, CD 96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

In one embodiment, the intracellular domain of a subject CAR comprises a 4-1BB domain comprising the amino acid sequence set forth below:

```
                                                (SEQ ID NO: 92)
KRGRKKLLYIFKQPFMRPVQTTQEEDGCSCRFPEEEEGGCEL,
``` which may be encoded by the nucleic acid sequence set forth below:

```
                                                (SEQ ID NO: 93)
AAACGGGGCAGAAAGAAACTCCTGTATATATTCAAACAACCATTTATGAG

ACCAGTACAAACTACTCAAGAGGAAGACGGCTGTAGCTGCCGATTTCCAG

AAGAAGAAGAAGGAGGATGTGAACTG,
``` or the nucleic acid sequence set forth below:

```
                                                (SEQ ID NO: 94)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG.
```

Tolerable variations of the intracellular domain will be known to those of skill in the art, while maintaining its intended function. For example, in some embodiments, a subject CAR of the present invention comprises an intracellular domain comprising a 4-1BB domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:92. In one embodiment, the CAR comprises an intracellular domain comprising a 4-1BB domain comprising the amino acid sequence set forth in SEQ ID NO:92.

In some embodiments, a subject CAR of the present invention comprises an intracellular domain comprising a 4-1BB domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NOs:93 or 94. In one embodiment, the CAR comprises an intracellular domain comprising a 4-1BB domain encoded by the nucleic acid sequence set forth in SEQ ID NOs:93 or 94.

In one embodiment, the intracellular domain of a subject CAR comprises an ICOS domain comprising the amino acid sequence set forth below:

```
                                               (SEQ ID NO: 203)
TKKKYSSSVHDPNGEYMFMRAVNTAKKSRLTDVTL,
``` which may be encoded by the nucleic acid sequence set forth below:

```
                                               (SEQ ID NO: 204)
ACAAAAAAGAAGTATTCATCCAGTGTGCACGACCCTAACGGTGAATACAT

GTTCATGAGAGCAGTGAACACAGCCAAAAAATCCAGACTCACAGATGTGA

CCCTA.
```

Tolerable variations of the intracellular domain will be known to those of skill in the art, while maintaining its intended function. For example, in some embodiments, a subject CAR of the present invention comprises an intracellular domain comprising an ICOS domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:203. In one embodiment, the CAR comprises an intracellular domain comprising an ICOS domain comprising the amino acid sequence set forth in SEQ ID NO:203.

In some embodiments, a subject CAR of the present invention comprises an intracellular domain comprising an ICOS domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:204. In one embodiment, the CAR comprises an intracellular domain comprising an ICOS domain encoded by the nucleic acid sequence set forth in SEQ ID NO:204.

In one embodiment, the intracellular domain of a subject CAR comprises a variant ICOS domain comprising the amino acid sequence set forth below:

```
                                                (SEQ ID NO: 95)
TKKKYSSSVHDPNGEYMNMRAVNTAKKSRLTDVTL,
``` which may be encoded by the nucleic acid sequence set forth below:

```
                                                (SEQ ID NO: 96)
ACAAAAAAGAAGTATTCATCCAGTGTGCACGACCCTAACGGTGAATACAT

GAACATGAGAGCAGTGAACACAGCCAAAAAATCCAGACTCACAGATGTGA

CCCTA.
```

The variant ICOS domain is also referred to herein as ICOS(YMNM).

Tolerable variations of the intracellular domain will be known to those of skill in the art, while maintaining its intended function. For example, in some embodiments, a subject CAR of the present invention comprises an intracellular domain comprising an ICOS domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:95. In one embodiment, the CAR comprises an intracellular domain comprising an ICOS domain comprising the amino acid sequence set forth in SEQ ID NO:95.

In some embodiments, a subject CAR of the present invention comprises an intracellular domain comprising an ICOS domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:96. In one embodiment, the CAR comprises an intracellular domain comprising an ICOS domain encoded by the nucleic acid sequence set forth in SEQ ID NO:96.

In one embodiment, the intracellular domain of a subject CAR comprises a CD3 zeta domain comprising the amino acid sequence set forth below:

(SEQ ID NO: 97)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR, which may be encoded by the nucleic acid sequence set forth below:

(SEQ ID NO: 98)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC, or the nucleic acid sequence set forth below:

(SEQ ID NO: 99)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGACG

TTTTGGACAAGAGACGTGGCCGGGACCCTGAGATGGGGGGAAAGCCGAGA

AGGAAGAACCCTCAGGAAGGCCTGTACAACGAACTGCAGAAAGATAAGAT

GGCGGAGGCCTACAGTGAGATTGGGATGAAAGGCGAGCGCCGGAGGGGCA

AGGGGCACGACGGCCTTTACCAGGGTCTCAGTACAGCCACCAAGGACACC

TACGACGCCCTTCACATGCAGGCCCTGCCCCCTCGC.

Tolerable variations of the intracellular domain will be known to those of skill in the art, while maintaining its intended function. For example, in some embodiments, a subject CAR of the present invention comprises an intracellular domain comprising a CD3 zeta domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:97. In one embodiment, a subject CAR of the present invention comprises an intracellular domain comprising a CD3 zeta domain comprising the amino acid sequence set forth in SEQ ID NO:97.

In some embodiments, a subject CAR of the present invention comprises an intracellular domain comprising a CD3 zeta domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NOs:98 or 99. In one embodiment, a subject CAR of the present invention comprises an intracellular domain comprising a CD3 zeta domain encoded by the nucleic acid sequence set forth in SEQ ID NOs:98 or 99

A CD3 zeta domain may comprise an amino acid sequence set forth below:

(SEQ ID NO: 100)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR, which may be encoded by the nucleic acid sequence set forth below:

(SEQ ID NO: 101)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC.

Tolerable variations of the intracellular domain will be known to those of skill in the art, while maintaining its intended function. For example, in some embodiments, a subject CAR of the present invention comprises an intracellular domain comprising a CD3 zeta domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:100. In one embodiment, a subject CAR of the present invention comprises an intracellular domain comprising a CD3 zeta domain comprising the amino acid sequence set forth in SEQ ID NO:100.

In some embodiments, a subject CAR of the present invention comprises an intracellular domain comprising a CD3 zeta domain encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:101. In one embodiment, a subject CAR of the present invention comprises an intracellular domain comprising a CD3 zeta domain encoded by the nucleic acid sequence set forth in SEQ ID NO:101.

In one embodiment, the CAR comprises an intracellular domain comprising a CD3 zeta domain comprising the amino acid sequence set forth in SEQ ID NOs:97 or 100.

In one exemplary embodiment, the intracellular domain of a subject CAR comprises a 4-1BB domain and a CD3 zeta domain, comprising the amino acid sequence set forth below:

(SEQ ID NO: 102)
KRGRKKLLYIFKQPFMRPVQTTQEEDGCSCRFPEEEEGGCELRVKFSRSA

DAPAYKQGQNQLYNELNLGRREEYDVLDKRRGRDPEMGGKPRRKNPQEGL

YNELQKDKMAEAYSEIGMKGERRRGKGHDGLYQGLSTATKDTYDALHMQA

LPPR, which may be encoded by the nucleic acid sequence set forth below:

(SEQ ID NO: 103)
AAACGGGGCAGAAAGAAACTCCTGTATATATTCAAACAACCATTTATGAG

ACCAGTACAAACTACTCAAGAGGAAGACGGCTGTAGCTGCCGATTTCCAG

AAGAAGAAGAAGGAGGATGTGAACTGAGAGTGAAGTTCAGCAGGAGCGCA

GACGCCCCCGCGTACAAGCAGGGCCAGAACCAGCTCTATAACGAGCTCAA

TCTAGGACGAAGAGAGGAGTACGACGTTTTGGACAAGAGACGTGGCCGGG

ACCCTGAGATGGGGGGAAAGCCGAGAAGGAAGAACCCTCAGGAAGGCCTG

TACAACGAACTGCAGAAAGATAAGATGGCGGAGGCCTACAGTGAGATTGG

GATGAAAGGCGAGCGCCGGAGGGGCAAGGGGCACGACGGCCTTTACCAGG

GTCTCAGTACAGCCACCAAGGACACCTACGACGCCCTTCACATGCAGGCC

CTGCCCCCTCGC, or the nucleic acid sequence set forth below:

(SEQ ID NO: 104)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTGAGAGTGAAGTTCAGCAGGAGCGCA

GACGCCCCCGCGTACAAGCAGGGCCAGAACCAGCTCTATAACGAGCTCAA

TCTAGGACGAAGAGAGGAGTACGATGTTTTGGACAAGAGACGTGGCCGGG

ACCCTGAGATGGGGGGAAAGCCGAGAAGGAAGAACCCTCAGGAAGGCCTG

TACAATGAACTGCAGAAAGATAAGATGGCGGAGGCCTACAGTGAGATTGG

GATGAAAGGCGAGCGCCGGAGGGGCAAGGGGCACGATGGCCTTTACCAGG

GTCTCAGTACAGCCACCAAGGACACCTACGACGCCCTTCACATGCAGGCC

CTGCCCCCTCGC.

Tolerable variations of the intracellular domain will be known to those of skill in the art, while maintaining its intended function. For example, in some embodiments, a subject CAR of the present invention comprises an intracellular domain comprising a 4-1BB domain and a CD3 zeta domain, comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:102. In one embodiment, the CAR comprises an intracellular domain comprising a 4-1BB domain and a CD3 zeta domain, comprising the amino acid sequence set forth in SEQ ID NO:102.

In some embodiments, a subject CAR of the present invention comprises an intracellular domain comprising a 4-1BB domain and a CD3 zeta domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NOs:103 or 104. In one embodiment, the CAR comprises an intracellular domain comprising a 4-1BB domain and a CD3 zeta domain, encoded by the nucleic acid sequence set forth in SEQ ID NOs:103 or 104.

In one exemplary embodiment, the intracellular domain of a subject CAR comprises an ICOS domain and a CD3 zeta domain, comprising the amino acid sequence set forth below:

(SEQ ID NO: 205)
TKKKYSSSVHDPNGEYMFMRAVNTAKKSRLTDVTLRVKFSRSADAPAYQQ

GQNQLYNELNLGRREEYDVLDKRRGRDPEMGGKPQRRKNPQEGLYNELQK

DKMAEAYSEIGMKGERRRGKGHDGLYQGLSTATKDTYDALHMQALPPR, which may be encoded by the nucleic acid sequence set forth below:

(SEQ ID NO: 206)
ACAAAAAAGAAGTATTCATCCAGTGTGCACGACCCTAACGGTGAATACAT

GTTCATGAGAGCAGTGAACACAGCCAAAAAATCCAGACTCACAGATGTGA

CCCTAAGAGTGAAGTTCAGCAGGAGCGCAGACGCCCCCGCGTACCAGCAG

GGCCAGAACCAGCTCTATAACGAGCTCAATCTAGGACGAAGAGAGGAGTA

CGATGTTTTGGACAAGAGACGTGGCCGGGACCCTGAGATGGGGGGAAAGC

CGCAGAGAAGGAAGAACCCTCAGGAAGGCCTGTACAATGAACTGCAGAAA

GATAAGATGGCGGAGGCCTACAGTGAGATTGGGATGAAAGGCGAGCGCCG

GAGGGGCAAGGGGCACGATGGCCTTTACCAGGGTCTCAGTACAGCCACCA

AGGACACCTACGACGCCCTTCACATGCAGGCCCTGCCCCCTCGC.

Tolerable variations of the intracellular domain will be known to those of skill in the art, while maintaining its intended function. For example, in some embodiments, a subject CAR of the present invention comprises an intracellular domain comprising an ICOS domain and a CD3 zeta domain, comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:205. In one embodiment, the CAR comprises an intracellular domain comprising an ICOS domain and a CD3 zeta domain, comprising the amino acid sequence set forth in SEQ ID NO:205.

In some embodiments, a subject CAR of the present invention comprises an intracellular domain comprising an ICOS domain and a CD3 zeta domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:206. In one embodiment, the CAR comprises an intracellular domain comprising an ICOS domain and a CD3 zeta domain, encoded by the nucleic acid sequence set forth in SEQ ID NO:206.

In one exemplary embodiment, the intracellular domain of a subject CAR comprises a variant ICOS domain and a CD3 zeta domain, comprising the amino acid sequence set forth below:

(SEQ ID NO: 207)
TKKKYSSSVHDPNGEYMNMRAVNTAKKSRLTDVTLRVKFSRSADAPAYQQ

GQNQLYNELNLGRREEYDVLDKRRGRDPEMGGKPQRRKNPQEGLYNELQK

DKMAEAYSEIGMKGERRRGKGHDGLYQGLSTATKDTYDALHMQALPPR, which may be encoded by the nucleic acid sequence set forth below:

(SEQ ID NO: 208)
ACAAAAAAGAAGTATTCATCCAGTGTGCACGACCCTAACGGTGAATACAT

GAACATGAGAGCAGTGAACACAGCCAAAAAATCCAGACTCACAGATGTGA

CCCTAAGAGTGAAGTTCAGCAGGAGCGCAGACGCCCCCGCGTACCAGCAG

GGCCAGAACCAGCTCTATAACGAGCTCAATCTAGGACGAAGAGAGGAGTA

CGATGTTTTGGACAAGAGACGTGGCCGGGACCCTGAGATGGGGGGAAAGC

CGCAGAGAAGGAAGAACCCTCAGGAAGGCCTGTACAATGAACTGCAGAAA

GATAAGATGGCGGAGGCCTACAGTGAGATTGGGATGAAAGGCGAGCGCCG

GAGGGGCAAGGGGCACGATGGCCTTTACCAGGGTCTCAGTACAGCCACCA

AGGACACCTACGACGCCCTTCACATGCAGGCCCTGCCCCCTCGC.

Tolerable variations of the intracellular domain will be known to those of skill in the art, while maintaining its intended function. For example, in some embodiments, a subject CAR of the present invention comprises an intracellular domain comprising a variant ICOS domain and a CD3 zeta domain, comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:207. In one embodiment, the CAR comprises an intracellular domain comprising a variant ICOS domain and a CD3 zeta domain, comprising the amino acid sequence set forth in SEQ ID NO:207.

In some embodiments, a subject CAR of the present invention comprises an intracellular domain comprising a variant ICOS domain and a CD3 zeta domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:208. In one embodiment, the CAR comprises an intracellular domain comprising a variant ICOS domain and a CD3 zeta domain, encoded by the nucleic acid sequence set forth in SEQ ID NO:208.

CAR Sequences

A subject CAR of the present invention may be selected from the group consisting of a J591 murine PSMA-CAR, a humanized J591 PSMA-CAR, a 1C3 human PSMA-CAR, a 2A10 human PSMA-CAR, a 2F5 human PSMA-CAR, and a 2C6 human PSMA-CAR.

In one embodiment, a subject CAR of the present invention is a J591 murine PSMA-CAR. In one embodiment, the J591 murine PSMA-CAR comprises the amino acid sequence set forth below:

(SEQ ID NO: 105)
MALPVTALLLPLALLLHAARPGSDIVMTQSHKFMSTSVGDRVSIICKASQ

DVGTAVDWYQQKPGQSPKLLIYWASTRHTGVPDRFTGSGSGTDFTLTITN

VQSEDLADYFCQQYNSYPLTFGAGTMLDLKGGGGSGGGGSSGGGSEVQLQ

QSGPELVKPGTSVRISCKTSGYTFTEYTIHWVKQSHGKSLEWIGNINPNN

GGTTYNQKFEDKATLTVDKSSSTAYMELRSLTSEDSAVYYCAAGWNFDYW

GQGTTLTVSSASSGTTTPAPRPPTPAPTIASQPLSLRPEACRPAAGGAVH

TRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPR, which may be encoded by the nucleic acid sequence set forth below:

(SEQ ID NO: 106)
ATGGCCCTGCCTGTGACAGCCCTGCTGCTGCCTCTGGCTCTGCTGCTGCA

CGCCGCCAGACCTGGATCTGACATTGTGATGACCCAGTCTCACAAATTCA

TGTCCACATCAGTAGGAGACAGGGTCAGCATCATCTGTAAGGCCAGTCAA

GATGTGGGTACTGCTGTAGACTGGTATCAACAGAAACCAGGACAATCTCC

TAAACTACTGATTTATTGGGCATCCACTCGGCACACTGGAGTCCCTGATC

GCTTCACAGGCAGTGGATCTGGGACAGACTTCACTCTCACCATTACTAAC

GTTCAGTCTGAAGACTTGGCAGATTATTTCTGTCAGCAATATAACAGCTA

TCCTCTCACGTTCGGTGCTGGGACCATGCTGGACCTGAAAGGAGGCGGAG

GATCTGGCGGCGGAGGAAGTTCTGGCGGAGGCAGCGAGGTGCAGCTGCAG

CAGAGCGGACCCGAGCTCGTGAAGCCTGGAACAAGCGTGCGGATCAGCTG

CAAGACCAGCGGCTACACCTTCACCGAGTACACCATCCACTGGGTCAAGC

AGTCCCACGGCAAGAGCCTGGAGTGGATCGGCAATATCAACCCCAACAAC

GGCGGCACCACCTACAACCAGAAGTTCGAGGACAAGGCCACCCTGACCGT

GGACAAGAGCAGCAGCACCGCCTACATGGAACTGCGGAGCCTGACCAGCG

-continued

```
AGGACAGCGCCGTGTACTATTGTGCCGCCGGTTGGAACTTCGACTACTGG

GGCCAGGGCACAACCCTGACAGTGTCTAGCGCTAGCTCCGGAACCACGAC

GCCAGCGCCGCGACCACCAACACCGGCGCCCACCATCGCGTCGCAGCCCC

TGTCCCTGCGCCCAGAGGCGTGCCGGCCAGCGGCGGGGGCGCAGTGCAC

ACGAGGGGGCTGGACTTCGCCTGTGATATCTACATCTGGGCGCCCTTGGC

CGGGACTTGTGGGGTCCTTCTCCTGTCACTGGTTATCACCCTTTACTGCA

AACGGGGCAGAAAGAAACTCCTGTATATATTCAAACAACCATTTATGAGA

CCAGTACAAACTACTCAAGAGGAAGACGGCTGTAGCTGCCGATTTCCAGA

AGAAGAAGAAGGAGGATGTGAACTGAGAGTGAAGTTCAGCAGGAGCGCAG

ACGCCCCCGCGTACAAGCAGGGCCAGAACCAGCTCTATAACGAGCTCAAT

CTAGGACGAAGAGAGGAGTACGACGTTTTGGACAAGAGACGTGGCCGGGA

CCCTGAGATGGGGGAAAGCCGAGAAGGAAGAACCCTCAGGAAGGCCTGT

ACAACGAACTGCAGAAAGATAAGATGGCGGAGGCCTACAGTGAGATTGGG

ATGAAAGGCGAGCGCCGGAGGGGCAAGGGGCACGACGGCCTTTACCAGGG

TCTCAGTACAGCCACCAAGGACACCTACGACGCCCTTCACATGCAGGCCC

TGCCCCCTCGC.
```

In one embodiment, a subject CAR of the present invention is a humanized PSMA-CAR, e.g., a humanized J591 PSMA-CAR. In such an embodiment, the humanized PSMA-CAR comprises any of the heavy and light chain variable regions disclosed in PCT Publication Nos. WO2017212250A1 and WO2018033749A1. For example, a humanized PSMA-CAR of the present invention can comprise an scFv comprising any of the heavy and light chain variable regions disclosed therein, see, e.g., sequences set forth in Table 19 of the present disclosure.

In one embodiment, a subject CAR of the present invention is a 1C3 human PSMA-CAR. In one embodiment, the 1C3 human PSMA-CAR comprises the amino acid sequence set forth below:

(SEQ ID NO: 107)
MALPVTALLLPLALLLHAARPQVQLVESGGGVVQPGRSLRLSCAASGFTF

SSYAMHWVRQAPGKGLEWVAVISYDGNNKYYADSVKGRFTISRDNSKNTL

YLQMNSLRAEDTAVYYCARAVPWGSRYYYYGMDVWGQGTTVTVSSGGGGS

GGGGSGGGGSAIQLTQSPSSLSASVGDRVTITCRASQGISSALAWYQQKS

GKAPKLLIFDASSLESGVPSRFSGSGSGTDFTLTISSLQPEDFATYYCQQ

FNSYPLTFGGGTKVEIKTTTPAPRPPTPAPTIASQPLSLRPEACRPAAGG

AVHTRGLDFACDIYIWAPLAGTCGVLLLSLVITLYCKRGRKKLLYIFKQP

FMRPVQTTQEEDGCSCRFPEEEEGGCELRVKFSRSADAPAYKQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR, which may be encoded by the nucleic acid sequence set forth below:

(SEQ ID NO: 108)
ATGGCCTTACCAGTGACCGCCTTGCTCCTGCCGCTGGCCTTGCTGCTCCA

CGCCGCCAGGCCGCAGGTGCAACTGGTGGAGTCTGGGGGAGGCGTGGTCC

AGCCTGGGAGGTCCCTGAGACTCTCCTGTGCAGCCTCTGGATTCACCTTC

AGTAGCTATGCTATGCACTGGGTCCGCCAGGCTCCAGGCAAGGGGCTGGA

GTGGGTGGCAGTTATATCATATGATGGAAACAATAAATACTACGCAGACT

CCGTGAAGGGCCGATTCACCATCTCCAGAGACAATTCCAAGAACACGCTG

TATCTGCAAATGAACAGCCTGAGAGCTGAGGACACGGCTGTGTATTACTG

TGCGAGAGCCGTCCCCTGGGGATCGAGGTACTACTACTACGGTATGGACG

TCTGGGGCCAAGGGACCACGGTCACCGTCTCCTCAGGTGGCGGTGGCTCG

GGCGGTGGTGGGTCGGGTGGCGGCGGATCTGCCATCCAGTTGACCCAGTC

TCCATCCTCCCTGTCTGCATCTGTAGGAGACAGAGTCACCATCACTTGCC

GGGCAAGTCAGGGCATTAGCAGTGCTTTAGCCTGGTATCAGCAGAAATCA

GGGAAAGCTCCTAAGCTCCTGATCTTTGATGCCTCCAGTTTGGAAAGTGG

GGTCCCATCAAGGTTCAGCGGCAGTGGATCTGGGACAGATTTCACTCTCA

CCATCAGCAGCCTGCAGCCTGAAGATTTTGCAACTTATTACTGTCAACAG

TTTAACAGTTATCCTCTCACTTTCGGCGGAGGGACCAAGGTGGAGATCAA

AACCACGACGCCAGCGCCGCGACCACCAACACCGGCGCCCACCATCGCGT

CGCAGCCCCTGTCCCTGCGCCCAGAGGCGTGCCGGCCAGCGGCGGGGGGC

GCAGTGCACACGAGGGGGCTGGACTTCGCCTGTGATATCTACATCTGGGC

GCCCTTGGCCGGGACTTGTGGGGTCCTTCTCCTGTCACTGGTTATCACCC

TTTACTGCAAACGGGGCAGAAAGAAACTCCTGTATATATTCAAACAACCA

TTTATGAGACCAGTACAAACTACTCAAGAGGAAGACGGCTGTAGCTGCCG

ATTTCCAGAAGAAGAAGAAGGAGGATGTGAACTGAGAGTGAAGTTCAGCA

GGAGCGCAGACGCCCCCGCGTACAAGCAGGGCCAGAACCAGCTCTATAAC

GAGCTCAATCTAGGACGAAGAGAGGAGTACGACGTTTTGGACAAGAGACG

TGGCCGGGACCCTGAGATGGGGGGAAAGCCGAGAAGGAAGAACCCTCAGG

AAGGCCTGTACAACGAACTGCAGAAAGATAAGATGGCGGAGGCCTACAGT

GAGATTGGGATGAAAGGCGAGCGCCGGAGGGGCAAGGGGCACGACGGCCT

TTACCAGGGTCTCAGTACAGCCACCAAGGACACCTACGACGCCCTTCACA

TGCAGGCCCTGCCCCCTCGC.

In one embodiment, a subject CAR of the present invention is a 2A10 human PSMA-CAR. In one embodiment, the 2A10 human PSMA-CAR comprises the amino acid sequence set forth below:

(SEQ ID NO: 109)
MALPVTALLLPLALLLHAARPEVQLVQSGAEVKKPGESLKISCKGSGYSF

TSNWIGWVRQMPGKGLEWMGIIYPGDSDTRYSPSFQGQVTISADKSISTA

YLQWSSLKASDTAMYYCARQTGFLWSSDLWGRGTLVTVSSGGGGSGGGGS

GGGGSAIQLTQSPSSLSASVGDRVTITCRASQDISSALAWYQQKPGKAPK

LLIYDASSLESGVPSRFSGYGSGTDFTLTINSLQPEDFATYYCQQFNSYP

LTFGGGTKVEIKTTTPAPRPPTPAPTIASQPLSLRPEACRPAAGGAVHTR

GLDFACDIYIWAPLAGTCGVLLLSLVITLYCKRGRKKLLYIFKQPFMRPV

-continued

QTTQEEDGCSCRFPEEEEGGCELRVKFSRSADAPAYKQGQNQLYNELNLG

RREEYDVLDKRRGRDPEMGGKPRRKNPQEGLYNELQKDKMAEAYSEIGMK

GERRRGKGHDGLYQGLSTATKDTYDALHMQALPPR, which may be encoded by the nucleic acid sequence set forth below:

(SEQ ID NO: 110)
ATGGCCTTACCAGTGACCGCCTTGCTCCTGCCGCTGGCCTTGCTGCTCCA
CGCCGCCAGGCCGGAGGTGCAGCTGGTGCAGTCTGGAGCAGAGGTGAAAA
AGCCCGGGGAGTCTCTGAAGATCTCCTGTAAGGGTTCTGGATACAGCTTT
ACCAGTAACTGGATCGGCTGGGTGCGCCAGATGCCCGGGAAAGGCCTGGA
GTGGATGGGGATCATCTATCCTGGTGACTCTGATACCAGATACAGCCCGT
CCTTCCAAGGCCAGGTCACCATCTCAGCCGACAAGTCCATCAGCACCGCC
TACCTGCAGTGGAGCAGCCTGAAGGCCTCGGACACCGCCATGTATTACTG
TGCGAGGCAAACTGGTTTCCTCTGGTCCTCCGATCTCTGGGGCCGTGGCA
CCCTGGTCACTGTCTCCTCAGGTGGCGGTGGCTCGGGCGGTGGTGGGTCG
GGTGGCGGCGGATCTGCCATCCAGTTGACCCAGTCTCCATCCTCCCTGTC
TGCATCTGTAGGAGACAGAGTCACCATCACTTGCCGGGCAAGTCAGGACA
TTAGCAGTGCTTTAGCCTGGTATCAACAGAAACCAGGGAAAGCTCCTAAG
CTCCTGATCTATGATGCCTCCAGTTTGGAAAGTGGGGTCCCATCAAGGTT
CAGCGGCTATGGATCTGGGACAGATTTCACTCTCACCATCAACAGCCTGC
AGCCTGAAGATTTTGCAACTTATTACTGTCAACAGTTTAATAGTTACCCG
CTCACTTTCGGCGGAGGGACCAAGGTGGAGATCAAAACCACGACGCCAGC
GCCGCGACCACCAACACCGGCGCCCACCATCGCGTCGCAGCCCCTGTCCC
TGCGCCCAGAGGCGTGCCGGCCAGCGGCGGGGGGCGCAGTGCACACGAGG
GGGCTGGACTTCGCCTGTGATATCTACATCTGGGCGCCCTTGGCCGGGAC
TTGTGGGGTCCTTCTCCTGTCACTGGTTATCACCCTTTACTGCAAACGGG
GCAGAAAGAAACTCCTGTATATATTCAAACAACCATTTATGAGACCAGTA
CAAACTACTCAAGAGGAAGACGGCTGTAGCTGCCGATTTCCAGAAGAAGA
AGAAGGAGGATGTGAACTGAGAGTGAAGTTCAGCAGGAGCGCAGACGCCC
CCGCGTACAAGCAGGGCCAGAACCAGCTCTATAACGAGCTCAATCTAGGA
CGAAGAGAGGAGTACGACGTTTTGGACAAGAGACGTGGCCGGGACCCTGA
GATGGGGGGAAAGCCGAGAAGGAAGAACCCTCAGGAAGGCCTGTACAACG
AACTGCAGAAAGATAAGATGGCGGAGGCCTACAGTGAGATTGGGATGAAA
GGCGAGCGCCGGAGGGGCAAGGGGCACGACGGCCTTTACCAGGGTCTCAG
TACAGCCACCAAGGACACCTACGACGCCCTTCACATGCAGGCCCTGCCCC
TCGC.

In one embodiment, a subject CAR of the present invention is a 2F5 human PSMA-CAR. In one embodiment, the 2F5 human PSMA-CAR comprises a 4-1BB domain and a CD3 zeta domain comprising the amino acid sequence set forth below:

(SEQ ID NO: 111)
MALPVTALLLPLALLLHAARPEVQLVQSGAEVKKPGESLKISCKGSGYSF
TSNWIGWVRQMPGKGLEWMGIIYPGDSDTRYSPSFQGQVTISADKSISTA
YLQWNSLKASDTAMYYCARQTGFLWSFDLWGRGTLVTVSSGGGGSGGGGS
GGGGSAIQLTQSPSSLSASVGDRVTITCRASQDISSALAWYQQKPGKAPK
LLIYDASSLESGVPSRFSGSGSGTDFTLTISSLQPEDFATYYCQQFNSYP
LTFGGGTKVEIKIKTTTPAPRPPTPAPTIASQPLSLRPEACRPAAGGAVH
TRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELN
LGRREEYDVLDKRRGRDPEMGGKPRRKNPQEGLYNELQKDKMAEAYSEIG
MKGERRRGKGHDGLYQGLSTATKDTYDALHMQALPPR, which may be encoded by the nucleic acid sequence set forth below:

(SEQ ID NO: 112)
ATGGCCTTACCAGTGACCGCCTTGCTCCTGCCGCTGGCCTTGCTGCTCCA
CGCCGCCAGGCCGGAGGTGCAGCTGGTGCAGTCTGGAGCAGAGGTGAAAA
AGCCCGGGGAGTCTCTGAAGATCTCCTGTAAGGGTTCTGGATACAGTTTT
ACCAGCAACTGGATCGGCTGGGTGCGCCAGATGCCCGGGAAAGGCCTGGA
GTGGATGGGGATCATCTATCCTGGTGACTCTGATACCAGATACAGCCCGT
CCTTCCAAGGCCAGGTCACCATCTCAGCCGACAAGTCCATCAGCACCGCC
TACCTGCAGTGGAACAGCCTGAAGGCCTCGGACACCGCCATGTATTACTG
TGCGAGACAAACTGGTTTCCTCTGGTCCTTCGATCTCTGGGGCCGTGGCA
CCCTGGTCACTGTCTCCTCAGGTGGCGGTGGCTCGGGCGGTGGTGGGTCG
GGTGGCGGCGGATCTGCCATCCAGTTGACCCAGTCTCCATCCTCCCTGTC
TGCATCTGTAGGAGACAGAGTCACCATCACTTGCCGGGCAAGTCAGGACA
TTAGCAGTGCTTTAGCCTGGTATCAGCAGAAACCGGGGAAAGCTCCTAAG
CTCCTGATCTATGATGCCTCCAGTTTGGAAAGTGGGGTCCCATCAAGGTT
CAGCGGCAGTGGATCTGGGACAGATTTCACTCTCACCATCAGCAGCCTGC
AGCCTGAAGATTTTGCAACTTATTACTGTCAACAGTTTAATAGTTACCCG
CTCACTTTCGGCGGAGGGACCAAGGTGGAGATCAAAATCAAAACCACGAC
GCCAGCGCCGCGACCACCAACACCGGCGCCCACCATCGCGTCGCAGCCCC
TGTCCCTGCGCCCAGAGGCGTGCCGGCCAGCGGCGGGGGGCGCAGTGCAC
ACGAGGGGGCTGGACTTCGCCTGTGATATCTACATCTGGGCGCCCTTGGC
CGGGACTTGTGGGGTCCTTCTCCTGTCACTGGTTATCACCCTTTACTGCA
AACGGGGCAGAAAGAAACTCCTGTATATATTCAAACAACCATTTATGAGA
CCAGTACAAACTACTCAAGAGGAAGACGGCTGTAGCTGCCGATTTCCAGA
AGAAGAAGGAGGATGTGAACTGAGAGTGAAGTTCAGCAGGAGCGCAG
ACGCCCCGCGTACAAGCAGGGCCAGAACCAGCTCTATAACGAGCTCAAT
CTAGGACGAAGAGAGGAGTACGACGTTTTGGACAAGAGACGTGGCCGGGA
CCCTGAGATGGGGGGAAAGCCGAGAAGGAAGAACCCTCAGGAAGGCCTGT
ACAACGAACTGCAGAAAGATAAGATGGCGGAGGCCTACAGTGAGATTGGG
ATGAAAGGCGAGCGCCGGAGGGGCAAGGGGCACGACGGCCTTTACCAGGG

TCTCAGTACAGCCACCAAGGACACCTACGACGCCCTTCACATGCAGGCCC

TGCCCCCTCGC.

In one embodiment, a subject CAR of the present invention is a 2F5 human PSMA-CAR. In one embodiment, the 2F5 human PSMA-CAR comprises an ICOS domain and a CD3 zeta domain comprising the amino acid sequence set forth below:

(SEQ ID NO: 209)
MALPVTALLLPLALLLHAARPEVQLVQSGAEVKKPGESLKISCKGSGYSF

TSNWIGWVRQMPGKGLEWMGIIYPGDSDTRYSPSFQGQVTISADKSISTA

YLQWNSLKASDTAMYYCARQTGFLWSFDLWGRGTLVTVSSGGGGSGGGGS

GGGGSAIQLTQSPSSLSASVGDRVTITCRASQDISSALAWYQQKPGKAPK

LLIYDASSLESGVPSRFSGSGSGTDFTLTISSLQPEDFATYYCQQFNSYP

LTFGGGTKVEIKIKTTTPAPRPPTPAPTIASQPLSLRPEACRPAAGGAVH

TRGLDFACDFWLPIGCAAFVVVCILGCILICWLTKKKYSSSVHDPNGEYM

FMRAVNTAKKSRLTDVTLRVKFSRSADAPAYQQGQNQLYNELNLGRREEY

DVLDKRRGRDPEMGGKPQRRKNPQEGLYNELQKDKMAEAYSEIGMKGERR

RGKGHDGLYQGLSTATKDTYDALHMQALPPR, which may be encoded by the nucleic acid sequence set forth below:

(SEQ ID NO: 210)
ATGGCCTTACCAGTGACCGCCTTGCTCCTGCCGCTGGCCTTGCTGCTCCA

CGCCGCCAGGCCGGAGGTGCAGCTGGTGCAGTCTGGAGCAGAGGTGAAAA

AGCCCGGGGAGTCTCTGAAGATCTCCTGTAAGGGTTCTGGATACAGTTTT

ACCAGCAACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TACCTGCAGTGGAACAGCCTGAAGGCCTCGGACACCGCCATGTATTACTG

TGCGAGACAAACTGGTTTCCTCTGGTCCTTCGATCTCTGGGGCCGTGGCA

CCCTGGTCACTGTCTCCTCAGGTGGCGGTGGCTCGGGCGGTGGTGGGTCG

GGTGGCGGCGGATCTGCCATCCAGTTGACCCAGTCTCCATCCTCCCTGTC

TGCATCTGTAGGAGACAGAGTCACCATCACTTGCCGGGCAAGTCAGGACA

TTAGCAGTGCTTTAGCCTGGTATCAGCAGAAACCGGGGAAAGCTCCTAAG

CTCCTGATCTATGATGCCTCCAGTTTGGAAAGTGGGGTCCCATCAAGGTT

CAGCGGCAGTGGATCTGGGACAGATTTCACTCTCACCATCAGCAGCCTGC

AGCCTGAAGATTTTGCAACTTATTACTGTCAACAGTTTAATAGTTACCCG

CTCACTTTCGGCGGAGGGACCAAGGTGGAGATCAAAATCAAAACCACGAC

GCCAGCGCCGCGACCACCAACACCGGCGCCCACCATCGCGTCGCAGCCCC

TGTCCCTGCGCCCAGAGGCGTGCCGGCCAGCGGCGGGGGGCGCAGTGCAC

ACGAGGGGGCTGGACTTCGCCTGTGATTTCTGGTTACCCATAGGATGTGC

AGCCTTTGTTGTAGTCTGCATTTTGGGATGCATACTTATTTGTTGGCTTA

CAAAAAAGAAGTATTCATCCAGTGTGCACGACCCTAACGGTGAATACATG

TTCATGAGAGCAGTGAACACAGCCAAAAAATCCAGACTCACAGATGTGAC

CCTAAGAGTGAAGTTCAGCAGGAGCGCAGACGCCCCCGCGTACCAGCAGG

GCCAGAACCAGCTCTATAACGAGCTCAATCTAGGACGAAGAGAGGAGTAC

GATGTTTTGGACAAGAGACGTGGCCGGGACCCTGAGATGGGGGGAAAGCC

GCAGAGAAGGAAGAACCCTCAGGAAGGCCTGTACAATGAACTGCAGAAAG

ATAAGATGGCGGAGGCCTACAGTGAGATTGGGATGAAAGGCGAGCGCCGG

AGGGGCAAGGGGCACGATGGCCTTTACCAGGGTCTCAGTACAGCCACCAA

GGACACCTACGACGCCCTTCACATGCAGGCCCTGCCCCCTCGC.

In one embodiment, a subject CAR of the present invention is a 2F5 human PSMA-CAR. In one embodiment, the 2F5 human PSMA-CAR comprises a variant ICOS domain and a CD3 zeta domain comprising the amino acid sequence set forth below:

(SEQ ID NO: 211)
MALPVTALLLPLALLLHAARPEVQLVQSGAEVKKPGESLKISCKGSGYSF

TSNWIGWVRQMPGKGLEWMGIIYPGDSDTRYSPSFQGQVTISADKSISTA

YLQWNSLKASDTAMYYCARQTGFLWSFDLWGRGTLVTVSSGGGGSGGGGS

GGGGSAIQLTQSPSSLSASVGDRVTITCRASQDISSALAWYQQKPGKAPK

LLIYDASSLESGVPSRFSGSGSGTDFTLTISSLQPEDFATYYCQQFNSYP

LTFGGGTKVEIKIKTTTPAPRPPTPAPTIASQPLSLRPEACRPAAGGAVH

TRGLDFACDFWLPIGCAAFVVVCILGCILICWLTKKKYSSSVHDPNGEYM

NMRAVNTAKKSRLTDVTLRVKFSRSADAPAYQQGQNQLYNELNLGRREEY

DVLDKRRGRDPEMGGKPQRRKNPQEGLYNELQKDKMAEAYSEIGMKGERR

RGKGHDGLYQGLSTATKDTYDALHMQALPPR, which may be encoded by the nucleic acid sequence set forth below:

(SEQ ID NO: 212)
ATGGCCTTACCAGTGACCGCCTTGCTCCTGCCGCTGGCCTTGCTGCTCCA

CGCCGCCAGGCCGGAGGTGCAGCTGGTGCAGTCTGGAGCAGAGGTGAAAA

AGCCCGGGGAGTCTCTGAAGATCTCCTGTAAGGGTTCTGGATACAGTTTT

ACCAGCAACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TACCTGCAGTGGAACAGCCTGAAGGCCTCGGACACCGCCATGTATTACTG

TGCGAGACAAACTGGTTTCCTCTGGTCCTTCGATCTCTGGGGCCGTGGCA

CCCTGGTCACTGTCTCCTCAGGTGGCGGTGGCTCGGGCGGTGGTGGGTCG

GGTGGCGGCGGATCTGCCATCCAGTTGACCCAGTCTCCATCCTCCCTGTC

TGCATCTGTAGGAGACAGAGTCACCATCACTTGCCGGGCAAGTCAGGACA

TTAGCAGTGCTTTAGCCTGGTATCAGCAGAAACCGGGGAAAGCTCCTAAG

CTCCTGATCTATGATGCCTCCAGTTTGGAAAGTGGGGTCCCATCAAGGTT

CAGCGGCAGTGGATCTGGGACAGATTTCACTCTCACCATCAGCAGCCTGC

AGCCTGAAGATTTTGCAACTTATTACTGTCAACAGTTTAATAGTTACCCG

-continued

```
CTCACTTTCGGCGGAGGGACCAAGGTGGAGATCAAAATCAAAACCACGAC

GCCAGCGCCGCGACCACCAACACCGGCGCCCACCATCGCGTCGCAGCCCC

TGTCCCTGCGCCCAGAGGCGTGCCGGCCAGCGGCGGGGGCGCAGTGCAC

ACGAGGGGGCTGGACTTCGCCTGTGATTTCTGGTTACCCATAGGATGTGC

AGCCTTTGTTGTAGTCTGCATTTTGGGATGCATACTTATTTGTTGGCTTA

CAAAAAAGAAGTATTCATCCAGTGTGCACGACCCTAACGGTGAATACATG

AACATGAGAGCAGTGAACACAGCCAAAAAATCCAGACTCACAGATGTGAC

CCTAAGAGTGAAGTTCAGCAGGAGCGCAGACGCCCCCGCGTACCAGCAGG

GCCAGAACCAGCTCTATAACGAGCTCAATCTAGGACGAAGAGAGGAGTAC

GATGTTTTGGACAAGAGACGTGGCCGGGACCCTGAGATGGGGGAAAGCC

GCAGAGAAGGAAGAACCCTCAGGAAGGCCTGTACAATGAACTGCAGAAAG

ATAAGATGGCGGAGGCCTACAGTGAGATTGGGATGAAAGGCGAGCGCCGG

AGGGGCAAGGGGCACGATGGCCTTTACCAGGGTCTCAGTACAGCCACCAA

GGACACCTACGACGCCCTTCACATGCAGGCCCTGCCCCCTCGC.
```

In one embodiment, a subject CAR of the present invention is a 2C6 human PSMA-CAR. In one embodiment, the 2C6 human PSMA-CAR comprises the amino acid sequence set forth below:

(SEQ ID NO: 113)
```
MALPVTALLLPLALLLHAARPEVQLVQSGSEVKKPGESLKISCKGSGYSF

TNYWIGWVRQMPGKGLEWMGIIYPGDSDTRYSPSFQGQVTISADKSISTA

YLQWSSLKASDTAMYYCASPGYTSSWTSFDYWGQGTLVTVSSGGGGSGGG

GSGGGGSEIVLTQSPATLSLSPGERATLSCRASQSVSSYLAWYQQKPGQA

PRLLIYDASNRATGIPARFSGSGSGTDFTLTISSLEPEDFAVYYCQQRSN

WPLFTFGPGTKVDIKTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR,
``` which may be encoded by the nucleic acid sequence set forth below:

(SEQ ID NO: 114)
```
ATGGCCTTACCAGTGACCGCCTTGCTCCTGCCGCTGGCCTTGCTGCTCCA

CGCCGCCAGGCCGGAGGTGCAGCTGGTGCAGTCTGGATCAGAGGTGAAAA

AGCCCGGGGAGTCTCTGAAGATCTCCTGTAAGGGTTCTGGATACAGCTTT

ACCAACTACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TATCTGCAGTGGAGCAGCCTGAAGGCCTCGGACACCGCCATGTATTACTG

TGCGAGTCCCGGGTATACCAGCAGTTGGACTTCTTTTGACTACTGGGGCC

AGGGAACCCTGGTCACCGTCTCCTCAGGTGGCGGTGGCTCGGGCGGTGGT

GGGTCGGGTGGCGGCGGATCTGAAATTGTGTTGACACAGTCTCCAGCCAC

CCTGTCTTTGTCTCCAGGGGAAAGAGCCACCCTCTCCTGCAGGGCCAGTC

AGAGTGTTAGCAGCTACTTAGCCTGGTACCAACAGAAACCTGGCCAGGCT

CCCAGGCTCCTCATCTATGATGCATCCAACAGGGCCACTGGCATCCCAGC

CAGGTTCAGTGGCAGTGGGTCTGGGACAGACTTCACTCTCACCATCAGCA

GCCTAGAGCCTGAAGATTTTGCAGTTTATTACTGTCAGCAGCGTAGCAAC

TGGCCCCTATTCACTTTCGGCCCTGGGACCAAAGTGGATATCAAAACCAC

GACGCCAGCGCCGCGACCACCAACACCGGCGCCCACCATCGCGTCGCAGC

CCCTGTCCCTGCGCCCAGAGGCGTGCCGGCCAGCGGCGGGGGCGCAGTG

CACACGAGGGGCTGGACTTCGCCTGTGATATCTACATCTGGGCGCCCTT

GGCCGGGACTTGTGGGGTCCTTCTCCTGTCACTGGTTATCACCCTTTACT

GCAAACGGGGCAGAAAGAAACTCCTGTATATATTCAAACAACCATTTATG

AGACCAGTACAAACTACTCAAGAGGAAGACGGCTGTAGCTGCCGATTTCC

AGAAGAAGAAGAAGGAGGATGTGAACTGAGAGTGAAGTTCAGCAGGAGCG

CAGACGCCCCCGCGTACAAGCAGGGCCAGAACCAGCTCTATAACGAGCTC

AATCTAGGACGAAGAGAGGAGTACGACGTTTTGGACAAGAGACGTGGCCG

GGACCCTGAGATGGGGGGAAAGCCGAGAAGGAAGAACCCTCAGGAAGGCC

TGTACAACGAACTGCAGAAAGATAAGATGGCGGAGGCCTACAGTGAGATT

GGGATGAAAGGCGAGCGCCGGAGGGGCAAGGGGCACGACGGCCTTTACCA

GGGTCTCAGTACAGCCACCAAGGACACCTACGACGCCCTTCACATGCAGG

CCCTGCCCCCTCGC.
```

Tolerable variations of the sequences of the subject CARs will be known to those of skill in the art, while maintaining its function.

For example, in some embodiments, a subject CAR of the present invention is a J591 murine PSMA-CAR comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:105. In one embodiment, the CAR is a J591 murine PSMA-CAR comprising the amino acid sequence set forth in SEQ ID NO:105.

For example, in some embodiments, a subject CAR of the present invention is a humanized J591 PSMA-CAR. A humanized J591 PSMA-CAR comprises a humanized J591 PSMA binding domain comprising a heavy and light chain variable region selected from any of the heavy and light chain variable region sequences set forth in Table 19. In some embodiments, the humanized J591 PSMA-CAR comprises a 4-1BB domain and a CD3zeta domain.

For example, in some embodiments, a subject CAR of the present invention is a 1C3 human PSMA-CAR comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:107. In one embodiment, the CAR is a 1C3 human PSMA-CAR comprising the amino acid sequence set forth in SEQ ID NO:107.

For example, in some embodiments, a subject CAR of the present invention is a 2A10 human PSMA-CAR comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:109. In one embodiment, the CAR is a 2A10 human PSMA-CAR comprising the amino acid sequence set forth in SEQ ID NO:109.

For example, in some embodiments, a subject CAR of the present invention is a 2F5 human PSMA-CAR. In one embodiment, the CAR is a 2F5 human PSMA-CAR that comprises a 4-1BB domain and a CD3zeta domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:111. In one embodiment, the CAR is a 2F5 human PSMA-CAR that comprises a 4-1BB domain and a CD3zeta domain comprising the amino acid sequence set forth in SEQ ID NO:111. In one embodiment, the CAR is a 2F5 human PSMA-CAR that comprises an ICOS domain and a CD3zeta domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:209. In one embodiment, the CAR is a 2F5 human PSMA-CAR that comprises an ICOS domain and a CD3zeta domain comprising the amino acid sequence set forth in SEQ ID NO:209. In one embodiment, the CAR is a 2F5 human PSMA-CAR that comprises a variant ICOS domain and a CD3zeta domain comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:211. In one embodiment, the CAR is a 2F5 human PSMA-CAR that comprises a variant ICOS domain and a CD3zeta domain comprising the amino acid sequence set forth in SEQ ID NO:211. For example, in some embodiments, a subject CAR of the present invention is a 2C6 human PSMA-CAR comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:113. In one embodiment, the CAR is a 2C6 human PSMA-CAR comprising the amino acid sequence set forth in SEQ ID NO:113.

In some embodiments, a subject CAR of the present invention is a J591 murine PSMA-CAR encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:106. In one embodiment, the CAR is a J591 murine PSMA-CAR encoded by the nucleic acid sequence set forth in SEQ ID NO:106.

For example, in some embodiments, a subject CAR of the present invention is a 1C3 human PSMA-CAR encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:108. In one embodiment, the CAR is a 1C3 human PSMA-CAR encoded by the nucleic acid sequence set forth in SEQ ID NO:108. For example, in some embodiments, a subject CAR of the present invention is a 2A10 human PSMA-CAR encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:110. In one embodiment, the CAR is a 2A10 human PSMA-CAR encoded by the nucleic acid sequence set forth in SEQ ID NO:110. For example, in some embodiments, a subject CAR of the present invention is a 2F5 human PSMA-CAR. In one embodiment, the CAR is a 2F5 human PSMA-CAR that comprises a 4-1BB domain and a CD3zeta domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:112. In one embodiment, the CAR is a 2F5 human PSMA-CAR that comprises a 4-1BB domain and a CD3zeta domain, encoded by the nucleic acid sequence set forth in SEQ ID NO:112. In one embodiment, the CAR is a 2F5 human PSMA-CAR that comprises an ICOS domain and a CD3zeta domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:210. In one embodiment, the CAR is a 2F5 human PSMA-CAR that comprises an ICOS domain and a CD3zeta domain, encoded by the nucleic acid sequence set forth in SEQ ID NO:210. In one embodiment, the CAR is a 2F5 human PSMA-CAR that comprises a variant ICOS domain and a CD3zeta domain, encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:212. In one embodiment, the CAR is a 2F5 human PSMA-CAR that comprises a variant ICOS domain and a CD3zeta domain, encoded by the nucleic acid sequence set forth in SEQ ID NO:212. For example, in some embodiments, a subject CAR of the present invention is a 2C6 human PSMA-CAR encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:114. In one embodiment, the CAR is a 2C6 human PSMA-CAR encoded by the nucleic acid sequence set forth in SEQ ID NO:114.

In certain embodiments, a subject CAR of the present invention may comprise any one of the amino acid sequences corresponding to SEQ ID NOs: 209, 211, or 227-236.

| SEQ ID NO: | CAR | Sequence |
|---|---|---|
| 227 | PD1-CD28-2F5-ICOSz | MQIPQAPWPVVWAVLQLGWRPGWFLDSPDRPWNPPTFS PALLVVTEGDNATFTCSFSNTSESFVLNWYRMSPSNQTDK LAAFPEDRSQPGQDCRFRVTQLPNGRDFHMSVVRARRND SGTYLCGAISLAPKAQIKESLRAELRVTERRAEVPTAHPSP SPRPAGQFQTLVFWVLVVVGGVLACYSLLVTVAFIIFWVR SKRSRLLHSDYMNMTPRRPGPTRKHYQPYAPPRDFAAYR SVKQTLNFDLLKLAGDVESNPGPMALPVTALLLPLALLLH AARPEVQLVQSGAEVKKPGESLKISCKGSGYSFTSNWIGW VRQMPGKGLEWMGIIYPGDSDTRYSPSFQGQVTISADKSI STAYLQWNSLKASDTAMYYCARQTGFLWSFDLWGRGTL VTVSSGGGGSGGGGSGGGGSAIQLTQSPSSLSASVGDRVT ITCRASQDISSALAWYQQKPGKAPKLLIYDASSLESGVPSR FSGSGSGTDFTLTISSLQPEDFATYYCQQFNSYPLTFGGGT KVEIKIKTTTPAPRPPTPAPTIASQPLSLRPEACRPAAGGAV HTRGLDFACDFWLPIGCAAFVVVCILGCILICWLTKKKYS SSVHDPNGEYMFMRAVNTAKKSRLTDVTLRVKFSRSADA PAYQQGQNQLYNELNLGRREEYDVLDKRRGRDPEMGGK PQRRKNPQEGLYNELQKDKMAEAYSEIGMKGERRRGKG HDGLYQGLSTATKDTYDALHMQALPPR |
| 228 | PD1*CD28-2F5-ICOSz | MQIPQAPWPVVWAVLQLGWRPGWFLDSPDRPWNPPTFS PALLVVTEGDNATFTCSFSNTSESFVLNWYRMSPSNQTDK LAAFPEDRSQPGQDCRFRVTQLPNGRDFHMSVVRARRND SGTYLCGAISLAPKLQIKESLRAELRVTERRAEVPTAHPSP SPRPAGQFQTLVVGVVGGLLGSLVLLVWVLAVIRSKRSR LLHSDYMNMTPRRPGPTRKHYQPYAPPRDFAAYRSVKQT LNFDLLKLAGDVESNPGPMALPVTALLLPLALLLHAARPE VQLVQSGAEVKKPGESLKISCKGSGYSFTSNWIGWVRQM PGKGLEWMGIIYPGDSDTRYSPSFQGQVTISADKSISTAYL QWNSLKASDTAMYYCARQTGFLWSFDLWGRGTLVTVSS GGGGSGGGGSGGGGSAIQLTQSPSSLSASVGDRVTITCRA SQDISSALAWYQQKPGKAPKLLIYDASSLESGVPSRFSGSG SGTDFTLTISSLQPEDFATYYCQQFNSYPLTFGGGTKVEIKI KTTTPAPRPPTPAPTIASQPLSLRPEACRPAAGGAVHTRGL DFACDFWLPIGCAAFVVVCILGCILICWLTKKKYSSSVHD PNGEYMFMRAVNTAKKSRLTDVTLRVKFSRSADAPAYQ QGQNQLYNELNLGRREEYDVLDKRRGRDPEMGGKPQRR KNPQEGLYNELQKDKMAEAYSEIGMKGERRRGKGHDGL YQGLSTATKDTYDALHMQALPPR |
| 229 | PD1*BB-2F5-ICOSz | MQIPQAPWPVVWAVLQLGWRPGWFLDSPDRPWNPPTFS PALLVVTEGDNATFTCSFSNTSESFVLNWYRMSPSNQTDK LAAFPEDRSQPGQDCRFRVTQLPNGRDFHMSVVRARRND SGTYLCGAISLAPKLQIKESLRAELRVTERRAEVPTAHPSP SPRPAGQFQTLVIYIWAPLAGTCGVLLLSLVITLYCKKRGR KKLLYIFKQPFMRPVQTTQEEDGCSCRFPEEEEGGCELVK QTLNFDLLKLAGDVESNPGPMALPVTALLLPLALLLHAA RPEVQLVQSGAEVKKPGESLKISCKGSGYSFTSNWIGWVR QMPGKGLEWMGIIYPGDSDTRYSPSFQGQVTISADKSIST AYLQWNSLKASDTAMYYCARQTGFLWSFDLWGRGTLVT VSSGGGGSGGGGSGGGGSAIQLTQSPSSLSASVGDRVTIT CRASQDISSALAWYQQKPGKAPKLLIYDASSLESGVPSRF SGSGSGTDFTLTISSLQPEDFATYYCQQFNSYPLTFGGGTK VEIKIKTTTPAPRPPTPAPTIASQPLSLRPEACRPAAGGAVH TRGLDFACDFWLPIGCAAFVVVCILGCILICWLTKKKYSSS VHDPNGEYMFMRAVNTAKKSRLTDVTLRVKFSRSADAP AYQQGQNQLYNELNLGRREEYDVLDKRRGRDPEMGGKP QRRKNPQEGLYNELQKDKMAEAYSEIGMKGERRRGKGH DGLYQGLSTATKDTYDALHMQALPPR |

| SEQ ID NO: | CAR | Sequence |
|---|---|---|
| 230 | TIM3-CD28-2F5-ICOSz | MFSHLPFDCVLLLLLLLTRSSEVEYRAEVGQNAYLPCFY TPAAPGNLVPVCWGKGACPVFECGNVVLRTDERDVNYW TSRYWLNGDFRKGDVSLTIENVTLADSGIYCCRIQIPGIMN DEKFNLKLVIKPAKVTPAPTRQRDFTAAFPRMLTTRGHGP AETQTLGSLPDINLTQISTLANELRDSRLANDLRDSGATIR FWVLVVVGGVLACYSLLVTVAFIIFWVRSKRSLLHSDY MNMTPRRPGPTRKHYQPYAPPRDFAAYRSVKQTLNFDLL KLAGDVESNPGPMALPVTALLLPLALLLHAARPEVQLVQ SGAEVKKPGESLKISCKGSGYSFTSNWIGWVRQMPGKGL EWMGIIYPGDSDTRYSPSFQGQVTISADKSISTAYLQWNSL KASDTAMYYCARQTGFLWSFDLWGRGTLVTVSSGGGGS GGGGSGGGGSAIQLTQSPSSLSASVGDRVTITCRASQDISS ALAWYQQKPGKAPKLLIYDASSLESGVPSRFSGSGSGTDF TLTISSLQPEDFATYYCQQFNSYPLTFGGGTKVEIKIKTTTP APRPPTPAPTIASQPLSLRPEACRPAAGGAVHTRGLDFACD FWLPIGCAAFVVVCILGCILICWLTKKKYSSSVHDPNGEY MFMRAVNTAKKSRLTDVTLRVKFSRSADAPAYQQGQNQ LYNELNLGRREEYDVLDKRRGRDPEMGGKPQRRKNPQE GLYNELQKDKMAEAYSEIGMKGERRRGKHDGLYQGLS TATKDTYDALHMQALPPR |
| 231 | PD1\*BB-TIM3-CD28-2F5-ICOSz | MQIPQAPWPVVWAVLQLGWRPGWFLDSPDRPWNPPTFS PALLVVTEGDNATFTCSFSNTSESFVLNWYRMSPSNQTDK LAAFPEDRSQPGQDCRFRVTQLPNGRDFHMSVVRARRND SGTYLCGAISLAPKLQIKESLRAELRVTERRAEVPTAHPSP SPRPAGQFQTLVIYIWAPLAGTCGVLLLSLVITLYCKKRGR KKLLYIFKQPFMRPVQTTQEEDGCSCRFPEEEEGGCELVK QTLNFDLLKLAGDVESNPGPMFSHLPFDCVLLLLLLLTR SSEVEYRAEVGQNAYLPCFYTPAAPGNLVPVCWGKGACP VFECGNVVLRTDERDVNYWTSRYWLNGDFRKGDVSLTIE NVTLADSGIYCCRIQIPGIMNDEKFNLKLVIKPAKVTPAPT RQRDFTAAFPRMLTTRGHGPAETQTLGSLPDINLTQISTLA NELRDSRLANDLRDSGATIRFWVLVVVGGVLACYSLLVT VAFIIFWVRSKRSLLHSDYMNMTPRRPGPTRKHYQPYAP PRDFAAYRSVKQTLNFDLLKLAGDVESNPGPMALPVTAL LLPLALLLHAARPEVQLVQSGAEVKKPGESLKISCKGSGY SFTSNWIGWVRQMPGKGLEWMGIIYPGDSDTRYSPSFQG QVTISADKSISTAYLQWNSLKASDTAMYYCARQTGFLWS FDLWGRGTLVTVSSGGGGSGGGGSGGGGSAIQLTQSPSSL SASVGDRVTITCRASQDISSALAWYQQKPGKAPKLLIYDA SSLESGVPSRFSGSGSGTDFTLTISSLQPEDFATYYCQQFNS YPLTFGGGTKVEIKIKTTTPAPRPPTPAPTIASQPLSLRPEA CRPAAGGAVHTRGLDFACDFWLPIGCAAFVVVCILGCILI CWLTKKKYSSSVHDPNGEYMFMRAVNTAKKSRLTDVTL RVKFSRSADAPAYQQGQNQLYNELNLGRREEYDVLDKR RGRDPEMGGKPQRRKNPQEGLYNELQKDKMAEAYSEIG MKGERRRGKHDGLYQGLSTATKDTYDALHMQALPPR |
| 232 | PD1-CD28-2F5-ICOSz YMNM | MQIPQAPWPVVWAVLQLGWRPGWFLDSPDRPWNPPTFS PALLVVTEGDNATFTCSFSNTSESFVLNWYRMSPSNQTDK LAAFPEDRSQPGQDCRFRVTQLPNGRDFHMSVVRARRND SGTYLCGAISLAPKAQIKESLRAELRVTERRAEVPTAHPSP SPRPAGQFQTLVFWVLVVVGGVLACYSLLVTVAFIIFWVR SKRSRLLHSDYMNMTPRRPGPTRKHYQPYAPPRDFAAYR SVKQTLNFDLLKLAGDVESNPGPMALPVTALLLPLALLLH AARPEVQLVQSGAEVKKPGESLKISCKGSGYSFTSNWIGW VRQMPGKGLEWMGIIYPGDSDTRYSPSFQGQVTISADKSI STAYLQWNSLKASDTAMYYCARQTGFLWSFDLWGRGTL VTVSSGGGGSGGGGSGGGGSAIQLTQSPSSLSASVGDRVT ITCRASQDISSALAWYQQKPGKAPKLLIYDASSLESGVPSR FSGSGSGTDFTLTISSLQPEDFATYYCQQFNSYPLTFGGGT KVEIKIKTTTPAPRPPTPAPTIASQPLSLRPEACRPAAGGAV HTRGLDFACDFWLPIGCAAFVVVCILGCILICWLTKKKYS SSVHDPNGEYMNMRAVNTAKKSRLTDVTLRVKFSRSAD APAYQQGQNQLYNELNLGRREEYDVLDKRRGRDPEMGG KPQRRKNPQEGLYNELQKDKMAEAYSEIGMKGERRRGK GHDGLYQGLSTATKDTYDALHMQALPPR |
| 233 | PD1\*CD28-2F5-ICOSz YMNM | MQIPQAPWPVVWAVLQLGWRPGWFLDSPDRPWNPPTFS PALLVVTEGDNATFTCSFSNTSESFVLNWYRMSPSNQTDK LAAFPEDRSQPGQDCRFRVTQLPNGRDFHMSVVRARRND SGTYLCGAISLAPKLQIKESLRAELRVTERRAEVPTAHPSP SPRPAGQFQTLVVGVVGGLLGSLVLLVWVLAVIRSKRSR LLHSDYMNMTPRRPGPTRKHYQPYAPPRDFAAYRSVKQT LNFDLLKLAGDVESNPGPMALPVTALLLPLALLLHAARPE VQLVQSGAEVKKPGESLKISCKGSGYSFTSNWIGWVRQM |

| SEQ ID NO: | CAR | Sequence |
|---|---|---|
| | | PGKGLEWMGIIYPGDSDTRYSPSFQGQVTISADKSISTAYL
QWNSLKASDTAMYYCARQTGFLWSFDLWGRGTLVTVSS
GGGGSGGGGSGGGGSAIQLTQSPSSLSASVGDRVTITCRA
SQDISSALAWYQQKPGKAPKLLIYDASSLESGVPSRFSGSG
SGTDFTLTISSLQPEDFATYYCQQFNSYPLTFGGGTKVEIKI
KTTTPAPRPPTPAPTIASQPLSLRPEACRPAAGGAVHTRGL
DFACDFWLPIGCAAFVVVCILGCILICWLTKKKYSSSVHD
PNGEYMNMRAVNTAKKSRLTDVTLRVKFSRSADAPAYQ
QGQNQLYNELNLGRREEYDVLDKRRGRDPEMGGKPQRR
KNPQEGLYNELQKDKMAEAYSEIGMKGERRRGKHDGL
YQGLSTATKDTYDALHMQALPPR |
| 234 | PD1*BB-
2F5-ICOSz
YMNM | MQIPQAPWPVVWAVLQLGWRPGWFLDSPDRPWNPPTFS
PALLVVTEGDNATFTCSFSNTSESFVLNWYRMSPSNQTDK
LAAFPEDRSQPGQDCRFRVTQLPNGRDFHMSVVRARRND
SGTYLCGAISLAPKLQIKESLRAELRVTERRAEVPTAHPSP
SPRPAGQFQTLVIYIWAPLAGTCGVLLLSLVITLYCKKRGR
KKLLYIFKQPFMRPVQTTQEEDGCSCRFPEEEEGGCELVK
QTLNFDLLKLAGDVESNPGPMALPVTALLLPLALLLHAA
RPEVQLVQSGAEVKKPGESLKISCKGSGYSFTSNWIGWVR
QMPGKGLEWMGIIYPGDSDTRYSPSFQGQVTISADKSIST
AYLQWNSLKASDTAMYYCARQTGFLWSFDLWGRGTLVT
VSSGGGGSGGGGSGGGGSAIQLTQSPSSLSASVGDRVTIT
CRASQDISSALAWYQQKPGKAPKLLIYDASSLESGVPSRF
SGSGSGTDFTLTISSLQPEDFATYYCQQFNSYPLTFGGGTK
VEIKIKTTTPAPRPPTPAPTIASQPLSLRPEACRPAAGGAVH
TRGLDFACDFWLPIGCAAFVVVCILGCILICWLTKKKYSSS
VHDPNGEYMNMRAVNTAKKSRLTDVTLRVKFSRSADAP
AYQQGQNQLYNELNLGRREEYDVLDKRRGRDPEMGGKP
QRRKNPQEGLYNELQKDKMAEAYSEIGMKGERRRGKGH
DGLYQGLSTATKDTYDALHMQALPPR |
| 235 | TIM3-CD28-
2F5-ICOSz
YMNM | MFSHLPFDCVLLLLLLLTRSSEVEYRAEVGQNAYLPCFY
TPAAPGNLVPVCWGKGACPVFECGNVVLRTDERDVNYW
TSRYWLNGDFRKGDVSLTIENVTLADSGIYCCRIQIPGIMN
DEKFNLKLVIKPAKVTPAPTRQRDFTAAFPRMLTTRGHGP
AETQTLGSLPDINLTQISTLANELRDSRLANDLRDSGATIR
FWVLVVVGGVLACYSLLVTVAFIIFWVRSKRSLLHSDY
MNMTPRRPGPTRKHYQPYAPPRDFAAYRSVKQTLNFDLL
KLAGDVESNPGPMALPVTALLLPLALLLHAARPEVQLVQ
SGAEVKKPGESLKISCKGSGYSFTSNWIGWVRQMPGKGL
EWMGIIYPGDSDTRYSPSFQGQVTISADKSISTAYLQWNSL
KASDTAMYYCARQTGFLWSFDLWGRGTLVTVSSGGGGS
GGGGSGGGGSAIQLTQSPSSLSASVGDRVTITCRASQDISS
ALAWYQQKPGKAPKLLIYDASSLESGVPSRFSGSGSGTDF
TLTISSLQPEDFATYYCQQFNSYPLTFGGGTKVEIKIKTTTP
APRPPTPAPTIASQPLSLRPEACRPAAGGAVHTRGLDFACD
FWLPIGCAAFVVVCILGCILICWLTKKKYSSSVHDPNGEY
MNMRAVNTAKKSRLTDVTLRVKFSRSADAPAYQQGQNQ
LYNELNLGRREEYDVLDKRRGRDPEMGGKPQRRKNPQE
GLYNELQKDKMAEAYSEIGMKGERRRGKHDGLYQGLS
TATKDTYDALHMQALPPR |
| 236 | PD1*BB-
TIM3-CD28-
2F5-ICOSz
YMNM | MQIPQAPWPVVWAVLQLGWRPGWFLDSPDRPWNPPTFS
PALLVVTEGDNATFTCSFSNTSESFVLNWYRMSPSNQTDK
LAAFPEDRSQPGQDCRFRVTQLPNGRDFHMSVVRARRND
SGTYLCGAISLAPKLQIKESLRAELRVTERRAEVPTAHPSP
SPRPAGQFQTLVIYIWAPLAGTCGVLLLSLVITLYCKKRGR
KKLLYIFKQPFMRPVQTTQEEDGCSCRFPEEEEGGCELVK
QTLNFDLLKLAGDVESNPGPMFSHLPFDCVLLLLLLLTR
SSEVEYRAEVGQNAYLPCFYTPAAPGNLVPVCWGKGACP
VFECGNVVLRTDERDVNYWTSRYWLNGDFRKGDVSLTIE
NVTLADSGIYCCRIQIPGIMNDEKFNLKLVIKPAKVTPAPT
RQRDFTAAFPRMLTTRGHGPAETQTLGSLPDINLTQISTLA
NELRDSRLANDLRDSGATIRFWVLVVVGGVLACYSLLVT
VAFIIFWVRSKRSLLHSDYMNMTPRRPGPTRKHYQPYAP
PRDFAAYRSVKQTLNFDLLKLAGDVESNPGPMALPVTAL
LLPLALLLHAARPEVQLVQSGAEVKKPGESLKISCKGSGY
SFTSNWIGWVRQMPGKGLEWMGIIYPGDSDTRYSPSFQG
QVTISADKSISTAYLQWNSLKASDTAMYYCARQTGFLWS
FDLWGRGTLVTVSSGGGGSGGGGSGGGGSAIQLTQSPSSL
SASVGDRVTITCRASQDISSALAWYQQKPGKAPKLLIYDA
SSLESGVPSRFSGSGSGTDFTLTISSLQPEDFATYYCQQFNS
YPLTFGGGTKVEIKIKTTTPAPRPPTPAPTIASQPLSLRPEA
CRPAAGGAVHTRGLDFACDFWLPIGCAAFVVVCILGCILI
CWLTKKKYSSSVHDPNGEYMNMRAVNTAKKSRLTDVTL |

-continued

| SEQ ID NO: | CAR | Sequence |
|---|---|---|
| | | RVKFSRSADAPAYQQGQNQLYNELNLGRREEYDVLDKR RGRDPEMGGKPQRRKNPQEGLYNELQKDKMAEAYSEIG MKGERRRGKGHDGLYQGLSTATKDTYDALHMQALPPR |

Accordingly, the present invention provides a modified immune cell or precursor cell thereof, e.g., a modified T cell, comprising a chimeric antigen receptor (CAR) having affinity for a prostate-specific membrane antigen (PSMA) on a target cell (e.g., a prostate cancer cell). In some embodiments, the CAR comprises a PSMA binding domain. In some embodiments, the CAR comprises a murine PSMA binding domain. In one embodiment, the CAR comprises a J591 murine PSMA binding domain. In one embodiment, the CAR comprises a humanized J591 PSMA binding domain. In some embodiments, the CAR comprises a human PSMA binding domain. In some embodiments, the CAR comprises a human PSMA binding domain selected from the group consisting of a 1C3, a 2A10, a 2F5, and a 2C6 human PSMA binding domain.

Accordingly, a subject CAR of the present invention comprises a PSMA binding domain and a transmembrane domain. In one embodiment, the CAR comprises a PSMA binding domain and a transmembrane domain, wherein the transmembrane domain comprises a CD8 hinge region. In one embodiment, the CAR comprises a PSMA binding domain and a transmembrane domain, wherein the transmembrane domain comprises a CD8 transmembrane domain. In one embodiment, the CAR comprises a PSMA binding domain and a transmembrane domain, wherein the transmembrane domain comprises a CD8 hinge region and a CD8 transmembrane domain.

Accordingly, a subject CAR of the present invention comprises a PSMA binding domain, a transmembrane domain, and an intracellular domain. In one embodiment, the CAR comprises a PSMA binding domain, a transmembrane domain, and an intracellular domain, wherein the intracellular domain comprises a 4-1BB domain. In one embodiment, the CAR comprises a PSMA binding domain, a transmembrane domain, and an intracellular domain, wherein the intracellular domain comprises a CD3 zeta domain. In one embodiment, the CAR comprises a PSMA binding domain, a transmembrane domain, and an intracellular domain, wherein the intracellular domain comprises a 4-1BB domain and a CD3 zeta domain.

C. Dominant Negative Receptors and Switch Receptors

The present invention provides compositions and methods for modified immune cells or precursors thereof, e.g., modified T cells, comprising a dominant negative receptor and/or a switch receptor. Thus, in some embodiments, the immune cell has been genetically modified to express the dominant negative receptor and/or switch receptor. As used herein, the term "dominant negative receptor" refers to a molecule designed to reduce the effect of a negative signal transduction molecule, e.g., the effect of a negative signal transduction molecule on a modified immune cell of the present invention. A dominant negative receptor of the present invention may bind a negative signal transduction molecule, e.g., TGF-β or PD-1, by virtue of an extracellular domain associated with the negative signal, and reduce the effect of the negative signal transduction molecule. Such dominant negative receptors are described herein. For example, a modified immune cell comprising a dominant negative receptor may bind a negative signal transduction molecule in the microenvironment of the modified immune cell, and reduce the effect the negative signal transduction molecule may have on the modified immune cell.

A switch receptor of the present invention may be designed to, in addition to reducing the effects of a negative signal transduction molecule, to convert the negative signal into a positive signal, by virtue of comprising an intracellular domain associated with the positive signal. Switch receptors designed to convert a negative signal into a positive signal are described herein. Accordingly, switch receptors comprise an extracellular domain associated with a negative signal and/or an intracellular domain associated with a positive signal.

Tumor cells generate an immunosuppressive microenvironment that serves to protect them from immune recognition and elimination. This immunosuppressive microenvironment can limit the effectiveness of immunosuppressive therapies such as CAR-T cell therapy. The secreted cytokine Transforming Growth Factor β (TGFβ) directly inhibits the function of cytotoxic T cells and additionally induces regulatory T cell formation to further suppress immune responses. T cell immunosuppression due to TGFβ in the context of prostate cancers has been previously demonstrated (Donkor et al., 2011; Shalapour et al., 2015). To reduce the immunosuppressive effects of TGFβ, immune cells can be modified to express a dominant negative receptor that is a dominant negative receptor for TGF-β.

In some embodiments, the dominant negative receptor is a truncated variant of a wild-type protein associated with a negative signal. In some embodiments, the dominant negative receptor is a dominant negative receptor for TGF-β. Accordingly, in some embodiments, the dominant negative receptor for TGF-β is a truncated variant of a wild-type TGF-β receptor. In some embodiments, the dominant negative receptor is a truncated dominant negative variant of the TGF-β receptor type II (TGFβRII-DN). In one embodiment, the TGFβRII-DN comprises the amino acid sequence set forth below:

(SEQ ID NO: 115)
MGRGLLRGLWPLHIVLWTRIASTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDLLLVIFQVTGISLLPPLGVAISVIIIFYCYRVNRQQKLSSS

G, which may be encoded by the nucleic acid sequence set forth below:

(SEQ ID NO: 116)
ATGGGTCGGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACTGCTACCGCGTTAACCGGCAGCAGAAGCTGAGTTCATCC

GGA.

Tolerable variations of the sequence of TGFβRII-DN will be known to those of skill in the art, while maintaining its intended function. For example, in some embodiments, a dominant negative receptor of the present invention is TGFβRII-DN comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO:115 In one embodiment, the dominant negative receptor is TGFβRII-DN comprising the amino acid sequence set forth in SEQ ID NO:115.

In some embodiments, a dominant negative receptor of the present invention is TGFβRII-DN encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:116. In one embodiment, the dominant negative receptor is TGFβRII-DN encoded by the nucleic acid sequence set forth in SEQ ID NO:116.

In one embodiment, a switch receptor suitable for use in the present invention is a PD1-CTM-CD28 receptor. The PD1-CTM-CD28 receptor converts a negative PD1 signal into a positive CD28 signal when expressed in a cell. The PD1-CTM-CD28 receptor comprises a variant of the PD1 extracellular domain, a CD28 transmembrane domain, and a CD28 cytoplasmic domain. In one embodiment, the PD1-CTM-CD28 receptor comprises an amino acid sequence set forth below:

(SEQ ID NO: 117)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVFWVLVVVGGVLACYSLLVTVAFIIFWVRSK

RSRLLHSDYMNMTPRRPGPTRKHYQPYAPPRDFAAYRS, which may be encoded by the nucleic acid sequence set forth below:

(SEQ ID NO: 118)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCC.

Tolerable variations of the PD1-CTM-CD28 receptor will be known to those of skill in the art, while maintaining its intended biological activity (e.g., converting a negative PD1 signal into a positive CD28 signal when expressed in a cell). Accordingly, a PD1-CTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CTM-CD28 receptor amino acid sequence set forth in SEQ ID NO:117. Accordingly, a PD1-CTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CTM-CD28 receptor nucleic acid sequence set forth in SEQ ID NO:118.

In one embodiment, a switch receptor suitable for use in the present invention is a PD1-PTM-CD28 receptor. The PD1-PTM-CD28 receptor converts a negative PD1 signal into a positive CD28 signal when expressed in a cell. The PD1-PTM-CD28 receptor comprises a variant of the PD1 extracellular domain, a PD1 transmembrane domain, and a CD28 cytoplasmic domain. In one embodiment, the PD1-PTM-CD28 receptor comprises an amino acid sequence set forth below:

(SEQ ID NO: 119)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKLQIKESLRAELRVTERRAE

VPTAHPSPSPRPAGQFQTLVVGVVGGLLGSLVLLVWVLAVIRSKRSRLLH

SDYMNMTPRRPGPTRKHYQPYAPPRDFAAYRS, which may be encoded by the nucleic acid sequence set forth below:

(SEQ ID NO: 120)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA

TTACCAGCCCTATGCCCCACCACGCGACTTCGCAGCCTATCGCTCC.

Tolerable variations of the PD1-PTM-CD28 receptor will be known to those of skill in the art, while maintaining its intended biological activity (e.g., converting a negative PD1 signal into a positive CD28 signal when expressed in a cell). Accordingly, a PD1-PTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-PTM-CD28 receptor amino acid sequence set forth in SEQ ID NO:119. Accordingly, a PD1-PTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-PTM-CD28 receptor nucleic acid sequence set forth in SEQ ID NO:120.

In one embodiment, a switch receptor suitable for use in the present invention is a PD1$^{A132L}$-PTM-CD28 receptor. The PD1$^{A132L}$-PTM-CD28 receptor converts a negative PD1 signal into a positive CD28 signal when expressed in a cell. A point mutation at amino acid position 132, substituting alanine with leucine (A132L), of PD1 was found to increase its affinity with PD-L1 by two fold (see, e.g., Zhang et al., Immunity (2004) 20(3), 337-347). The PD1$^{A132L}$-PTM-CD28 receptor comprises a variant of the PD1 extracellular domain that has an amino acid substitution at position 132 (A132L), a PD1 transmembrane domain, and a CD28 cytoplasmic domain. In one embodiment, the PD1$^{A132L}$-PTM-CD28 receptor comprises an amino acid sequence set forth below:

(SEQ ID NO: 121)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKLQIKESLRAELRVTERRAE

VPTAHPSPSPRPAGQFQTLVVGVVGGLLGSLVLLVWVLAVIRSKRSRLLH

SDYMNMTPRRPGPTRKHYQPYAPPRDFAAYRS, which may be encoded by the nucleic acid sequence set forth below:

(SEQ ID NO: 122)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA

TTACCAGCCCTATGCCCCACCACGCGACTTCGCAGCCTATCGC.

Tolerable variations of the PD1$^{A132L}$-PTM-CD28 receptor will be known to those of skill in the art, while maintaining its intended biological activity (e.g., converting a negative PD1 signal into a positive CD28 signal when expressed in a cell). Accordingly, a PD1$^{A132L}$-PTM-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-PTM-CD28 receptor amino acid sequence set forth in SEQ ID NO:121. Accordingly, a PD1$^{A132L}$-PTM-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-PTM-CD28 receptor nucleic acid sequence set forth in SEQ ID NO:122.

In one embodiment, a switch receptor suitable for use in the present invention is a PD1-4-1BB receptor. The PD1-4-1BB receptor (also referred to herein as PD1-BB) converts a negative PD1 signal into a positive 4-1BB signal when expressed in a cell. In one embodiment, the PD1-4-1BB receptor comprises an amino acid sequence set forth below:

(SEQ ID NO: 213)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVIYIWAPLAGTCGVLLLSLVITLYCKKRGRK

KLLYIFKQPFMRPVQTTQEEDGCSCRFPEEEEGGCEL, which may be encoded by the nucleic acid sequence set forth below:

(SEQ ID NO: 214)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTG.

Tolerable variations of the PD1-4-1BB receptor will be known to those of skill in the art, while maintaining its intended biological activity (e.g., converting a negative PD1 signal into a positive 4-1BB signal when expressed in a cell). Accordingly, a PD1-4-1BB receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-4-1BB receptor amino acid sequence set forth in SEQ ID NO:213. Accordingly, a PD1-4-1BB receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-4-1BB receptor nucleic acid sequence set forth in SEQ ID NO:214.

In one embodiment, a switch receptor suitable for use in the present invention is a PD1$^{A132L}$-4-1BB receptor. The PD1$^{A132L}$-4-1BB receptor (also referred to herein as PD1*BB) converts a negative PD1 signal into a positive 4-1BB signal when expressed in a cell. In one embodiment, the PD1$^{A132L}$-4-1BB receptor comprises an amino acid sequence set forth below:

(SEQ ID NO: 215)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKLQIKESLRAELRVTERRAE

VPTAHPSPSPRPAGQFQTLVIYIWAPLAGTCGVLLLSLVITLYCKKRGRK

KLLYIFKQPFMRPVQTTQEEDGCSCRFPEEEEGGCEL, which may be encoded by the nucleic acid sequence set forth below:

(SEQ ID NO: 216)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTG.

Tolerable variations of the PD1$^{A132L}$-4-1BB receptor will be known to those of skill in the art, while maintaining its intended biological activity (e.g., converting a negative PD1 signal into a positive 4-1BB signal when expressed in a cell). Accordingly, a PD1$^{A132L}$-4-1BB receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-4-1BB receptor amino acid sequence set forth in SEQ ID NO:215. Accordingly, a PD1$^{A132L}$-4-1BB receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-4-1BB receptor nucleic acid sequence set forth in SEQ ID NO:216.

In one embodiment, a switch receptor suitable for use in the present invention is a TGFβR-IL12Rβ1 receptor. The TGFβR-IL12Rβ1 receptor converts a negative TGF-β signal into a positive IL-12 signal when expressed in a cell. In one embodiment, the TGFβR-IL12Rβ1 receptor comprises an amino acid sequence set forth below:

(SEQ ID NO: 123)
MEAAVAAPRPRLLLLVLAAAAAAAAALLPGATALQCFCHLCTKDNFTCVT

DGLCFVSVTETTDKVIHNSMCIAEIDLIPRDRPFVCAPSSKTGSVTTTYC

CNQDHCNKIELPTTVKSSPGLGPVELAAVIAGPVCFVCISLMLMVYIRAA

RHLCPPLPTPCASSAIEFPGGKETWQWINPVDFQEEASLQEALVVEMSWD

KGERTEPLEKTELPEGAPELALDTELSLEDGDRCKAKM, which may be encoded by the nucleic acid sequence set forth below:

(SEQ ID NO: 124)
ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGTAAAGTC

ATCACCTGGCCTTGGTCCTGTGGAACTGGCAGCTGTCATTGCTGGACCAG

TGTGCTTCGTCTGCATCTCACTCATGTTGATGGTCTATATCAGGGCCGCA

CGGCACCTGTGCCCGCCGCTGCCCACACCCTGTGCCAGCTCCGCCATTGA

GTTCCCTGGAGGGAAGGAGACTTGGCAGTGGATCAACCCAGTGGACTTCC

AGGAAGAGGCATCCCTGCAGGAGGCCCTGGTGGTAGAGATGTCCTGGGAC

AAAGGCGAGAGGACTGAGCCTCTCGAGAAGACAGAGCTACCTGAGGGTGC

CCCTGAGCTGGCCCTGGATACAGAGTTGTCCTTGGAGGATGGAGACAGGT

GCAAGGCCAAGATG.

Tolerable variations of the TGFβR-IL12Rβ1 receptor will be known to those of skill in the art, while maintaining its intended biological activity (e.g., converting a negative TGF-β signal into a positive IL-12 signal when expressed in a cell). Accordingly, a TGFβR-IL12Rβ1 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ1 receptor amino acid sequence set forth in SEQ ID NO:123. Accordingly, a TGFβR-IL12Rβ1 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ1 receptor nucleic acid sequence set forth in SEQ ID NO:124.

In one embodiment, a switch receptor suitable for use in the present invention is a TGFβR-IL12Rβ2 receptor. The TGFβR-IL12Rβ2 receptor converts a negative TGF-β signal into a positive IL-12 signal when expressed in a cell. In one embodiment, the TGFβR-IL12Rβ2 receptor comprises an amino acid sequence set forth below:

(SEQ ID NO: 125)
MGRGLLRGLWPLHIVLWTRIASTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDLLLVIFQVTGISLLPPLGVAISVIIIFYQQKVFVLLAALRP

QWCSREIPDPANSTCAKKYPIAEEKTQLPLDRLLIDWPTPEDPEPLVISE

VLHQVTPVFRHPPCSNWPQREKGIQGHQASEKDMMHSASSPPPPRALQAE

SRQLVDLYKVLESRGSDPKPENPACPWTVLPAGDLPTHDGYLPSNIDDLP

SHEAPLADSLEELEPQHISLSVFPSSSLHPLTFSCGDKLTLDQLKMRCDS

LML, which may be encoded by the nucleic acid sequence set forth below:

(SEQ ID NO: 126)
ATGGGTCGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACCAGCAAAAGGTGTTTGTTCTCCTAGCAGCCCTCAGACCT

CAGTGGTGTAGCAGAGAAATTCCAGATCCAGCAAATAGCACTTGCGCTAA

GAAATATCCCATTGCAGAGGAGAAGACACAGCTGCCCTTGGACAGGCTCC

TGATAGACTGGCCCACGCCTGAAGATCCTGAACCGCTGGTCATCAGTGAA

GTCCTTCATCAAGTGACCCCAGTTTTCAGACATCCCCCCTGCTCCAACTG

GCCACAAAGGGAAAAAGGAATCCAAGGTCATCAGGCCTCTGAGAAAGACA

TGATGCACAGTGCCTCAAGCCCACCACCTCCAAGAGCTCTCCAAGCTGAG

```
AGCAGACAACTGGTGGATCTGTACAAGGTGCTGGAGAGCAGGGGCTCCGA

CCCAAAGCCAGAAAACCCAGCCTGTCCCTGGACGGTGCTCCCAGCAGGTG

ACCTTCCCACCCATGATGGCTACTTACCCTCCAACATAGATGACCTCCCC

TCACATGAGGCACCTCTCGCTGACTCTCTGGAAGAACTGGAGCCTCAGCA

CATCTCCCTTTCTGTTTTCCCCTCAAGTTCTCTTCACCCACTCACCTTCT

CCTGTGGTGATAAGCTGACTCTGGATCAGTTAAAGATGAGGTGTGACTCC

CTCATGCTC.
```

Tolerable variations of the TGFβR-IL12Rβ2 receptor will be known to those of skill in the art, while maintaining its intended biological activity (e.g., converting a negative TGF-β signal into a positive IL-12 signal when expressed in a cell). Accordingly, a TGFβR-IL12Rβ2 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ2 receptor amino acid sequence set forth in SEQ ID NO:125. Accordingly, a TGFβR-IL12Rβ2 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-IL12Rβ2 receptor nucleic acid sequence set forth in SEQ ID NO:126.

In one embodiment, a switch receptor suitable for use in the present invention is a TIM3-CD28 receptor. The TIM3-CD28 receptor converts a negative TIM-3 signal into a positive CD28 signal when expressed in a cell. In one embodiment, the TIM3-CD28 receptor comprises an amino acid sequence set forth below:

(SEQ ID NO: 127)

MFSHLPFDCVLLLLLLLLTRSSEVEYRAEVGQNAYLPCFYTPAAPGNLVP

VCWGKGACPVFECGNVVLRTDERDVNYWTSRYWLNGDFRKGDVSLTIENV

TLADSGIYCCRIQIPGIMNDEKFNLKLVIKPAKVTPAPTRQRDFTAAFPR

MLTTRGHGPAETQTLGSLPDINLTQISTLANELRDSRLANDLRDSGATIR

FWVLVVVGGVLACYSLLVTVAFIIFWVRSKRSRLLHSDYMNMTPRRPGPT

RKHYQPYAPPRDFAAYRS, which may be encoded by the nucleic acid sequence set forth below:

(SEQ ID NO: 128)

ATGTTTTCACATCTTCCCTTTGACTGTGTCCTGCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC

GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

-continued

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCC.

Tolerable variations of the TIM3-CD28 receptor will be known to those of skill in the art, while maintaining its intended biological activity (e.g., converting a negative TIM-3 signal into a positive CD28 signal when expressed in a cell). Accordingly, a TIM3-CD28 receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TIM3-CD28 receptor amino acid sequence set forth in SEQ ID NO:127. Accordingly, a TIM3-CD28 receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TIM3-CD28 receptor nucleic acid sequence set forth in SEQ ID NO:128.

Other suitable dominant negative receptors and switch receptors for use in the present invention are described in PCT Publication No. WO2013019615A2, the disclosure of which is incorporated herein by reference.

D. Bispecific Antibodies

The present invention provides compositions and methods for modified immune cells or precursors thereof, e.g., modified T cells, comprising a nucleic acid encoding a bispecific antibody. Thus, in some embodiments, the immune cell has been genetically modified to express the bispecific antibody. A "bispecific antibody," as used herein, refers to an antibody having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al.

(1985) Science 229:81. Bispecific antibodies include bispecific antibody fragments. See, e.g., Holliger et al. (1993) Proc. Natl. Acad. Sci. U.S.A. 90:6444-48, Gruber et al. (1994) J. Immunol. 152:5368.

In certain embodiments, the modified cell of the present invention comprises a CAR having affinity for a prostate specific membrane antigen (PSMA) on a target cell and a bispecific antibody. In certain embodiments, the modified cell of the present invention secretes a bispecific antibody.

In one embodiment, the bispecific antibody comprises a first antigen binding domain that binds to a first antigen and a second antigen binding domain that binds to a second antigen. In some embodiments, the bispecific antibody comprises an antigen binding domain comprising a first and a second single chain variable fragment (scFv) molecules. In one embodiment, the first and a second antigen binding domains bind an antigen on a target cell and an antigen on an activating T cell.

In one embodiment, the bispecific antibody comprises specificity to at least one antigen on an activating T cell. The activating T cell antigen includes antigens found on the surface of a T cell that can activate another cell. The activating T cell antigen may bind a co-stimulatory molecule. A costimulatory molecule is a cell surface molecule, other than an antigen receptor or their ligands, that is required for an efficient response of lymphocytes to an antigen. Examples of the activating T cell antigen can include but are not limited to CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, or any fragment thereof. In some embodiments, the bispecific antibody comprises specificity to the T cell antigen CD28.

Other costimulatory elements are also within the scope of the invention. In these examples, the bispecific antibody recognizes a T cell antigen and may be referred to as a Bispecific T Cell Engager (BiTE). However, the present invention is not limited by the use of any particular bispecific antibody. Rather, any bispecific antibody or BiTE can be used. The bispecific antibody or BiTE molecule may also be expressed as a soluble protein with specificity for at least one target cell associated antigen.

In one embodiment, the bispecific antibody comprises more than one antigen binding domain. In this embodiment, at least one antigen binding domain includes a synthetic antibody, human antibody, a humanized antibody, single chain variable fragment, single domain antibody, an antigen binding fragment thereof, and any combination thereof. Techniques for making human and humanized antibodies are described elsewhere herein.

In some embodiments, the bispecific antibody comprises more than one antigen binding domain, wherein at least one antigen binding domain binds to a negative signal transduction molecule (e.g., a negative signal transduction molecule that may be found in the microenvironment of the cell secreting the bispecific antibody) or an interacting partner thereof (e.g., receptor). In some embodiments, at least one antigen binding domain of the bispecific antibody binds to TGF-β or an interacting partner thereof (e.g., receptor). In some embodiments, at least one antigen binding domain of the bispecific antibody binds to PD-1 or an interacting partner thereof. In one embodiment, at least one antigen binding domain of the bispecific antibody binds to TGF-βR. In another embodiment, at least one antigen binding domain of the bispecific antibody binds to PD-L1.

In some embodiments, the bispecific antibody comprises at least one antigen binding domain that binds to a molecule on a T cell and activates the T cell. For example, a bispecific antibody of the present disclosure may comprise a super-agonistic anti-CD28 binding domain as described in U.S. Pat. No. 7,585,960, contents of which are incorporated herein in its entirety.

In some embodiments, the bispecific antibody comprises at least one antigen binding domain that binds PD-L1. For example, a bispecific antibody of the present disclosure may comprise, without limitation, a PD-L1 binding domain derived from 10A5, 13G4, or 1B12 as described in PCT Publication No. WO2007005874A2, contents of which are incorporated herein in its entirety. In some embodiments, the bispecific antibody comprises at least one antigen binding domain that binds a TGF-β receptor, e.g., TGFβRII. For example, a bispecific antibody of the present disclosure may comprise, without limitation, a TGFβRII binding domain derived from TGF1 or TGF3 as described in U.S. Pat. No. 8,147,834, contents of which are incorporated herein in its entirety.

Accordingly, in one embodiment, a bispecific antibody of the present disclosure comprises at least one antigen binding domain that binds PD-L1 or TGFβRII, and an antigen binding domain that binds CD28.

In some embodiments, the target cell antigen may be the same antigen that a T cell receptor binds to or may be a different antigen. The target cell antigen includes any tumor associated antigen (TAA) or viral, bacterial and parasitic antigen, or any fragment thereof. The target cell antigen may include any type of ligand that defines the target cell. For example, the target cell antigen may be chosen to recognize a ligand that acts as a cell marker on target cells associated with a particular disease state. Thus, cell markers may act as ligands for the antigen binding domain in the bispecific antibody, including those associated with viral, bacterial and parasitic infections, autoimmune disease and cancer cells.

In some embodiments, the target cell antigen is the same antigen as the activating T cell antigen including, but not limited to, CD3, CD4, CD8, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and fragments thereof. In one aspect, the invention includes a nucleic acid encoding a bispecific antibody comprising bispecificity for an antigen on a target cell and an antigen on an activating T cell, wherein the T cell transiently secretes the bispecific antibody. Techniques for engineering and expressing bispecific antibodies include, but are not limited to, recombinant co-expression of two immunoglobulin heavy chain-light chain pairs having different specificities (see, e.g., Milstein and Cuello, Nature 305: 537 (1983), WO 93/08829, and Traunecker et al, EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al, Science 229:81 (1985)); using leucine zippers to produce bispecific antibodies (see, e.g., Kostelny et al, J. Immunol. 148(5): 1547-1553 (1992)); using "diabody" technology for making bispecific antibody fragments (see, e.g., Hollinger et al, Proc. Natl. Acad. Sci. USA, 90:6444-6448 (1993)); and using single-chain Fv (scFv) dimers (see, e.g. Gruber et al, J. Immunol, 152:5368 (1994)); and preparing trispecific antibodies as described, e.g., in Tutt et al. J.

Immunol. 147: 60 (1991). Engineered antibodies with three or more functional antigen binding sites, including "Octopus antibodies," are also included herein (see, e.g. US 2006/0025576A1). Bispecific antibodies can be constructed by linking two different antibodies, or portions thereof. For example, a bispecific antibody can comprise Fab, F(ab')2, Fab', scFv, and sdAb from two different antibodies.

A bispecific antibody of the present invention includes a bispecific antibody having affinity for PD-L1 and CD28. In one embodiment, a 13G4-1211 PD-L1/CD28 bispecific antibody of the present invention comprises an amino acid sequence set forth below:

(SEQ ID NO: 129)
MGWSCIILFLVATATGVHSAIQLTQSPSSLSASVGDRVTITCRASQGISS

ALAWYQQKPGKAPKLLIYDASSLESGVPSRFSGSGSGTDFTLTISSLQPE

DFATYYCQQFNSYPFTFGPGTKVDIKSGGGGSEVQLVESGGGLVQPGRSL

RLSCAASGITFDDYGMHWVRQAPGKGLEWVSGISWNRGRIEYADSVKGRF

TISRDNAKNSLYLQMNSLRAEDTALYYCAKGRFRYFDWFLDYWGQGTLVT

VSSGGGGSQVQLVQSGAEVKKPGASVKVSCKASGYTFTSYYIHWVRQAPG

QGLEWIGCIYPGNVNTNYNEKFKDRATLTVDTSISTAYMELSRLRSDDTA

VYFCTRSHYGLDWNFDVWGQGTTVTVSSVEGGSGGSGGSGGSGGVMDDIQ

MTQSPSSLSASVGDRVTITCHASQNIYVWLNWYQQKPGKAPKLLIYKASN

LHTGVPSRFSGSGSGTDFTLTISSLQPEDFATYYCQQGQTYPYTFGGGTK

VEI, which may be encoded by the nucleic acid sequence set forth below:

(SEQ ID NO: 130)
ATGGGGTGGTCGTGTATCATCCTGTTCCTGGTCGCGACAGCAACCGGCGT

GCATTCGGCCATACAGCTGACCCAGAGCCCCTCCTCCCTCTCCGCTTCCG

TGGGGGACCGCGTGACAATCACGTGCCGCGCCAGCCAGGGAATCTCCTCG

GCCCTCGCCTGGTACCAGCAGAAACCCGGGAAGGCTCCCAAGCTGCTCAT

CTACGATGCCTCCTCGCTTGAGTCGGGCGTGCCATCCAGGTTCTCCGGAT

CCGGGTCCGGAACCGACTTTACACTCACGATTTCCTCTCTGCAGCCCGAG

GACTTCGCCACATACTACTGTCAGCAGTTCAACTCCTACCCATTCACCTT

CGGCCCGGGCACCAAGGTGGACATCAAGTCTGGCGGGGAGGCTCCGAAG

TCCAGCTCGTGGAATCCGGGGCGGTCTCGTGCAGCCAGGCCGGAGTCTG

CGCCTGTCTTGCGCTGCCTCGGGGATCACTTTCGACGACTACGGCATGCA

TTGGGTTCGCCAGGCCCCAGGGAAGGGGTTGGAGTGGGTCAGTGGCATTT

CATGGAACAGGGGGCGCATCGAATACGCCGACTCCGTTAAGGGCAGATTC

ACCATCTCGCGCGATAACGCCAAAAACAGTCTCTACCTCCAGATGAACTC

GCTTCGAGCAGAGGATACTGCCCTGTACTATTGCGCGAAGGGACGCTTCC

GCTACTTTGACTGGTTTCTGGACTACTGGGGCCAGGGGACACTGGTGACG

GTGTCGTCGGGGGGCGGGGGAGTCAGGTGCAGCTGGTGCAGTCCGGAGC

CGAGGTAAAGAAGCCAGGCGCTTCCGTCAAGGTGTCATGCAAGGCCTCAG

GCTACACCTTCACAAGCTATTACATCCACTGGGTGCGCCAAGCTCCCGGT

CAGGGCTTGGAGTGGATCGGGTGCATTTACCCAGGGAACGTCAACACAAA

CTACAACGAGAAGTTCAAGGATCGGGCAACCCTGACCGTGGACACATCCA

TCTCTACCGCCTACATGGAGCTGTCACGCCTGCGCTCTGATGACACCGCA

GTGTACTTCTGTACCAGGAGTCACTACGGCCTGGACTGGAACTTTGATGT

CTGGGGCCAGGGAACCACCGTGACGGTGTCCAGTGTGGAGGGCGGTAGTG

GCGGCTCTGGTGGGTCCGGAGGCTCAGGCGGCGTGATGGATGACATTCAG

ATGACCCAGAGTCCCTCCTCCCTCTCCGCTTCCGTCGGAGACCGCGTGAC

CATCACTTGTCACGCCTCACAGAATATCTACGTGTGGCTGAACTGGTACC

AACAGAAGCCCGGCAAGGCCCCCAAGCTGCTTATCTATAAAGCGTCCAAC

CTCCACACGGGAGTCCCTTCCCGCTTCTCCGGATCCGGCAGTGGGACGGA

CTTCACACTCACAATCTCGTCGCTGCAGCCAGAGGACTTTGCGACGTACT

ACTGCCAGCAGGGCCAGACCTACCCATATACTTTCGGCGGCGGGACCAAG

GTGGAGAT.

Tolerable variations of the 13G4-1211 PD-L1/CD28 bispecific antibody will be known to those of skill in the art, while maintaining its intended biological activity (e.g., binding to PD-L1 and CD28). Accordingly, a 13G4-1211 PD-L1/CD28 bispecific antibody of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 13G4-1211 PD-L1/CD28 bispecific antibody amino acid sequence set forth in SEQ ID NO:129. Accordingly, a 13G4-1211 PD-L1/CD28 bispecific antibody of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 13G4-1211 PD-L1/CD28 bispecific antibody nucleic acid sequence set forth in SEQ ID NO:130.

A bispecific antibody of the present invention includes a bispecific antibody having affinity for PD-L1 and CD28. In one embodiment, a 10A5-1412 PD-L1/CD28 bispecific antibody of the present invention comprises an amino acid sequence set forth below:

(SEQ ID NO: 131)
MGWSCIILFLVATATGVHSDIQMTQSPSSLSASVGDRVTITCRASQGISS

WLAWYQQKPEKAPKSLIYAASSLQSGVPSRFSGSGSGTDFTLTISSLQPE

DFATYYCQQYNSYPYTFGQGTKLEIKSGGGGSQVQLVQSGAEVKKPGASV

KVSCKASGYTFTSYDVHWVRQAPGQRLEWMGWLHADTGITKFSQKFQGRV

TITRDTSASTAYMELSSLRSEDTAVYYCARERIQLWFDYWGQGTLVTVSS

GGGGSQVQLVQSGAEVKKPGASVKVSCKASGYTFTSYYIHWVRQAPGQGL

EWIGCIYPGNVNTNYNEKFKDRATLTVDTSISTAYMELSRLRSDDTAVYF

CTRSHYGLDWNFDVWGQGTTVTVSSVEGGSGGSGGSGGSGGVMDDIQMTQ

-continued

SPSSLSASVGDRVTITCHASQNIYVWLNWYQQKPGKAPKLLIYKASNLHT

GVPSRFSGSGSGTDFTLTISSLQPEDFATYYCQQGQTYPYTFGGGTKVE

I, which may be encoded by the nucleic acid sequence set forth below:

(SEQ ID NO: 132)
ATGGGCTGGAGTTGCATCATTCTCTTCCTCGTGGCGACCGCAACAGGGGT

GCACTCCGACATCCAGATGACCCAGTCCCCGAGTTCCCTGTCTGCTTCCG

TGGGAGATCGCGTGACTATCACCTGCCGGGCTTCCCAGGGCATCTCTTCC

TGGCTGGCGTGGTACCAGCAGAAACCAGAAAAGGCTCCTAAGTCCCTGAT

CTACGCAGCTTCGTCCCTCCAATCCGGCGTCCCCTCTCGCTTCTCCGGCT

CCGGATCCGGCACCGACTTCACGCTGACAATCTCGAGTTTGCAGCCCGAG

GACTTCGCCACCTACTACTGCCAGCAGTACAACTCCTACCCTTACACCTT

CGGCCAGGGCACAAAGCTCGAAATCAAGTCGGGGGGGGCGGGTCGCAGG

TCCAGCTGGTGCAGTCCGGCGCCGAAGTCAAGAAGCCCGGAGCAAGTGTG

AAAGTGTCGTGCAAGGCAAGTGGGTATACCTTCACCTCATACGACGTACA

CTGGGTGCGCCAGGCGCCCGGTCAGCGCCTTGAGTGGATGGGCTGGCTCC

ACGCCGACACCGGCATTACCAAGTTCTCTCAGAAGTTCCAGGGAAGAGTG

ACCATAACACGCGACACCAGTGCTTCCACAGCTTACATGGAACTTTCGAG

TCTGAGATCCGAGGACACAGCCGTGTATTACTGTGCCCGTGAGCGCATCC

AGCTGTGGTTCGACTACTGGGGCAGGGCACCCTCGTGACGGTGTCGTCG

GGGGGCGGGGGGAGTCAGGTGCAGCTGGTGCAGTCCGGAGCCGAGGTAAA

GAAGCCAGGCGCTTCCGTCAAGGTGTCATGCAAGGCCTCAGGCTACACCT

TCACAAGCTATTACATCCACTGGGTGCGCCAAGCTCCCGGTCAGGGCTTG

GAGTGGATCGGGTGCATTTACCCAGGGAACGTCAACACAAACTACAACGA

GAAGTTCAAGGATCGGGCAACCCTGACCGTGGACACATCCATCTCTACCG

CCTACATGGAGCTGTCACGCCTGCGCTCTGATGACACCGCAGTGTACTTC

TGTACCAGGAGTCACTACGGCCTGGACTGGAACTTTGATGTCTGGGGCCA

GGGAACCACCGTGACGGTGTCCAGTGTGGAGGGCGGTAGTGGCGGCTCTG

GTGGGTCCGAGGCTCAGGCGGCGTGATGATGACATTCAGATGACCCAG

AGTCCCTCCTCCCTCTCCGCTTCCGTCGGAGACCGCGTGACCATCACTTG

TCACGCCTCACAGAATATCTACGTGTGGCTGAACTGGTACCAACAGAAGC

CCGGCAAGGCCCCCAAGCTGCTTATCTATAAAGCGTCCAACCTCCACACG

GGAGTCCCTTCCCGCTTCTCCGGATCCGGCAGTGGGACGGACTTCACACT

CACAATCTCGTCGCTGCAGCCAGAGGACTTTGCGACGTACTACTGCCAGC

AGGGCCAGACCTACCCATATACTTTCGGCGGCGGGACCAAGGTGGAGAT.

Tolerable variations of the 10A5-1412 PD-L1/CD28 bispecific antibody will be known to those of skill in the art, while maintaining its intended biological activity (e.g., binding to PD-L1 and CD28). Accordingly, a 10A5-1412 PD-L1/CD28 bispecific antibody of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 10A5-1412 PD-L1/CD28 bispecific antibody amino acid sequence set forth in SEQ ID NO:131. Accordingly, a 10A5-1412 PD-L1/CD28 bispecific antibody of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 10A5-1412 PD-L1/CD28 bispecific antibody nucleic acid sequence set forth in SEQ ID NO:132.

A bispecific antibody of the present invention includes a bispecific antibody having affinity for PD-L1 and CD28. In one embodiment, a 1B12-1412 PD-L1/CD28 bispecific antibody of the present invention comprises an amino acid sequence set forth below:

(SEQ ID NO: 133)
MGWSCIILFLVATATGVHSEIVLTQSPATLSLSPGERATLSCRASQSVSS

YLAWYQQKPGQAPRLLIYDASNRATGIPARFSGSGSGTDFTLTISSLEPE

DFAVYYCQQRSNWPTFGQGTKVEIKSGGGGSQVQLVQSGAEVKKPGSSVK

VSCKTSGDTFSSYAISWVRQAPGQGLEWMGGIIPIFGRAHYAQKFQGRVT

ITADESTSTAYMELSSLRSEDTAVYFCARKFHFVSGSPFGMDVWGQGTVT

VSSGGSSGGGGSQVQLVQSGAEVKKPGASVKVSCKASGYTFTSYYIHWVR

QAPGQGLEWIGCIYPGNVNTNYNEKFKDRATLTVDTSISTAYMELSRLRS

DDTAVYFCTRSHYGLDWNFDVWGQGTTVTVSSVEGGSGGSGGSGGSGGVM

DDIQMTQSPSSLSASVGDRVTITCHASQNIYVWLNWYQQKPGKAPKLLIY

KASNLHTGVPSRFSGSGSGTDFTLTISSLQPEDFATYYCQQGQTYPYTFG

GGTKVEI, which may be encoded by the nucleic acid sequence set forth below:

(SEQ ID NO: 134)
ATGGGCTGGAGTTGCATCATCCTCTTTCTAGTCGCCACGGCCACCGGCGT

ACACTCAGAGATCGTGCTGACACAGTCGCCTGCGACGCTGTCGCTCAGTC

CAGGGGAGCGCGCTACTCTCTCCTGCCGCGCGTCGCAGAGCGTGTCGTCC

TACTTGGCCTGGTACCAGCAGAAGCCTGGCCAGGCTCCGCGCCTGCTGAT

ATACGACGCCTCGAACAGAGCCACGGGCATCCCCGCCCGTTTTAGTGGCT

CCGGGTCGGGGACCGACTTCACTCTGACAATCTCATCCCTCGAGCCCGAG

GATTTCGCCGTGTACTACTGTCAGCAGCGCTCGAATTGGCCAACCTTCGG

GCAGGGGACGAAAGTTGAGATCAAAAGCGGCGGCGGGGGCAGCCAGGTCC

AGCTCGTCCAGTCTGGCGCCGAGGTCAAAAAGCCGGGCTCTTCGGTCAAG

GTCTCCTGCAAGACTTCCGGCGACACCTTCTCCTCCTATGCTATCTCCTG

GGTGCGGCAGGCCCCGGGCAGGGCCTGGAGTGGATGGGAGGCATCATCC

CAATCTTTGGGAGGGCCCACTACGCCCAGAAGTTCCAGGGACGCGTGACA

ATCACCGCAGACGAGTCCACATCCACTGCCTACATGGAGTTGTCCTCGCT

-continued

```
CCGGTCGGAGGATACTGCCGTGTACTTCTGCGCCCGGAAGTTCCACTTCG
TGTCAGGCTCCCCCTTCGGGATGGACGTGTGGGGACAAGGAACCGTGACG
GTGTCGTCGGGGGGCTCGTCGGGGGGCGGGGGGAGTCAGGTGCAGCTGGT
GCAGTCCGGAGCCGAGGTAAAGAAGCCAGGCGCTTCCGTCAAGGTGTCAT
GCAAGGCCTCAGGCTACACCTTCACAAGCTATTACATCCACTGGGTGCGC
CAAGCTCCCGGTCAGGGCTTGGAGTGGATCGGGTGCATTTACCCAGGGAA
CGTCAACACAAACTACAACGAGAAGTTCAAGGATCGGGCAACCCTGACCG
TGGACACATCCATCTCTACCGCCTACATGGAGCTGTCACGCCTGCGCTCT
GATGACACCGCAGTGTACTTCTGTACCAGGAGTCACTACGGCCTGGACTG
GAACTTTGATGTCTGGGGCCAGGGAACCACCGTGACGGTGTCCAGTGTGG
AGGGCGGTAGTGGCGGCTCTGGTGGGTCCGGAGGCTCAGGCGGCGTGATG
GATGACATTCAGATGACCCAGAGTCCCTCCTCCCTCTCCGCTTCCGTCGG
AGACCGCGTGACCATCACTTGTCACGCCTCACAGAATATCTACGTGTGGC
TGAACTGGTACCAACAGAAGCCCGGCAAGGCCCCCAAGCTGCTTATCTAT
AAAGCGTCCAACCTCCACACGGGAGTCCCTTCCCGCTTCTCCGGATCCGG
CAGTGGGACGGACTTCACACTCACAATCTCGTCGCTGCAGCCAGAGGACT
TTGCGACGTACTACTGCCAGCAGGGCCAGACCTACCCATATACTTTCGGC
GGCGGGACCAAGGTGGAGAT.
```

Tolerable variations of the 1B12-1412 PD-L1/CD28 bispecific antibody will be known to those of skill in the art, while maintaining its intended biological activity (e.g., binding to PD-L1 and CD28). Accordingly, a 1B12-1412 PD-L1/CD28 bispecific antibody of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 1B12-1412 PD-L1/CD28 bispecific antibody amino acid sequence set forth in SEQ ID NO:133. Accordingly, a 1B12-1412 PD-L1/CD28 bispecific antibody of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 1B12-1412 PD-L1/CD28 bispecific antibody nucleic acid sequence set forth in SEQ ID NO:134.

A bispecific antibody of the present invention includes a bispecific antibody having affinity for TGF-β receptor type II (TGFβRII) and CD28. In one embodiment, a TGFβR-1-1412 TGFβRII/CD28 bispecific antibody of the present invention comprises an amino acid sequence set forth below:

(SEQ ID NO: 135)
```
MGWSCIILFLVATATGVHSEIVLTQSPATLSLSPGERATLSCRASQSVRS
YLAWYQQKPGQAPRLLIYDASNRATGIPARFSGSGSGTDFTLTISSLEPE
DFAVYYCQQRSNWPPTFGQGTKVEIKSGGGGSQLQVQESGPGLVKPSETL
SLTCTVSGGSISNSYFSWGWIRQPPGKGLEWIGSFYYGEKTYYNPSLKSR
ATISIDTSKSQFSLKLSSVTAADTAVYYCPRGPTMIRGVIDSWGQGTLVT
VSSGGGGSQVQLVQSGAEVKKPGASVKVSCKASGYTFTSYYIHWVRQAPG
QGLEWIGCIYPGNVNTNYNEKFKDRATLTVDTSISTAYMELSRLRSDDTA
VYFCTRSHYGLDWNFDVWGQGTTVTVSSVEGGSGGSGGSGGSGGVMDDIQ
MTQSPSSLSASVGDRVTITCHASQNIYVWLNWYQQKPGKAPKLLIYKASN
LHTGVPSRFSGSGSGTDFTLTISSLQPEDFATYYCQQGQTYPYTFGGGTK
VEIK,
``` which may be encoded by the nucleic acid sequence set forth below:

(SEQ ID NO: 136)
```
ATGGGTTGGTCCTGCATCATCCTGTTTCTCGTGGCCACCGCCACCGGCGT
GCACTCCGAAATTGTGTTGACACAGTCTCCAGCCACCCTGTCTTTGTCTC
CAGGGGAAAGAGCCACCCTCTCCTGCAGGGCCAGTCAGAGTGTTCGCAGC
TACTTAGCCTGGTACCAACAGAAACCTGGCCAGGCTCCCAGGCTCCTCAT
CTATGATGCATCCAACAGGGCCACTGGCATCCCAGCCAGGTTCAGTGGCA
GTGGGTCTGGGACAGACTTCACTCTCACCATCAGCAGCCTAGAGCCTGAA
GATTTTGCAGTTTATTACTGTCAGCAGCGTAGCAACTGGCCTCCGACGTT
CGGCCAAGGGACCAAGGTGGAAATCAAAAGTGGAGGGGGCGGTTCACAGC
TGCAGGTGCAGGAGTCGGGCCCAGGACTGGTGAAGCCTTCGGAGACCCTG
TCCCTCACCTGCACTGTCTCTGGTGGCTCCATCAGCAACAGTTATTTCTC
CTGGGGCTGGATCCGCCAGCCCCCAGGGAAGGGACTGGAGTGGATTGGGA
GTTTCTATTATGGTGAAAAAACCTACTACAACCCGTCCCTCAAGAGCCGA
GCCACCATATCCATTGACACGTCCAAGAGCCAGTTCTCCCTGAAGCTGAG
CTCTGTGACCGCCGCAGACACGGCTGTGTATTACTGTCCGAGAGGGCCTA
CTATGATTCGGGGAGTTATAGACTCCTGGGGCCAGGGAACCCTGGTGACG
GTGTCGTCGGGGGGCGGGGGAGTCAGGTGCAGCTGGTGCAGTCCGGAGC
CGAGGTAAAGAAGCCAGGCGCTTCCGTCAAGGTGTCATGCAAGGCCTCAG
GCTACACCTTCACAAGCTATTACATCCACTGGGTGCGCCAAGCTCCCGGT
CAGGGCTTGGAGTGGATCGGGTGCATTTACCCAGGGAACGTCAACACAAA
CTACAACGAGAAGTTCAAGGATCGGGCAACCCTGACCGTGGACACATCCA
TCTCTACCGCCTACATGGAGCTGTCACGCCTGCGCTCTGATGACACCGCA
GTGTACTTCTGTACCAGGAGTCACTACGGCCTGGACTGGAACTTTGATGT
CTGGGGCCAGGGAACCACCGTGACGGTGTCCAGTGTGGAGGGCGGTAGTG
GCGGCTCTGGTGGGTCCGGAGGCTCAGGCGGCGTGATGGATGACATTCAG
ATGACCCAGAGTCCCTCCTCCCTCTCCGCTTCCGTCGGAGACCGCGTGAC
CATCACTTGTCACGCCTCACAGAATATCTACGTGTGGCTGAACTGGTACC
AACAGAAGCCCGGCAAGGCCCCCAAGCTGCTTATCTATAAAGCGTCCAAC
CTCCACACGGGAGTCCCTTCCCGCTTCTCCGGATCCGGCAGTGGGACGGA
CTTCACACTCACAATCTCGTCGCTGCAGCCAGAGGACTTTGCGACGTACT
```

ACTGCCAGCAGGGCCAGACCTACCCATATACTTTCGGCGGCGGGACCAAG

GTGGAGATTAAG.

Tolerable variations of the TGFβR-1-1412 TGFβRII/ CD28 bispecific antibody will be known to those of skill in the art, while maintaining its intended biological activity (e.g., binding to TGFβRII and CD28). Accordingly, a TGFβR-1-1412 TGFβRII/CD28 bispecific antibody of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-1-1412 TGFβRII/CD28 bispecific antibody amino acid sequence set forth in SEQ ID NO:135. Accordingly, a TGFβR-1-1412 TGFβRII/CD28 bispecific antibody of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-1-1412 TGFβRII/CD28 bispecific antibody nucleic acid sequence set forth in SEQ ID NO:136.

A bispecific antibody of the present invention includes a bispecific antibody having affinity for TGF-β receptor type II (TGFβRII) and CD28. In one embodiment, a TGFβR-3-1412 TGFβRII/CD28 bispecific antibody of the present invention comprises an amino acid sequence set forth below:

(SEQ ID NO: 137)

MGWSCIILFLVATATGVHSEIVLTQSPATLSLSPGERATLSCRASQSVRS

FLAWYQQKPGQAPRLLIYDASNRATGIPARFSGSGSGTDFTLTISSLEPE

DFAVYYCQQRSNWPPTFGQGTKVEIKSGGGGSQLQLQESGPGLVKPSETL

SLTCTVSGGSISSSSYSWGWIRQPPGKGLEWIGSFYYSGITYYSPSLKSR

IIISEDTSKNQFSLKLSSVTAADTAVYYCASGFTMIRGALDYWGQGTLVT

VSSGGGGSQVQLVQSGAEVKKPGASVKVSCKASGYTFTSYYIHWVRQAPG

QGLEWIGCIYPGNVNTNYNEKFKDRATLTVDTSISTAYMELSRLRSDDTA

VYFCTRSHYGLDWNFDVWGQGTTVTVSSVEGGSGGSGGSGGSGGVMDDIQ

MTQSPSSLSASVGDRVTITCHASQNIYVWLNWYQQKPGKAPKLLIYKASN

LHTGVPSRFSGSGSGTDFTLTISSLQPEDFATYYCQQGQTYPYTFGGGTK

VEIK, which may be encoded by the nucleic acid sequence set forth below:

(SEQ ID NO: 138)

ATGGGTTGGTCCTGCATCATCCTGTTTCTCGTGGCCACCGCCACCGGCGT

GCACTCCGAAATTGTGTTGACACAGTCTCCAGCCACCCTGTCTTTGTCTC

CAGGGGAAAGAGCCACCCTCTCCTGCAGGGCCAGTCAGAGTGTTAGAAGT

TTCTTAGCCTGGTACCAACAGAAACCTGGCCAGGCTCCCAGGCTCCTCAT

-continued

CTATGATGCATCCAACAGGGCCACTGGCATCCCAGCCAGGTTCAGTGGCA

GTGGGTCTGGGACAGACTTCACTCTCACCATCAGCAGCCTAGAGCCTGAA

GATTTTGCAGTTTATTACTGTCAGCAGCGTAGCAACTGGCCTCCGACGTT

CGGCCAAGGGACCAAGGTGGAAATCAAAAGTGGAGGGGGCGGTTCACAGC

TACAGCTGCAGGAGTCGGGCCCAGGACTGGTGAAGCCTTCGGAGACCCTA

TCCCTCACCTGCACTGTCTCTGGTGGCTCCATCAGCAGTAGTAGTTACTC

CTGGGGCTGGATCCGCCAGCCCCCAGGGAAGGGCCTGGAGTGGATTGGGA

GTTTCTATTACAGTGGGATCACCTACTACAGCCCGTCCCTCAAGAGTCGA

ATTATCATATCCGAAGACACGTCCAAGAACCAGTTCTCCCTGAAGCTGAG

TTCTGTGACCGCCGCAGACACGGCTGTGTATTACTGTGCGAGCGGGTTTA

CTATGATTCGGGGAGCCCTTGACTACTGGGGCCAGGGAACCCTGGTGACG

GTGTCGTCGGGGGGCGGGGGGAGTCAGGTGCAGCTGGTGCAGTCCGGAGC

CGAGGTAAAGAAGCCAGGCGCTTCCGTCAAGGTGTCATGCAAGGCCTCAG

GCTACACCTTCACAAGCTATTACATCCACTGGGTGCGCCAAGCTCCCGGT

CAGGGCTTGGAGTGGATCGGGTGCATTTACCCAGGGAACGTCAACACAAA

CTACAACGAGAAGTTCAAGGATCGGGCAACCCTGACCGTGGACACATCCA

TCTCTACCGCCTACATGGAGCTGTCACGCCTGCGCTCTGATGACACCGCA

GTGTACTTCTGTACCAGGAGTCACTACGGCCTGGACTGGAACTTTGATGT

CTGGGGCCAGGGAACCACCGTGACGGTGTCCAGTGTGGAGGGCGGTAGTG

GCGGCTCTGGTGGGTCCGGAGGCTCAGGCGGCGTGATGGATGACATTCAG

ATGACCCAGAGTCCCTCCTCCCTCTCCGCTTCCGTCGGAGACCGCGTGAC

CATCACTTGTCACGCCTCACAGAATATCTACGTGTGGCTGAACTGGTACC

AACAGAAGCCCGGCAAGGCCCCCAAGCTGCTTATCTATAAAGCGTCCAAC

CTCCACACGGGAGTCCCTTCCCGCTTCTCCGGATCCGGCAGTGGGACGGA

CTTCACACTCACAATCTCGTCGCTGCAGCCAGAGGACTTTGCGACGTACT

ACTGCCAGCAGGGCCAGACCTACCCATATACTTTCGGCGGCGGGACCAAG

GTGGAGATTAAG.

Tolerable variations of the TGFβR-3-1412 TGFβRII/CD28 bispecific antibody will be known to those of skill in the art, while maintaining its intended biological activity (e.g., binding to TGFβRII and CD28). Accordingly, a TGFβR-3-1412 TGFβRII/CD28 bispecific antibody of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-3-1412 TGFβRII/CD28 bispecific antibody amino acid sequence set forth in SEQ ID NO:137. Accordingly, a TGFβR-3-1412 TGFβRII/CD28 bispecific antibody of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβR-3-1412 TGFβRII/CD28 bispecific antibody nucleic acid sequence set forth in SEQ ID NO:138.

Other suitable bispecific antibodies for use in the present invention are described in PCT Publication No. WO2016122738A1, the disclosure of which is incorporated herein by reference.

E. Nucleic Acids and Expression Vectors

The present invention provides a nucleic acid encoding a CAR and/or a dominant negative receptor and/or a switch receptor. In one embodiment, a nucleic acid of the present disclosure comprises a nucleic acid sequence encoding a subject CAR of the present invention (e.g., PSMA-CAR). In one embodiment, a nucleic acid of the present disclosure comprises a nucleic acid sequence encoding a dominant negative receptor and/or a switch receptor (e.g., a PD1-PTM-CD28 receptor).

In some embodiments, a nucleic acid of the present disclosure provides for the production of a CAR and/or dominant negative receptor and/or a switch receptor as described herein, e.g., in a mammalian cell. In some embodiments, a nucleic acid of the present disclosure provides for amplification of the CAR and/or dominant negative receptor and/or a switch receptor-encoding nucleic acid.

As described herein, a subject CAR comprises an antigen binding domain, a transmembrane domain, and an intracellular domain. Accordingly, the present disclosure provides a nucleic acid encoding an antigen binding domain, a transmembrane domain, and an intracellular domain of a subject CAR. As described herein, various dominant negative receptors and switch receptors are provided. Accordingly, the present invention provides a nucleic acid encoding a dominant negative receptor and/or a switch receptor.

In some embodiments, the nucleic acid encoding a CAR is separate from the nucleic acid encoding a dominant negative receptor and/or a switch receptor. In an exemplary embodiment, the nucleic acid encoding a CAR, and the nucleic acid encoding a dominant negative receptor and/or a switch receptor, resides within the same nucleic acid.

In some embodiments, a nucleic acid of the present invention comprises a nucleic acid comprising a CAR coding sequence and a dominant negative receptor and/or a switch receptor coding sequence. In some embodiments, a nucleic acid of the present invention comprises a nucleic acid comprising a CAR coding sequence and a dominant negative receptor and/or a switch receptor coding sequence that is separated by a linker. A linker for use in the present invention (e.g., in the context of linking a CAR coding sequence and a dominant negative receptor and/or a switch receptor coding sequence) allows for multiple proteins to be encoded by the same nucleic acid sequence (e.g., a multicistronic or bicistronic sequence), which are translated as a polyprotein that is dissociated into separate protein components. For example, a linker for use in a nucleic acid of the present disclosure comprising a CAR coding sequence and a dominant negative receptor and/or a switch receptor coding sequence, allows for the CAR and dominant negative receptor and/or switch receptor to be translated as a polyprotein that is dissociated into separate CAR and dominant negative receptor and/or switch receptor components.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAV0, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a nucleic acid of the present disclosure comprises a nucleic acid sequence comprising a CAR coding sequence and a dominant negative receptor and/or a switch receptor coding sequence that is separated by a linker comprising a T2A peptide sequence. In some embodiments, the T2A peptide sequence comprises the amino acid sequence EGRGSLLTCGDVEENPGP (SEQ ID NO:139), which may be encoded by the nucleic acid sequence GAGGGCAGAGGAAGTCTTCTAACATGCGGTGACGTGGAGGAGAATCCCGGCCCT (SEQ ID NO:140). In some embodiments, the linker comprising a T2A peptide sequence may further comprise a spacer sequence as described herein. For example, the linker comprising a T2A peptide sequence may further comprise a spacer sequence comprising the amino acid sequence SGRSGGG (SEQ ID NO:141), which may be encoded by the nucleic acid sequence TCCGGAAGATCTGGCGGCGGA (SEQ ID NO:142).

In some embodiments, a nucleic acid of the present disclosure comprises a nucleic acid sequence comprising a CAR coding sequence and a dominant negative receptor and/or a switch receptor coding sequence that is separated by a linker comprising a F2A peptide sequence. In some embodiments, the F2A peptide sequence comprises the amino acid sequence VKQTLNFDLLKLAGDVESNPGP (SEQ ID NO:143), which may be encoded by the nucleic acid sequence (SEQ ID NO: 144)
GTGAAACAGACTTTGAATTTTGACCTTCTCAAGTTGGCGGGAGACGTGGA

GTCCAACCCAGGGCCG.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X-Lys-Arg (SEQ ID NO:145) or Arg-X-Arg-Arg (SEQ ID NO:146), and Arg-X-X-Arg (SEQ ID NO:147), such as an Arg-Gln-Lys-Arg (SEQ ID NO:148), where X is any naturally occurring amino acid. Another example of a furin cleavage site is X1-Arg-X2-X3-Arg (SEQ ID NO:149), where X1 is Lys or Arg, X2 is any naturally occurring amino acid, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:1) and (GGGS)n (SEQ ID NO:2), where n represents an integer of at least 1. Exemplary spacer sequences can comprise amino acid sequences including, without limitation, GGSG (SEQ ID NO:4), GGSGG (SEQ ID NO:5), GSGSG (SEQ ID NO:6), GSGGG (SEQ ID NO:7), GGGSG (SEQ ID NO:8), GSSSG (SEQ ID NO:9), and the like. Those of skill in the art would be able to select the appropriate spacer sequence for use in the present invention.

In some embodiments, a nucleic acid of the present disclosure comprises a nucleic acid sequence comprising a CAR coding sequence and a dominant negative receptor and/or a switch receptor coding sequence that is separated by a Furin-(G4S)2-T2A (F-GS2-T2A) linker. The F-GS2-T2A linker may be encoded by the nucleic acid sequence (SEQ ID NO: 150)
CGTGCGAAGAGGGGCGGCGGGGGCTCCGGCGGGGGAGGCAGTGAGGGCCG

CGGCTCCCTGCTGACCTGCGGAGATGTAGAAGAGAACCCAGGCCCC, and may comprise the amino acid sequence RAKRGGGGSGGGGSEGRGSLLTCGDVEENPGP (SEQ ID NO:151). Those of skill in the art would appreciate that linkers of the present invention may include tolerable sequence variations.

In some embodiments, the present invention provides a nucleic acid comprising a nucleic acid sequence encoding a dominant negative receptor and/or a switch receptor as described herein. In some embodiments, a nucleic acid comprises a nucleic acid sequence encoding a dominant negative receptor and/or a switch receptor and a nucleic acid sequence encoding a CAR as described herein (e.g., a PSMA-CAR). In one embodiment, the nucleic acid sequence encoding the dominant negative receptor and/or the switch receptor and the nucleic acid sequence encoding the CAR resides on separate nucleic acids. In one embodiment, the nucleic acid sequence encoding the dominant negative receptor and/or the switch receptor and the nucleic acid sequence encoding the CAR resides within the same nucleic acid. In such an embodiment, the nucleic acid sequence encoding the dominant negative receptor and/or the switch receptor and the nucleic acid sequence encoding the CAR is separated by a linker as described herein.

For example, a nucleic acid of the present disclosure may comprise a nucleic acid sequence encoding a dominant receptor, a linker, and a nucleic acid sequence encoding a CAR. In one embodiment, the linker comprises a nucleic acid sequence encoding a 2A peptide (e.g., T2A). In an exemplary embodiment, a nucleic acid of the present disclosure may comprise a nucleic acid sequence encoding a dominant negative receptor and/or a switch receptor and a nucleic acid sequence encoding a CAR separated by a linker sequence comprising a nucleic acid sequence encoding T2A.

Accordingly, in one embodiment, a nucleic acid of the present disclosure comprises from 5' to 3': a nucleic acid sequence encoding a dominant negative receptor and/or a switch receptor, a nucleic acid sequence encoding a linker, and a nucleic acid sequence encoding a CAR. In one embodiment, a nucleic acid of the present disclosure comprises from 5' to 3': a nucleic acid sequence encoding a CAR, a nucleic acid sequence encoding a linker, and a nucleic acid sequence encoding a dominant negative receptor and/or a switch receptor.

In some embodiments, a nucleic acid of the present disclosure comprises from 5' to 3': a nucleic acid sequence encoding a dominant negative receptor and/or a switch receptor, a nucleic acid sequence encoding a linker comprising T2A, and a nucleic acid sequence encoding a CAR. In one embodiment, the dominant negative receptor is TGFβRII-DN. In one embodiment, the CAR is a murine J591 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising T2A, and a nucleic acid sequence encoding a murine J591 PSMA-CAR. In one embodiment, the nucleic acid comprising from 5' to 3': a nucleic acid sequence encoding TGFβRII-DN, a nucleic acid sequence encoding a linker comprising T2A, and a nucleic acid sequence encoding a murine J591 PSMA-CAR, comprises the nucleic acid sequence set forth below:

(SEQ ID NO: 152)
ATGGGTCGGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACTGCTACCGCGTTAACCGGCAGCAGAAGCTGAGTTCATCC

GGAAGATCTGGCGGCGGAGAGGGCAGAGGAAGTCTTCTAACATGCGGTGA

-continued
```
CGTGGAGGAGAATCCCGGCCCTAGAGCCACCATGGCCCTGCCTGTGACAG
CCCTGCTGCTGCCTCTGGCTCTGCTGCTGCACGCCGCCAGACCTGGATCT
GACATTGTGATGACCCAGTCTCACAAATTCATGTCCACATCAGTAGGAGA
CAGGGTCAGCATCATCTGTAAGGCCAGTCAAGATGTGGGTACTGCTGTAG
ACTGGTATCAACAGAAACCAGGACAATCTCCTAAACTACTGATTTATTGG
GCATCCACTCGGCACACTGGAGTCCCTGATCGCTTCACAGGCAGTGGATC
TGGGACAGACTTCACTCTCACCATTACTAACGTTCAGTCTGAAGACTTGG
CAGATTATTTCTGTCAGCAATATAACAGCTATCCTCTCACGTTCGGTGCT
GGGACCATGCTGGACCTGAAAGGAGGCGGAGGATCTGGCGGCGGAGGAAG
TTCTGGCGGAGGCAGCGAGGTGCAGCTGCAGCAGAGCGGACCCGAGCTCG
TGAAGCCTGGAACAAGCGTGCGGATCAGCTGCAAGACCAGCGGCTACACC
TTCACCGAGTACACCATCCACTGGGTCAAGCAGTCCCACGGCAAGAGCCT
GGAGTGGATCGGCAATATCAACCCCAACAACGGCGGCACCACCTACAACC
AGAAGTTCGAGGACAAGGCCACCCTGACCGTGGACAAGAGCAGCAGCACC
GCCTACATGGAACTGCGGAGCCTGACCAGCGAGGACAGCGCCGTGTACTA
TTGTGCCGCCGGTTGGAACTTCGACTACTGGGGCCAGGGCACAACCCTGA
CAGTGTCTAGCGCTAGCTCCGGAACCACGACGCCAGCGCCGCGACCACCA
ACACCGGCGCCCACCATCGCGTCGCAGCCCCTGTCCCTGCGCCCAGAGGC
GTGCCGGCCAGCGGCGGGGGCGCAGTGCACACGAGGGGGCTGGACTTCG
CCTGTGATATCTACATCTGGGCGCCCTTGGCCGGGACTTGTGGGGTCCTT
CTCCTGTCACTGGTTATCACCCTTTACTGCAAACGGGGCAGAAAGAAACT
CCTGTATATATTCAAACAACCATTTATGAGACCAGTACAAACTACTCAAG
AGGAAGACGGCTGTAGCTGCCGATTTCCAGAAGAAGAAGAAGGAGGATGT
GAACTGAGAGTGAAGTTCAGCAGGAGCGCAGACGCCCCCGCGTACAAGCA
GGGCCAGAACCAGCTCTATAACGAGCTCAATCTAGGACGAAGAGAGGAGT
ACGACGTTTTGGACAAGAGACGTGGCCGGGACCCTGAGATGGGGGGAAAG
CCGAGAAGGAAGAACCCTCAGGAAGGCCTGTACAACGAACTGCAGAAAGA
TAAGATGGCGGAGGCCTACAGTGAGATTGGGATGAAAGGCGAGCGCCGGA
GGGGCAAGGGGCACGACGGCCTTTACCAGGGTCTCAGTACAGCCACCAAG
GACACCTACGACGCCCTTCACATGCAGGCCCTGCCCCCTCGC.
```

In one embodiment, the CAR is a humanized J591 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising a 2A peptide (e.g., T2A), and a nucleic acid sequence encoding a humanized J591 PSMA-CAR. In one embodiment, a nucleic acid of the present disclosure comprises from 5' to 3': a nucleic acid encoding a humanized PSMA-CAR, a nucleic acid encoding a linker comprising a 2A peptide (e.g., T2A), and a nucleic acid encoding a dominant negative receptor and/or a switch receptor.

In one embodiment, the CAR is a humanized J591 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising T2A, and a nucleic acid sequence encoding a humanized J591 PSMA-CAR. In one embodiment, the nucleic acid comprising from 5' to 3': a nucleic acid sequence encoding TGFβRII-DN, a nucleic acid sequence encoding a linker comprising T2A, and a nucleic acid sequence encoding a humanized J591 PSMA-CAR.

The humanized PSMA-CAR can comprise any of the heavy and light chain variable regions disclosed in PCT Publication Nos. WO2017212250A1 and WO2018033749A1. For example, the humanized PSMA-CAR of the present invention can comprise an scFv comprising any of the heavy and light chain variable regions disclosed therein. In some embodiments, the humanized J591 PSMA-CAR comprises a humanized J591 PSMA binding domain comprising a heavy and light chain variable region selected from any of the heavy and light chain variable region sequences set forth in Table 19.

In one embodiment, the CAR is a human 1C3 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising T2A, and a nucleic acid sequence encoding a human 1C3 PSMA-CAR. In one embodiment, the nucleic acid comprising from 5' to 3': a nucleic acid sequence encoding TGFβRII-DN, a nucleic acid sequence encoding a linker comprising T2A, and a nucleic acid sequence encoding a human 1C3 PSMA-CAR, comprises the nucleic acid sequence set forth below:

(SEQ ID NO: 153)
```
ATGGGTCGGGGCTGCTCAGGGGCCTGTGGCCGCTGCACATCGTCCTGTG
GACGCGTATCGCCAGCACGATCCCACCGCACGTTCAGAAGTCGGTTAATA
ACGACATGATAGTCACTGACAACAACGGTGCAGTCAAGTTTCCACAACTG
TGTAAATTTTGTGATGTGAGATTTTCCACCTGTGACAACCAGAAATCCTG
CATGAGCAACTGCAGCATCACCTCCATCTGTGAGAAGCCACAGGAAGTCT
GTGTGGCTGTATGGAGAAAGAATGACGAGAACATAACACTAGAGACAGTT
TGCCATGACCCCAAGCTCCCCTACCATGACTTTATTCTGGAAGATGCTGC
TTCTCCAAAGTGCATTATGAAGGAAAAAAAAAAGCCTGGTGAGACTTTCT
TCATGTGTTCCTGTAGCTCTGATGAGTGCAATGACAACATCATCTTCTCA
GAAGAATATAACACCAGCAATCCTGACTTGTTGCTAGTCATATTTCAAGT
GACAGGCATCAGCCTCCTGCCACCACTGGGAGTTGCCATATCTGTCATCA
TCATCTTCTACTGCTACCGCGTTAACCGGCAGCAGAAGCTGAGTTCATCC
GGAAGATCTGGCGGCGGAGAGGGCAGAGGAAGTCTTCTAACATGCGGTGA
CGTGGAGGAGAATCCCGGCCCTAGAGCCACCATGGCCTTACCAGTGACCG
CCTTGCTCCTGCCGCTGGCCTTGCTGCTCCACGCCGCCAGGCCGCAGGTG
CAACTGGTGGAGTCTGGGGGAGGCGTGGTCCAGCCTGGGAGGTCCCTGAG
ACTCTCCTGTGCAGCCTCTGGATTCACCTTCAGTAGCTATGCTATGCACT
GGGTCCGCCAGGCTCCAGGCAAGGGGCTGGAGTGGGTGGCAGTTATATCA
TATGATGGAAACAATAAATACTACGCAGACTCCGTGAAGGGCCGATTCAC
CATCTCCAGAGACAATTCCAAGAACACGCTGTATCTGCAAATGAACAGCC
TGAGAGCTGAGGACACGGCTGTGTATTACTGTGCGAGAGCCGTCCCCTGG
GGATCGAGGTACTACTACTACGGTATGGACGTCTGGGGCCAAGGGACCAC
GGTCACCGTCTCCTCAGGTGGCGGTGGCTCGGGCGGTGGTGGGTCGGGTG
```

```
GCGGCGGATCTGCCATCCAGTTGACCCAGTCTCCATCCTCCCTGTCTGCA

TCTGTAGGAGACAGAGTCACCATCACTTGCCGGGCAAGTCAGGGCATTAG

CAGTGCTTTAGCCTGGTATCAGCAGAAATCAGGGAAAGCTCCTAAGCTCC

TGATCTTTGATGCCTCCAGTTTGGAAAGTGGGGTCCCATCAAGGTTCAGC

GGCAGTGGATCTGGGACAGATTTCACTCTCACCATCAGCAGCCTGCAGCC

TGAAGATTTTGCAACTTATTACTGTCAACAGTTTAACAGTTATCCTCTCA

CTTTCGGCGGAGGGACCAAGGTGGAGATCAAAACCACGACGCCAGCGCCG

CGACCACCAACACCGGCGCCCACCATCGCGTCGCAGCCCCTGTCCCTGCG

CCCAGAGGCGTGCCGGCCAGCGGCGGGGGCGCAGTGCACACGAGGGGGC

TGGACTTCGCCTGTGATATCTACATCTGGGCGCCCTTGGCCGGGACTTGT

GGGGTCCTTCTCCTGTCACTGGTTATCACCCTTTACTGCAAACGGGGCAG

AAAGAAACTCCTGTATATATTCAAACAACCATTTATGAGACCAGTACAAA

CTACTCAAGAGGAAGACGGCTGTAGCTGCCGATTTCCAGAAGAAGAAGAA

GGAGGATGTGAACTGAGAGTGAAGTTCAGCAGGAGCGCAGACGCCCCCGC

GTACAAGCAGGGCCAGAACCAGCTCTATAACGAGCTCAATCTAGGACGAA

GAGAGGAGTACGACGTTTTGGACAAGAGACGTGGCCGGGACCCTGAGATG

GGGGGAAAGCCGAGAAGGAAGAACCCTCAGGAAGGCCTGTACAACGAACT

GCAGAAAGATAAGATGGCGGAGGCCTACAGTGAGATTGGGATGAAAGGCG

AGCGCCGGAGGGGCAAGGGGCACGACGGCCTTTACCAGGGTCTCAGTACA

GCCACCAAGGACACCTACGACGCCCTTCACATGCAGGCCCTGCCCCCTCG

C.
```

In one embodiment, the CAR is a human 2A10 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising T2A, and a nucleic acid sequence encoding a human 2A10 PSMA-CAR. In one embodiment, the nucleic acid comprising from 5' to 3': a nucleic acid sequence encoding TGFβRII-DN, a nucleic acid sequence encoding a linker comprising T2A, and a nucleic acid sequence encoding a human 2A10 PSMA-CAR, comprises the nucleic acid sequence set forth below:

```
                                    (SEQ ID NO: 154)
ATGGGTCGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACTGCTACCGCGTTAACCGGCAGCAGAAGCTGAGTTCATCC

GGAAGATCTGGCGGCGGAGAGGGCAGAGGAAGTCTTCTAACATGCGGTGA

CGTGGAGGAGAATCCCGGCCCTAGAGCCACCATGGCCTTACCAGTGACCG

CCTTGCTCCTGCCGCTGGCCTTGCTGCTCCACGCCGCCAGGCCGGAGGTG

CAGCTGGTGCAGTCTGGAGCAGAGGTGAAAAAGCCCGGGGAGTCTCTGAA

GATCTCCTGTAAGGGTTCTGGATACAGCTTTACCAGTAACTGGATCGGCT

GGGTGCGCCAGATGCCCGGGAAAGGCCTGGAGTGGATGGGGATCATCTAT

CCTGGTGACTCTGATACCAGATACAGCCCGTCCTTCCAAGGCCAGGTCAC

CATCTCAGCCGACAAGTCCATCAGCACCGCCTACCTGCAGTGGAGCAGCC

TGAAGGCCTCGGACACCGCCATGTATTACTGTGCGAGGCAAACTGGTTTC

CTCTGGTCCTCCGATCTCTGGGCCGTGGCACCCTGGTCACTGTCTCCTC

AGGTGGCGGTGGCTCGGGCGGTGGTGGGTCGGGTGGCGGCGGATCTGCCA

TCCAGTTGACCCAGTCTCCATCCTCCCTGTCTGCATCTGTAGGAGACAGA

GTCACCATCACTTGCCGGGCAAGTCAGGACATTAGCAGTGCTTTAGCCTG

GTATCAACAGAAACCAGGGAAAGCTCCTAAGCTCCTGATCTATGATGCCT

CCAGTTTGGAAAGTGGGGTCCCATCAAGGTTCAGCGGCTATGGATCTGGG

ACAGATTTCACTCTCACCATCAACAGCCTGCAGCCTGAAGATTTTGCAAC

TTATTACTGTCAACAGTTTAATAGTTACCCGCTCACTTTCGGCGGAGGGA

CCAAGGTGGAGATCAAAACCACGACGCCAGCGCCGCGACCACCAACACCG

GCGCCCACCATCGCGTCGCAGCCCCTGTCCCTGCGCCCAGAGGCGTGCCG

GCCAGCGGCGGGGGCGCAGTGCACACGAGGGGGCTGGACTTCGCCTGTG

ATATCTACATCTGGGCGCCCTTGGCCGGGACTTGTGGGGTCCTTCTCCTG

TCACTGGTTATCACCCTTTACTGCAAACGGGGCAGAAAGAAACTCCTGTA

TATATTCAAACAACCATTTATGAGACCAGTACAAACTACTCAAGAGGAAG

ACGGCTGTAGCTGCCGATTTCCAGAAGAAGAAGAAGGAGGATGTGAACTG

AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGACG

TTTTGGACAAGAGACGTGGCCGGGACCCTGAGATGGGGGGAAAGCCGAGA

AGGAAGAACCCTCAGGAAGGCCTGTACAACGAACTGCAGAAAGATAAGAT

GGCGGAGGCCTACAGTGAGATTGGGATGAAAGGCGAGCGCCGGAGGGGCA

AGGGGCACGACGGCCTTTACCAGGGTCTCAGTACAGCCACCAAGGACACC

TACGACGCCCTTCACATGCAGGCCCTGCCCCCTCGC.
```

In one embodiment, the CAR is a human 2F5 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising T2A, and a nucleic acid sequence encoding a human 2F5 PSMA-CAR. In one embodiment, the nucleic acid comprising from 5' to 3': a nucleic acid sequence encoding TGFβRII-DN, a nucleic acid sequence encoding a linker comprising T2A, and a nucleic acid sequence encoding a human 2F5 PSMA-CAR, comprises the nucleic acid sequence set forth below:

(SEQ ID NO: 155)
ATGGGTCGGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACTGCTACCGCGTTAACCGGCAGCAGAAGCTGAGTTCATCC

GGAAGATCTGGCGGCGGAGAGGGCAGAGGAAGTCTTCTAACATGCGGTGA

CGTGGAGGAGAATCCCGGCCCTAGAGCCACCATGGCCTTACCAGTGACCG

CCTTGCTCCTGCCGCTGGCCTTGCTGCTCCACGCCGCCAGGCCGGAGGTG

CAGCTGGTGCAGTCTGGAGCAGAGGTGAAAAAGCCCGGGGAGTCTCTGAA

GATCTCCTGTAAGGGTTCTGGATACAGTTTTACCAGCAACTGGATCGGCT

GGGTGCGCCAGATGCCCGGGAAAGGCCTGGAGTGGATGGGGATCATCTAT

CCTGGTGACTCTGATACCAGATACAGCCCGTCCTTCCAAGGCCAGGTCAC

CATCTCAGCCGACAAGTCCATCAGCACCGCCTACCTGCAGTGGAACAGCC

TGAAGGCCTCGGACACCGCCATGTATTACTGTGCGAGACAAACTGGTTTC

CTCTGGTCCTTCGATCTCTGGGCCGTGGCACCCTGGTCACTGTCTCCTC

AGGTGGCGGTGGCTCGGGCGGTGTGGGTCGGTGGCGGCGGATCTGCCA

TCCAGTTGACCCAGTCTCCATCCTCCCTGTCTGCATCTGTAGGAGACAGA

GTCACCATCACTTGCCGGGCAAGTCAGGACATTAGCAGTGCTTTAGCCTG

GTATCAGCAGAAACCGGGGAAAGCTCCTAAGCTCCTGATCTATGATGCCT

CCAGTTTGGAAAGTGGGGTCCCATCAAGGTTCAGCGGCAGTGGATCTGGG

ACAGATTTCACTCTCACCATCAGCAGCCTGCAGCCTGAAGATTTTGCAAC

TTATTACTGTCAACAGTTTAATAGTTACCCGCTCACTTTCGGCGGAGGGA

CCAAGGTGGAGATCAAAATCAAAACCACGACGCCAGCGCCGCGACCACCA

ACACCGGCGCCCACCATCGCGTCGCAGCCCCTGTCCCTGCGCCCAGAGGC

GTGCCGGCCAGCGGCGGGGGCGCAGTGCACACGAGGGGCTGGACTTCG

CCTGTGATATCTACATCTGGGCGCCCTTGGCCGGGACTTGTGGGGTCCTT

CTCCTGTCACTGGTTATCACCCTTTACTGCAAACGGGGCAGAAAGAAACT

CCTGTATATATTCAAACAACCATTTATGAGACCAGTACAAACTACTCAAG

AGGAAGACGGCTGTAGCTGCCGATTTCCAGAAGAAGAAGAAGGAGGATGT

GAACTGAGAGTGAAGTTCAGCAGGAGCGCAGACGCCCCCGCGTACAAGCA

GGGCCAGAACCAGCTCTATAACGAGCTCAATCTAGGACGAAGAGAGGAGT

ACGACGTTTTGGACAAGAGACGTGGCCGGGACCCTGAGATGGGGGGAAAG

CCGAGAAGGAAGAACCCTCAGGAAGGCCTGTACAACGAACTGCAGAAAGA

TAAGATGGCGGAGGCCTACAGTGAGATTGGGATGAAAGGCGAGCGCCGGA

GGGGCAAGGGGCACGACGGCCTTTACCAGGGTCTCAGTACAGCCACCAAG

GACACCTACGACGCCCTTCACATGCAGGCCCTGCCCCCTCGC.

In one embodiment, the CAR is a human 2C6 PSMA-CAR. Accordingly, in an exemplary embodiment, a nucleic acid of the present invention comprises from 5' to 3': a nucleic acid sequence encoding TGFβRII-DN, a nucleic acid sequence encoding a linker comprising T2A, and a nucleic acid sequence encoding a human 2C6 PSMA-CAR. In one embodiment, the nucleic acid comprising from 5' to 3': a nucleic acid sequence encoding TGFβRII-DN, a nucleic acid sequence encoding a linker comprising T2A, and a nucleic acid sequence encoding a human 2C6 PSMA-CAR, comprises the nucleic acid sequence set forth below:

(SEQ ID NO: 156)
ATGGGTCGGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACTGCTACCGCGTTAACCGGCAGCAGAAGCTGAGTTCATCC

GGAAGATCTGGCGGCGGAGAGGGCAGAGGAAGTCTTCTAACATGCGGTGA

CGTGGAGGAGAATCCCGGCCCTAGAGCCACCATGGCCTTACCAGTGACCG

CCTTGCTCCTGCCGCTGGCCTTGCTGCTCCACGCCGCCAGGCCGGAGGTG

CAGCTGGTGCAGTCTGGATCAGAGGTGAAAAAGCCCGGGGAGTCTCTGAA

GATCTCCTGTAAGGGTTCTGGATACAGCTTTACCAACTACTGGATCGGCT

GGGTGCGCCAGATGCCCGGGAAAGGCCTGGAGTGGATGGGGATCATCTAT

CCTGGTGACTCTGATACCAGATACAGCCCGTCCTTCCAAGGCCAGGTCAC

CATCTCAGCCGACAAGTCCATCAGCACCGCCTATCTGCAGTGGAGCAGCC

TGAAGGCCTCGGACACCGCCATGTATTACTGTGCGAGTCCCGGGTATACC

AGCAGTTGGACTTCTTTTGACTACTGGGGCCAGGGAACCCTGGTCACCGT

CTCCTCAGGTGGCGGTGGCTCGGGCGGTGTGGGTCGGTGGCGGCGGAT

CTGAAATTGTGTTGACACAGTCTCCAGCCACCCTGTCTTTGTCTCCAGGG

GAAAGAGCCACCCTCTCCTGCAGGGCCAGTCAGAGTGTTAGCAGCTACTT

AGCCTGGTACCAACAGAAACCTGGCCAGGCTCCCAGGCTCCTCATCTATG

ATGCATCCAACAGGGCCACTGGCATCCCAGCCAGGTTCAGTGGCAGTGGG

TCTGGGACAGACTTCACTCTCACCATCAGCAGCCTAGAGCCTGAAGATTT

TGCAGTTTATTACTGTCAGCAGCGTAGCAACTGGCCCCTATTCACTTTCG

```
GCCCTGGGACCAAAGTGGATATCAAAACCACGACGCCAGCGCCGCGACCA

CCAACACCGGCGCCCACCATCGCGTCGCAGCCCCTGTCCCTGCGCCCAGA

GGCGTGCCGGCCAGCGGCGGGGGGCGCAGTGCACACGAGGGGGCTGGACT

TCGCCTGTGATATCTACATCTGGGCGCCCTTGGCCGGGACTTGTGGGGTC

CTTCTCCTGTCACTGGTTATCACCCTTTACTGCAAACGGGGCAGAAAGAA

ACTCCTGTATATATTCAAACAACCATTTATGAGACCAGTACAAACTACTC

AAGAGGAAGACGGCTGTAGCTGCCGATTTCCAGAAGAAGAAGAAGGAGGA

TGTGAACTGAGAGTGAAGTTCAGCAGGAGCGCAGACGCCCCCGCGTACAA

GCAGGGCCAGAACCAGCTCTATAACGAGCTCAATCTAGGACGAAGAGAGG

AGTACGACGTTTTGGACAAGAGACGTGGCCGGGACCCTGAGATGGGGGGA

AAGCCGAGAAGGAAGAACCCTCAGGAAGGCCTGTACAACGAACTGCAGAA

AGATAAGATGGCGGAGGCCTACAGTGAGATTGGGATGAAAGGCGAGCGCC

GGAGGGGCAAGGGGCACGACGGCCTTTACCAGGGTCTCAGTACAGCCACC

AAGGACACCTACGACGCCCTTCACATGCAGGCCCTGCCCCCTCGC.
```

Tolerable variations of the nucleic acid sequence encoding for TGFβRII-DN and a PSMA-CAR will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in any one of SEQ ID NOs:152-156. In one embodiment, the nucleic acid sequence encoding for TGFβRII-DN and murine J591 PSMA-CAR comprises the nucleic acid sequence set forth in SEQ ID NO:152. In one embodiment, the nucleic acid sequence encoding for TGFβRII-DN and human 1C3 PSMA-CAR comprises the nucleic acid sequence set forth in SEQ ID NO:153. In one embodiment, the nucleic acid sequence encoding for TGFβRII-DN and human 2A10 PSMA-CAR comprises the nucleic acid sequence set forth in SEQ ID NO:154. In one embodiment, the nucleic acid sequence encoding for TGFβRII-DN and human 2F5 PSMA-CAR comprises the nucleic acid sequence set forth in SEQ ID NO:155. In one embodiment, the nucleic acid sequence encoding for TGFβRII-DN and human 2C6 PSMA-CAR comprises the nucleic acid sequence set forth in SEQ ID NO:156.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1-CTM-CD28. In one embodiment, the CAR is a human 1C3 PSMA-CAR. Accordingly, in an exemplary embodiment, a nucleic acid of the present invention comprises from 5' to 3': a nucleic acid sequence encoding PD1-CTM-CD28, a nucleic acid sequence encoding a linker comprising F2A, and a nucleic acid sequence encoding a human 1C3 PSMA-CAR. In one embodiment, the nucleic acid comprising from 5' to 3': a nucleic acid sequence encoding PD1-CTM-CD28, a nucleic acid sequence encoding a linker comprising F2A, and a nucleic acid sequence encoding a human 1C3 PSMA-CAR, comprises the nucleic acid sequence set forth below:

```
                                           (SEQ ID NO: 157)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCCGTGAAACAGACTTTGAATTTTGACCTTCTCAAGTTG

GCGGGAGACGTGGAGTCCAACCCAGGGCCGATGGCCTTACCAGTGACCGC

CTTGCTCCTGCCGCTGGCCTTGCTGCTCCACGCCGCCAGGCCGCAGGTGC

AACTGGTGGAGTCTGGGGGAGGCGTGGTCCAGCCTGGGAGGTCCCTGAGA

CTCTCCTGTGCAGCCTCTGGATTCACCTTCAGTAGCTATGCTATGCACTG

GGTCCGCCAGGCTCCAGGCAAGGGGCTGGAGTGGGTGGCAGTTATATCAT

ATGATGGAAACAATAAATACTACGCAGACTCCGTGAAGGGCCGATTCACC

ATCTCCAGAGACAATTCCAAGAACACGCTGTATCTGCAAATGAACAGCCT

GAGAGCTGAGGACACGGCTGTGTATTACTGTGCGAGAGCCGTCCCCTGGG

GATCGAGGTACTACTACTACGGTATGGACGTCTGGGGCCAAGGGACCACG

GTCACCGTCTCCTCAGGTGGCGGTGGCTCGGGCGGTGGTGGGTCGGGTGG

CGGCGGATCTGCCATCCAGTTGACCCAGTCTCCATCCTCCCTGTCTGCAT

CTGTAGGAGACAGAGTCACCATCACTTGCCGGGCAAGTCAGGGCATTAGC

AGTGCTTTAGCCTGGTATCAGCAGAAATCAGGGAAAGCTCCTAAGCTCCT

GATCTTTGATGCCTCCAGTTTGGAAAGTGGGGTCCCATCAAGGTTCAGCG

GCAGTGGATCTGGGACAGATTTCACTCTCACCATCAGCAGCCTGCAGCCT

GAAGATTTTGCAACTTATTACTGTCAACAGTTTAACAGTTATCCTCTCAC

TTTCGGCGGAGGGACCAAGGTGGAGATCAAAACCACGACGCCAGCGCCGC

GACCACCAACACCGGCGCCCACCATCGCGTCGCAGCCCCTGTCCCTGCGC

CCAGAGGCGTGCCGGCCAGCGGCGGGGGCGCAGTGCACACGAGGGGGCT

GGACTTCGCCTGTGATATCTACATCTGGGCGCCCTTGGCCGGGACTTGTG

GGGTCCTTCTCCTGTCACTGGTTATCACCCTTTACTGCAAACGGGGCAGA

AAGAAACTCCTGTATATATTCAAACAACCATTTATGAGACCAGTACAAAC

TACTCAAGAGGAAGATGGCTGTAGCTGCCGATTTCCAGAAGAAGAAGAAG

GAGGATGTGAACTGAGAGTGAAGTTCAGCAGGAGCGCAGACGCCCCCGCG

TACAAGCAGGGCCAGAACCAGCTCTATAACGAGCTCAATCTAGGACGAAG
```

```
AGAGGAGTACGATGTTTTGGACAAGAGACGTGGCCGGGACCCTGAGATGG

GGGGAAAGCCGAGAAGGAAGAACCCTCAGGAAGGCCTGTACAATGAACTG

CAGAAAGATAAGATGGCGGAGGCCTACAGTGAGATTGGGATGAAAGGCGA

GCGCCGGAGGGGCAAGGGGCACGATGGCCTTTACCAGGGTCTCAGTACAG

CCACCAAGGACACCTACGACGCCCTTCACATGCAGGCCCTGCCCCCTCG

C.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1-CTM-CD28. In one embodiment, the CAR is a human 2A10 PSMA-CAR. Accordingly, in an exemplary embodiment, a nucleic acid of the present invention comprises from 5' to 3': a nucleic acid sequence encoding PD1-CTM-CD28, a nucleic acid sequence encoding a linker comprising F2A, and a nucleic acid sequence encoding a human 2A10 PSMA-CAR. In one embodiment, the nucleic acid comprising from 5' to 3': a nucleic acid sequence encoding PD1-CTM-CD28, a nucleic acid sequence encoding a linker comprising F2A, and a nucleic acid sequence encoding a human 2A10 PSMA-CAR, comprises the nucleic acid sequence set forth below:

```
                                            (SEQ ID NO: 158)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCCGTGAAACAGACTTTGAATTTTGACCTTCTCAAGTTG

GCGGGAGACGTGGAGTCCAACCCAGGGCCGATGGCCTTACCAGTGACCGC

CTTGCTCCTGCCGCTGGCCTTGCTGCTCCACGCCGCCAGGCCGGAGGTGC

AGCTGGTGCAGTCTGGAGCAGAGGTGAAAAAGCCCGGGGAGTCTCTGAAG

ATCTCCTGTAAGGGTTCTGGATACAGCTTTACCAGTAACTGGATCGGCTG

GGTGCGCCAGATGCCCGGGAAAGGCCTGGAGTGGATGGGGATCATCTATC

CTGGTGACTCTGATACCAGATACAGCCCGTCCTTCCAAGGCCAGGTCACC

ATCTCAGCCGACAAGTCCATCAGCACCGCCTACCTGCAGTGGAGCAGCCT
```

```
                                            -continued
GAAGGCCTCGGACACCGCCATGTATTACTGTGCGAGGCAAACTGGTTTCC

TCTGGTCCTCCGATCTCTGGGGCCGTGGCACCCTGGTCACTGTCTCCTCA

GGTGGCGGTGGCTCGGGCGGTGGTGGGTCGGGTGGCGGCGGATCTGCCAT

CCAGTTGACCCAGTCTCCATCCTCCCTGTCTGCATCTGTAGGAGACAGAG

TCACCATCACTTGCCGGGCAAGTCAGGACATTAGCAGTGCTTTAGCCTGG

TATCAACAGAAACCAGGGAAAGCTCCTAAGCTCCTGATCTATGATGCCTC

CAGTTTGGAAAGTGGGGTCCCATCAAGGTTCAGCGGCTATGGATCTGGGA

CAGATTTCACTCTCACCATCAACAGCCTGCAGCCTGAAGATTTTGCAACT

TATTACTGTCAACAGTTTAATAGTTACCCGCTCACTTTCGGCGGAGGGAC

CAAGGTGGAGATCAAAACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGGCGCAGTGCACACGAGGGGGCTGGACTTCGCCTGTGA

TATCTACATCTGGGCGCCCTTGGCCGGGACTTGTGGGGTCCTTCTCCTGT

CACTGGTTATCACCCTTTACTGCAAACGGGGCAGAAAGAAACTCCTGTAT

ATATTCAAACAACCATTTATGAGACCAGTACAAACTACTCAAGAGGAAGA

TGGCTGTAGCTGCCGATTTCCAGAAGAAGAAGAAGGAGGATGTGAACTGA

GAGTGAAGTTCAGCAGGAGCGCAGACGCCCCCGCGTACAAGCAGGGCCAG

AACCAGCTCTATAACGAGCTCAATCTAGGACGAAGAGAGGAGTACGATGT

TTTGGACAAGAGACGTGGCCGGGACCCTGAGATGGGGGGAAAGCCGAGAA

GGAAGAACCCTCAGGAAGGCCTGTACAATGAACTGCAGAAAGATAAGATG

GCGGAGGCCTACAGTGAGATTGGGATGAAAGGCGAGCGCCGGAGGGGCAA

GGGGCACGATGGCCTTTACCAGGGTCTCAGTACAGCCACCAAGGACACCT

ACGACGCCCTTCACATGCAGGCCCTGCCCCCTCGC.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1-CTM-CD28. In one embodiment, the CAR is a human 2F5 PSMA-CAR. Accordingly, in an exemplary embodiment, a nucleic acid of the present invention comprises from 5' to 3': a nucleic acid sequence encoding PD1-CTM-CD28, a nucleic acid sequence encoding a linker comprising F2A, and a nucleic acid sequence encoding a human 2F5 PSMA-CAR. In one embodiment, the nucleic acid comprising from 5' to 3': a nucleic acid sequence encoding PD1-CTM-CD28, a nucleic acid sequence encoding a linker comprising F2A, and a nucleic acid sequence encoding a human 2F5 PSMA-CAR, comprises the nucleic acid sequence set forth below:

```
                                            (SEQ ID NO: 159)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG
```

```
CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCCGTGAAACAGACTTTGAATTTTGACCTTCTCAAGTTG

GCGGGAGACGTGGAGTCCAACCCAGGGCCGATGGCCTTACCAGTGACCGC

CTTGCTCCTGCCGCTGGCCTTGCTGCTCCACGCCGCCAGGCCGGAGGTGC

AGCTGGTGCAGTCTGGAGCAGAGGTGAAAAAGCCCGGGGAGTCTCTGAAG

ATCTCCTGTAAGGGTTCTGGATACAGTTTTACCAGCAACTGGATCGGCTG

GGTGCGCCAGATGCCCGGGAAAGGCCTGGAGTGGATGGGGATCATCTATC

CTGGTGACTCTGATACCAGATACAGCCCGTCCTTCCAAGGCCAGGTCACC

ATCTCAGCCGACAAGTCCATCAGCACCGCCTACCTGCAGTGGAACAGCCT

GAAGGCCTCGGACACCGCCATGTATTACTGTGCGAGACAAACTGGTTTCC

TCTGGTCCTTCGATCTCTGGGGCCGTGGCACCCTGGTCACTGTCTCCTCA

GGTGGCGGTGGCTCGGGCGGTGGTGGGTCGGGTGGCGGCGGATCTGCCAT

CCAGTTGACCCAGTCTCCATCCTCCCTGTCTGCATCTGTAGGAGACAGAG

TCACCATCACTTGCCGGGCAAGTCAGGACATTAGCAGTGCTTTAGCCTGG

TATCAGCAGAAACCGGGGAAAGCTCCTAAGCTCCTGATCTATGATGCCTC

CAGTTTGGAAAGTGGGGTCCCATCAAGGTTCAGCGGCAGTGGATCTGGGA

CAGATTTCACTCTCACCATCAGCAGCCTGCAGCCTGAAGATTTTGCAACT

TATTACTGTCAACAGTTTAATAGTTACCCGCTCACTTTCGGCGGAGGGAC

CAAGGTGGAGATCAAAATCAAAACCACGACGCCAGCGCCGCGACCACCAA

CACCGGCGCCCACCATCGCGTCGCAGCCCCTGTCCCTGCGCCCAGAGGCG

TGCCGGCCAGCGGCGGGGGGCGCAGTGCACACGAGGGGGCTGGACTTCGC

CTGTGATATCTACATCTGGGCGCCCTTGGCCGGGACTTGTGGGGTCCTTC

TCCTGTCACTGGTTATCACCCTTTACTGCAAACGGGGCAGAAAGAAACTC

CTGTATATATTCAAACAACCATTTATGAGACCAGTACAAACTACTCAAGA

GGAAGATGGCTGTAGCTGCCGATTTCCAGAAGAAGAAGAAGGAGGATGTG

AACTGAGAGTGAAGTTCAGCAGGAGCGCAGACGCCCCCGCGTACAAGCAG

GGCCAGAACCAGCTCTATAACGAGCTCAATCTAGGACGAAGAGAGGAGTA

CGATGTTTTGGACAAGAGACGTGGCCGGGACCCTGAGATGGGGGGAAAGC

CGAGAAGGAAGAACCCTCAGGAAGGCCTGTACAATGAACTGCAGAAAGAT

AAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGG

ACACCTACGACGCCCTTCACATGCAGGCCCTGCCCCCTCGC.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1-CTM-CD28. In one embodiment, the CAR is a human 2C6 PSMA-CAR. Accordingly, in an exemplary embodiment, a nucleic acid of the present invention comprises from 5' to 3': a nucleic acid sequence encoding PD1-CTM-CD28, a nucleic acid sequence encoding a linker comprising F2A, and a nucleic acid sequence encoding a human 2C6 PSMA-CAR. In one embodiment, the nucleic acid comprising from 5' to 3': a nucleic acid sequence encoding PD1-CTM-CD28, a nucleic acid sequence encoding a linker comprising F2A, and a nucleic acid sequence encoding a human 2C6 PSMA-CAR, comprises the nucleic acid sequence set forth below:

```
                                           (SEQ ID NO: 160)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCCGTGAAACAGACTTTGAATTTTGACCTTCTCAAGTTG

GCGGGAGACGTGGAGTCCAACCCAGGGCCGATGGCCTTACCAGTGACCGC

CTTGCTCCTGCCGCTGGCCTTGCTGCTCCACGCCGCCAGGCCGGAGGTGC

AGCTGGTGCAGTCTGGATCAGAGGTGAAAAAGCCCGGGGAGTCTCTGAAG

ATCTCCTGTAAGGGTTCTGGATACAGCTTTACCAACTACTGGATCGGCTG

GGTGCGCCAGATGCCCGGGAAAGGCCTGGAGTGGATGGGGATCATCTATC

CTGGTGACTCTGATACCAGATACAGCCCGTCCTTCCAAGGCCAGGTCACC

ATCTCAGCCGACAAGTCCATCAGCACCGCCTATCTGCAGTGGAGCAGCCT

GAAGGCCTCGGACACCGCCATGTATTACTGTGCGAGTCCGGGTATACCA

GCAGTTGGACTTCTTTTGACTACTGGGGCCAGGGAACCCTGGTCACCGTC

TCCTCAGGTGGCGGTGGCTCGGGCGGTGGTGGGTCGGGTGGCGGCGGATC

TGAAATTGTGTTGACACAGTCTCCAGCCACCCTGTCTTTGTCTCCAGGGG

AAAGAGCCACCCTCTCCTGCAGGGCCAGTCAGAGTGTTAGCAGCTACTTA

GCCTGGTACCAACAGAAACCTGGCCAGGCTCCCAGGCTCCTCATCTATGA

TGCATCCAACAGGGCCACTGGCATCCCAGCCAGGTTCAGTGGCAGTGGGT

CTGGGACAGACTTCACTCTCACCATCAGCAGCCTAGAGCCTGAAGATTTT

GCAGTTTATTACTGTCAGCAGCGTAGCAACTGGCCCCTATTCACTTTCGG
```

-continued
CCCTGGGACCAAAGTGGATATCAAAACCACGACGCCAGCGCCGCGACCAC

CAACACCGGCGCCCACCATCGCGTCGCAGCCCCTGTCCCTGCGCCCAGAG

GCGTGCCGGCCAGCGGCGGGGGCGCAGTGCACACGAGGGGGCTGGACTT

CGCCTGTGATATCTACATCTGGGCGCCCTTGGCCGGGACTTGTGGGGTCC

TTCTCCTGTCACTGGTTATCACCCTTTACTGCAAACGGGGCAGAAAGAAA

CTCCTGTATATATTCAAACAACCATTTATGAGACCAGTACAAACTACTCA

AGAGGAAGATGGCTGTAGCTGCCGATTTCCAGAAGAAGAAGAAGGAGGAT

GTGAACTGAGAGTGAAGTTCAGCAGGAGCGCAGACGCCCCCGCGTACAAG

CAGGGCCAGAACCAGCTCTATAACGAGCTCAATCTAGGACGAAGAGAGGA

GTACGATGTTTTGGACAAGAGACGTGGCCGGGACCCTGAGATGGGGGGAA

AGCCGAGAAGGAAGAACCCTCAGGAAGGCCTGTACAATGAACTGCAGAAA

GATAAGATGGCGGAGGCCTACAGTGAGATTGGGATGAAAGGCGAGCGCCG

GAGGGGCAAGGGGCACGATGGCCTTTACCAGGGTCTCAGTACAGCCACCA

AGGACACCTACGACGCCCTTCACATGCAGGCCCTGCCCCCTCGC.

Tolerable variations of the nucleic acid sequence encoding PD1-CTM-CD28 and a PSMA-CAR will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in any one of SEQ ID NOs:157-160. In one embodiment, the nucleic acid sequence encoding for PD1-CTM-CD28 and human 1C3 PSMA-CAR comprises the nucleic acid sequence set forth in SEQ ID NO:157. In one embodiment, the nucleic acid sequence encoding for PD1-CTM-CD28 and human 2A10 PSMA-CAR comprises the nucleic acid sequence set forth in SEQ ID NO:158. In one embodiment, the nucleic acid sequence encoding for PD1-CTM-CD28 and human 2F5 PSMA-CAR comprises the nucleic acid sequence set forth in SEQ ID NO:159. In one embodiment, the nucleic acid sequence encoding for PD1-CTM-CD28 and human 2C6 PSMA-CAR comprises the nucleic acid sequence set forth in SEQ ID NO:160.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-PTM-CD28. In one embodiment, the CAR is a human 1C3 PSMA-CAR. Accordingly, in an exemplary embodiment, a nucleic acid of the present invention comprises from 5' to 3': a nucleic acid sequence encoding PD1$^{A132L}$-PTM-CD28, a nucleic acid sequence encoding a linker comprising F2A, and a nucleic acid sequence encoding a human 1C3 PSMA-CAR. In one embodiment, the nucleic acid comprising from 5' to 3': a nucleic acid sequence encoding PD1$^{A132L}$-PTM-CD28, a nucleic acid sequence encoding a linker comprising F2A, and a nucleic acid sequence encoding a human 1C3 PSMA-CAR, comprises the nucleic acid sequence set forth below:

(SEQ ID NO: 161)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA

TTACCAGCCCTATGCCCCACCACGCGACTTCGCAGCCTATCGCTCCGTGA

AACAGACTTTGAATTTTGACCTTCTCAAGTTGGCGGGAGACGTGGAGTCC

AACCCAGGGCCGATGGCCTTACCAGTGACCGCCTTGCTCCTGCCGCTGGC

CTTGCTGCTCCACGCCGCCAGGCCGCAGGTGCAACTGGTGGAGTCTGGGG

GAGGCGTGGTCCAGCCTGGGAGGTCCCTGAGACTCTCCTGTGCAGCCTCT

GGATTCACCTTCAGTAGCTATGCTATGCACTGGGTCCGCCAGGCTCCAGG

CAAGGGGCTGGAGTGGGTGGCAGTTATATCATATGATGGAAACAATAAAT

ACTACGCAGACTCCGTGAAGGGCCGATTCACCATCTCCAGAGACAATTCC

AAGAACACGCTGTATCTGCAAATGAACAGCCTGAGAGCTGAGGACACGGC

TGTGTATTACTGTGCGAGAGCCGTCCCCTGGGGATCGAGGTACTACTACT

ACGGTATGGACGTCTGGGGCCAAGGGACCACGGTCACCGTCTCCTCAGGT

GGCGGTGGCTCGGGCGGTGGTGGGTCGGGTGGCGGCGGATCTGCCATCCA

GTTGACCCAGTCTCCATCCTCCCTGTCTGCATCTGTAGGAGACAGAGTCA

CCATCACTTGCCGGGCAAGTCAGGGCATTAGCAGTGCTTTAGCCTGGTAT

CAGCAGAAATCAGGGAAAGCTCCTAAGCTCCTGATCTTTGATGCCTCCAG

TTTGGAAAGTGGGGTCCCATCAAGGTTCAGCGGCAGTGGATCTGGGACAG

ATTTCACTCTCACCATCAGCAGCCTGCAGCCTGAAGATTTTGCAACTTAT

TACTGTCAACAGTTTAACAGTTATCCTCTCACTTTCGGCGGAGGGACCAA

GGTGGAGATCAAAACCACGACGCCAGCGCCGCGACCACCAACACCGGCGC

CCACCATCGCGTCGCAGCCCCTGTCCCTGCGCCCAGAGGCGTGCCGGCCA

GCGGCGGGGGCGCAGTGCACACGAGGGGGCTGGACTTCGCCTGTGATAT

CTACATCTGGGCGCCCTTGGCCGGGACTTGTGGGGTCCTTCTCCTGTCAC

TGGTTATCACCCTTTACTGCAAACGGGGCAGAAAGAAACTCCTGTATATA

TTCAAACAACCATTTATGAGACCAGTACAAACTACTCAAGAGGAAGATGG

CTGTAGCTGCCGATTTCCAGAAGAAGAAGAAGGAGGATGTGAACTGAGAG

TGAAGTTCAGCAGGAGCGCAGACGCCCCCGCGTACAAGCAGGGCCAGAAC

CAGCTCTATAACGAGCTCAATCTAGGACGAAGAGAGGAGTACGATGTTTT

-continued
GGACAAGAGACGTGGCCGGGACCCTGAGATGGGGGAAAGCCGAGAAGGA

AGAACCCTCAGGAAGGCCTGTACAATGAACTGCAGAAAGATAAGATGGCG

GAGGCCTACAGTGAGATTGGGATGAAAGGCGAGCGCCGGAGGGGCAAGGG

GCACGATGGCCTTTACCAGGGTCTCAGTACAGCCACCAAGGACACCTACG

ACGCCCTTCACATGCAGGCCCTGCCCCCTCGC.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-PTM-CD28. In one embodiment, the CAR is a human 2A10 PSMA-CAR. Accordingly, in an exemplary embodiment, a nucleic acid of the present invention comprises from 5' to 3': a nucleic acid sequence encoding PD1$^{A132L}$-PTM-CD28, a nucleic acid sequence encoding a linker comprising F2A, and a nucleic acid sequence encoding a human 2A10 PSMA-CAR. In one embodiment, the nucleic acid comprising from 5' to 3': a nucleic acid sequence encoding PD1$^{A132L}$-PTM-CD28, a nucleic acid sequence encoding a linker comprising F2A, and a nucleic acid sequence encoding a human 2A10 PSMA-CAR, comprises the nucleic acid sequence set forth below:

(SEQ ID NO: 162)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA

TTACCAGCCCTATGCCCCACCACGCGACTTCGCAGCCTATCGCTCCGTGA

AACAGACTTTGAATTTTGACCTTCTCAAGTTGGCGGGAGACGTGGAGTCC

AACCCAGGGCCGATGGCCTTACCAGTGACCGCCTTGCTCCTGCCGCTGGC

CTTGCTGCTCCACGCCGCCAGGCCGGAGGTGCAGCTGGTGCAGTCTGGAG

CAGAGGTGAAAAGCCCGGGGAGTCTCTGAAGATCTCCTGTAAGGGTTCT

GGATACAGCTTTACCAGTAACTGGATCGGCTGGGTGCGCCAGATGCCCGG

GAAAGGCCTGGAGTGGATGGGGATCATCTATCCTGGTGACTCTGATACCA

GATACAGCCCGTCCTTCCAAGGCCAGGTCACCATCTCAGCCGACAAGTCC

ATCAGCACCGCCTACCTGCAGTGGAGCAGCCTGAAGGCCTCGGACACCGC

CATGTATTACTGTGCGAGGCAAACTGGTTTCCTCTGGTCCTCCGATCTCT

-continued
GGGGCCGTGGCACCCTGGTCACTGTCTCCTCAGGTGGCGGTGGCTCGGGC

GGTGGTGGGTCGGGTGGCGGCGGATCTGCCATCCAGTTGACCCAGTCTCC

ATCCTCCCTGTCTGCATCTGTAGGAGACAGAGTCACCATCACTTGCCGGG

CAAGTCAGGACATTAGCAGTGCTTTAGCCTGGTATCAACAGAAACCAGGG

AAAGCTCCTAAGCTCCTGATCTATGATGCCTCCAGTTTGGAAAGTGGGGT

CCCATCAAGGTTCAGCGGCTATGGATCTGGGACAGATTTCACTCTCACCA

TCAACAGCCTGCAGCCTGAAGATTTTGCAACTTATTACTGTCAACAGTTT

AATAGTTACCCGCTCACTTTCGGCGGAGGGACCAAGGTGGAGATCAAAAC

CACGACGCCAGCGCCGCGACCACCAACACCGGCGCCCACCATCGCGTCGC

AGCCCCTGTCCCTGCGCCCAGAGGCGTGCCGGCCAGCGGCGGGGGGCGCA

GTGCACACGAGGGGGCTGGACTTCGCCTGTGATATCTACATCTGGGCGCC

CTTGGCCGGGACTTGTGGGGTCCTTCTCCTGTCACTGGTTATCACCCTTT

ACTGCAAACGGGGCAGAAAGAAACTCCTGTATATATTCAAACAACCATTT

ATGAGACCAGTACAAACTACTCAAGAGGAAGATGGCTGTAGCTGCCGATT

TCCAGAAGAAGAAGAAGGAGGATGTGAACTGAGAGTGAAGTTCAGCAGGA

GCGCAGACGCCCCCGCGTACAAGCAGGGCCAGAACCAGCTCTATAACGAG

CTCAATCTAGGACGAAGAGAGGAGTACGATGTTTTGGACAAGAGACGTGG

CCGGGACCCTGAGATGGGGGAAAGCCGAGAAGGAAGAACCCTCAGGAAG

GCCTGTACAATGAACTGCAGAAAGATAAGATGGCGGAGGCCTACAGTGAG

ATTGGGATGAAAGGCGAGCGCCGGAGGGGCAAGGGGCACGATGGCCTTTA

CCAGGGTCTCAGTACAGCCACCAAGGACACCTACGACGCCCTTCACATGC

AGGCCCTGCCCCCTCGC.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-PTM-CD28. In one embodiment, the CAR is a human 2F5 PSMA-CAR. Accordingly, in an exemplary embodiment, a nucleic acid of the present invention comprises from 5' to 3': a nucleic acid sequence encoding PD1$^{A132L}$-PTM-CD28, a nucleic acid sequence encoding a linker comprising F2A, and a nucleic acid sequence encoding a human 2F5 PSMA-CAR. In one embodiment, the nucleic acid comprising from 5' to 3': a nucleic acid sequence encoding PD1$^{A132L}$-PTM-CD28, a nucleic acid sequence encoding a linker comprising F2A, and a nucleic acid sequence encoding a human 2F5 PSMA-CAR, comprises the nucleic acid sequence set forth below:

(SEQ ID NO: 163)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

```
CCCAACGGGCGTGACTTCCACATGAGCGTGGTCAGGGCCCGGCGCAATGA
CAGCGGCACCTACCTCTGTGGGGCCATCTCCCTGGCCCCCAAGCTGCAGA
TCAAAGAGAGCCTGCGGGCAGAGCTCAGGGTGACAGAGAGAAGGGCAGAA
GTGCCCACAGCCCACCCCAGCCCCTCACCCAGGCCAGCCGGCCAGTTCCA
AACCCTGGTGGTTGGTGTCGTGGGCGGCCTGCTGGGCAGCCTGGTGCTGC
TAGTCTGGGTCCTGGCCGTCATCAGGAGTAAGAGGAGCAGGCTCCTGCAC
AGTGACTACATGAACATGACTCCCCGCCGCCCCGGGCCCACCCGCAAGCA
TTACCAGCCCTATGCCCCACCACGCGACTTCGCAGCCTATCGCTCCGTGA
AACAGACTTTGAATTTTGACCTTCTCAAGTTGGCGGGAGACGTGGAGTCC
AACCCAGGGCCGATGGCCTTACCAGTGACCGCCTTGCTCCTGCCGCTGGC
CTTGCTGCTCCACGCCGCCAGGCCGGAGGTGCAGCTGGTGCAGTCTGGAG
CAGAGGTGAAAAAGCCCGGGGAGTCTCTGAAGATCTCCTGTAAGGGTTCT
GGATACAGTTTTACCAGCAACTGGATCGGCTGGGTGCGCCAGATGCCCGG
GAAAGGCCTGGAGTGGATGGGGATCATCTATCCTGGTGACTCTGATACCA
GATACAGCCCGTCCTTCCAAGGCCAGGTCACCATCTCAGCCGACAAGTCC
ATCAGCACCGCCTACCTGCAGTGGAACAGCCTGAAGGCCTCGGACACCGC
CATGTATTACTGTGCGAGACAAACTGGTTTCCTCTGGTCCTTCGATCTCT
GGGGCCGTGGCACCCTGGTCACTGTCTCCTCAGGTGGCGGTGGCTCGGGC
GGTGGTGGGTCGGGTGGCGGCGGATCTGCCATCCAGTTGACCCAGTCTCC
ATCCTCCCTGTCTGCATCTGTAGGAGACAGAGTCACCATCACTTGCCGGG
CAAGTCAGGACATTAGCAGTGCTTTAGCCTGGTATCAGCAGAAACCGGGG
AAAGCTCCTAAGCTCCTGATCTATGATGCCTCCAGTTTGGAAAGTGGGGT
CCCATCAAGGTTCAGCGGCAGTGGATCTGGGACAGATTTCACTCTCACCA
TCAGCAGCCTGCAGCCTGAAGATTTTGCAACTTATTACTGTCAACAGTTT
AATAGTTACCCGCTCACTTTCGGCGGAGGGACCAAGGTGGAGATCAAAAT
CAAAACCACGACGCCAGCGCCGCGACCACCAACACCGGCGCCCACCATCG
CGTCGCAGCCCCTGTCCCTGCGCCCAGAGGCGTGCCGGCCAGCGGCGGGG
GGCGCAGTGCACACGAGGGGGCTGGACTTCGCCTGTGATATCTACATCTG
GGCGCCCTTGGCCGGGACTTGTGGGGTCCTTCTCCTGTCACTGGTTATCA
CCCTTTACTGCAAACGGGGCAGAAAGAAACTCCTGTATATATTCAAACAA
CCATTTATGAGACCAGTACAAACTACTCAAGAGGAAGATGGCTGTAGCTG
CCGATTTCCAGAAGAAGAAGAAGGAGGATGTGAACTGAGAGTGAAGTTCA
GCAGGAGCGCAGACGCCCCCGCGTACAAGCAGGGCCAGAACCAGCTCTAT
AACGAGCTCAATCTAGGACGAAGAGAGGAGTACGATGTTTTGGACAAGAG
ACGTGGCCGGGACCCTGAGATGGGGGGAAAGCCGAGAAGGAAGAACCCTC
AGGAAGGCCTGTACAATGAACTGCAGAAAGATAAGATGGCGGAGGCCTAC
AGTGAGATTGGGATGAAAGGCGAGCGCCGGAGGGGCAAGGGGCACGATGG
CCTTTACCAGGGTCTCAGTACAGCCACCAAGGACACCTACGACGCCCTTC
ACATGCAGGCCCTGCCCCCTCGC.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-PTM-CD28. In one embodiment, the CAR is a human 2C6 PSMA-CAR. Accordingly, in an exemplary embodiment, a nucleic acid of the present invention comprises from 5' to 3': a nucleic acid sequence encoding PD1$^{A132L}$-PTM-CD28, a nucleic acid sequence encoding a linker comprising F2A, and a nucleic acid sequence encoding a human 2C6 PSMA-CAR. In one embodiment, the nucleic acid comprising from 5' to 3': a nucleic acid sequence encoding PD1$^{A132L}$-PTM-CD28, a nucleic acid sequence encoding a linker comprising F2A, and a nucleic acid sequence encoding a human 2C6 PSMA-CAR, comprises the nucleic acid sequence set forth below:

(SEQ ID NO: 164)
```
ATGCAGATCCCACAGGCGCCCTGGCCAGTCGTCTGGGCGGTGCTACAACT
GGGCTGGCGGCCAGGATGGTTCTTAGACTCCCCAGACAGGCCCTGGAACC
CCCCCACCTTCTCCCCAGCCCTGCTCGTGGTGACCGAAGGGGACAACGCC
ACCTTCACCTGCAGCTTCTCCAACACATCGGAGAGCTTCGTGCTAAACTG
GTACCGCATGAGCCCCAGCAACCAGACGGACAAGCTGGCCGCCTTCCCCG
AGGACCGCAGCCAGCCCGGCCAGGACTGCCGCTTCCGTGTCACACAACTG
CCCAACGGGCGTGACTTCCACATGAGCGTGGTCAGGGCCCGGCGCAATGA
CAGCGGCACCTACCTCTGTGGGGCCATCTCCCTGGCCCCCAAGCTGCAGA
TCAAAGAGAGCCTGCGGGCAGAGCTCAGGGTGACAGAGAGAAGGGCAGAA
GTGCCCACAGCCCACCCCAGCCCCTCACCCAGGCCAGCCGGCCAGTTCCA
AACCCTGGTGGTTGGTGTCGTGGGCGGCCTGCTGGGCAGCCTGGTGCTGC
TAGTCTGGGTCCTGGCCGTCATCAGGAGTAAGAGGAGCAGGCTCCTGCAC
AGTGACTACATGAACATGACTCCCCGCCGCCCCGGGCCCACCCGCAAGCA
TTACCAGCCCTATGCCCCACCACGCGACTTCGCAGCCTATCGCTCCGTGA
AACAGACTTTGAATTTTGACCTTCTCAAGTTGGCGGGAGACGTGGAGTCC
AACCCAGGGCCGATGGCCTTACCAGTGACCGCCTTGCTCCTGCCGCTGGC
CTTGCTGCTCCACGCCGCCAGGCCGGAGGTGCAGCTGGTGCAGTCTGGAT
CAGAGGTGAAAAAGCCCGGGGAGTCTCTGAAGATCTCCTGTAAGGGTTCT
GGATACAGCTTTACCAACTACTGGATCGGCTGGGTGCGCCAGATGCCCGG
GAAAGGCCTGGAGTGGATGGGGATCATCTATCCTGGTGACTCTGATACCA
GATACAGCCCGTCCTTCCAAGGCCAGGTCACCATCTCAGCCGACAAGTCC
ATCAGCACCGCCTATCTGCAGTGGAGCAGCCTGAAGGCCTCGGACACCGC
CATGTATTACTGTGCGAGTCCCGGGTATACCAGCAGTTGGACTTCTTTTG
ACTACTGGGGCCAGGGAACCCTGGTCACCGTCTCCTCAGGTGGCGGTGGC
TCGGGCGGTGGTGGGTCGGGTGGCGGCGGATCTGAAATTGTGTTGACACA
GTCTCCAGCCACCCTGTCTTTGTCTCCAGGGGAAAGAGCCACCCTCTCCT
GCAGGGCCAGTCAGAGTGTTAGCAGCTACTTAGCCTGGTACCAACAGAAA
CCTGGCCAGGCTCCCAGGCTCCTCATCTATGATGCATCCAACAGGGCCAC
TGGCATCCCAGCCAGGTTCAGTGGCAGTGGGTCTGGGACAGACTTCACTC
TCACCATCAGCAGCCTAGAGCCTGAAGATTTTGCAGTTTATTACTGTCAG
CAGCGTAGCAACTGGCCCCTATTCACTTTCGGCCCTGGGACCAAAGTGGA
```

```
TATCAAAACCACGACGCCAGCGCCGCGACCACCAACACCGGCGCCCACCA

TCGCGTCGCAGCCCCTGTCCCTGCGCCCAGAGGCGTGCCGGCCAGCGGCG

GGGGGCGCAGTGCACACGAGGGGGCTGGACTTCGCCTGTGATATCTACAT

CTGGGCGCCCTTGGCCGGGACTTGTGGGGTCCTTCTCCTGTCACTGGTTA

TCACCCTTTACTGCAAACGGGGCAGAAAGAAACTCCTGTATATATTCAAA

CAACCATTTATGAGACCAGTACAAACTACTCAAGAGGAAGATGGCTGTAG

CTGCCGATTTCCAGAAGAAGAAGAAGGAGGATGTGAACTGAGAGTGAAGT

TCAGCAGGAGCGCAGACGCCCCCGCGTACAAGCAGGGCCAGAACCAGCTC

TATAACGAGCTCAATCTAGGACGAAGAGAGGAGTACGATGTTTTGGACAA

GAGACGTGGCCGGGACCCTGAGATGGGGGAAAGCCGAGAAGGAAGAACC

CTCAGGAAGGCCTGTACAATGAACTGCAGAAAGATAAGATGGCGGAGGCC

TACAGTGAGATTGGGATGAAAGGCGAGCGCCGGAGGGGCAAGGGCACGA

TGGCCTTTACCAGGGTCTCAGTACAGCCACCAAGGACACCTACGACGCCC

TTCACATGCAGGCCCTGCCCCCTCGC.
```

Tolerable variations of the nucleic acid sequence encoding PD1$^{A132L}$-PTM-CD28 and a PSMA-CAR will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in any one of SEQ ID NOs:161-164. In one embodiment, the nucleic acid sequence encoding for PD1$^{A132L}$-PTM-CD28 and human 1C3 PSMA-CAR comprises the nucleic acid sequence set forth in SEQ ID NO:161. In one embodiment, the nucleic acid sequence encoding for PD1$^{A132L}$-PTM-CD28 and human 2A10 PSMA-CAR comprises the nucleic acid sequence set forth in SEQ ID NO:162. In one embodiment, the nucleic acid sequence encoding for PD1$^{A132L}$-PTM-CD28 and human 2F5 PSMA-CAR comprises the nucleic acid sequence set forth in SEQ ID NO:163. In one embodiment, the nucleic acid sequence encoding for PD1$^{A132L}$-PTM-CD28 and human 2C6 PSMA-CAR comprises the nucleic acid sequence set forth in SEQ ID NO:164.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is TIM3-CD28. In one embodiment, the CAR is a human 1C3 PSMA-CAR. Accordingly, in an exemplary embodiment, a nucleic acid of the present invention comprises from 5' to 3': a nucleic acid sequence encoding TIM3-CD28, a nucleic acid sequence encoding a linker comprising F2A, and a nucleic acid sequence encoding a human 1C3 PSMA-CAR. In one embodiment, the nucleic acid comprising from 5' to 3': a nucleic acid sequence encoding TIM3-CD28, a nucleic acid sequence encoding a linker comprising F2A, and a nucleic acid sequence encoding a human 1C3 PSMA-CAR, comprises the nucleic acid sequence set forth below:

```
                                         (SEQ ID NO: 165)
ATGTTTTCACATCTTCCCTTTGACTGTGTCCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC

GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCGGGCCCACC

CGCAAGCATTACCAGCCCTATGCCCCACCACGCGACTTCGCAGCCTATCG

CTCCGTGAAACAGACTTTGAATTTTGACCTTCTCAAGTTGGCGGGAGACG

TGGAGTCCAACCCAGGGCCGATGGCCTTACCAGTGACCGCCTTGCTCCTG

CCGCTGGCCTTGCTGCTCCACGCCGCCAGGCCGCAGGTGCAACTGGTGGA

GTCTGGGGGAGGCGTGGTCCAGCCTGGGAGGTCCCTGAGACTCTCCTGTG

CAGCCTCTGGATTCACCTTCAGTAGCTATGCTATGCACTGGGTCCGCCAG

GCTCCAGGCAAGGGGCTGGAGTGGGTGGCAGTTATATCATATGATGGAAA

CAATAAATACTACGCAGACTCCGTGAAGGGCCGATTCACCATCTCCAGAG

ACAATTCCAAGAACACGCTGTATCTGCAAATGAACAGCCTGAGAGCTGAG

GACACGGCTGTGTATTACTGTGCGAGAGCCGTCCCCTGGGGATCGAGGTA

CTACTACTACGGTATGGACGTCTGGGGCCAAGGGACCACGGTCACCGTCT

CCTCAGGTGGCGGTGGCTCGGGCGGTGGTGGGTCGGGTGGCGGCGGATCT

GCCATCCAGTTGACCCAGTCTCCATCCTCCCTGTCTGCATCTGTAGGAGA

CAGAGTCACCATCACTTGCCGGGCAAGTCAGGGCATTAGCAGTGCTTTAG

CCTGGTATCAGCAGAAATCAGGGAAAGCTCCTAAGCTCCTGATCTTTGAT

GCCTCCAGTTTGGAAAGTGGGGTCCCATCAAGGTTCAGCGGCAGTGGATC

TGGGACAGATTTCACTCTCACCATCAGCAGCCTGCAGCCTGAAGATTTTG

CAACTTATTACTGTCAACAGTTTAACAGTTATCCTCTCACTTTCGGCGGA

GGGACCAAGGTGGAGATCAAAACCACGACGCCAGCGCCGCGACCACCAAC

ACCGGCGCCCACCATCGCGTCGCAGCCCCTGTCCCTGCGCCCAGAGGCGT

GCCGGCCAGCGGCGGGGGGCGCAGTGCACACGAGGGGGCTGGACTTCGCC

TGTGATATCTACATCTGGGCGCCCTTGGCCGGGACTTGTGGGGTCCTTCT

CCTGTCACTGGTTATCACCCTTTACTGCAAACGGGGCAGAAAGAAACTCC

TGTATATATTCAAACAACCATTTATGAGACCAGTACAAACTACTCAAGAG

GAAGACGGCTGTAGCTGCCGATTTCCAGAAGAAGAAGAAGGAGGATGTGA
```

```
ACTGAGAGTGAAGTTCAGCAGGAGCGCAGACGCCCCCGCGTACAAGCAGG

GCCAGAACCAGCTCTATAACGAGCTCAATCTAGGACGAAGAGAGGAGTAC

GACGTTTTGGACAAGAGACGTGGCCGGGACCCTGAGATGGGGGAAAGCC

GAGAAGGAAGAACCCTCAGGAAGGCCTGTACAACGAACTGCAGAAAGATA

AGATGGCGGAGGCCTACAGTGAGATTGGGATGAAAGGCGAGCGCCGGAGG

GGCAAGGGGCACGACGGCCTTTACCAGGGTCTCAGTACAGCCACCAAGGA

CACCTACGACGCCCTTCACATGCAGGCCCTGCCCCCTCGC.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is TIM3-CD28. In one embodiment, the CAR is a human 2A10 PSMA-CAR. Accordingly, in an exemplary embodiment, a nucleic acid of the present invention comprises from 5' to 3': a nucleic acid sequence encoding TIM3-CD28, a nucleic acid sequence encoding a linker comprising F2A, and a nucleic acid sequence encoding a human 2A10 PSMA-CAR. In one embodiment, the nucleic acid comprising from 5' to 3': a nucleic acid sequence encoding TIM3-CD28, a nucleic acid sequence encoding a linker comprising F2A, and a nucleic acid sequence encoding a human 2A10 PSMA-CAR, comprises the nucleic acid sequence set forth below:

```
                                        (SEQ ID NO: 166)
ATGTTTTCACATCTTCCCTTTGACTGTGTCCTGCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC

GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCCGTGAAACAGACTTTGAATTTTGACCTTCTCAAGTTGGCGGGAGACG

TGGAGTCCAACCCAGGGCCGATGGCCTTACCAGTGACCGCCTTGCTCCTG

CCGCTGGCCTTGCTGCTCCACGCCGCCAGGCCGGAGGTGCAGCTGGTGCA

GTCTGGAGCAGAGGTGAAAAAGCCCGGGGAGTCTCTGAAGATCTCCTGTA

AGGGTTCTGGATACAGCTTTACCAGTAACTGGATCGGCTGGGTGCGCCAG
```

```
                                        -continued
ATGCCCGGGAAAGGCCTGGAGTGGATGGGGATCATCTATCCTGGTGACTC

TGATACCAGATACAGCCCGTCCTTCCAAGGCCAGGTCACCATCTCAGCCG

ACAAGTCCATCAGCACCGCCTACCTGCAGTGGAGCAGCCTGAAGGCCTCG

GACACCGCCATGTATTACTGTGCGAGGCAAACTGGTTTCCTCTGGTCCTC

CGATCTCTGGGGCCGTGGCACCCTGGTCACTGTCTCCTCAGGTGGCGGTG

GCTCGGGCGGTGGTGGGTCGGGTGGCGGCGGATCTGCCATCCAGTTGACC

CAGTCTCCATCCTCCCTGTCTGCATCTGTAGGAGACAGAGTCACCATCAC

TTGCCGGGCAAGTCAGGACATTAGCAGTGCTTTAGCCTGGTATCAACAGA

AACCAGGGAAAGCTCCTAAGCTCCTGATCTATGATGCCTCCAGTTTGGAA

AGTGGGGTCCCATCAAGGTTCAGCGGCTATGGATCTGGGACAGATTTCAC

TCTCACCATCAACAGCCTGCAGCCTGAAGATTTTGCAACTTATTACTGTC

AACAGTTTAATAGTTACCCGCTCACTTTCGGCGGAGGGACCAAGGTGGAG

ATCAAAACCACGACGCCAGCGCCGCGACCACCAACACCGGCGCCCACCAT

CGCGTCGCAGCCCCTGTCCCTGCGCCCAGAGGCGTGCCGGCCAGCGGCGG

GGGGCGCAGTGCACACGAGGGGGCTGGACTTCGCCTGTGATATCTACATC

TGGGCGCCCTTGGCCGGGACTTGTGGGGTCCTTCTCCTGTCACTGGTTAT

CACCCTTTACTGCAAACGGGGCAGAAAGAAACTCCTGTATATATTCAAAC

AACCATTTATGAGACCAGTACAAACTACTCAAGAGGAAGATGGCTGTAGC

TGCCGATTTCCAGAAGAAGAAGAAGGAGGATGTGAACTGAGAGTGAAGTT

CAGCAGGAGCGCAGACGCCCCCGCGTACAAGCAGGGCCAGAACCAGCTCT

ATAACGAGCTCAATCTAGGACGAAGAGAGGAGTACGATGTTTTGGACAAG

AGACGTGGCCGGGACCCTGAGATGGGGGGAAAGCCGAGAAGGAAGAACCC

TCAGGAAGGCCTGTACAATGAACTGCAGAAAGATAAGATGGCGGAGGCCT

ACAGTGAGATTGGGATGAAAGGCGAGCGCCGGAGGGGCAAGGGGCACGAT

GGCCTTTACCAGGGTCTCAGTACAGCCACCAAGGACACCTACGACGCCCT

TCACATGCAGGCCCTGCCCCCTCGC.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is TIM3-CD28. In one embodiment, the CAR is a human 2F5 PSMA-CAR. Accordingly, in an exemplary embodiment, a nucleic acid of the present invention comprises from 5' to 3': a nucleic acid sequence encoding TIM3-CD28, a nucleic acid sequence encoding a linker comprising F2A, and a nucleic acid sequence encoding a human 2F5 PSMA-CAR. In one embodiment, the nucleic acid comprising from 5' to 3': a nucleic acid sequence encoding TIM3-CD28, a nucleic acid sequence encoding a linker comprising F2A, and a nucleic acid sequence encoding a human 2F5 PSMA-CAR, comprises the nucleic acid sequence set forth below:

```
                                        (SEQ ID NO: 167)
ATGTTTTCACATCTTCCCTTTGACTGTGTCCTGCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC
```

```
GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCCGTGAAACAGACTTTGAATTTTGACCTTCTCAAGTTGGCGGGAGACG

TGGAGTCCAACCCAGGGCCGATGGCCTTACCAGTGACCGCCTTGCTCCTG

CCGCTGGCCTTGCTGCTCCACGCCGCCAGGCCGGAGGTGCAGCTGGTGCA

GTCTGGAGCAGAGGTGAAAAAGCCCGGGGAGTCTCTGAAGATCTCCTGTA

AGGGTTCTGGATACAGTTTTACCAGCAACTGGATCGGCTGGGTGCGCCAG

ATGCCCGGGAAAGGCCTGGAGTGGATGGGGATCATCTATCCTGGTGACTC

TGATACCAGATACAGCCCGTCCTTCCAAGGCCAGGTCACCATCTCAGCCG

ACAAGTCCATCAGCACCGCCTACCTGCAGTGGAACAGCCTGAAGGCCTCG

GACACCGCCATGTATTACTGTGCGAGACAAACTGGTTTCCTCTGGTCCTT

CGATCTCTGGGCCGTGGCACCCTGGTCACTGTCTCCTCAGGTGGCGGTG

GCTCGGGCGGTGGTGGGTCGGGTGGCGGCGGATCTGCCATCCAGTTGACC

CAGTCTCCATCCTCCCTGTCTGCATCTGTAGGAGACAGAGTCACCATCAC

TTGCCGGGCAAGTCAGGACATTAGCAGTGCTTTAGCCTGGTATCAGCAGA

AACCGGGGAAAGCTCCTAAGCTCCTGATCTATGATGCCTCCAGTTTGGAA

AGTGGGGTCCCATCAAGGTTCAGCGGCAGTGGATCTGGGACAGATTTCAC

TCTCACCATCAGCAGCCTGCAGCCTGAAGATTTTGCAACTTATTACTGTC

AACAGTTTAATAGTTACCCGCTCACTTTCGGCGGAGGGACCAAGGTGGAG

ATCAAAATCAAAACCACGACGCCAGCGCCGCGACCACCAACACCGGCGCC

CACCATCGCGTCGCAGCCCCTGTCCCTGCGCCCAGAGGCGTGCCGGCCAG

CGGCGGGGGCGCAGTGCACACGAGGGGGCTGGACTTCGCCTGTGATATC

TACATCTGGGCGCCCTTGGCCGGGACTTGTGGGGTCCTTCTCCTGTCACT

GGTTATCACCCTTTACTGCAAACGGGGCAGAAAGAAACTCCTGTATATAT

TCAAACAACCATTTATGAGACCAGTACAAACTACTCAAGAGGAAGACGGC

TGTAGCTGCCGATTTCCAGAAGAAGAAGAAGGAGGATGTGAACTGAGAGT

GAAGTTCAGCAGGAGCGCAGACGCCCCCGCGTACAAGCAGGGCCAGAACC

AGCTCTATAACGAGCTCAATCTAGGACGAAGAGAGGAGTACGACGTTTTG

GACAAGAGACGTGGCCGGGACCCTGAGATGGGGGGAAAGCCGAGAAGGAA

GAACCCTCAGGAAGGCCTGTACAACGAACTGCAGAAAGATAAGATGGCGG

AGGCCTACAGTGAGATTGGGATGAAAGGCGAGCGCCGGAGGGGCAAGGGG

CACGACGGCCTTTACCAGGGTCTCAGTACAGCCACCAAGGACACCTACGA

CGCCCTTCACATGCAGGCCCTGCCCCCTCGC.
```

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is TIM3-CD28. In one embodiment, the CAR is a human 2C6 PSMA-CAR. Accordingly, in an exemplary embodiment, a nucleic acid of the present invention comprises from 5' to 3': a nucleic acid sequence encoding TIM3-CD28, a nucleic acid sequence encoding a linker comprising F2A, and a nucleic acid sequence encoding a human 2C6 PSMA-CAR. In one embodiment, the nucleic acid comprising from 5' to 3': a nucleic acid sequence encoding TIM3-CD28, a nucleic acid sequence encoding a linker comprising F2A, and a nucleic acid sequence encoding a human 2C6 PSMA-CAR, comprises the nucleic acid sequence set forth below:

```
(SEQ ID NO: 168)
ATGTTTTCACATCTTCCCTTTGACTGTGTCCTGCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC

GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCCGTGAAACAGACTTTGAATTTTGACCTTCTCAAGTTGGCGGGAGACG

TGGAGTCCAACCCAGGGCCGATGGCCTTACCAGTGACCGCCTTGCTCCTG

CCGCTGGCCTTGCTGCTCCACGCCGCCAGGCCGGAGGTGCAGCTGGTGCA

GTCTGGATCAGAGGTGAAAAAGCCCGGGGAGTCTCTGAAGATCTCCTGTA

AGGGTTCTGGATACAGCTTTACCAACTACTGGATCGGCTGGGTGCGCCAG

ATGCCCGGGAAAGGCCTGGAGTGGATGGGGATCATCTATCCTGGTGACTC

TGATACCAGATACAGCCCGTCCTTCCAAGGCCAGGTCACCATCTCAGCCG

ACAAGTCCATCAGCACCGCCTATCTGCAGTGGAGCAGCCTGAAGGCCTCG

GACACCGCCATGTATTACTGTGCGAGTCCCGGGTATACCAGCAGTTGGAC
```

-continued

```
TTCTTTTGACTACTGGGGCCAGGGAACCCTGGTCACCGTCTCCTCAGGTG
GCGGTGGCTCGGGCGGTGGTGGGTCGGGTGGCGGCGGATCTGAAATTGTG
TTGACACAGTCTCCAGCCACCCTGTCTTTGTCTCCAGGGGAAAGAGCCAC
CCTCTCCTGCAGGGCCAGTCAGAGTGTTAGCAGCTACTTAGCCTGGTACC
AACAGAAACCTGGCCAGGCTCCCAGGCTCCTCATCTATGATGCATCCAAC
AGGGCCACTGGCATCCCAGCCAGGTTCAGTGGCAGTGGGTCTGGGACAGA
CTTCACTCTCACCATCAGCAGCCTAGAGCCTGAAGATTTTGCAGTTTATT
ACTGTCAGCAGCGTAGCAACTGGCCCCTATTCACTTTCGGCCCTGGGACC
AAAGTGGATATCAAAACCACGACGCCAGCGCCGCGACCACCAACACCGGC
GCCCACCATCGCGTCGCAGCCCCTGTCCCTGCGCCCAGAGGCGTGCCGGC
CAGCGGCGGGGGCGCAGTGCACACGAGGGGGCTGGACTTCGCCTGTGAT
ATCTACATCTGGGCGCCCTTGGCCGGGACTTGTGGGGTCCTTCTCCTGTC
ACTGGTTATCACCCTTTACTGCAAACGGGGCAGAAAGAAACTCCTGTATA
TATTCAAACAACCATTTATGAGACCAGTACAAACTACTCAAGAGGAAGAC
GGCTGTAGCTGCCGATTTCCAGAAGAAGAAGAAGGAGGATGTGAACTGAG
AGTGAAGTTCAGCAGGAGCGCAGACGCCCCCGCGTACAAGCAGGGCCAGA
ACCAGCTCTATAACGAGCTCAATCTAGGACGAAGAGAGGAGTACGACGTT
TTGGACAAGAGACGTGGCCGGGACCCTGAGATGGGGGGAAAGCCGAGAAG
GAAGAACCCTCAGGAAGGCCTGTACAACGAACTGCAGAAAGATAAGATGG
CGGAGGCCTACAGTGAGATTGGGATGAAAGGCGAGCGCCGGAGGGGCAAG
GGGCACGACGGCCTTTACCAGGGTCTCAGTACAGCCACCAAGGACACCTA
CGACGCCCTTCACATGCAGGCCCTGCCCCCTCGC.
```

Tolerable variations of the nucleic acid sequence encoding TIM3-CD28 and a PSMA-CAR will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in any one of SEQ ID NOs:165-168. In one embodiment, the nucleic acid sequence encoding for TIM3-CD28 and human 1C3 PSMA-CAR comprises the nucleic acid sequence set forth in SEQ ID NO:165. In one embodiment, the nucleic acid sequence encoding for TIM3-CD28 and human 2A10 PSMA-CAR comprises the nucleic acid sequence set forth in SEQ ID NO:166. In one embodiment, the nucleic acid sequence encoding for TIM3-CD28 and human 2F5 PSMA-CAR comprises the nucleic acid sequence set forth in SEQ ID NO:167. In one embodiment, the nucleic acid sequence encoding for TIM3-CD28 and human 2C6 PSMA-CAR comprises the nucleic acid sequence set forth in SEQ ID NO:168.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1-CTM-CD28. In one embodiment, the CAR is a human 2F5 PSMA-CAR comprising an ICOS domain and a CD3zeta domain. Accordingly, in an exemplary embodiment, a nucleic acid of the present invention comprises from 5' to 3': a nucleic acid sequence encoding PD1-CTM-CD28, a nucleic acid sequence encoding a linker comprising F2A, and a nucleic acid sequence encoding a human 2F5 PSMA-CAR comprising an ICOS domain and a CD3zeta domain. In one embodiment, the nucleic acid comprising from 5' to 3': a nucleic acid sequence encoding PD1-CTM-CD28, a nucleic acid sequence encoding a linker comprising F2A, and a nucleic acid sequence encoding a human 2F5 PSMA-CAR comprising an ICOS domain and a CD3zeta domain, comprises the nucleic acid sequence set forth below:

(SEQ ID NO: 217)
```
ATGCAGATCCCACAGGCGCCCTGGCCAGTCGTCTGGGCGGTGCTACAACT
GGGCTGGCGGCCAGGATGGTTCTTAGACTCCCCAGACAGGCCCTGGAACC
CCCCCACCTTCTCCCCAGCCCTGCTCGTGGTGACCGAAGGGGACAACGCC
ACCTTCACCTGCAGCTTCTCCAACACATCGGAGAGCTTCGTGCTAAACTG
GTACCGCATGAGCCCCAGCAACCAGACGGACAAGCTGGCCGCCTTCCCCG
AGGACCGCAGCCAGCCCGGCCAGGACTGCCGCTTCCGTGTCACACAACTG
CCCAACGGGCGTGACTTCCACATGAGCGTGGTCAGGGCCCGGCGCAATGA
CAGCGGCACCTACCTCTGTGGGGCCATCTCCCTGGCCCCCAAGGCGCAGA
TCAAAGAGAGCCTGCGGGCAGAGCTCAGGGTGACAGAGAGAAGGGCAGAA
GTGCCCACAGCCCACCCCAGCCCCTCACCCAGGCCAGCCGGCCAGTTCCA
AACCCTGGTGTTTTGGGTGCTGGTGGTGGTTGGTGGAGTCCTGGCTTGCT
ATAGCTTGCTAGTAACAGTGGCCTTTATTATTTTCTGGGTGAGGAGTAAG
AGGAGCAGGCTCCTGCACAGTGACTACATGAACATGACTCCCCGCCGCCC
CGGGCCCACCCGCAAGCATTACCAGCCCTATGCCCCACCACGCGACTTCG
CAGCCTATCGCTCCGTGAAACAGACTTTGAATTTTGACCTTCTCAAGTTG
GCGGGAGACGTGGAGTCCAACCCAGGGCCGATGGCCTTACCAGTGACCGC
CTTGCTCCTGCCGCTGGCCTTGCTGCTCCACGCCGCCAGGCCGGAGGTGC
AGCTGGTGCAGTCTGGAGCAGAGGTGAAAAAGCCCGGGGAGTCTCTGAAG
ATCTCCTGTAAGGGTTCTGGATACAGTTTTACCAGCAACTGGATCGGCTG
GGTGCGCCAGATGCCCGGGAAAGGCCTGGAGTGGATGGGGATCATCTATC
CTGGTGACTCTGATACCAGATACAGCCCGTCCTTCCAAGGCCAGGTCACC
ATCTCAGCCGACAAGTCCATCAGCACCGCCTACCTGCAGTGGAACAGCCT
GAAGGCCTCGGACACCGCCATGTATTACTGTGCGAGACAAACTGGTTTCC
TCTGGTCCTTCGATCTCTGGGGCCGTGGCACCCTGGTCACTGTCTCCTCA
GGTGGCGGTGGCTCGGGCGGTGGTGGGTCGGGTGGCGGCGGATCTGCCAT
CCAGTTGACCCAGTCTCCATCCTCCCTGTCTGCATCTGTAGGAGACAGAG
TCACCATCACTTGCCGGGCAAGTCAGGACATTAGCAGTGCTTTAGCCTGG
TATCAGCAGAAACCGGGGAAAGCTCCTAAGCTCCTGATCTATGATGCCTC
CAGTTTGGAAAGTGGGGTCCCATCAAGGTTCAGCGGCAGTGGATCTGGGA
CAGATTTCACTCTCACCATCAGCAGCCTGCAGCCTGAAGATTTTGCAACT
TATTACTGTCAACAGTTTAATAGTTACCCGCTCACTTTCGGCGGAGGGAC
CAAGGTGGAGATCAAAATCAAAACCACGACGCCAGCGCCGCGACCACCAA
```

```
CACCGGCGCCCACCATCGCGTCGCAGCCCCTGTCCCTGCGCCCAGAGGCG

TGCCGGCCAGCGGCGGGGGGCGCAGTGCACACGAGGGGGCTGGACTTCGC

CTGTGATTTCTGGTTACCCATAGGATGTGCAGCCTTTGTTGTAGTCTGCA

TTTTGGGATGCATACTTATTTGTTGGCTTACAAAAAAGAAGTATTCATCC

AGTGTGCACGACCCTAACGGTGAATACATGTTCATGAGAGCAGTGAACAC

AGCCAAAAAATCCAGACTCACAGATGTGACCCTAAGAGTGAAGTTCAGCA

GGAGCGCAGACGCCCCCGCGTACCAGCAGGGCCAGAACCAGCTCTATAAC

GAGCTCAATCTAGGACGAAGAGAGGAGTACGATGTTTTGGACAAGAGACG

TGGCCGGGACCCTGAGATGGGGGGAAAGCCGCAGAGAAGGAAGAACCCTC

AGGAAGGCCTGTACAATGAACTGCAGAAAGATAAGATGGCGGAGGCCTAC

AGTGAGATTGGGATGAAAGGCGAGCGCCGGAGGGGCAAGGGGCACGATGG

CCTTTACCAGGGTCTCAGTACAGCCACCAAGGACACCTACGACGCCCTTC

ACATGCAGGCCCTGCCCCCTCGC.
```

Tolerable variations of the nucleic acid sequence encoding PD1-CTM-CD28 and a human 2F5 PSMA-CAR comprising an ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:217. In one embodiment, the nucleic acid sequence encoding for PD1-CTM-CD28 and human 2F5 PSMA-CAR comprising an ICOS domain and a CD3zeta domain comprises the nucleic acid sequence set forth in SEQ ID NO:217.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1-CTM-CD28. In one embodiment, the CAR is a human 2F5 PSMA-CAR comprising a variant ICOS domain and a CD3zeta domain. Accordingly, in an exemplary embodiment, a nucleic acid of the present invention comprises from 5' to 3': a nucleic acid sequence encoding PD1-CTM-CD28, a nucleic acid sequence encoding a linker comprising F2A, and a nucleic acid sequence encoding a human 2F5 PSMA-CAR comprising a variant ICOS domain and a CD3zeta domain. In one embodiment, the nucleic acid comprising from 5' to 3': a nucleic acid sequence encoding PD1-CTM-CD28, a nucleic acid sequence encoding a linker comprising F2A, and a nucleic acid sequence encoding a human 2F5 PSMA-CAR comprising a variant ICOS domain and a CD3zeta domain, comprises the nucleic acid sequence set forth below:

```
                                    (SEQ ID NO: 218)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCCGTGAAACAGACTTTGAATTTTGACCTTCTCAAGTTG

GCGGAGACGTGGAGTCCAACCCAGGGCCGATGGCCTTACCAGTGACCGC

CTTGCTCCTGCCGCTGGCCTTGCTGCTCCACGCCGCCAGGCCGGAGGTGC

AGCTGGTGCAGTCTGGAGCAGAGGTGAAAAAGCCCGGGGAGTCTCTGAAG

ATCTCCTGTAAGGGTTCTGGATACAGTTTTACCAGCAACTGGATCGGCTG

GGTGCGCCAGATGCCCGGGAAAGGCCTGGAGTGGATGGGGATCATCTATC

CTGGTGACTCTGATACCAGATACAGCCCGTCCTTCCAAGGCCAGGTCACC

ATCTCAGCCGACAAGTCCATCAGCACCGCCTACCTGCAGTGGAACAGCCT

GAAGGCCTCGGACACCGCCATGTATTACTGTGCGAGACAAACTGGTTTCC

TCTGGTCCTTCGATCTCTGGGGCCGTGGCACCCTGGTCACTGTCTCCTCA

GGTGGCGGTGGCTCGGGCGGTGGTGGGTCGGGTGGCGGCGGATCTGCCAT

CCAGTTGACCCAGTCTCCATCCTCCCTGTCTGCATCTGTAGGAGACAGAG

TCACCATCACTTGCCGGGCAAGTCAGGACATTAGCAGTGCTTTAGCCTGG

TATCAGCAGAAACCGGGGAAAGCTCCTAAGCTCCTGATCTATGATGCCTC

CAGTTTGGAAAGTGGGGTCCCATCAAGGTTCAGCGGCAGTGGATCTGGGA

CAGATTTCACTCTCACCATCAGCAGCCTGCAGCCTGAAGATTTTGCAACT

TATTACTGTCAACAGTTTAATAGTTACCCGCTCACTTTCGGCGGAGGGAC

CAAGGTGGAGATCAAAATCAAAACCACGACGCCAGCGCCGCGACCACCAA

CACCGGCGCCCACCATCGCGTCGCAGCCCCTGTCCCTGCGCCCAGAGGCG

TGCCGGCCAGCGGCGGGGGGCGCAGTGCACACGAGGGGGCTGGACTTCGC

CTGTGATTTCTGGTTACCCATAGGATGTGCAGCCTTTGTTGTAGTCTGCA

TTTTGGGATGCATACTTATTTGTTGGCTTACAAAAAAGAAGTATTCATCC

AGTGTGCACGACCCTAACGGTGAATACATGAACATGAGAGCAGTGAACAC

AGCCAAAAAATCCAGACTCACAGATGTGACCCTAAGAGTGAAGTTCAGCA

GGAGCGCAGACGCCCCCGCGTACCAGCAGGGCCAGAACCAGCTCTATAAC

GAGCTCAATCTAGGACGAAGAGAGGAGTACGATGTTTTGGACAAGAGACG

TGGCCGGGACCCTGAGATGGGGGGAAAGCCGCAGAGAAGGAAGAACCCTC

AGGAAGGCCTGTACAATGAACTGCAGAAAGATAAGATGGCGGAGGCCTAC
```

```
AGTGAGATTGGGATGAAAGGCGAGCGCCGGAGGGGCAAGGGGCACGATGG

CCTTTACCAGGGTCTCAGTACAGCCACCAAGGACACCTACGACGCCCTTC

ACATGCAGGCCCTGCCCCCTCGC.
```

Tolerable variations of the nucleic acid sequence encoding PD1-CTM-CD28 and a human 2F5 PSMA-CAR comprising a variant ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:218. In one embodiment, the nucleic acid sequence encoding for PD1-CTM-CD28 and human 2F5 PSMA-CAR comprising a variant ICOS domain and a CD3zeta domain comprises the nucleic acid sequence set forth in SEQ ID NO:218.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-PTM-CD28. In one embodiment, the CAR is a human 2F5 PSMA-CAR comprising an ICOS domain and a CD3zeta domain. Accordingly, in an exemplary embodiment, a nucleic acid of the present invention comprises from 5' to 3': a nucleic acid sequence encoding PD1$^{A132L}$-PTM-CD28, a nucleic acid sequence encoding a linker comprising F2A, and a nucleic acid sequence encoding a human 2F5 PSMA-CAR comprising an ICOS domain and a CD3zeta domain. In one embodiment, the nucleic acid comprising from 5' to 3': a nucleic acid sequence encoding PD1$^{A132L}$-PTM-CD28, a nucleic acid sequence encoding a linker comprising F2A, and a nucleic acid sequence encoding a human 2F5 PSMA-CAR comprising an ICOS domain and a CD3zeta domain, comprises the nucleic acid sequence set forth below:

```
                                    (SEQ ID NO: 219)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA
```

```
                                    -continued
TTACCAGCCCTATGCCCCACCACGCGACTTCGCAGCCTATCGCTCCGTGA

AACAGACTTTGAATTTTGACCTTCTCAAGTTGGCGGGAGACGTGGAGTCC

AACCCAGGGCCGATGGCCTTACCAGTGACCGCCTTGCTCCTGCCGCTGGC

CTTGCTGCTCCACGCCGCCAGGCCGGAGGTGCAGCTGGTGCAGTCTGGAG

CAGAGGTGAAAAAGCCCGGGGAGTCTCTGAAGATCTCCTGTAAGGGTTCT

GGATACAGTTTTACCAGCAACTGGATCGGCTGGGTGCGCCAGATGCCCGG

GAAAGGCCTGGAGTGGATGGGGATCATCTATCCTGGTGACTCTGATACCA

GATACAGCCCGTCCTTCCAAGGCCAGGTCACCATCTCAGCCGACAAGTCC

ATCAGCACCGCCTACCTGCAGTGGAACAGCCTGAAGGCCTCGGACACCGC

CATGTATTACTGTGCGAGACAAACTGGTTTCCTCTGGTCCTTCGATCTCT

GGGGCCGTGGCACCCTGGTCACTGTCTCCTCAGGTGGCGGTGGCTCGGGC

GGTGGTGGGTCGGGTGGCGGCGGATCTGCCATCCAGTTGACCCAGTCTCC

ATCCTCCCTGTCTGCATCTGTAGGAGACAGAGTCACCATCACTTGCCGGG

CAAGTCAGGACATTAGCAGTGCTTTAGCCTGGTATCAGCAGAAACCGGGG

AAAGCTCCTAAGCTCCTGATCTATGATGCCTCCAGTTTGGAAAGTGGGGT

CCCATCAAGGTTCAGCGGCAGTGGATCTGGGACAGATTTCACTCTCACCA

TCAGCAGCCTGCAGCCTGAAGATTTTGCAACTTATTACTGTCAACAGTTT

AATAGTTACCCGCTCACTTTCGGCGGAGGGACCAAGGTGGAGATCAAAAT

CAAAACCACGACGCCAGCGCCGCGACCACCAACACCGGCGCCCACCATCG

CGTCGCAGCCCCTGTCCCTGCGCCCAGAGGCGTGCCGGCCAGCGGCGGGG

GGCGCAGTGCACACGAGGGGGCTGGACTTCGCCTGTGATTTCTGGTTACC

CATAGGATGTGCAGCCTTTGTTGTAGTCTGCATTTTGGGATGCATACTTA

TTTGTTGGCTTACAAAAAAGAAGTATTCATCCAGTGTGCACGACCCTAAC

GGTGAATACATGTTCATGAGAGCAGTGAACACAGCCAAAAAATCCAGACT

CACAGATGTGACCCTAAGAGTGAAGTTCAGCAGGAGCGCAGACGCCCCCG

CGTACCAGCAGGGCCAGAACCAGCTCTATAACGAGCTCAATCTAGGACGA

AGAGAGGAGTACGATGTTTTGGACAAGAGACGTGGCCGGGACCCTGAGAT

GGGGGGAAAGCCGCAGAGAAGGAAGAACCCTCAGGAAGGCCTGTACAATG

AACTGCAGAAAGATAAGATGGCGGAGGCCTACAGTGAGATTGGGATGAAA

GGCGAGCGCCGGAGGGGCAAGGGGCACGATGGCCTTTACCAGGGTCTCAG

TACAGCCACCAAGGACACCTACGACGCCCTTCACATGCAGGCCCTGCCCC

CTCGC.
```

Tolerable variations of the nucleic acid sequence encoding PD1$^{A132L}$-PTM-CD28 and a human 2F5 PSMA-CAR comprising an ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:219. In one embodiment, the nucleic acid sequence encoding for PD1$^{A132L}$-PTM-CD28 and human 2F5 PSMA-CAR comprising an ICOS domain and a CD3zeta domain comprises the nucleic acid sequence set forth in SEQ ID NO:219.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-PTM-CD28. In one embodiment, the CAR is a human 2F5 PSMA-CAR comprising a variant ICOS domain and a CD3zeta domain. Accordingly, in an exemplary embodiment, a nucleic acid of the present invention comprises from 5' to 3': a nucleic acid sequence encoding PD1$^{A132L}$-PTM-CD28, a nucleic acid sequence encoding a linker comprising F2A, and a nucleic acid sequence encoding a human 2F5 PSMA-CAR comprising a variant ICOS domain and a CD3zeta domain. In one embodiment, the nucleic acid comprising from 5' to 3': a nucleic acid sequence encoding PD1$^{A132L}$-PTM-CD28, a nucleic acid sequence encoding a linker comprising F2A, and a nucleic acid sequence encoding a human 2F5 PSMA-CAR comprising a variant ICOS domain and a CD3zeta domain, comprises the nucleic acid sequence set forth below:

(SEQ ID NO: 220)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA

TTACCAGCCCTATGCCCACCACGCGACTTCGCAGCCTATCGCTCCGTGA

AACAGACTTTGAATTTTGACCTTCTCAAGTTGGCGGGAGACGTGGAGTCC

AACCCAGGGCCGATGGCCTTACCAGTGACCGCCTTGCTCCTGCCGCTGGC

CTTGCTGCTCCACGCCGCCAGGCCGGAGGTGCAGCTGGTGCAGTCTGGAG

CAGAGGTGAAAAAGCCCGGGGAGTCTCTGAAGATCTCCTGTAAGGGTTCT

GGATACAGTTTTACCAGCAACTGGATCGGCTGGGTGCGCCAGATGCCCGG

GAAAGGCCTGGAGTGGATGGGGATCATCTATCCTGGTGACTCTGATACCA

GATACAGCCCGTCCTTCCAAGGCCAGGTCACCATCTCAGCCGACAAGTCC

ATCAGCACCGCCTACCTGCAGTGGAACAGCCTGAAGGCCTCGGACACCGC

CATGTATTACTGTGCGAGACAAACTGGTTTCCTCTGGTCCTTCGATCTCT

GGGGCCGTGGCACCCTGGTCACTGTCTCCTCAGGTGGCGGTGGCTCGGGC

GGTGGTGGGTCGGGTGGCGGCGGATCTGCCATCCAGTTGACCCAGTCTCC

-continued
ATCCTCCCTGTCTGCATCTGTAGGAGACAGAGTCACCATCACTTGCCGGG

CAAGTCAGGACATTAGCAGTGCTTTAGCCTGGTATCAGCAGAAACCGGGG

AAAGCTCCTAAGCTCCTGATCTATGATGCCTCCAGTTTGGAAAGTGGGGT

CCCATCAAGGTTCAGCGGCAGTGGATCTGGGACAGATTTCACTCTCACCA

TCAGCAGCCTGCAGCCTGAAGATTTTGCAACTTATTACTGTCAACAGTTT

AATAGTTACCCGCTCACTTTCGGCGGAGGGACCAAGGTGGAGATCAAAAT

CAAAACCACGACGCCAGCGCCGCGACCACCAACACCGGCGCCCACCATCG

CGTCGCAGCCCCTGTCCCTGCGCCCAGAGGCGTGCCGGCCAGCGGCGGGG

GGCGCAGTGCACACGAGGGGGCTGGACTTCGCCTGTGATTTCTGGTTACC

CATAGGATGTGCAGCCTTTGTTGTAGTCTGCATTTTGGGATGCATACTTA

TTTGTTGGCTTACAAAAAAGAAGTATTCATCCAGTGTGCACGACCCTAAC

GGTGAATACATGAACATGAGAGCAGTGAACACAGCCAAAAAATCCAGACT

CACAGATGTGACCCTAAGAGTGAAGTTCAGCAGGAGCGCAGACGCCCCCG

CGTACCAGCAGGGCCAGAACCAGCTCTATAACGAGCTCAATCTAGGACGA

AGAGAGGAGTACGATGTTTTGGACAAGAGACGTGGCCGGGACCCTGAGAT

GGGGGGAAAGCCGCAGAGAAGGAAGAACCCTCAGGAAGGCCTGTACAATG

AACTGCAGAAAGATAAGATGGCGGAGGCCTACAGTGAGATTGGGATGAAA

GGCGAGCGCCGGAGGGGCAAGGGGCACGATGGCCTTTACCAGGGTCTCAG

TACAGCCACCAAGGACACCTACGACGCCCTTCACATGCAGGCCCTGCCCC

CTCGC.

Tolerable variations of the nucleic acid sequence encoding PD1$^{A132L}$-PTM-CD28 and a human 2F5 PSMA-CAR comprising a variant ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:220. In one embodiment, the nucleic acid sequence encoding for PD1$^{A132L}$-PTM-CD28 and human 2F5 PSMA-CAR comprising a variant ICOS domain and a CD3zeta domain comprises the nucleic acid sequence set forth in SEQ ID NO:220.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-4-1BB. In one embodiment, the CAR is a human 2F5 PSMA-CAR comprising an ICOS domain and a CD3zeta domain. Accordingly, in an exemplary embodiment, a nucleic acid of the present invention comprises from 5' to 3': a nucleic acid sequence encoding PD1$^{A132L}$-4-1BB, a nucleic acid sequence encoding a linker comprising F2A, and a nucleic acid sequence encoding a human 2F5 PSMA-CAR comprising an ICOS domain and a CD3zeta domain. In one embodiment, the nucleic acid comprising from 5' to 3': a nucleic acid sequence encoding PD1$^{A132L}$-4-1BB, a nucleic acid sequence encoding a linker comprising F2A, and a nucleic acid sequence encoding a human 2F5 PSMA- CAR comprising an ICOS domain and a CD3zeta domain, comprises the nucleic acid sequence set forth below:

(SEQ ID NO: 221)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTGGTGAAACAGACTTTGAATTTTGACCTTCTCAAGTTGGCG

GGAGACGTGGAGTCCAACCCAGGGCCGATGGCCTTACCAGTGACCGCTT

GCTCCTGCCGCTGGCCTTGCTGCTCCACGCCGCCAGGCCGGAGGTGCAGC

TGGTGCAGTCTGGAGCAGAGGTGAAAAAGCCCGGGGAGTCTCTGAAGATC

TCCTGTAAGGGTTCTGGATACAGTTTTACCAGCAACTGGATCGGCTGGGT

GCGCCAGATGCCCGGGAAAGGCCTGGAGTGGATGGGGATCATCTATCCTG

GTGACTCTGATACCAGATACAGCCCGTCCTTCCAAGGCCAGGTCACCATC

TCAGCCGACAAGTCCATCAGCACCGCCTACCTGCAGTGGAACAGCCTGAA

GGCCTCGGACACCGCCATGTATTACTGTGCGAGACAAACTGGTTTCCTCT

GGTCCTTCGATCTCTGGGGCCGTGGCACCCTGGTCACTGTCTCCTCAGGT

GGCGGTGGCTCGGGCGGTGGTGGGTCGGGTGGCGGCGGATCTGCCATCCA

GTTGACCCAGTCTCCATCCTCCCTGTCTGCATCTGTAGGAGACAGAGTCA

CCATCACTTGCCGGGCAAGTCAGGACATTAGCAGTGCTTTAGCCTGGTAT

CAGCAGAAACCGGGGAAAGCTCCTAAGCTCCTGATCTATGATGCCTCCAG

TTTGGAAAGTGGGGTCCCATCAAGGTTCAGCGGCAGTGGATCTGGGACAG

ATTTCACTCTCACCATCAGCAGCCTGCAGCCTGAAGATTTTGCAACTTAT

TACTGTCAACAGTTTAATAGTTACCCGCTCACTTTCGGCGGAGGGACCAA

GGTGGAGATCAAAATCAAAACCACGACGCCAGCGCCGCGACCACCAACAC

CGGCGCCCACCATCGCGTCGCAGCCCCTGTCCCTGCGCCCAGAGGCGTGC

CGGCCAGCGGCGGGGGCGCAGTGCACACGAGGGGGCTGGACTTCGCCTG

TGATTTCTGGTTACCCATAGGATGTGCAGCCTTTGTTGTAGTCTGCATTT

TGGGATGCATACTTATTTGTTGGCTTACAAAAAAGAAGTATTCATCCAGT

GTGCACGACCCTAACGGTGAATACATGTTCATGAGAGCAGTGAACACAGC

CAAAAAATCCAGACTCACAGATGTGACCCTAAGAGTGAAGTTCAGCAGGA

-continued

GCGCAGACGCCCCCGCGTACCAGCAGGGCCAGAACCAGCTCTATAACGAG

CTCAATCTAGGACGAAGAGAGGAGTACGATGTTTTGGACAAGAGACGTGG

CCGGGACCCTGAGATGGGGGGAAAGCCGCAGAGAAGGAAGAACCCTCAGG

AAGGCCTGTACAATGAACTGCAGAAAGATAAGATGGCGGAGGCCTACAGT

GAGATTGGGATGAAAGGCGAGCGCCGGAGGGGCAAGGGGCACGATGGCCT

TTACCAGGGTCTCAGTACAGCCACCAAGGACACCTACGACGCCCTTCACA

TGCAGGCCCTGCCCCCTCGC.

Tolerable variations of the nucleic acid sequence encoding PD1$^{A132L}$-4-1BB and a human 2F5 PSMA-CAR comprising an ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:221. In one embodiment, the nucleic acid sequence encoding for PD1$^{A132L}$-4-1BB and human 2F5 PSMA-CAR comprising an ICOS domain and a CD3zeta domain comprises the nucleic acid sequence set forth in SEQ ID NO:221.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is PD1$^{A132L}$-4-1BB. In one embodiment, the CAR is a human 2F5 PSMA-CAR comprising a variant ICOS domain and a CD3zeta domain. Accordingly, in an exemplary embodiment, a nucleic acid of the present invention comprises from 5' to 3': a nucleic acid sequence encoding PD1$^{A132L}$-4-1BB, a nucleic acid sequence encoding a linker comprising F2A, and a nucleic acid sequence encoding a human 2F5 PSMA-CAR comprising a variant ICOS domain and a CD3zeta domain. In one embodiment, the nucleic acid comprising from 5' to 3': a nucleic acid sequence encoding PD1$^{A132L}$-4-1BB, a nucleic acid sequence encoding a linker comprising F2A, and a nucleic acid sequence encoding a human 2F5 PSMA-CAR comprising a variant ICOS domain and a CD3zeta domain, comprises the nucleic acid sequence set forth below:

(SEQ ID NO: 222)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

-continued
```
GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTGGTGAAACAGACTTTGAATTTTGACCTTCTCAAGTTGGCG

GGAGACGTGGAGTCCAACCCAGGGCCGATGGCCTTACCAGTGACCGCCTT

GCTCCTGCCGCTGGCCTTGCTGCTCCACGCCGCCAGGCCGGAGGTGCAGC

TGGTGCAGTCTGGAGCAGAGGTGAAAAAGCCCGGGGAGTCTCTGAAGATC

TCCTGTAAGGGTTCTGGATACAGTTTTACCAGCAACTGGATCGGCTGGGT

GCGCCAGATGCCCGGGAAAGGCCTGGAGTGGATGGGGATCATCTATCCTG

GTGACTCTGATACCAGATACAGCCCGTCCTTCCAAGGCCAGGTCACCATC

TCAGCCGACAAGTCCATCAGCACCGCCTACCTGCAGTGGAACAGCCTGAA

GGCCTCGGACACCGCCATGTATTACTGTGCGAGACAAACTGGTTTCCTCT

GGTCCTTCGATCTCTGGGGCCGTGGCACCCTGGTCACTGTCTCCTCAGGT

GGCGGTGGCTCGGGCGGTGGTGGGTCGGGTGGCGGCGGATCTGCCATCCA

GTTGACCCAGTCTCCATCCTCCCTGTCTGCATCTGTAGGAGACAGAGTCA

CCATCACTTGCCGGGCAAGTCAGGACATTAGCAGTGCTTTAGCCTGGTAT

CAGCAGAAACCGGGGAAAGCTCCTAAGCTCCTGATCTATGATGCCTCCAG

TTTGGAAAGTGGGGTCCCATCAAGGTTCAGCGGCAGTGGATCTGGGACAG

ATTTCACTCTCACCATCAGCAGCCTGCAGCCTGAAGATTTTGCAACTTAT

TACTGTCAACAGTTTAATAGTTACCCGCTCACTTTCGGCGGAGGGACCAA

GGTGGAGATCAAATCAAAACCACGACGCCAGCGCCGCGACCACCAACAC

CGGCGCCCACCATCGCGTCGCAGCCCCTGTCCCTGCGCCCAGAGGCGTGC

CGGCCAGCGGCGGGGGCGCAGTGCACACGAGGGGGCTGGACTTCGCCTG

TGATTTCTGGTTACCCATAGGATGTGCAGCCTTTGTTGTAGTCTGCATTT

TGGGATGCATACTTATTTGTTGGCTTACAAAAAAGAAGTATTCATCCAGT

GTGCACGACCCTAACGGTGAATACATGAACATGAGAGCAGTGAACACAGC

CAAAAAATCCAGACTCACAGATGTGACCCTAAGAGTGAAGTTCAGCAGGA

GCGCAGACGCCCCGCGTACCAGCAGGGCCAGAACCAGCTCTATAACGAG

CTCAATCTAGGACGAAGAGAGGAGTACGATGTTTTGGACAAGAGACGTGG

CCGGGACCCTGAGATGGGGGGAAAGCCGCAGAGAAGGAAGAACCCTCAGG

AAGGCCTGTACAATGAACTGCAGAAAGATAAGATGGCGGAGGCCTACAGT

GAGATTGGGATGAAAGGCGAGCGCCGGAGGGGCAAGGGGCACGATGGCCT

TTACCAGGGTCTCAGTACAGCCACCAAGGACACCTACGACGCCCTTCACA

TGCAGGCCCTGCCCCCTCGC.
```

Tolerable variations of the nucleic acid sequence encoding PD1$^{A132L}$-4-1BB and a human 2F5 PSMA-CAR comprising a variant ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:222. In one embodiment, the nucleic acid sequence encoding for PD1$^{A132L}$-4-1BB and human 2F5 PSMA-CAR comprising a variant ICOS domain and a CD3zeta domain comprises the nucleic acid sequence set forth in SEQ ID NO:222.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is TIM3-CD28. In one embodiment, the CAR is a human 2F5 PSMA-CAR comprising an ICOS domain and a CD3zeta domain. Accordingly, in an exemplary embodiment, a nucleic acid of the present invention comprises from 5' to 3': a nucleic acid sequence encoding TIM3-CD28, a nucleic acid sequence encoding a linker comprising F2A, and a nucleic acid sequence encoding a human 2F5 PSMA-CAR comprising an ICOS domain and a CD3zeta domain. In one embodiment, the nucleic acid comprising from 5' to 3': a nucleic acid sequence encoding TIM3-CD28, a nucleic acid sequence encoding a linker comprising F2A, and a nucleic acid sequence encoding a human 2F5 PSMA-CAR comprising an ICOS domain and a CD3zeta domain, comprises the nucleic acid sequence set forth below:

```
                                     (SEQ ID NO: 223)
ATGTTTTCACATCTTCCCTTTGACTGTGTCCTGCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC

GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCCGTGAAACAGACTTTGAATTTTGACCTTCTCAAGTTGGCGGGAGACG

TGGAGTCCAACCCAGGGCCGATGGCCTTACCAGTGACCGCCTTGCTCCTG

CCGCTGGCCTTGCTGCTCCACGCCGCCAGGCCGGAGGTGCAGCTGGTGCA

GTCTGGAGCAGAGGTGAAAAAGCCCGGGGAGTCTCTGAAGATCTCCTGTA

AGGGTTCTGGATACAGTTTTACCAGCAACTGGATCGGCTGGGTGCGCCAG

ATGCCCGGGAAAGGCCTGGAGTGGATGGGGATCATCTATCCTGGTGACTC

TGATACCAGATACAGCCCGTCCTTCCAAGGCCAGGTCACCATCTCAGCCG
```

```
ACAAGTCCATCAGCACCGCCTACCTGCAGTGGAACAGCCTGAAGGCCTCG

GACACCGCCATGTATTACTGTGCGAGACAAACTGGTTTCCTCTGGTCCTT

CGATCTCTGGGGCCGTGGCACCCTGGTCACTGTCTCCTCAGGTGGCGGTG

GCTCGGGCGGTGGTGGGTCGGGTGGCGGCGGATCTGCCATCCAGTTGACC

CAGTCTCCATCCTCCCTGTCTGCATCTGTAGGAGACAGAGTCACCATCAC

TTGCCGGGCAAGTCAGGACATTAGCAGTGCTTTAGCCTGGTATCAGCAGA

AACCGGGGAAAGCTCCTAAGCTCCTGATCTATGATGCCTCCAGTTTGGAA

AGTGGGGTCCCATCAAGGTTCAGCGGCAGTGGATCTGGGACAGATTTCAC

TCTCACCATCAGCAGCCTGCAGCCTGAAGATTTTGCAACTTATTACTGTC

AACAGTTTAATAGTTACCCGCTCACTTTCGGCGGAGGGACCAAGGTGGAG

ATCAAAATCAAAACCACGACGCCAGCGCCGCGACCACCAACACCGGCGCC

CACCATCGCGTCGCAGCCCCTGTCCCTGCGCCCAGAGGCGTGCCGGCCAG

CGGCGGGGGCGCAGTGCACACGAGGGGGCTGGACTTCGCCTGTGATTTC

TGGTTACCCATAGGATGTGCAGCCTTTGTTGTAGTCTGCATTTTGGGATG

CATACTTATTTGTTGGCTTACAAAAAAGAAGTATTCATCCAGTGTGCACG

ACCCTAACGGTGAATACATGTTCATGAGAGCAGTGAACACAGCCAAAAAA

TCCAGACTCACAGATGTGACCCTAAGAGTGAAGTTCAGCAGGAGCGCAGA

CGCCCCCGCGTACCAGCAGGGCCAGAACCAGCTCTATAACGAGCTCAATC

TAGGACGAAGAGAGGAGTACGATGTTTTGGACAAGAGACGTGGCCGGGAC

CCTGAGATGGGGGAAAGCCGCAGAGAAGGAAGAACCCTCAGGAAGGCCT

GTACAATGAACTGCAGAAAGATAAGATGGCGGAGGCCTACAGTGAGATTG

GGATGAAAGGCGAGCGCCGGAGGGGCAAGGGGCACGATGGCCTTTACCAG

GGTCTCAGTACAGCCACCAAGGACACCTACGACGCCCTTCACATGCAGGC

CCTGCCCCCTCGC.
```

Tolerable variations of the nucleic acid sequence encoding TIM3-CD28 and a human 2F5 PSMA-CAR comprising an ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:223. In one embodiment, the nucleic acid sequence encoding for TIM3-CD28 and human 2F5 PSMA-CAR comprising an ICOS domain and a CD3zeta domain comprises the nucleic acid sequence set forth in SEQ ID NO:223.

In some embodiments, a nucleic acid of the present disclosure comprises from 5' to 3': a nucleic acid sequence encoding a switch receptor, a nucleic acid sequence encoding a linker comprising F2A, and a nucleic acid sequence encoding a CAR. In one embodiment, the switch receptor is TIM3-CD28. In one embodiment, the CAR is a human 2F5 PSMA-CAR comprising a variant ICOS domain and a CD3zeta domain. Accordingly, in an exemplary embodiment, a nucleic acid of the present invention comprises from 5' to 3': a nucleic acid sequence encoding TIM3-CD28, a nucleic acid sequence encoding a linker comprising F2A, and a nucleic acid sequence encoding a human 2F5 PSMA-CAR comprising a variant ICOS domain and a CD3zeta domain. In one embodiment, the nucleic acid comprising from 5' to 3': a nucleic acid sequence encoding TIM3-CD28, a nucleic acid sequence encoding a linker comprising F2A, and a nucleic acid sequence encoding a human 2F5 PSMA-CAR comprising a variant ICOS domain and a CD3zeta domain, comprises the nucleic acid sequence set forth below:

```
                                        (SEQ ID NO: 224)
ATGTTTTCACATCTTCCCTTTGACTGTGTCCTGCTGCTGCTGCTGCTACT

ACTTACAAGGTCCTCAGAAGTGGAATACAGAGCGGAGGTCGGTCAGAATG

CCTATCTGCCCTGCTTCTACACCCCAGCCGCCCCAGGGAACCTCGTGCCC

GTCTGCTGGGGCAAAGGAGCCTGTCCTGTGTTTGAATGTGGCAACGTGGT

GCTCAGGACTGATGAAAGGGATGTGAATTATTGGACATCCAGATACTGGC

TAAATGGGGATTTCCGCAAAGGAGATGTGTCCCTGACCATAGAGAATGTG

ACTCTAGCAGACAGTGGGATCTACTGCTGCCGAATCCAAATCCCAGGCAT

AATGAATGATGAAAAATTTAACCTGAAGTTGGTCATCAAACCAGCCAAGG

TCACCCCTGCACCGACTCGGCAGAGAGACTTCACTGCAGCCTTTCCAAGG

ATGCTTACCACCAGGGGACATGGCCCAGCAGAGACACAGACACTGGGGAG

CCTCCCTGACATAAATCTAACACAAATATCCACATTGGCCAATGAGTTAC

GGGACTCTAGGTTGGCCAATGACTTACGGGACTCCGGAGCAACCATCAGA

TTTTGGGTGCTGGTGGTGGTTGGTGGAGTCCTGGCTTGCTATAGCTTACT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCCGTGAAACAGACTTTGAATTTTGACCTTCTCAAGTTGGCGGGAGACG

TGGAGTCCAACCCAGGGCCGATGGCCTTACCAGTGACCGCCTTGCTCCTG

CCGCTGGCCTTGCTGCTCCACGCCGCCAGGCCGGAGGTGCAGCTGGTGCA

GTCTGGAGCAGAGGTGAAAAAGCCCGGGGAGTCTCTGAAGATCTCCTGTA

AGGGTTCTGGATACAGTTTTACCAGCAACTGGATCGGCTGGGTGCGCCAG

ATGCCCGGGAAAGGCCTGGAGTGGATGGGGATCATCTATCCTGGTGACTC

TGATACCAGATACAGCCCGTCCTTCCAAGGCCAGGTCACCATCTCAGCCG

ACAAGTCCATCAGCACCGCCTACCTGCAGTGGAACAGCCTGAAGGCCTCG

GACACCGCCATGTATTACTGTGCGAGACAAACTGGTTTCCTCTGGTCCTT

CGATCTCTGGGGCCGTGGCACCCTGGTCACTGTCTCCTCAGGTGGCGGTG

GCTCGGGCGGTGGTGGGTCGGGTGGCGGCGGATCTGCCATCCAGTTGACC

CAGTCTCCATCCTCCCTGTCTGCATCTGTAGGAGACAGAGTCACCATCAC

TTGCCGGGCAAGTCAGGACATTAGCAGTGCTTTAGCCTGGTATCAGCAGA

AACCGGGGAAAGCTCCTAAGCTCCTGATCTATGATGCCTCCAGTTTGGAA

AGTGGGGTCCCATCAAGGTTCAGCGGCAGTGGATCTGGGACAGATTTCAC

TCTCACCATCAGCAGCCTGCAGCCTGAAGATTTTGCAACTTATTACTGTC

AACAGTTTAATAGTTACCCGCTCACTTTCGGCGGAGGGACCAAGGTGGAG
```

-continued
ATCAAAATCAAAACCACGACGCCAGCGCCGCGACCACCAACACCGGCGCC

CACCATCGCGTCGCAGCCCCTGTCCCTGCGCCCAGAGGCGTGCCGGCCAG

CGGCGGGGGCGCAGTGCACACGAGGGGGCTGGACTTCGCCTGTGATTTC

TGGTTACCCATAGGATGTGCAGCCTTTGTTGTAGTCTGCATTTTGGGATG

CATACTTATTTGTTGGCTTACAAAAAAGAAGTATTCATCCAGTGTGCACG

ACCCTAACGGTGAATACATGAACATGAGAGCAGTGAACACAGCCAAAAAA

TCCAGACTCACAGATGTGACCCTAAGAGTGAAGTTCAGCAGGAGCGCAGA

CGCCCCCGCGTACCAGCAGGGCCAGAACCAGCTCTATAACGAGCTCAATC

TAGGACGAAGAGAGGAGTACGATGTTTTGGACAAGAGACGTGGCCGGGAC

CCTGAGATGGGGGAAAGCCGCAGAGAAGGAAGAACCCTCAGGAAGGCCT

GTACAATGAACTGCAGAAAGATAAGATGGCGGAGGCCTACAGTGAGATTG

GGATGAAAGGCGAGCGCCGGAGGGGCAAGGGGCACGATGGCCTTTACCAG

GGTCTCAGTACAGCCACCAAGGACACCTACGACGCCCTTCACATGCAGGC

CCTGCCCCCTCGC.

Tolerable variations of the nucleic acid sequence encoding TIM3-CD28 and a human 2F5 PSMA-CAR comprising a variant ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:224. In one embodiment, the nucleic acid sequence encoding for TIM3-CD28 and human 2F5 PSMA-CAR comprising a variant ICOS domain and a CD3zeta domain comprises the nucleic acid sequence set forth in SEQ ID NO:224.

In some embodiments, a nucleic acid of the present disclosure comprises from 5' to 3': a nucleic acid sequence encoding a first switch receptor, a nucleic acid sequence encoding a first linker comprising F2A, a nucleic acid sequence encoding a second switch receptor, a nucleic acid encoding a second linker comprising F2A, and a nucleic acid sequence encoding a CAR. In one embodiment, the first switch receptor is TIM3-CD28, and the second switch receptor is PD1$^{A132L}$-4-1BB. In one embodiment, the first switch receptor is PD1$^{A132L}$-4-1BB, and the second switch receptor is TIM3-CD28. In one embodiment, the CAR is a human 2F5 PSMA-CAR comprising an ICOS domain and a CD3zeta domain. In one embodiment, the first and second linkers are the same. In one embodiment, the first and second linkers are different. Accordingly, in an exemplary embodiment, a nucleic acid of the present invention comprises from 5' to 3': a nucleic acid sequence encoding PD1$^{A132L}$-4-1BB, a nucleic acid sequence encoding a first linker comprising F2A, a nucleic acid sequence encoding TIM3-CD28, a nucleic acid sequence encoding a second linker comprising F2A, and a nucleic acid sequence encoding a human 2F5 PSMA-CAR comprising an ICOS domain and a CD3zeta domain. In one embodiment, the nucleic acid comprising from 5' to 3': a nucleic acid sequence encoding PD1$^{A132L}$-4-1BB, a nucleic acid sequence encoding a first linker comprising F2A, a nucleic acid sequence encoding TIM3-CD28, a nucleic acid encoding a second linker comprising F2A, and a nucleic acid sequence encoding a human 2F5 PSMA-CAR comprising an ICOS domain and a CD3zeta domain, comprises the nucleic acid sequence set forth below:

(SEQ ID NO: 225)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTGGTGAAGCAGACGTTGAACTTCGATTTGCTCAAACTTGCC

GGTGACGTGGAATCCAATCCGGGGCCGATGTTTTCACATCTTCCCTTTGA

CTGTGTCCTGCTGCTGCTGCTGCTACTACTTACAAGGTCCTCAGAAGTGG

AATACAGAGCGGAGGTCGGTCAGAATGCCTATCTGCCCTGCTTCTACACC

CCAGCCGCCCCAGGGAACCTCGTGCCCGTCTGCTGGGGCAAAGGAGCCTG

TCCTGTGTTTGAATGTGGCAACGTGGTGCTCAGGACTGATGAAAGGGATG

TGAATTATTGGACATCCAGATACTGGCTAAATGGGGATTTCCGCAAAGGA

GATGTGTCCCTGACCATAGAGAATGTGACTCTAGCAGACAGTGGGATCTA

CTGCTGCCGAATCCAAATCCCAGGCATAATGAATGATGAAAAATTTAACC

TGAAGTTGGTCATCAAACCAGCCAAGGTCACCCCTGCACCGACTCGGCAG

AGAGACTTCACTGCAGCCTTTCCAAGGATGCTTACCACCAGGGGACATGG

CCCAGCAGAGACACAGACACTGGGGAGCCTCCCTGACATAAATCTAACAC

AAATATCCACATTGGCCAATGAGTTACGGGACTCTAGGTTGGCCAATGAC

TTACGGGACTCCGGAGCAACCATCAGATTTTGGGTGCTGGTGGTGGTTGG

TGGAGTCCTGGCTTGCTATAGCTTACTAGTAACAGTGGCCTTTATTATTT

TCTGGGTGAGGAGTAAGAGGAGCAGGCTCCTGCACAGTGACTACATGAAC

ATGACTCCCCGCCGCCCCGGGCCCACCCGCAAGCATTACCAGCCCTATGC

CCCACCACGCGACTTCGCAGCCTATCGCTCCGTGAAACAGACTTTGAATT

TTGACCTTCTCAAGTTGGCGGGAGACGTGGAGTCCAACCCAGGGCCGATG

GCCTTACCAGTGACCGCCTTGCTCCTGCCGCTGGCCTTGCTGCTCCACGC

CGCCAGGCCGGAGGTGCAGCTGGTGCAGTCTGGAGCAGAGGTGAAAAAGC

CCGGGGAGTCTCTGAAGATCTCCTGTAAGGGTTCTGGATACAGTTTTACC

AGCAACTGGATCGGCTGGGTGCGCCAGATGCCCGGGAAAGGCCTGGAGTG

```
GATGGGGATCATCTATCCTGGTGACTCTGATACCAGATACAGCCCGTCCT

TCCAAGGCCAGGTCACCATCTCAGCCGACAAGTCCATCAGCACCGCCTAC

CTGCAGTGGAACAGCCTGAAGGCCTCGGACACCGCCATGTATTACTGTGC

GAGACAAACTGGTTTCCTCTGGTCCTTCGATCTCTGGGGCCGTGGCACCC

TGGTCACTGTCTCCTCAGGTGGCGGTGGCTCGGGCGGTGGTGGGTCGGGT

GGCGGCGGATCTGCCATCCAGTTGACCCAGTCTCCATCCTCCCTGTCTGC

ATCTGTAGGAGACAGAGTCACCATCACTTGCCGGGCAAGTCAGGACATTA

GCAGTGCTTTAGCCTGGTATCAGCAGAAACCGGGGAAAGCTCCTAAGCTC

CTGATCTATGATGCCTCCAGTTTGGAAAGTGGGGTCCCATCAAGGTTCAG

CGGCAGTGGATCTGGGACAGATTTCACTCTCACCATCAGCAGCCTGCAGC

CTGAAGATTTTGCAACTTATTACTGTCAACAGTTTAATAGTTACCCGCTC

ACTTTCGGCGGAGGGACCAAGGTGGAGATCAAAATCAAAACCACGACGCC

AGCGCCGCGACCACCAACACCGGCGCCCACCATCGCGTCGCAGCCCCTGT

CCCTGCGCCCAGAGGCGTGCCGGCCAGCGGCGGGGGCGCAGTGCACACG

AGGGGGCTGGACTTCGCCTGTGATTTCTGGTTACCCATAGGATGTGCAGC

CTTTGTTGTAGTCTGCATTTTGGGATGCATACTTATTTGTTGGCTTACAA

AAAAGAAGTATTCATCCAGTGTGCACGACCCTAACGGTGAATACATGTTC

ATGAGAGCAGTGAACACAGCCAAAAAATCCAGACTCACAGATGTGACCCT

AAGAGTGAAGTTCAGCAGGAGCGCAGACGCCCCCGCGTACCAGCAGGGCC

AGAACCAGCTCTATAACGAGCTCAATCTAGGACGAAGAGAGGAGTACGAT

GTTTTGGACAAGAGACGTGGCCGGGACCCTGAGATGGGGGGAAAGCCGCA

GAGAAGGAAGAACCCTCAGGAAGGCCTGTACAATGAACTGCAGAAAGATA

AGATGGCGGAGGCCTACAGTGAGATTGGGATGAAAGGCGAGCGCCGGAGG

GGCAAGGGGCACGATGGCCTTTACCAGGGTCTCAGTACAGCCACCAAGGA

CACCTACGACGCCCTTCACATGCAGGCCCTGCCCCCTCGC.
```

Tolerable variations of the nucleic acid sequence encoding $PD1^{4132L}$-4-1BB, TIM3-CD28, and a human 2F5 PSMA-CAR comprising an ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:225. In one embodiment, the nucleic acid sequence encoding for $PD1^{4132L}$-4-1BB, TIM3-CD28, and a human 2F5 PSMA-CAR comprising an ICOS domain and a CD3zeta domain comprises the nucleic acid sequence set forth in SEQ ID NO:225.

In some embodiments, a nucleic acid of the present disclosure comprises from 5' to 3': a nucleic acid sequence encoding a first switch receptor, a nucleic acid sequence encoding a first linker comprising F2A, a nucleic acid sequence encoding a second switch receptor, a nucleic acid encoding a second linker comprising F2A, and a nucleic acid sequence encoding a CAR. In one embodiment, the first switch receptor is TIM3-CD28, and the second switch receptor is $PD1^{4132L}$-4-1BB. In one embodiment, the first switch receptor is $PD1^{4132L}$-4-1BB, and the second switch receptor is TIM3-CD28. In one embodiment, the CAR is a human 2F5 PSMA-CAR comprising a variant ICOS domain and a CD3zeta domain. In one embodiment, the first and second linkers are the same. In one embodiment, the first and second linkers are different. Accordingly, in an exemplary embodiment, a nucleic acid of the present invention comprises from 5' to 3': a nucleic acid sequence encoding $PD1^{4132L}$-4-1BB, a nucleic acid sequence encoding a first linker comprising F2A, a nucleic acid sequence encoding TIM3-CD28, a nucleic acid sequence encoding a second linker comprising F2A, and a nucleic acid sequence encoding a human 2F5 PSMA-CAR comprising a variant ICOS domain and a CD3zeta domain. In one embodiment, the nucleic acid comprising from 5' to 3': a nucleic acid sequence encoding $PD1^{4132L}$-4-1BB, a nucleic acid sequence encoding a first linker comprising F2A, a nucleic acid sequence encoding TIM3-CD28, a nucleic acid encoding a second linker comprising F2A, and a nucleic acid sequence encoding a human 2F5 PSMA-CAR comprising a variant ICOS domain and a CD3zeta domain, comprises the nucleic acid sequence set forth below:

```
                                          (SEQ ID NO: 226)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTGGTGAAGCAGACGTTGAACTTCGATTTGCTCAAACTTGCC

GGTGACGTGGAATCCAATCCGGGGCCGATGTTTTCACATCTTCCCTTTGA

CTGTGTCCTGCTGCTGCTGCTGCTACTACTTACAAGGTCCTCAGAAGTGG

AATACAGAGCGGAGGTCGGTCAGAATGCCTATCTGCCCTGCTTCTACACC

CCAGCCGCCCCAGGGAACCTCGTGCCCGTCTGCTGGGGCAAAGGAGCCTG

TCCTGTGTTTGAATGTGGCAACGTGGTGCTCAGGACTGATGAAAGGGATG

TGAATTATTGGACATCCAGATACTGGCTAAATGGGGATTTCCGCAAAGGA

GATGTGTCCCTGACCATAGAGAATGTGACTCTAGCAGACAGTGGGATCTA

CTGCTGCCGAATCCAAATCCCAGGCATAATGAATGATGAAAAATTTAACC

TGAAGTTGGTCATCAAACCAGCCAAGGTCACCCCTGCACCGACTCGGCAG

AGAGACTTCACTGCAGCCTTTCCAAGGATGCTTACCACCAGGGGACATGG

CCCAGCAGAGACACAGACACTGGGGAGCCTCCCTGACATAAATCTAACAC
```

-continued

```
AAATATCCACATTGGCCAATGAGTTACGGGACTCTAGGTTGGCCAATGAC

TTACGGGACTCCGGAGCAACCATCAGATTTTGGGTGCTGGTGGTGGTTGG

TGGAGTCCTGGCTTGCTATAGCTTACTAGTAACAGTGGCCTTTATTATTT

TCTGGGTGAGGAGTAAGAGGAGCAGGCTCCTGCACAGTGACTACATGAAC

ATGACTCCCCGCCGCCCGGGCCCACCCGCAAGCATTACCAGCCCTATGC

CCCACCACGCGACTTCGCAGCCTATCGCTCCGTGAAACAGACTTTGAATT

TTGACCTTCTCAAGTTGGCGGGAGACGTGGAGTCCAACCCAGGGCCGATG

GCCTTACCAGTGACCGCCTTGCTCCTGCCGCTGGCCTTGCTGCTCCACGC

CGCCAGGCCGGAGGTGCAGCTGGTGCAGTCGGAGCAGAGGTGAAAAAGC

CCGGGGAGTCTCTGAAGATCTCCTGTAAGGGTTCTGGATACAGTTTTACC

AGCAACTGGATCGGCTGGGTGCGCCAGATGCCCGGGAAAGGCCTGGAGTG

GATGGGGATCATCTATCCTGGTGACTCTGATACCAGATACAGCCCGTCCT

TCCAAGGCCAGGTCACCATCTCAGCCGACAAGTCCATCAGCACCGCCTAC

CTGCAGTGGAACAGCCTGAAGGCCTCGGACACCGCCATGTATTACTGTGC

GAGACAAACTGGTTTCCTCTGGTCCTTCGATCTCTGGGGCCGTGGCACCC

TGGTCACTGTCTCCTCAGGTGGCGGTGGCTCGGGCGGTGGTGGGTCGGGT

GGCGGCGGATCTGCCATCCAGTTGACCCAGTCTCCATCCTCCCTGTCTGC

ATCTGTAGGAGACAGAGTCACCATCACTTGCCGGGCAAGTCAGGACATTA

GCAGTGCTTTAGCCTGGTATCAGCAGAAACCGGGGAAAGCTCCTAAGCTC

CTGATCTATGATGCCTCCAGTTTGGAAAGTGGGGTCCCATCAAGGTTCAG

CGGCAGTGGATCTGGGACAGATTTCACTCTCACCATCAGCAGCCTGCAGC

CTGAAGATTTTGCAACTTATTACTGTCAACAGTTTAATAGTTACCCGCTC

ACTTTCGGCGGAGGGACCAAGGTGGAGATCAAAATCAAAACCACGACGCC

AGCGCCGCGACCACCAACACCGGCGCCCACCATCGCGTCGCAGCCCCTGT

CCCTGCGCCCAGAGGCGTGCCGGCCAGCGGCGGGGGCGCAGTGCACACG

AGGGGGCTGGACTTCGCCTGTGATTTCTGGTTACCCATAGGATGTGCAGC

CTTTGTTGTAGTCTGCATTTTGGGATGCATACTTATTTGTTGGCTTACAA

AAAAGAAGTATTCATCCAGTGTGCACGACCCTAACGGTGAATACATGAAC

ATGAGAGCAGTGAACACAGCCAAAAAATCCAGACTCACAGATGTGACCCT

AAGAGTGAAGTTCAGCAGGAGCGCAGACGCCCCCGCGTACCAGCAGGGCC

AGAACCAGCTCTATAACGAGCTCAATCTAGGACGAAGAGAGGAGTACGAT

GTTTTGGACAAGAGACGTGGCCGGGACCCTGAGATGGGGGAAAGCCGCA

GAGAAGGAAGAACCCTCAGGAAGGCCTGTACAATGAACTGCAGAAAGATA

AGATGGCGGAGGCCTACAGTGAGATTGGGATGAAAGGCGAGCGCCGGAGG

GGCAAGGGGCACGATGGCCTTTACCAGGGTCTCAGTACAGCCACCAAGGA

CACCTACGACGCCCTTCACATGCAGGCCCTGCCCCCTCGC.
```

Tolerable variations of the nucleic acid sequence encoding PD1$^{A132L}$-4-1BB, TIM3-CD28, and a human 2F5 PSMA-CAR comprising a variant ICOS domain and a CD3zeta domain will be known to those of skill in the art. For example, in some embodiments, the nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO:226. In one embodiment, the nucleic acid sequence encoding for PD1$^{A132L}$-4-1BB, TIM3-CD28, and a human 2F5 PSMA-CAR comprising a variant ICOS domain and a CD3zeta domain comprises the nucleic acid sequence set forth in SEQ ID NO:226.

In some embodiments, a nucleic acid of the present disclosure may be operably linked to a transcriptional control element, e.g., a promoter, and enhancer, etc. Suitable promoter and enhancer elements are known to those of skill in the art.

For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., alac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as Escherichia coli include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a TCR/CAR inducible expression cassette. In one embodiment, the TCR/CAR inducible expression cassette is for the production of a transgenic polypeptide product that is released upon TCR/CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the TCR/CAR and/or the dominant negative receptor and/or switch receptor into an immune cell or precursor thereof (e.g., a T cell). Accordingly, an expression vector (e.g., a lentiviral vector) of the present invention may comprise a nucleic acid encoding for a TCR/CAR and/or the dominant negative receptor and/or switch receptor. In some embodiments, the expression vector (e.g., lentiviral vector) will comprise additional elements that will aid in the functional expression of the TCR/CAR and/or the dominant negative receptor and/or switch receptor encoded therein. In some embodiments, an expression vector comprising a nucleic acid encoding for a TCR/CAR and/or the dominant negative receptor and/or switch receptor further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a TCR/CAR and/or the dominant negative receptor and/or switch receptor encoding nucleic acid sequence). Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a TCR/CAR and/or the dominant negative receptor and/or switch receptor.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a TCR/CAR and/or the dominant negative receptor and/or switch receptor of the present disclosure. Methods for introducing RNA into a host cell are known in the art. See, e.g., Zhao et al. Cancer Res. (2010) 15: 9053. Introducing RNA comprising a nucleotide sequence encoding a TCR/CAR and/or the dominant negative receptor and/or switch receptor of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a TCR/CAR and/or the dominant negative receptor and/or switch receptor of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

F. Modified Immune Cells

The present invention provides a modified immune cell or precursor cell thereof (e.g., a T cell), comprising a CAR and/or a dominant negative receptor and/or a switch receptor. Accordingly, such modified cells possess the specificity directed by the CAR that is expressed therein. For example, a modified cell of the present invention comprising a PSMA-CAR possesses specificity for PSMA on a target cell.

In some embodiments, a modified cell of the present invention comprises a CAR. In one embodiment, a modified cell of the present invention comprises a CAR having affinity for a prostate-specific membrane antigen (PSMA) on a target cell. In some embodiments, a modified cell of the present invention comprises a dominant negative receptor and/or a switch receptor. In one embodiment, a modified cell of the present invention comprises a dominant negative receptor capable of reducing the effect of a negative signal transduction molecule in the microenvironment. In one embodiment, a modified cell of the present invention comprises a switch receptor capable of reducing the effect of a negative signal transduction molecule in the microenvironment, and converting the negative signal into a positive signal within the modified cell. In some embodiments, a modified cell of the present invention comprises a CAR and a dominant negative receptor and/or a switch receptor. In one embodiment, a modified cell of the present invention comprises a CAR having affinity for PSMA on a target cell, and a dominant negative receptor and/or a switch receptor. Modified cells comprising a dominant negative receptor and/or a switch receptor of the present invention are able to engage negative signal transduction molecules (e.g., inhibitory ligands) in the microenvironment by virtue of their respective extracellular domains. In some embodiments, a modified cell of the present invention comprising a dominant negative receptor is capable of reducing the effect of a negative signal transduction molecule in the microenvironment, wherein the dominant negative receptor comprises an extracellular domain associated with the negative signal. In some embodiments, a modified cell of the present invention comprising a switch receptor is capable of converting the effect of a negative signal transduction molecule in the microenvironment into a positive signal, wherein the switch receptor comprises an extracellular domain associated with the negative signal and an intracellular domain associated with the positive signal.

In an exemplary embodiment, a modified cell of the present invention comprises a dominant negative receptor that is capable of reducing the effect of a negative signal transduction molecule. In one embodiment, a modified cell of the present invention comprises TGFβRII-DN.

In an exemplary embodiment, a modified cell of the present invention comprises a switch receptor that is capable of converting the effect of a negative signal transduction molecule into a positive (e.g., activating) signal within the modified cell. In one embodiment, a modified cell of the present invention comprises PD1-CTM-CD28. In one embodiment, a modified cell of the present invention comprises PD1$^{A132L}$-PTM-CD28. In one embodiment, a modified cell of the present invention comprises TIM3-CD28.

In an exemplary embodiment, a modified cell of the present invention comprises a PSMA-CAR and a dominant negative receptor that is capable of reducing the effect of a negative signal transduction molecule. In one embodiment, a modified cell of the present invention comprises a murine J591 PSMA-CAR and TGFβRII-DN. In one embodiment, a modified cell of the present invention comprises a humanized J591 PSMA-CAR and TGFβRII-DN. In one embodiment, a modified cell of the present invention comprises a human 1C3 PSMA-CAR and TGFβRII-DN. In one embodiment, a modified cell of the present invention comprises a human 2A10 PSMA-CAR and TGFβRII-DN. In one embodiment, a modified cell of the present invention comprises a human 2F5 PSMA-CAR and TGFβRII-DN. In one embodiment, a modified cell of the present invention comprises a human 2C6 PSMA-CAR and TGFβRII-DN. Such modified cells (e.g., modified T cells) in addition to having affinity for PSMA on a target cell, are capable of reducing inhibitory TGF-β signals from the microenvironment they reside in.

In an exemplary embodiment, a modified cell of the present invention comprises a PSMA-CAR and a switch receptor that is capable of converting the inhibitory effect of a negative signal transduction molecule into a positive signal within the modified cell. In one embodiment, a modified cell of the present invention comprises a murine J591 PSMA-CAR and PD1-CTM-CD28. In one embodiment, a modified cell of the present invention comprises a humanized J591 PSMA-CAR and PD1-PTM-CD28. In one embodiment, a modified cell of the present invention comprises a human 1C3 PSMA-CAR and PD1-CTM-CD28. In one embodiment, a modified cell of the present invention comprises a human 2A10 PSMA-CAR and PD1-CTM-CD28. In one embodiment, a modified cell of the present invention comprises a human 2F5 PSMA-CAR and PD1-CTM-CD28. In one embodiment, a modified cell of the present invention comprises a human 2C6 PSMA-CAR and PD1-CTM-CD28. In one embodiment, a modified cell of the present invention comprises a murine J591 PSMA-CAR and PD1$^{A132L}$-PTM-CD28. In one embodiment, a modified cell of the present invention comprises a humanized J591 PSMA-CAR and PD1$^{A132L}$-PTM-CD28. In one embodiment, a modified cell of the present invention comprises a human 1C3 PSMA-CAR and PD1$^{A132L}$-PTM-CD28. In one embodiment, a modified cell of the present invention comprises a human 2A10 PSMA-CAR and PD1$^{A132L}$-PTM-CD28. In one embodiment, a modified cell of the present invention comprises a human 2F5 PSMA-CAR and PD1$^{A132L}$-PTM-CD28. In one embodiment, a modified cell of the present invention comprises a human 2C6 PSMA-CAR and PD1$^{A132L}$-PTM-CD28. In one embodiment, a modified cell of the present invention comprises a murine J591 PSMA-CAR and TIM3-CD28. In one embodiment, a modified cell of the present invention comprises a humanized J591 PSMA-CAR and TIM3-CD28. In one embodiment, a modified cell of the present invention comprises a human 1C3 PSMA-CAR and TIM3-CD28. In one embodiment, a modified cell of the present invention comprises a human 2A10 PSMA-CAR and TIM3-CD28. In one embodiment, a modified cell of the present invention comprises a human 2F5 PSMA-CAR and TIM3-CD28. In one embodiment, a modified cell of the present invention comprises a human 2C6 PSMA-CAR and TIM3-CD28. In one embodiment, a modified cell of the present invention comprises a murine J591 PSMA-CAR and PD1-4-1BB. In one embodiment, a modified cell of the present invention comprises a humanized J591 PSMA-CAR and PD1-4-1BB. In one embodiment, a modified cell of the present invention comprises a human 1C3 PSMA-CAR and PD1-4-1BB. In one embodiment, a modified cell of the present invention comprises a human 2A10 PSMA-CAR and PD1-4-1BB. In one embodiment, a modified cell of the present invention comprises a human 2F5 PSMA-CAR and PD1-4-1BB. In one embodiment, a modified cell of the present invention comprises a human 2C6 PSMA-CAR and PD1-4-1BB. In one embodiment, a modified cell of the present invention comprises a murine J591 PSMA-CAR and PD1$^{A132L}$-4-1BB. In one embodiment, a modified cell of the present invention comprises a humanized J591 PSMA-CAR and PD1$^{A132L}$-4-1BB. In one embodiment, a modified cell of the present invention comprises a human 1C3 PSMA-CAR and PD1$^{A132L}$-4-1BB. In one embodiment, a modified cell of the present invention comprises a human 2A10 PSMA-CAR and PD1$^{A132L}$-4-1BB. In one embodiment, a modified cell of the present invention comprises a human 2F5 PSMA-CAR and PD1$^{A132L}$-4-1BB. In one embodiment, a modified cell of the present invention comprises a human 2C6 PSMA-CAR and PD1$^{A132L}$-4-1BB. In one embodiment, a modified cell of the present invention comprises a murine J591 PSMA-CAR and TGFβR-IL12Rβ1. In one embodiment, a modified cell of the present invention comprises a humanized J591 PSMA-CAR and TGFβR-IL12Rβ1. In one embodiment, a modified cell of the present invention comprises a human 1C3 PSMA-CAR and TGFβR-IL12Rβ1. In one embodiment, a modified cell of the present invention comprises a human 2A10 PSMA-CAR and TGFβR-IL12Rβ1. In one embodiment, a modified cell of the present invention comprises a human 2F5 PSMA-CAR and TGFβR-IL12Rβ1. In one embodiment, a modified cell of the present invention comprises a human 2C6 PSMA-CAR and TGFβR-IL12Rβ1. In one embodiment, a modified cell of the present invention comprises a murine J591 PSMA-CAR and TGFβR-IL12Rβ2. In one embodiment, a modified cell of the present invention comprises a humanized J591 PSMA-CAR and TGFβR-IL12Rβ2. In one embodiment, a modified cell of the present invention comprises a human 1C3 PSMA-CAR and TGFβR-IL12Rβ2. In one embodiment, a modified cell of the present invention comprises a human 2A10 PSMA-CAR and TGFβR-IL12Rβ2. In one embodiment, a modified cell of the present invention comprises a human 2F5 PSMA-CAR and TGFβR-IL12Rβ2. In one embodiment, a modified cell of the present invention comprises a human 2C6 PSMA-CAR and TGFβR-IL12Rβ2. Such modified cells (e.g., modified T cells) in addition to having affinity for PSMA on a target cell, are capable of converting inhibitory PD-1 or TGFβ signals from the microenvironment into a positive (e.g., activating) signal within the modified cell. Such modified cells (e.g., modified T cells) in addition to having affinity for PSMA on a target cell, are capable of converting inhibitory PD-1 or TIM-3 signals from the microenvironment into a positive (e.g., activating) CD28 signal within the modified cell.

In an exemplary embodiment, a modified cell of the present invention comprises a nucleic acid encoding a bispecific antibody. In one embodiment, such modified cells can secrete the bispecific antibody outside of the modified cell. In one embodiment, a modified cell of the present invention comprises a nucleic acid encoding a bispecific antibody, wherein the bispecific antibody comprises more than one antigen binding domain, wherein at least one antigen binding domain binds to a negative signal transduction molecule (e.g., a negative signal transduction molecule found in the microenvironment of the modified cell), and at least one antigen binding domain binds a co-stimulatory molecule on the surface of the modified cell. In one embodiment, a modified cell of the present invention comprises a nucleic acid encoding a 13G4-1211 PD-L1/CD28 bispecific antibody as described herein. In one embodiment, a modified cell of the present invention comprises a nucleic acid encoding a 10A5-1412 PD-L1/CD28 bispecific antibody as described herein. In one embodiment, a modified cell of the present invention comprises a nucleic acid encoding a 1B12-1412 PD-L1/CD28 bispecific antibody as described herein. In one embodiment, a modified cell of the present invention comprises a nucleic acid encoding a TGFβR-1-1412 TGFβRII/CD28 bispecific antibody as described herein. In one embodiment, a modified cell of the present invention comprises a nucleic acid encoding a TGFβR-3-1412 TGFβRII/CD28 bispecific antibody as described herein.

In an exemplary embodiment, a modified cell of the present invention comprises a PSMA-CAR, a dominant negative receptor and/or a switch receptor, and may further comprise a nucleic acid encoding a bispecific antibody. Such modified cells (e.g., modified T cells) in addition to having affinity for PSMA on a target cell, are capable of reducing inhibitory signals from the microenvironment they reside in, and secreting the bispecific antibody into the microenvironment they reside in. In such cells, the activity of the bispecific antibody may further increase the activation of the modified cell (e.g., modified T cell). In one embodiment, a modified cell of the present invention comprises a PSMA-CAR selected from the group consisting of a murine J591 PSMA-CAR, a humanized J591 PSMA-CAR, a human 1C3 PSMA-CAR, a human 2A10 PSMA-CAR, a human 2F5 PSMA-CAR, and a human 2C6 PSMA-CAR; TGFβRII-DN; and expresses and secretes a bispecific antibody selected from the group consisting of a 13G4-1211 PD-L1/CD28 bispecific antibody, a 10A5-1412 PD-L1/CD28 bispecific antibody, a 1B12-1412 PD-L1/CD28 bispecific antibody, a TGFβR-1-1412 TGFβRII/CD28 bispecific antibody, and a TGFβR-3-1412 TGFβRII/CD28 bispecific antibody.

In an exemplary embodiment, a modified cell of the present invention comprises a PSMA-CAR, a switch receptor, and may further comprise a nucleic acid encoding a bispecific antibody. Such modified cells (e.g., modified T cells) in addition to having affinity for PSMA on a target cell, are capable of converting inhibitory signals from the microenvironment they reside in into a positive (e.g., activating) signal within the modified cell, and secreting the bispecific antibody into the microenvironment they reside in. In such cells, the activity of the bispecific antibody may further increase the activation of the modified cell (e.g., modified T cell). In one embodiment, a modified cell of the present invention comprises a PSMA-CAR selected from the group consisting of a murine J591 PSMA-CAR, a humanized J591 PSMA-CAR, a human 1C3 PSMA-CAR, a human 2A10 PSMA-CAR, a human 2F5 PSMA-CAR, and a human 2C6 PSMA-CAR; a switch receptor selected from the group consisting of a PD1-CTM-CD28 switch receptor, a PD1A132L-PTM-CD28 switch receptor, and a TIM3-CD28 switch receptor; and expresses and secretes a bispecific antibody selected from the group consisting of a 13G4-1211 PD-L1/CD28 bispecific antibody, a 10A5-1412 PD-L1/CD28 bispecific antibody, a 1B12-1412 PD-L1/CD28 bispecific antibody, a TGFβR-1-1412 TGFβRII/CD28 bispecific antibody, and a TGFβR-3-1412 TGFβRII/CD28 bispecific antibody.

Any modified cell comprising a PSMA-CAR of the present invention, a dominant negative receptor and/or a switch receptor of the present invention, and/or expresses and secretes a bispecific antibody of the present invention is envisioned, and can readily be understood and made by a person of skill in the art in view of the disclosure herein.

G. Methods of Producing Modified Immune Cells

The present invention provides methods for producing or generating a modified immune cell or precursor thereof (e.g., a T cell) of the invention for tumor immunotherapy, e.g., adoptive immunotherapy. The cells generally are engineered by introducing one or more nucleic acids encoding a subject CAR, dominant negative receptor and/or switch receptor, and/or bispecific antibody, and/or combinations thereof.

In some embodiments, one or more nucleic acids encoding the subject CAR, dominant negative receptor and/or switch receptor, and/or bispecific antibody is introduced into a cell by an expression vector. Expression vectors comprising a nucleic acid sequence encoding a subject CAR, dominant negative receptor and/or switch receptor, and/or bispecific antibody, and/or combinations thereof, of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the subject CAR, dominant negative receptor and/or switch receptor, and/or bispecific antibody, and/or combinations thereof, in the host cell. In some embodiments, the adenovirus genome is a 36 kb, linear, double stranded DNA, where a foreign DNA sequence (e.g., a nucleic acid encoding a subject CAR, dominant negative receptor and/or switch receptor, and/or bispecific antibody, and/or combinations thereof) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus, which takes advantage of the adenovirus coupled systems. This AAV expression vector has a high frequency of integration into the host genome. It can infect non-dividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding a subject CAR, dominant negative receptor and/or switch receptor, and/or bispecific antibody, and/or combinations thereof) into the viral genome at certain locations to produce a virus that is replication defective. Though the retrovirus vectors are able to infect a broad variety of cell types, integration and stable expression of the subject CAR, dominant negative receptor and/or switch receptor, and/or bispecific antibody, and/or combinations thereof, requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a subject CAR, dominant negative receptor and/or switch receptor, and/or bispecific antibody, and/or combinations thereof (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides genetically engineered cells which include and stably express a subject CAR, dominant negative receptor and/or switch receptor, and/or bispecific antibody, and/or combinations thereof, of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Modified cells (e.g., comprising a subject CAR, dominant negative receptor and/or switch receptor, and/or expresses and secretes a bispecific antibody, and/or combinations thereof) may be produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a subject CAR, dominant negative receptor and/or switch receptor, and/or bispecific antibody, and/or combinations thereof, of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5'

UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a subject CAR, dominant negative receptor and/or switch receptor, and/or bispecific antibody, and/or combinations thereof, of the present disclosure will be RNA, e.g., in vitro synthesized RNA. Methods for in vitro synthesis of RNA are known in the art; any known method can be used to synthesize RNA comprising a sequence encoding a subject CAR, dominant negative receptor and/or switch receptor, and/or bispecific antibody, and/or combinations thereof. Methods for introducing RNA into a host cell are known in the art. See, e.g., Zhao et al. Cancer Res. (2010) 15: 9053. Introducing RNA comprising a nucleotide sequence encoding a subject CAR, dominant negative receptor and/or switch receptor, and/or bispecific antibody, and/or combinations thereof, into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a subject CAR, dominant negative receptor and/or switch receptor, and/or bispecific antibody, and/or combinations thereof.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the Med-Pulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the subject CAR, dominant negative receptor and/or switch receptor, and/or bispecific antibody, and/or combinations thereof. In some embodiments, the cells (e.g. T cells) can be incubated or cultivated prior to, during or subsequent to the introduction of the nucleic acid molecule encoding the subject CAR, dominant negative receptor and/or switch receptor, and/or bispecific antibody, and/or combinations thereof, such as prior to, during or subsequent to the transduction of the cells with a viral vector (e.g. lentiviral vector) encoding the subject CAR, dominant negative receptor and/or switch receptor, and/or bispecific antibody, and/or combinations thereof. In some embodiments, the method includes activating or stimulating cells with a stimulating or activating agent (e.g. anti-CD3/anti-CD28 antibodies) prior to introducing the nucleic acid molecule encoding the subject CAR, dominant negative receptor and/or switch receptor, and/or bispecific antibody, and/or combinations thereof.

In some embodiments, where the nucleic acid sequences encoding the subject CAR, dominant negative receptor and/or switch receptor, and/or bispecific antibody, and/or combinations thereof, of the present invention reside on one or more separate nucleic acid sequences, the order of introducing each of the one or more nucleic acid sequences may vary. For example, a nucleic acid sequence encoding a subject CAR and dominant negative receptor and/or switch receptor may first be introduced into the host cell, followed by introduction of a nucleic acid sequence encoding a subject bispecific antibody. For example, a nucleic acid sequence encoding a subject bispecific antibody may first be introduced into the host cell, followed by introduction of a nucleic acid sequence encoding a subject CAR and dominant negative receptor and/or switch receptor. In some embodiments, each of the one or more nucleic acid sequences are introduced into the host cell simultaneously. Those of skill in the art will be able to determine the order in which each of the one or more nucleic acid sequences are introduced into the host cell.

H. Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker$^-$) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNA-BEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L−CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

I. Expansion of Immune Cells

Whether prior to or after modification of cells to express a subject CAR, dominant negative receptor, and/or switch receptor, and/or bispecific antibody, and/or combinations thereof, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or an antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). In one embodiment, human T regulatory cells are expanded via anti-CD3 antibody coated K562 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

J. Methods of Treatment

The modified cells (e.g., T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells.

Also included is a method of treating a disease or condition in a subject in need thereof comprising administering to the subject a modified cell (e.g., modified T cell) of the present invention. In one embodiment, the method of treating a disease or condition in a subject in need thereof comprises administering to the subject a modified cell (e.g., a modified T cell) comprising a subject CAR, dominant negative receptor and/or switch receptor, and/or a bispecific antibody, and/or combinations thereof. In one embodiment, the method of treating a disease or condition in a subject in need thereof comprises administering to the subject a modified cell (e.g., a modified T cell) comprising a subject CAR (e.g., a CAR having affinity for PSMA on a target cell) and a dominant negative receptor and/or switch receptor. In one embodiment, the method of treating a disease or condition in a subject in need thereof comprises administering to the subject a modified cell (e.g., a modified T cell) comprising a subject CAR (e.g., a CAR having affinity for PSMA on a target cell), a dominant negative receptor and/or switch receptor, and wherein the modified cell is capable of expressing and secreting a bispecific antibody.

Methods for administration of immune cells for adoptive cell therapy are known and may be used in connection with the provided methods and compositions. For example, adoptive T cell therapy methods are described, e.g., in U.S. Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g., the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Prostate adenocarcinoma is an extremely common and lethal disease. Prostate cancer is the most common malignancy among men. Prostate cancer is the second-leading cause of cancer-related deaths among men, accounting for an estimated 10% of annual male cancer deaths. PSMA is highly expressed in malignant prostate tissue, with low-levels of expression in some normal human tissues. Under normal physiologic conditions, PSMA is expressed in the prostate gland (secretory acinar epithelium), kidney (proximal tubules), nervous system glia (astrocytes and Schwann cells), and the small intestine (jejunal brush border). PSMA is much more highly expressed in prostate epithelium and is significantly upregulated in malignant prostate tissues. PSMA expression in normal cells has been found to be 100-fold to 1000-fold less than in prostate carcinoma cells. PSMA expression increases significantly during the transformation from benign prostatic hyperplasia to prostatic adenocarcinoma. PSMA expression has been found to be directly correlated with the histologic grade of malignant prostate tissue and increases with more advanced disease (i.e. highest PSMA expression found in prostate cancer metastases in lymph node and bone).

In one embodiment, the methods of the invention are useful for treating prostate cancer, for example advanced castrate-resistant prostate cancer. It should be readily understood by one of ordinary skill in the art that any type of cancer wherein the PSMA tumor antigen is expressed, can be treated using the methods of the present invention. For example, neovascular expression of PSMA was found in non-small cell lung cancer, see, e.g., PLoS One. 2017 Oct. 27; 12(10). Accordingly, the methods of the invention may also be useful for treating non-small cell lung cancer (NSCLC).

In certain exemplary embodiments, the modified immune cells of the invention are used to treat prostate cancer. In one embodiment, a method of the present disclosure is used to treat castrate-resistant prostate cancer. In one embodiment, a method of the present disclosure is used to treat advanced castrate-resistant prostate cancer. In one embodiment, a method of the present disclosure is used to treat metastatic castrate-resistant prostate cancer. In one embodiment, a method of the present disclosure is used to treat metastatic castrate-resistant prostate cancer, wherein the patient with metastatic castrate-resistant prostate cancer has ≥10% tumor cells expressing PSMA. In one embodiment, a method of the present disclosure is used to treat castrate-resistant prostate adenocarcinoma, wherein the patient has castrate levels of testosterone (e.g., <50 ng/mL) with or without the use of androgen deprivation therapy.

In certain embodiments, the subject is provided a secondary treatment. Secondary treatments include but are not limited to chemotherapy, radiation, surgery, and medications.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, alymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg, $10^4$, and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells. In an exemplary embodiment, a suitable dosage is from about $1\times10^7$ total cells to about $3\times10^7$ total cells.

In some embodiments, the dose of total cells and/or dose of individual sub-populations of cells is within a range of between at or about $1\times10^5$ cells/m² to about $1\times10^{11}$ cells/m². In an exemplary embodiment, the dose of total cells and/or dose of individual sub-populations of cells is within a range of between at or about $1\times10^7$/m² to at or about $3\times10^7$/m². In an exemplary embodiment, the dose of total cells and/or dose of individual sub-populations of cells is within a range of between at or about $1\times10^8$/m² to at or about $3\times10^8$/m². In some embodiments, the dose of total cells and/or dose of individual sub-populations of cells is the maximum tolerated dose by a given patient.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or $CD8^+$ cells/kg, $1.5\times10^5$ $CD4^+$ and/or $CD8^+$ cells/kg, $2\times10^5$ $CD4^+$ and/or $CD8^+$ cells/kg, or $1\times10^6$ $CD4^+$ and/or $CD8^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ $CD4^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNy, IL-2, and TNF. In some aspects the biological activity is measured by assessing clinical outcome, such as reduction in tumor burden or load.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, for a subject having castrate-resistant prostate cancer, the subject receives lymphodepleting chemotherapy prior to the administration of the modified T cells. In an exemplary embodiment, for a subject having castrate-resistant prostate cancer, the subject receives lymphodepleting chemotherapy including at or about 500 mg/m$^2$ to at or about 1 g/m$^2$ of cyclophosphamide by intravenous infusion. In an exemplary embodiment, for a subject having castrate-resistant prostate cancer, the subject receives lymphodepleting chemotherapy including at or about 500 mg/m$^2$ to at or about 1 g/m$^2$ of cyclophosphamide by intravenous infusion about 3 days (±1 day) prior to administration of the modified T cells. In an exemplary embodiment, for a subject having castrate-resistant prostate cancer, the subject receives lymphodepleting chemotherapy including at or about 500 mg/m$^2$ to at or about 1 g/m$^2$ of cyclophosphamide by intravenous infusion up to 4 days prior to administration of the modified T cells. In an exemplary embodiment, for a subject having castrate-resistant prostate cancer, the subject receives lymphodepleting chemotherapy including at or about 500 mg/m$^2$ to at or about 1 g/m$^2$ of cyclophosphamide by intravenous infusion 4 days prior to administration of the modified T cells. In an exemplary embodiment, for a subject having castrate-resistant prostate cancer, the subject receives lymphodepleting chemotherapy including at or about 500 mg/m$^2$ to at or about 1 g/m$^2$ of cyclophosphamide by intravenous infusion 3 days prior to administration of the modified T cells. In an exemplary embodiment, for a subject having castrate-resistant prostate cancer, the subject receives lymphodepleting chemotherapy including at or about 500 mg/m$^2$ to at or about 1 g/m$^2$ of cyclophosphamide by intravenous infusion 2 days prior to administration of the modified T cells.

In an exemplary embodiment, for a subject having castrate-resistant prostate cancer, the subject receives lymphodepleting chemotherapy including 300 mg/m$^2$ of cyclophosphamide by intravenous infusion 3 days prior to administration of the modified T cells. In an exemplary embodiment, for a subject having castrate-resistant prostate cancer, the subject receives lymphodepleting chemotherapy including 300 mg/m$^2$ of cyclophosphamide by intravenous infusion for 3 days prior to administration of the modified T cells.

In an exemplary embodiment, for a subject having castrate-resistant prostate cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having castrate-resistant prostate cancer, the subject receives lymphodepleting chemotherapy including fludarabine at a dose of 30 mg/m$^2$ for 3 days.

In an exemplary embodiment, for a subject having castrate-resistant prostate cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having castrate-resistant prostate cancer, the subject receives lymphodepleting chemotherapy including cyclophosphamide at a dose of about 300 mg/m²/day, and fludarabine at a dose of 30 mg/m² for 3 days.

It is known in the art that one of the adverse effects following infusion of CAR T cells is the onset of immune activation, known as cytokine release syndrome (CRS). CRS is immune activation resulting in elevated inflammatory cytokines. Clinical and laboratory measures range from mild CRS (constitutional symptoms and/or grade-2 organ toxicity) to severe CRS (sCRS; grade≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

In some embodiments, the methods of the invention involve selecting and treating a subject having failed at least one prior course of standard of cancer therapy. For example, a suitable subject may have had a confirmed diagnosis of relapsed prostate cancer. In some embodiments, the methods of the invention involve selecting and treating a subject having had at least one prior course of standard of cancer therapy. For example, a suitable subject may have had prior therapy with at least one standard 17α lyase inhibitor or second-generation anti-androgen therapy for the treatment of metastatic castrate resistant prostate cancer.

In an exemplary embodiment, a suitable subject is a subject having metastatic castrate resistant prostate cancer. In an exemplary embodiment, a suitable subject is a subject having metastatic castrate resistant prostate cancer having ≥10% tumor cells expressing PSMA as demonstrated by immunohistochemistry analysis on fresh tissue.

In some embodiments, a suitable subject is a subject that has radiographic evidence of osseous metastatic disease and/or measurable, non-osseous metastatic disease (nodal or visceral).

In some embodiments, a suitable subject is a subject that has an ECOG performance status of 0-1.

In some embodiments, a suitable subject is a subject that has adequate organ function, as defined by: serum creatinine≤1.5 mg/dl or creatinine clearance≥60 cc/min; and/or serum total bilirubin<1.5×ULN; serum ALT/AST<2×ULN.

In some embodiments, a suitable subject is a subject that has adequate hematologic reserve as defined by: Hgb>10 g/dl; PLT>100 k/ul; and/or ANC>1.5 k/ul.

In some embodiments, a suitable subject is a subject that is not transfusion dependent.

In some embodiments, a suitable subject is a subject that has evidence of progressive castrate resistant prostate adenocarcinoma, as defined by: castrate levels of testosterone (<50 ng/ml) with or without the use of androgen deprivation therapy; and/or evidence of one of the following measures of progressive disease: soft tissue progression by RECIST 1.1 criteria, osseous disease progression with 2 or more new lesions on bone scan (as per PCWG2 criteria), increase in serum PSA of at least 25% and an absolute increase of 2 ng/ml or more from nadir (as per PCWG2 criteria).

In some embodiments, a suitable subject has had previous treatment with at least one second-generation androgen signaling inhibitor. In some embodiments, a suitable subject has had previous treatment with abiraterone. In some embodiments, a suitable subject has had previous treatment with enzalutamide.

In some embodiments, a suitable subject has ≥10% tumor cells expressing PSMA by immunohistochemistry (IHC) on a metastatic tissue biopsy.

In some embodiments, a suitable subject has radiographic evidence for metastatic disease (osseous or nodal/visceral).

In some embodiments, a suitable subject has ≤4 lines of therapy for metastatic CRPC.

K. Pharmaceutical Compositions and Formulations

Also provided are populations of immune cells of the invention, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

RNA CAR Construct Design:

Four human scFvs specifically targeting human PSMA, 1C3, 2A10, 2C6 and 2F5, were synthesized from IDT as gBlocks. CARs with 4-1BB-zeta (BBZ) were assembled by overlapping PCR and cloned into the RNA in vitro transcription vector pD-A. The pD-A vector was optimized for T cell transfection, CAR expression and RNA production. The four human PSMA CARs and one mouse PSMA CAR (J591) were linearized by SpeI digestion prior to RNA IVT. The T7 mScript Standard mRNA Production System (Cellscript, Inc., Madison, Wis.) was utilized to generate capped/tailed IVT RNA. The IVT RNA was purified by RNeasy Mini Kit (Qiagen, Inc., Valencia, Calif.). Purified RNA was eluted in RNase-free water at 1-2 mg/mL and stored at −80° C. until use. RNA integrity was confirmed by 260/280 absorbance and visually on an Agarose gel.

Lenti CAR Construct Design:

All PSMA CARs were subcloned into pTRPE Lenti vectors. Switch receptor: PD1.CD28-F2A (SW), PD1$^{A132L}$PTM.CD28-F2A (SW*) and a dominant negative TGFRβII sequence, dnTGFRβII-T2A (dn), were then subcloned into each Lenti vector followed by human PSMA scFv.

Examples of sequences comprised by a Lenti vector are as follows:

1C3
(SEQ ID NO: 169)
ATGGCCTTACCAGTGACCGCCTTGCTCCTGCCGCTGGCCTTGCTGCTCCA

CGCCGCCAGGCCGCAGGTGCAACTGGTGGAGTCTGGGGGAGGCGTGGTCC

AGCCTGGGAGGTCCCTGAGACTCTCCTGTGCAGCCTCTGGATTCACCTTC

AGTAGCTATGCTATGCACTGGGTCCGCCAGGCTCCAGGCAAGGGGCTGGA

GTGGGTGGCAGTTATATCATATGATGGAAACAATAAATACTACGCAGACT

CCGTGAAGGGCCGATTCACCATCTCCAGAGACAATTCCAAGAACACGCTG

TATCTGCAAATGAACAGCCTGAGAGCTGAGGACACGGCTGTGTATTACTG

TGCGAGAGCCGTCCCCTGGGGATCGAGGTACTACTACTACGGTATGGACG

TCTGGGGCCAAGGGACCACGGTCACCGTCTCCTCAGGTGGCGGTGGCTCG

GGCGGTGGTGGGTCGGGTGGCGGCGGATCTGCCATCCAGTTGACCCAGTC

TCCATCCTCCCTGTCTGCATCTGTAGGAGACAGAGTCACCATCACTTGCC

GGGCAAGTCAGGGCATTAGCAGTGCTTTAGCCTGGTATCAGCAGAAATCA

GGGAAAGCTCCTAAGCTCCTGATCTTTGATGCCTCCAGTTTGGAAAGTGG

GGTCCCATCAAGGTTCAGCGGCAGTGGATCTGGGACAGATTTCACTCTCA

CCATCAGCAGCCTGCAGCCTGAAGATTTTGCAACTTATTACTGTCAACAG

TTTAACAGTTATCCTCTCACTTTCGGCGGAGGGACCAAGGTGGAGATCAA

AACCACGACGCCAGCGCCGCG

2A10
(SEQ ID NO: 170)
ATGGCCTTACCAGTGACCGCCTTGCTCCTGCCGCTGGCCTTGCTGCTCCA

CGCCGCCAGGCCGGAGGTGCAGCTGGTGCAGTCTGGAGCAGAGGTGAAAA

AGCCCGGGGAGTCTCTGAAGATCTCCTGTAAGGGTTCTGGATACAGCTTT

ACCAGTAACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TACCTGCAGTGGAGCAGCCTGAAGGCCTCGGACACCGCCATGTATTACTG

TGCGAGGCAAACTGGTTTCCTCTGGTCCTCCGATCTCTGGGGCCGTGGCA

CCCTGGTCACTGTCTCCTCAGGTGGCGGTGGCTCGGGCGGTGGTGGGTCG

GGTGGCGGCGGATCTGCCATCCAGTTGACCCAGTCTCCATCCTCCCTGTC

TGCATCTGTAGGAGACAGAGTCACCATCACTTGCCGGGCAAGTCAGGACA

TTAGCAGTGCTTTAGCCTGGTATCAACAGAAACCAGGGAAAGCTCCTAAG

CTCCTGATCTATGATGCCTCCAGTTTGGAAAGTGGGGTCCCATCAAGGTT

CAGCGGCTATGGATCTGGGACAGATTTCACTCTCACCATCAACAGCCTGC

AGCCTGAAGATTTTGCAACTTATTACTGTCAACAGTTTAATAGTTACCCG

CTCACTTTCGGCGGAGGGACCAAGGTGGAGATCAAAACCACGACGCCAGC

GCCGCG

2F5
(SEQ ID NO: 171)
ATGGCCTTACCAGTGACCGCCTTGCTCCTGCCGCTGGCCTTGCTGCTCCA

CGCCGCCAGGCCGGAGGTGCAGCTGGTGCAGTCTGGAGCAGAGGTGAAAA

AGCCCGGGGAGTCTCTGAAGATCTCCTGTAAGGGTTCTGGATACAGTTTT

ACCAGCAACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TACCTGCAGTGGAACAGCCTGAAGGCCTCGGACACCGCCATGTATTACTG

TGCGAGACAAACTGGTTTCCTCTGGTCCTTCGATCTCTGGGGCCGTGGCA

CCCTGGTCACTGTCTCCTCAGGTGGCGGTGGCTCGGGCGGTGGTGGGTCG

GGTGGCGGCGGATCTGCCATCCAGTTGACCCAGTCTCCATCCTCCCTGTC

TGCATCTGTAGGAGACAGAGTCACCATCACTTGCCGGGCAAGTCAGGACA

TTAGCAGTGCTTTAGCCTGGTATCAGCAGAAACCGGGGAAAGCTCCTAAG

CTCCTGATCTATGATGCCTCCAGTTTGGAAAGTGGGGTCCCATCAAGGTT

CAGCGGCAGTGGATCTGGGACAGATTTCACTCTCACCATCAGCAGCCTGC

-continued

AGCCTGAAGATTTTGCAACTTATTACTGTCAACAGTTTAATAGTTACCCG

CTCACTTTCGGCGGAGGGACCAAGGTGGAGATCAAAATCAAAACCACGAC

GCCAGCGCCGCG

2C6

(SEQ ID NO: 172)

ATGGCCTTACCAGTGACCGCCTTGCTCCTGCCGCTGGCCTTGCTGCTCCA

CGCCGCCAGGCCGGAGGTGCAGCTGGTGCAGTCTGGATCAGAGGTGAAAA

AGCCCGGGGAGTCTCTGAAGATCTCCTGTAAGGGTTCTGGATACAGCTTT

ACCAACTACTGGATCGGCTGGGTGCGCCAGATGCCCGGGAAAGGCCTGGA

GTGGATGGGGATCATCTATCCTGGTGACTCTGATACCAGATACAGCCCGT

CCTTCCAAGGCCAGGTCACCATCTCAGCCGACAAGTCCATCAGCACCGCC

TATCTGCAGTGGAGCAGCCTGAAGGCCTCGGACACCGCCATGTATTACTG

TGCGAGTCCCGGGTATACCAGCAGTTGGACTTCTTTTGACTACTGGGGCC

AGGGAACCCTGGTCACCGTCTCCTCAGGTGGCGGTGGCTCGGGCGGTGGT

GGGTCGGGTGGCGGCGGATCTGAAATTGTGTTGACACAGTCTCCAGCCAC

CCTGTCTTTGTCTCCAGGGGAAAGAGCCACCCTCTCCTGCAGGGCCAGTC

AGAGTGTTAGCAGCTACTTAGCCTGGTACCAACAGAAACCTGGCCAGGCT

CCCAGGCTCCTCATCTATGATGCATCCAACAGGGCCACTGGCATCCCAGC

CAGGTTCAGTGGCAGTGGGTCTGGGACAGACTTCACTCTCACCATCAGCA

GCCTAGAGCCTGAAGATTTTGCAGTTTATTACTGTCAGCAGCGTAGCAAC

TGGCCCCTATTCACTTTCGGCCCTGGGACCAAAGTGGATATCAAAACCAC

GACGCCAGCGCCGCG

PD1.CD28-F2A (SW)

(SEQ ID NO: 173)

ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCCGTGAAACAGACTTTGAATTTTGACCTTCTCAAGTTG

GCGGGAGACGTGGAGTCCAACCCAGGGCCG

PD1$^{A132L}$-PTM.CD28-F2A (SW*)

(SEQ ID NO: 174)

ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGGTTGGTGTCGTGGGCGGCCTGCTGGGCAGCCTGGTGCTGC

TAGTCTGGGTCCTGGCCGTCATCAGGAGTAAGAGGAGCAGGCTCCTGCAC

AGTGACTACATGAACATGACTCCCCGCCGCCCCGGGCCCACCCGCAAGCA

TTACCAGCCCTATGCCCCACCACGCGACTTCGCAGCCTATCGCTCCGTGA

AACAGACTTTGAATTTTGACCTTCTCAAGTTGGCGGGAGACGTGGAGTCC

AACCCAGGGCCG dnTGFβRII-T2A (dn)

(SEQ ID NO: 175)

ATGGGTCGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACTGCTACCGCGTTAACCGGCAGCAGAAGCTGAGTTCATCC

GGAAGATCTGGCGGCGAGAGGGCAGAGGAAGTCTTCTAACATGCGGTGA

CGTGGAGGAGAATCCCGGCCCTAGAGCCACC

Transduction Protocol:

Bulk T cells (CD4 and CD8) obtained from the Human Immunology Core were diluted to $10^6$ cells/mL, and stimulated with CD3/28 beads (T cell expanders, Invitrogen) at a cell:bead ratio of 1:3. Transductions of packaged lentiviral vectors were performed on day 1 post-stimulation using a MOI of 3:1, and allowed to expand in a 37° C./5% $CO_2$ incubator.

Transduction Efficacy:

The CAR transduction efficacy was evaluated by flow cytometry using Biotin-SP-AffiniPure Goat Anti-Mouse IgG (Cat #: 115-065-072, Jackson ImmunoResearch Labs) or Biotin-SP-AffiniPure Rabbit Anti-Human IgG (Cat #: 309-065-082, Jackson ImmunoResearch Labs) followed by Streptavidin APC (Cat #: 17-4317-82, eBioscience) or Streptavidin PE (Cat #: 554061, BD Pharmingen). APC anti-human CD279 (PD-1) antibody (Cat #: 329908, BioLegend) and Human TGF-beta RII APC-conjugated Antibody (Catalog # FAB241A, R&D systems) were used to examine the switch receptor or dominant negative TGFRβII portion.

T Cell Expansion:

Cells were fed and split every 2 days starting at day 3 post stimulation. T cells were de-beaded at day 4 and frozen at day 10 for later use.

RNA Electroporation:

Resting T cells were electroporated with 10 or 20 μg IVT PSMA RNA CARs using BTX830 at 500 V and 700 μs. Nalm6.CBG or K562 cells were electroporated with 5 μg or 15 μg PSMA IVT RNA using BTX830 at 300 V and 500 μs. PC3.PSMA cells were electroporated with 0.5 μg, 2 μg or 5 μg PDL1 IVT RNA using BTX830 at 300 V and 500 μs. Following electroporation, the cells were immediately placed in pre-warmed culture media at 37° C. and 5% $CO_2$. 18 hr later, PSMA or PDL1 electroporated tumor cells were stained by APC anti-human PSMA (FOLH1) antibody (Cat #: 342507, BioLegend) or APC anti-human CD274 (PDL-1 or B7-H1) antibody (Cat #: 17-5983-42, BD Biosciences) and analyzed by Flow Cytometry.

Cell Counting:

At various time-points during the expansion-resting cycles, cells were gently mixed and a 40 μL aliquot of cells was collected from known culture volume and placed into accuvettes (Beckman Coulter) with 20 mL Isoton II Diluent Buffer for counting using a Coulter Multisizer 3 (Beckman Coulter) in accordance with the CCI laboratory SOP. These assays determined cell concentration, total cell numbers, growth rates, and cell volumes and were used to calculate dilution volumes and determine when cells were rested for freezing.

Quantitative-PCR:

Primary cells or tumor cell lines were lysed and passed through QIA shredder (Cat #79656). Total RNA was extracted by RNeasy Mini kit (Cat #74104) according to the manufacturer's protocol. Reverse transcription (Cat #: 11904-018, Invitrogen) was performed to obtain cDNA. cDNA was subjected to quantitative PCR with primers specific for PSMA: (F primer: AGGAAGTCTCAAAGT-GCCCT (SEQ ID NO:176), R primer: GAACAACAGCT-GCTCCACTC (SEQ ID NO:177)) or GAPDH: (F primer: GCTACACTGAGCACCAGGTGGTCTC (SEQ ID NO:178), R primer: CCCAGCAGT-GAGGGTCTCTCTCTTC (SEQ ID NO:179)).

ELISA for IL-2 and IFN-γ:

The T cells or target cells were washed and suspended in R10 medium at $1\times10^6$ cells/mL. Approximately 0.1 mL of each cell line was added to a well of a 96-well plate (Corning) and incubated at 37° C. for 18 to 20 hours. The supernatant was harvested and subjected to ELISA.

Cd107A Assay:

An E:T ratio of 1:2 ($5\times10^4$ effectors: $1\times10^5$ targets) of cells were prepared in 100 μL of R10 medium and plated in a 96 well plate. 10 μL of phycoerythrin-labeled anti-CD107a Ab was added and the plate was incubated at 37° C. for 1 hour. Golgi Stop (2 ul Golgi Stop in 3 ml R10 medium, 10 ul/well; BD Biosciences, 51-2092KZ) was added and the plate was incubated for another 2.5 hours. Then 2 μL FITC-anti-CD8 (Cat #: 551347, BD Pharmingen) and 2 uL APC-anti-CD3 (Cat #: 555342, BD Pharmingen) was added and incubated at 37° C. for 30 min. After incubation, the samples were washed with FACS buffer and analyzed by flow cytometry.

Luciferase Based CTL Assay:

Nalm6-CBG, PC3-CBG, PC3.PSMA-CBG tumor cells were resuspended at $1\times10^5$ cells/mL in R10 medium and incubated with different ratios of T cells (e.g. 10:1, 5:1, 2.5 etc.) for 18 hr at 37° C. Equal volume of substrate was added and the luminescence was immediately determined. Results are reported as percent killing based on luciferase activity in wells with only tumor in the absence of T cells (% killing=100−((RLU from well with effector and target cell co-culture)/(RLU from well with target cells)×100)).

PC3.PSMA Tumor Model:

2E6 PC3.PSMA.7SC cells transduced with click beetle were injected to the mice (i.v.), and 28 days later, 2E6 PSMA CAR-T positive transduced T cells were injected to the tumor bearing mice (i.v.). Bioluminescence imaging (BLI) was conducted at multiple time points.

The results of the experiments are now described.

Example 1: Human RNA PSMA CARs Have Equivalent Anti-Tumor Activity as Mouse RNA PSMA CAR, J591

Figure 1B:
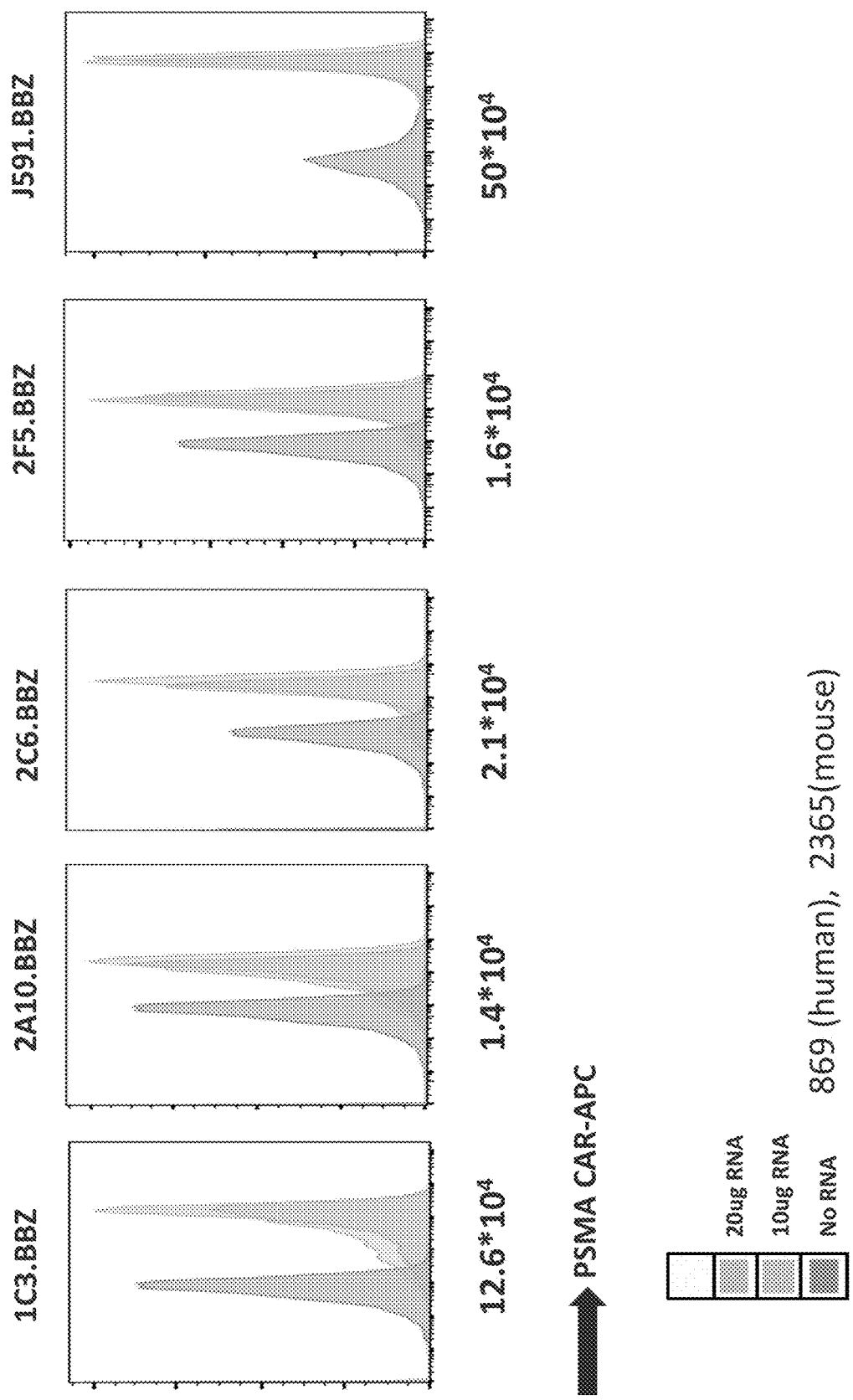
FIG. 1B shows results using purified PSMA RNA CARs electroporated into ND444 T cells and CAR expression examined by Flow Cytometry. The mean fluorescence intensity is labeled below the graph.

Four human RNA CARs targeting PSMA were constructed using one of four scFv sequences, 1C3 (SEQ ID NO:169), 2A10 (SEQ ID NO:170), 2C6 (SEQ ID NO:172) and 2F5 (SEQ ID NO:171), (from U.S Patent Application, US 2009/0297438 A1, incorporated by reference herein in its entirety). ScFvs were linked to a CD8 transmembrane domain and 4-1BB and CD3 zeta intracellular signaling domains. Purified RNA was visualized on an Agarose gel (FIG. 1A) and electroporated into resting human primary T cells. All CARs had nearly 100% CAR expression under the condition tested. 10 ug of IVT RNA CARs, whether it was human or mouse PSMA CAR, reached maximal mean fluorescence intensity (MFI) for CAR expression; thus, 10 ug IVT RNA was used for further experiments (FIG. 1B). CAR expression varied among different human CARs, the highest MFI for CAR expression being 1C3.BBZ. The MFI for mouse J591 CAR expression was 4 fold higher than that of 1C3.BBZ; however, since the species of antibody origins differ, 10 ug mouse J591 RNA CAR was also used for further experiments.

Figure 1C:
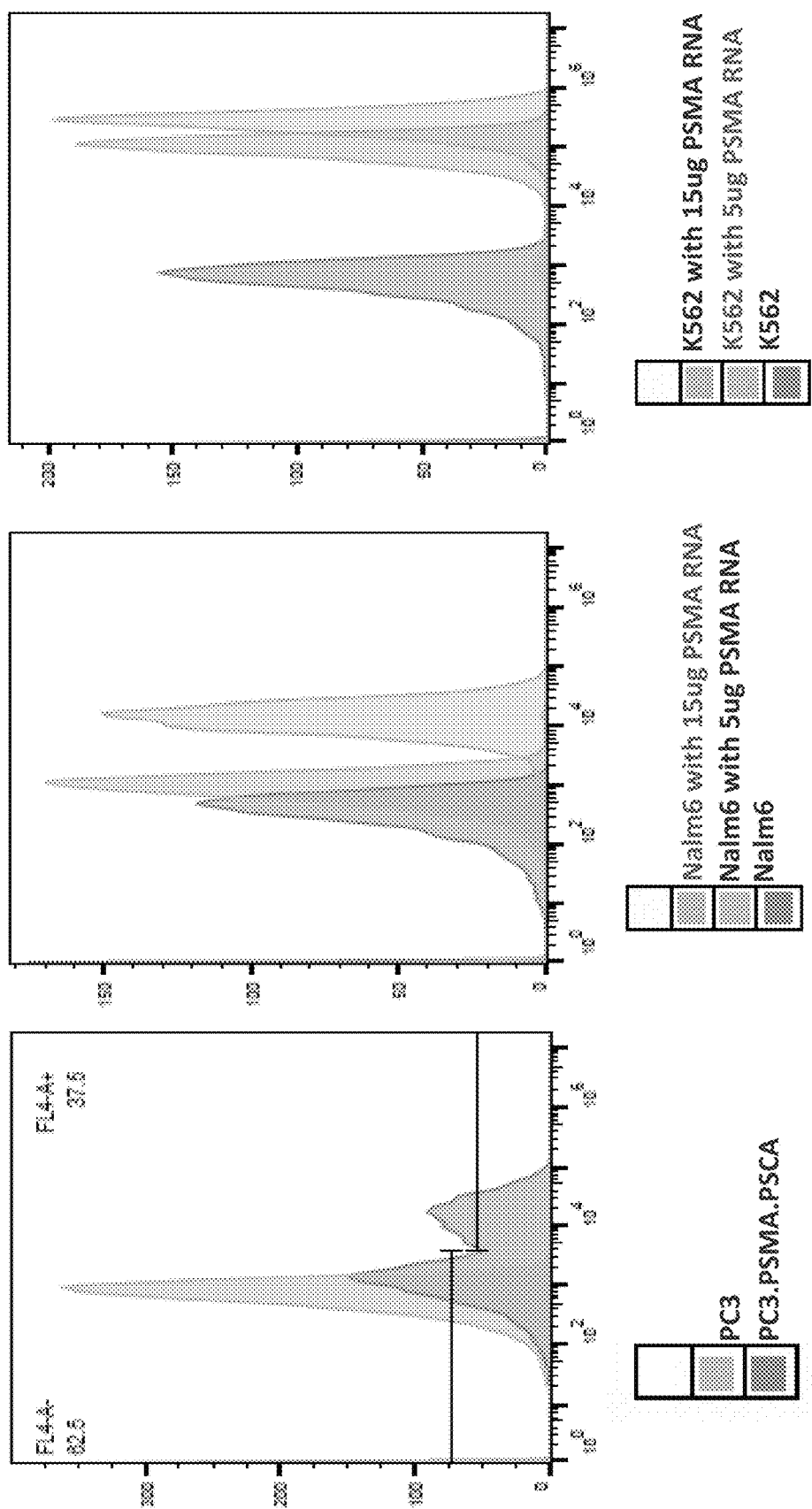
FIG. 1C illustrates PSMA expression. Purified full length PSMA RNA were electroporated into Nalm6 or K562 cells (middle and right panel). PSMA expression was examined by Flow Cytometry.

Full length PSMA was cloned into a PD-A vector for optimal RNA expression. Purified RNA was visualized on an Agarose gel (FIG. 1A), electroporated into Nalm6.CBG or K562 tumor cells and the expression of PSMA was analyzed by flow cytometry (FIG. 1C). 15 ug and 5 ug PSMA RNA was used for further experiments for Nalm6.CBG and K562 tumor cells respectively. PC3.PSMA.PSCA.CBG tumor cells were constructed previously with diminishing PSMA expression (37.5%) (FIG. 1C). Limited dilutions were performed for PC3.PSMA.CBG tumor cell line and 7 single cell clones were isolated and combined to be a new cell line, PC3.PSMA.7SC.CBG (FIG. 1D).

Figure 2A:
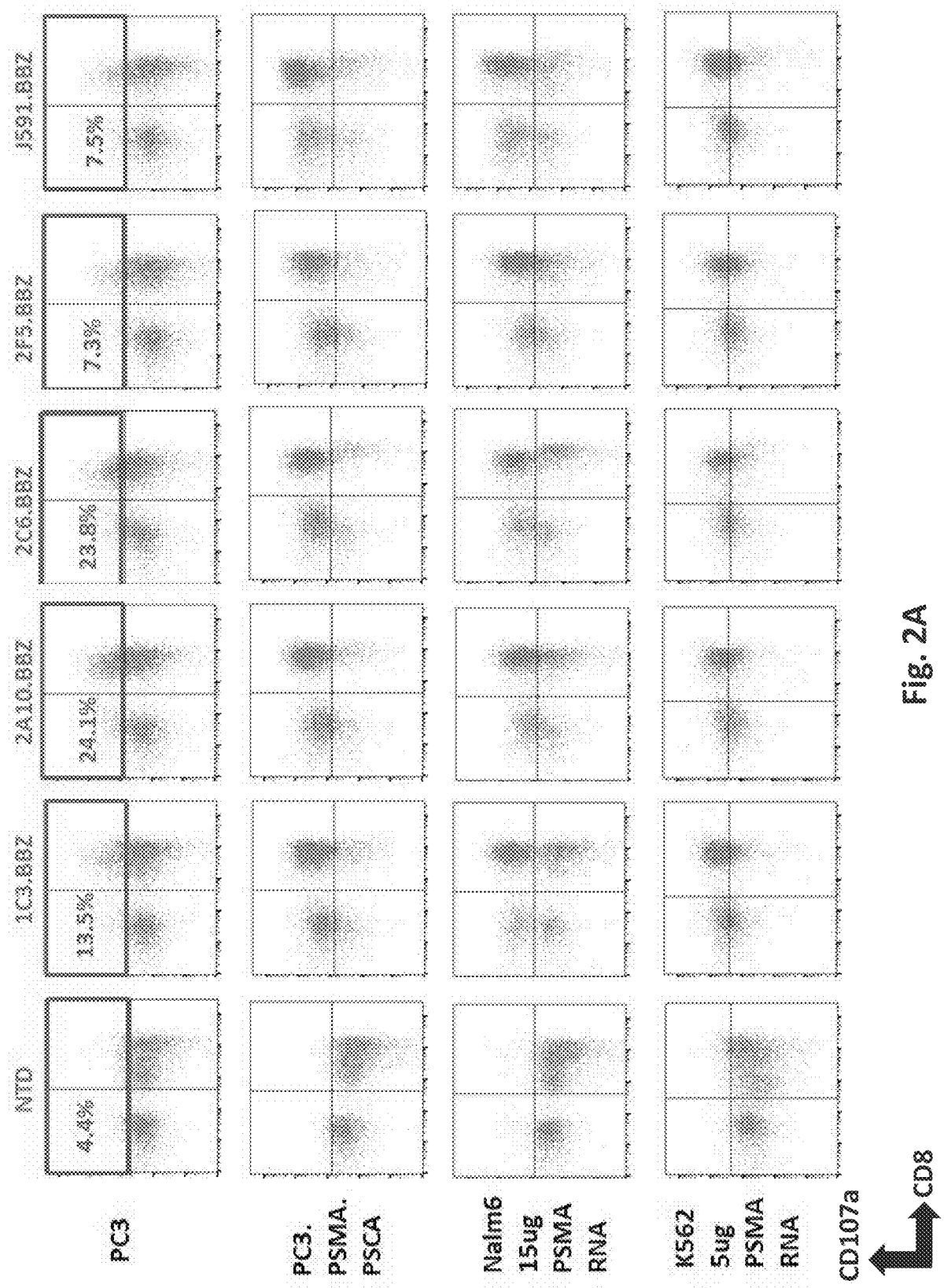
FIG. 2A illustrates results using various PSMA RNA CARs incubated with tumor cells and CD107a assays performed. The cells were gated by CD3.
Figure 2B:
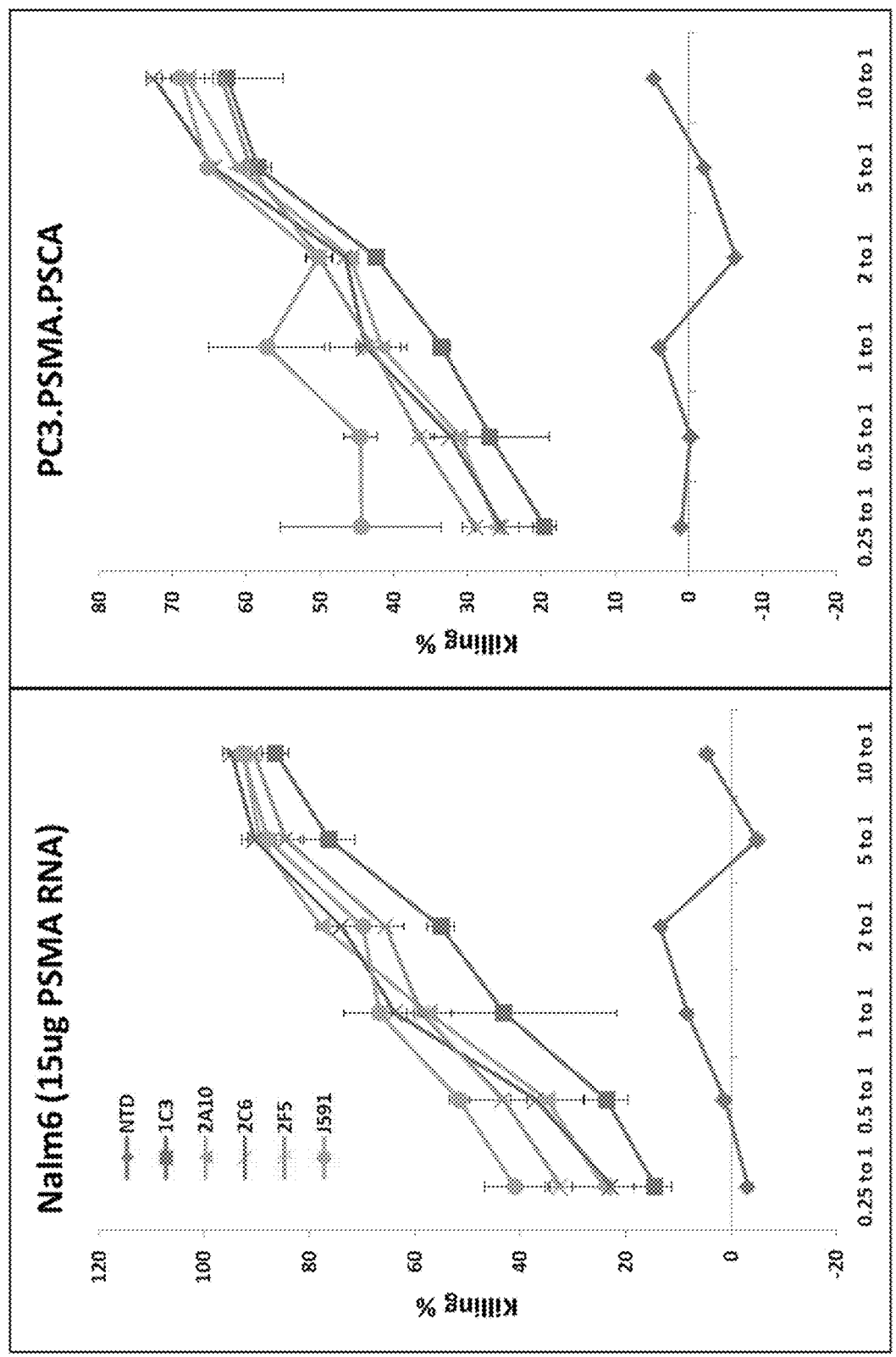
FIG. 2B illustrates results using various PSMA RNA CARs incubated with tumor cells and Luciferase based CTL assays performed. Results are reported as percent killing based on luciferase activity in wells with only tumor in the absence of T cells.
Figure 2C:
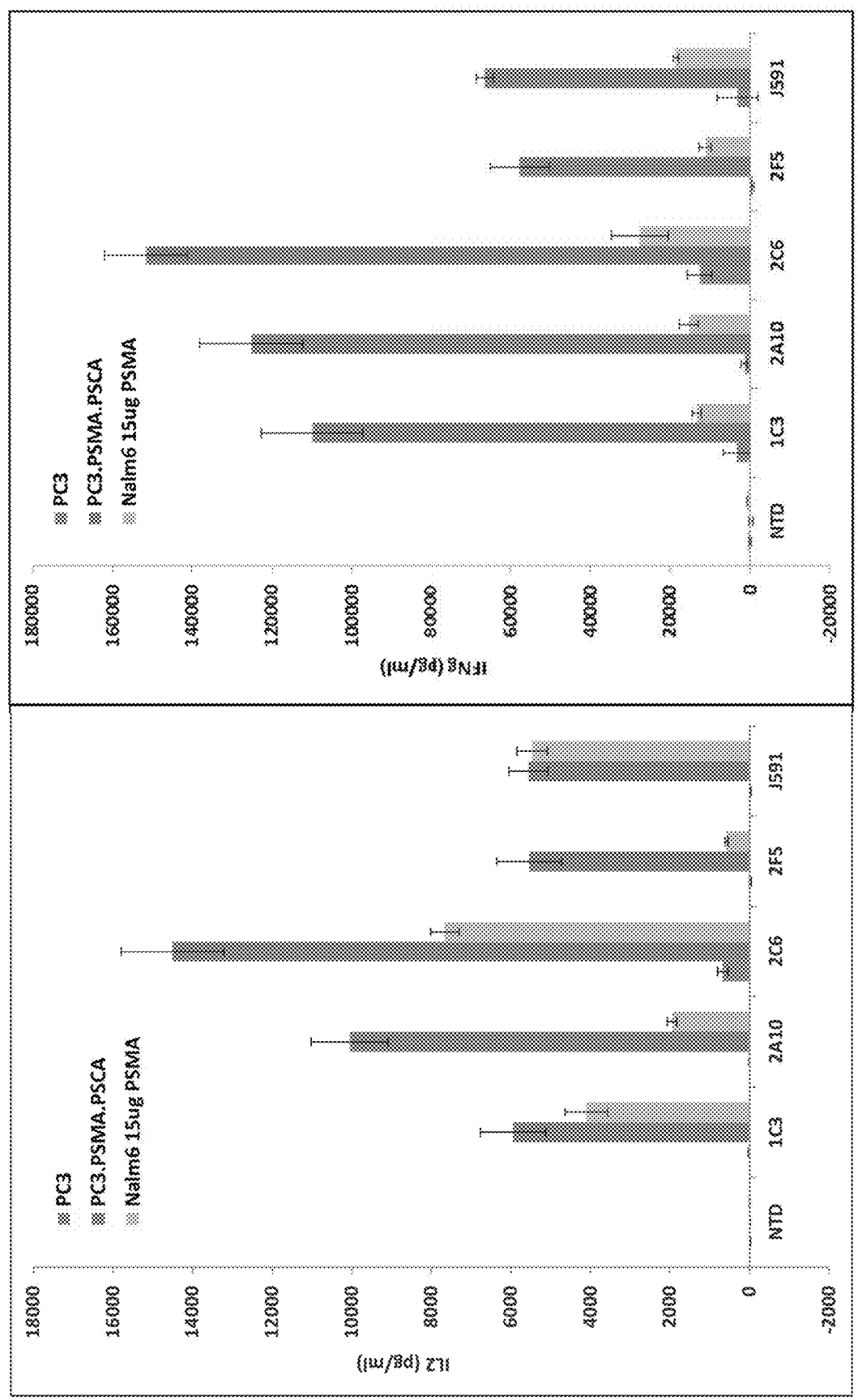
FIG. 2C shows results using various PSMA RNA CARs incubated with tumor cells and ELISA assays performed. (IL-2, left panel; IFN-γ, right panel).

Nalm6.CBG or K562 electroporated with PSMA RNA, PC3 or PC3.PSMA.PSCA.CBG tumor cells were co-cultured with various PSMA RNA CARs. CD107a assays, Luciferase based CTL assays and ELISA assays were performed to determine the functionality of the four new human CARs. All four human PSMA CARs had equivalent de-granulation activity as mouse PSMA CAR, J591, when co-cultured with PSMA positive cells (FIG. 2A). However, three out of four human PSMA CARs exerted higher nonspecific activation toward PC3 cells than J591 CAR (FIG. 2A). All four human CARs had comparable cytotoxicity and anti-tumor activity toward PSMA positive cells compared with the J591 CAR (FIG. 2B and FIG. 2C). Cytokine production was PSMA target specific for 1C3.BBZ, 2A10.BBZ and 2F5.BBZ CARs (FIG. 2C).

Example 2: Human Lenti PSMA CARs Specifically Target PSMA Positive Cells

Figure 3A:
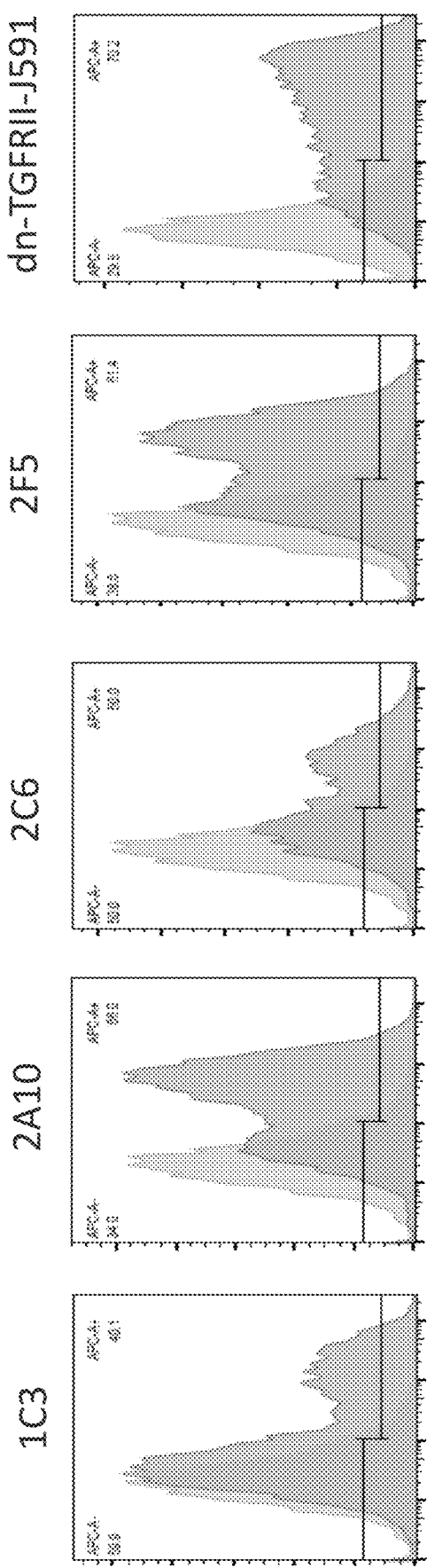
FIG. 3A illustrates results using PSMA Lenti CARs constructed and transduced into primary human T cells (MOI=3). CAR expression was examined by Flow Cytometry on day 8.
Figure 3B:
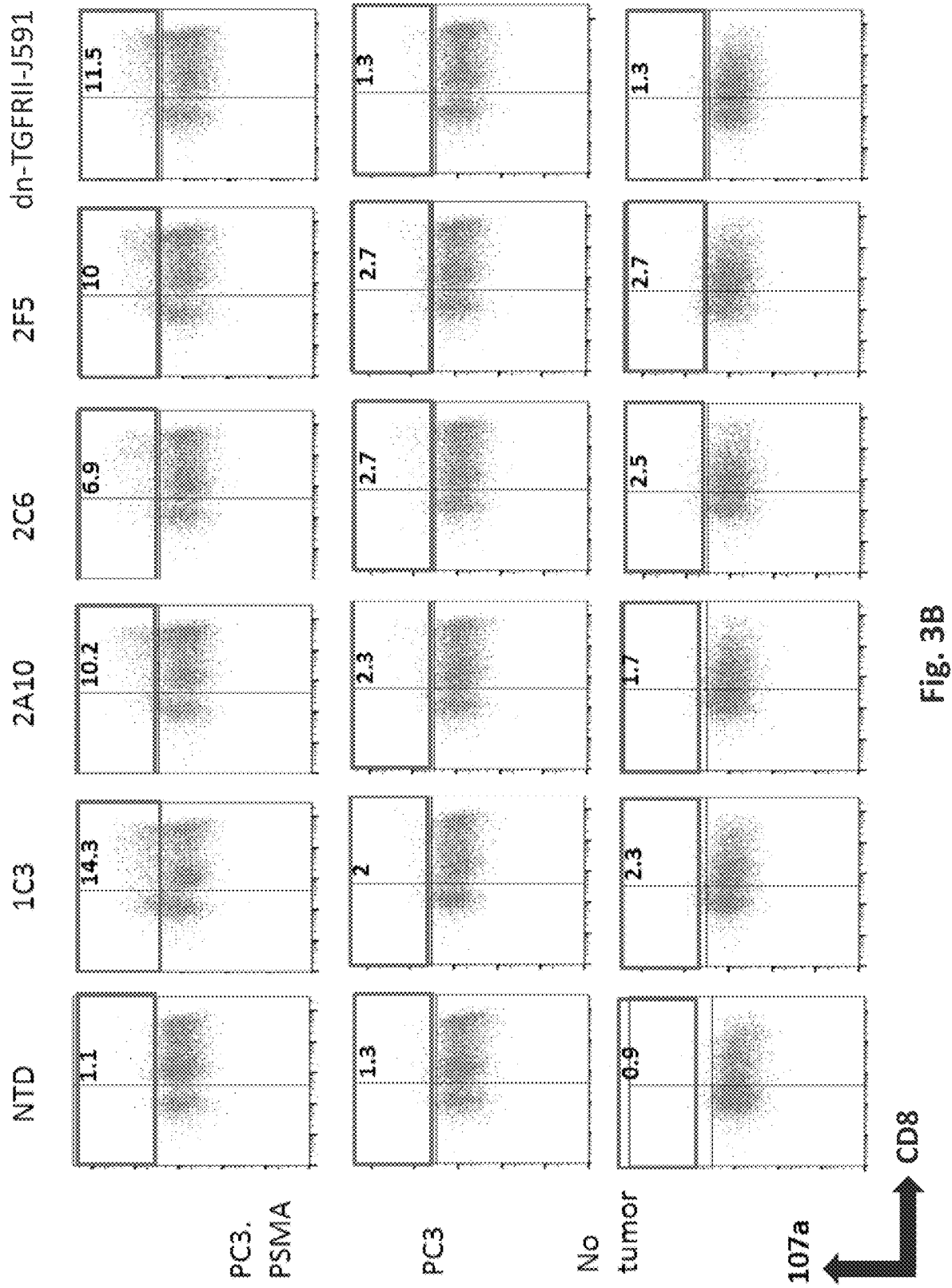
FIG. 3B shows results using various PSMA Lenti CARs incubated with or without tumor cells and CD107a assays performed. The cells were gated by CD3. Results from day 12 are shown.
Figure 3C:
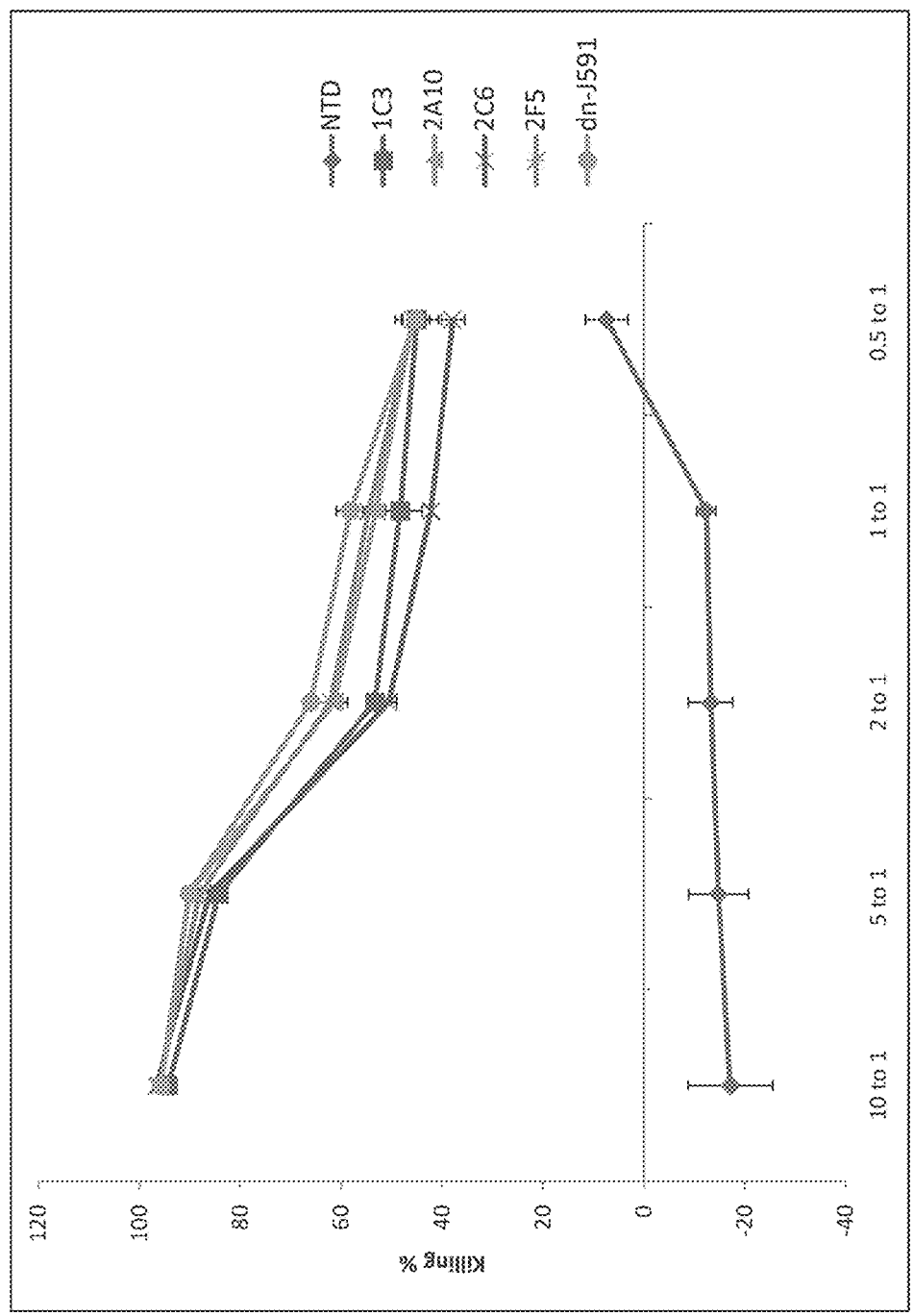
FIG. 3C shows results using various PSMA Lenti CARs incubated with tumor cells and Luciferase based CTL assays performed. Results are reported as percent killing based on luciferase activity in wells with only tumor in the absence of T cells. Results from day 12 are shown.
Figure 3D:
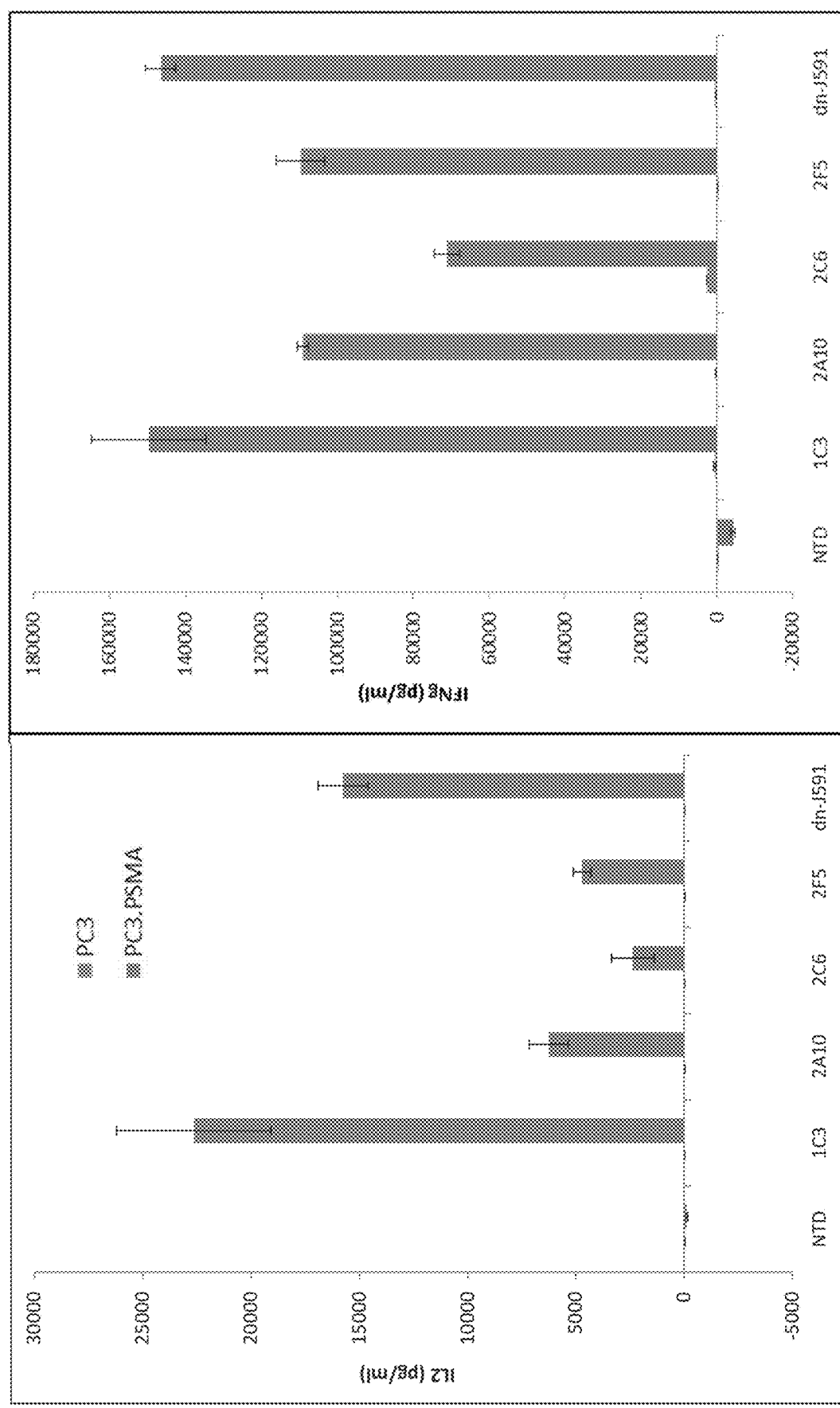
FIG. 3D illustrates results using various PSMA Lenti CARs incubated with PC3 or PC3.PSMA cells and ELISA assays performed (IL-2, left panel; IFN-γ, right panel). Results from day 12 are shown.

The four human PSMA CARs were subcloned into pTRPE Lenti vector. Primary human T cells transduced with human PSMA CARs had different CAR expression levels: 40% for 1C3.BBZ, 66% for 2A10.BBZ, 50% for 2C6.BBZ and 61% for 2F5.BBZ (FIG. 3A). A dominant negative TGFRβII sequence was linked to the mouse J591.BBZ CAR via a T2A sequence (dnTGFR(3II-J591.BBZ). Nalm6.CBG electroporated with PSMA RNA, PC3 or PC3.PSMA.CBG cells were co-cultured with various PSMA Lenti CARs. CD107a assays, Luciferase based CTL assays and ELISA assays were performed to determine the functionality of the four new human PSMA Lenti CARs, and compared with mouse J591 CAR. 1C3.BBZ, 2A10.BBZ and 2F5.BBZ exerted similar anti-tumor activity in the de-granulation assay and Luciferase based Killing assay as dnTGFRβII-J591 (FIG. 3B and FIG. 3C). In terms of cytokine production, all four human PSMA Lenti CARs elicited specific IL-2 and INF-γ production but the amount varied among the human CARs (FIG. 3D).

Figure 4A:
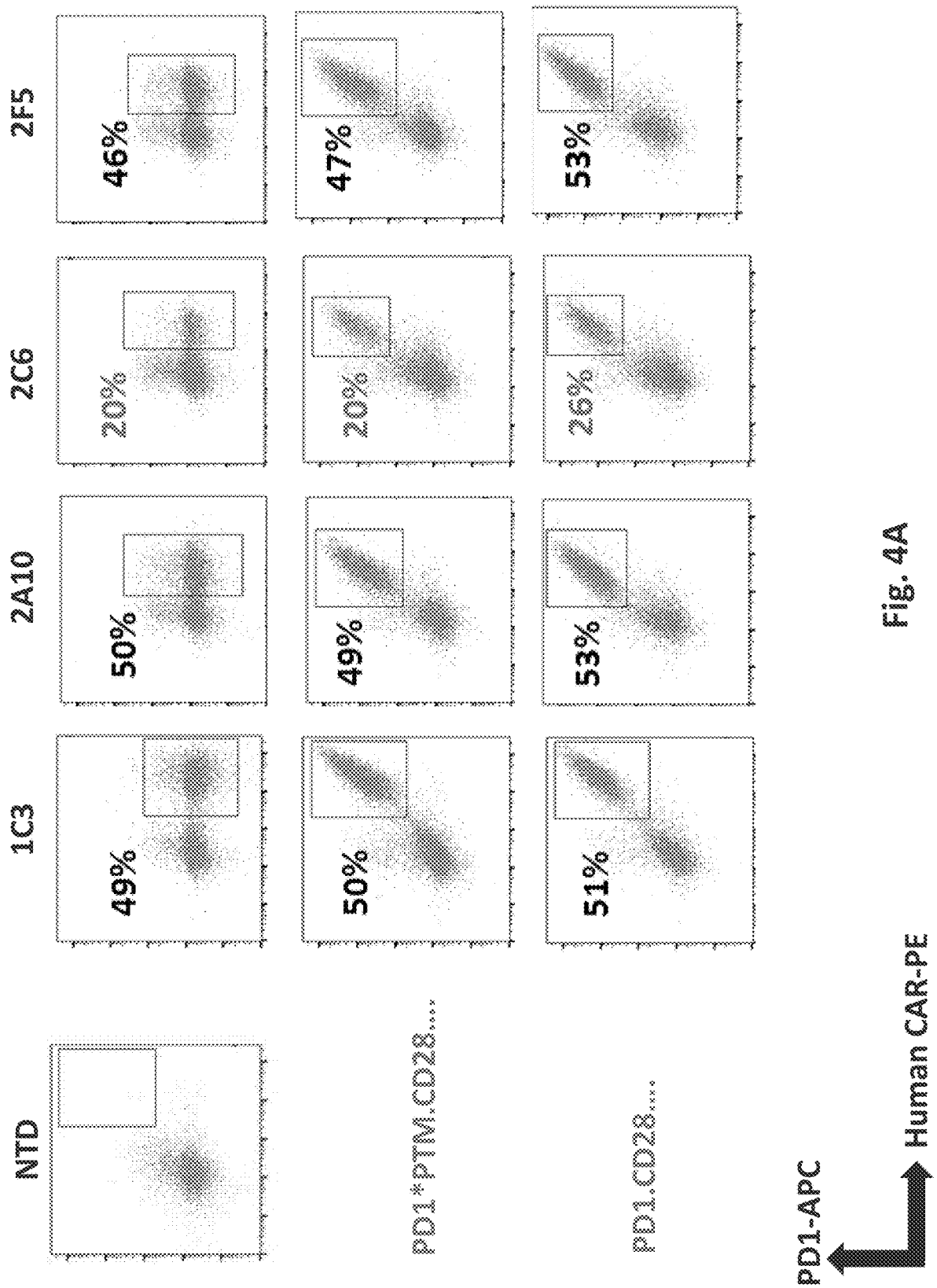
FIG. 4A illustrates results using switch receptors, PD1*PTM.CD28 or PD1.CD28 linked to each human PSMA Lenti CARs via F2A and transduced into primary human T cells. PD1 and CAR expression were examined by Flow Cytometry on day 12.
Figure 4B:
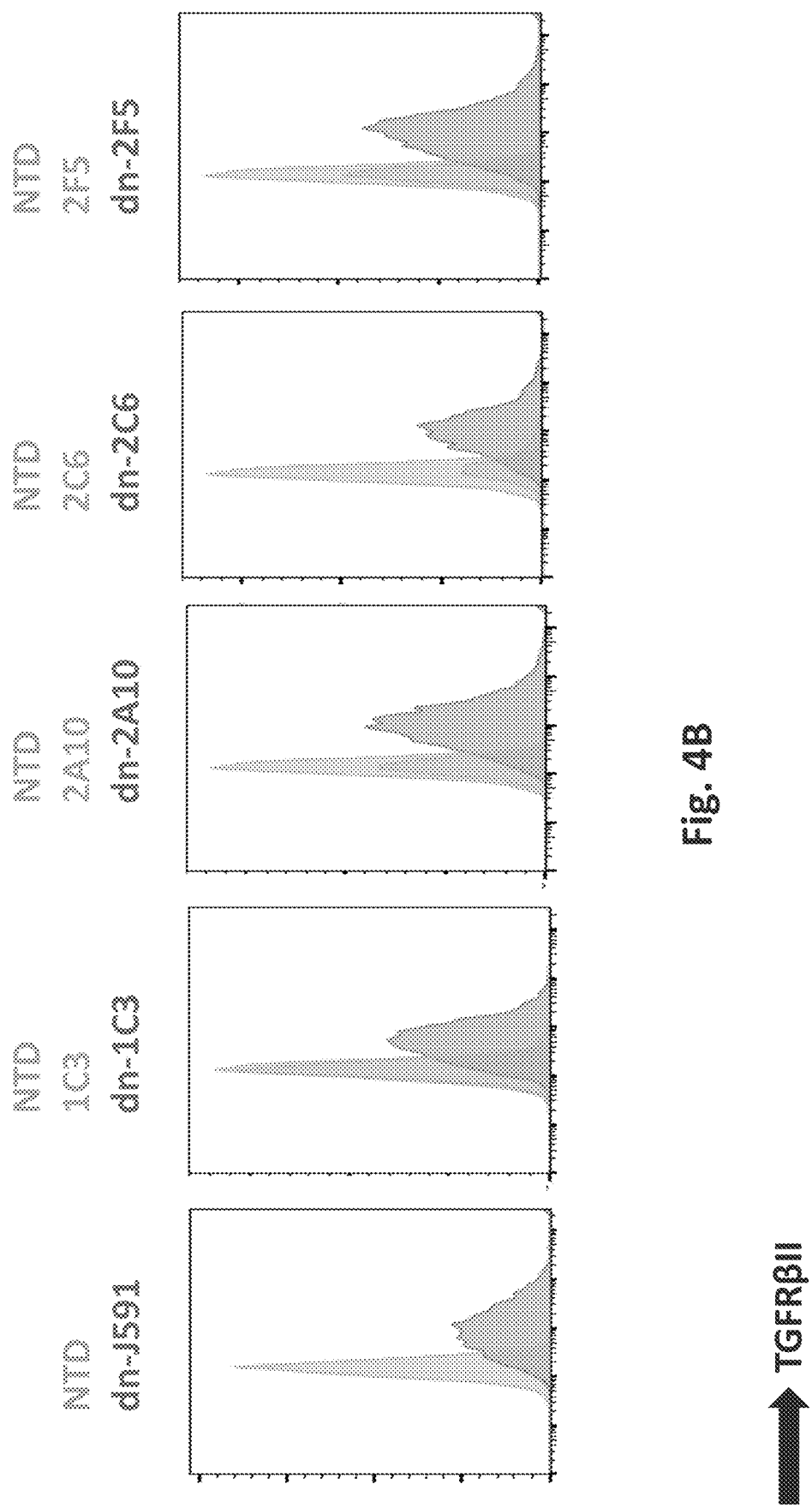
FIG. 4B illustrates results using a dominant negative (dn) transforming growth factor β receptor II (TGFRβII) sequence linked to each human PSMA Lenti CAR via T2A. Dn-TGFRβII-PSMA CAR transduced T cells were analyzed by Flow Cytometry on day 7.

Example 3: Construction of Switch Receptor or Dominant Negative-TGFRβII Linked-Human Lenti CARs A switch receptor (PD1.CD28), comprising a truncated extracellular domain of PD1 and the transmembrane and cytoplasmic signaling domains of CD28 was designed and linked to each human PSMA CAR via a T2A sequence. A point mutation at the 132 (99 for mouse) position from Alanine to Leucine on PD1 increases its affinity with PDL1 by two fold (Zhang et al. Immunity 20, 337-347, 2004). Thus, the second version of switch receptor, "PD1$^{A132L}$PTM.CD28" (with truncated extracellular and transmembrane domains of PD1 and cytoplasmic signaling domain of CD28) was linked to each human PSMA CAR. The dominant negative TGFRβII sequence was subcloned into each human PSMA CARs as well. Flow cytometry was performed to examine the transduction efficiency of each switch receptor-CAR (FIG. 4A) and dnTGFRβII CAR (FIG. 4B). A distinct CAR/PD1 double positive population was observed for all switch receptor-CAR transduced T cells. The transduction efficiency was similar between the human PSMA Lenti CARs and their two switch receptor counterparts (FIG. 4A). Each 2C6 CAR had the lowest transduction efficiency. There was no separate dnTGFRβII population but a clear shift was observed for each dnTGFRβII-linked human PSMA CAR (FIG. 4B).

Figure 4C:
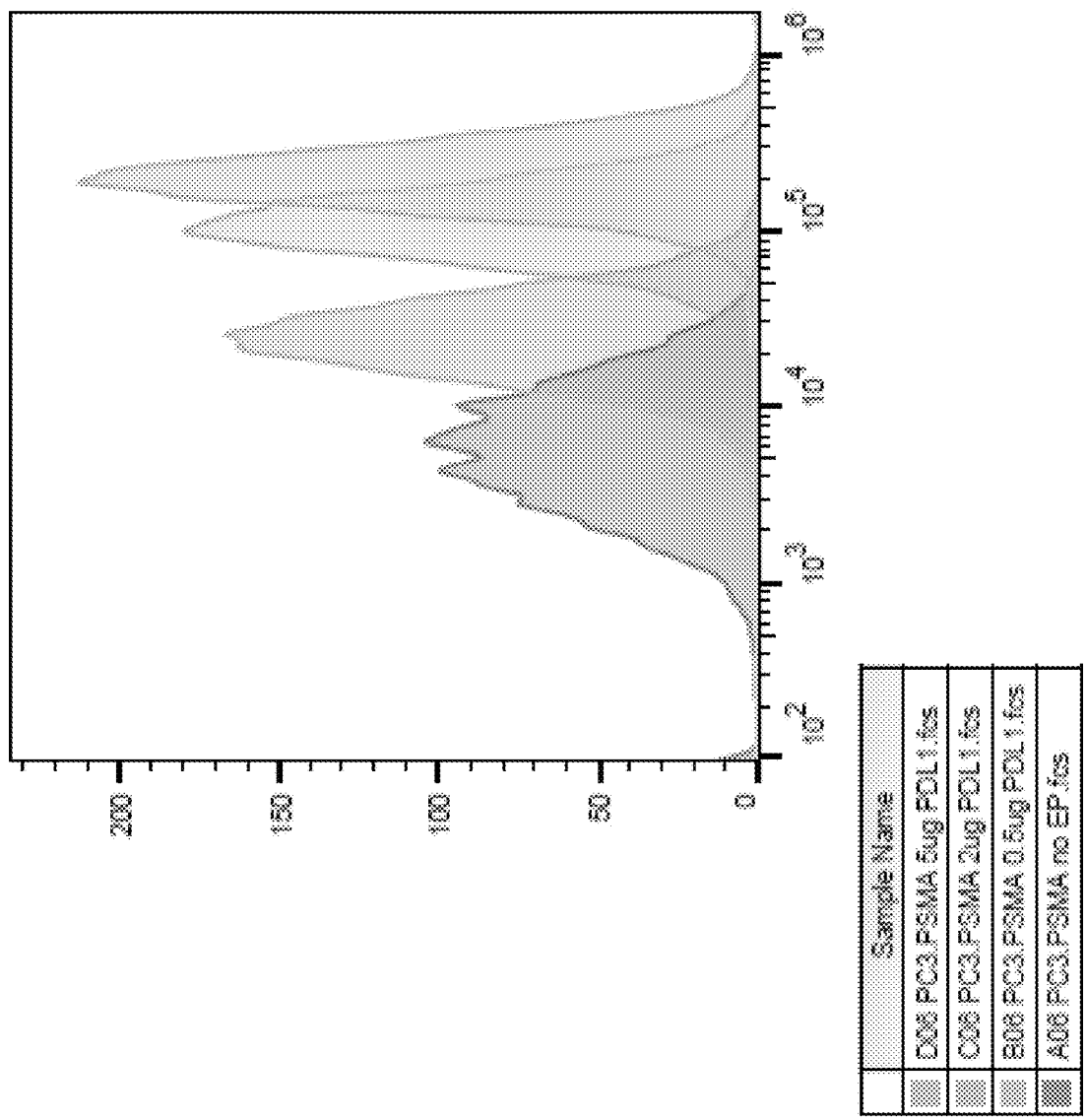
FIG. 4C illustrates results using various amounts of purified full length PDL1 RNA electroporated into PC3.PSMA cells and PDL1 expression examined by Flow Cytometry on day 13.
Figure 4D:
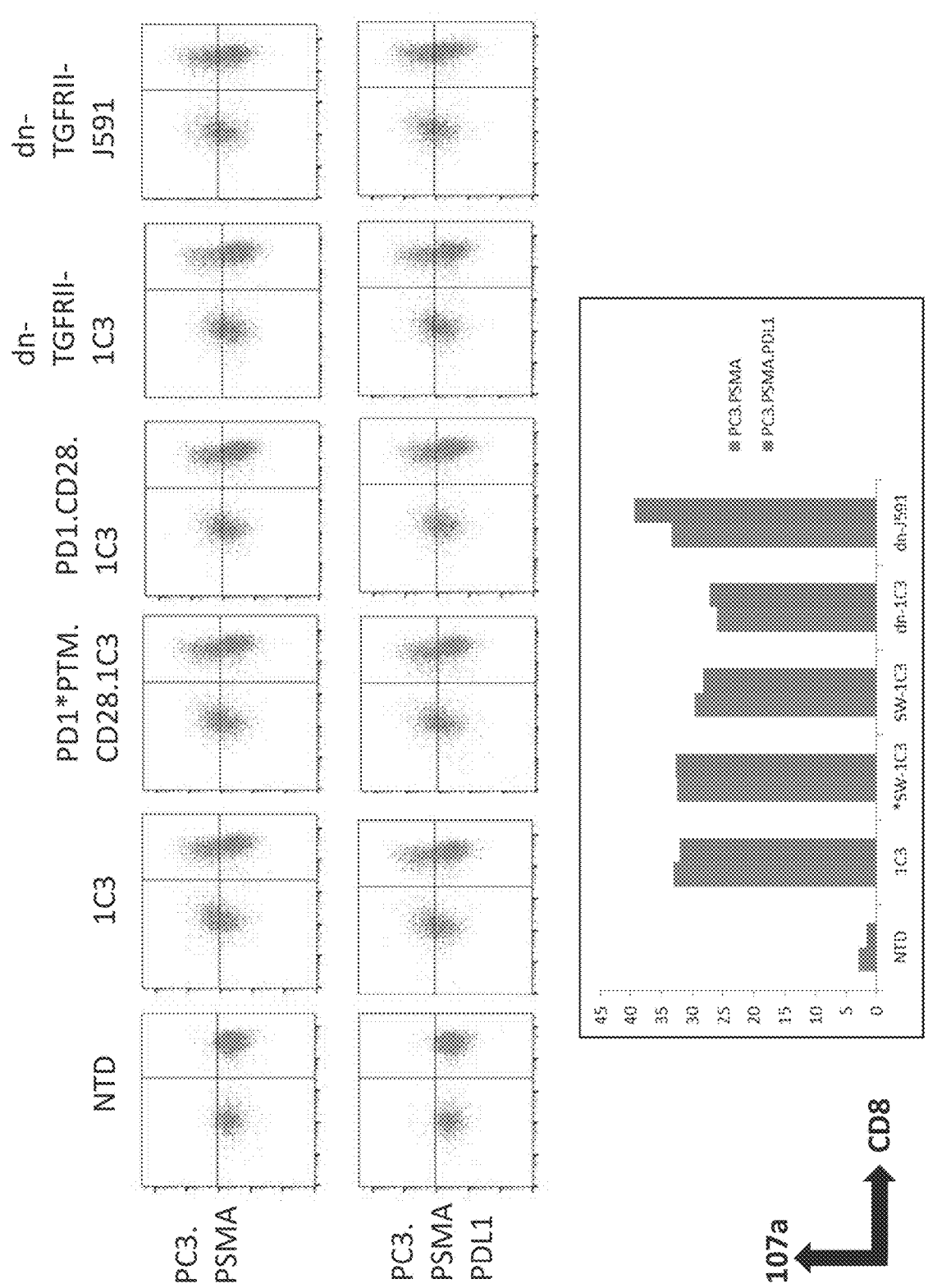
FIG. 4D shows results using various PSMA Lenti CARs incubated with PC3.PSMA or PDL1 electroporated PC3.PSMA cells and CD107a assays performed. The cells were gated by CD3. Results from day 14 are shown.
Figure 4E:
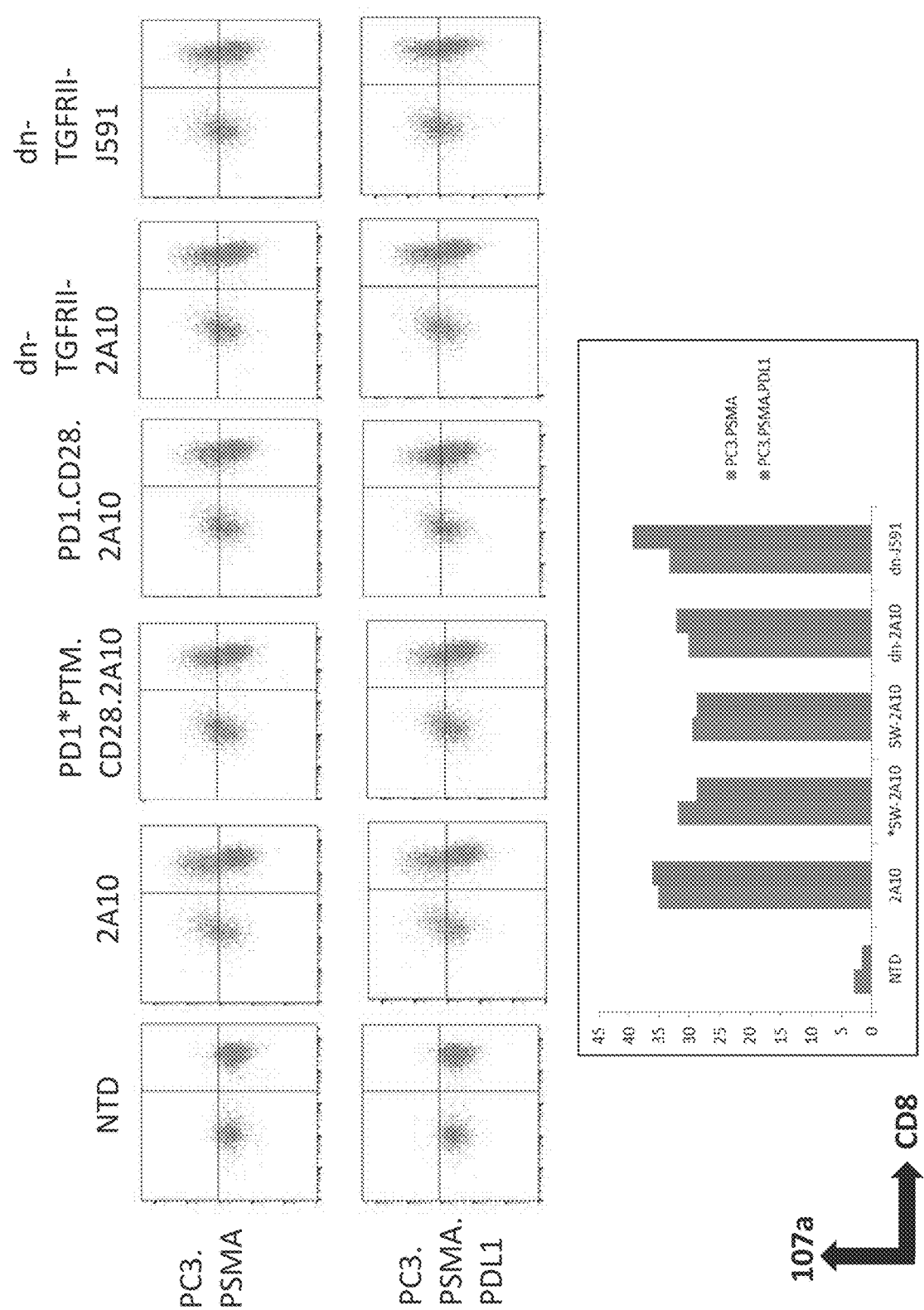
FIG. 4E shows results using various PSMA Lenti CARs incubated with PC3.PSMA or PDL1 electroporated PC3.PSMA cells and CD107a assays performed. The cells were gated by CD3. Results from day 14 are shown.
Figure 4G:
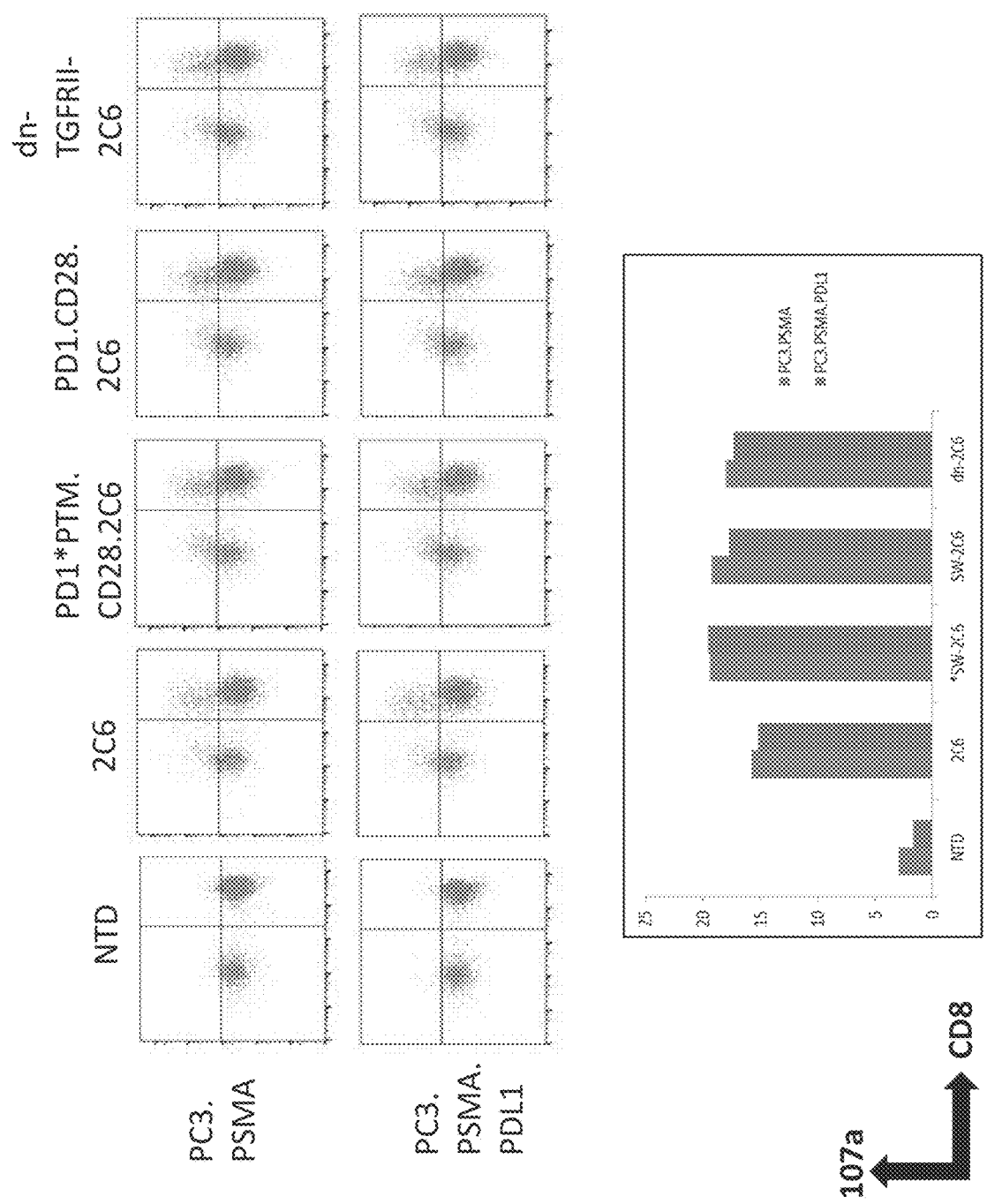
FIG. 4G shows results using various PSMA Lenti CARs incubated with PC3.PSMA or PDL1 electroporated PC3.PSMA cells and CD107a assays performed. The cells were gated by CD3. Results from day 14 are shown.
Figure 4H:
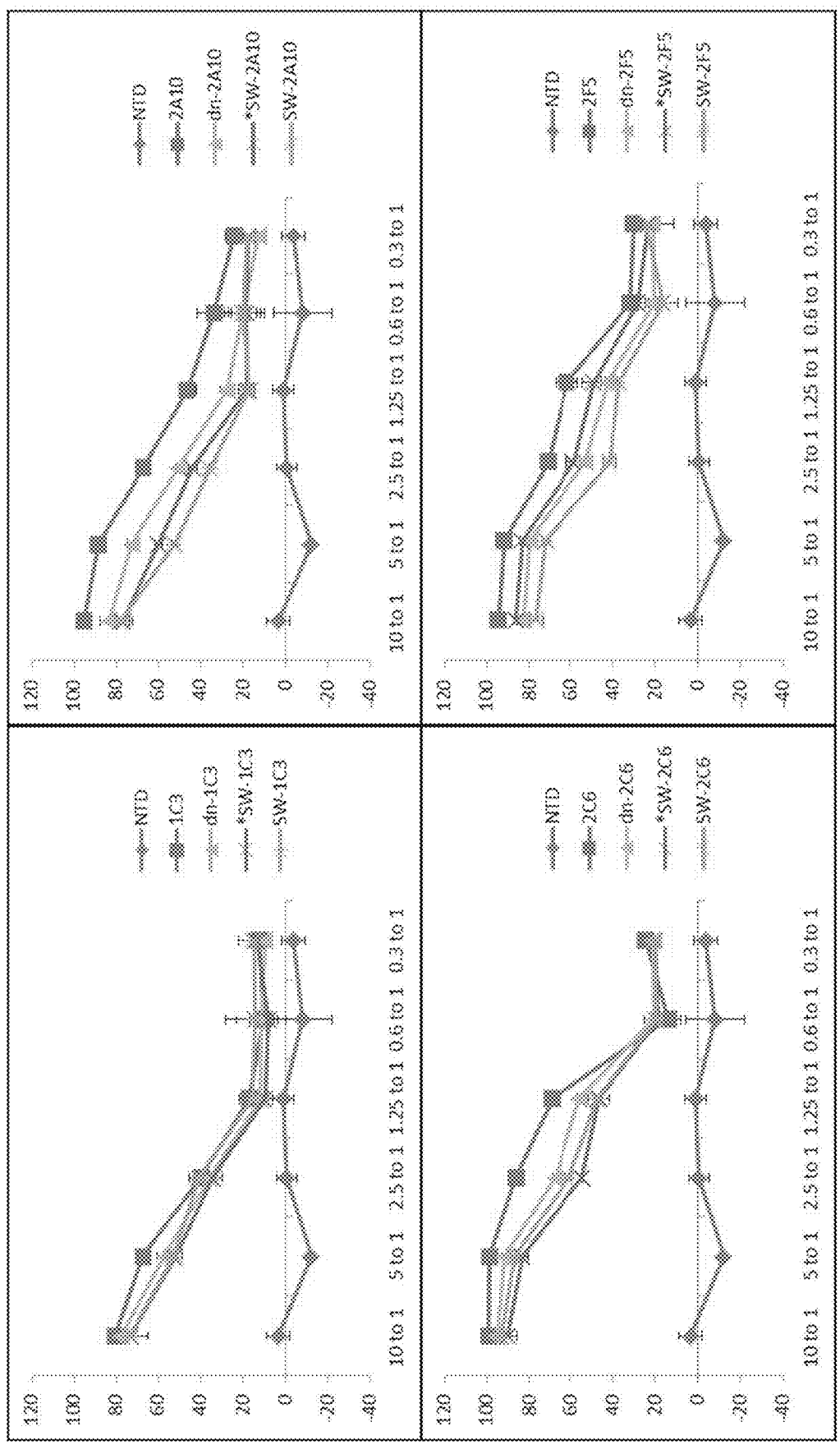
FIG. 4H shows results using various PSMA Lenti CARs incubated with PC3.PSMA cells and Luciferase based CTL assays performed. Results are reported as percent killing based on luciferase activity in wells with only tumor in the absence of T cells.
Figure 4I:
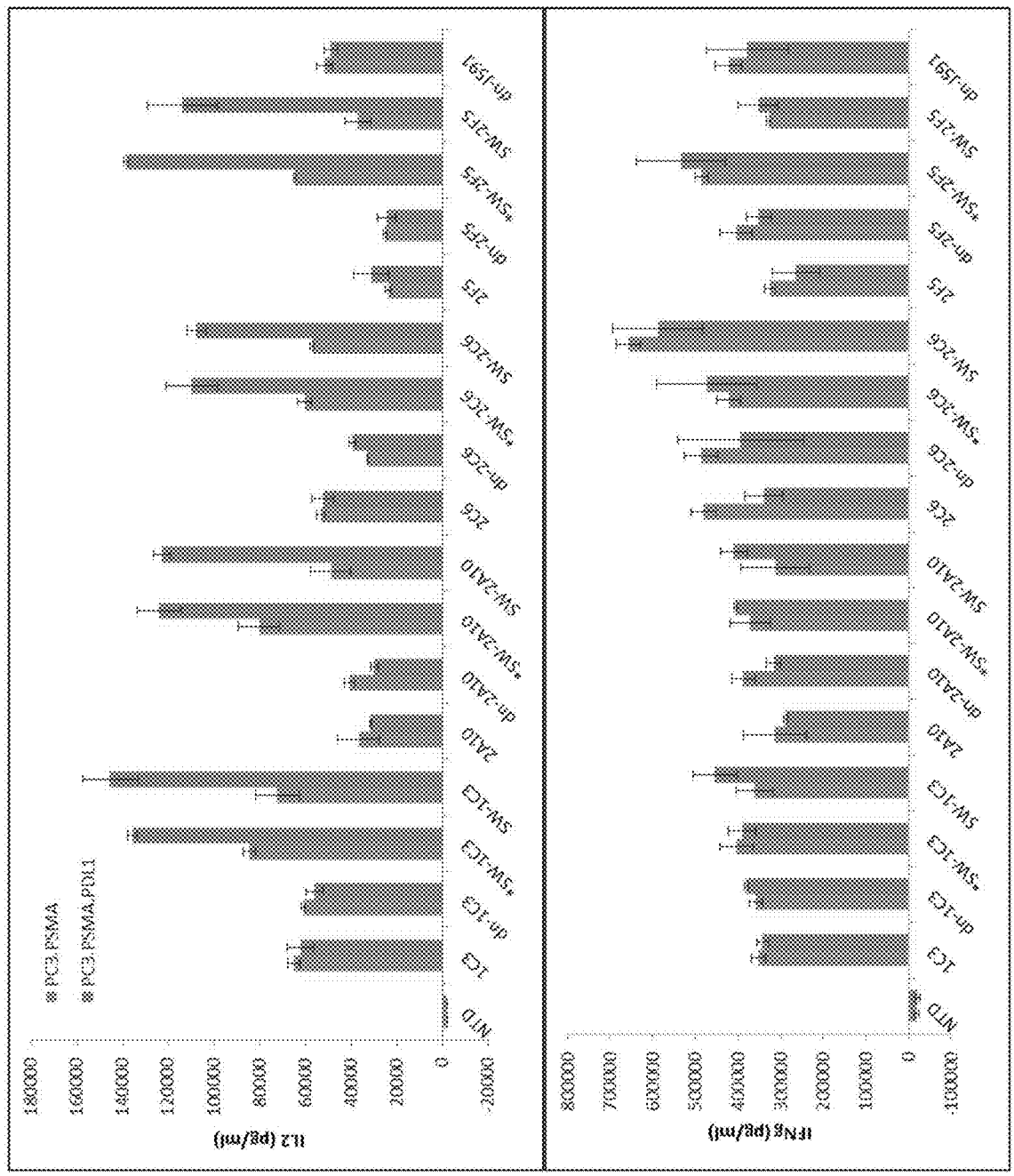
FIG. 4I shows results using various PSMA Lenti CARs incubated with PC3.PSMA or PDL1 electroporated PC3.PSMA cells and ELISA assays performed. (IL-2, top panel; IFN-γ, bottom panel).

To examine the functionality of the switch receptors, various amounts of PDL1 RNA, 0.5 ug, 2 ug, and 5 ug, were electroporated into PC3.PSMA cells (FIG. 4C). The PC3.PSMA cells electroporated with 5 ug PDL1 RNA were co-cultured with each PSMA CAR. dnTGFRβII-J591.BBZ was normalized to a transduction efficiency of 50% prior to the co-cultured experiment. Three out of four human PSMA CARs and their switch receptors or dnTGFRβII counterparts showed comparable de-granulation activity with dnTGFRβII-J591.BBZ CAR when co-cultured with PSMA positive cells (FIG. 4D, FIG. 4E, and FIG. 4F). 2C6.BBZ CAR and its relevant counterparts demonstrated a lower degranulation activity which might be due to lower transduction efficiency (FIG. 4G). All four human PSMA CARs and their switch receptor or dnTGFRβII counterparts showed similar cytotoxicity toward PC3.PSMA cells (FIG. 4H). All human PSMA CARs elicited comparable amounts of cytokine with dnTGFRβII-J591.BBZ CAR (FIG. 4I). Each switch receptor CAR secreted almost two fold higher IL-2 compared with their non-switch receptor or dnTGFRβII CAR counterparts when co-cultured with PDL1 electroporated PC3.PSMA cells (FIG. 4I).

Example 4: PC3.PSMA.7SC Xenograft Model

Figure 5A:
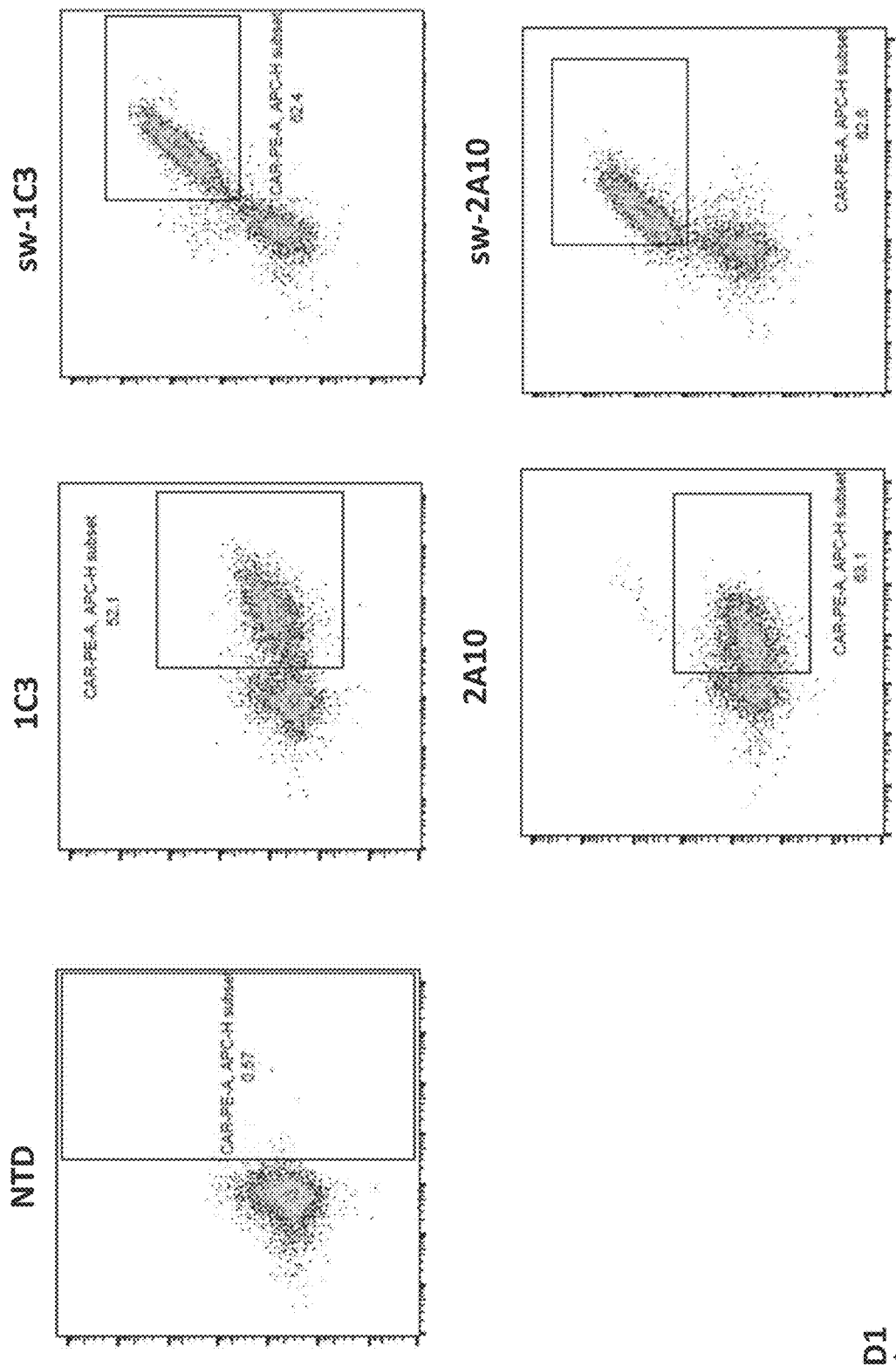
FIG. 5A shows results using switch receptor PD1.CD28 linked to each human PSMA Lenti CARs via F2A transduced into primary human T cells. PD1 and CAR expression were examined by Flow Cytometry.
Figure 5B:
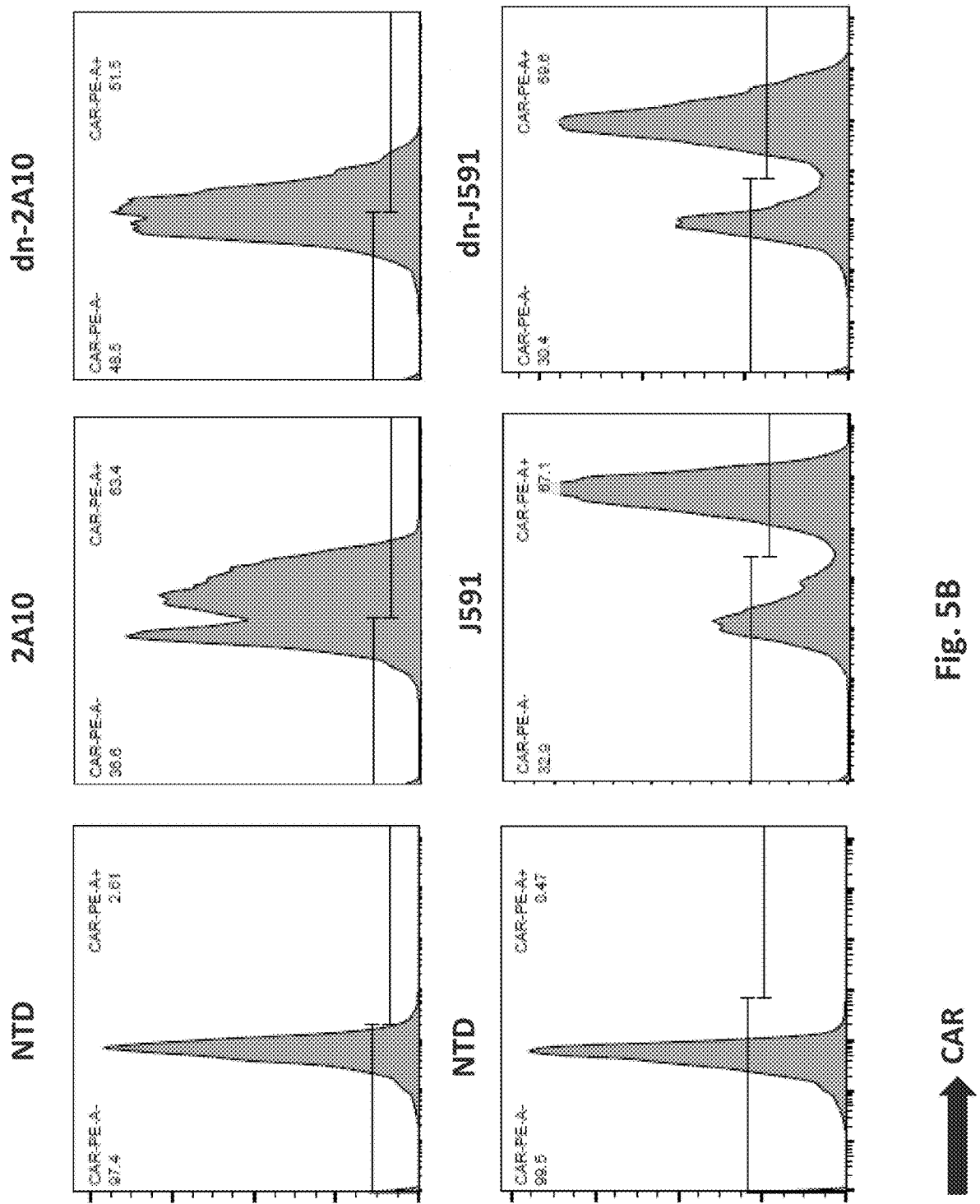
FIG. 5B shows results using a dominant negative (dn) TGFRβII sequence linked to human 2A10 PSMA Lenti CARs via T2A. CARs transduced T cells were analyzed by Flow Cytometry.
Figure 5C:
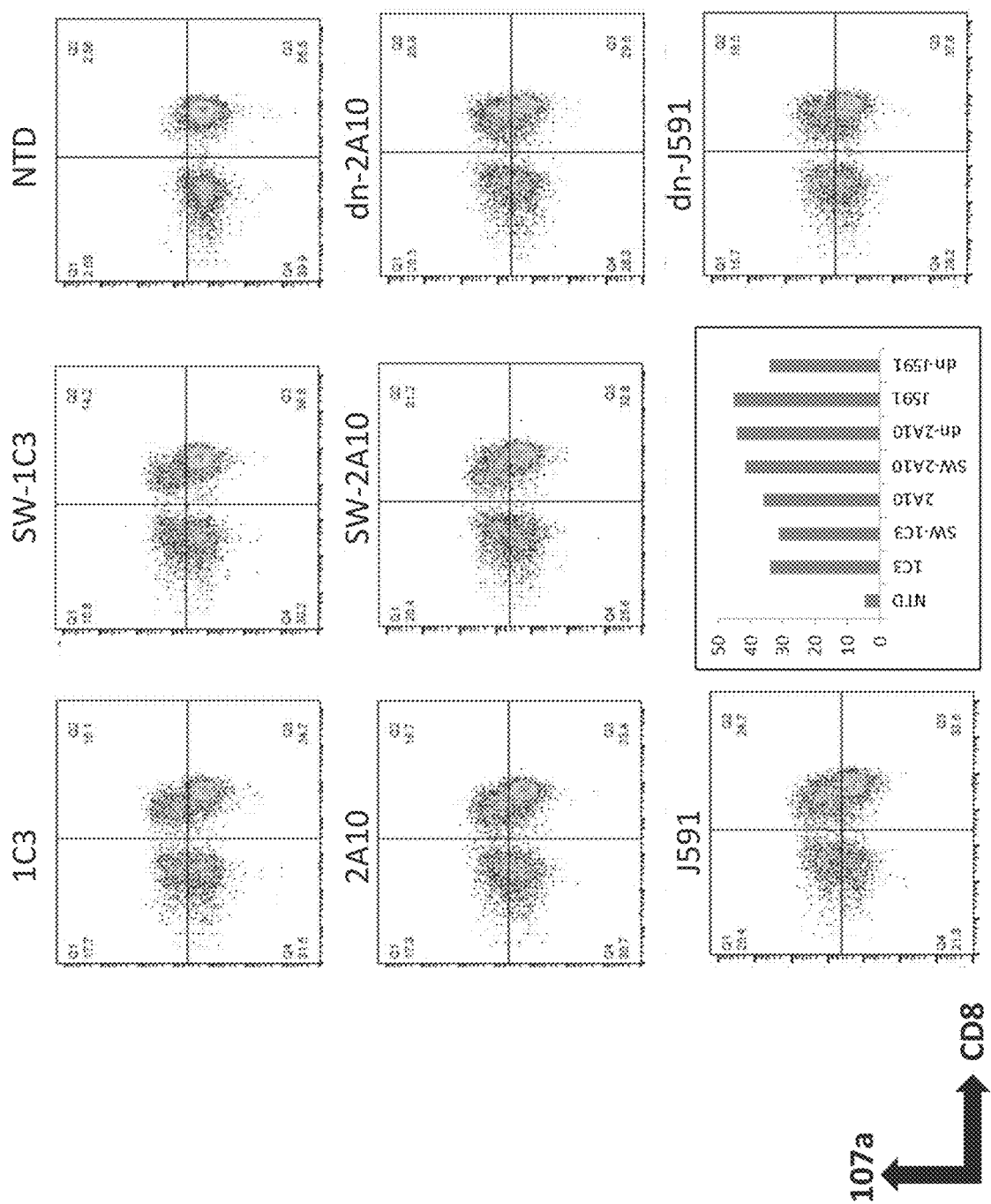
FIG. 5C shows results using various PSMA Lenti CARs incubated with PC3.PSMA.7SC cells and CD107a assays performed. The cells were gated by CD3.
Figure 5D:
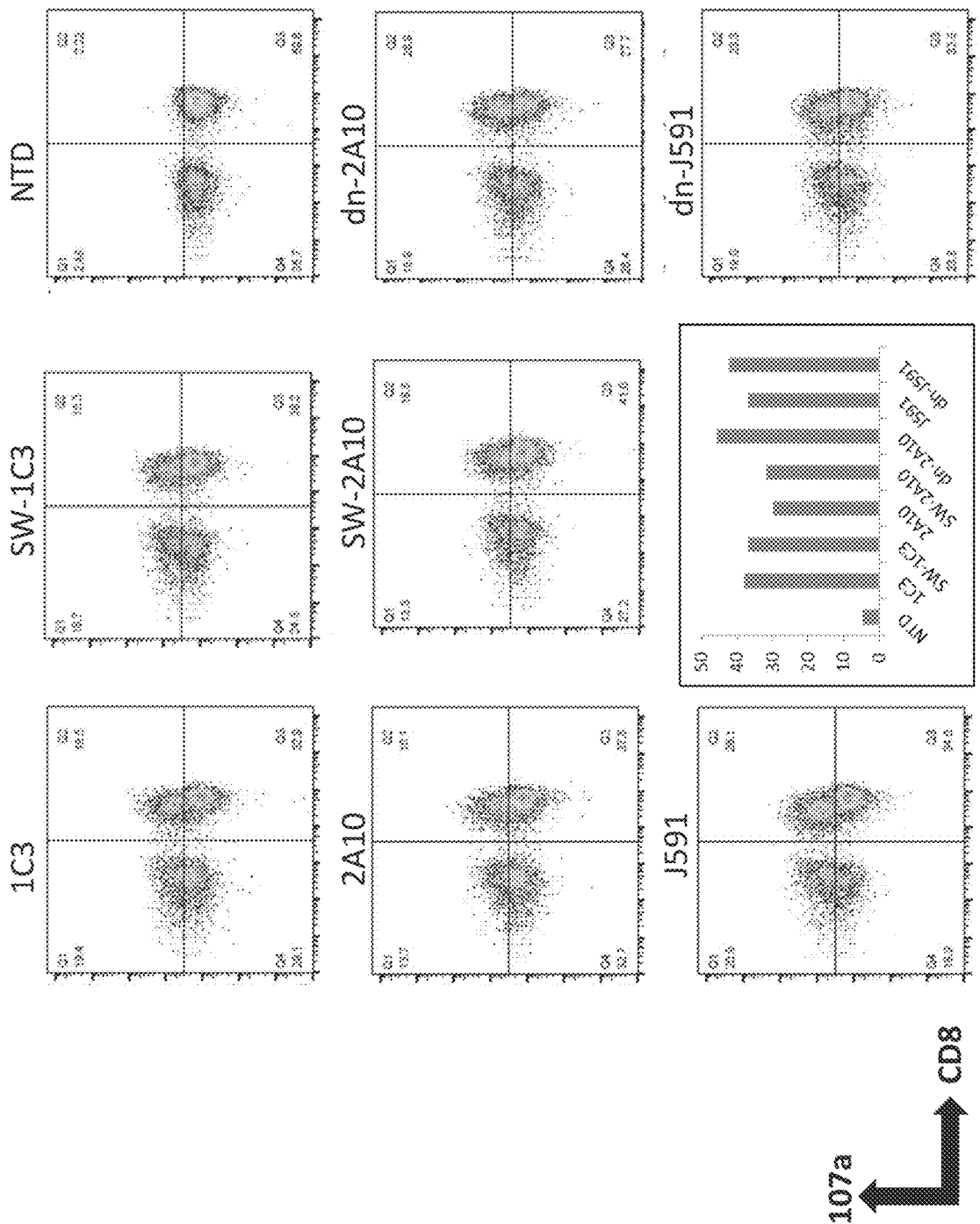
FIG. 5D shows results using various PSMA Lenti CARs were incubated with PDL1 electroporated PC3.PSMA.7SC cells and CD107a assay was performed. The cells were gated by CD3.
Figure 5E:
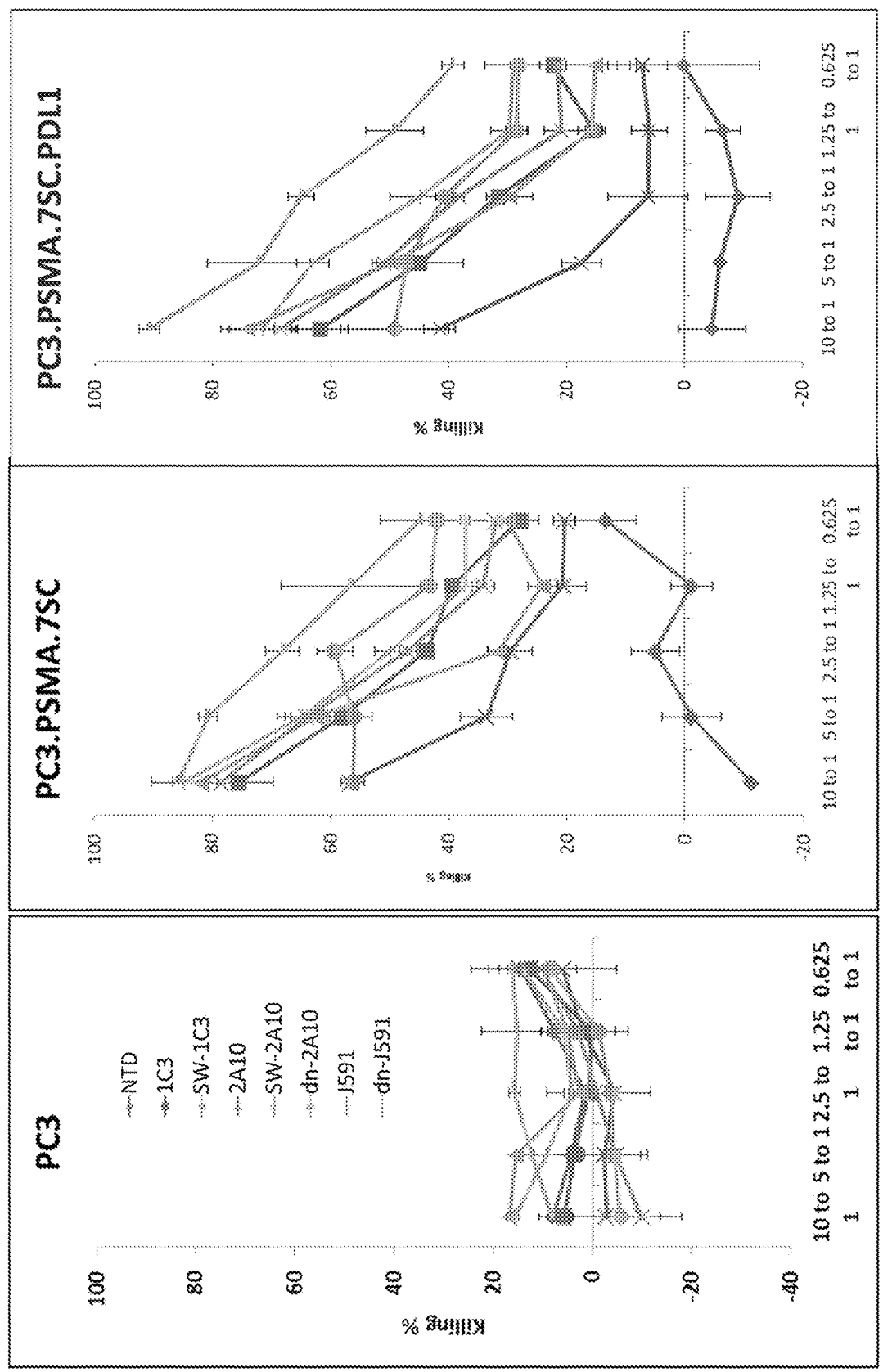
FIG. 5E shows results using various PSMA Lenti CARs incubated with tumor cells and Luciferase based CTL assays performed. Results are reported as percent killing based on luciferase activity in wells with only tumor in the absence of T cells.

The following six human PSMA CARs were selected for use in PC3.PSMA.7SC mouse xenograft model: 1C3.BBZ, PD1CD28.1C3.BBZ, 2A10.BBZ, PD1CD28.2A10.BBZ, dnTGFRβII-2A10.BBZ and dnTGFRβII-J591.BBZ. CAR expression was tested by flow cytometry (FIG. 5A and FIG. 5B). Mouse J591.BBZ Lenti CAR was included in the functional test. All the PSMA CARs tested showed similar degranulation activity in the CD107a assay (FIG. 5C and FIG. 5D) and comparable killing activity in the Luciferase based CTL assay, with 2A10.BBZ being the lowest and dnTGFRβII-J591.BBZ being the highest (FIG. 5E). Each switch receptor CAR secreted almost two fold higher IL-2 comparing with their non-switch receptor or dnTGFRβII CAR counterparts when co-cultured with PDL1 electroporated PC3.PSMA.7SC cells (FIG. 5F).

Figure 5G:
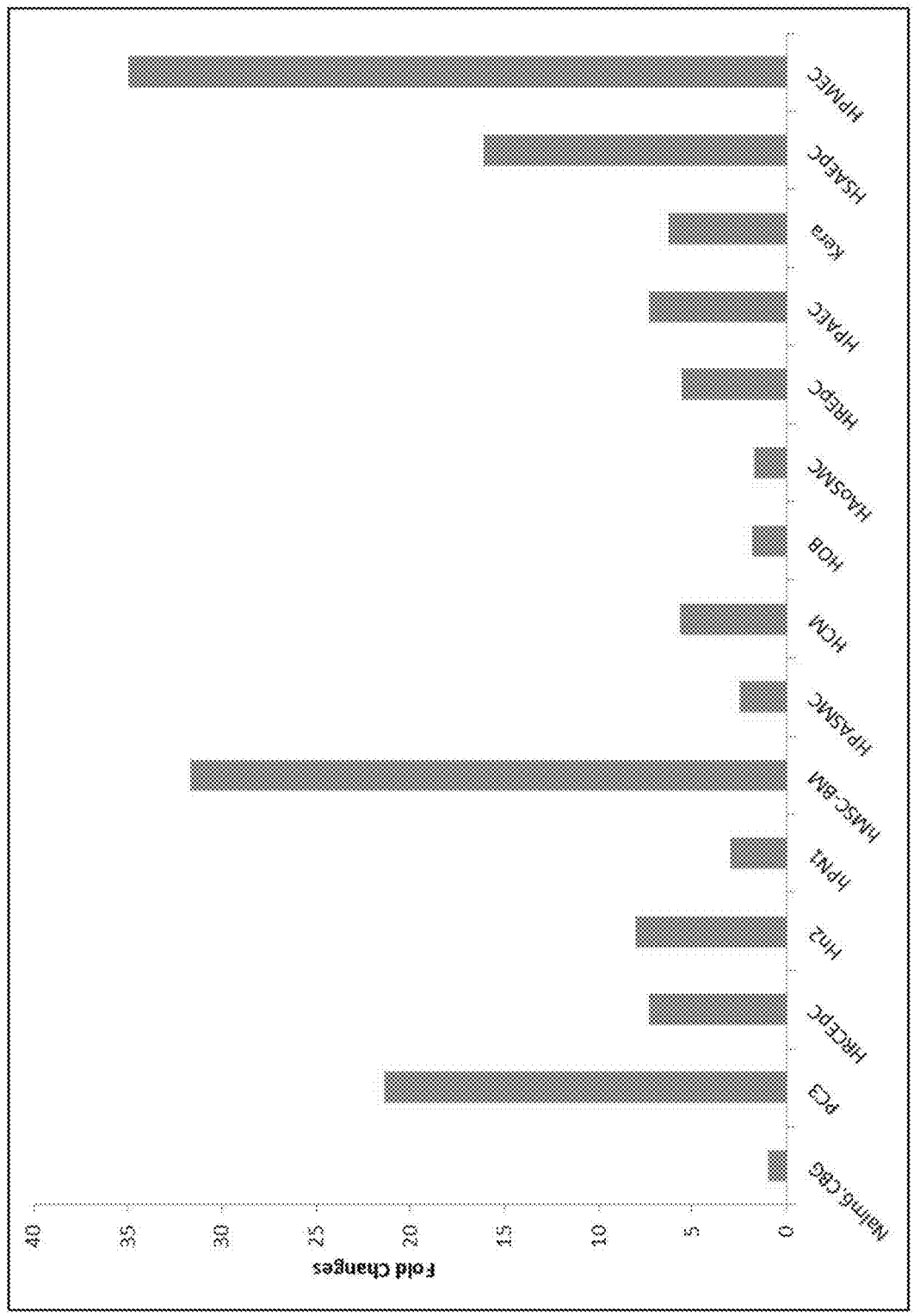
FIG. 5G shows results using quantitative PCR for PSMA expression. The fold changes (delta delta CT) were normalized to Nalm6.CBG cells. See Table 1 for the abbreviations.
Figure 5I:
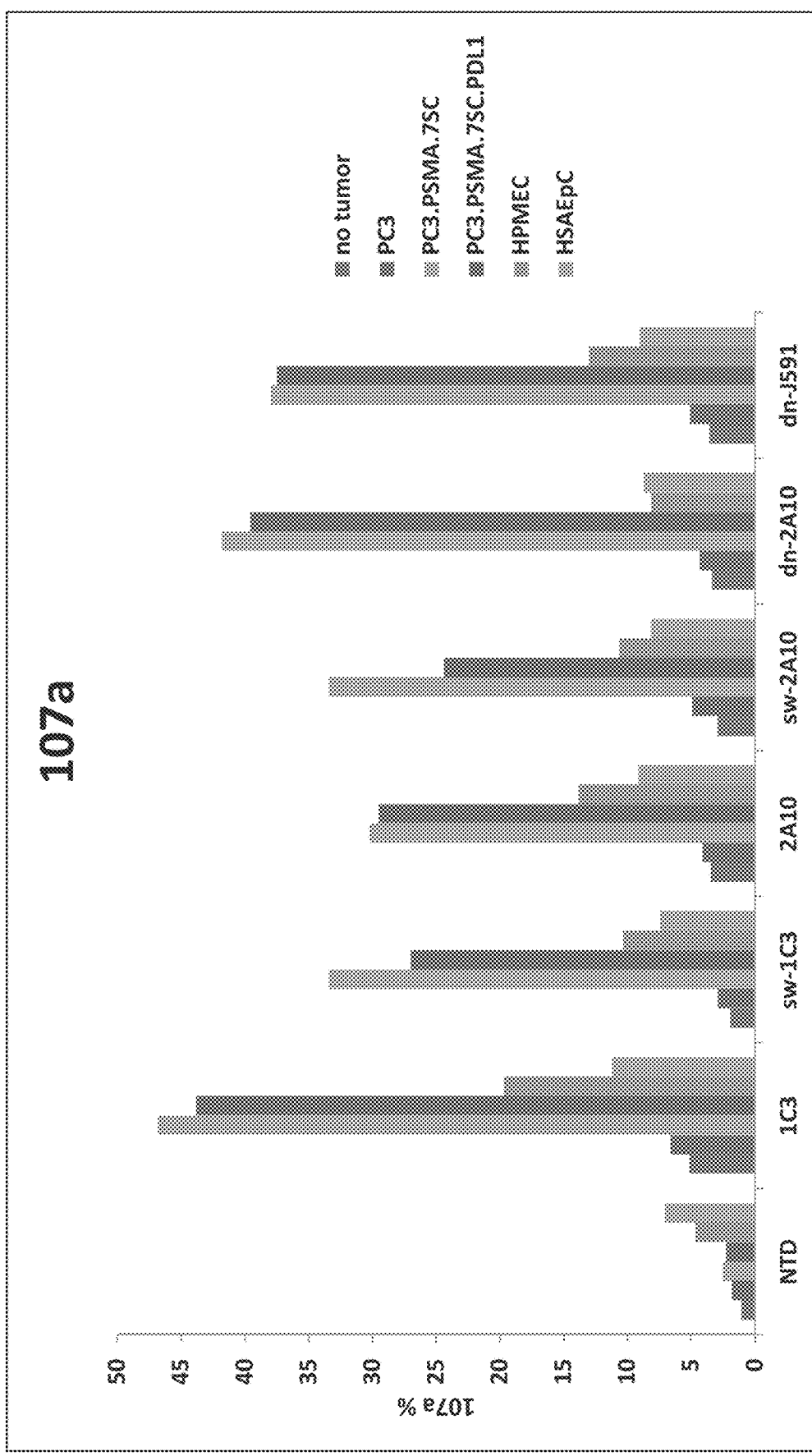
FIG. 5I shows quantitative data from the experiments shown in FIG. 5H. HSAEpC: Human Small Airway Epithelial Cells. HPMEC: Human Pulmonary Microvascular Endothelial Cells.
Figure 5J:
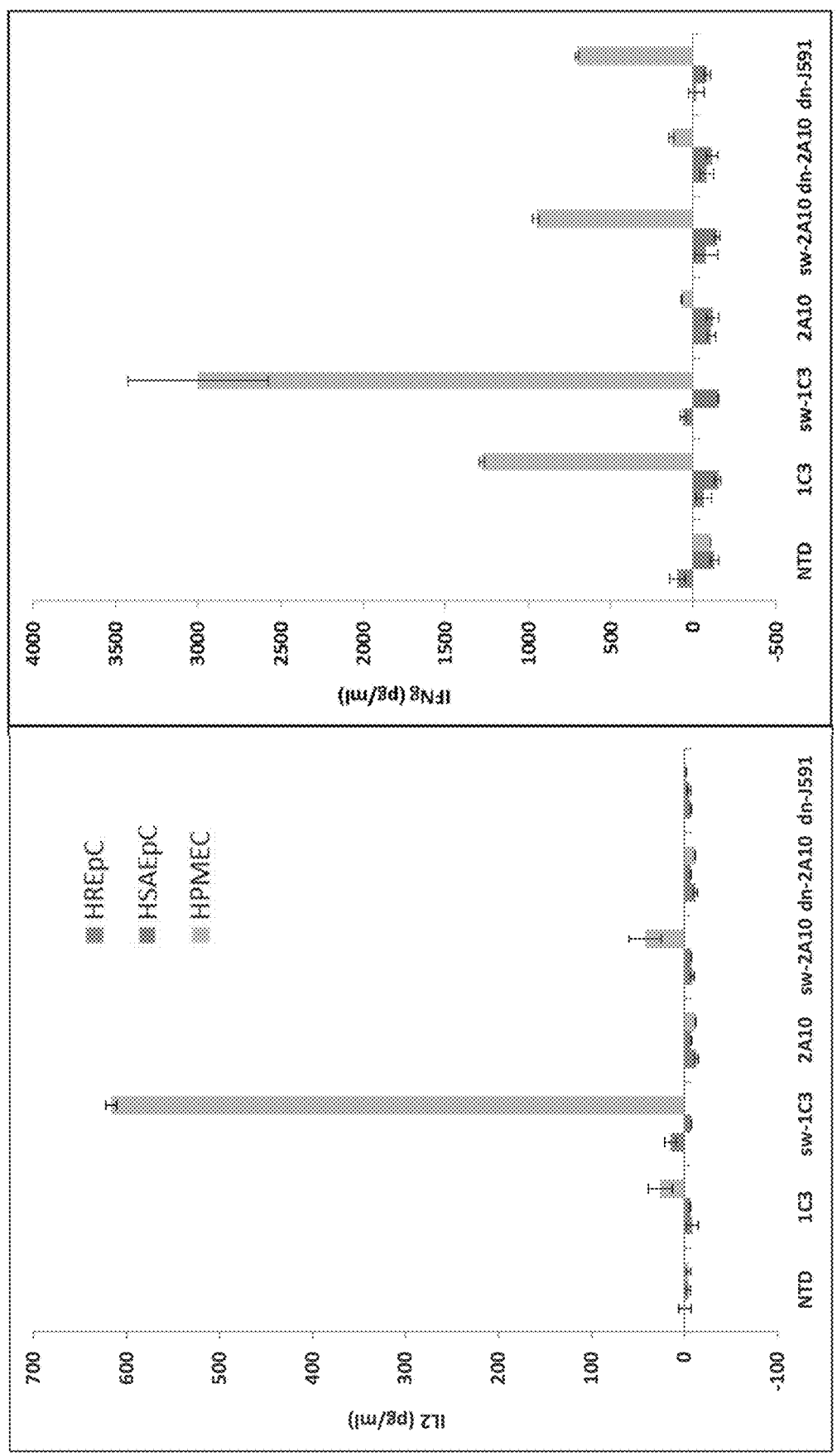
FIG. 5J shows results using various PSMA Lenti CARs incubated with primary human cells and ELISA assays performed. (IL-2, left panel; IFN-γ, right panel). HREpC: Human Renal Epithelial Cells. HSAEpC: Human Small Airway Epithelial Cells. HPMEC: Human Pulmonary Microvascular Endothelial Cells.

To ensure the safety of using the above-mentioned human PSMA CARs, a panel of primary human cells (Table 1) was tested for PSMA expression by quantitative PCR (FIG. 5G). Normalized by Nalm6.CBG, all primary cells tested had various PSMA expression levels even for PC3 cells which only had limited reactivity toward PSMA RNA CARs (FIG. 2A) but not PSMA Lenti CARs (FIG. 5H) (PSMA expression is 1800 fold higher for PC3.PSMA than PC3 cells). HREpC, HSAEpC and HPMEC human primary were co-cultured with above-mentioned CARs. CD107a and ELISA assays were performed. All PSMA CARs tested had minimal detectable de-granulation activity when co-culturing with HPMEC (FIG. 5H and FIG. 5I). PD1CD28.1C3.BBZ elicited increased IL-2, compared with 1C3.BBZ when co-cultured with HPMEC (FIG. 5J). Even though the level of cytokine elicited by primary human cells, specifically, HPMEC is negligible when compared to that by PC3.PSMA.7SC (FIG. 5J as compared to FIG. 5F).

TABLE 1

| Primary human cells tested for PSMA expression | |
| --- | --- |
| HRCEpC | Human Renal Cortical Epithelial Cells |
| Hn2 | Primary human Neuron |
| hNP1 | Human Neuronal progenitors |
| hMSC-BM | Human Mesenchymal Stem Cells from Bone Marrow |
| HPASMC | Human Pulmonary Artery Smooth Muscle Cells |
| HCM | Human cardiac myocytes |
| HOB | Human Osteoblasts |
| HAoSMC | Human Aortic Smooth Muscle Cells |
| HREpC | Human Renal Epithelial Cells |
| HPAEC | Human Pulmonary Artery Endothelial Cells |
| Kera | Kerotinocyte |
| HSAEpC | Human Small Airway Epithelial Cells |
| HPMEC | Human Pulmonary Microvascular Endothelial Cells |

Figure 5K:
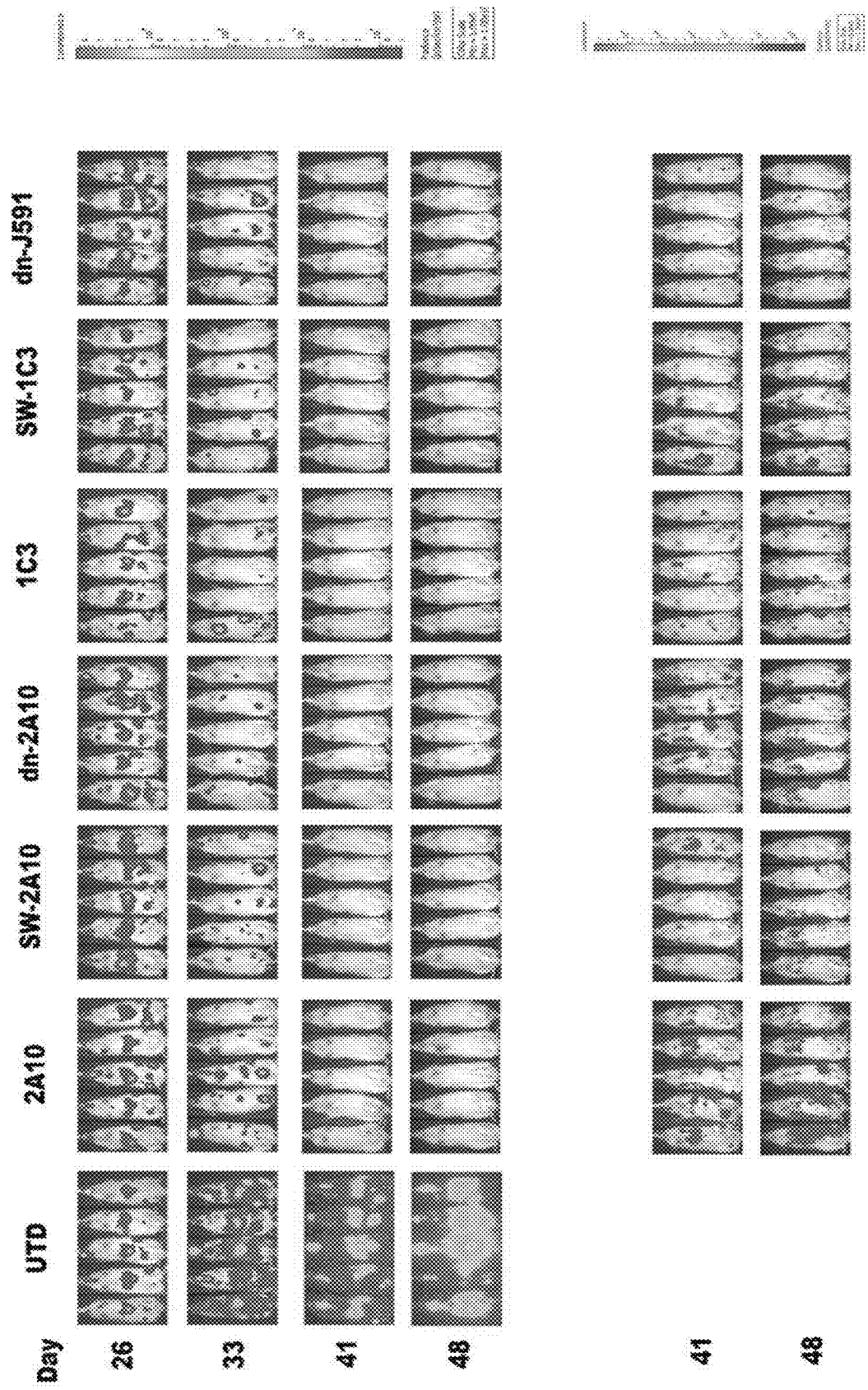
FIG. 5K shows results using $2 \times 10^6$ PC3.PSMA.7SC cells transduced with click beetle and injected into mice (i.v.). 27 days later, $2 \times 10^6$ PSMA CAR-T positive transduced T cells were injected to the tumor bearing mice (i.v.). Bioluminescence imaging (BLI) was conducted at multiple time points. Upper panel with a minimal average radiance of $5 \times 10^5$; Lower panel with a minimal average radiance of $3 \times 10^5$.
Figure 5L:
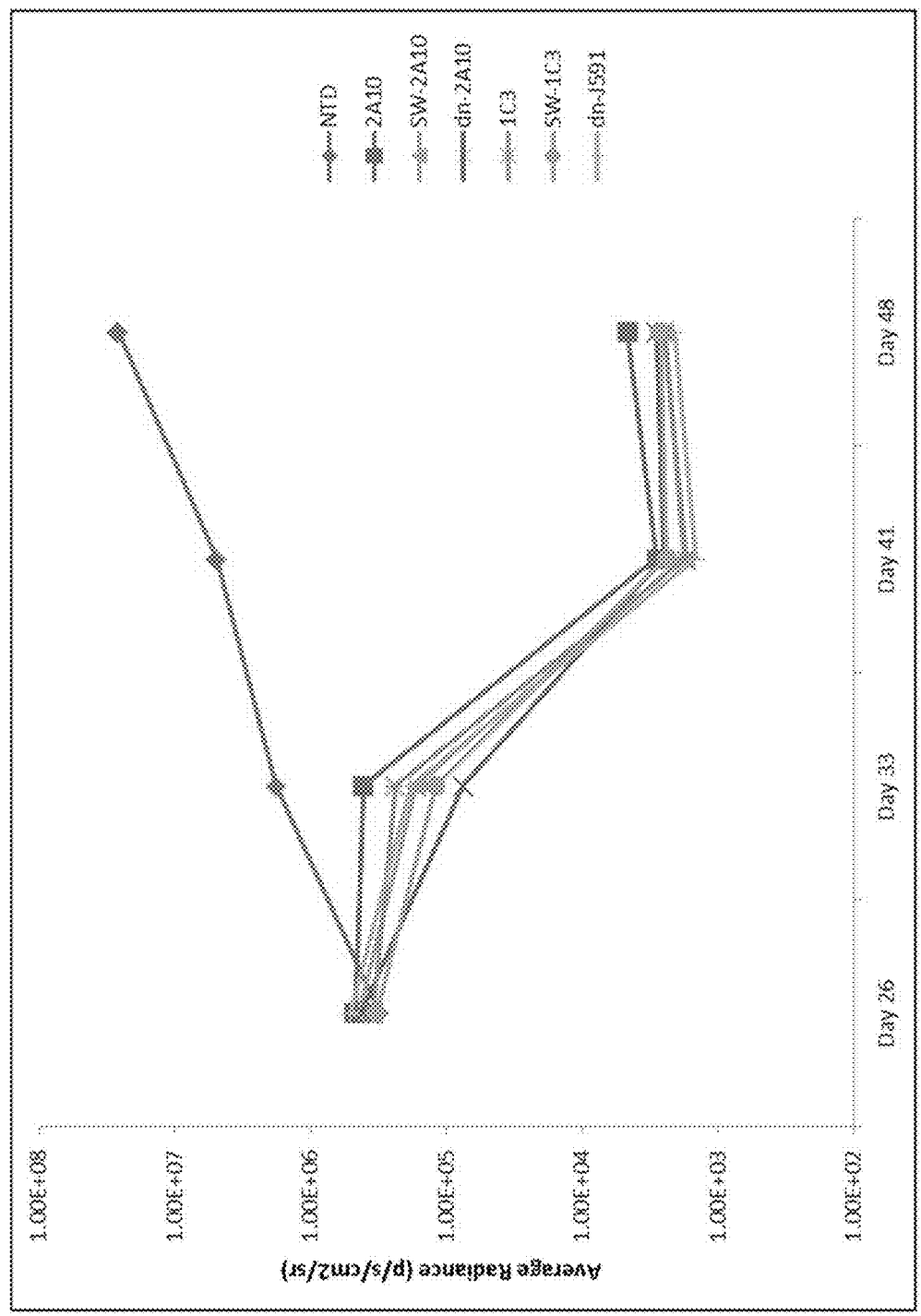
FIG. 5L illustrates quantitative average radiances of FIG. 5K.

The in vivo NSG mouse experiment was designed for 7 groups (five mice per group) to test the six above-mentioned PSMA CARs plus a non-transduced control group. 2E6 PC3.PSMA.7SC cells transduced with click beetle green were injected in the mice (i.v.) and 28 days later, 2E6 CAR positive transduced T cells were injected into the tumor bearing mice (i.v.). Bioluminescence imaging (BLI) was conducted at different time points: day 27, 34, 42, 49 post tumor injection (FIG. 5K and FIG. 5L). Without being bound by any theory, the results of this experiment indicated that all the PSMA CARs tested had comparable anti-tumor activity as dnTGFRβII.J591.BBZ.

FIG. 6 shows the different domains of a dnTGFRII-T2A PSMA-CAR construct, and a pTRPE dnTGFRII-T2A PSMA CAR vector map.

Example 5: In Vivo Tumor Control by PSMA CAR-T Cells

Transduction Protocol:

Bulk T cells (CD4 and CD8) obtained from the Human Immunology Core were diluted to $10^6$ cells/ml, and stimulated with CD3/28 beads (T cell expanders, Invitrogen) at a cell:bead ratio of 1:3. Transductions of packaged lentiviral vectors were performed on day 1 post-stimulation using a MOI of 3:1, and allowed to expand in a 37° C./5% $CO_2$ incubator.

Transduction Efficacy:

The transduction efficacy was evaluated by flow cytometry using the PE anti-human TCR Vβ8 antibody (Cat #: 348104, BioLegend) and APC anti-human CD279 (PD-1) antibody (Cat #: 329908, BioLegend).

T Cell Expansion:

Cells were fed and split every 2 days starting day 3 post stimulation. T cells were de-beaded at day 3 or day 4 and frozen at day 12 for later use.

Cell Counting:

At various time-points during the expansion-resting cycles, cells were gently mixed and a 40 µl aliquot of cells was collected from known culture volume and placed into accuvettes (Beckman Coulter) with 20 ml Isoton II Diluent Buffer for counting using a Coulter Multisizer 3 (Beckman Coulter) in accordance with the CCI laboratory SOP. These assays determined cell concentration, total cell numbers, growth rates, and cell volumes and were used to calculate dilution volumes and determine when cells were rested for freezing.

ELISA for IL-2 and IFNγ:

The T cells were washed and suspended in R10 medium at $1\times10^6$ cells/ml. Approximately 0.1 ml of each cell line was added to a well of a 96-well plate (Corning) and incubated at 37° C. for 18 to 20 hours. The supernatant was harvested and subjected to ELISA.

Cd107A Assay:

The cells were plated at an effector:target (E:T) cell ratio of 1:1 ($10^5$ effectors:$10^5$ targets) in 160 µl of R/10 medium in a 96-well plate. An anti-CD107a antibody was added and incubated with the cells for 1 hour at 37° C. before Golgi Stop was added and incubated for an additional 2.5 hours. The anti-CD8 and anti-CD3 antibodies were added and incubated at 37° C. for 30 min. After incubation, the samples were washed once and subjected to flow cytometry with a BD Accuri C6. The data were analyzed with the FlowJo software.

PC3-PMSA Tumor Models:

1E6 PC3-PMSA-CBG were injected to the mice subcutaneously (s.c.), and 21 days later, lentiviral transduced T cells were injected to the tumor bearing mice intravenously (i.v.). Bioluminescence imaging (BLI) and tumor measurements were conducted at multiple time points.

Results:

The sequences set forth in Table 2 were generated and tested for their ability to control tumors in vivo.

TABLE 2

PSMA CAR in combination with various switch receptor sequences

| SEQ ID NO: | Fig. Ref. | Sequence | CAR | Switch | Description |
|---|---|---|---|---|---|
| 111 or 112 | B | 2F5BBZ | 2F5BBZ | N/A | comprises a 2F5 scFv, a 4-1BB costimulatory domain, and a CD3 zeta intracellular signaling domain |
| 159 | C | PD1CD28. 2F5BBZ | 2F5BBZ | PD1-CD28 | comprises a PD1-CD28 switch and a 2F5BBZ PSMA CAR |
| 163 | D | PD1*CD28. 2F5BBZ | 2F5BBZ | PD1$^{A132L}$-CD28 | comprises a PD1$^{A132L}$-CD28 switch and a 2F5BBZ PSMA CAR |
| 209 or 210 | E | 2F5ICOSz | 2F5ICOSz | N/A | comprises a 2F5 scFv, an ICOS costimulatory domain, and a CD3 zeta intracellular signaling domain |
| 211 or 212 | F | 2F5ICOSzYMNM | 2F5ICOSzYMNM | N/A | comprises a 2F5 scFv, a variant ICOS costimulatory domain comprising a YMNM motif, and a CD3 zeta intracellular signaling domain |
| 217 or 227 | G | PD1CD28. 2F5ICOSz | 2F5ICOSz | PD1-CD28 | comprises a PD1-CD28 switch and a 2F5ICOSz PSMA CAR |
| 218 or 232 | H | PD1CD28. 2F5ICOSzYMNM | 2F5ICOSzYMNM | PD1-CD28 | comprises a PD1-CD28 switch and a 2F5ICOSzYMNM PSMA CAR |
| 219 or 233 | I | PD1*CD28. 2F5ICOSz | 2F5ICOSz | PD1$^{A132L}$-CD28 | comprises a PD1$^{A132L}$-CD28 switch and a 2F5ICOSz PSMA CAR |
| 220 | J | PD1*CD28. 2F5ICOSzYMNM | 2F5ICOSzYMNM | PD1$^{A132L}$-CD28 | comprises a PD1$^{A132L}$-CD28 switch and a 2F5ICOSzYMNM PSMA CAR |
| 221 or 229 | K | PD1*BB. 2F5ICOSz | 2F5ICOSz | PD1$^{A132L}$-41BB | comprises a PD1$^{A132L}$-41BB switch and a 2F5ICOSz PSMA CAR |

TABLE 2-continued

PSMA CAR in combination with various switch receptor sequences

| SEQ ID NO: | Fig. Ref. | Sequence | CAR | Switch | Description |
|---|---|---|---|---|---|
| 222 or 234 | L | PD1*BB. 2F5ICOSzYMNM | 2F5ICOSzYMNM | PD1$^{A132L}$-41BB | comprises a PD1$^{A132L}$-41BB switch and a 2F5ICOSzYMNM PSMA CAR |
| 223 | M | TIM3CD28. 2F5ICOSz | 2F5ICOSz | TIM3-CD28 | comprises a TIM3-CD28 switch and a 2F5ICOSz PSMA CAR |
| 224 or 235 | N | TIM3CD28. 2F5ICOSzYMNM | 2F5ICOSzYMNM | TIM3-CD28 | comprises a TIM3-CD28 switch and a 2F5ICOSzYMNM PSMA CAR |
| 225 | O | PD1*BB. TIM3CD28. 2F5ICOSz | 2F5ICOSz | PD1$^{A132L}$-41BB; and TIM3-CD28 | comprises a PD1$^{A132L}$-41BB switch, a TIM3-CD28 switch, and a 2F5ICOSz PSMA CAR |
| 226 or 236 | P | PD1*BB. TIM3CD28. 2F5ICOSzYMNM | 2F5ICOSzYMNM | PD1$^{A132L}$-41BB; and TIM3-CD28 | comprises a PD1$^{A132L}$-41BB switch, a TIM3-CD28 switch, and a 2F5ICOSzYMNM PSMA CAR |

Figure 7:
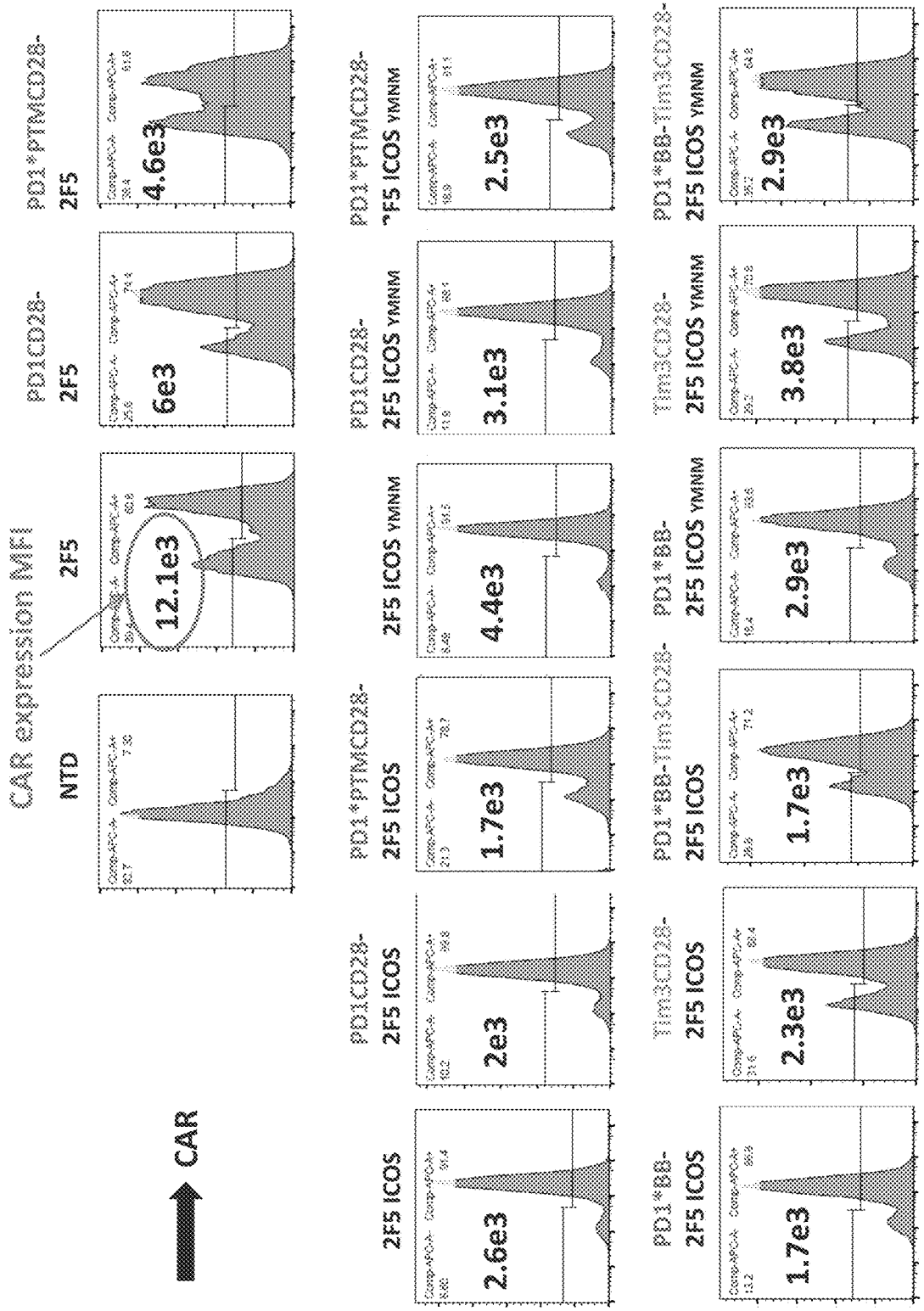
FIG. 7 shows flow cytometry examination of CAR expression in T cells transduced with 2F5 PSMA CAR alone (2F5 ICOS), or co-transduced 2F5 PSMA CAR together with various switch receptors, as indicated.
Figure 8:
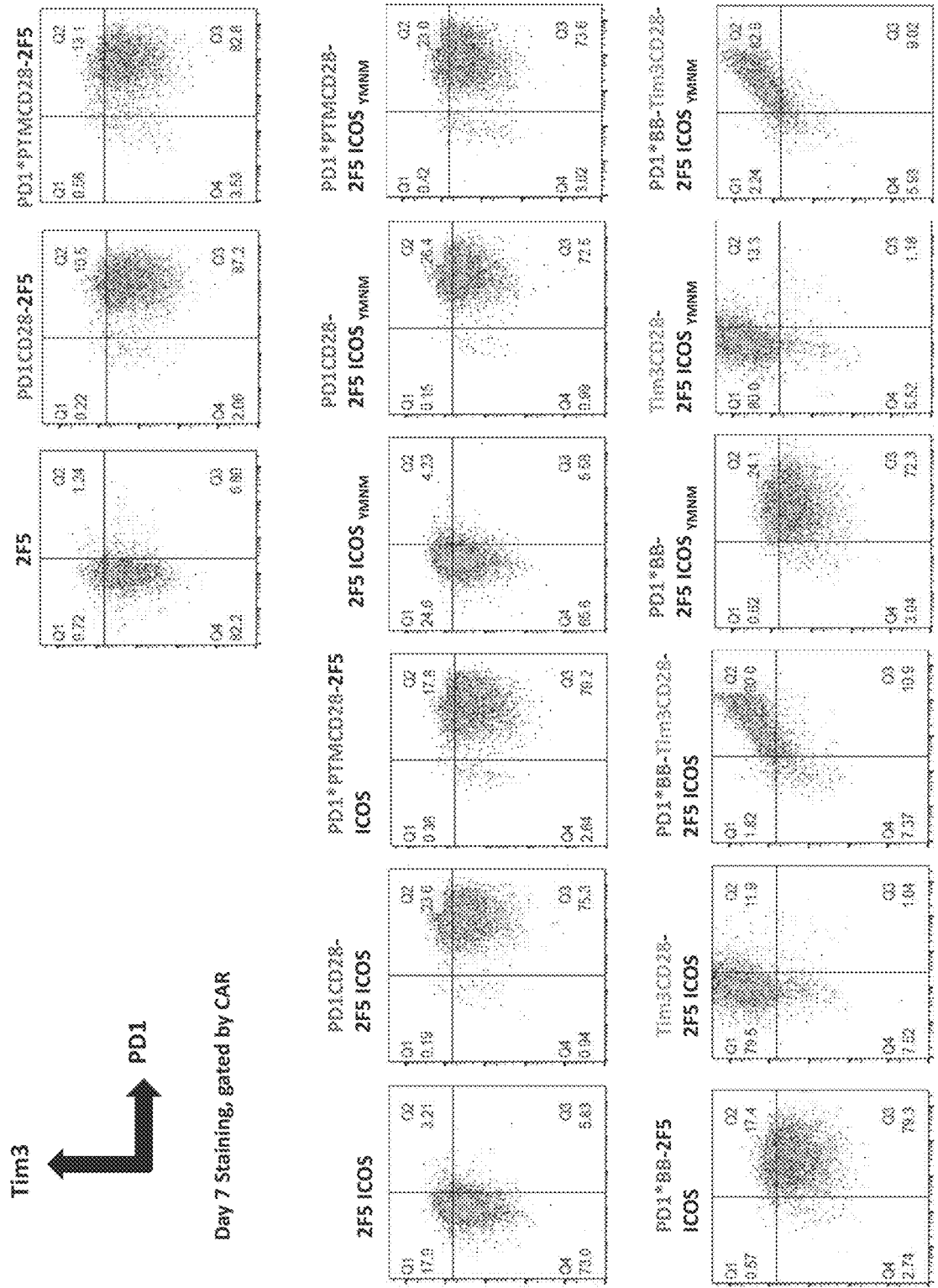
FIG. 8 shows flow cytometry examination of PD1 and Tim3 expression of T cells transduced with 2F5 PSMA CAR alone (2F5 ICOS), or co-transduced 2F5 PSMA CAR together with various switch receptors, as indicated.
Figure 9:
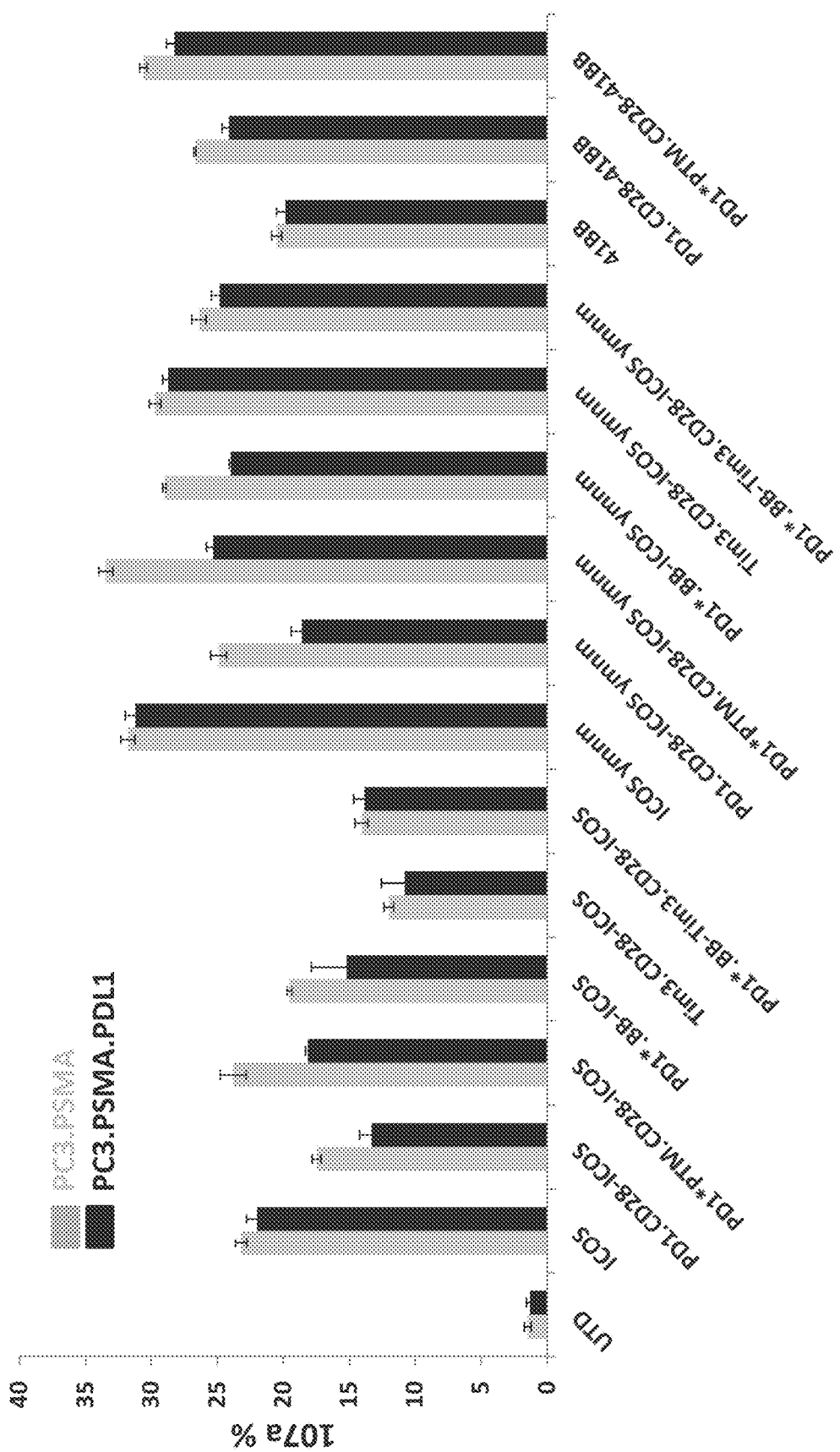
FIG. 9 is a graph depicting CD107a expression in T cells transduced with 2F5 PSMA ICOS-CAR alone (ICOS), PSMA 41BB-CAR alone (41BB), or co-transduced 2F5 PSMA CAR together with various switch receptors, as indicated. UTD means untransduced.
Figure 10:
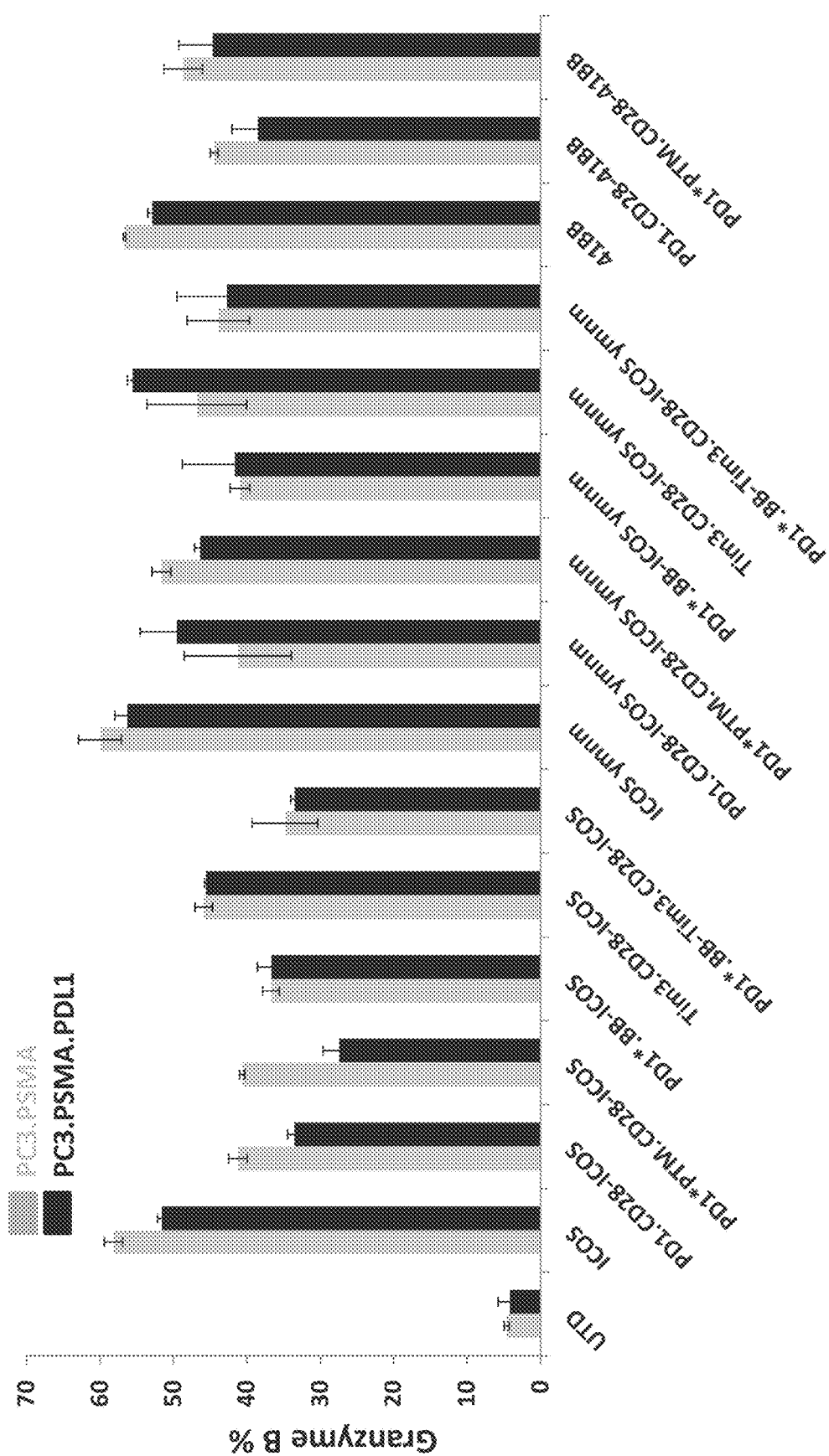
FIG. 10 is a graph depicting granzyme B expression in T cells transduced with 2F5 PSMA ICOS-CAR alone (ICOS), PSMA 41BB-CAR alone (41BB), or co-transduced 2F5 PSMA CAR together with various switch receptors, as indicated. UTD means untransduced.
Figure 11A:
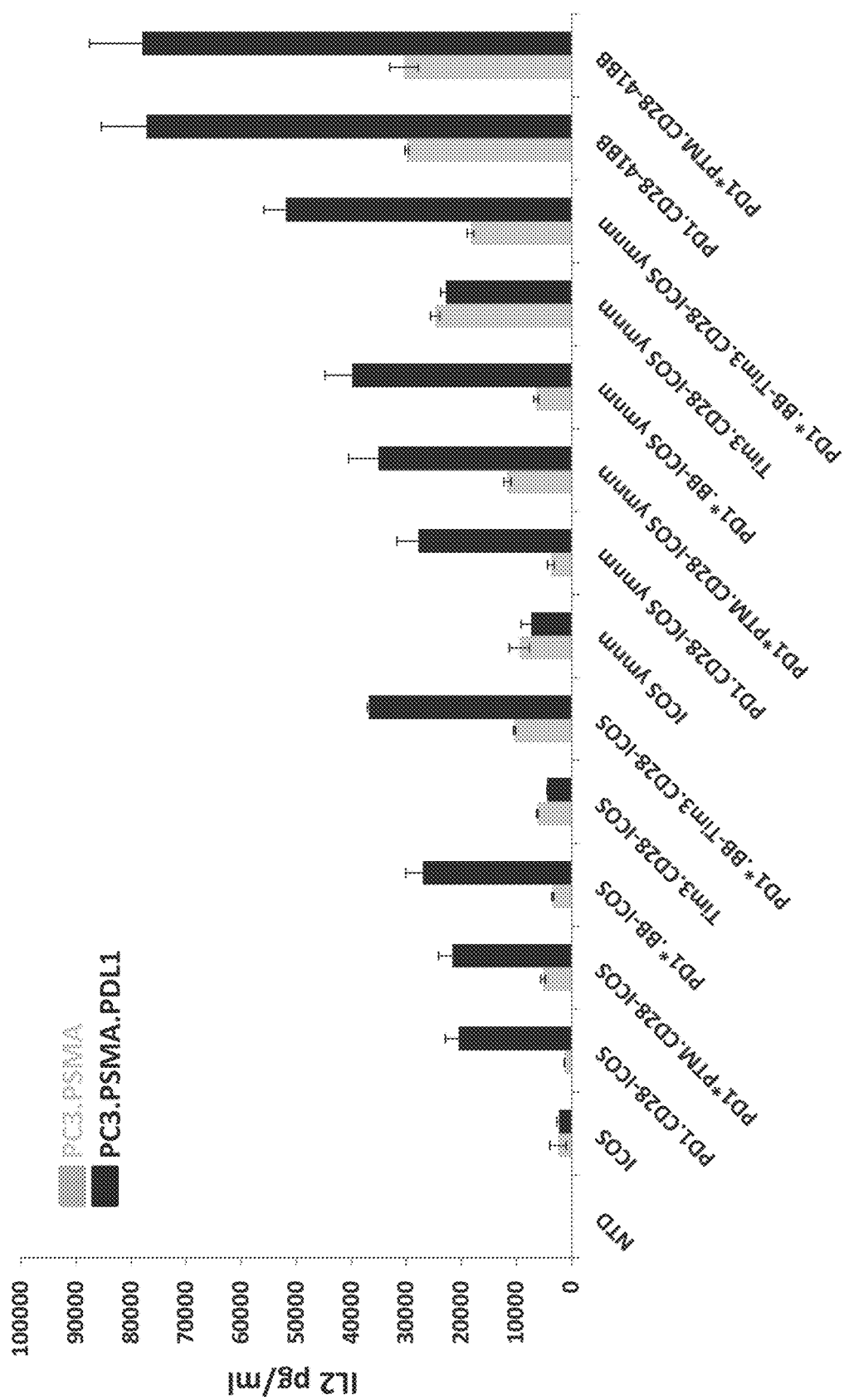
FIG. 11A is a graph depicting IL-2 secretion of T cells transduced with 2F5 PSMA ICOS-CAR alone (ICOS), PSMA 41BB-CAR alone (41BB), or co-transduced 2F5 PSMA CAR together with various switch receptors, as indicated. NTD means untransduced.
Figure 11B:
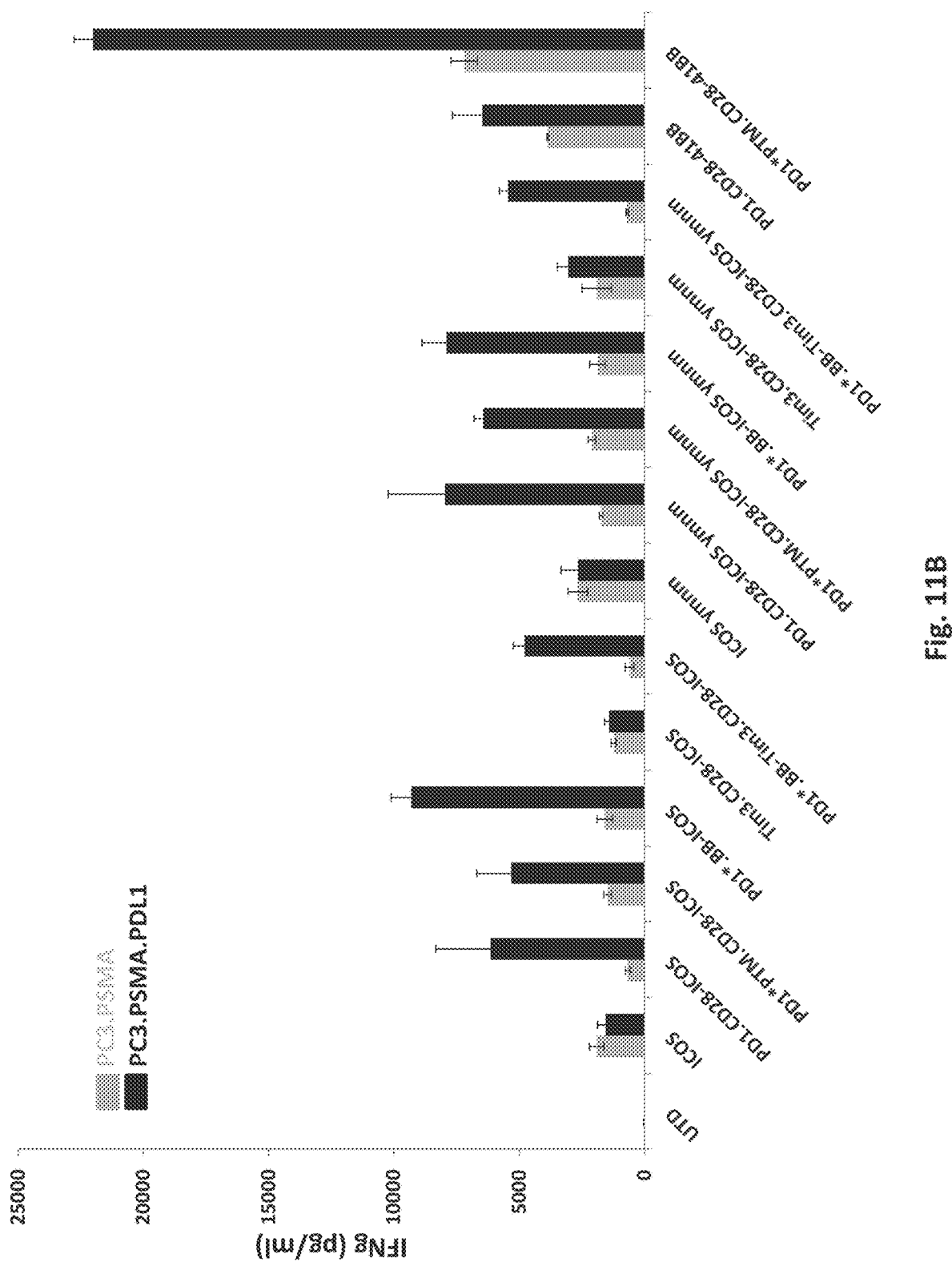
FIG. 11B is a graph depicting IFNgamma secretion of T cells transduced with 2F5 PSMA ICOS-CAR alone (ICOS), PSMA 41BB-CAR alone (41BB), or co-transduced 2F5 PSMA CAR together with various switch receptors, as indicated. UTD means untransduced.

PSMA CARs with either ICOS or ICOS.YMNM signaling domain and combination of CAR+PD1 (or Tim3) switch receptors were constructed and cloned into a lentiviral vector (see, Table 2 for sequences). The CAR expression levels in transduced T cells were comparable for most of the CAR constructs (FIG. 7), and the switch receptors were expressed properly (FIG. 8). When stimulated with PSMA positive cell lines PC3.PSMA or PC3.PSMA.PD-L1 and examined for CD107a upregulation, PSMA CAR with ICOS.YMNM signaling domain (ICOS ymnm) showed significantly higher CD107a expression compared to wild type ICOS (ICOS) or 4-1BB (41BB) CARs (FIG. 9). GranzymeB expression for both ICOS and ICOS.YMNM PSMA CARs were similar to 4-1BB PSMA CAR (FIG. 10). Cytokine production (IL-2 and IFN-gamma) of the PD1 switch receptors co-transduced with PSMA CARs comprising ICOS, ICOS.YMNM, or 4-1BB were significantly higher when stimulated with PD-L1 expressing PC3.PSMA cells (FIGS. 11A and 11B).

Figure 12A:
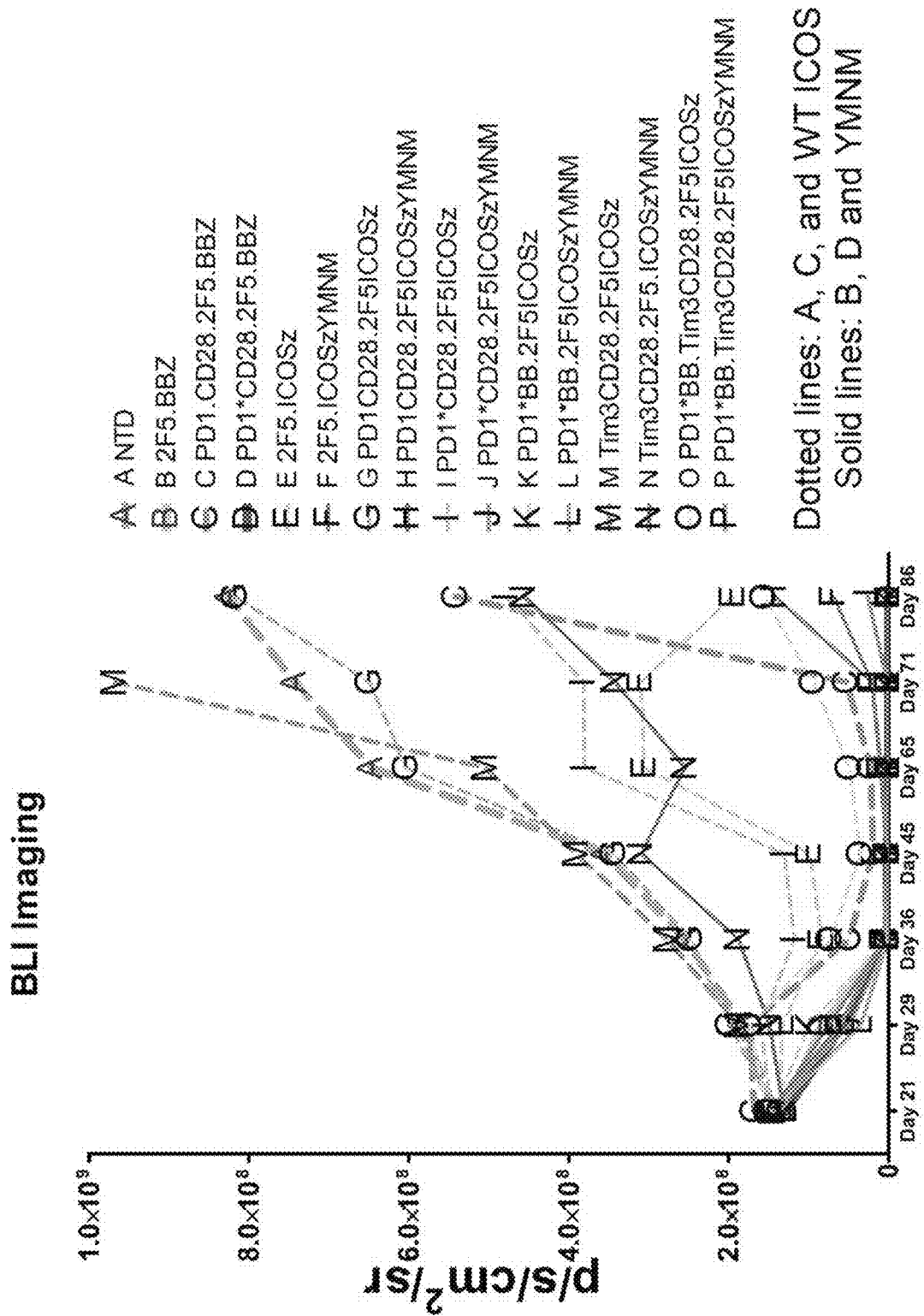
FIG. 12A is a graph depicting the quantification of bioluminescence obtained from imaging of NSG mice bearing PC3-PSMA.CBG induced tumors treated with T cells transduced as indicated.
Figure 12B:
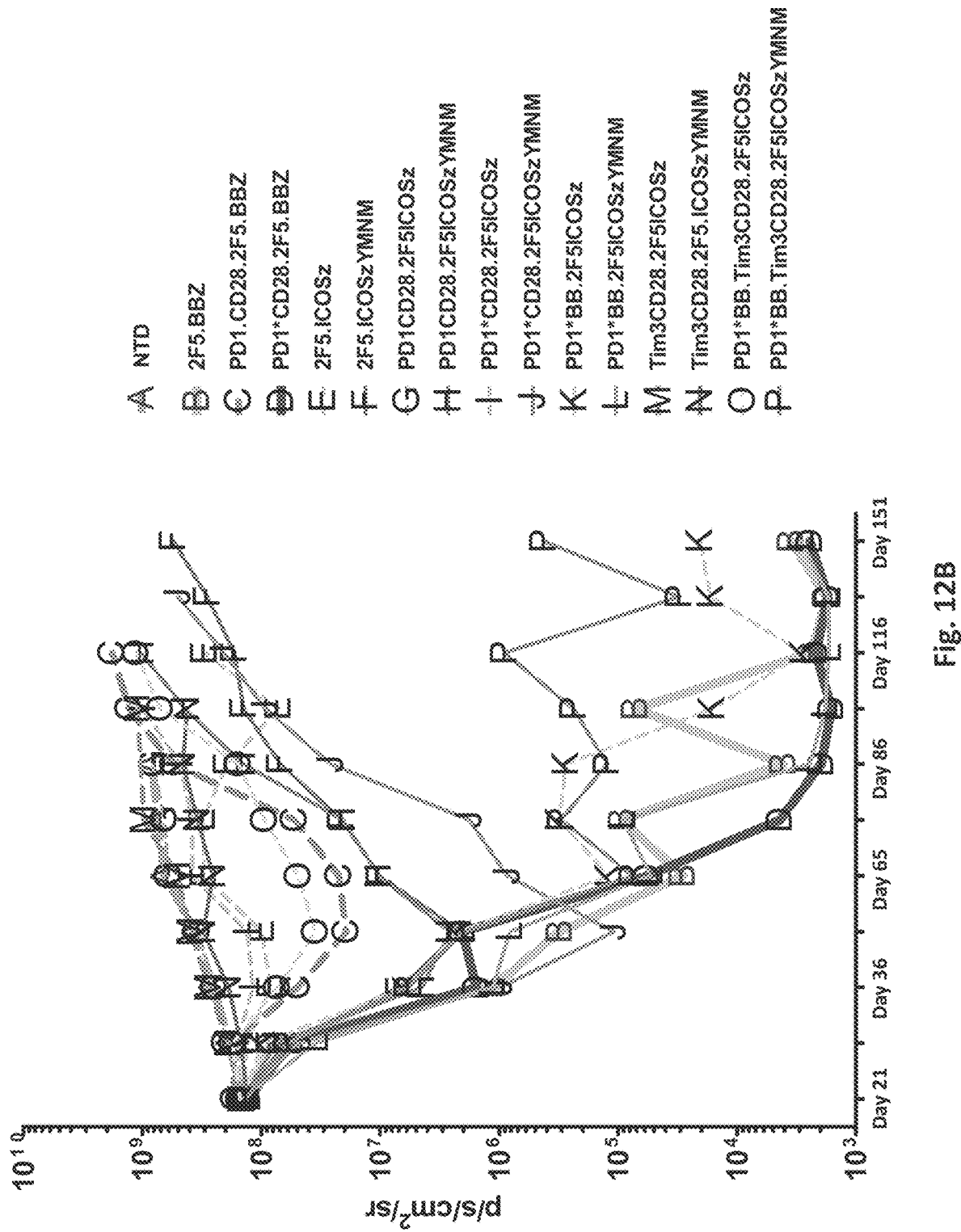
FIG. 12B is a graph depicting the quantification of bioluminescence obtained from imaging of NSG mice bearing PC3-PSMA.CBG induced tumors treated with T cells transduced as indicated.
Figure 13:
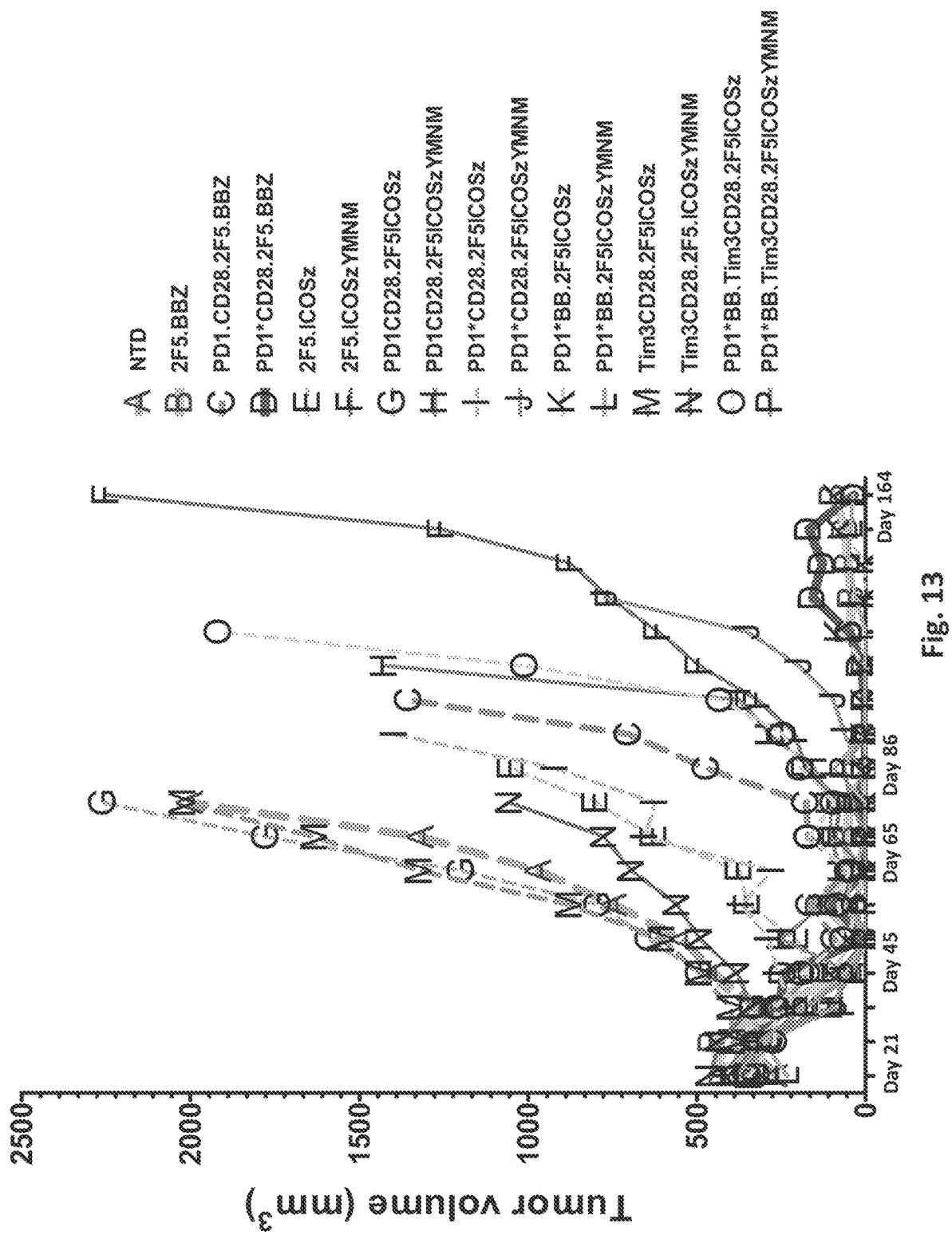
FIG. 13 is a graph depicting tumor sizes of NSG mice bearing PC3-PSMA.CBG induced tumors treated with T cells transduced as indicated.
Figure 14A:
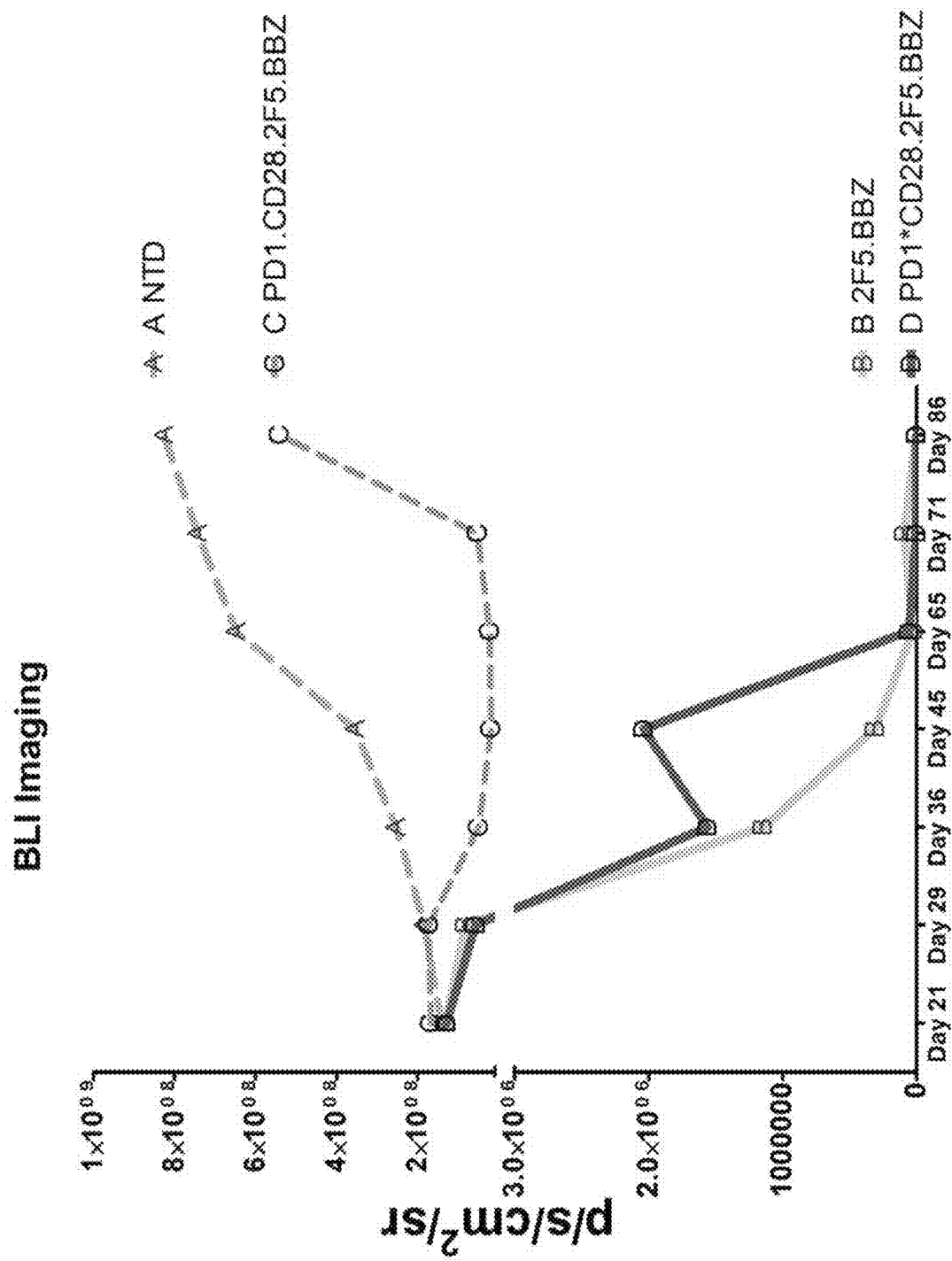
FIG. 14A is a graph depicting the quantification of bioluminescence obtained from imaging of NSG mice bearing PC3-PSMA.CBG induced tumors treated with T cells transduced as indicated.
Figure 14B:
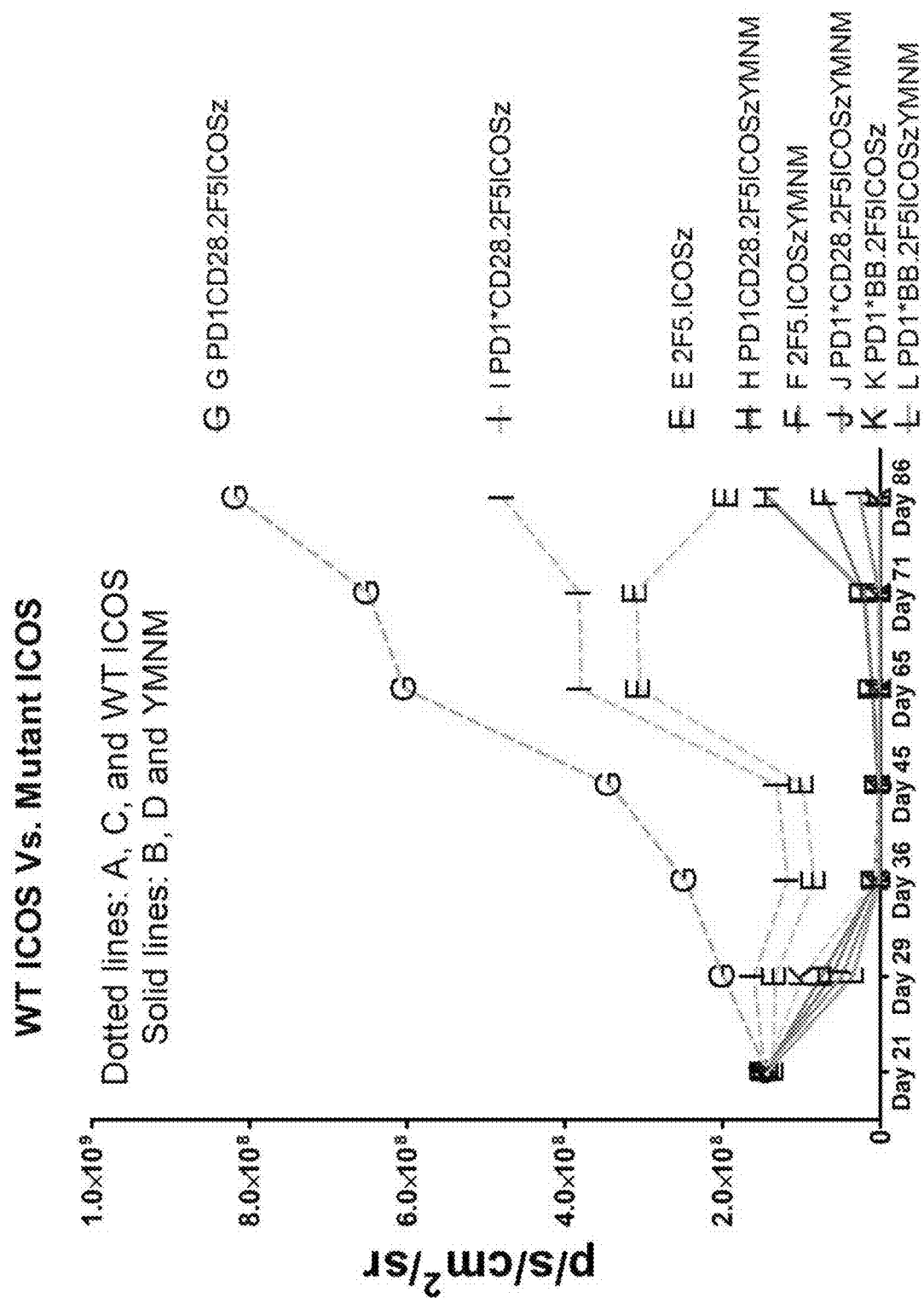
FIG. 14B is a graph depicting the quantification of bioluminescence obtained from imaging of NSG mice bearing PC3-PSMA.CBG induced tumors treated with T cells transduced as indicated.
Figure 14C:
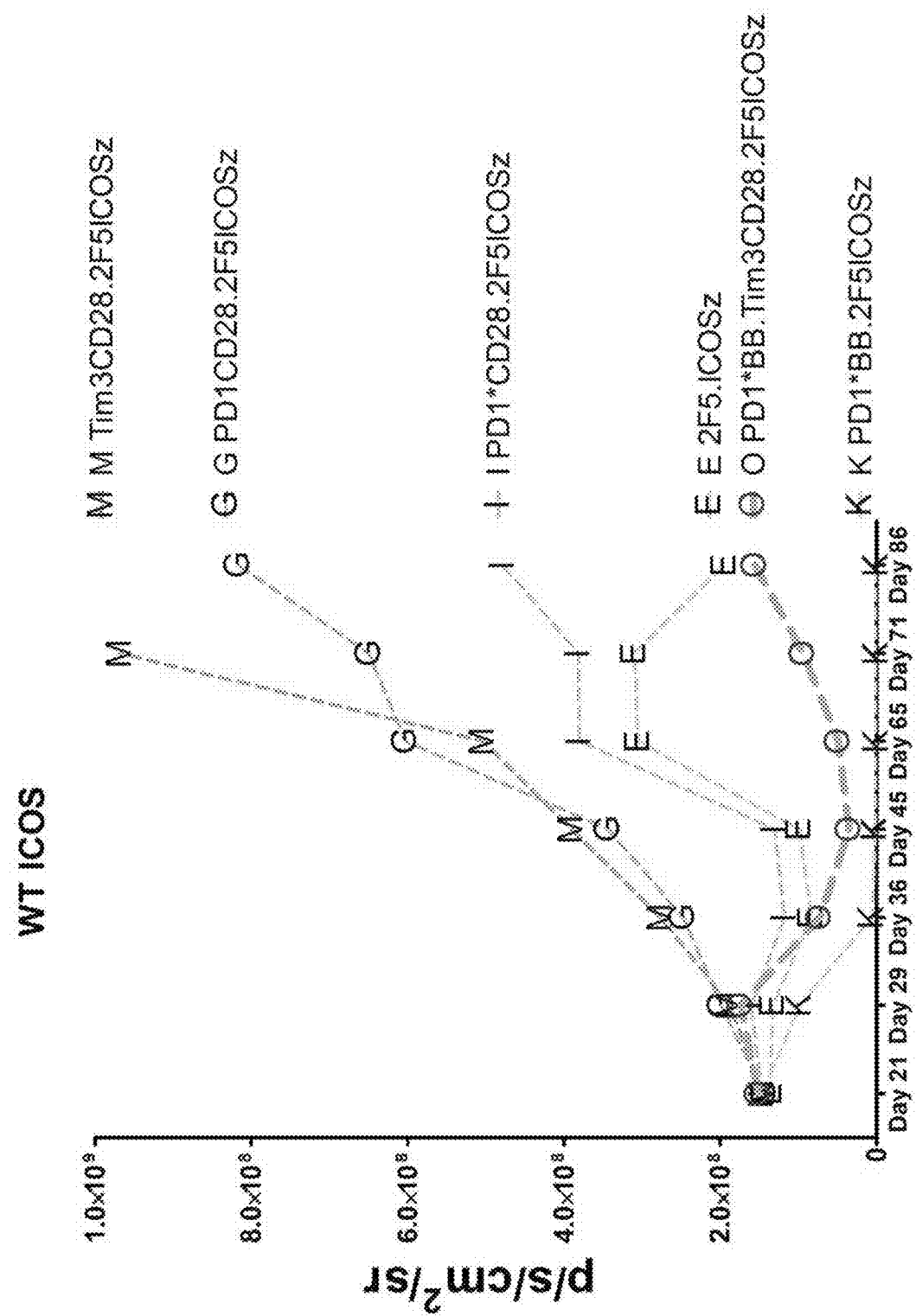
FIG. 14C is a graph depicting the quantification of bioluminescence obtained from imaging of NSG mice bearing PC3-PSMA.CBG induced tumors treated with T cells transduced as indicated.
Figure 14D:
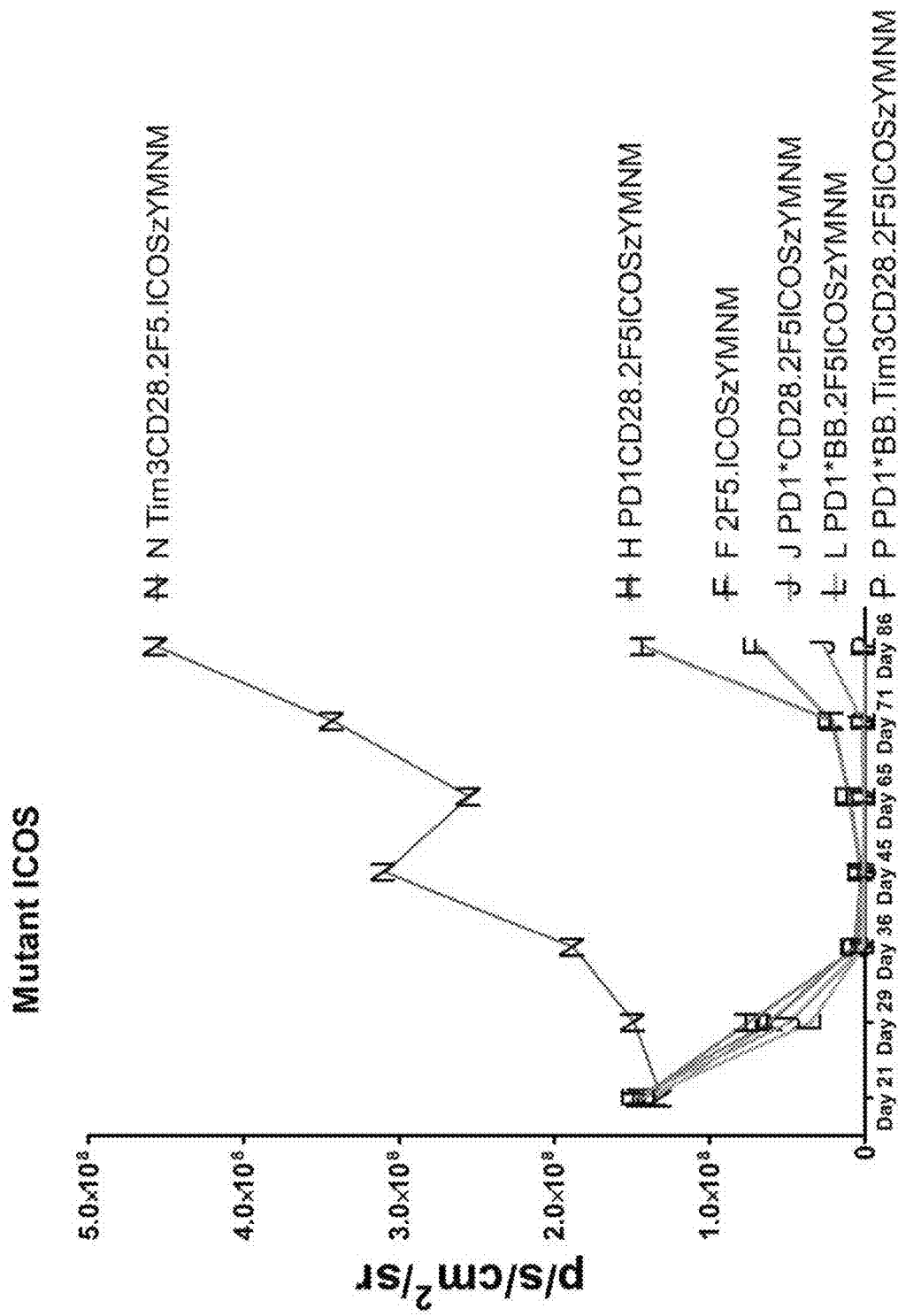
FIG. 14D is a graph depicting the quantification of bioluminescence obtained from imaging of NSG mice bearing PC3-PSMA.CBG induced tumors treated with T cells transduced as indicated.
Figure 14E:
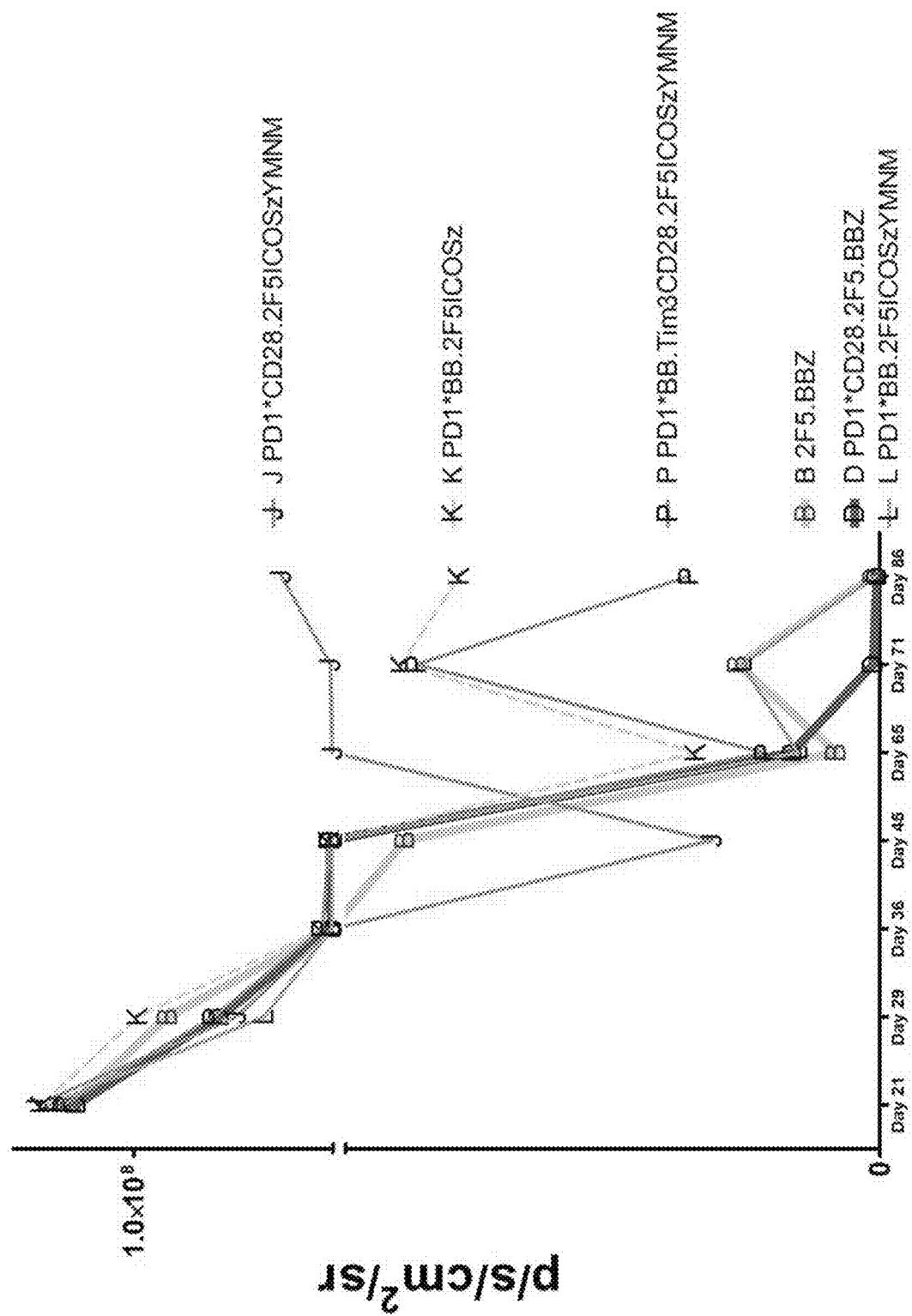
FIG. 14E is a graph depicting the quantification of bioluminescence obtained from imaging of NSG mice bearing PC3-PSMA.CBG induced tumors treated with T cells transduced as indicated.
Figure 14F:
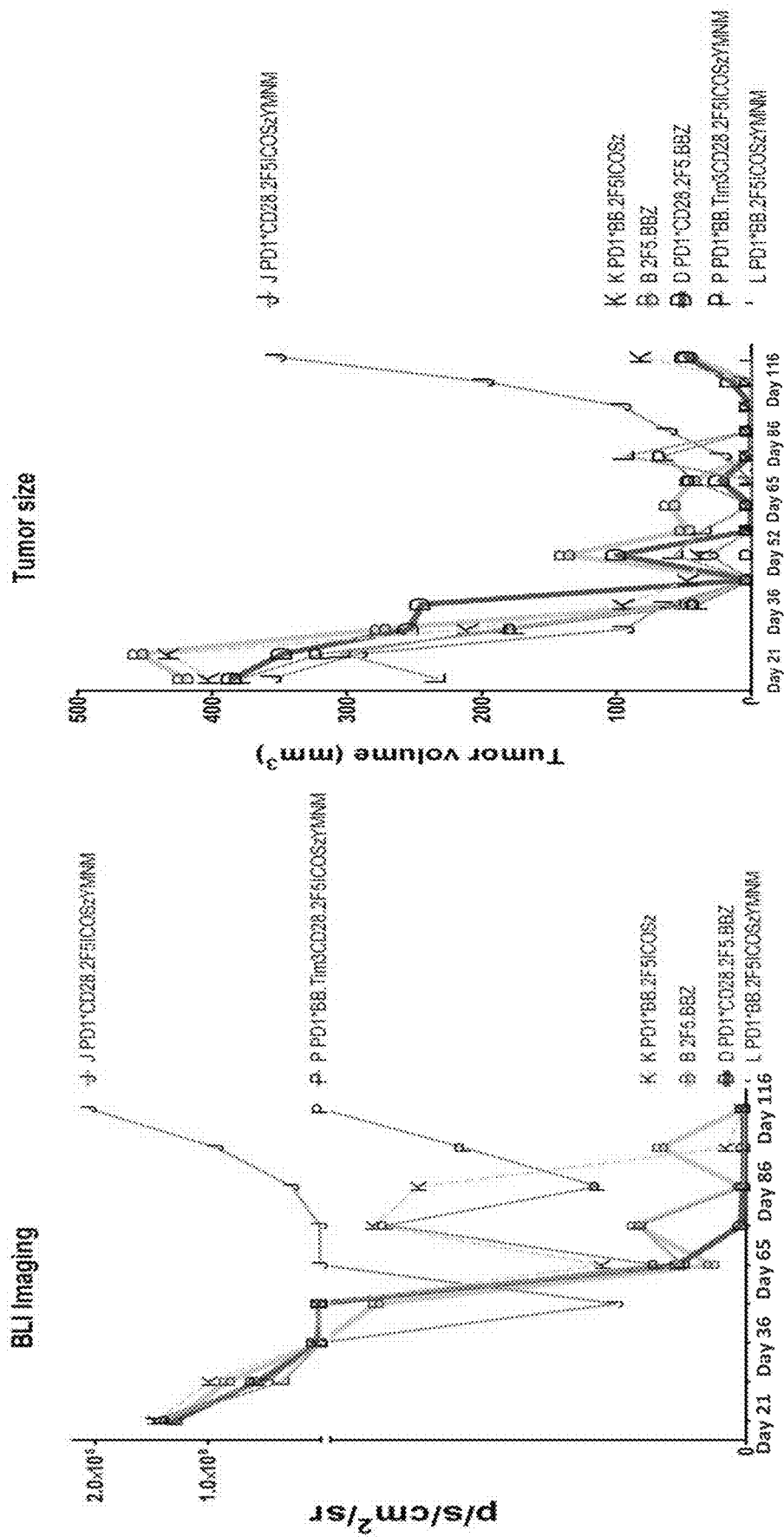
FIG. 14F is a graph depicting the quantification of bioluminescence (left) and tumor size (right) obtained from imaging of NSG mice bearing PC3-PSMA.CBG induced tumors treated with T cells transduced as indicated.

FIG. 12 and shows the quantification of bioluminescence imaging of NSG mice bearing PC3-PSMA.CBG induced tumors treated with T cells transduced with the CARs as indicated, up to 86 days (FIG. 12A), and up to 151 days (FIG. 12B). FIG. 13 shows the tumor size of NSG mice bearing PC3-PSMA.CBG induced tumors treated with T cells transduced with the CARs as indicated, up to 164 days. As shown, both ICOS (2F5.ICOSz) and ICOS.YMNM PSMA CARs (2F5.ICOSzYMNM) showed worse tumor control than the 4-1BB PSMA CAR (2F5.BBZ). The PD1-CD28 switch receptor improved the PSMA CAR with 4-1BB costimulatory domain (PD1.CD28.2F5.BBZ), but not for ICOS (PD1CD28.2F5ICOSz) or ICOS.YMNM (PD1CD28.2F5ICOSzYMNM) PSMA CARs. Both PD1.CD28.2F5.BBZ and PD1CD28.2F5ICOSzYMNM showed inferior tumor control compared to 4-1BB PMSA CAR. When these ICOS based CARs were co-delivered to T cells with a high affinity PD1 switch receptor with 4-1BB signaling domain (PD1*BB), the tumor can be controlled as efficiently as 4-1BB PMSA CAR. As shown in FIGS. 14A-14F, T cells co-delivered with ICOS.YMNM CAR and PD1 switch receptor with 4-1BB signaling domain (PD1*BB.2F5ICOSzYMNM) eliminated tumors. FIG. 14G provides a list of the T cells in order of tumor control capabilities.

Example 7: PSMA CAR-T Cells to Co-Express Bispecific Antibodies for PD1 to CD28 Switch or TGF Beta Receptor II to CD28 Switch Five bispecific antibodies using scFvs that could bind PD-L1 (10A5, 13G4 and 1B12, see, e.g., PCT Publication No. WO2007005874A2) or TGF beta receptor II (aTGFbRII-1 and aTGFbRII-3 (TGFb1 and TGFb3, see, e.g., U.S. Pat. No. 8,147,834) and an anti-CD28 scFv (1412, see, e.g., U.S. Pat. No. 7,585,960) were designed and the genes were synthesized by PCR. Sequence verified DNA was cloned into PGEM.64A based RNA in vitro transcription vector to generate pGEM.aTGFbR-1-1412 and pGEM.aTGFbR-3-1412. See, e.g., PCT Publication No. WO2016122738A1.

PSMA CAR-T cells are generated that co-express a bispecific antibody selected from the above described.

Example 8: Manufacture and Administration of Clinical CART-PSMA-TGFβRDN Autologous T Cells CART-PSMA-TGFβRDN investigational cell product manufacturing, final formulation, testing, and labeling were performed as described below, according to The Clinical Cell and Vaccine Production Facility's (CVPF) standard operating protocols (SOPs). The CVPF is a unit within the Division of Transfusion Medicine and Therapeutic Pathology in the Department of Pathology and Laboratory Medicine at the University of Pennsylvania. Within the Division, in addition to the CVPF and the apheresis collection facility, there is a separate hematopoietic stem cell processing laboratory that is responsible for bone marrow and peripheral blood stem cell products primarily dedicated to support the clinical hematopoietic stem cell transplantation service. The CVPF is a registered HCT Facility and accredited by the Foundation for the Accreditation of Cellular Therapy (FACT).

Dynabeads CD3/C28 CTS™ (formerly named ClinExVivo) beads were used for T cell activations and expansions.

CART-PSMA-TGFβRDN investigational product manufacturing was initiated from a leukapheresis product. Based on the constitution of the leukaphereis product, as assessed by Beckman Coulter Multisizer and BD FACS Calibur devices, the following occured: depletion of monocytes via counterflow centrifugal elutriation on the TerumoBCT Elutra, which employs a single use closed system disposable set, washing step using a semi-automated, closed-system device Haemonetics CellSaver 5, and/or Ficoll separation of the buffy fraction of the PBMCs. On day 0, the CART-PSMATGFβRDN manufacturing process was initiated with activation of T lymphocytes with the Dynabeads CD3/CD28 CTS beads. The PSMA-TGFbRIIDN CAR LV vector was added on Day 1 at the total final MOI. Vector transduction occured between days 1 and 3. On day 3, the cells were washed and media was replaced. Cultures were allowed to continue expansion in the GE Wave Bioreactor System. On the final day of the culture, cells were harvested and concentrated using the Cell Saver Prior to harvest, the cell product was placed on the Baxter MaxSep for removal of the Dynabeads CD3/CD28 CTS beads. Following bead removal, the cell expansion was washed using the Haemonetics Cell Saver 5 to remove residual vector, viral particles, and cell debris. CART-PSMA-TGFβRDN cells were resuspended in cryopreservation media containing 31.25% Plasmalyte-A, 31.25% Dextrose 5%, 0.45% NaCl, 1% Dextran 40 and 5% Dextrose, 5% Human Serum Albumin, and 7.5% DMSO. Cells were frozen in Cryostore Ethylene-Vinyl Acetate (EVA) (OriGen Biomedical) or equivalent clear bags using a controlled-rate freezer.

Cryopreserved CART-PSMA-TGFβRDN:

Each infusion bag contained ~10-50 mL of cells. Cryopreserved cells were also retained in small aliquots in identical cell concentrations to the infusion dose and used as sentinel vials for performing a viability and endotoxin test prior to infusions, and for stability testing.

Leukapheresis Collection and Cell Separation/Enrichment:

Autologous peripheral blood lymphocytes were obtained via leukapheresis collection at the Apheresis Unit at the Hospital of the University of Pennsylvania (HUP). Cryopreserved historical apheresis products collected from the patient prior to study entry may be usable for CART-PSMA-TGFβRDN cell manufacturing. If used, the sample must have been collected at an appropriately certified apheresis center and the product must have met adequate mononuclear cell yields.

Approximately 10-15 L of blood was processed on the COBE Spectra Apheresis System or equivalent system to obtain a population of approximately $5 \times 10^9$ white blood cells. In addition to the screening testing requirements provided in the protocol, blood from all apheresis donors underwent infectious disease testing performed by the American Red Cross National Testing Laboratory.

The apheresis product was transported in an insulated container to the CVPF, and temperature was logged upon receipt. Samples were removed for bacterial and fungal cultures, real-time phenotyping by flow cytometry, and research and correlative study purposes. Apheresis products were cryopreserved or processed by elutriation. After Elutriation or cell washing, the cell number was determined on the Coulter Multisizer M3/M4 and viability by trypan blue dye exclusion assay. Elutriated products were cryopreserved or proceeded to further processing. Cryopreserved apheresis or elutriated products were thawed and washed prior to culture to remove cryopreservation medium. These products were then processed via either 1) washing and seeding of elutriated lymphocytes, 2) positive selection with CD3/CD28 beads, or 3) Ficoll based gradient separation for further T-cell selection.

Culture Initiation and Expansion:

Enriched lymphocytes were stimulated with Dynabeads CD3/CD28 CTS in static tissue culture flasks at an approximate range of $8 \times 10^5$-$1 \times 10^6$ cells in XVIVO-15 media supplemented with 5% human AB Serum, 2 mM L-GlutaMAX, 20 mM Hepes, 1 mM Sodium Pyruvate, 1% MEM Vitamin Essential Mixture, 10 mM N-Acetylcysteine, and 100 IU/ml IL-2 (Modified X-VIVO 15 Media). Beads were added at a 3:1 bead to cell ratio. On day 5 of culture, if an acceptable cell number was achieved, cells were transferred to the WAVE 2/10EH Bioreactor for expansion to the appropriate cell number allowing for harvest, electroporation, sampling and final formulation. On the final day of the culture, cells were harvested and concentrated using the Cell Saver Wash system. Prior to harvest, the cell product was placed on the Baxter MaxSep for removal of the anti-CD3/CD28 magnetic microbeads. Post-harvest, the expanded T cells were resuspended at $2 \times 10^6$ cells per mL of X-VIVO media supplemented with 5% Human AB Serum. Cells were placed in a 37° C. incubator overnight.

CART-PSMA-TGFBRDN Dose Formulation:

The dose formulation started at a dose of $1-3 \times 10^7/m^2$ CART-PSMA-TGFBRDN cells for one cohort, and a dose of $1-3 \times 10^8/m^2$ for other cohorts. Dosing was based on anti-PSMA CAR expression. The total dose was formulated as a single dose.

Final Formulation:

Post-incubation, after all release testing samples and archives were removed, the cells were resuspended in infusible cryopreservation media containing 31.25% PlasmaLyte-A, 31.25% Dextrose (5%) in NaCl (0.45%), 7.5% DMSO, 5% Human Serum Albumin, and 1% Low Molecular Weight Dextran (LMD).

Product Administration:

Cell thawing: The cells were thawed at the CVPF or at the bedside using a water bath or comparable device maintained at 36° C. to 38° C. by trained personnel. There should be no frozen clumps left in the container by the time it is connected to the I.V. tube. If the CART-PSMA-TGFβRDN cell product appeared to have a damaged or leaking bag, or be compromised, it was not infused, and was returned to the CVPF.

Administration: The infusion took place in an isolated room in the CTRC or elsewhere in the Hospital of the University of Pennsylvania, using precautions for immunosuppressed patients. Prior to the infusion, two individuals independently verified the information on the infusion product label in the presence of the subject and confirmed that the information is correctly matched to the participant. Cells were infused within approximately 30 minutes after thaw. The CART cells were infused intravenously into an 18 gauge intravenous catheter, either through a peripheral vein (preferred) or central vein. Macrodrip intravenous tubing was used to infuse the CART cells by gravity (i.e., without an infusion pump) at a rate of approximately ~10 mL/minute through a latex free-Y-type blood set with a 3-way stopcock. A leukoreduction filter was not used for the infusion of the CART cell product. Emergency medical equipment (i.e., emergency trolley) was available during the infusion in case the subject had an allergic response, or severe hypotensive crisis, or any other reaction to the infusion. Vital signs (temperature, respiration rate, pulse, blood pressure, and oxygen saturation by pulse oximetry) were measured prior, and after the infusion. If the subject's vital signs were not satisfactory and stable, vital signs were continually monitored at a minimum of every hour or as clinically indicated until stable. The subject was discharged after the physician managing their care has determined the subject was in satisfactory condition.

Example 9: CART-PSMA-TGFβRDN Clinical Trial Design

This protocol tested the safety of 2 dose-levels of CART-PSMA-TGFβRDN cells administered intravenously alone or after lymphodepletion with a moderate dose of cyclophosphamide administered three days prior to CART-PSMA-TGFβRDN cells. The dose escalation followed a 3+3 design. CART-PSMA-TGFβRDN cells were permanently modified to be directed to the PSMA protein with an anti-PSMA CAR fused to the signaling domains of 4-1BB and TCR. The study population included patients with castrate resistant prostate cancer with radiographic evidence of lymph node, visceral, or osseous metastases. All patients must have progressed after therapy with at least one standard 17α lyase inhibitor or second-generation anti-androgen therapy.

The date the first patient was dosed was Aug. 31, 2017.

As part of informed consent, subjects were asked for permission to test their tumor for PSMA as one of the eligibility criteria. Evaluation of PSMA expression on a fresh tumor biopsy was preferred; however, if a biopsy was not feasible or clinically appropriate, then archived tissue from a recent metastatic tissue biopsy was used to determine eligibility if obtained within prior 90 days.

Patients with confirmed ≥10% of tumor cells with PSMA expression and who meet all other inclusion criteria were eligible to participate.

Cohort 1 subjects (N=3 or 6) received a single dose of $1-3\times10^7/m^2$ lentivirally transduced CART-PSMA-TGFβRDN cells on day 0 without any conditioning chemotherapeutic regimen. If the number of manufactured CAR T cells did not meet the pre-specified minimum infused dose of $1\times10^7/m^2$ cells, then the dose was not administered, and the subject was replaced in the study. If 1 DLT/3 subjects occurs, the study enrolls an additional 3 subjects at this dose level. If 0 DLT/3 subjects or 1 DLT/6 subjects occurs, the study advances to Cohort 2. If 2 DLT/3 subjects occurs at dose of $1-3\times10^7/m^2$ cells, then enrollment in this Cohort is stopped and the dose is de-escalated by 10-fold to $1-3\times10^6$ cells/$m^2$ (Cohort-1). In this situation, up to 6 subjects are enrolled in Cohort-1.

Cohort 2 subjects (N=3 or 6) received a single dose of $1-3\times10^8/m^2$ lentivirally transduced CART-PSMA-TGFβRDN cells on day 0 without any conditioning chemotherapeutic regimen. If the number of manufactured CAR T cells did not meet the protocol-specified minimum of $1\times10^8/m^2$ cells, but does meet the minimum dose requirement of at least $1\times10^7/m^2$ cells, then the subject receives the dose and was not included in the DLT assessment for Cohort 2. This subject would be replaced for DLT assessment at this dose. If, the number of manufactured CAR T cells did not meet the pre-specified minimum infused dose as outlined for Cohort 1, then no dose was administered, and the subject was replaced in the study. If 1 DLT/3 subjects occurs, the study enrolls an additional 3 subjects at this dose level. If 0 DLT/3 subjects or 1 DLT/6 subjects occur, the study advances to Cohort 3. If 2 DLT/3 subjects occur, then the study stops and declares maximum tolerated dose (MTD).

Cohorts 1 and 2 served to identify the MTD of CART-PSMA-TGFβRDN cells. The MTD is defined as the highest dose at which 0/3 or 1/6 DLTs occur.

Cohort 3 subjects (N=3 or 6) received a single infusion at the MTD of lentivirally transduced CART-PSMA-TGFβRDN cells on day 0, following a single dose of 1.0 gram/$m^2$ of cyclophosphamide administered up to 4 days prior to the CAR T cells (day −3±1 day). If 0 DLT/3 subjects occur, the study enrolls an additional 3 patients to confirm tolerability. If 1 DLT/3 subject occurs, the study enrolls an additional 3 subjects at this dose level. If two of the initial three subjects experience a DLT, three additional patients are accrued with a dose-reduction in the lymphodepleting chemotherapy to 500 mg/$m^2$ administered up to 4 days prior to the CAR T cells (day −3±1 day).

Subjects were enrolled serially. Infusions were staggered to allow assessment of DLTs for cohort progression, expansion, or dose de-escalation. The infusions for the first 2 subjects in each cohort were staggered by 28 days; the second subject was not infused until 28 days after the infusion of the first subject. The 2nd and 3rd subjects in each cohort were infused and followed in parallel but only after the 1st subject in that cohort completed the day 28 visit without DLT.

DLT was defined as any new grade 3 or greater adverse event at least possibly related to the T cell regimen that occured within 28 days of T cell infusion. If 1 DLT occurs in the first 3 subjects treated at a dose level, the study enrolls an additional 3 subjects at that dose level. If 2 DLT/3 subjects occur, then the study stops and declares maximum tolerated dose, except for Cohort 1, where a 10-fold dose de-escalation occurs. If 0 DLT/3 subjects or 1 DLT/6 subjects at a dose level, the study advances to the next Cohort. For cohort 3, if two of the initial three subjects experience a DLT, three additional patients are accrued with a dose-reduction in the lymphodepleting chemotherapy to 500 mg/$m^2$ administered up to 4 days prior to the CART cells (day −3±1 day). Otherwise, if 0-1 DLT/3 subjects occur in cohort 3, the study enrolls an additional 3 patients to confirm tolerability.

Subjects were followed up for safety assessments and research assessments. Subjects returned for study follow-up on Days 1, 3, 7, 10, 14, 21, and 28 for safety assessments. On Day 28 (±5), disease staging was performed with a CT chest/abdomen/pelvis, bone scan, and serum PSA. The reasons for this early imaging assessment at day 28 were to assess for systemic inflammation effects and to monitor disease status at the time of the expected homing of CART-PSMA-TGFβRDN cells. Repeat disease assessments (including imaging) were performed at Months 3 and 6 and as standard of care thereafter. If a subject had relevant imaging data (CT abd/pelvis, MRI abd/pelvis, bone scan) within 4 weeks of Month 3 and/or 6 performed as part of their standard of care, this was not repeated at Month 3 and/or 6.

Adverse event reporting began at the time of consent and continues until the subject is off-study. While on study, subjects were continually reassessed for evidence of acute and cumulative toxicity. Upon discontinuation from the primary follow-up phase, subjects enter long-term follow-up for up to 5 years from their CART-PSMA-TGFβRDN infusion. During long-term follow-up, subjects are monitored for delayed adverse events that may be associated with the administration of the CART-PSMA-TGFβRDN cells.

Peripheral blood samples were obtained at defined time points to monitor for measures of safety and efficacy. Additional blood and tissue samples (e.g. fluids, tissue biopsy) that were obtained for clinical indications may also be sent for research analysis. At any time that tissue or body fluids were obtained (for example, drainage of pleural fluid or ascites fluid), fluid samples that would otherwise be discarded were used instead for research purposes. These studies include, but were not limited to, CART-PSMA-TGFβRDN cell persistence by Q-PCR and inflammation marker assessment with a Luminex-based cytokine and chemokine panel.

In case of unexpected AEs, additional blood and tissues were collected for research analysis, focused at evaluating the potential causality of the unexpected event with the infused CART-PSMA-TGFβRDN cells. The additional samples collected for research did not exceed 3 tablespoons of blood twice in one week, and one tissue sample collection procedure for per month.

Inclusion Criteria:
1. Metastatic castrate resistant prostate cancer
2. ≥10% tumor cells expressing PSMA as demonstrated by immunohistochemistry analysis on biopsied tissue.
3. Radiographic evidence of osseous metastatic disease and/or measurable, non-osseous metastatic disease (nodal or visceral)
4. Patients≥18 years of age
5. ECOG performance status of 0-1
6. Adequate organ function, as defined by:
   a. Serum creatinine≤1.5 mg/dl or creatinine clearance≥60 cc/min
   b. Serum total bilirubin<1.5×ULN
   c. Serum ALT/AST<2×ULN
7. Adequate hematologic reserve within 4 weeks of study enrollment as defined by:
   a. Hgb>10 g/dl
   b. PLT>100 k/ul
   c. ANC>1.5 k/ul
   Note: Subjects must not be transfusion dependent
8. Evidence of progressive castrate resistant prostate adenocarcinoma, as defined by:
   a. Castrate levels of testosterone (<50 ng/ml) with or without the use of androgen-deprivation therapy AND
   b. Evidence of one of the following measures of progressive disease in the 12 weeks preceding study enrollment:
      i. soft tissue progression by RECIST 1.1 criteria
      ii. osseous disease progression with 2 or more new lesions on bone scan (as per PCWG2 criteria)
      iii. increase in serum PSA of at least 25% and an absolute increase of 2 ng/ml or more from nadir (as per PCWG2 criteria)
9. Prior therapy with at least one standard 17α lyase inhibitor or second-generation anti-androgen therapy for the treatment of metastatic castrate resistant prostate cancer
10. Provides written informed consent
11. Subjects of reproductive potential must agree to use acceptable birth control methods.

Exclusion Criteria:
1. Prior treatment with an immune-based therapy for the treatment of prostate cancer, including cancer vaccine therapies (such as SipuleucelT, PROSTVAC), immune checkpoint inhibitors, radium-223 and immunoconjugate therapies
2. History of an active non-curative non-prostate primary malignancy within the prior 5 years
3. Subjects who require the chronic use of systemic corticosteroid therapy
4. Subjects who have received >3 prior therapies for the treatment of castrate resistant prostate cancer (excluding luteinizing hormone-releasing hormone agonists or antagonists, or first generation anti-androgen therapies). This includes subjects who received Taxotere in non-castrate resistant setting.
5. Subjects with Class III/IV cardiovascular disability according to the New York Heart Association Classification (see Attachment 2)
6. Subjects with symptomatic vertebral metastases affecting spinal cord function (as determined by clinical history, physical exam, or MRI imaging)
7. History of active autoimmune disease requiring immunosuppressive therapy
8. Patients with ongoing or active infection.
9. History of allergy or hypersensitivity to study product excipients (human serum albumin, DMSO, and Dextran 40)
10. Active hepatitis B, hepatitis C or HIV infection.

Example 10: Phase 1 Clinical Safety Data

A total of six subjects have been infused and two subjects remain on study as of Jul. 25, 2018. Three subjects were infused in Cohort 1 and three subjects were infused in Cohort 2. Thus, Cohort 2 was filled. In contract to Cohort 1, all three subjects infused in Cohort 2 experienced cytokine release syndrome (CRS): two subjects had grade 3 CRS and one subject had grade 1 CRS, all of which developed within 12 hours CAR T cell infusion. These toxicities were managed per protocol/institutional guidelines and resolved. Thus, Cohort 2 was completed without a DLT.

The study Site Initiation Visit was held on Wednesday, Feb. 22, 2017 and the study was activated on Mar. 8, 2017. As of Jul. 25, 2018, the clinical site consented 8 subjects. Of the 8 subjects consented there was 1 screen failure, 1 subject withdrew prior to treatment, and 6 subjects were infused.

Table 3 shows a summary of the demographics of screened subjects (N=8).

TABLE 3

Demographics of screened subjects

| | Subject ID | Cohort | Sex (F/M) | Age at Consent | Race | Screen Fail (Y/N) | Reason for Screen Fail | Infused (Y/N) | Reason for End of Study |
|---|---|---|---|---|---|---|---|---|---|
| 1 | 32816-01 | N/A | M | 66 | Caucasian | Y | Excluded based on prior immune therapy | N | Screen Failure |
| 2 | 32816-02 | 1 | M | 55 | Caucasian | N | N/A | Y | Death; Neutropenic Sepsis* |
| 3 | 32816-03 | N/A | M | 67 | Caucasian | N | N/A | N | Subject Withdrew Consent |
| 4 | 32816-04 | 1 | M | 50 | Caucasian | N | N/A | Y | Death; Disease Progression* |

TABLE 3-continued

Demographics of screened subjects

| | Subject ID | Cohort | Sex (F/M) | Age at Consent | Race | Screen Fail (Y/N) | Reason for Screen Fail | Infused (Y/N) | Reason for End of Study |
|---|---|---|---|---|---|---|---|---|---|
| 5 | 32816-05 | 1 | M | 71 | Caucasian | N | N/A | Y | Disease Progression |
| 6 | 32816-06 | 2 | M | 72 | Caucasian | N | N/A | Y | Disease Progression |
| 7 | 32816-07 | 2 | M | 73 | Caucasian | N | N/A | Y | Active on Study |
| 8 | 32816-08 | 2 | M | 64 | Caucasian | N | | Y | Active on Study |

N/A = not applicable
*Death occurred during long term follow up. Therefore, this event did not qualify as a PDAE and determined unrelated to the IP.

Table 4 shows a summary of the current protocol status for infused subjects (N=6).

TABLE 4

Current protocol status for infused subjects

| | Subject ID | Last Study Visit/ Date of Last Visit in Primary Study | Off-Study Date/ Reason | Protocol Deviation (Y/N) | Adverse Events (Y/N) | Related Adverse Events (Y/N) | Serious Adverse Events (Y/N) | Study Status |
|---|---|---|---|---|---|---|---|---|
| 1 | 32816-02 | Day 28/ Sep. 29, 2017 | Nov. 16, 2017/Death (Neutropenic Sepsis) | N | Y | Y | Y | Off-Study |
| 2 | 32816-04 | Month 3/ Feb. 15, 2018 | May 19, 2018/Death (Disease Progression) | N | Y | N | N | Off-Study |
| 3 | 32816-05 | Month 6/ May 22, 2018 | Jun. 13, 2018/Disease Progression | N | Y | Y | Y | Off-Study |
| 4 | 32816-06 | Day 28/ Jul. 13, 2018 | Jul. 17, 2018/Disease Progression | Y | Y | Y | Y | Off-Study |
| 5 | 32816-07 | Month 2/ Jul. 9, 2018 | N/A | N | Y | Y | Y | On-Study |
| 6 | 32816-08 | Day 28/ Jul. 25, 2018 | N/A | Y | Y | Y | Y | On-Study |

Table 5 shows a summary of deviations or exceptions for infused subjects (N=6).

TABLE 5

Deviations or exceptions for infused subjects

| Subject ID | Protocol Exception or Deviation | Date Exception or Deviation Identified | Description of Exception or Deviation | Status of Exception or Deviation |
|---|---|---|---|---|
| 32816-02 | Exception | Apr. 24, 2017 | Subject had repeate screening biopsy as initial biopsied material was determined to be insufficient for PSMA expression analysis as it contained fat, marrow tissue | Sponsor approved; approved by all local regulatory review communities |
| 32816-04 | | | No Deviations or Exceptions to report | |
| 32816-05 | | | No Deviations or Exceptions to report | |
| 32816-06 | Deviation | Jun. 12, 2018 | Subject was infused on Jun. 11, 2018; the vital signs source documentation was lost during the subject's transfer to the ICU and therefore there is no record of the subject's protocol-required pre- and post-infusion vital signs | Sponsor acknowledgment communicated to the site Aug. 7, 2018; did not require real time reporting as it did not affect subject safety. Corrective and preventative action plan being implemented. |

TABLE 5-continued

Deviations or exceptions for infused subjects

| Subject ID | Protocol Exception or Deviation | Date Exception or Deviation Identified | Description of Exception or Deviation | Status of Exception or Deviation |
|---|---|---|---|---|
| 32816-07 | | | No Deviations or Exceptions to report | |
| 32816-08 | Deviation | Mar. 29, 2018 | The study pathologist performed PSMA expression testing on a specimen collected as standard of care prior to the patient signing the pre-screening informed consent form | Sponsor approved; IRB approved; did not require real time reporting as it did not affect subject safety. Corrective and preventative action plan implemented. |

Table 6 shows a summary of infusion dates and doses among infused subjects (N=6).

TABLE 6

PSMA-TGFβRDN infusion dates and dose summary among infused subjects

| | Subject ID | Cohort | Infusion Date | Cells Infused | | | | Transduction Efficiency | |
|---|---|---|---|---|---|---|---|---|---|
| | | | | Total Cell Dose | Total CART-PSMA-TGFβRDN Cell Dose | CART-PSMA-TGFβRDN Cell Dose/m² | Met Target Dose (Y/N) | % s cFv Flow (%) | Met Target % scFv Flow (Y/N) |
| 1 | 32816-02 | 1 | Aug. 31, 2017 | $9.25 \times 10^7$ | $5.61 \times 10^7$ | $3 \times 10^7/m^2$ | Y | 60.5 | Y |
| 2 | 32816-04 | 1 | Nov. 13, 2017 | $1.20 \times 10^8$ | $7.56 \times 10^7$ | $3 \times 10^7/m^2$ | Y | 62.9 | Y |
| 3 | 32816-05 | 1 | Nov. 20, 2017 | $7.66 \times 10^7$ | $5.58 \times 10^7$ | $3 \times 10^7/m^2$ | Y | 72.7 | Y |
| 4 | 32816-06 | 2 | Jun. 11, 2018 | $1.05 \times 10^9$ | $7.29 \times 10^8$ | $3 \times 10^8/m^2$ | Y | 69.7 | Y |
| 5 | 32816-07 | 2 | May 7, 2018 | $1.18 \times 10^9$ | $6.60 \times 10^8$ | $3 \times 10^8/m^2$ | Y | 56.1 | Y |
| 6 | 32816-08 | 2 | Jun. 27, 2018 | $1.13 \times 10^9$ | $6.36 \times 10^8$ | $3 \times 10^8/m^2$ | Y | 56.4 | Y |

Table 7 is a summary of disease response for infused subjects (N=6).

TABLE 7

Disease response for infused subjects

| | Subject ID | Cohort | Response Criteria | Overall Tumor Response | | | |
|---|---|---|---|---|---|---|---|
| | | | | Day 28 | Month 2 | Month 3 | Month 6 |
| 1 | 32816-02 | 1 | RECIST 1.1 | NE | N/A | N/A | N/A |
| | | | Bone Scan | New Lesions | N/A | N/A | N/A |
| 2 | 32816-04 | 1 | RECIST 1.1 | NE | Not Assessed | PD | N/A |
| | | | Bone Scan | No New Lesions | Not Assessed | New Lesions | N/A |
| 3 | 32816-05 | 1 | RECIST 1.1 | SD | Not Assessed | SD | PD |
| | | | Bone Scan | New Lesions | Not Assessed | New Lesions | No New Lesions |
| 4 | 32816-06 | 2 | RECIST 1.1 | PD | N/A | N/A | N/A |
| | | | Bone Scan | Not Assessed | N/A | N/A | N/A |
| 5 | 32816-07 | 2 | RECIST 1.1 | SD | Not Assessed | Pending | Pending |
| | | | Bone Scan | No New Lesions | Not Assessed | Pending | Pending |

TABLE 7-continued

Disease response for infused subjects

| | | | Overall Tumor Response | | | |
|---|---|---|---|---|---|---|
| Subject ID | Cohort | Response Criteria | Day 28 | Month 2 | Month 3 | Month 6 |
| 6 32816-08 | 2 | RECIST 1.1 Bone Scan | PD New Lesions Pending | Pending Pending | Pending Pending | Pending Pending |

NE = Not Evaluable
PD = Progressive Disease
SD = Stable Disease
Pending = Subject has not yet reached this time point
Not Assessed = An assessment was not done at this time point
N/A = Not applicable/Subject discontinued primary follow-up prior to this time point Table 8 is a summary of serum PSA levels for infused subjects (N=6).

TABLE 8

Serum PSA levels for infused patients (data provided in ng/mL)

| | Subject ID | Cohort | Screening | Pre-Infusion Safety | Day 28 | Month 2 | Month 3 | Month 6 | Unscheduled |
|---|---|---|---|---|---|---|---|---|---|
| 1 | 32816-02 | 1 | 163.80 | 237.80 | 167.40 | 317.1¥ | N/A | N/A | (Day +20): 162.20 |
| 2 | 32816-04 | 1 | 9.35 | 7.60 | 10.45 | 19.79 | 38.11 | N/A | — |
| 3 | 32816-05 | 1 | 17.83 | 10.47 | 14.01 | 11.75 | 18.77 | 47.31 | — |
| 4 | 32816-06 | 2 | 14.26 | 41.75 | 132.20 | N/A | N/A | N/A | — |
| 5 | 32816-07 | 2 | 219.30 | 324.30 | 340.50 | 372.50 | Pending | Pending | (Day +10): 286.80 (Day +14): 285.40 (Day +21): 341.60 |
| 6 | 32816-08 | 2 | 70.56 | 134.50 | 197.10 | Pending | Pending | Pending | — |

N/A = not applicable
¥ = Subject entered LTFU on Nov. 1, 2017; Month 2 PSA was drawn on Nov. 2, 2017
— = no unscheduled data for this subject
Pending = subject has not yet reached this time point Table 9 is a summary showing PSMA-TGFβRDN cell marking in the peripheral blood by iPCR for infused subjects (N=6).

TABLE 9

PSMA-TGFβRDN cell marking in the peripheral blood by qPCR for infused subjects (data provided in copies/microgram genomic DNA)

| Subject ID | Cohort | Pre-Infusion Safety | Day 0 pre | Day 0 post | Day 1 | Day 3 | Day 7 | Day 10 | Day 14 | Day 21 | Day 28 | Month 2 | Month 3 | Month 6 |
|---|---|---|---|---|---|---|---|---|---|---|---|---|---|---|
| 32816-02 | 1 | ND | ND | 85.15 | 4.53 | 101.82 | 343.70 | 1412.81 | 110.46 | 11.46 | 8.04 | N/A | N/A | N/A |
| 32816-04 | 1 | ND | ND | 151.6 | ND | 25.90 | 417.31 | 3351.64 | 216.02 | 27.02 | ND | ND | ND | N/A |
| 32816-05 | 1 | ND | ND | 46.99 | 5.95 | 9.23 | ND | 33.38 | 43.61 | 7.85 | 14.50 | ND | ND | ND |
| 32816-06 | 2 | ND | ND | 394.94 | 16.87 | 201.73 | 3099.79 | 1084.13 | 218.64 | Not Collected | 26.96 | N/A | N/A | N/A |

TABLE 9-continued

PSMA-TGFβRDN cell marking in the peripheral blood by qPCR for infused subjects (data provided in copies/microgram genomic DNA)

| Subject ID | Cohort | Pre-Infusion Safety | Day 0 pre | Day 0 post | Day 1 | Day 3 | Day 7 | Day 10 | Day 14 | Day 21 | Day 28 | Month 2 | Month 3 | Month 6 |
|---|---|---|---|---|---|---|---|---|---|---|---|---|---|---|
| 32816-07 | 2 | ND | ND | 530.57 | 16.27 | 89.39 | 457.40 | 151.45 | 84.31 | 43.40 | 14.50 | Not Yet Resulted | Pending | Pending |
| 32816-08 | 2 | ND | ND | 422.92 | 63.32 | 96.76 | 253.85 | 217.28 | 114.46 | 72.06 | Not Yet Resulted | Pending | Pending | Pending |

ND = not detected
N/A = not applicable - subject discontinued primary follow-up priot to this visit
Pending = subject has not yet reached this time point
Not Collected = Research samples were not collected for analysis
Not Yet Resulted = Sample has not yet been tested Table 10 is a summary showing PSMA-TGFβRDN cell marking in other tissues by qPCR for infused subjects (N=6).

TABLE 10

PSMA-TGFβRDN cell marking in other tissues by qPCR for infused subjects (data provided in copies/microgram genomic DNA)

| Subject ID | Cohort | Time Point | Sample Type | Results |
|---|---|---|---|---|
| 32816-02 | 1 | Day 10 | Tumor (1A FFPE tissue curls) | 122.32 |
|  |  |  | Tumor (2A FFPE tissue culrs) | 57.99 |
|  |  | Day 21 | Other (BMBMX core cells) | ND |
|  |  |  | Other (Marrow) | 27.12 |
|  |  | Month 2 | Other (BMBMX core cells) | ND |
| 32816-04 | 1 | Day 10 | Tumor (HS17-37343-1A Right Iliac) | 133.36 |
|  |  |  | Tumor (HS17-37343-1B Right Iliac) | 211.16 |
| 32816-05 | 1 | Day 10 | Tumor (Retroperitoneal lymph node) | 758.51 |
| 32816-06 | 2 | Day 10 | Tumor BX curls | 98.24 |
| 32816-07 | 2 | Day 10 | Tumor BX curls | ND |
| 32816-08 | 2 |  | No other tissue data at this time |  |

FFPE = Formalin-fixed, paraffin embedded
BMBMX = Bone marrow biopsy
BX = Biopsy
ND = Not detected Table 11 is a summary showing percent PSMA positive tumor cells for enrolled subjects as determined by immunohistochemistry (N=7).

TABLE 11

Percent PSMA positive tumor cells for enrolled subjects

|  | Subject ID | Cohort | Timepoint | Sample Type | Location | Results (%) |
|---|---|---|---|---|---|---|
| 1 | 32816-02 | 1 | Screening | Fresh | Right iliac bone | ND, biopsy insufficient |
|  |  |  | Screening | Fresh | Bladder | 100 |
|  |  |  | Day 10 | Fresh | Bladder | 100 |
| 2 | 32816-03 | NA | Screening | Fresh | Right external iliac lymph node | 100 |
| 3 | 32816-04 | 1 | Screening | Archived | Iliac bone | 30 |
|  |  |  | Day 10 | Fresh | Left iliac bone | 75 |
| 4 | 32816-05 | 1 | Screening | Fresh | Left retroperitoneal lymph node | 100 |
|  |  |  | Day 10 | Fresh | Left retroperitoneal lymph node | 100 |
| 5 | 32816-06 | 2 | Screening | Fresh | Para aortic lymph node | 25 |
|  |  |  | Day 10 | Fresh | Para aortic lymph node | 100 |
| 6 | 32816-07 | 2 | Screening | Fresh | Posterior vertebra | 100 |
|  |  |  | Day 10 | Fresh | L1 vertebra | 80 |
| 7 | 32816-08 | 2 | Screening | Fresh | Bladder | 100 |
|  |  |  | Day 10 | Fresh | Primary | 70-80 |

NA = Not assigned
ND = Not detected

Example 11: Phase 1 Clinical Trial of PSMA-Directed/TGFβ-Insensitive CAR-T Cells in Metastatic Castration-Resistant Prostate Cancer Background:

Adoptive immunotherapy with CAR-T cells has transformative potential for the treatment of cancer. A primary challenge to the success of these therapies in prostate cancer is the immunosuppressive microenvironment, including high levels of TGFβ, encountered by re-directed T cells upon tumor infiltration. Importantly, these immunosuppressive functions of TGFβ can be inhibited in T cells using a dominant negative TGFβ receptor (TGFβRdn), thereby enhancing antitumor immunity. In in vivo disseminated tumor models, co-expression of TGFβRdn on PSMA-directed CAR-T cells led to increased T cell proliferation, enhanced cytokine secretion, long-term persistence, and greater induction of tumor eradication. Mechanisms of adaptive tumor resistance are unknown.

Figure 15A:
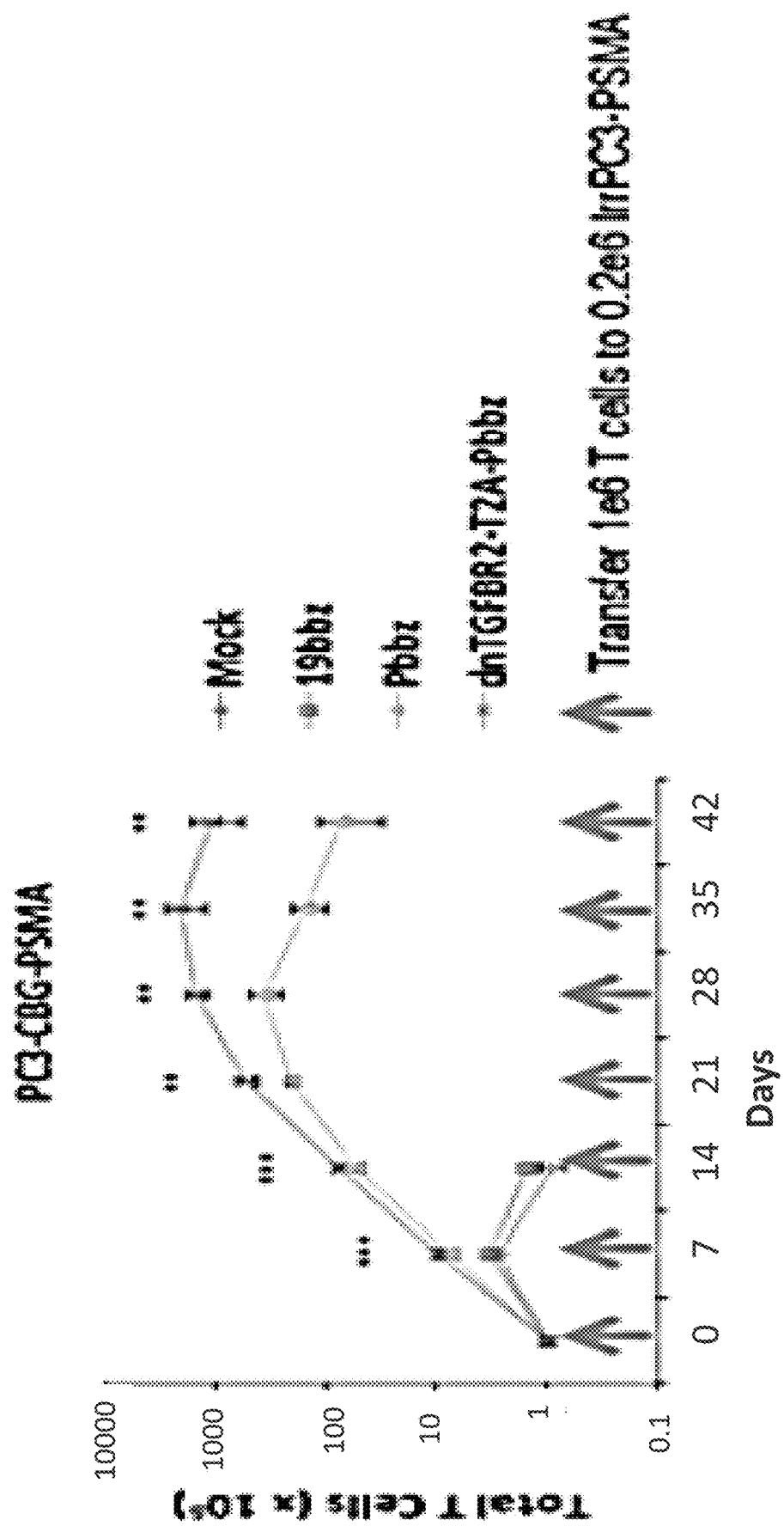
FIG. 15A is a graph showing that CART-PSMA-TGFβRdn cells (dnT-GFBR2-T2A-Pbbz) demonstrated enhanced antigen-specific proliferation versus CART-PSMA (Pbbz) over 42 days co-culture and repetitive stimulation with PSMA-expressing tumor cells (arrows). CD19-BBz CART (19bbz) and transduced T cells (mock) were used as controls.
Figure 15B:
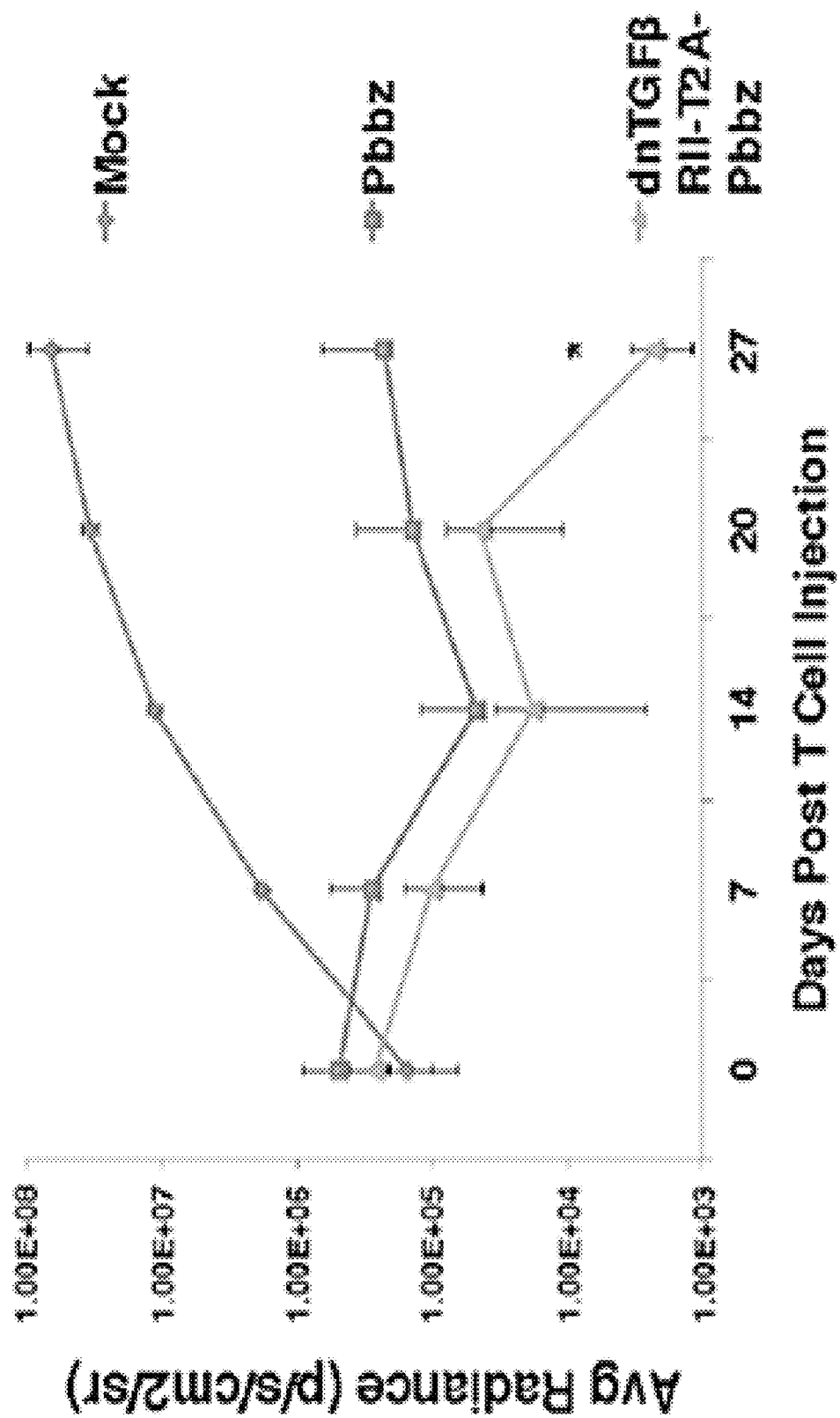
FIG. 15B is a graph showing the average radiance detected in tumor-bearing mice up to 27 days post T cell injection with CART-PSMA-TGFβRdn cells (dnTGFBR2-T2A-Pbbz), CART-PSMA cells (Pbbz), and untransduced cells used as control (mock).
Figure 15C:
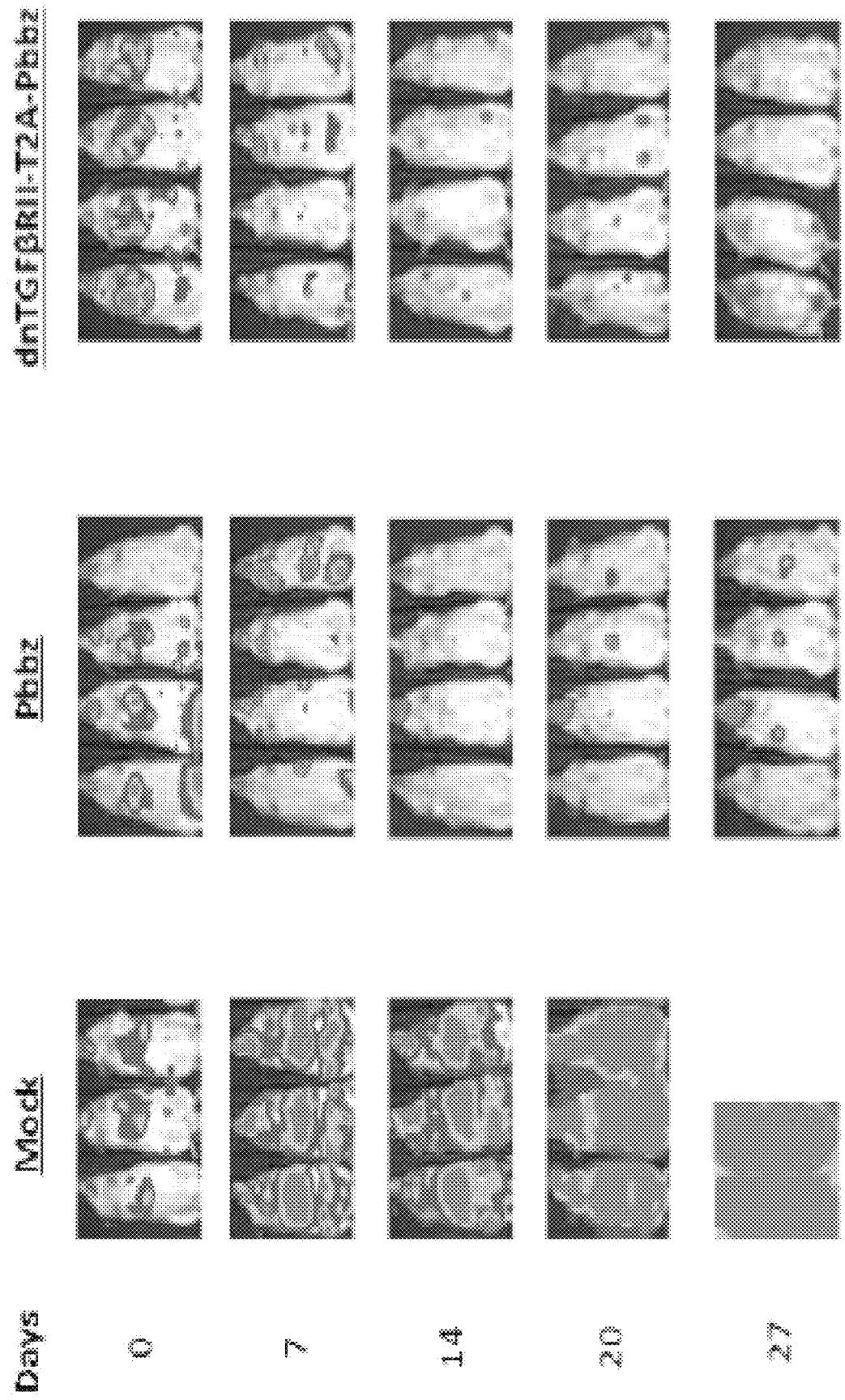
FIG. 15C are photographs showing the location and systemic burden of tumor with weekly Bioluminescence imaging (BLI) assessment.

FIG. 15 shows the efficacy of CART-PSMA-TGFβRdn cells in in vivo disseminated tumor models. FIG. 15A is a graph showing that CART-PSMA-TGFβRdn cells demonstrated enhanced antigen-specific proliferation versus CART-PSMA over 42 days co-culture and repetitive stimulation with PSMA-expressing tumor cells. FIG. 15B is a graph showing that in vivo, CART-PSMA-TGFβRdn cells demonstrated significantly increased tumor reduction compared to CART-PSMA, as measured by BLI imaging weekly to assess tumor burden. FIG. 15C are photographs showing the location and systemic burden of tumor with weekly BLI assessment. Abbreviations used in FIG. 15: Pbbz=CAR-T PSMA; dnTGFBR2-T2A-Pbbz=CART-PSMA-TGFβRdn; 19bbz=anti-CD19 CAR.

Study Design:

Study Overview: A first-in-human phase 1 clinical trial was initiated to evaluate the safety and preliminary efficacy of lentivirally-transduced PSMA-directed/TGFβ-insensitive CAR-T cells (CART-PSMA-TGFβRdn) in men with treatment-refractory metastatic castrate resistant prostate cancer (CRPC) (NCT03089203). In preliminary dose-escalation cohorts, patients received a single dose of $1-3\times10^7/m^2$ (Cohort 1) or $1-3\times10^8/m^2$ (Cohort 2) CART-PSMA-TGFβRdn cells without lymphodepleting chemotherapy in a 3+3 design. In Cohort 3, patients receive the maximum tolerated dose (MTD) of CART-PSMA-TGFβRdn cells following lymphodepleting chemotherapy with Cyclophosphamide 300 mg/m² and Fludarabine 30 mg/m² for 3 days. All treated patients underwent metastatic tumor biopsies at baseline, as well as on day +10 following the CAR-T cell infusion.

Key Eligibility Criteria:

Metastatic CRPC, with previous treatment with at least one second-generation androgen signaling inhibitor (abiraterone or enzalutamide); ≥10% tumor cells expressing PSMA by IHC on metastatic tissue biopsy; radiographic evidence for metastatic disease (osseous or nodal/visceral); ≤4 lines of therapy for metastatic CRPC.

Figure 16:
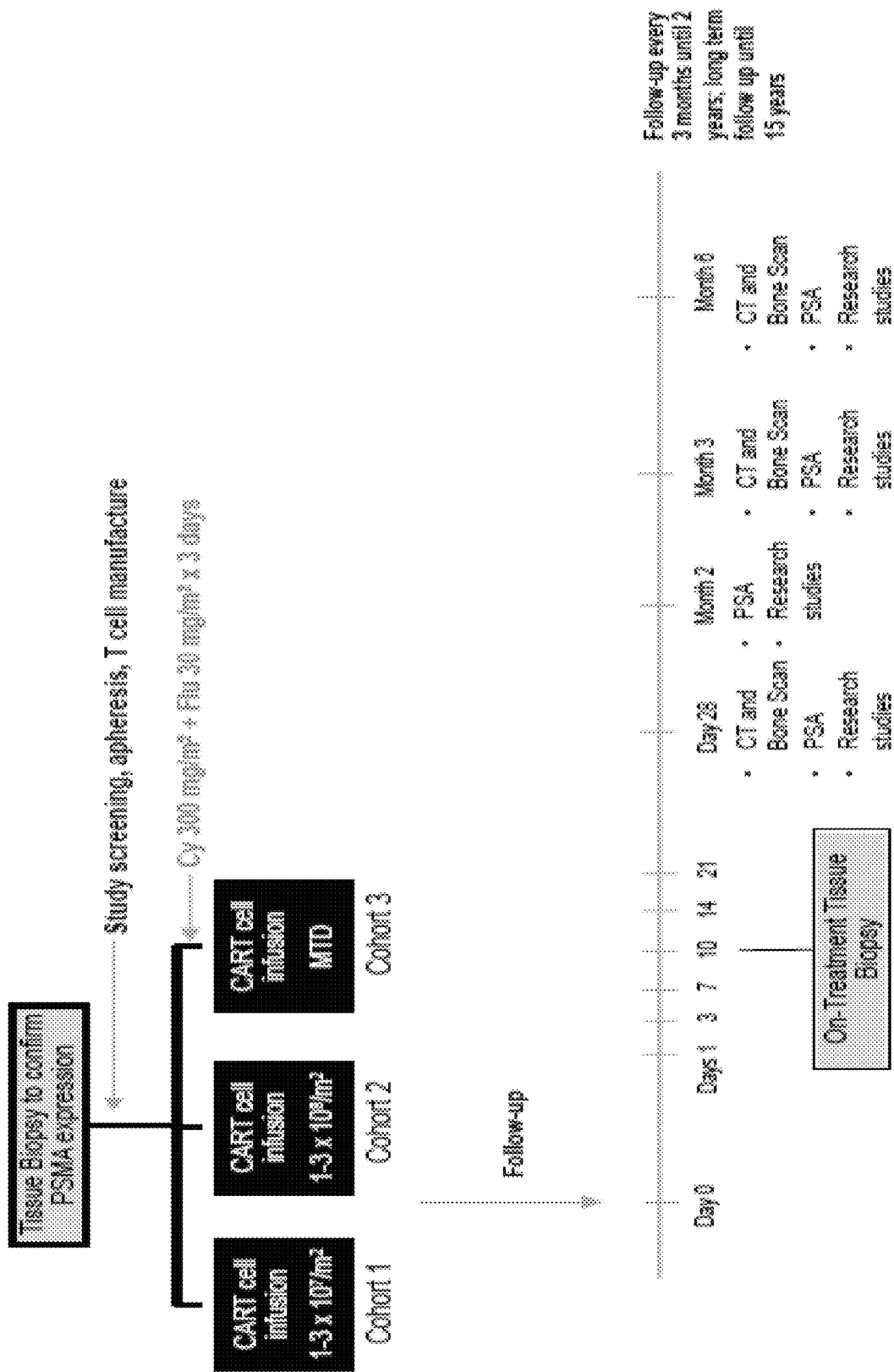
FIG. 16 illustrates the study schema used in a phase 1 clinical trial.

Study Schema:

FIG. 16 shows the study schema used in this clinical trial.

Correlative Analyses:

Quantitative PCR of CART-PSMA-TGFβRdn DNA was performed at serial timepoints to evaluate for CAR-T expansion and persistence in peripheral blood and trafficking to target tissues. Bioactivity of CART-PSMA-TGFβRdn cells in peripheral blood was evaluated through Luminex analyses of immune and inflammatory factors. Circulating tumor material was collected at serial time points and correlated with clinical response.

Study Status and Preliminary Findings:

Six patients received CART-PSMA-TGFβRdn cell infusions at the specified dose levels (Cohort 1, N=3; Cohort 2, N=3). All CART-PSMA-TGFβRdn infusion products met target transduction efficiency. No dose limiting toxicities were observed in preliminary dose escalation.

Figure 17:
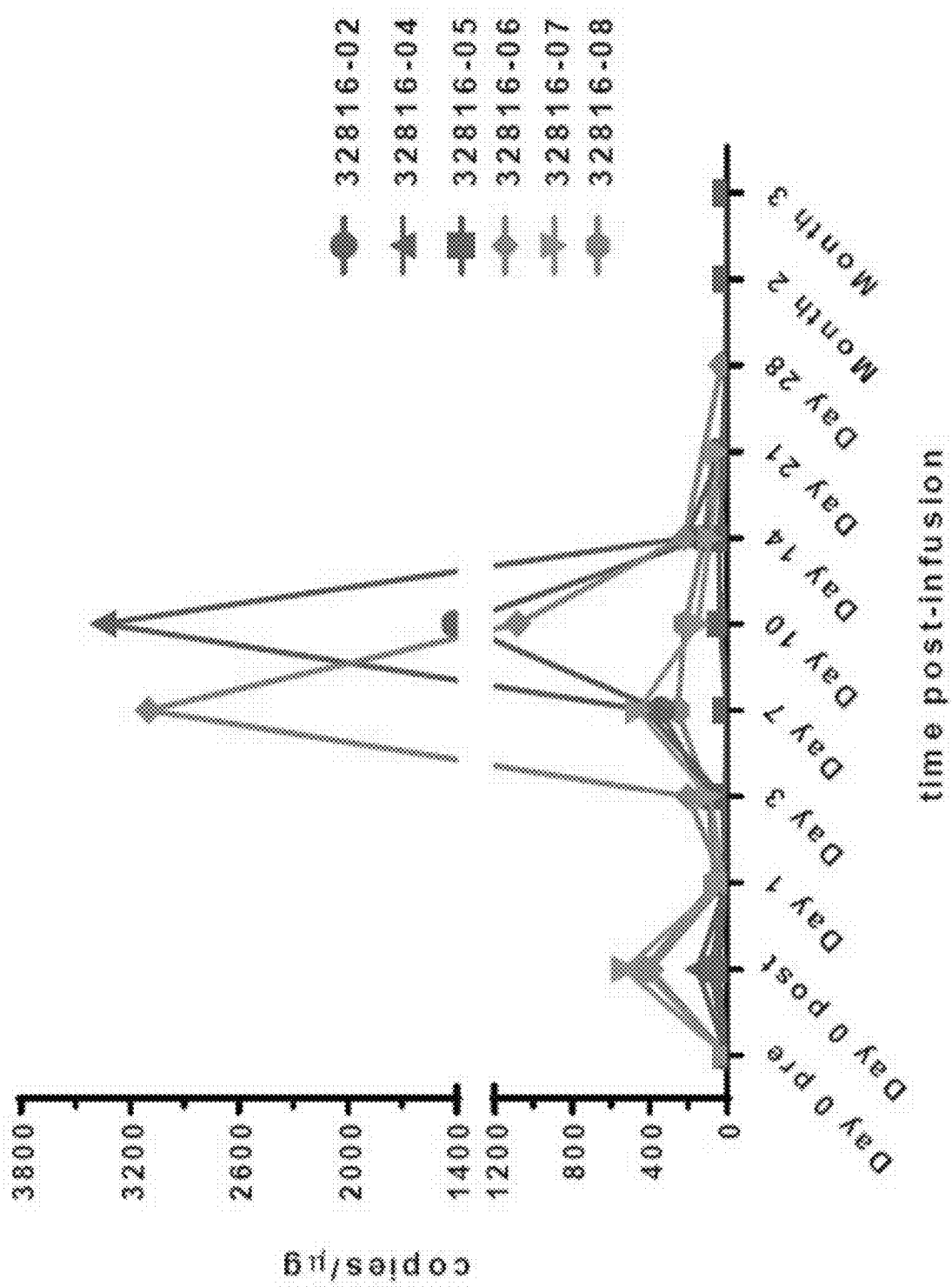
FIG. 17 is a graph showing the evaluation of CAR-T cellular kinetics via qPCR of CART-PSMA-TGFβRdn DNA in subjects. Subjects 32816-02, -04, and -05 are in Cohort 1, and subjects 32816-06, -07, and -08 are in Cohort 2.

Evaluation of CAR-T cellular kinetics via qPCR of CART-PSMA-TGFβRdn DNA demonstrated peripheral blood T cell expansion (FIG. 17), as well as tumor tissue trafficking in post-treatment tumor biopsies (Table 17).

TABLE 17

CART-PSMA-TGFβRDN cell trafficking: qPCR detection in tissue biopsy samples in infused subjects

| Subject ID | Cohort | Time Point | Sample Type | Results* |
|---|---|---|---|---|
| 32816-02 | 1 | Day 10 | Bladder (FFPE tissue curls) | 122.32 |
|  |  |  | Bladder (FFPE tissue curls) | 57.99 |
|  |  | Day 21 | Bone marrow biopsy core | ND |
|  |  |  | Bone marrow | 27.12 |
|  |  | Month 2 | Bone marrow biopsy core | ND |
| 32816-04 | 1 | Day 10 | Bone (FFPE tissue curls) | 133.36 |
|  |  |  | Bone (FFPE tissue curls) | 211.16 |
| 32816-05 | 1 | Day 10 | Lymph node (FFPE tissue) | 758.51 |
| 32816-06 | 2 | Day 10 | Lymph node (FFPE tissue) | 98.24 |
| 32816-07 | 2 | Day 10 | Bone (FFPE tissue curls) | ND |
| 32816-08 | 2 |  | Data analysis pending |  |

*copies/ug gDNA
FFPE = formalin-fixed, paraffin embedded
ND = not detected

In Cohort 2, two patients developed anticipated Grade 3 cytokine release syndrome (CRS), which is a critical marker of biologic activity with CAR-T therapy, and one patient developed Grade 3 CAR-T neurotoxicity requiring corticosteroids.

Figure 18A:
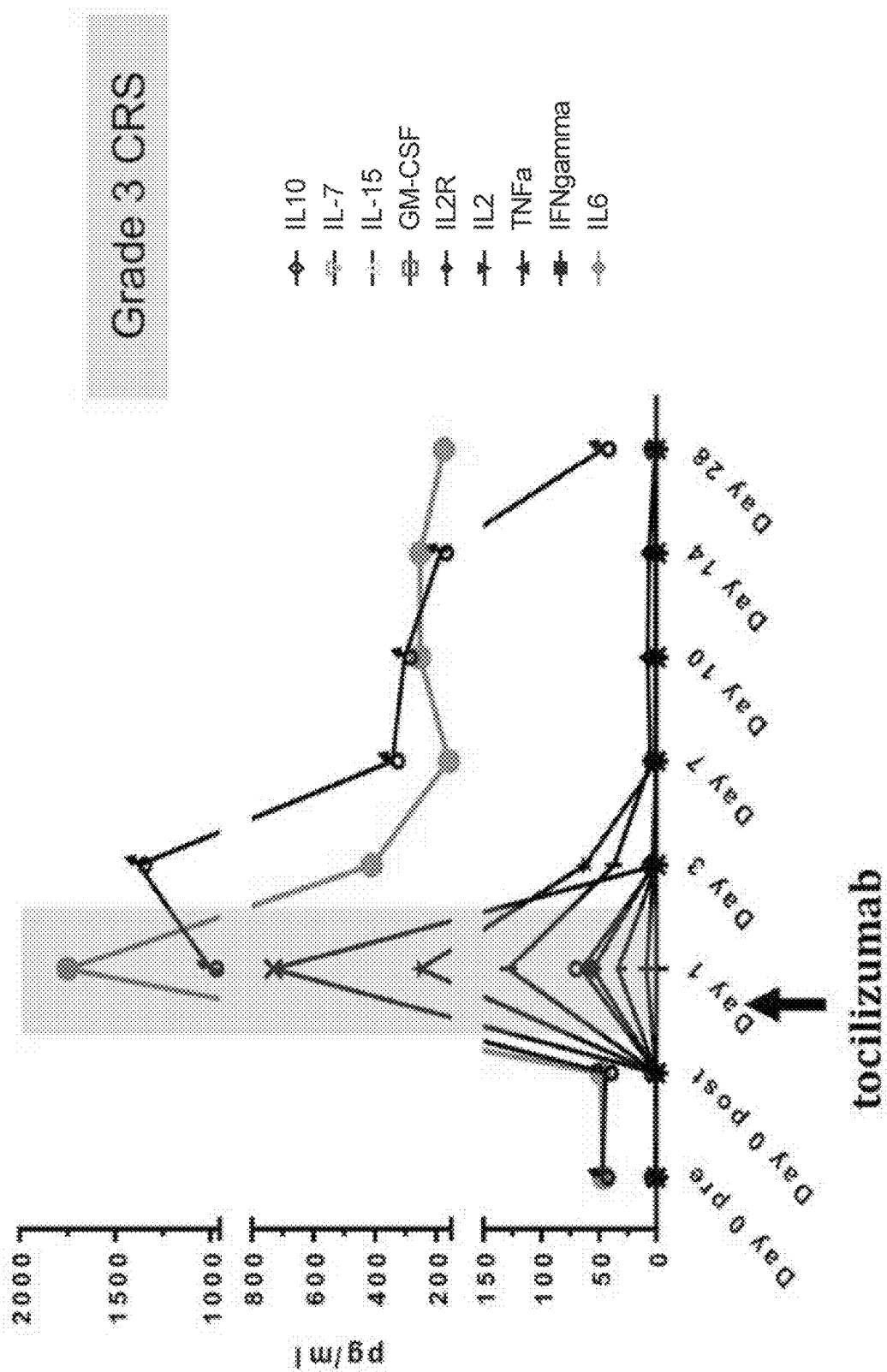
FIG. 18A is a graph showing marked increases in inflammatory cytokines (IL-6, IL-15, IL-2, IFNgamma) and ferritin, correlating with a grade 3 cytokine release syndrome event in subject 32816-06.
Figure 18B:
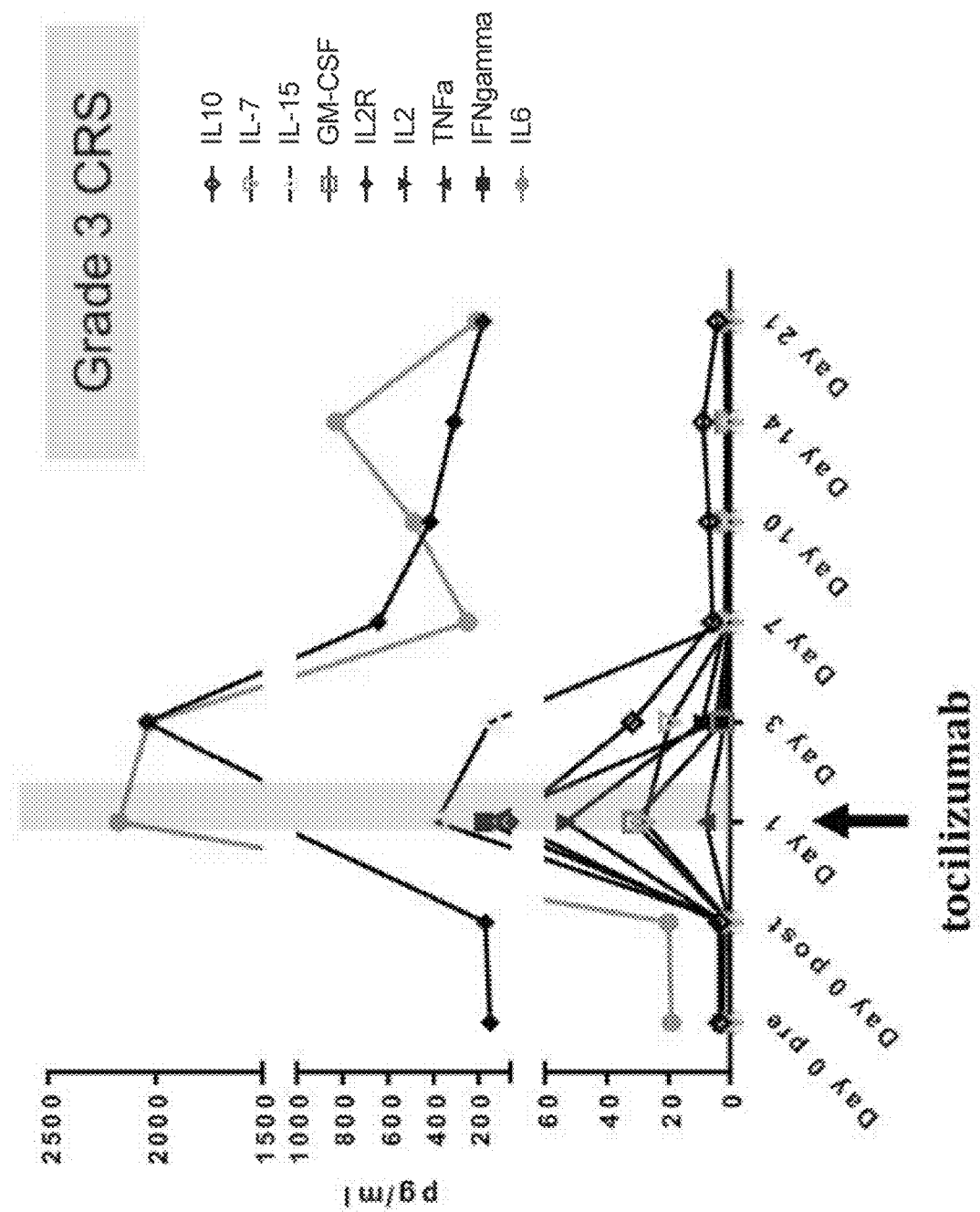
FIG. 18B is a graph showing marked increases in inflammatory cytokines (IL-6, IL-15, IL-2, IFNgamma) and ferritin, correlating with a grade 3 cytokine release syndrome event in subject 32816-07.

Marked increases in inflammatory cytokines (IL-6, IL-15, IL-2, IFNgamma) and ferritin correlated with all Grade 3 CRS events (Subject 32816-06: FIG. 18A; and subject 32816-07: FIG. 18B). All CRS events rapidly resolved with tocilizumab (anti-IL6R) rescue.

Cohort 3 enrollment (MTD with lymphodepleting chemotherapy) begain in September 2018.

Example 12: Cohorts 1 and 2 Observations and Case Study

Figure 19:
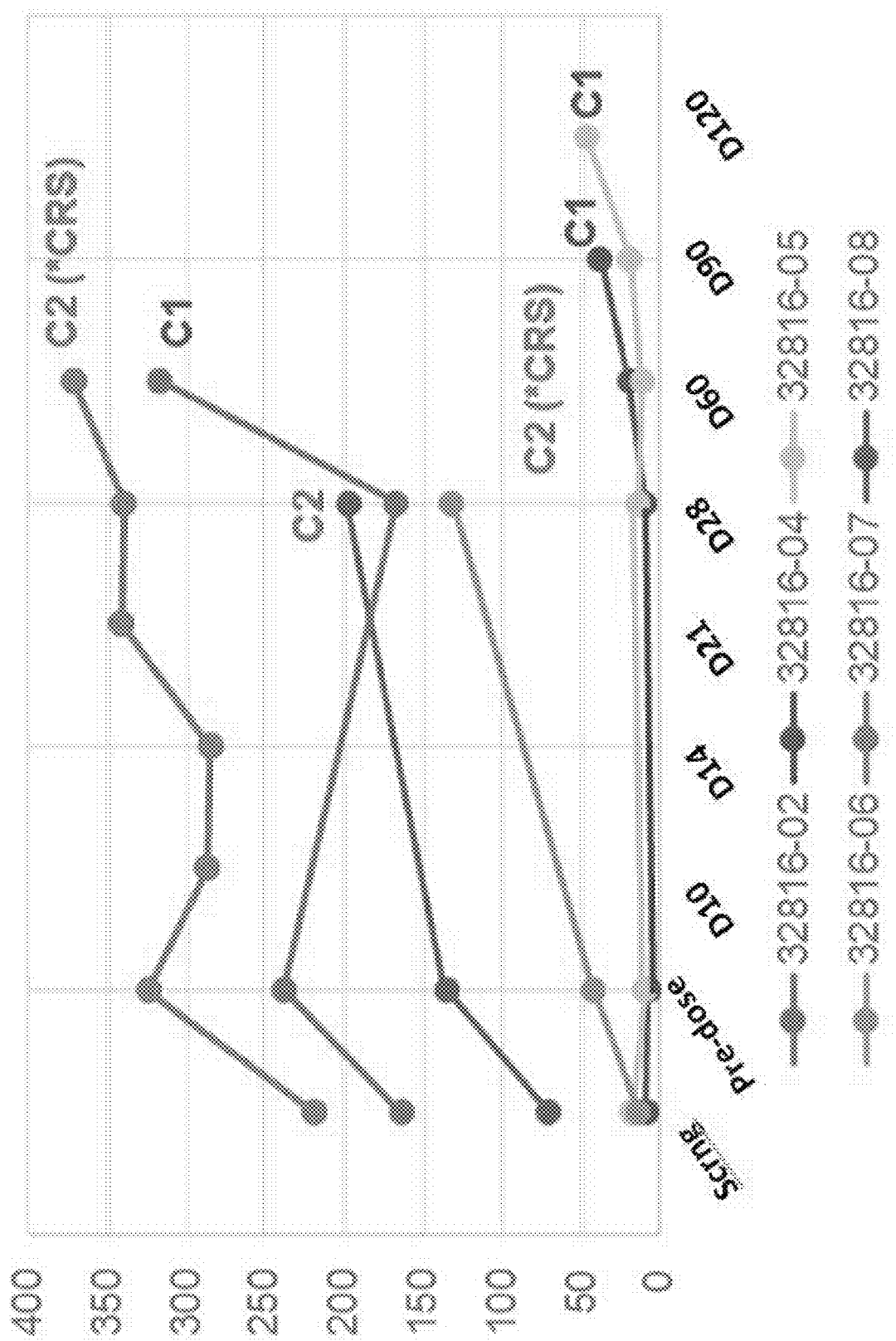
FIG. 19 is a graph showing the prostate specific antigen (PSA) response among Cohort 1 and Cohort 2 patients.

FIG. 19 shows a graph of prostate specific antigen (PSA) response among Cohort 1 and Cohort 2 patients.

Subject 32816-07:

74 year old with metastatic castration resistant prostate cancer (mCRPC; initial diagnosis: May 2014). Fever to 103F several hours post-PSMA-TGFβRDN CART infusion (no lymphodepletion) was observed. Hypotension was observed approximately 6 hours post-PSMA-TGFβRDN CART at 83/44 mmHg nadir. Hypotension was managed with crystalloid infusion (no pharmacologic management required during ICU admission) and tocilizumab with resolution by the following day after PSMA-TGFβRDN CART infusion.

Figure 20B:
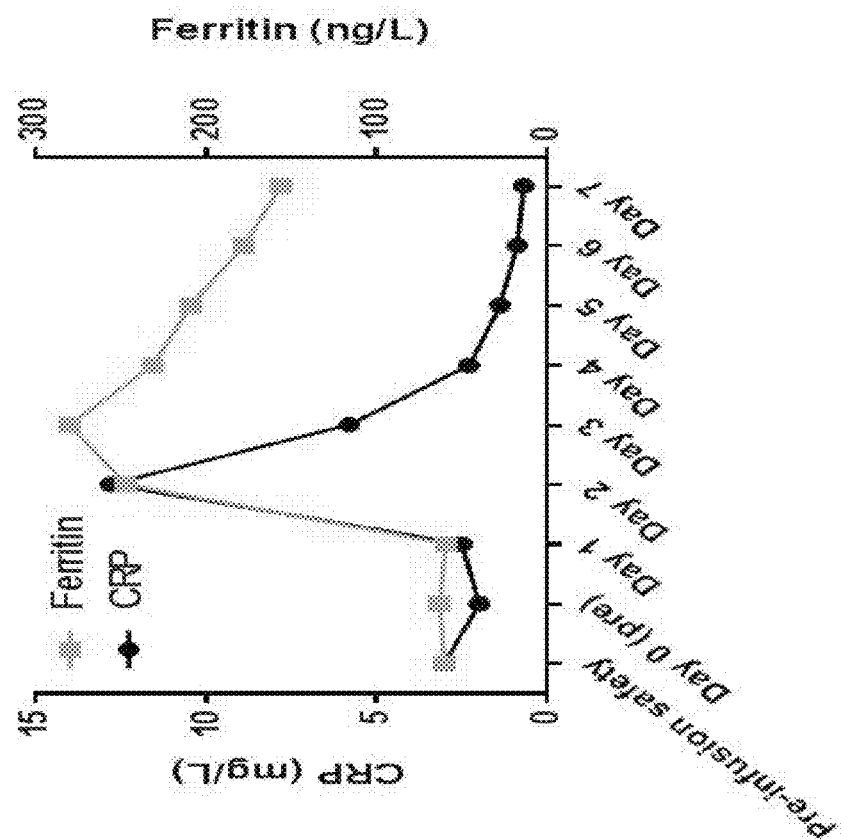
FIG. 20B is a graph showing that cytokine release syndrome management was accompanied by transient PSA decrease, as measured by the level of C-reactive protein (CRP; left y-axis in mg/L) and the level of serum ferritin (right y-axis in ng/L).
Figure 20A:
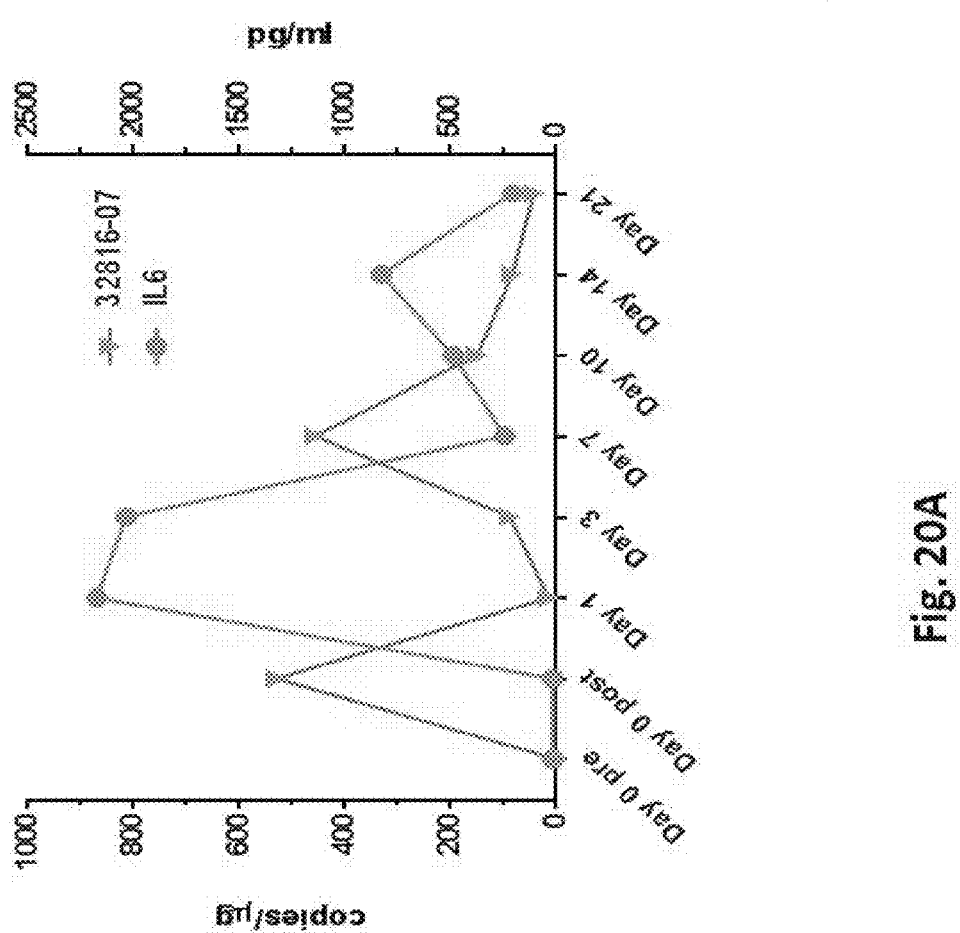
FIG. 20A is a graph showing the expression of PSMA-TGFβRDN CART (left y-axis in copies/ug of genomic DNA) and the level of IL-6 (right y-axis in pg/ml) in subject 32816-07, indicating cytokine release syndrome exhibited in subject one day post-infusion.

Cytokine release syndrome (CRS) was observed in patient 32816-07 following PSMA-TGFβRDN CART-infusion (FIG. 20A). In FIG. 20A, the left y-axis indicates the level of PSMA-TGFβRDN CART in peripheral blood in copies/ug of genomic DNA (32816-07), and the right y-axis indicates the level of IL-6 in pg/ml (IL6). CRS was accompanied by transient PSA decrease (FIG. 20B). In FIG. 20B, the left y-axis indicates the serum level of C-reactive protein (CRP) in mg/L and the right y-axis indicates the serum level of ferritin in ng/L.

Figure 21:
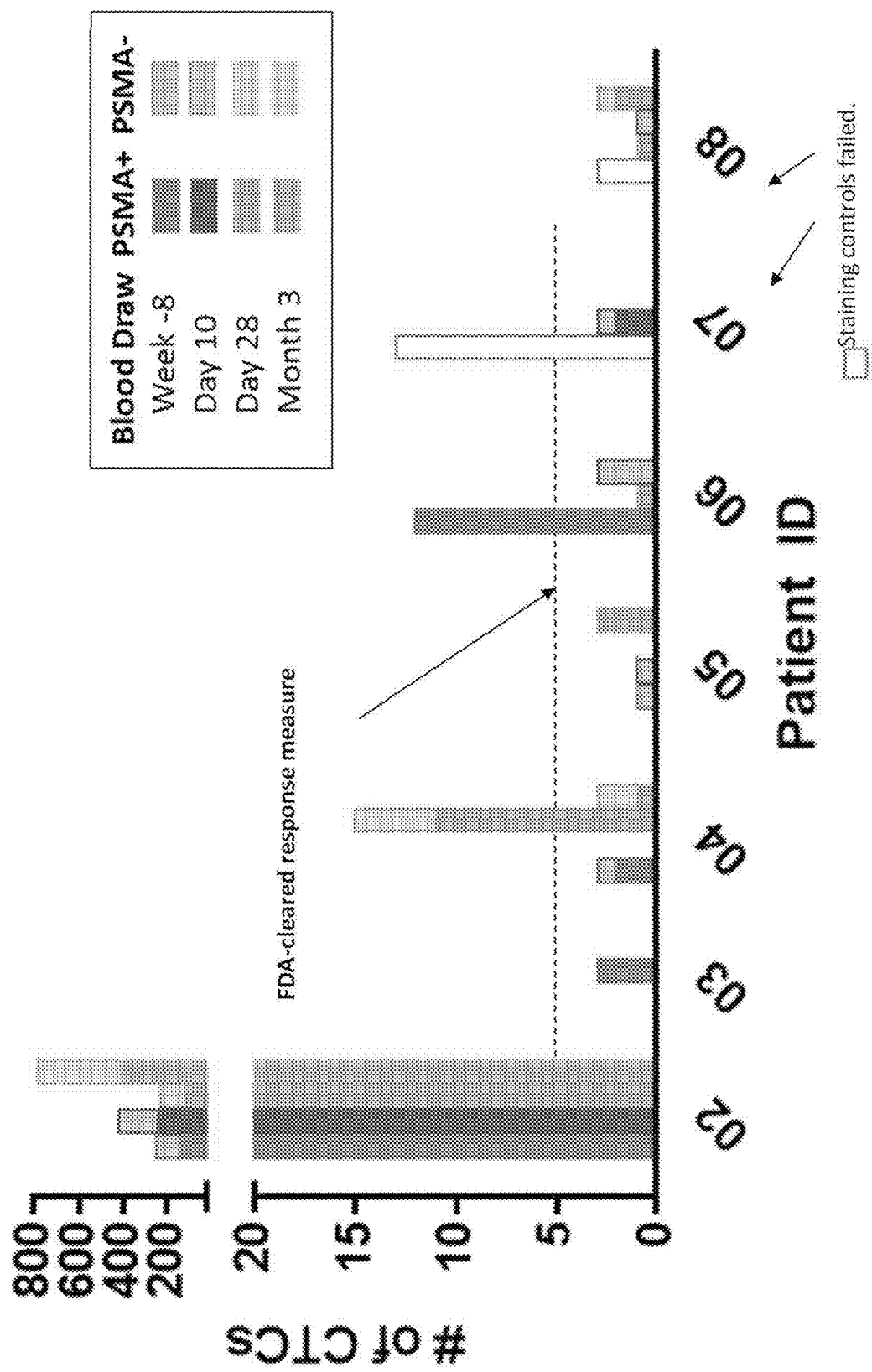
FIG. 21 is a graph showing the number of PSMA-positive circulating tumor cells (CTCs) detected in each subject over time.

PSMA Positive CTC Observations in Cohorts 1 and 2:

Table 18 shows a summary of the number of PSMA-positive circulating tumor cells (CTCs) detected in each subject across various time points, the data of which is graphed in FIG. 21.

TABLE 18

PSMA-positive CTCs in Cohorts 1 and 2

| Cohort | Subject ID | Week −8 Screening | | Day 10 Post-Infusion | | Day 28 Post-Infusion | | Month 3 Post-Infusion | |
|---|---|---|---|---|---|---|---|---|---|
| | | Total CTC | # PSMA + CTCs (%) | Total CTC | # PSMA + CTCs (%) | Total CTC | # PSMA + CTCs (%) | Total CTC | # PSMA + CTCs (%) |
| 1 | 32816-02 | 248 | 144 (58.1%) | 421 | 241 (57.2%) | 230 | 117 (50.9%) | 788 | 409 (51.9%) |
| | 32816-03 | 3 | 3 (100.0%) | | | Off study | | | |
| | 32816-04 | 3 | 2 (66.7%) | 0 | 0 | 15 | 11 (73.3%) | 3 | 1 (33.3%) |
| | 32816-05 | 1 | 0 (0.0%) | 1 | 0 (0.0%) | 0 | 0 | 3 | 3 (100.0%) |
| 2 | 32816-06 | 12 | 12 (100.0%) | 3 | 0 | 0 | 0 | 0 | Off study |
| | 32816-07 | 13 | — | 3 | 2 | 0 | 0 | 0 | 0 |
| | 32816-08 | 3 | — | | | Pending | | | |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A modified T cell, comprising:
    a chimeric antigen receptor (CAR) having affinity for a prostate specific membrane antigen (PSMA) on a target cell, wherein the CAR comprises the amino acid sequence set forth in SEQ ID NO:105; and
    a dominant negative receptor consisting of the amino acid sequence set forth in SEQ ID NO:115.

2. The modified T cell of claim 1, wherein the modified T cell is derived from a human.

3. The modified T cell of claim 1, wherein the modified T cell is an autologous cell.

* * * * *